(12) United States Patent
Wang et al.

(10) Patent No.: US 8,877,796 B2
(45) Date of Patent: Nov. 4, 2014

(54) SPIRO-OXINDOLE MDM2 ANTAGONISTS

(71) Applicant: The Regents of the University of Machigan, Ann Arbor, MI (US)

(72) Inventors: Shaomeng Wang, Saline, MI (US); Shanghai Yu, Ann Arbor, MI (US); Wei Sun, Yunnan (CN); Sanjeev Kumar, Ann Arbor, MI (US); Duxin Sun, Ann Arbor, MI (US); Peng Zou, Ann Arbor, MI (US); Donna McEachern, Ann Arbor, MI (US); Yujun Zhao, Ann Arbor, MI (US)

(73) Assignee: The Regents of the University of Michigan, Ann Arbor, MI (US)

( * ) Notice: Subject to any disclaimer, the term of this patent is extended or adjusted under 35 U.S.C. 154(b) by 0 days.

(21) Appl. No.: 13/944,587

(22) Filed: Jul. 17, 2013

(65) Prior Publication Data
US 2013/0296303 A1 Nov. 7, 2013

Related U.S. Application Data

(63) Continuation of application No. 12/945,511, filed on Nov. 12, 2010, now Pat. No. 8,518,984.

(60) Provisional application No. 61/260,685, filed on Nov. 12, 2009, provisional application No. 61/263,662, filed on Nov. 23, 2009.

(51) Int. Cl.
| | |
|---|---|
| *C07D 487/10* | (2006.01) |
| *A61K 31/407* | (2006.01) |
| *A61K 31/454* | (2006.01) |
| *C07D 495/10* | (2006.01) |
| *A61K 45/06* | (2006.01) |
| *A61K 31/496* | (2006.01) |
| *C07D 491/107* | (2006.01) |
| *A61K 31/5377* | (2006.01) |
| *A61K 31/675* | (2006.01) |

(52) U.S. Cl.
CPC ............ *C07D 487/10* (2013.01); *A61K 31/454* (2013.01); *C07D 495/10* (2013.01); *A61K 45/06* (2013.01); *A61K 31/496* (2013.01); *C07D 491/107* (2013.01); *A61K 31/407* (2013.01); *A61K 31/5377* (2013.01); *A61K 31/675* (2013.01)
USPC ........................... 514/409; 548/409; 548/411

(58) Field of Classification Search
None
See application file for complete search history.

(56) References Cited

U.S. PATENT DOCUMENTS

| | | | |
|---|---|---|---|
| 3,219,661 A | 11/1965 | Shavel, Jr. et al. | |
| 6,617,346 B1 | 9/2003 | Kong et al. | |
| 6,734,302 B2 | 5/2004 | Kong et al. | |
| 6,916,833 B2 | 7/2005 | Kim et al. | |
| 7,060,713 B2 | 6/2006 | Kim et al. | |
| 7,083,983 B2 | 8/2006 | Lane et al. | |
| 7,125,659 B1 | 10/2006 | Kiyoi et al. | |
| 7,132,421 B2 | 11/2006 | Fotouhi et al. | |
| 7,425,638 B2 | 9/2008 | Haley et al. | |
| 7,495,007 B2 | 2/2009 | Chen et al. | |
| 7,553,833 B2 | 6/2009 | Liu et al. | |
| 7,576,082 B2 | 8/2009 | Luk et al. | |
| 7,625,895 B2 | 12/2009 | Dominique et al. | |
| 7,638,548 B2 | 12/2009 | Liu et al. | |
| 7,723,372 B2 | 5/2010 | Liu | |
| 7,737,174 B2 | 6/2010 | Wang et al. | |
| 7,759,383 B2 | 7/2010 | Wang et al. | |
| 7,776,875 B2 | 8/2010 | Chen et al. | |
| 7,834,179 B2 | 11/2010 | Liu et al. | |
| 7,928,233 B2 | 4/2011 | Chen et al. | |
| 8,053,475 B2 | 11/2011 | Klein | |
| 8,058,269 B2 | 11/2011 | Chen et al. | |
| 8,076,482 B2 | 12/2011 | Chen et al. | |
| 8,088,815 B2 | 1/2012 | Bartkovitz et al. | |
| 8,088,931 B2 | 1/2012 | Wang et al. | |
| 8,134,001 B2 | 3/2012 | Ding et al. | |
| 8,222,288 B2 | 7/2012 | Wang et al. | |
| 8,518,984 B2 | 8/2013 | Wang et al. | |
| 8,629,141 B2 | 1/2014 | Wang et al. | |
| 8,680,132 B2 | 3/2014 | Wang et al. | |
| 2002/0039790 A1 | 4/2002 | Keplinger et al. | |
| 2002/0132977 A1 | 9/2002 | Yuan et al. | |
| 2004/0171035 A1 | 9/2004 | Huang et al. | |
| 2005/0137137 A1 | 6/2005 | Lane et al. | |
| 2005/0227932 A1 | 10/2005 | Lu et al. | |
| 2005/0288287 A1 | 12/2005 | Fotouhi et al. | |

(Continued)

FOREIGN PATENT DOCUMENTS

| | | |
|---|---|---|
| CN | 1410401 A | 4/2003 |
| EP | 2 298 778 A1 | 3/2011 |

(Continued)

OTHER PUBLICATIONS

Alper, P. B. et al., "Facile, Novel Methodology for the Synthesis of Spiro[pyrrolidin-3,3'-oxindoles]: Catalyzed Ring Expansion Reactions of Cyclopropanes by Aldimines," *Angew. Chem. Int. Ed.* 38:3186-3189, Wiley-VCH Verlag GmbH (1999).

(Continued)

*Primary Examiner* — Michael Barker
(74) *Attorney, Agent, or Firm* — Casimir Jones SC

(57) ABSTRACT

Provided herein are compounds, compositions, and methods in the field of medicinal chemistry. The compounds and compositions provided herein relate to spiro-oxindoles which function as antagonists of the interaction between p53 and MDM2, and their use as therapeutics for the treatment of cancer and other diseases.

23 Claims, 50 Drawing Sheets

(56) References Cited

U.S. PATENT DOCUMENTS

| | | | |
|---|---|---|---|
| 2006/0211718 | A1 | 9/2006 | Weissman et al. |
| 2006/0211757 | A1* | 9/2006 | Wang et al. .................. 514/409 |
| 2006/0241017 | A1 | 10/2006 | Chandran |
| 2006/0287244 | A1 | 12/2006 | Chandran |
| 2007/0249564 | A1 | 10/2007 | Erion et al. |
| 2008/0039472 | A1 | 2/2008 | Lacrampe et al. |
| 2008/0171723 | A1 | 7/2008 | Khan |
| 2008/0261917 | A1 | 10/2008 | Willems et al. |
| 2008/0280769 | A1 | 11/2008 | Doemling |
| 2009/0030181 | A1 | 1/2009 | Han et al. |
| 2009/0143364 | A1 | 6/2009 | Fotouhi et al. |
| 2009/0149493 | A1 | 6/2009 | Lacrampe et al. |
| 2009/0227542 | A1 | 9/2009 | Khan |
| 2009/0312310 | A1 | 12/2009 | Kawato et al. |
| 2010/0048593 | A1 | 2/2010 | Weissman et al. |
| 2010/0216770 | A1 | 8/2010 | Storck et al. |
| 2011/0201635 | A1 | 8/2011 | Liu et al. |
| 2011/0251252 | A1 | 10/2011 | Wang et al. |
| 2011/0269809 | A1 | 11/2011 | Chu et al. |
| 2012/0046306 | A1 | 2/2012 | Bartkovitz et al. |
| 2012/0071499 | A1 | 3/2012 | Chu et al. |
| 2012/0101092 | A1 | 4/2012 | Wang et al. |
| 2012/0122947 | A1 | 5/2012 | Wang et al. |
| 2012/0289494 | A1 | 11/2012 | Wang et al. |
| 2013/0030173 | A1 | 1/2013 | Wang et al. |

FOREIGN PATENT DOCUMENTS

| | | |
|---|---|---|
| GB | 1056537 | 1/1967 |
| JP | 40-23184 | 10/1965 |
| JP | 44-4986 | 2/1969 |
| RU | 2 084 449 C1 | 7/1997 |
| RU | 2186776 C2 | 10/2002 |
| WO | WO 98/00409 A1 | 1/1998 |
| WO | WO 99/12904 A1 | 3/1999 |
| WO | WO 03/051360 A1 | 6/2003 |
| WO | WO 2005/046575 A2 | 5/2005 |
| WO | WO 2005/110992 A1 | 11/2005 |
| WO | WO 2006/125784 A1 | 11/2006 |
| WO | WO 2008/106507 A2 | 9/2008 |
| WO | WO 2008/119741 A2 | 10/2008 |
| WO | WO 2008/125487 A1 | 10/2008 |
| WO | WO 2009/156735 A2 | 12/2009 |
| WO | WO 2011/067185 A1 | 6/2011 |
| WO | WO 2011/106650 A2 | 9/2011 |

OTHER PUBLICATIONS

Azmi, A.S. et al., "MDM2 inhibitor MI-319 in combination with cisplatin is an effective treatment for pancreatic cancer independent of p53 function," *Eur. J. Cancer* 46:1122-1131, Elsevier Ltd. (2010).
Ban, Y. and Oishi, T., "The Synthesis of 3-Spiro-oxindole Derivatives. I. Syntheses of 1-Methyl-2', 3', 10',10'α-tetrahydrospiro[indoline-3,1'(5'H)-pyrrolo[1,2-b]-isoquinoline]-2-one and its Homologs," *Chem. Pharm. Bull.* 4:441-445, Pharmaceutical Society of Japan (1963).
Barakat, K. et al., "Ensemble-based virtual screening reveals dual-inhibitors for the p53-MDM2/MDMX interactions," *Journal of Molecular Graphics & Modelling* 28:555-568, Elsevier Inc. (2010).
Baxter, E.W. and Reitz, A.B, "Reductive aminations of carbonyl compounds with borohydride and borane reducing agents. Organic reactions" (Hoboken, NJ, United States), 59, (2002) (online); Found from database ASC on STN, CA: 149-5759820 (2010).
Canner, J.A. et al., "MI-63: A novel small-molecule inhibitor targets MDM2 and induces apoptosis in embryonal and alveolar rhabdomyosarcoma cells with wild-type p53," *Br. J Cancer* 101:774-781, Cancer Research UK (2009).
Chène, P., "Inhibiting the p53-MDM2 Interaction: An Important Target for Cancer Therapy," *Nature Reviews: Cancer* 3:102-109, Nature Publishing Group, London, UK (2003).
Cochard, F. et al., "Synthesis of Substituted 1,2,3,4-Tetrahydro-1-thiacarbazole and Spiro[pyrrolidinone-3,3'-indolinones] through a Common Intermediate Obtained by Condensation of Indolin-2-one, (Aryl)aldehydes, and Meldrum's Acid," *Eur. J. Org. Chem.* 20:3481-3490, Wiley-VCH Verlag GmbH (2002).
Cossy, J. et al., "A Convenient Route to Spiropyrrolidinyl-Oxindole Alkaloids via C-3 Substituted Ene-Pyrrolidine Carbamate Radical Cyclization," *Tetrahedron Letters* 39:2331-2332, Elsevier Science Ltd. (1998).
Cui, C-B et al., "Isolation, Structure Determination and Biological Activities of Novel Mammalian Cell Cycle Inhibitors, Spirotryprostatins A & B, Tryprostatins A & B and Related New Diketopiperazine Derivatives Produced by a Fungus, *Aspergillus fumigatus,*" *Symposium on the Chemistry of Natural Products* 38:49-54 (1996).
Ding, K. et al., "Structure-Based Design of Spiro-oxindoles as Potent, Specific Small-Molecule Inhibitors of the MDM2-p53 Interaction," *J. Med. Chem.* 49:3432-3435, American Chemical Society (2006).
Ding, K. et al., "Structure-Based Design of Potent Non-Peptide MDM2 Inhibitors," *J. Am. Chem. Soc.* 127:10130-10131, American Chemical Society (2005).
Ding, K. et al., "Synthesis of spirooxindoles via asymmetric 1,3-dipolar cycloaddition," *Tetrahedron Letters* 46:5949-5951, Elsevier Ltd. (2005).
Döé de Maindreville, M. and Lévy, J., "Synthèses en série indolique. VII. Synthése et transformation chimiques de l'enchaînement tétracyclique commun aux alcaloïdes á chromophore ester an ilinoacrylique," *Bulletin de la Société Chimique de France* 5-6:179-184, Societe Francaise De Chimie (1981).
Dörnyei, G. et al., "Intramolecular Mannich Reaction of 2-Oxotryptamine and Homologues with Oxo Reagents Yielding Spiro Compounds. Part II," *Collect. Czech Chem. Commun.* 67:1669-1680, Nakladatelstvi Ceskoslovenski Akademie Ved. (2002).
Edmondson, S. et al., "Total Synthesis of Spirotryprostatin A, Leading to the Discovery of Some Biologically Promising Analogs," *J. Am. Chem. Soc.* 121:2147-2155, American Chemical Society (1999).
García-Echeverría, C. et al., "Discovery of Potent Antagonists of the Interaction between Human Double Minute 2 and Tumor Suppressor p53," *J. Med.* 43:3205-3208, American Chemical Society (2000).
Giese, B. et al., Radical cyclization reactions, Organic reactions (Hoboken, NJ, United States), 48 (1996) (online); Found from database ASC on STN, CA: 149:5550940 (2010).
Grigg, R. et al., "Spiro-oxindoles via bimetallic [Pd(0)/Ag(I)] catalytic intramolecular Heck-1,3-dipolar cycloaddition cascade reactions," *Tetrahedron Letters* 43:2605-2608, Elsevier Science Ltd. (2002).
Harley-Mason, J. and Ingleby, R.F.J., "Hydroxytryptamines, Part IV. Synthesis and Reactions of 2-3'-Oxindolylethylamines," *J. Chem. Soc.* 3639-3642, Chemical Society of Great Britain, London, UK (1958).
Incze, M. et al., "Intramolecular Mannich Reaction of 2-Oxotryptamines with Acetone Yielding Spiro[indole-3,3'-pyrrolidin]-2-ones," *Collect. Czech Chem. Commun.* 64:408-416, Institute of Organic Chemistry and Biochemistry, Academy of Sciences of the Czech Republic, Prague (1999).
Jones, R.I. et al., "Inhibition of the p53 E3 Ligase HDM-2 induces Apoptosis and DNA Damage-Independent p53 Phosphorylation in Mantle Cell Lymphoma," *Clin. Cancer Res.* 14:5416-5425, American Association of Cancer Research (2008).
Kabankin, A.S., et al., "Analysis of Structure—Hepatoprotective Activity Relationship for Indole Derivatives." *Chemical and Pharmaceutical Magazine*, 39:24-28 (2005).
Kuroda, M. et al., "Cytotoxic Alkaloids from the Barks of *Ochrosia elliptica,*" *Natural Medicines* 53:272 (1999).
Kussie, P.H. et al., "Structure of the MDM2 Oncoprotein Bound to the p53 Tumor Suppressor Transactivation Domain," *Science* 274:948-953, American Association for the Advancement of Science (1996).
Leclercq, J., et al., "Screening of Cytotoxic Activities of *Strychnos* Alkaloids (Methods and Results)," *J. Ethnopharmacology* 15:305-316, Elsevier Scientific Publishers Ireland Ltd. (1986).
Lizos, D. et al., "A novel and economical route to (±)-horsfiline using an aryl iodoazide tandem radical cyclisation strategy," *Chem. Commun.* 2732-2733, The Royal Society of Chemistry (2001).

(56) References Cited

OTHER PUBLICATIONS

Lizos, D.E. and Murphy, J.A., "Concise synthesis of (±)-horsfiline and (±)-coerulescine by tandem cyclisation of iodoaryl alkenyl azides," *Org. Biomol. Chem.* 1: 117-122, The Royal Society of Chemistry (2003).

Lu, Y. et al., "Discovery of a Nanomolar Inhibitor of the Human Murine Double Minute 2 (MDM2)-p53 Interaction through an Integrated, Virtual Database Screening Strategy," *J. Med. Chem.* 49:3759-3762, American Chemical Society (2006).

Marti, C. and Carreira, E.M., "Construction of Spiro[pyrrolidine-3,3'-oxindoles] — Recent Applications to the Synthesis of Oxindole Alkaloids." *Eur. J. Org. Chem.* 2209-2219, Wiley-VCH Verlag GmbH & Co. (2003).

Miyake, F.Y. et al., "Preparation and Synthetic Applications of 2-Halotryptophan Methyl Esters: Synthesis of Spirotryprostatin B," *Angew. Chem. Int. Ed.* 43:5357-5360, Wiley-VCH Verlag GmbH & Co. (2004).

Mohammad, R.M. et al., "An MDM2 antagonist (MI-319) restores p53 functions and increases the life span of orally treated follicular lymphoma bearing animals," *Mol. Canc.* 8:115, BioMed Central (2009).

Muhammad, I., "Investigation of Uña De Gato I. 7-Deoxyloganic acid and $^{15}$N NMR spectropscopic studies on pentacyclic oxindole alkaloids from *Uncaria tomentosa*," *Phytochemistry* 57:781-785, Elsevier Science Ltd. (2001).

Nikolovska-Coleska, Z. et al., "Development and optimization of a binding assay for the XIAP BIR3 domain using fluorescence polarization," *Analytical Biochemistry* 332:261-273, Elsevier Inc. (2004).

Onishi T. et al., "Concise, asymmetric total synthesis of spirotryprostatin A," *Tetrahedron* 60:9503-9515, Elsevier Ltd. (2004).

Onishi, T. et al., "Concise, Asymmetric Total Synthesis of Spirotryprostatin A," *Org. Lett.* 5:3135-3137, American Chemical Society (2003).

Pellegrini, C. et al., "Synthesis of the Oxindole Alkaloid (–)-Horsfiline," *Tetrahedron: Asymmetry* 5:1979-1992, Elsevier Science Ltd. (1994).

Pellegrini, C. et al., "Total Synthesis of (+)-Elacomine and ( )-Isoelacomine, Two Hitherto Unnamed Oxindole Alkaloids from *Elaeagnus commutata*," *Helv. Chim. Acta* 79:151-168, Schweizerische Chemische Gessellschaft, Basel (1996).

Rothweiler, U. et al., "Isoquinolin-1-one inhibitors of the MDM2-p53 interaction," *ChemMedChem* 3:1118-1128, Wiley-VCH Verlag GmbH & Co. (2008).

Saddler, C. et al., "Comprehensive biomarker and genomic analysis identities p53 status as the major determinant of response to MDM2 inhibitors in chronic lymphocytic leukemia," *Blood* 111:1584-1593, The American Society of Hematology (2008).

Samudio, I.J. et al., "Activation of p53 signaling by MI-63 induces apoptosis in acute myeloid leukemia cells," *Leukemia & Lymphoma* 51:911-919, Informa Healthcare USA, Inc. (2010).

Schubert, M.A. and Müller-Goymann, C.C. "Solvent injection as a new approach for manufacturing lipid nanoparticles—evaluation of the method and process parameters," *European Journal of Pharmaceutics and Biopharmaceutics* 55:125-131, Elsevier Science B.V. (2003).

Sebahar P.R. and Williams, R.M., "The Synthesis of Spirooxindole Pyrrolidines Via an Asymmetric Azomethine Ylide [1,3]-Dipolar Cycloaddition Reaction," *Heterocycles* 58:563-575, Elsevier Science (2002).

Sebahar, P.R. et al., "Asymmetric, stereocontrolled total synthesis of (+) and (–)-spirotryprostatin B via a diastereoselective azomethine ylide [1,3]-dipolar cycloaddition reaction," *Tetrahedron* 58:6311-6322, Elsevier Science Ltd. (2002).

Sebahar P.R. and Williams, R.M., "The Asymmetric Total Synthesis of (+)- and (–)-Spirotryprostatin B," *J. Am. Chem. Soc.* 122:5666-5667, American Chemical Society (2000).

Shangary, S. et al., "Reactivation of p53 by a specific MDM2 antagonist (MI-43) leads to p21-mediated cell cycle arrest and selective cell death in colon cancer," *Mol. Cancer Ther.* 7:1533-1542, American Association for Cancer Research (2008).

Shangary, S. et al., "Temporal activation of p53 by a specific MDM2 inhibitor is selectively toxic to tumors and leads to complete tumor growth inhibition," *Proc. Nat. Acad. Sci. (USA)* 105:3933-3938, The National Academy of Sciences of the USA (2008).

Sharma, P. et al., "Alkaloids of *Amsonia brevifolia*," *Phytochemistry* 27:3649-3652, Pergamon Press (1988).

Somet, M. et al., "Preparation and a Novel Rearrangement Reaction of 1,2,3,4- tetrahydro-9-hydroxy-β-carboline, and Their Applications for the Total Synthesis of (±)-Cocrulescinc," *Heterocycles* 53:7-10, Elsevier Science (2000).

Sun, S.H. et al., "A small molecule that disrupts Mdm2-p53 binding activates p53, induces apoptosis and sensitizes lung cancer cells to chemotherapy," *Cancer Biology & Therapy* 7:845-852, Landes Bioscience (2008).

Usui, T. et al., "Tryprostatin A, a specific and novel inhibitor of microtubule assembly," *Biochem. J.* 333:543-548, The Biochemical Society, London (1998).

van Tamelen, E.E. et al., "Spiro[Pyrrolidine-3 : 3'-Oxindole and -2'-*Pseudo*-Indoxyl]," *Chemistry & Industry* 1145-1146, Society of Chemical Industry, London (1956).

Vassilev, L.T. et al., "In Vivo Activation of the p53 Pathway by Small-Molecule Antagonists of MDM2," *Science* 303:844-848, American Association for the Advancement of Science (2004).

Vogelstein, B. et al., "Surfing the p53 network," *Nature* 408:307-310, Nature Publishing Group (2000).

Wade, M. et al., "BH3 activation blocks Hdmx suppression of apoptosis and cooperates with Nutlin to induce cell death," *Cell Cycle* 7:1973-1982, Landes Bioscience (2008).

Wang, H. and Ganesan, A., "A Biomimetic Total Synthesis of (–)-Spirotryprostatin B and Related Studies," *J. Org. Chem.* 65:4685-4693, The American Chemical Society (2000).

Wu, K-M and Farrelly, J.G, "Regulatory perspectives of Type II prodrug development and time-dependent toxicity management: Nonclinical Pharm/Tox analysis and the role of comparative toxicology" *Toxicology* 236: 1-6, Elsevier Ireland Ltd. (2007).

Wu, X. et al., "The p53-mdm-2 autoregulatory feedback loop," *Genes & Development* 7:1126-1132, Cold Spring Harbor Laboratory Press (1993).

Yu, S. et al., "Potent and Orally Active Small-Molecule Inhibitors of the MDM2—p53 Interaction," *J. Med. Chem.* 52:7970-7973, American Chemical Society (2009).

Antonchick, A.P. et al., "Highly enantioselective synthesis and cellular evaluation of spirooxindoles inspired by natural products," *Nature Chemistry* 2:735-740, Macmillan Publishers Limited (Sep. 2010; published online Jul. 11, 2010).

Chen, X.-H. et al., "Organocatalytic Synthesis of Spiro[pyrrolidin-3,3'-oxindoles] with High Enantiopurity and Structural Diversity," *J. Am. Chem. Soc.* 131:13819-13825, American Chemical Society (2009).

Dudkina, A.S. and Lindsley, C.W., "Small Molecule Protein-Protein Inhibitors for the p53-MDM2 Interaction," *Current Topics in Medicinal Chemistry* 7:952-960, Bentham Science Publishers Ltd. (2007).

Galliford, C.V. and Scheidt, K.A., "Pyrrolidinyl-Spirooxindole Natural Products as Inspirations for the Development of Potential Therapeutic Agents," *Angew. Chem. Int. Ed.* 46:8748-8758, Wiley-VCH Verlag GmbH & Co. KGaA, Weinheim (2007).

Jansen, A.B.A. and Richards, C.G., "A Synthesis of Some Spiro [Indoline-3,3'- Pyrrolidines]," *Tetrahedron* 21:1327-1331, Pergamon Press Ltd. (1965).

Kang, T.-H. et al., "Pteropodine and isopteropodine positively modulate the function of rat muscarinic $M_1$ and 5-$HT_2$ receptors expressed in *Xenopus* oocyte," *Eur. J. Pharmacol.* 444:39-45, Elsevier Science B.V. (2002).

Lo, M. M.-C. et al., "A Library of Spirooxindoles Based on a Stereoselective Three-Component Coupling Reaction," *J. Am. Chem. Soc.* 126:16077-16086, American Chemical Society (2004).

Seaton, J.C. et al., "The Structure and Stereoisomerism of Three Mitragyna Alkaloids," *Can. J. Chem.* 38:1035-1042, NRC Research Press, Ottawa (1960).

(56) References Cited

OTHER PUBLICATIONS

Seto, M. et al., "The Synthesis of 3-Spirooxindole Derivatives. IX. The Reactions of 2-Hydroxytryptamine with Hemiacetals," *Chem. Pharm. Bull.* 24:1393-1397, Pharmaceutical Society of Japan, Tokyo (1976).

Trost, B.M. and Brennan, M.K., "Asymmetric Syntheses of Oxindole and Indole Spirocyclic Alkaloid Natural Products," *Synthesis* 18:3003-3025, Thieme Stuttgart, New York (2009).

van Tamelen, E.E. et al., "Total Synthesis of Rhyncophyllol and dl-Isorhyncophyllol," *J. Am. Chem. Soc.* 91:7333-7341, American Chemical Society (1969).

von Nussbaum, F. And Danishefsky, S.J., "A Rapid Total Synthesis of Spirotryprostatin B: Proof of its Relative and Absolute Stereochemistry," *Angew. Chem. Int. Ed.* 39:2175-2178, Wiley-VCH Verlag GmbH, Weinheim (2000).

Wenkert, E. et al., "3-Hydroxymethyleneoxindole and its Derivatives," *J. Am. Chem. Soc.* 81:3763-3768, American Chemical Society (1959).

Office Action mailed Feb. 19, 2013, for U.S. Appl. No. 13/294,315, inventors Wang, S. et al., filed Nov. 11, 2011, U.S. Patent and Trademark Office, Alexandria, VA.

* cited by examiner

SJSA-1; t = 10 h

SPIRO-OXINDOLE MDM2 ANTAGONISTS

CROSS-REFERENCE TO RELATED APPLICATIONS

This application is a continuation of pending U.S. patent application Ser. No. 12/945,511, filed Nov. 12, 2010, which claims priority to U.S. Provisional Patent Application No. 61/260,685, filed Nov. 12, 2009, and U.S. Provisional Patent Application No. 61/263,662, filed Nov. 23, 2009.

STATEMENT REGARDING FEDERALLY SPONSORED RESEARCH OR DEVELOPMENT

This invention was made with government support under CA121279; CA069568; and CA097248 awarded by the National Institutes of Health. The government has certain rights in the invention.

BACKGROUND

The aggressive cancer cell phenotype is the result of a variety of genetic and epigenetic alterations leading to deregulation of intracellular signaling pathways (Ponder, *Nature* 411:336 (2001)). Cancer cells typically fail to execute an apoptotic program, and lack of appropriate apoptosis due to defects in the normal apoptosis machinery is considered a hallmark of cancer (Lowe et al., *Carcinogenesis* 21:485 (2000)). The inability of cancer cells to execute an apoptotic program due to defects in the normal apoptotic machinery is often associated with an increase in resistance to chemotherapy, radiation, or immunotherapy-induced apoptosis. Primary or acquired resistance of human cancer of different origins to current treatment protocols due to apoptosis defects is a major problem in current cancer therapy (Lowe et al., *Carcinogenesis* 21:485 (2000); Nicholson, *Nature* 407:810 (2000)). Accordingly, current and future efforts towards designing and developing new molecular target-specific anticancer therapies to improve survival and quality of life of cancer patients must include strategies that specifically target cancer cell resistance to apoptosis.

The p53 tumor suppressor plays a central role in controlling cell cycle progression, senescence, and apoptosis (Vogelstein et al., *Nature* 408:307 (2000); Goberdhan, *Cancer Cell* 7:505 (2005)). MDM2 and p53 are part of an auto-regulatory feed-back loop (Wu et al., *Genes Dev.* 7:1126 (1993)). MDM2 is transcriptionally activated by p53 and MDM2, in turn, inhibits p53 activity by at least three mechanisms (Wu et al., *Genes Dev.* 7:1126 (1993). First, MDM2 protein directly binds to the p53 transactivation domain and thereby inhibits p53-mediated transactivation. Second, MDM2 protein contains a nuclear export signal sequence, and upon binding to p53, induces the nuclear export of p53, preventing p53 from binding to the targeted DNAs. Third, MDM2 protein is an E3 ubiquitin ligase and upon binding to p53 is able to promote p53 degradation.

Although high-affinity peptide-based inhibitors of MDM2 have been successfully designed in the past (Garcia-Echeverria et al., *Med. Chem.* 43:3205 (2000)), these inhibitors are not suitable therapeutic molecules because of their poor cell permeability and in vivo bioavailability. Despite intensive efforts by the pharmaceutical industry, high throughput screening strategies have had very limited success in identifying potent, non-peptide small molecule inhibitors. Accordingly, there is a need for non-peptide, drug-like, small molecule inhibitors of the p53-MDM2 interaction.

The structural basis of the interaction p53 and MDM2 has been established by x-ray crystallography (Kussie et al., *Science* 274:948 (1996)).

Spiro-oxindole-based antagonists of the p53-MDM2 interaction are described in U.S. Pat. Nos. 7,759,383 B2 and 7,737,174 B2.

SUMMARY OF THE INVENTION

The present disclosure contemplates that exposure of animals suffering from cancer to therapeutically effective amounts of drug(s) (e.g., small molecules) that increase the function(s) of p53 and p53-related proteins (e.g., p63, p73) inhibits the growth of cancer cells or supporting cells. In some embodiments, the compounds provided herein inhibit the interaction between p53 or p53-related proteins and MDM2 or MDM2-related proteins (e.g., MDMX) Inhibiting the interaction between p53 or p53-related proteins and MDM2 or MDM2-related proteins inhibits the growth of cancer cells or supporting cells and/or renders such cells as a population more susceptible to the cell death-inducing activity of cancer therapeutic drugs or radiation therapies. In some embodiments, the inhibitors provided herein prolong the half-life of p53 by interfering with the p53-MDM2 interaction that would normally promote degradation of p53 The compounds provided herein satisfy an unmet need for the treatment of multiple cancer types, either when administered as monotherapy to induce senescence, cell growth inhibition, apoptosis and/or cell cycle arrest in cancer cells, or when administered in a temporal relationship with additional agent(s), such as other cell death-inducing or cell cycle disrupting cancer therapeutic drugs or radiation therapies (combination therapies), so as to render a greater proportion of the cancer cells or supportive cells susceptible to executing the apoptosis program compared to the corresponding proportion of cells in an animal treated only with the cancer therapeutic drug or radiation therapy alone.

In some embodiments, treatment of animals with a therapeutically effective amount of one or more compounds provided herein and an anticancer agent produces a greater antitumor activity and clinical benefit in such animals compared to those treated with the compound or anticancer drugs/radiation alone. Put another way, because the compounds provided herein can lower the apoptotic threshold of cells that express p53 or p53-related protein, the proportion of cells that successfully execute the apoptosis program in response to the apoptosis inducing activity of anticancer drugs/radiation will be increased when used in combination with one or more of the compounds provided herein. Alternatively, the compounds provided herein can be used to allow administration of a lower, and therefore less toxic and more tolerable, dose of an anticancer drug and/or radiation to produce the same tumor response/clinical benefit as the conventional dose of the anticancer drug/radiation alone. Since the doses for all approved anticancer drugs and radiation treatments are known, the present compounds, compositions, and methods provided herein can be used with one or more approved anticancer drugs and/or radiation treatment. Also, since the compounds provided herein may act at least in part by stimulating the pro-apoptotic and/or cell cycle-inhibiting activities of p53 and p53-related proteins, the exposure of cancer cells and supporting cells to therapeutically effective amounts of the compounds can be temporally linked to coincide with the attempts of cells to execute the apoptosis program in response to the anticancer drug or radiation therapy. Thus, in some embodiments, administering the compounds or compositions provided herein in combination with other known anticancer drugs provide especially efficacious therapeutic practices.

In other embodiments, the inhibitors of the interaction between p53 or p53-related proteins and MDM2 and MDM2-related proteins provided herein may protect normal (e.g., non-hyperproliferative) cells from the toxic effects of certain chemotherapeutic agents and radiation, possibly through the ability of the inhibitors to induce cell cycle arrest of normal cells. For example, the inhibitors provided herein may cause cell cycle arrest in cells comprising wild-type or functional p53 (and/or wild-type or functional p53-related proteins) while having no or less effect on cancer cells comprising mutated, deleted, or otherwise non- or less functional p53 (and/or mutated, deleted, or otherwise non- or less functional p53-related proteins). This differential protective effect may allow for more effective treatment of cancer by allowing the use of higher doses or longer treatments of chemotherapeutic agents or treatments without increasing the toxic side effects of such treatment when administered in combination with inhibitors provided herein.

Applicants have found that certain spiro-oxindoles provided herein display an unexpected combination of drug-like properties. The unexpected combinations include, e.g., two or more of in vitro efficacy, in vivo efficacy, in vitro liver microsome stability, desirable absorption, distribution, metabolism, and excretion (ADME) properties. For example, certain spiro-oxindoles provided herein are more resistant to metabolic degradation e.g., as measured by in vitro liver microsomal stability and/or in vivo pharmacokinetics, and/or display improved in vivo efficacy as compared to known antagonists of the p53-MDM2 interaction.

Applicants have also found that metabolically cleavable groups can be used to increase the aqueous solubility of the parent molecule. Thus, in some embodiments, the spiro-oxindoles provided herein are useful prodrugs with improved aqueous solubility relative to the parent molecule.

In some embodiments, spiro-oxindoles provided herein have Formula I:

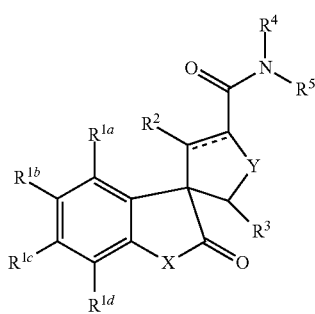

I wherein:
$R^{1a}$, $R^{1b}$, $R^{1c}$, and $R^{1d}$ are independently selected from the group consisting of hydrogen, halogen, hydroxy, amino, nitro, cyano, alkoxy, aryloxy, optionally substituted alkyl, haloalkyl, optionally substituted cycloalkyl, optionally substituted alkenyl, optionally substituted cycloalkenyl, optionally substituted aryl, optionally substituted heteroaryl, carboxamido, and sulfonamido;

$R^2$ is selected from the group consisting of optionally substituted aryl and optionally substituted heteroaryl;

$R^3$ is selected from the group consisting of optionally substituted alkyl, optionally substituted (cycloalkyl)alkyl, optionally substituted cycloalkyl, optionally substituted alkenyl, optionally substituted cycloalkenyl, optionally substituted aryl, and optionally substituted heteroaryl;

$R^4$ is selected from the group consisting of hydrogen and optionally substituted $C_1$-$C_6$ alkyl;

$R^5$ is selected from the group consisting of:

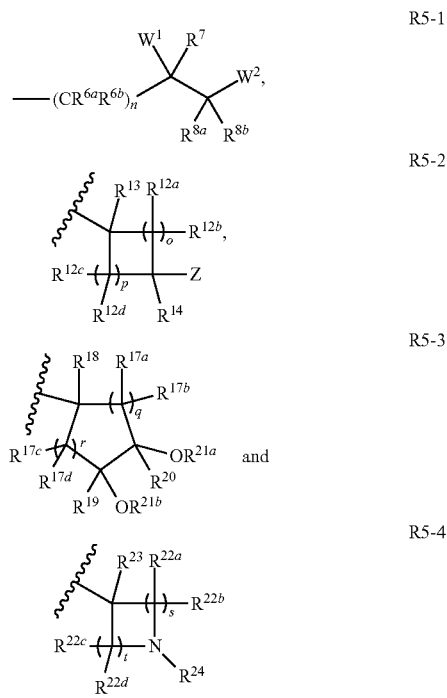

wherein:
each $R^{6a}$ and $R^{6b}$ is independently selected from the group consisting of hydrogen and optionally substituted $C_1$-$C_6$ alkyl;

$R^7$ is selected from the group consisting of hydrogen, optionally substituted $C_1$-$C_6$ alkyl, and optionally substituted cycloalkyl;

$R^{8a}$ and $R^{8b}$ are each independently selected from the group consisting of hydrogen, optionally substituted $C_1$-$C_6$ alkyl, and optionally substituted cycloalkyl; or $R^{8a}$ and $R^{8b}$ taken together with the carbon that they are attached form a 3- to 8-membered optionally substituted cycloalkyl;

$W^1$ is selected from the group consisting of $-OR^{9a}$ and $-NR^{9b}R^{9c}$;

$R^{9a}$ is hydrogen;

$R^{9b}$ is selected from the group consisting of hydrogen, optionally substituted alkyl, optionally substituted cycloalkyl, optionally substituted aryl, optionally substituted heteroaryl, $-SO_2R^{9d}$, and $-CONR^{9e}R^{9f}$;

$R^{9c}$ is selected from the group consisting of hydrogen, optionally substituted alkyl, optionally substituted cycloalkyl, optionally substituted aryl, and optionally substituted heteroaryl; or $R^{9b}$ and $R^{9c}$ taken together with the nitrogen atom to which they are attached form a 4- to 8-membered optionally substituted heterocyclo;

$R^{9d}$ is selected from the group consisting of optionally substituted alkyl and optionally substituted cycloalkyl;

$R^{9e}$ and $R^{9f}$ are each independently selected from the group consisting of hydrogen, optionally substituted alkyl, and optionally substituted cycloalkyl; or $R^{9e}$ and $R^{9f}$ taken together with the nitrogen atom to which they are attached form a 4- to 8-membered optionally substituted heterocyclo;

$W^2$ is selected from the group consisting of —$OR^{10}$ and —$NR^{11a}R^{11b}$;

with the proviso that when $W^1$ is –$OR^{9a}$ and $W^2$ is —$OR^{10}$ then at least one of $R^2$, $R^{8a}$, and $R^{8b}$ is other than hydrogen;

$R^{10}$ is hydrogen; or one of $R^{9a}$ and $R^{10}$ is hydrogen and the other is a metabolically cleavable group;

$R^{11a}$ is selected from the group consisting of hydrogen, optionally substituted alkyl, optionally substituted cycloalkyl, optionally substituted aryl, optionally substituted heteroaryl, —$SO_2R^{11c}$, and —$CONR^{11d}R^{11e}$;

$R^{11b}$ is selected from the group consisting of hydrogen, optionally substituted alkyl, optionally substituted cycloalkyl, optionally substituted aryl, and optionally substituted heteroaryl; or $R^{11a}$ and $R^{11b}$ taken together with the nitrogen atom to which they are attached form a 4- to 8-membered optionally substituted heterocyclo;

$R^{11c}$ is selected from the group consisting of optionally substituted alkyl and optionally substituted cycloalkyl;

$R^{11d}$ and $R^{11e}$ are each independently selected from the group consisting of hydrogen, optionally substituted alkyl, and optionally substituted cycloalkyl; or $R^{11d}$ and $R^{11e}$ taken together with the nitrogen atom to which they are attached form a 4- to 8-membered optionally substituted heterocyclo;

n is 1, 2, 3, 4, or 5;

each $R^{12a}$, $R^{12b}$, $R^{12c}$ and $R^{12d}$ is independently selected from the group consisting of hydrogen and optionally substituted $C_1$-$C_6$ alkyl;

$R^{13}$ is selected from the group consisting of hydrogen and optionally substituted $C_1$-$C_6$ alkyl;

$R^{14}$ is selected from the group consisting of hydrogen, optionally substituted $C_1$-$C_6$ alkyl, and optionally substituted cycloalkyl;

Z is selected from the group consisting of —$OR^{15}$ and —$NR^{16a}R^{16b}$; or Z and $R^{14}$ taken together form a carbonyl, i.e., a C=O, group.

$R^{15}$ is selected from the group consisting of hydrogen and metabolically cleavable group;

$R^{16a}$ is selected from the group consisting of —$SO_2R^{16c}$ and —$CONR^{16d}R^{16e}$;

$R^{16b}$ is selected from the group consisting of hydrogen and optionally substituted alkyl;

$R^{16c}$ is selected from the group consisting of optionally substituted alkyl, optionally substituted cycloalkyl, optionally substituted aryl, and optionally substituted heteroaryl;

$R^{16d}$ and $R^{16e}$ are each independently selected from the group consisting of hydrogen, optionally substituted alkyl, optionally substituted cycloalkyl, optionally substituted aryl, and optionally substituted heteroaryl; or $R^{16d}$ and $R^{16e}$ taken together with the nitrogen atom to which they are attached form a 4- to 8-membered heterocyclo;

o is 1, 2, or 3;

p is 0, 1, 2, or 3;

each $R^{17a}$, $R^{17b}$, $R^{17c}$ and $R^{17d}$ is independently selected from the group consisting of hydrogen and optionally substituted $C_1$-$C_6$ alkyl;

$R^{18}$ is selected from the group consisting of hydrogen and optionally substituted $C_1$-$C_6$ alkyl;

$R^{19}$ is selected from the group consisting of hydrogen, optionally substituted $C_1$-$C_6$ alkyl, and optionally substituted cycloalkyl;

$R^{20}$ is selected from the group consisting of hydrogen, optionally substituted $C_1$-$C_6$ alkyl, and optionally substituted cycloalkyl;

$R^{21a}$ and $R^{21b}$ are each hydrogen; or one of $R^{21a}$ and $R^{21b}$ is hydrogen and the other is metabolically cleavable group;

q is 0, 1, 2, or 3;

r is 1, 2, or 3;

each $R^{22a}$, $R^{22b}$, $R^{22c}$, and $R^{22d}$ is independently selected from the group consisting of hydrogen and optionally substituted $C_1$-$C_6$ alkyl;

$R^{23}$ is selected from the group consisting of hydrogen and optionally substituted $C_1$-$C_6$ alkyl;

$R^{24}$ is selected from the group consisting of —$SO_2R^{24a}$ and —$CONR^{24b}R^{24c}$;

$R^{24a}$ is selected from the group consisting of optionally substituted alkyl, optionally substituted cycloalkyl, optionally substituted aryl, and optionally substituted heteroaryl;

$R^{24b}$ and $R^{24c}$ are each independently selected from the group consisting of hydrogen, optionally substituted cycloalkyl, optionally substituted aryl, and optionally substituted heteroaryl; or $R^{24b}$ and $R^{24c}$ taken together with the nitrogen atom to which they are attached form a 4- to 8-membered heterocyclo;

s and t are each independently 1, 2, or 3;

X is selected from the group consisting of O, S, and NR';

Y is selected from the group consisting of O, S, and NR";

R' is selected from the group consisting of hydrogen, optionally substituted alkyl, aralkyl, and optionally substituted cycloalkyl;

R" is selected from the group consisting of hydrogen, optionally substituted alkyl, aralkyl, and optionally substituted cycloalkyl; and ⎓ represents a single or a double bond, or a pharmaceutically acceptable salt, solvate, or prodrug thereof, or a compound having the structure:

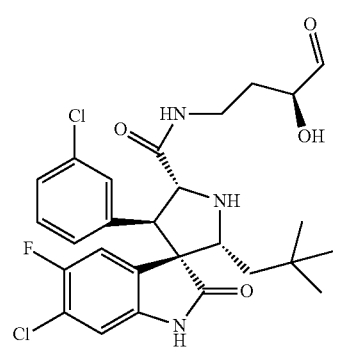

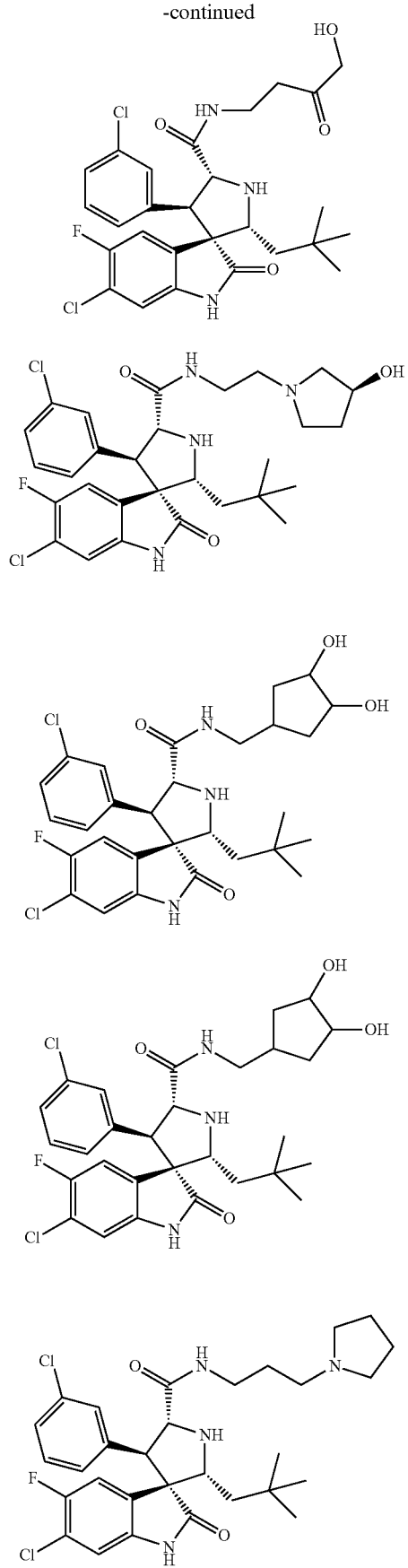
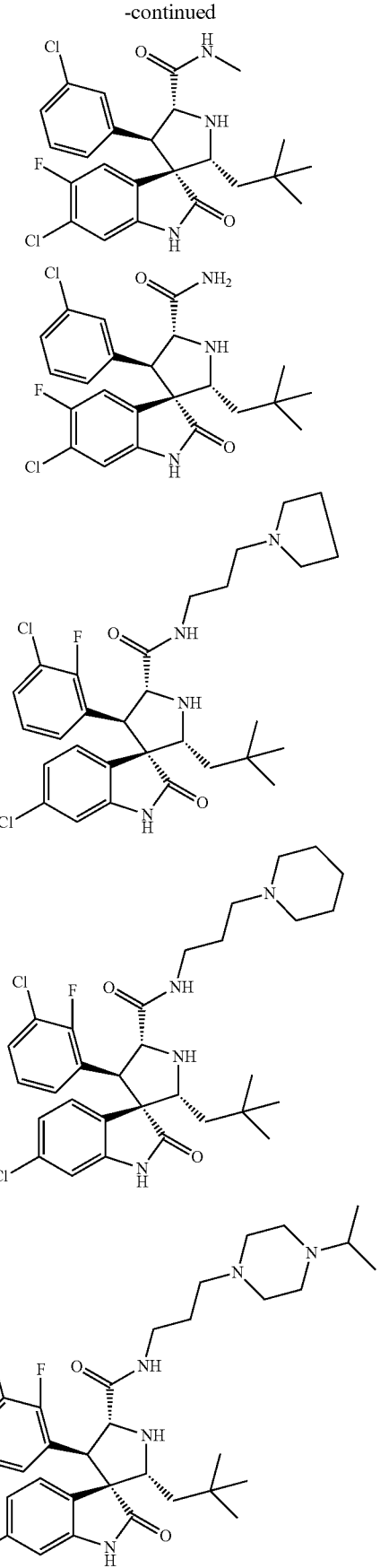

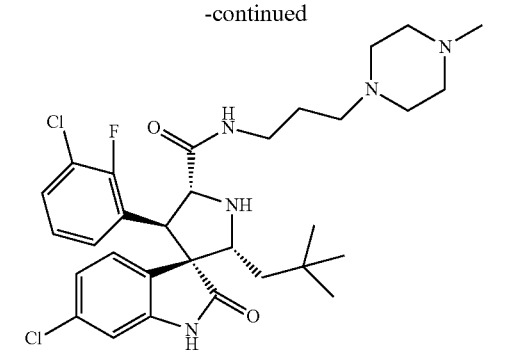
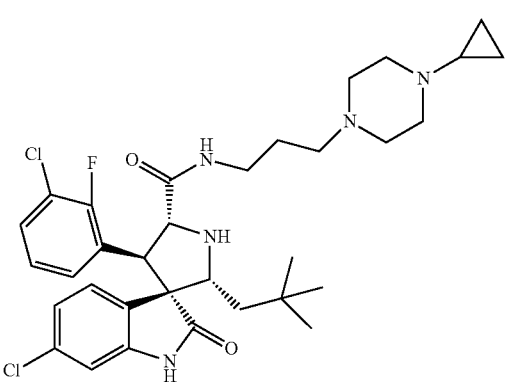
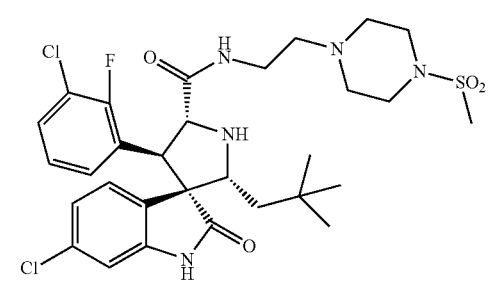
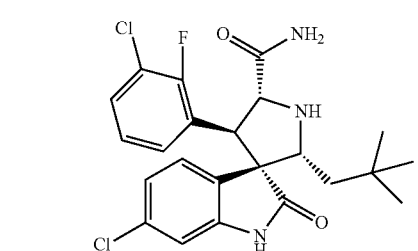
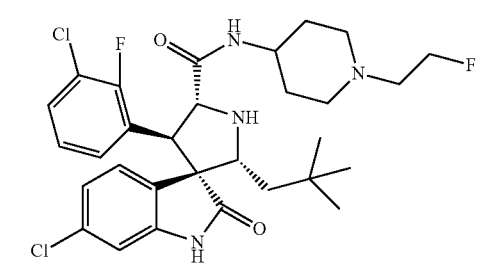
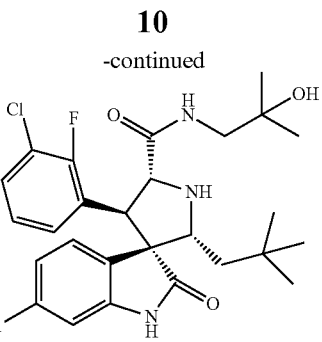
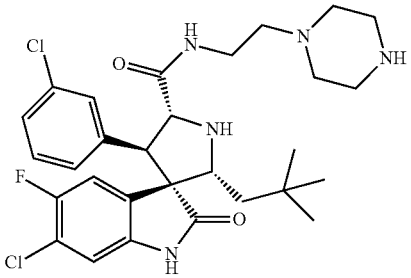
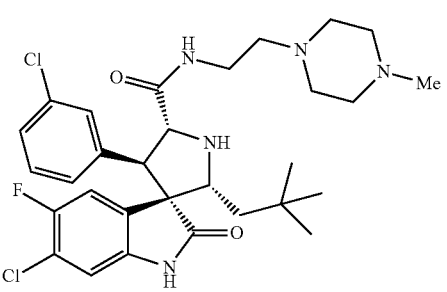
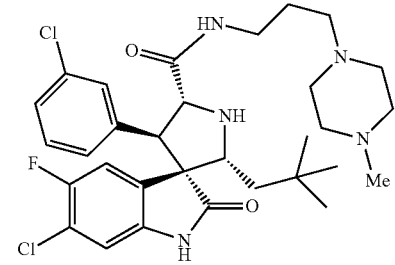
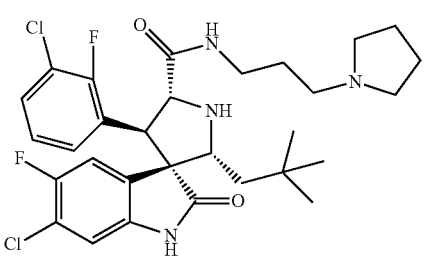
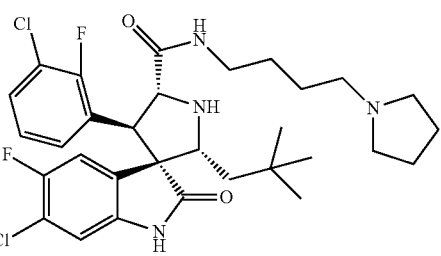

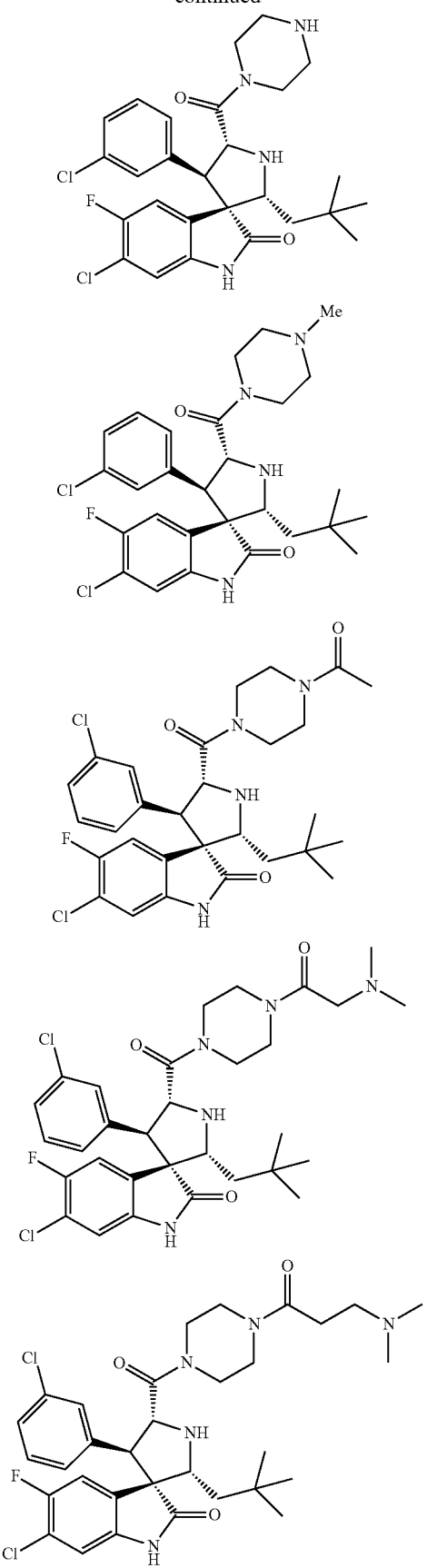
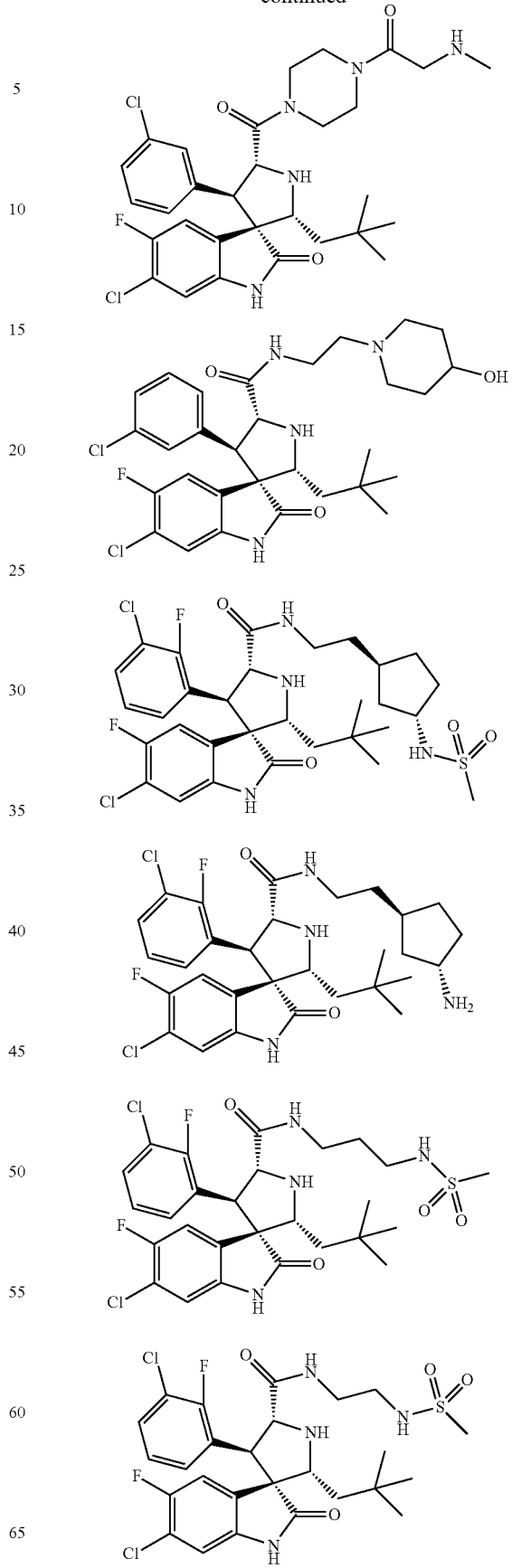

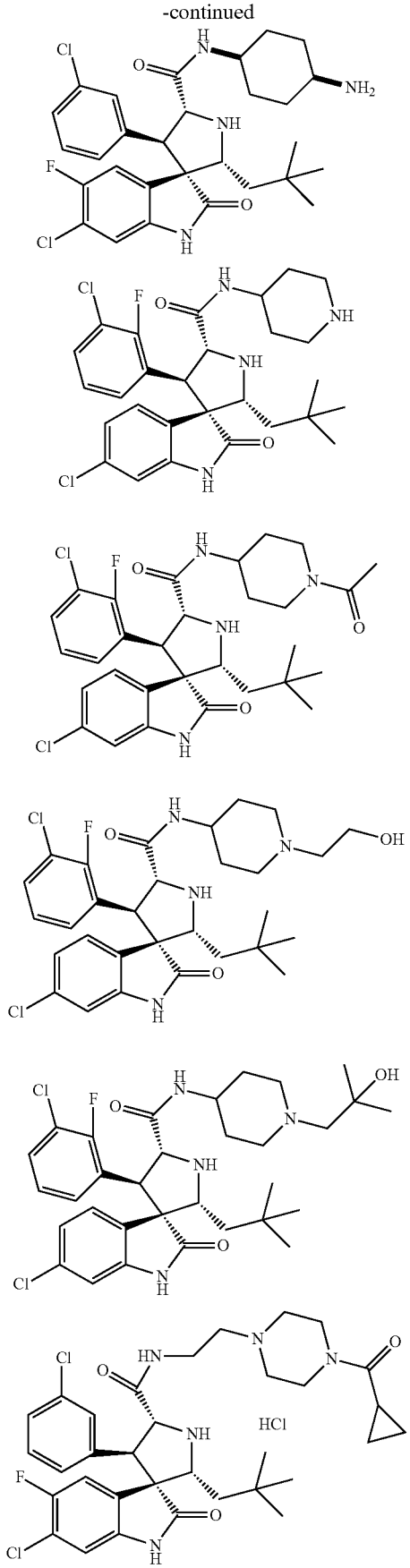

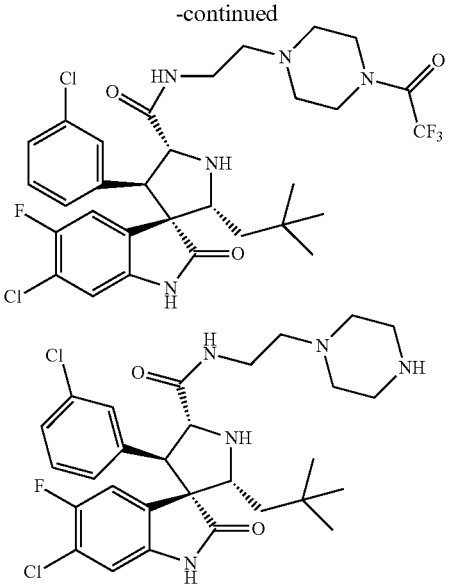

or a pharmaceutically acceptable salt, solvate, or prodrug thereof.

In some embodiments, the compounds provided herein inhibit the interaction between p53 or p53-related proteins and MDM2 or MDM2-related proteins.

In some embodiments, the compounds provided herein contain a metabolically cleavable group. In particular, in some embodiments, the compounds provided herein contain a hydroxy group of a hydroxycycloalkyl side chain that can be used to attach a metabolically cleavable group. Suitable metabolically cleavable groups include, but are not limited to, amino acid esters or phosphate esters.

In some embodiments, the compounds provided herein can be used to induce senescence, cell cycle arrest and/or apoptosis in cells containing functional p53 or p53-related proteins. Also provided herein are methods of using the compounds provided herein for sensitizing cells to additional agent(s), such as inducers of senescence, apoptosis and/or cell cycle arrest. The compounds provided herein can also be used to provide chemoprotection of normal cells through the induction of cell cycle arrest prior to treatment with chemotherapeutic agents. In one embodiment, the methods of rendering a normal cell resistant to chemotherapeutic agents or treatments comprises contacting the cell with one or more compounds provided herein. In one embodiment, methods of protecting normal cells in an animal having a hyperproliferative disease from the toxic side effects of chemotherapeutic agents or treatments, comprises administering to the animal a compound provided herein. Provided herein are methods for the treatment, amelioration, or prevention of disorders, side effects, or conditions caused by the administration of chemotherapeutic agents to normal cells comprising administering to an animal undergoing chemotherapy a compound provided herein. Examples of such disorders and conditions caused by chemotherapy include, without limitation, mucositis, stomatitis, xerostomia, gastrointestinal disorders, and alopecia.

The compounds provided herein are useful for the treatment, amelioration, or prevention of disorders, such as those responsive to induction of apoptotic cell death, e.g., disorders characterized by dysregulation of apoptosis, including hyperproliferative diseases such as cancer. In certain embodiments, the compounds can be used to treat, ameliorate, or prevent cancer that is characterized by resistance to cancer therapies (e.g., those cancer cells which are chemoresistant, radiation resistant, hormone resistant, and the like). In other embodiments, the compounds can be used to treat hyperproliferative diseases characterized by expression of functional p53 or p53-related proteins. In other embodiments, the compounds provided herein can be used to protect normal (e.g., non-hyperproliferative) cells from the toxic side effects of chemotherapeutic agents and treatments by the induction of cell cycle arrest in those cells.

In one embodiment, pharmaceutical compositions are provided. The pharmaceutical compositions can comprise one of more of the compounds provided herein in a pharmaceutically acceptable carrier.

In one embodiment, kits are provided. The kits can comprise one or more of the compounds provided herein and instructions for administering the compound to an animal. The kits may optionally contain other therapeutic agents, e.g., anticancer agents or apoptosis-modulating agents.

DETAILED DESCRIPTION OF THE INVENTION

Figure 1:
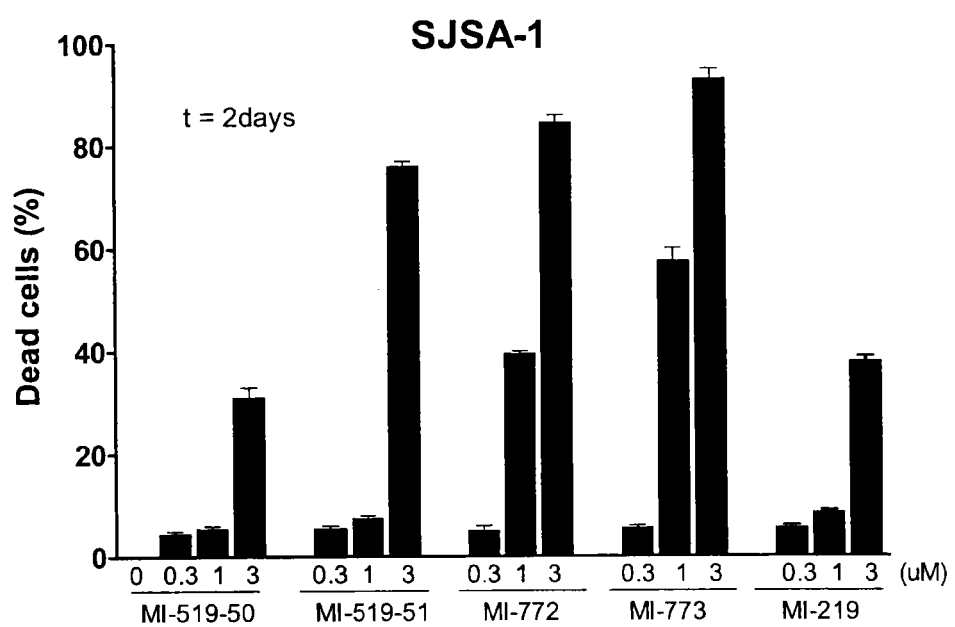
FIG. 1 is a bar graph showing the induction of cell death by MDM2 inhibitors in SJSA-1 cancer cells with wild-type p53.
Figure 2:
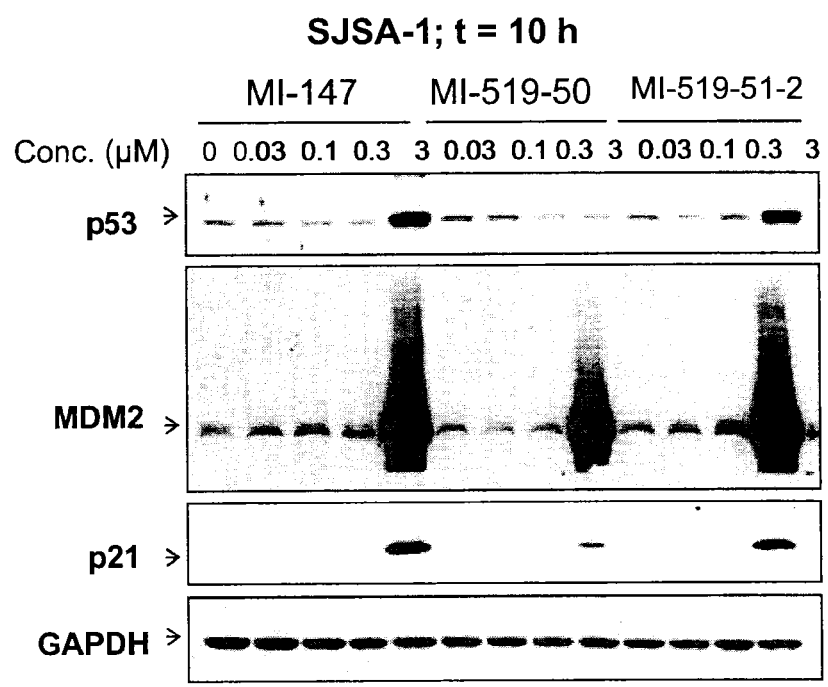
FIG. 2 is an illustration showing western blot analysis of p53 activation induced by MDM2 inhibitors in SJSA-1 cancer cells with wild-type p53.
Figure 3:
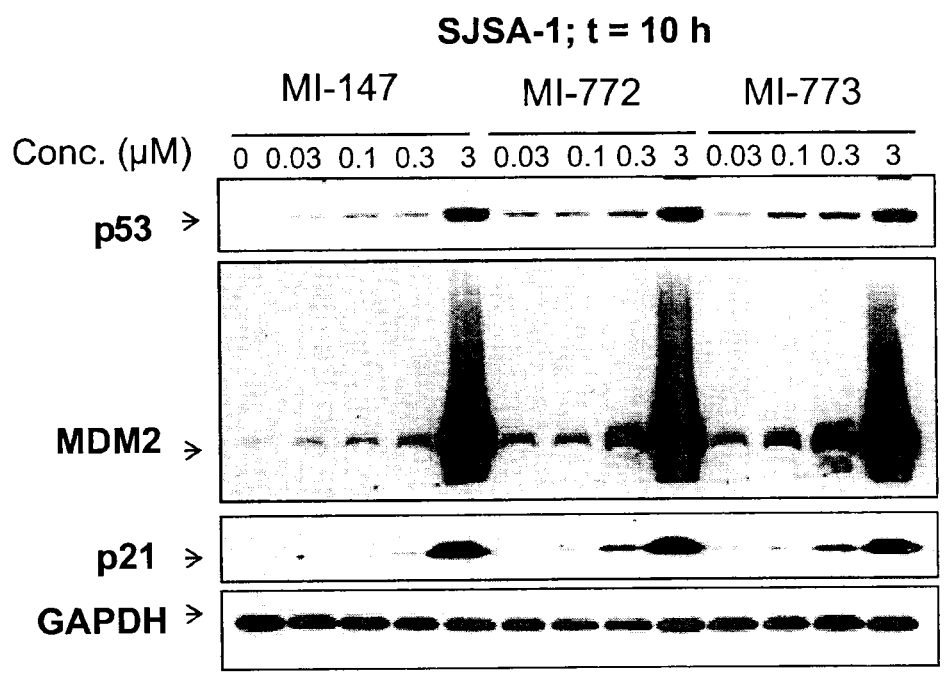
FIG. 3 is an illustration showing western blot analysis of p53 activation induced by MDM2 inhibitors in SJSA-1 cancer cells with wild-type p53.
Figure 4:
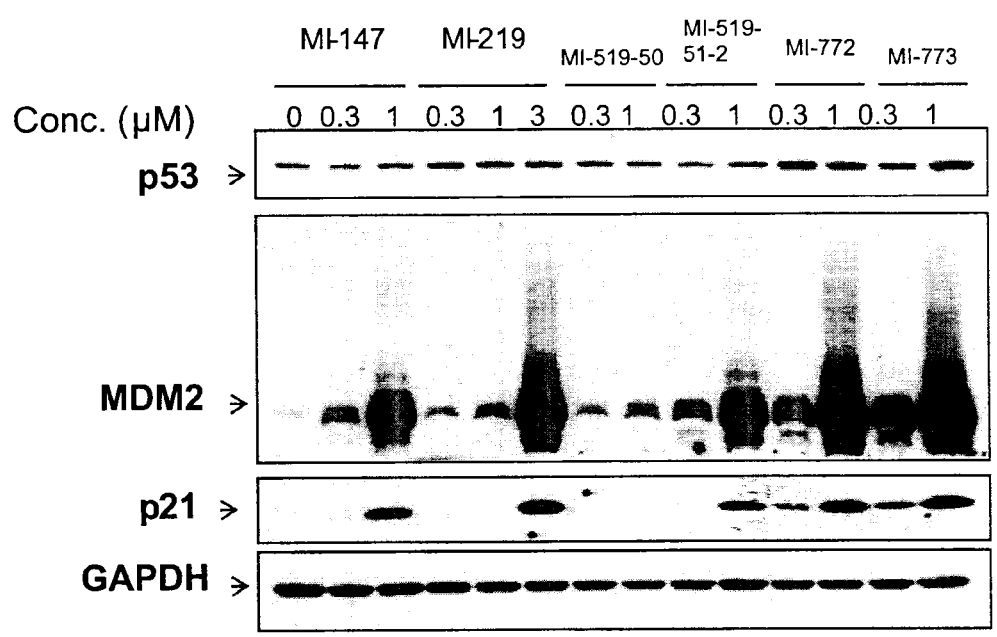
FIG. 4 is an illustration showing western blot analysis of p53 activation induced by MDM2 inhibitors in SJSA-1 cancer cells with wild-type p53.

Provided herein are compounds that inhibit the interaction between p53 or p53-related proteins and MDM2 or MDM2-related proteins. By inhibiting the negative effect of MDM2 or MDM2-related proteins on p53 or p53-related proteins, these compounds sensitize cells to inducers of apoptosis and/or cell cycle arrest. In some embodiments, the compounds provided herein induce apoptosis and/or cell cycle arrest.

Therefore, also provided herein are methods of sensitizing cells to inducers of apoptosis and/or cell cycle arrest and to methods of inducing apoptosis and/or cell cycle arrest in cells. In some embodiments, the methods comprise contacting the cells with one or more compounds provided herein alone or in combination with additional agent(s), e.g., an inducer of apoptosis or a cell cycle disrupter.

Also provided herein are methods of treating, ameliorating, or preventing disorders in an patient, comprising administering to the patient one or more compounds provided herein and additional agent(s), e.g., an inducer of apoptosis. Such disorders include those characterized by a dysregulation of apoptosis and those characterized by the proliferation of cells expressing functional p53 or p53-related proteins. In other embodiments, methods of protecting normal (e.g., non-hyperproliferative) cells in an animal from the toxic side effects of chemotherapeutic agents and treatments are provided. The methods comprise administering to the animal one or more compounds provided herein.

DEFINITIONS

The term "anticancer agent" as used herein, refers to any therapeutic agent (e.g., chemotherapeutic compound and/or molecular therapeutic compound), antisense therapy, radiation therapy, or surgical intervention, used in the treatment of hyperproliferative diseases such as cancer (e.g., in mammals, e.g., in humans).

The term "prodrug" as used herein, refers to a pharmacologically inactive derivative of a parent "drug" molecule that requires biotransformation (e.g., either spontaneous or enzymatic) within the target physiological system to release, or to convert (e.g., enzymatically, physiologically, mechanically, electromagnetically) the prodrug into the active drug. Prodrugs are designed to overcome problems associated with stability, water solubility, toxicity, lack of specificity, or limited bioavailability. Exemplary prodrugs comprise an active drug molecule itself and a chemical masking group (e.g., a group that reversibly suppresses the activity of the drug). Some prodrugs are variations or derivatives of compounds that have groups cleavable under metabolic conditions. Prodrugs can be readily prepared from the parent compounds using methods known in the art, such as those described in A Textbook of Drug Design and Development, Krogsgaard-Larsen and H. Bundgaard (eds.), Gordon & Breach, 1991, particularly Chapter 5: "Design and Applications of Pro-drugs"; Design of Prodrugs, H. Bundgaard (ed.), Elsevier, 1985; Prodrugs: Topical and Ocular Drug Delivery, K. B. Sloan (ed.), Marcel Dekker, 1998; Methods in Enzymology, K. Widder et al. (eds.), Vol. 42, Academic Press, 1985, particularly pp. 309-396; Burger's Medicinal Chemistry and Drug Discovery, 5th Ed., M. Wolff (ed.), John Wiley & Sons, 1995, particularly Vol. 1 and pp. 172-178 and pp. 949-982; Pro-Drugs as Novel Delivery Systems, T. Higuchi and V. Stella (eds.), Am. Chem. Soc., 1975; and Bioreversible Carriers in Drug Design, E. B. Roche (ed.), Elsevier, 1987.

Exemplary prodrugs become pharmaceutically active in vivo or in vitro when they undergo solvolysis under physiological conditions or undergo enzymatic degradation or other biochemical transformation (e.g., phosphorylation, hydrogenation, dehydrogenation, glycosylation). Prodrugs often offer advantages of water solubility, tissue compatibility, or delayed release in the mammalian organism. (See e.g., Bundgard, Design of Prodrugs, pp. 7-9, 21-24, Elsevier, Amsterdam (1985); and Silverman, The Organic Chemistry of Drug Design and Drug Action, pp. 352-401, Academic Press, San Diego, Calif. (1992)). Common prodrugs include acid derivatives such as esters prepared by reaction of parent acids with a suitable alcohol (e.g., a lower alkanol) or esters prepared by reaction of parent alcohol with a suitable carboxylic acid, (e.g., an amino acid), amides prepared by reaction of the parent acid compound with an amine, basic groups reacted to form an acylated base derivative (e.g., a lower alkylamide), or phosphorus-containing derivatives, e.g., phosphate, phosphonate, and phosphoramidate esters, including cyclic phosphate, phosphonate, and phosphoramidate, see, e.g., US 2007/0249564 A1.

The term "metabolically cleavable group" as used herein, refers to groups which can be cleaved from the parent molecule by metabolic processes and be substituted with hydrogen. Certain compounds containing metabolically cleavable groups may be prodrugs, i.e., they are pharmacologically inactive. Certain other compounds containing metabolically cleavable groups may be antagonists of the interaction between p53 and MDM2. In such cases, these compounds may have more, less, or equivalent activity of the parent molecule. Examples of metabolically cleavable groups include those derived from amino acids (see, e.g., US 2006/0241017 A1; US 2006/0287244 A1; and WO 2005/046575 A2) or phosphorus-containing compounds (see, e.g., U.S. 2007/0249564 A1) as illustrated in Scheme 1.

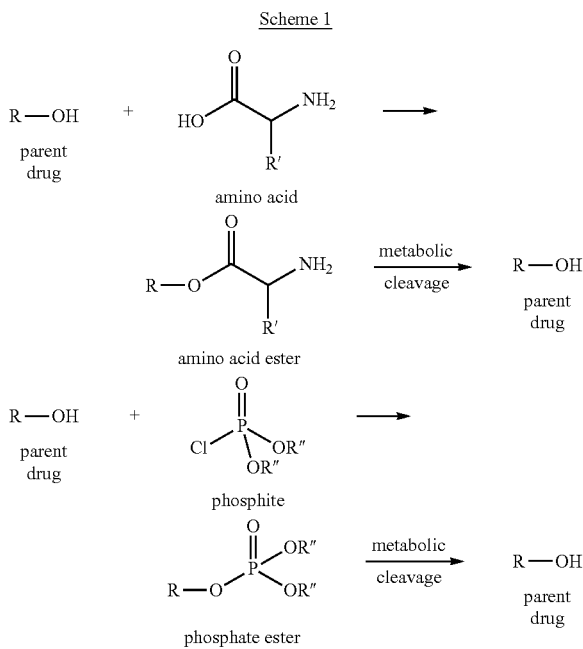

Scheme 1

The term "pharmaceutically acceptable salt" as used herein, refers to any salt (e.g., obtained by reaction with an acid or a base) of a compound provided herein that is physiologically tolerated in the target animal (e.g., a mammal). Salts of the compounds of provided herein may be derived from inorganic or organic acids and bases. Examples of acids include, but are not limited to, hydrochloric, hydrobromic, sulfuric, nitric, perchloric, fumaric, maleic, phosphoric, glycolic, lactic, salicylic, succinic, toluene-p-sulfonic, tartaric, acetic, citric, methanesulfonic, ethanesulfonic, formic, benzoic, malonic, sulfonic, naphthalene-2-sulfonic, benzenesulfonic acid, and the like. Other acids, such as oxalic, while not in themselves pharmaceutically acceptable, may be employed in the preparation of salts useful as intermediates in obtaining the compounds provided herein and their pharmaceutically acceptable acid addition salts.

Examples of bases include, but are not limited to, alkali metal (e.g., sodium) hydroxides, alkaline earth metal (e.g., magnesium) hydroxides, ammonia, and compounds of formula $NW_4^+$, wherein W is $C_{1-4}$ alkyl, and the like.

Examples of salts include, but are not limited to: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, flucoheptanoate, glycerophosphate, hemisulfate, heptanoate, hexanoate, chloride, bromide, iodide, 2-hydroxyethanesulfonate, lactate, maleate, mesylate, methanesulfonate, 2-naphthalenesulfonate, nicotinate, oxalate, palmoate, pectinate, persulfate, phenylpropionate, picrate, pivalate, propionate, succinate, tartrate, thiocyanate, tosylate, undecanoate, and the like. Other examples of salts include anions of the compounds provided herein compounded with a suitable cation such as $Na^+$, $NH_4^+$, and $NW_4^+$ (wherein W is a $C_{1-4}$ alkyl group), and the like. For therapeutic use, salts of the compounds provided herein are contemplated as being pharmaceutically acceptable. However, salts of acids and bases that are non-pharmaceutically acceptable may also find use, for example, in the preparation or purification of a pharmaceutically acceptable compound.

The term "solvate" as used herein, refers to the physical association of a compound provided herein with one or more solvent molecules, whether organic or inorganic. This physical association often includes hydrogen bonding. In certain instances, the solvate is capable of isolation, for example, when one or more solvate molecules are incorporated in the crystal lattice of the crystalline solid. "Solvate" encompasses both solution-phase and isolable solvates. Exemplary solvates include hydrates, ethanolates, and methanolates.

The term "monovalent pharmaceutically acceptable cation" as used herein refers to inorganic cations such as, but not limited to, alkaline metal ions, e.g., $Na^+$ and $K^+$, as well as organic cations such as, but not limited to, ammonium and substituted ammonium ions, e.g., $NH_4^+$, $NHMe_3^+$, $NH_2Me_2^+$, $NHMe_3^+$ and $NMe_4^+$.

The term "divalent pharmaceutically acceptable cation" as used herein refers to inorganic cations such as, but not limited to, alkaline earth metal cations, e.g., $Ca^{2+}$ and $Mg^{2+}$.

Examples of monovalent and divalent pharmaceutically acceptable cations are discussed, e.g., in Berge et al. *J. Pharm. Sci.*, 66:1-19 (1997).

The term "therapeutically effective amount," as used herein, refers to that amount of the therapeutic agent (including the compounds and compositions of matter provided herein) sufficient to result in amelioration of one or more symptoms of a disorder, or prevent advancement of a disorder, or cause regression of the disorder. For example, with respect to the treatment of cancer, in one embodiment, a therapeutically effective amount can refer to the amount of a therapeutic agent that decreases the rate of tumor growth, decreases tumor mass, decreases the number of metastases, increases time to tumor progression, increase tumor cell apoptosis, or increases survival time by at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100%.

The terms "sensitize" and "sensitizing," as used herein, refer to making, through the administration of a first therapeutic agent (e.g., a compound provided herein), an animal or a cell within an animal more susceptible, or more responsive, to the biological effects (e.g., promotion or retardation of an aspect of cellular function including, but not limited to, cell division, cell growth, proliferation, invasion, angiogenesis, necrosis, or apoptosis) of a second therapeutic agent. The sensitizing effect of a first agent on a target cell can be measured as the difference in the intended biological effect (e.g., promotion or retardation of an aspect of cellular function including, but not limited to, cell growth, proliferation, invasion, angiogenesis, or apoptosis) observed upon the administration of a second agent with and without administration of the first agent. The response of the sensitized cell can be increased by at least about 10%, at least about 20%, at least about 30%, at least about 40%, at least about 50%, at least about 60%, at least about 70%, at least about 80%, at least about 90%, at least about 100%, at least about 150%, at least about 200%, at least about 250%, at least 300%, at least about 350%, at least about 400%, at least about 450%, or at least about 500% over the response in the absence of the first agent.

The term "dysregulation of apoptosis," as used herein, refers to any aberration in the ability of (e.g., predisposition) a cell to undergo cell death via apoptosis. Dysregulation of apoptosis is associated with or induced by a variety of conditions, non-limiting examples of which include, autoimmune disorders (e.g., systemic lupus erythematosus, rheumatoid arthritis, graft-versus-host disease, myasthenia gravis, or Sjögren's syndrome), chronic inflammatory conditions (e.g., psoriasis, asthma or Crohn's disease), hyperproliferative disorders (e.g., tumors, B cell lymphomas, or T cell lymphomas), viral infections (e.g., herpes, papilloma, or HIV), and other conditions such as osteoarthritis and atherosclerosis. It should be noted that when the dysregulation is induced by or associated with a viral infection, the viral infection may or may not be detectable at the time dysregulation occurs or is observed. That is, viral-induced dysregulation can occur even after the disappearance of symptoms of viral infection.

The term "functional p53," as used herein, refers to wild-type p53 expressed at normal, high, or low levels and mutant or allelic variants of p53 that retain(s) at least about 5% of the activity of wild-type p53, e.g., at least about 10%, about 20%, about 30%, about 40%, about 50%, or more of wild-type activity.

The term "p53-related protein," as used herein, refers to proteins that have at least 25% sequence homology with p53, have tumor suppressor activity, and are inhibited by interaction with MDM2 or MDM2-related proteins. Examples of p53-related proteins include, but are not limited to, p63 and p73.

The term "MDM2-related protein," as used herein, refers to proteins that have at least 25% sequence homology with MDM2, and interact with and inhibit p53 or p53-related proteins. Examples of MDM2-related proteins include, but are not limited to, MDMX. The term "senescence" as used herein, refers to the phenomenon whereby non-cancerous diploid cells lose the ability to divide, and characterized in part by telomeric dysfunction or shortening.

The term "hyperproliferative disease," as used herein, refers to any condition in which a localized population of proliferating cells in an animal is not governed by the usual limitations of normal growth. Examples of hyperproliferative disorders include tumors, neoplasms, lymphomas, leukemias and the like. A neoplasm is said to be benign if it does not undergo invasion or metastasis and malignant if it does either of these. A "metastatic" cell means that the cell can invade neighboring body structures. Hyperplasia is a form of cell proliferation involving an increase in cell number in a tissue or organ without significant alteration in structure or function.

Metaplasia is a form of controlled cell growth in which one type of fully differentiated cell substitutes for another type of differentiated cell.

The pathological growth of activated lymphoid cells often results in an autoimmune disorder or a chronic inflammatory condition. As used herein, the term "autoimmune disorder" refers to any condition in which an organism produces antibodies or immune cells which recognize the organism's own molecules, cells or tissues. Non-limiting examples of autoimmune disorders include autoimmune hemolytic anemia, autoimmune hepatitis, Berger's disease or IgA nephropathy, celiac sprue, chronic fatigue syndrome, Crohn's disease, dermatomyositis, fibromyalgia, graft versus host disease, Grave's disease, Hashimoto's thyroiditis, idiopathic thrombocytopenia purpura, lichen planus, multiple sclerosis, myasthenia gravis, psoriasis, rheumatic fever, rheumatic arthritis, scleroderma, Sjögren's syndrome, systemic lupus erythematosus, type 1 diabetes, ulcerative colitis, vitiligo, and the like.

The term "neoplastic disease," as used herein, refers to any abnormal growth of cells being either benign (non-cancerous) or malignant (cancerous).

The term "normal cell," as used herein, refers to a cell that is not undergoing abnormal growth or division. Normal cells are non-cancerous and are not part of any hyperproliferative disease or disorder.

The term "anti-neoplastic agent," as used herein, refers to any compound that retards the proliferation, growth, or spread of a targeted (e.g., malignant) neoplasm.

The terms "prevent," "preventing," and "prevention," as used herein, refer to a decrease in the occurrence of pathological cells (e.g., hyperproliferative or neoplastic cells) in an animal. The prevention may be complete, e.g., the total absence of pathological cells in a subject. The prevention may also be partial, such that the occurrence of pathological cells in a subject is less than that which would have occurred without treatment with one or more compounds provided herein.

The term "apoptosis-modulating agents," as used herein, refers to agents which are involved in modulating (e.g., inhibiting, decreasing, increasing, promoting) apoptosis. Examples of apoptosis-modulating agents include proteins which comprise a death domain such as, but not limited to, Fas/CD95, TRAMP, TNF RI, DR1, DR2, DR3, DR4, DR5, DR6, FADD, and RIP. Other examples of apoptosis-modulating agents include, but are not limited to, TNFα, Fas ligand, antibodies to Fas/CD95 and other TNF family receptors, TRAIL (also known as Apo2 Ligand or Apo2L/TRAIL), antibodies to TRAIL-R1 or TRAIL-R2, Bcl-2, p53, BAX, BAD, Aid, CAD, PI3 kinase, PP1, and caspase proteins. Modulating agents broadly include agonists and antagonists of TNF family receptors and TNF family ligands. Apoptosis-modulating agents may be soluble or membrane bound (e.g. ligand or receptor). Apoptosis-modulating agents include those which are inducers of apoptosis, such as TNF or a TNF-related ligand, particularly a TRAMP ligand, a Fas/CD95 ligand, a TNFR-1 ligand, or TRAIL.

The term "pharmaceutically acceptable carrier" or "pharmaceutically acceptable vehicle" encompasses any of the standard pharmaceutical carriers, solvents, surfactants, or vehicles. Suitable pharmaceutically acceptable vehicles include aqueous vehicles and nonaqueous vehicles. Standard pharmaceutical carriers and their formulations are described in Remington's Pharmaceutical Sciences, Mack Publishing Co., Easton, Pa., 19th ed. 1995.

The term "alkyl" as used herein by itself or part of another group refers to a straight-chain or branched saturated aliphatic hydrocarbon having from one to eighteen carbons or the number of carbons designated (e.g., $C_1$-$C_{18}$ means 1 to 18 carbons). In one embodiment, the alkyl is a $C_1$-$C_{10}$ alkyl. In another embodiment, the alkyl is a $C_1$-$C_6$ alkyl. In another embodiment, the alkyl is a $C_1$-$C_4$ alkyl. Exemplary alkyl groups include methyl, ethyl, n-propyl, isopropyl, n-butyl, sec-butyl, isobutyl, tert-butyl, n-pentyl, n-hexyl, isohexyl, n-heptyl, 4,4-dimethylpentyl, n-octyl, 2,2,4-trimethylpentyl, nonyl, decyl and the like.

The term "optionally substituted alkyl" as used herein by itself or part of another group means that the alkyl as defined above is either unsubstituted or substituted with one, two or three substituents independently selected from hydroxy (i.e., —OH), nitro (i.e., —NO$_2$), cyano (i.e., —CN), optionally substituted cycloalkyl, optionally substituted heteroaryl, optionally substituted heterocyclo, alkoxy, aryloxy, aralkyloxy, alkylthio, carboxamido or sulfonamido. In one embodiment, the optionally substituted alkyl is substituted with two substituents. In another embodiment, the optionally substituted alkyl is substituted with one substituent. In another embodiment, the substituents are selected from hydroxyl (i.e., a hydroxyalkyl), optionally substituted cycloalkyl (i.e., a (cycloalkyl)alkyl), or amino (i.e., an aminoalkyl). Exemplary optionally substituted alkyl groups include —CH$_2$OCH$_3$, —CH$_2$CH$_2$NH$_2$, —CH$_2$CH$_2$NH(CH$_3$), —CH$_2$CH$_2$CN, —CH$_2$SO$_2$CH$_3$, hydroxymethyl, hydroxyethyl, hydroxypropyl, and the like.

The term "alkylenyl" as used herein by itself or part of another group refers to a divalent alkyl radical containing one, two, three, four, or more joined methylene groups. Exemplary alkylenyl groups include —(CH$_2$)—, —(CH$_2$)$_2$—, —(CH$_2$)$_3$—, —(CH$_2$)$_4$—, and the like.

The term "optionally substituted alkylenyl" as used herein by itself or part of another group means the alkylenyl as defined above is either unsubstituted or substituted with one, two, three, or four substituents independently selected from the group consisting of optionally substituted $C_1$-$C_6$ alkyl, optionally substituted cycloalkyl, optionally substituted aryl, and optionally substituted heteroaryl. In one embodiment, the optionally substituted $C_1$-$C_6$ alkyl is methyl. In one embodiment, the optionally substituted aryl is a phenyl optionally substituted with one or two halo groups. Exemplary optionally substituted alkylenyl groups include —CH(CH$_3$)—, —C(CH$_3$)$_2$—, —CH$_2$CH(CH$_3$)—, —CH$_2$CH(CH$_3$)CH$_2$—, —CH$_2$CH(Ph)CH$_2$—, —CH(CH$_3$)CH(CH$_3$)—, and the like.

The term "haloalkyl" as used herein by itself or part of another group refers to an alkyl as defined above having one to six halo substituents. In one embodiment, the haloalkyl has one, two or three halo substituents. Exemplary haloalkyl groups include trifluoromethyl, —CH$_2$CH$_2$F and the like.

The term "hydroxyalkyl" as used herein by itself or part of another group refers to an alkyl as defined above having one hydroxy substituent. Exemplary hydroxyalkyl groups include hydroxymethyl, hydroxyethyl, hydroxypropyl, and the like.

The term "dihydroxyalkyl" as used herein by itself or part of another group refers to alkyl as defined above having two hydroxyl substituents. Exemplary dihydroxyalkyl groups include —CH$_2$CH$_2$CCH$_3$(OH)CH$_2$OH, —CH$_2$CH$_2$CH(OH)CH(CH3)OH, —CH$_2$CH(CH$_2$OH)$_2$, —CH$_2$CH$_2$CH(OH)C(CH3)$_2$OH, —CH$_2$CH$_2$CCH$_3$(OH)CH(CH$_3$)OH, and the like, including stereoisomers thereof.

The term "hydroxycycloalkyl" as used herein by itself or part of another group refers to an optionally substituted cycloalkyl as defined below having a least one, e.g., one or two hydroxy substituents. Exemplary hydroxycycloalkyl groups include:

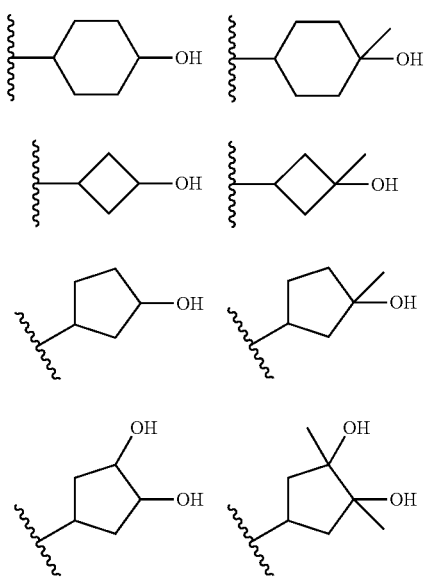

and the like, including stereoisomers thereof.

The term "optionally substituted (cycloalkyl)alkyl" as used herein by itself or part of another group refers to an optionally substituted alkyl as defined above having an optionally substituted cycloalkyl (as defined below) substituent. Exemplary optionally substituted (cycloalkyl)alkyl groups include:

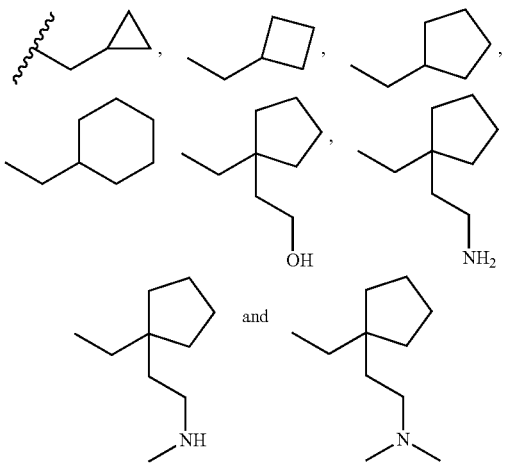

and the like, including stereoisomers thereof.

The term "aralkyl" as used herein by itself or part of another group refers to an optionally substituted alkyl as defined above having one, two or three optionally substituted aryl substituents. In one embodiment, the aralkyl has two optionally substituted aryl substituents. In another embodiment, the aralkyl has one optionally substituted aryl substituent. In another embodiment, the aralkyl is an aryl($C_1$-$C_4$ alkyl). In another embodiment, the aryl($C_1$-$C_4$ alkyl) has two optionally substituted aryl substituents. In another embodiment, the aryl($C_1$-$C_4$ alkyl) has one optionally substituted aryl substituent. Exemplary aralkyl groups include, for example, benzyl, phenylethyl, (4-fluorophenyl)ethyl, phenylpropyl, diphenylmethyl (i.e., Ph$_2$CH—), diphenylethyl (Ph$_2$CHCH$_2$—) and the like.

The term "cycloalkyl" as used herein by itself or part of another group refers to saturated and partially unsaturated (containing one or two double bonds) cyclic hydrocarbon groups containing one to three rings having from three to twelve carbon atoms (i.e., $C_3$-$C_{12}$ cycloalkyl) or the number of carbons designated. In one embodiment, the cycloalkyl has one ring. In another embodiment, the cycloalkyl is a $C_3$-$C_6$ cycloalkyl. Exemplary cycloalkyl groups include cyclopropyl, cyclobutyl, cyclopentyl, cyclohexyl, cycloheptyl, cyclooctyl, norbornyl, decalin, adamantyl and the like.

The term "optionally substituted cycloalkyl" as used herein by itself or part of another group means the cycloalkyl as defined above is either unsubstituted or substituted with one, two or three substituents independently selected from halo, nitro, cyano, hydroxy, amino, optionally substituted alkyl, haloalkyl, hydroxyalkyl, aminoalkyl, aralkyl, optionally substituted cycloalkyl, optionally substituted alkenyl, optionally substituted alkynyl, optionally substituted aryl, optionally substituted heteroaryl, optionally substituted heterocyclo, alkoxy, aryloxy, aralkyloxy, alkylthio, carboxamido or sulfonamido. The term "optionally substituted cycloalkyl" also means the cycloalkyl as defined above may be fused to an optionally substituted aryl. Exemplary optionally substituted cycloalkyl groups include

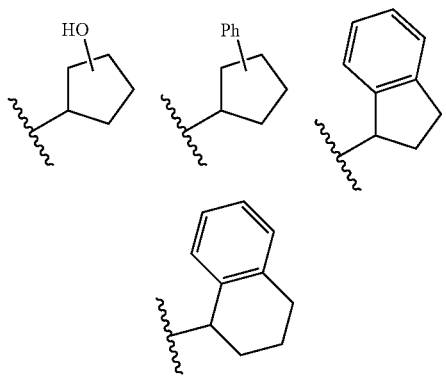

and the like.

The term "alkenyl" as used herein by itself or part of another group refers to an alkyl group as defined above containing one, two or three carbon-to-carbon double bonds.

In one embodiment, the alkenyl has one carbon-to-carbon double bond. Exemplary alkenyl groups include —CH=CH$_2$, —CH$_2$CH=CH$_2$, —CH$_2$CH$_2$CH=CH$_2$, —CH$_2$CH$_2$CH=CHCH$_3$ and the like.

The term "optionally substituted alkenyl" as used herein by itself or part of another group means the alkenyl as defined above is either unsubstituted or substituted with one, two or three substituents independently selected from halo, nitro, cyano, hydroxy, amino, optionally substituted alkyl, haloalkyl, hydroxyalkyl, aralkyl, optionally substituted cycloalkyl, optionally substituted alkenyl, optionally substituted alkynyl, optionally substituted aryl, optionally substituted heteroaryl, optionally substituted heterocyclo, alkoxy, aryloxy, aralkyloxy, alkylthio, carboxamido or sulfonamido. Exemplary optionally substituted alkenyl groups include —CH=CHPh, —CH$_2$CH=CHPh and the like.

The term "cycloalkenyl" as used herein by itself or part of another group refers to a cycloalkyl group as defined above containing one, two or three carbon-to-carbon double bonds. In one embodiment, the cycloalkenyl has one carbon-to-carbon double bond. Exemplary cycloalkenyl groups include cyclopentene, cyclohexene and the like.

The term "optionally substituted cycloalkenyl" as used herein by itself or part of another group means the cycloalkenyl as defined above is either unsubstituted or substituted with one, two or three substituents independently selected from halo, nitro, cyano, hydroxy, amino, optionally substituted alkyl, haloalkyl, hydroxyalkyl, aralkyl, optionally substituted cycloalkyl, optionally substituted alkenyl, optionally substituted alkynyl, optionally substituted aryl, optionally substituted heteroaryl, optionally substituted heterocyclo, alkoxy, aryloxy, aralkyloxy, alkylthio, carboxamido or sulfonamido.

The term "alkynyl" as used herein by itself or part of another group refers to an alkyl group as defined above containing one to three carbon-to-carbon triple bonds. In one embodiment, the alkynyl has one carbon-to-carbon triple bond. Exemplary alkynyl groups include —C≡CH, —C≡CCH$_3$, —CH$_2$C≡CH, —CH$_2$CH$_2$C≡CH and —CH$_2$CH$_2$C≡CCH$_3$.

The term "optionally substituted alkynyl" as used herein by itself or part of another group means the alkynyl as defined above is either unsubstituted or substituted with one, two or three substituents independently selected from halo, nitro, cyano, hydroxy, amino, optionally substituted alkyl, haloalkyl, hydroxyalkyl, aralkyl, optionally substituted cycloalkyl, optionally substituted alkenyl, optionally substituted alkynyl, optionally substituted aryl, optionally substituted heteroaryl, optionally substituted heterocyclo, alkoxy, aryloxy, aralkyloxy, alkylthio, carboxamido or sulfonamido. Exemplary optionally substituted alkenyl groups include —C≡Ph, —CH$_2$C≡CPh and the like.

The term "aryl" as used herein by itself or part of another group refers to monocyclic and bicyclic aromatic ring systems having from six to fourteen carbon atoms (i.e., $C_6$-$C_{14}$ aryl) such as phenyl (abbreviated as Ph), 1-naphthyl and 2-naphthyl and the like.

The term "optionally substituted aryl" as used herein by itself or part of another group means the aryl as defined above is either unsubstituted or substituted with one to five substituents independently selected from halo, nitro, cyano, hydroxy, amino, optionally substituted alkyl, haloalkyl, hydroxyalkyl, aralkyl, optionally substituted cycloalkyl, optionally substituted alkenyl, optionally substituted alkynyl, optionally substituted aryl, optionally substituted heteroaryl, optionally substituted heterocyclo, alkoxy, aryloxy, aralkyloxy, alkylthio, carboxamido or sulfonamido. In one embodiment, the optionally substituted aryl is an optionally substituted phenyl. In one embodiment, the optionally substituted phenyl has four substituents. In another embodiment, the optionally substituted phenyl has three substituents. In another embodiment, the optionally substituted phenyl has two substituents. In another embodiment, the optionally substituted phenyl has one substituent. Exemplary substituted aryl groups include 2-methylphenyl, 2-methoxyphenyl, 2-fluorophenyl, 2-chlorophenyl, 2-bromophenyl, 3-methylphenyl, 3-methoxyphenyl, 3-fluorophenyl, 3-chlorophenyl, 4-methylphenyl, 4-ethylphenyl, 4-methoxyphenyl, 4-fluorophenyl, 4-chlorophenyl, 2,6-di-fluorophenyl, 2,6-di-chlorophenyl, 2-methyl, 3-methoxyphenyl, 2-ethyl, 3-methoxyphenyl, 3,4-di-methoxyphenyl, 3,5-di-fluorophenyl 3,5-di-methylphenyl and 3,5-dimethoxy, 4-methylphenyl, 2-fluoro-3-chlorophenyl, 3-chloro-4-fluorophenyl and the like. The term optionally substituted aryl is meant to include groups having fused optionally substituted cycloalkyl and fused optionally substituted heterocyclo rings. Examples include

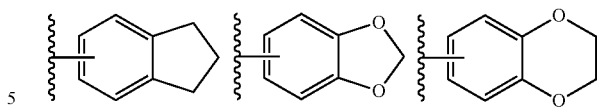

and the like.

The term "heteroaryl" as used herein by itself or part of another group refers to monocyclic and bicyclic aromatic ring systems having from five to fourteen carbon atoms (i.e., $C_5$-$C_{14}$ heteroaryl) and one, two, three or four heteroatoms independently selected from the group consisting of oxygen, nitrogen and sulfur. In one embodiment, the heteroaryl has three heteroatoms. In one embodiment, the heteroaryl has two heteroatoms. In one embodiment, the heteroaryl has one heteroatom. Exemplary heteroaryl groups include 1-pyrrolyl, 2-pyrrolyl, 3-pyrrolyl, 2-imidazolyl, 4-imidazolyl, pyrazinyl, 2-oxazolyl, 4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, purinyl, 2-benzimidazolyl, 4-benzimidazolyl, 5-benzimidazolyl, 2-benzthiazolyl, 4-benzthiazolyl, 5-benzthiazolyl, 5-indolyl, 3-indazolyl, 4-indazolyl, 5-indazolyl, 1-isoquinolyl, 5-isoquinolyl, 2-quinoxalinyl, 5-quinoxalinyl, 2-quinolyl 3-quinolyl, 6-quinolyl and the like. The term heteroaryl is meant to include possible N-oxides. Exemplary N-oxides include pyridyl N-oxide and the like.

The term "optionally substituted heteroaryl" as used herein by itself or part of another group means the heteroaryl as defined above is either unsubstituted or substituted with one to four substituents, typically one or two substituents, independently selected from halo, nitro, cyano, hydroxy, amino, optionally substituted alkyl, haloalkyl, hydroxyalkyl, aralkyl, optionally substituted cycloalkyl, optionally substituted alkenyl, optionally substituted alkynyl, optionally substituted aryl, optionally substituted heteroaryl, optionally substituted heterocyclo, alkoxy, aryloxy, aralkyloxy, alkylthio, carboxamido or sulfonamido. In one embodiment, the optionally substituted heteroaryl has one substituent. In another embodiment, the substituent is an optionally substituted aryl, aralkyl, or optionally substituted alkyl. In another embodiment, the substituent is an optionally substituted phenyl. Any available carbon or nitrogen atom may be substituted. Exemplary optionally substituted heteroaryl groups include

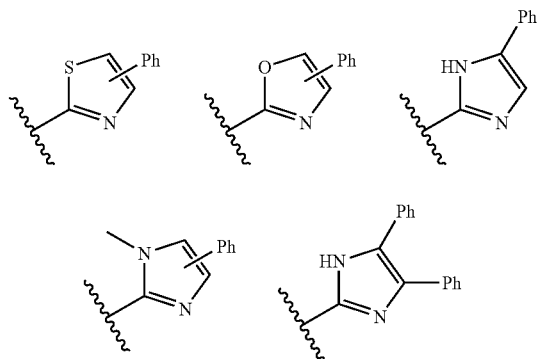

-continued

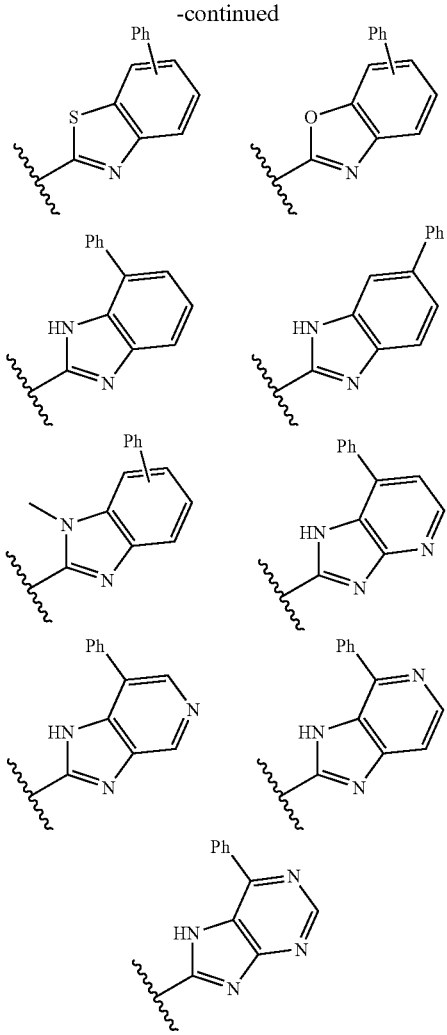

and the like.

The term "heterocyclo" as used herein by itself or part of another group refers to saturated and partially unsaturated (containing one or two double bonds) cyclic groups containing one to three rings having from two to twelve carbon atoms (i.e., $C_2$-$C_{12}$ heterocyclo) and one or two oxygen, sulfur or nitrogen atoms. The heterocyclo can be optionally linked to the rest of the molecule through a carbon or nitrogen atom. Exemplary heterocyclo groups include

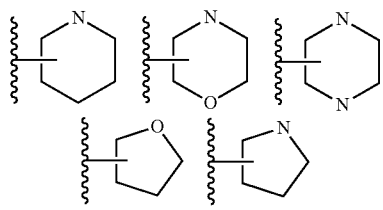

and the like.

The term "optionally substituted heterocyclo" as used herein by itself or part of another group means the heterocyclo as defined above is either unsubstituted or substituted with one to four substituents independently selected from halo, nitro, cyano, hydroxy, amino, optionally substituted alkyl, haloalkyl, hydroxyalkyl, aralkyl, optionally substituted cycloalkyl, optionally substituted alkenyl, optionally substituted alkynyl, optionally substituted aryl, optionally substituted heteroaryl, optionally substituted heterocyclo, alkoxy, aryloxy, aralkyloxy, alkylthio, carboxamido, sulfonamido, —$COR^c$, —$SO_2R^d$, —$N(R^e)COR^f$, —$N(R^e)SO_2R^g$ or —$N(R^e)C\!\!=\!\!N(R^h)$-amino, wherein $R^c$ is hydrogen, optionally substituted alkyl, optionally substituted aryl, or optionally substituted heteroaryl; $R^d$ is optionally substituted alkyl, optionally substituted aryl, or optionally substituted heteroaryl; $R^e$ is hydrogen, optionally substituted alkyl, optionally substituted aryl, or optionally substituted heteroaryl; $R^f$ is hydrogen, optionally substituted alkyl, optionally substituted aryl, or optionally substituted heteroaryl; $R^g$ is optionally substituted alkyl, optionally substituted aryl, or optionally substituted heteroaryl; and $R^h$ is hydrogen, —CN, optionally substituted alkyl, optionally substituted aryl, or optionally substituted heteroaryl. Substitution may occur on any available carbon or nitrogen atom. Exemplary substituted heterocyclo groups include

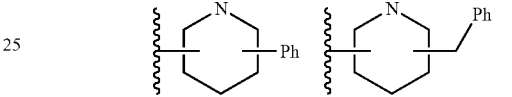

and the like. An optionally substituted heterocyclo may be fused to an aryl group to provide an optionally substituted aryl as described above.

The term "alkoxy" as used herein by itself or part of another group refers to a haloalkyl, optionally substituted alkyl, optionally substituted cycloalkyl, optionally substituted alkenyl or optionally substituted alkynyl attached to a terminal oxygen atom. Exemplary alkoxy groups include methoxy, tert-butoxy, —$OCH_2CH\!\!=\!\!CH_2$ and the like.

The term "aryloxy" as used herein by itself or part of another group refers to an optionally substituted aryl attached to a terminal oxygen atom. Exemplary aryloxy groups include phenoxy and the like.

The term "aralkyloxy" as used herein by itself or part of another group refers to an aralkyl attached to a terminal oxygen atom. Exemplary aralkyloxy groups include benzyloxy and the like.

The term "alkylthio" as used herein by itself or part of another group refers to a haloalkyl, aralkyl, optionally substituted alkyl, optionally substituted cycloalkyl, optionally substituted alkenyl or optionally substituted alkynyl attached to a terminal sulfur atom. Exemplary alkyl groups include —$SCH_3$ and the like.

The term "halo" or "halogen" as used herein by itself or part of another group refers to fluoro, chloro, bromo or iodo. In one embodiment, the halo is fluoro or chloro.

The term "amino" as used herein by itself or part of another group refers to a radical of formula —$NR^aR^b$ wherein $R^a$ and $R^b$ are independently hydrogen, haloalkyl, aralkyl, optionally substituted alkyl, optionally substituted cycloalkyl, optionally substituted heterocyclo, optionally substituted aryl or optionally substituted heteroaryl; or $R^a$ and $R^b$ taken together with the nitrogen atom to which they are attached form a four to seven membered optionally substituted heterocyclo. Exemplary amino groups include —$NH_2$, —$N(H)CH_3$, —$N(CH_3)_2$, $N(H)CH_2CH_3$, $N(CH_2CH_3)$, —$N(H)CH_2Ph$ and the like.

The term "carboxamido" as used herein by itself or part of another group refers to a radical of formula —CO-amino.

Exemplary carboxamido groups include —CONH$_2$, —CON(H)CH$_3$, —CON(H)Ph, —CON(H)CH$_2$CH$_2$Ph, —CON(CH$_3$)$_2$, CON(H)CHPh$_2$ and the like.

The term "sulfonamido" as used herein by itself or part of another group refers to a radical of formula —SO$_2$-amino. Exemplary sulfonamido groups include —SO$_2$NH$_2$, —SO$_2$N(H)CH$_3$, —SO$_2$N(H)Ph and the like.

The term "about," as used herein, includes the recited number ±10%. Thus, "about 10" means 9 to 11.

Certain of the compounds of the present disclosure may exist as stereoisomers including optical isomers and conformational isomers (or conformers). The disclosure includes all stereoisomers, both as pure individual stereoisomer preparations and enriched preparations of each, and both the racemic mixtures of such stereoisomers as well as the individual diastereomers and enantiomers that may be separated according to methods that are well known to those of skill in the art.

Compounds

In certain embodiments, compounds of Formula I are provided:

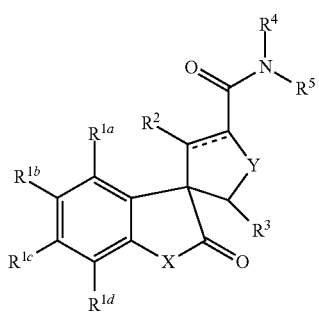

I wherein:

$R^{1a}$, $R^{1b}$, $R^{1c}$, and $R^{1d}$ are independently selected from the group consisting of hydrogen, halogen, hydroxy, amino, nitro, cyano, alkoxy, aryloxy, optionally substituted alkyl, haloalkyl, optionally substituted cycloalkyl, optionally substituted alkenyl, optionally substituted cycloalkenyl, optionally substituted aryl, optionally substituted heteroaryl, carboxamido, and sulfonamido;

$R^2$ is selected from the group consisting of optionally substituted aryl and optionally substituted heteroaryl;

$R^3$ is selected from the group consisting of optionally substituted alkyl, optionally substituted (cycloalkyl)alkyl, optionally substituted cycloalkyl, optionally substituted alkenyl, optionally substituted cycloalkenyl, optionally substituted aryl, and optionally substituted heteroaryl;

$R^4$ is selected from the group consisting of hydrogen and optionally substituted alkyl;

$R^5$ is selected from the group consisting of:

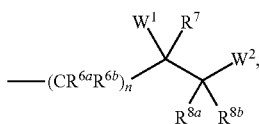

R5-1

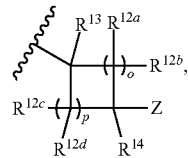

R5-2

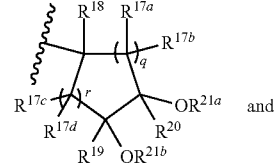

R5-3 and

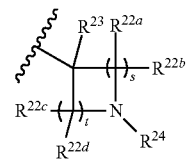

R5-4 wherein:

each $R^{6a}$ and $R^{6b}$ is independently selected from the group consisting of hydrogen and optionally substituted C$_1$-C$_6$ alkyl;

$R^7$ is selected from the group consisting of hydrogen, optionally substituted C$_1$-C$_6$ alkyl, and optionally substituted cycloalkyl;

$R^{8a}$ and $R^{8b}$ are each independently selected from the group consisting of hydrogen, optionally substituted C$_1$-C$_6$ alkyl, and optionally substituted cycloalkyl; or $R^{8a}$ and $R^{8b}$ taken together with the carbon that they are attached form a 3- to 8-membered optionally substituted cycloalkyl;

$W^1$ is selected from the group consisting of —OR$^{9a}$ and —NR$^{9b}$R$^{9c}$;

$R^{9a}$ is hydrogen;

$R^{9b}$ is selected from the group consisting of hydrogen, optionally substituted alkyl, optionally substituted cycloalkyl, optionally substituted aryl, optionally substituted heteroaryl, —SO$_2$R$^{9d}$, and —CONR$^{9e}$R$^{9f}$;

$R^{9c}$ is selected from the group consisting of hydrogen, optionally substituted alkyl, optionally substituted cycloalkyl, optionally substituted aryl, and optionally substituted heteroaryl; or $R^{9b}$ and $R^{9c}$ taken together with the nitrogen atom to which they are attached form a 4- to 8-membered optionally substituted heterocyclo;

$R^{9d}$ is selected from the group consisting of optionally substituted alkyl and optionally substituted cycloalkyl;

$R^{9e}$ and $R^{9f}$ are each independently selected from the group consisting of hydrogen, optionally substituted alkyl, and optionally substituted cycloalkyl; or $R^{9e}$ and $R^{9f}$ taken together with the nitrogen atom to which they are attached form a 4- to 8-membered optionally substituted heterocyclo;

$W^2$ is selected from the group consisting of —OR$^{10}$ and —NR$^{11a}$R$^{11b}$;

with the proviso that when $W^1$ is —OR$^{9a}$ and $W^2$ is —OR$^{10}$ then at least one of $R^7$, $R^{8a}$, and $R^{8b}$ is other than hydrogen;

$R^{10}$ is hydrogen; or one of $R^{9a}$ and $R^{10}$ is hydrogen and the other is a metabolically cleavable group;

R$^{11a}$ is selected from the group consisting of hydrogen, optionally substituted alkyl, optionally substituted cycloalkyl, optionally substituted aryl, optionally substituted heteroaryl, —SO$_2$R$^{11c}$, and —CONR$^{11d}$R$^{11e}$;

R$^{11b}$ is selected from the group consisting of hydrogen, optionally substituted alkyl, optionally substituted cycloalkyl, optionally substituted aryl, and optionally substituted heteroaryl; or R$^{11a}$ and R$^{11b}$ taken together with the nitrogen atom to which they are attached form a 4- to 8-membered optionally substituted heterocyclo;

R$^{11c}$ is selected from the group consisting of optionally substituted alkyl and optionally substituted cycloalkyl;

R$^{11d}$ and R$^{11e}$ are each independently selected from the group consisting of hydrogen, optionally substituted alkyl, and optionally substituted cycloalkyl; or R$^{11d}$ and R$^{11e}$ together with the nitrogen atom to which they are attached form a 4- to 8-membered optionally substituted heterocyclo;

n is 1, 2, 3, 4, or 5;

each R$^{12a}$, R$^{12b}$, R$^{12c}$ and R$^{12d}$ is independently selected from the group consisting of hydrogen and optionally substituted C$_1$-C$_6$ alkyl;

R$^{13}$ is selected from the group consisting of hydrogen and optionally substituted C1-C6 alkyl;

R$^{14}$ is selected from the group consisting of hydrogen, optionally substituted C$_1$-C$_6$ alkyl, and optionally substituted cycloalkyl;

Z is selected from the group consisting of —OR$^{15}$ and —NR$^{16a}$R$^{16b}$; or Z and R$^{14}$ taken together form a carbonyl, i.e., a C=O, group.

R$^{15}$ is selected from the group consisting of hydrogen and metabolically cleavable group;

R$^{16a}$ is selected from the group consisting of —SO$_2$R$^{16e}$ and —CONR$^{16d}$R$^{16e}$;

R$^{16b}$ is selected from the group consisting of hydrogen and optionally substituted alkyl;

R$^{16c}$ is selected from the group consisting of optionally substituted alkyl, optionally substituted cycloalkyl, optionally substituted aryl, and optionally substituted heteroaryl;

R$^{16d}$ and R$^{16e}$ are each independently selected from the group consisting of hydrogen, optionally substituted alkyl, optionally substituted cycloalkyl, optionally substituted aryl, and optionally substituted heteroaryl; or R$^{16d}$ and R$^{16e}$ taken together with the nitrogen atom to which they are attached form a 4- to 8-membered heterocyclo;

o is 1, 2, or 3;

p is 0, 1, 2, or 3;

each R$^{17a}$, R$^{17b}$, R$^{17c}$ and R$^{17d}$ is independently selected from the group consisting of hydrogen and optionally substituted C$_1$-C$_6$ alkyl;

R$^{18}$ is selected from the group consisting of hydrogen and optionally substituted C$_1$-C$_6$ alkyl;

R$^{19}$ is selected from the group consisting of hydrogen, optionally substituted C$_1$-C$_6$ alkyl, and optionally substituted cycloalkyl;

R$^{20}$ is selected from the group consisting of hydrogen, optionally substituted C$_1$-C$_6$ alkyl, and optionally substituted cycloalkyl;

R$^{21a}$ and R$^{21b}$ are each hydrogen; or one of R$^{21a}$ and R$^{21b}$ is hydrogen and the other is metabolically cleavable group;

q is 0, 1, 2, or 3;

r is 1, 2, or 3;

each R$^{22a}$, R$^{22b}$, R$^{22c}$, and R$^{22d}$ is independently selected from the group consisting of hydrogen and optionally substituted C$_1$-C$_6$ alkyl;

R$^{23}$ is selected from the group consisting of hydrogen and optionally substituted C$_1$-C$_6$ alkyl;

R$^{24}$ is selected from the group consisting of —SO$_2$R$^{24a}$ and —CONR$^{24b}$R$^{24c}$;

R$^{24a}$ is selected from the group consisting of optionally substituted alkyl, optionally substituted cycloalkyl, optionally substituted aryl, and optionally substituted heteroaryl;

R$^{24b}$ and R$^{24c}$ are each independently selected from the group consisting of hydrogen, optionally substituted cycloalkyl, optionally substituted aryl, and optionally substituted heteroaryl; or R$^{24b}$ and R$^{24c}$ taken together with the nitrogen atom to which they are attached form a 4- to 8-membered heterocyclo;

s and t are each independently 1, 2, or 3;

X is selected from the group consisting of O, S, and NR';

Y is selected from the group consisting of O, S, and NR";

R' is selected from the group consisting of hydrogen, optionally substituted alkyl, aralkyl, and optionally substituted cycloalkyl;

R" is selected from the group consisting of hydrogen, optionally substituted alkyl, aralkyl, and optionally substituted cycloalkyl; and ═══ represents a single or a double bond, or a pharmaceutically acceptable salt, solvate, or prodrug thereof, or a compound having the structure:

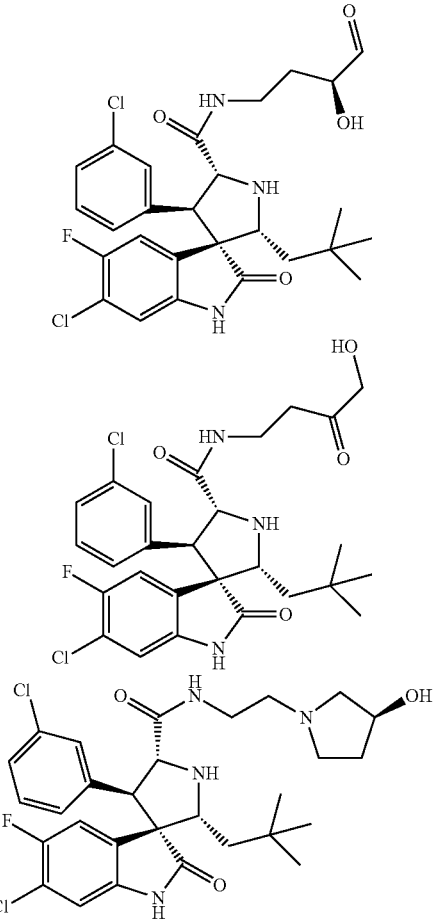

33
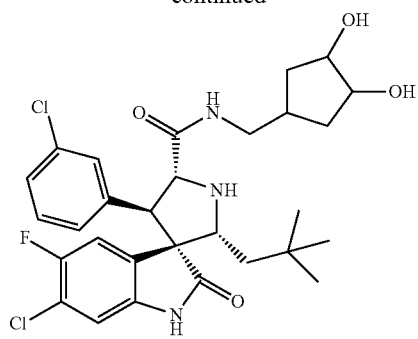
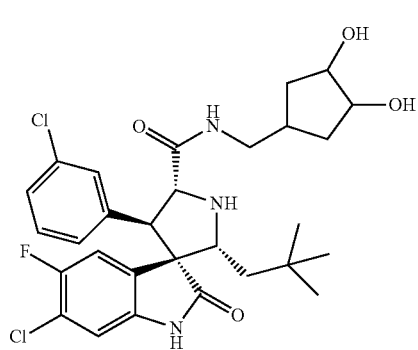
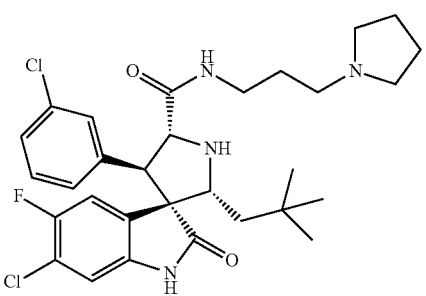
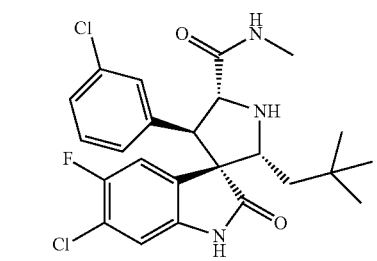
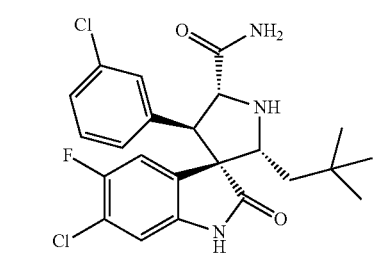
34
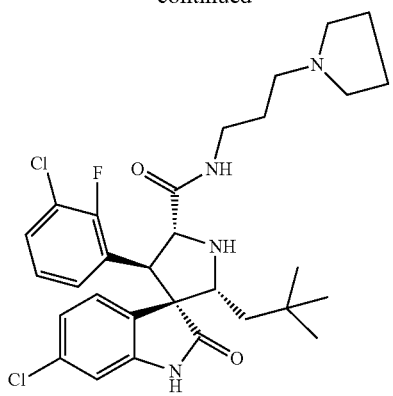
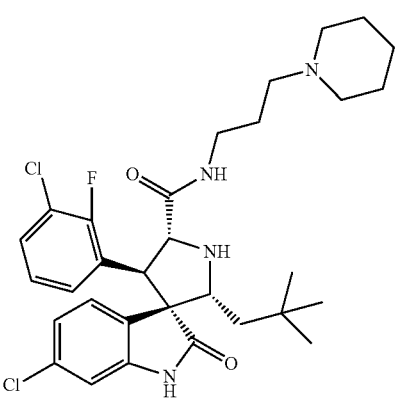
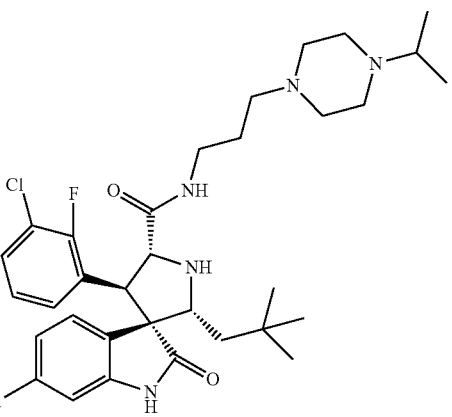
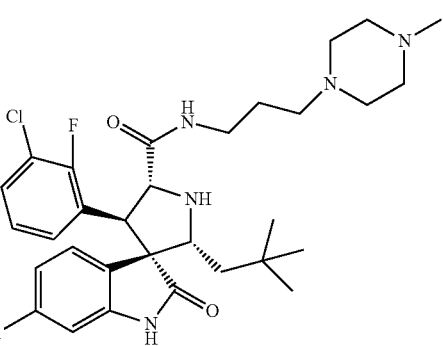

35
-continued
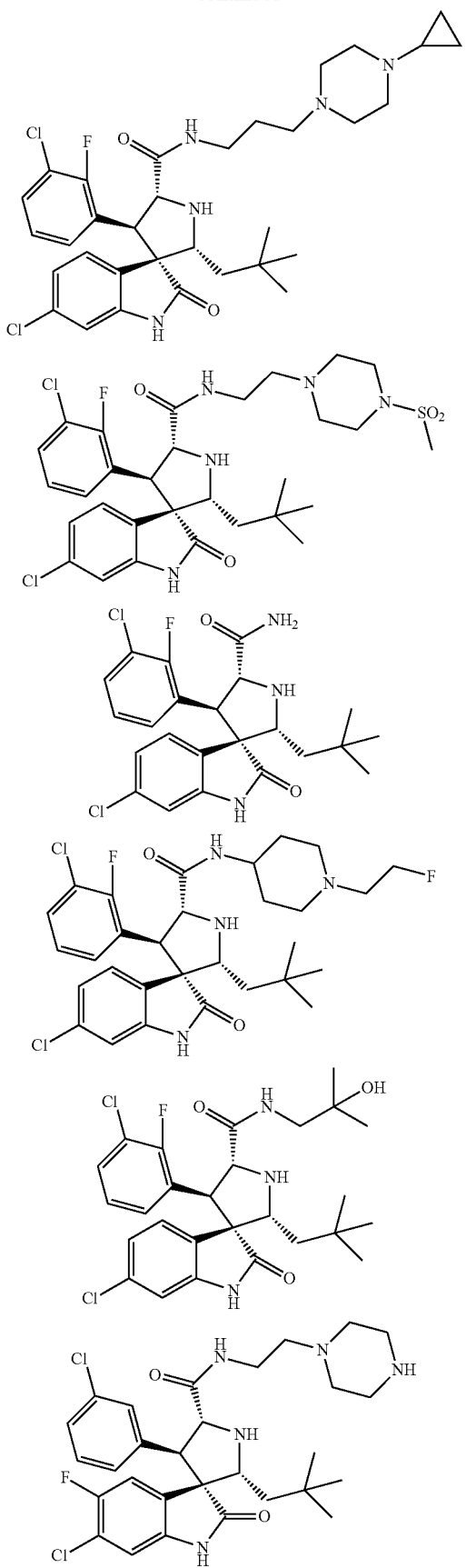
36
-continued
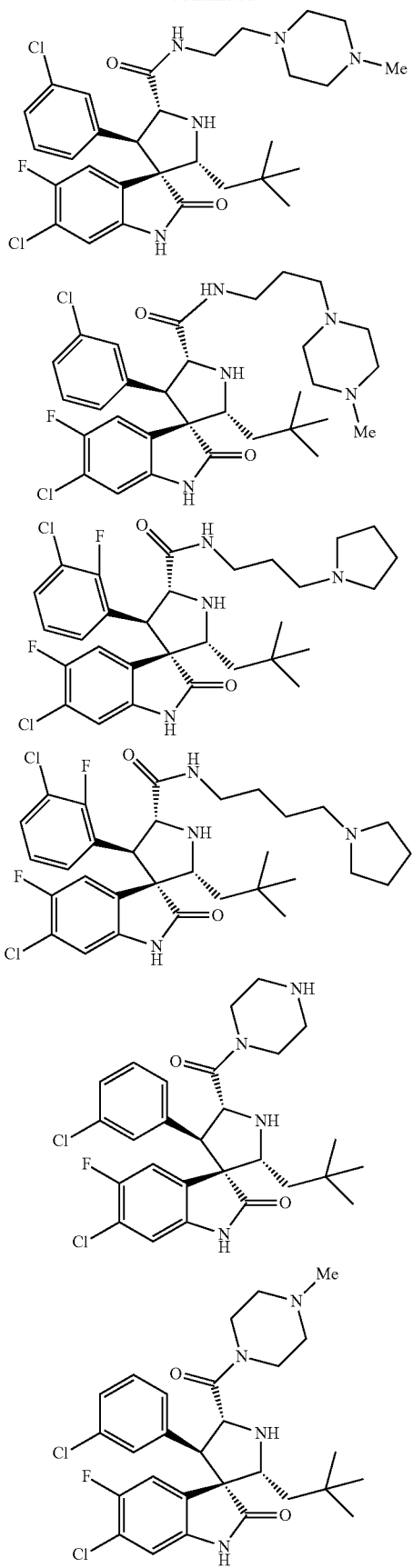

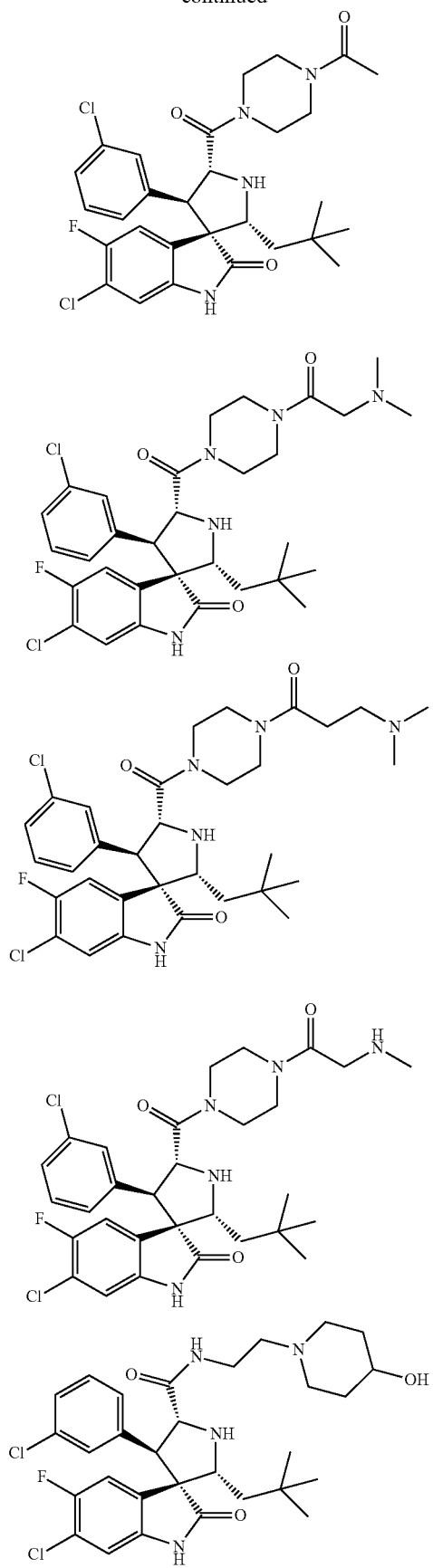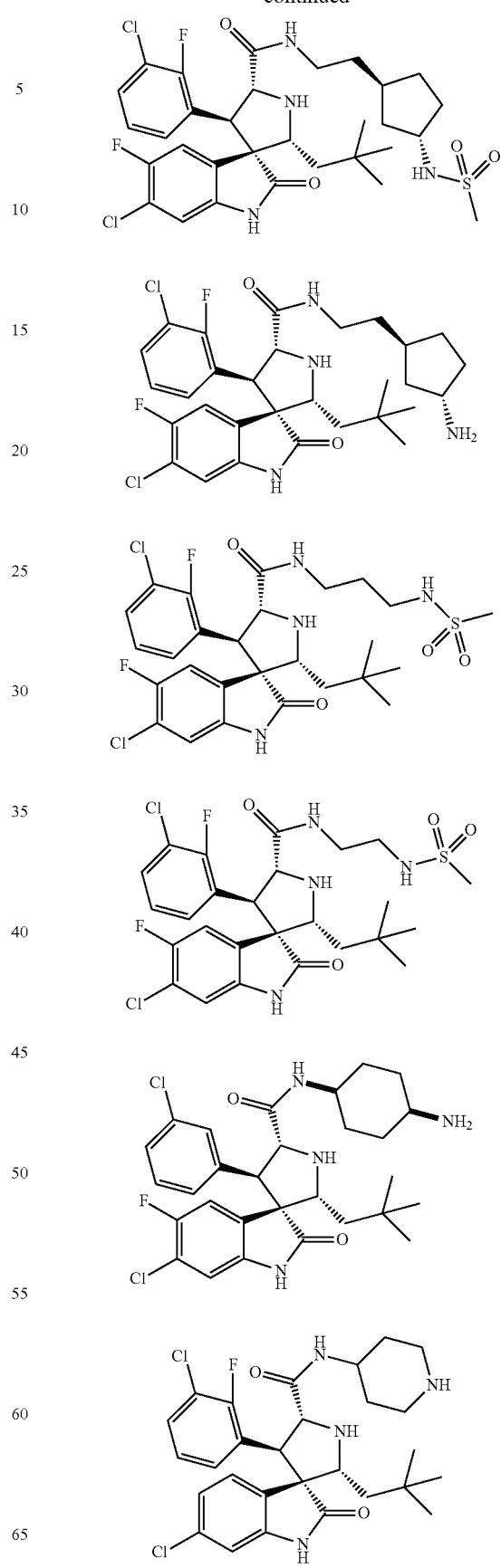

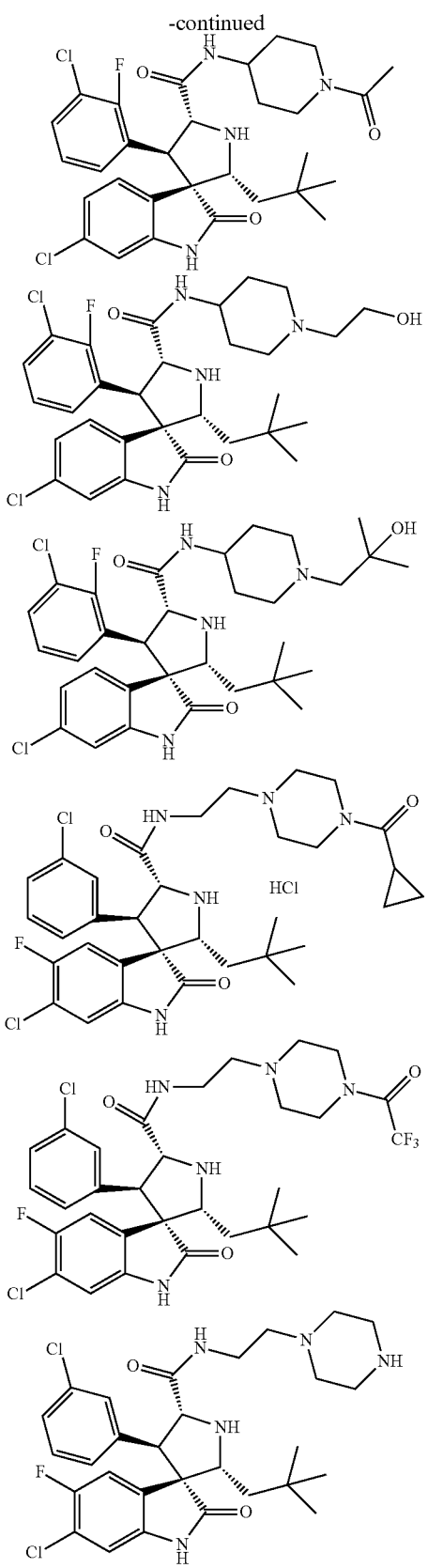

or a pharmaceutically acceptable salt, solvate, or prodrug thereof.

In certain embodiments, for the compounds of Formula I, ⸺ represents a single or a double bond.

In certain embodiments, the compound of Formula I is a mixture of stereoisomers, e.g., a mixture of diastereomers and/or enantiomers, e.g., a racemic mixture. In another such embodiment, the compound is a mixture of diastereomers. In another such embodiment, the compound is a mixture of enantiomers. In particular embodiments, the compound is a single enantiomer.

In certain embodiments, $R^5$ is selected from the group consisting of R5-1 and R5-2. In particular embodiments, $R^5$ is R5-2 and Z is —OH.

In certain embodiments, compounds of Formula Ia are provided:

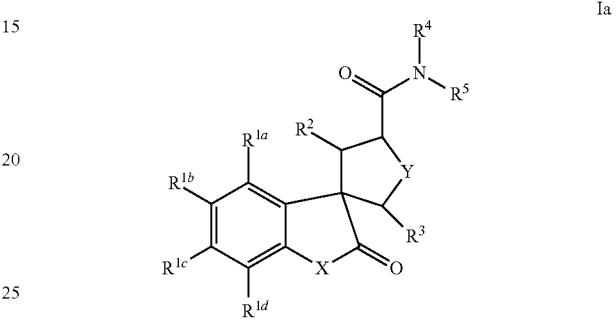

Ia wherein $R^{1a}$, $R^{1b}$, $R^{1c}$, $R^{1d}$, $R^2$, $R^3$, $R^4$, $R^5$, X, and Y have the meanings as described above for Formula I, or pharmaceutically acceptable salt, solvate, or prodrug thereof.

In certain embodiments, compounds of Formula Ib are provided:

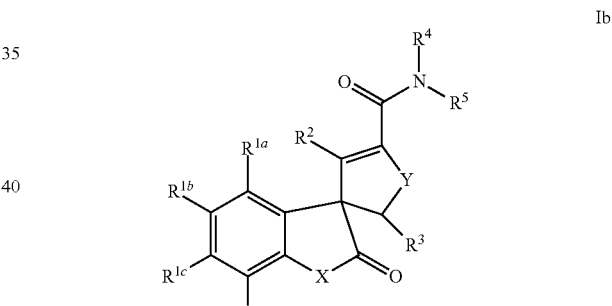

Ib wherein $R^{1a}$, $R^{1b}$, $R^{1c}$, $R^{1d}$, $R^2$, $R^3$, $R^4$, $R^5$, X, and Y have the meanings as described above for Formula I, or tautomer thereof, or a pharmaceutically acceptable salt, solvate, or prodrug thereof.

In certain embodiments, compounds of Formula II-XVII are provided:

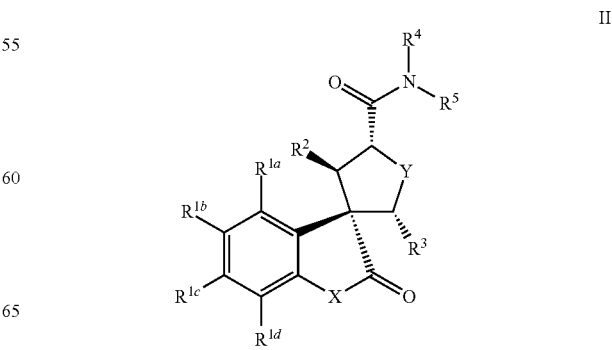

II

III
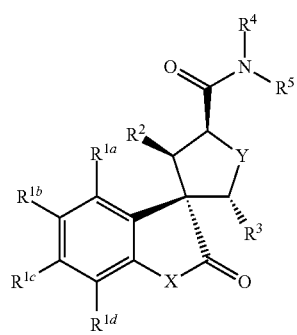
IV
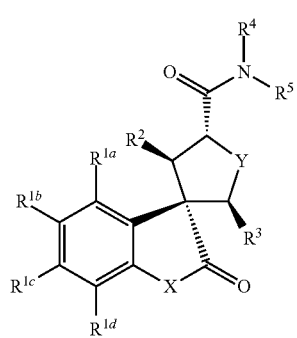
V
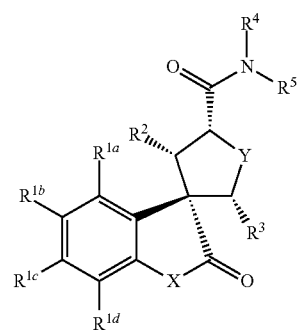
VI
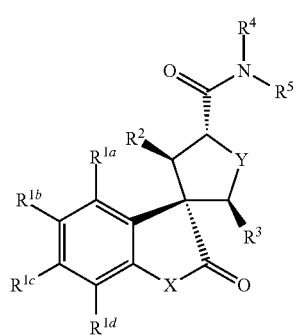
VII
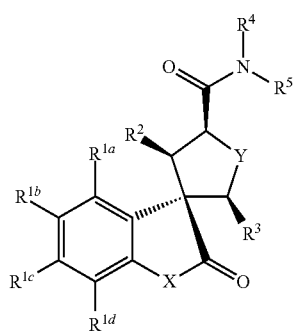
VIII
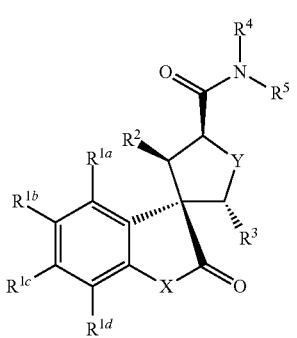
IX
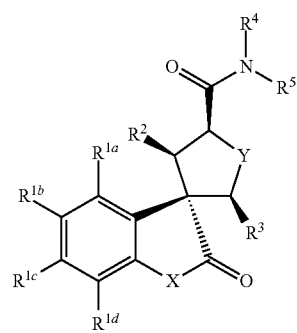
X
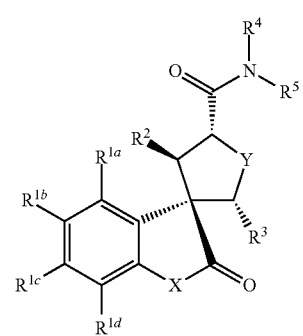

XI
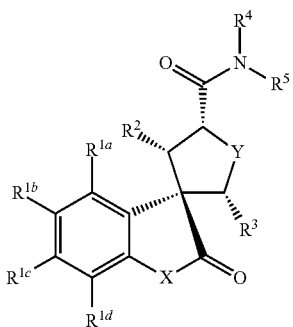

XII
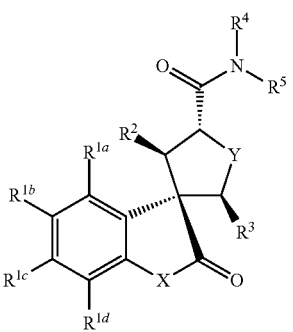

XIII
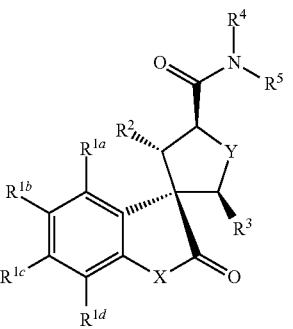

XIV
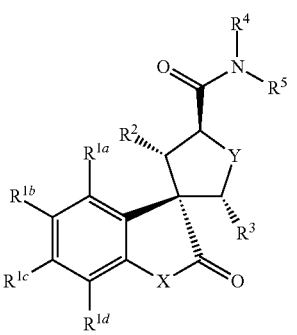

XV
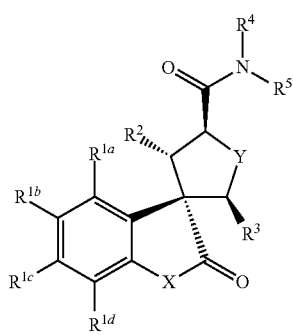

XVI
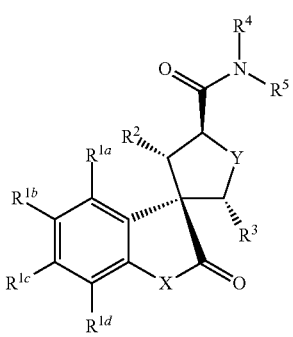

XVII
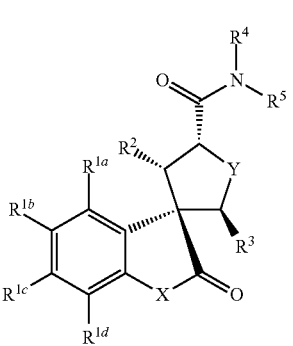

wherein $R^{1a}$, $R^{1b}$, $R^{1c}$, $R^{1d}$, $R^2$, $R^3$, $R^4$, $R^5$, X, A and Y have the meanings as described above for Formula I, or a pharmaceutically acceptable salt, solvate, or prodrug thereof.

In some embodiments, compounds of Formula II are provided, wherein $R^{1a}$, $R^{1b}$, $R^{1c}$, $R^{1d}$, $R^2$, $R^3$, $R^4$, $R^5$, X, and Y have the meanings as described above in connection with Formula I, or a pharmaceutically acceptable salt, solvate, or prodrug thereof.

In certain embodiments, compounds of Formulae I-XVII or a pharmaceutically acceptable salt, solvate, or prodrug thereof are provided. In some embodiments, compounds of Formula II or a pharmaceutically acceptable salt, solvate, or prodrug thereof are provided, wherein:

a) $R^{1a}$, $R^{1b}$, $R^{1c}$, and $R^{1d}$ are independently selected from the group consisting of hydrogen, fluoro, and chloro;

b) $R^{1a}$ and $R^{1d}$ are hydrogen; $R^{1b}$ is selected from the group consisting of hydrogen and fluoro; and $R^{1c}$ is selected from the group consisting of fluoro and chloro;

c) $R^2$ is optionally substituted phenyl;

d) $R^3$ is selected from the group consisting of optionally substituted alkyl, optionally substituted (cycloalkyl)alkyl, and optionally substituted cycloalkyl;

e) $R^4$ is hydrogen;

f) X is NH;

g) X is O;

h) X is S;
i) Y is O;
j) Y is S;
k) Y is NH; or
l) X and Y are NH;
or any combination thereof.

In certain embodiments, compounds of Formula II or a pharmaceutically acceptable salt, solvate, or prodrug thereof are provided, wherein $R^5$ is R5-1; $R^{6a}$ and $R^{6b}$ are hydrogen; $R^7$ is $C_1$-$C_4$ alkyl; $R^{8a}$ and $R^{8b}$ are hydrogen; W is —$OR^{10}$, $R^9$ and $R^{10}$ are hydrogen; and n is 2.

In certain embodiments, compounds of Formula II or a pharmaceutically acceptable salt, solvate, or prodrug thereof are provided, wherein $R^5$ is R5-1; $R^{6a}$ and $R^{6b}$ are hydrogen; $R^7$ is $C_1$-$C_4$ alkyl; $R^{8a}$ and $R^{8b}$ are hydrogen; W is —$NR^{11a}R^{11b}$, $R^9$ is hydrogen; and n is 2.

In certain embodiments, the compounds of Formula II or a pharmaceutically acceptable salt, solvate, or prodrug thereof are provided, wherein $R^5$ is R5-1; $R^{6a}$ and $R^{6b}$ are hydrogen; $R^2$ is $C_1$-$C_4$ alkyl; $R^{8a}$ and $R^{8b}$ are hydrogen; W is —$OR^{10}$, one of $R^9$ and $R^{10}$ is hydrogen and the other is a metabolically cleavable group; and n is 2.

In certain embodiments, compounds of Formula II or a pharmaceutically acceptable salt, solvate, or prodrug thereof are provided, wherein $R^5$ is R5-2; $R^{12a}$, $R^{12b}$, $R^{12c}$, and $R^{12d}$ are each hydrogen; $R^{13}$ is hydrogen; Z is —$OR^{15}$ and $R^{15}$ is hydrogen; o is 1 or 2; and p is 1 or 2.

In certain embodiments, compounds of Formula II or a pharmaceutically acceptable salt, solvate, or prodrug thereof are provided, wherein $R^5$ is R5-2; $R^{12a}$, $R^{12b}$, $R^{12c}$, and $R^{12d}$ are each hydrogen; $R^{13}$ is hydrogen; Z is —$NR^{16a}R^{16b}$; o is 1 or 2; and p is 1 or 2.

In certain embodiments, compounds of Formula II or a pharmaceutically acceptable salt, solvate, or prodrug thereof are provided, wherein $R^5$ is R5-2; $R^{12a}$, $R^{12b}$, $R^{12c}$, and $R^{12d}$ are each hydrogen; $R^{13}$ is hydrogen; Z is —$OR^{15}$ and $R^{15}$ a metabolically cleavable group; o is 1 or 2; and p is 1 or 2.

In certain embodiments, compounds of Formula II or a pharmaceutically acceptable salt, solvate, or prodrug thereof are provided, wherein $R^5$ is R5-3; $R^{17a}$, $R^{17b}$, $R^{17c}$, and $R^{17d}$ are each hydrogen; $R^{18}$, $R^{19}$, and $R^{20}$ are hydrogen; $R^{21a}$ and $R^{21b}$ are hydrogen; and q and r are 1.

In certain embodiments, compounds of Formula II or a pharmaceutically acceptable salt, solvate, or prodrug thereof are provided, wherein $R^5$ is R5-3; $R^{17a}$, $R^{17b}$, $R^{17c}$, and $R^{17d}$ are each hydrogen; $R^{18}$, $R^{19}$, and $R^{20}$ are hydrogen; one of $R^{21a}$ and $R^{21b}$ is hydrogen and the other is a metabolically cleavable group; and q and r are 1.

In certain embodiments, compounds of Formula II or a pharmaceutically acceptable salt, solvate, or prodrug thereof are provided, wherein $R^2$ is an optionally substituted aryl having the Formula R2-1:

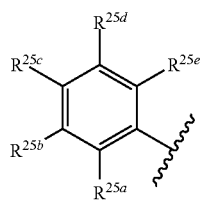

R2-1 and $R^{25a}$, $R^{25b}$, $R^{25c}$, $R^{25d}$, and $R^{25e}$ are each independently selected from the group consisting of hydrogen, halogen, hydroxy, nitro, amino, cyano, alkoxy, optionally substituted alkyl, haloalkyl, optionally substituted aryl, and optionally substituted heteroaryl. In particular embodiments, $R^{25a}$ is selected from the group consisting of hydrogen and fluoro; $R^{25b}$ is chloro; $R^{25c}$ is selected from the group consisting of hydrogen and fluoro; and $R^{25d}$ and $R^{25e}$ are hydrogen.

In certain embodiments, compounds of Formula II or a pharmaceutically acceptable salt, solvate, or prodrug thereof are provided, wherein $R^5$ is selected from the group consisting of:

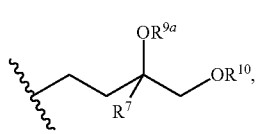

R5-5

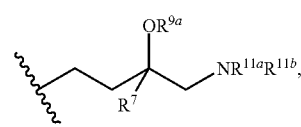

R5-6

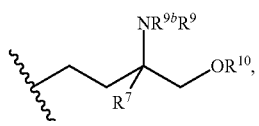

R5-7

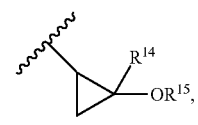

R5-8

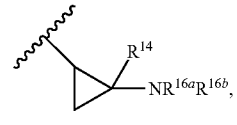

R5-9

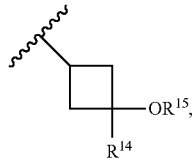

R5-10

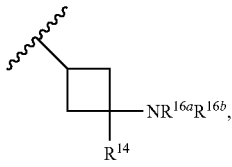

R5-11

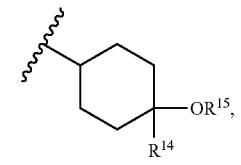

R5-12

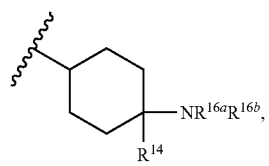

R5-13

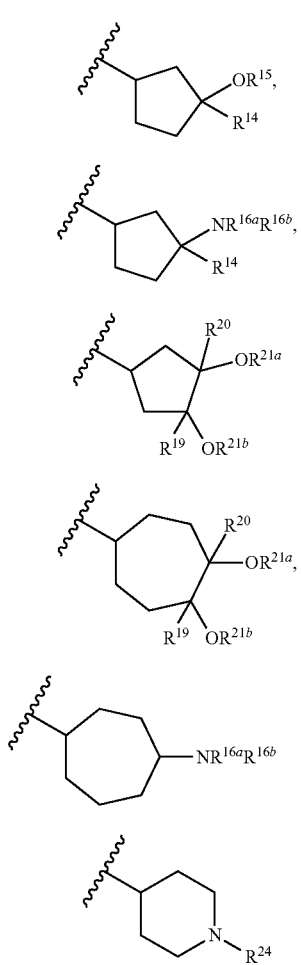

including stereoisomers, e.g., enantiomers, thereof, wherein:

$R^7$ is optionally substituted $C_1$-$C_4$ alkyl;

$R^{9a}$ and $R^{10}$ are each hydrogen; or one of $R^{9a}$ and $R^{10}$ is hydrogen and the other is a metabolically cleavable group;

$R^{9b}$ is selected from the group consisting of hydrogen, optionally substituted alkyl, optionally substituted cycloalkyl, optionally substituted aryl, optionally substituted heteroaryl, —$SO_2R^{9d}$, and —$CONR^{9e}R^{9f}$;

$R^{9c}$ is selected from the group consisting of hydrogen, optionally substituted alkyl, optionally substituted cycloalkyl, optionally substituted aryl, and optionally substituted heteroaryl; or $R^{9b}$ and $R^{9c}$ taken together with the nitrogen atom to which they are attached form a 4- to 8-membered optionally substituted heterocyclo;

$R^{9d}$ is selected from the group consisting of optionally substituted alkyl and optionally substituted cycloalkyl;

$R^{9e}$ and $R^{9f}$ are each independently selected from the group consisting of hydrogen, optionally substituted alkyl, and optionally substituted cycloalkyl; or $R^{9e}$ and $R^{9f}$ taken together with the nitrogen atom to which they are attached form a 4- to 8-membered optionally substituted heterocyclo;

$R^{11a}$ is selected from the group consisting of hydrogen, optionally substituted alkyl, optionally substituted cycloalkyl, optionally substituted aryl, optionally substituted heteroaryl, —$SO_2R^{11c}$, and —$CONR^{11d}R^{11e}$;

$R^{11b}$ is selected from the group consisting of hydrogen, optionally substituted alkyl, optionally substituted cycloalkyl, optionally substituted aryl, and optionally substituted heteroaryl; or $R^{11a}$ and $R^{11b}$ taken together with the nitrogen atom to which they are attached form a 4- to 8-membered optionally substituted heterocyclo;

$R^{11c}$ is selected from the group consisting of optionally substituted alkyl and optionally substituted cycloalkyl;

$R^{11d}$ and $R^{11e}$ are each independently selected from the group consisting of hydrogen, optionally substituted alkyl, and optionally substituted cycloalkyl; or $R^{11d}$ and $R^{11e}$ taken together with the nitrogen atom to which they are attached form a 4- to 8-membered optionally substituted heterocyclo;

$R^{14}$ is selected from the group consisting of hydrogen, $C_1$-$C_4$ alkyl, or $C_3$-$C_6$ cycloalkyl;

$R^{15}$ is hydrogen or a metabolically cleavable group;

$R^{16a}$ is selected from the group consisting of —$SO_2R^{16c}$ and —$CONR^{16d}R^{16e}$;

$R^{16b}$ is selected from the group consisting of hydrogen and optionally substituted alkyl;

$R^{16c}$ is selected from the group consisting of optionally substituted alkyl, optionally substituted cycloalkyl, optionally substituted aryl, and optionally substituted heteroaryl;

$R^{16d}$ and $R^{16e}$ are each independently selected from the group consisting of hydrogen, optionally substituted alkyl, optionally substituted cycloalkyl, optionally substituted aryl, and optionally substituted heteroaryl; or $R^{16d}$ and $R^{16e}$ taken together with the nitrogen atom to which they are attached form a 4- to 8-membered heterocyclo;

$R^{19}$ is selected from the group consisting of hydrogen, optionally substituted $C_1$-$C_6$ alkyl, and optionally substituted cycloalkyl;

$R^{20}$ is selected from the group consisting of hydrogen, optionally substituted $C_1$-$C_6$ alkyl, and optionally substituted cycloalkyl;

$R^{21a}$ and $R^{21b}$ are each hydrogen; or one of $R^{21a}$ and $R^{21b}$ is hydrogen and the other is metabolically cleavable group;

$R^{24}$ is selected from the group consisting of —$SO_2R^{24a}$ and —$CONR^{24b}R^{24c}$;

$R^{24a}$ is selected from the group consisting of optionally substituted alkyl, optionally substituted cycloalkyl, optionally substituted aryl, and optionally substituted heteroaryl; and $R^{24b}$ and $R^{24c}$ are each independently selected from the group consisting of hydrogen, optionally substituted cycloalkyl, optionally substituted aryl, and optionally substituted heteroaryl, or $R^{24b}$ and $R^{24c}$ taken together with the nitrogen atom to which they are attached form a 4- to 8-membered heterocyclo.

In certain embodiments, $R^5$ is selected from the group consisting of R5-5, R5-6, R5-10, R5-11, R5-12, R5-13, and R5-14.

In certain embodiments, $R^5$ is selected from the group consisting of R5-10 and R5-12 and $R^{14}$ is hydrogen or methyl and $R^{15}$ is hydrogen.

In certain embodiments, compounds of Formula II or a pharmaceutically acceptable salt, solvate, or prodrug thereof are provided, wherein $R^5$ is selected from the group consisting of:

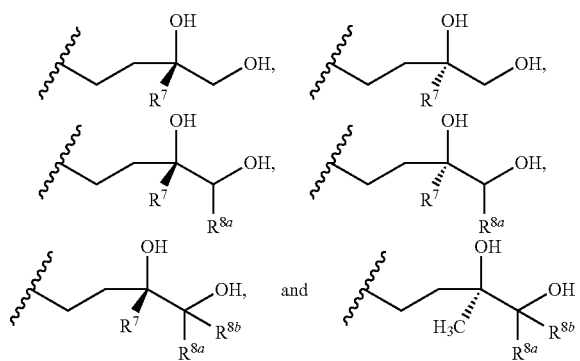

wherein:

R[7] is selected from the group consisting of methyl, ethyl, propyl, isopropyl, and cyclopropyl; and R[8a] and R[8b] are each independently selected from the group consisting of hydrogen, methyl, ethyl, propyl, isopropyl, and cyclopropyl.

In certain embodiments, compounds of Formula II or a pharmaceutically acceptable salt, solvate, or prodrug thereof are provided, wherein R[5] is selected from the group consisting of:

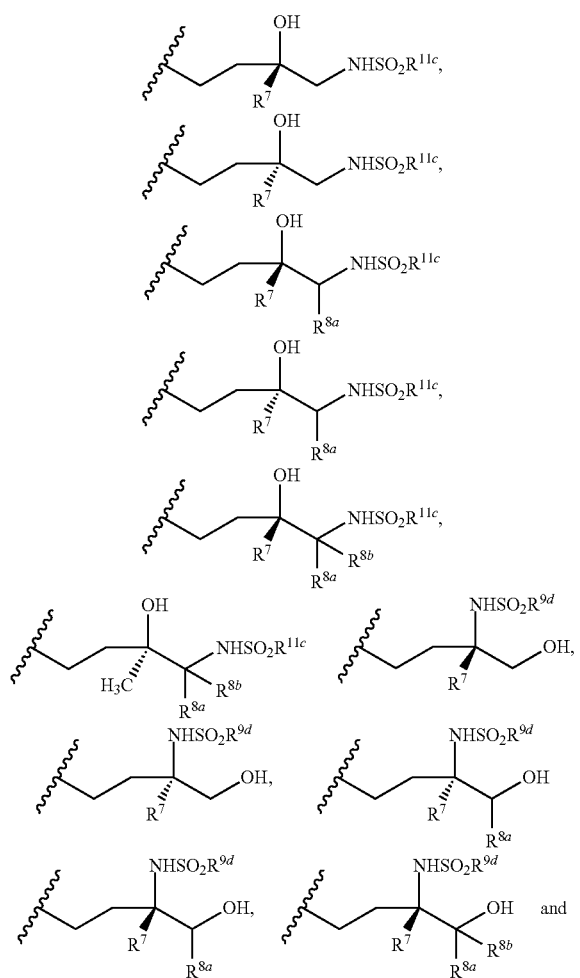

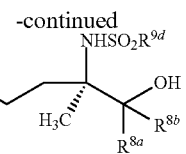

wherein:

R[7] is selected from the group consisting of methyl, ethyl, propyl, isopropyl, and cyclopropyl;

R[8a] and R[8b] are each independently is selected from the group consisting of hydrogen, methyl, ethyl, propyl, isopropyl, and cyclopropyl;

R[9d] is selected from the group consisting of methyl, trifluoromethyl, ethyl, propyl, isopropyl, and cyclopropyl; and R[11c] is selected from the group consisting of methyl, trifluoromethyl, ethyl, propyl, isopropyl, and cyclopropyl.

In certain embodiments, compounds of Formula II or a pharmaceutically acceptable salt, solvate, or prodrug thereof are provided, wherein R[5] is selected from the group consisting of:

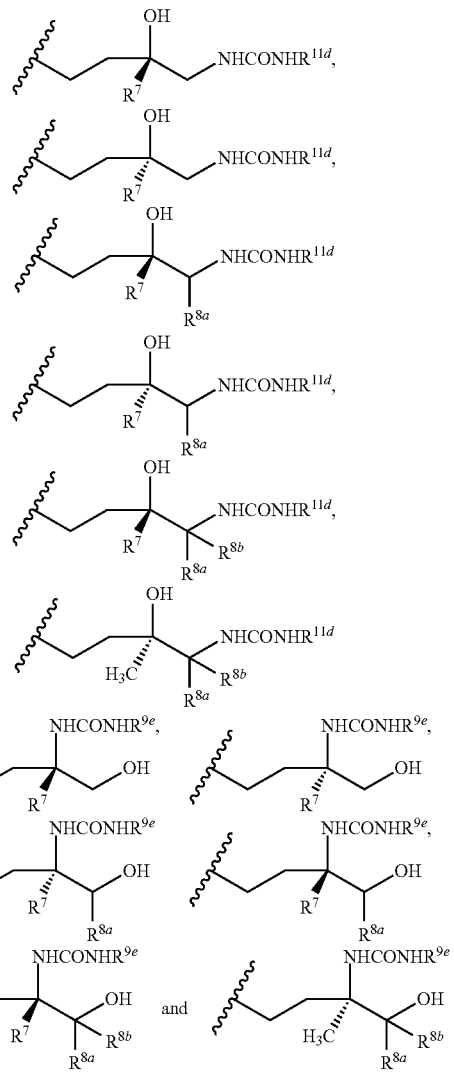

wherein:

R[7] is selected from the group consisting of methyl, ethyl, propyl, isopropyl, and cyclopropyl;

$R^{8a}$ and $R^{8b}$ are each independently is selected from the group consisting of hydrogen, methyl, ethyl, propyl, isopropyl, and cyclopropyl;

$R^{9c}$ is selected from the group consisting of methyl, trifluoromethyl, ethyl, propyl, isopropyl, and cyclopropyl; and $R^{11d}$ is selected from the group consisting of methyl, trifluoromethyl, ethyl, propyl, isopropyl, and cyclopropyl.

In certain embodiments, compounds of Formula II or a pharmaceutically acceptable salt, solvate, or prodrug thereof are provided, wherein $R^5$ is selected from the group consisting of:

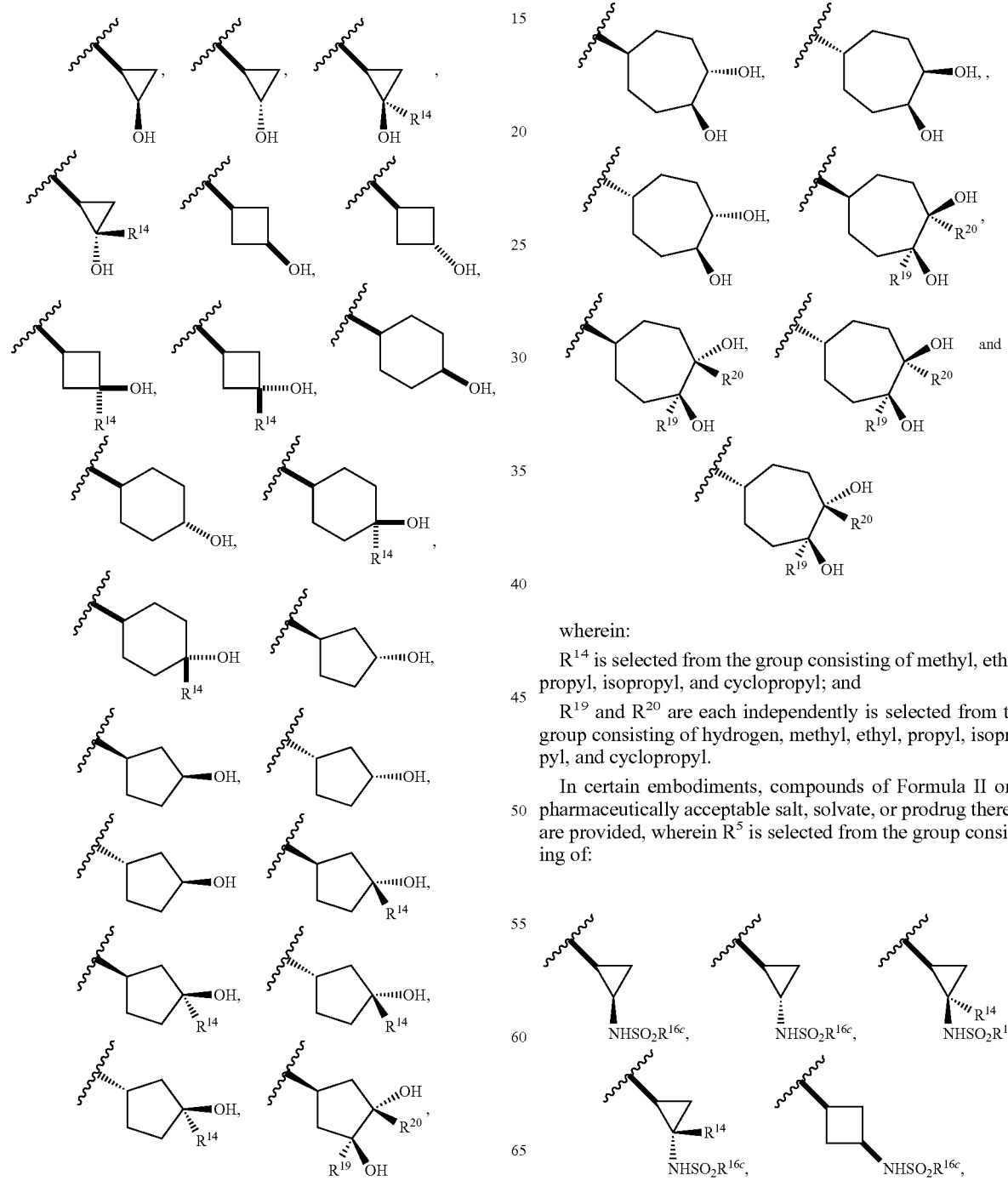

wherein:

$R^{14}$ is selected from the group consisting of methyl, ethyl, propyl, isopropyl, and cyclopropyl; and $R^{19}$ and $R^{20}$ are each independently is selected from the group consisting of hydrogen, methyl, ethyl, propyl, isopropyl, and cyclopropyl.

In certain embodiments, compounds of Formula II or a pharmaceutically acceptable salt, solvate, or prodrug thereof are provided, wherein $R^5$ is selected from the group consisting of:

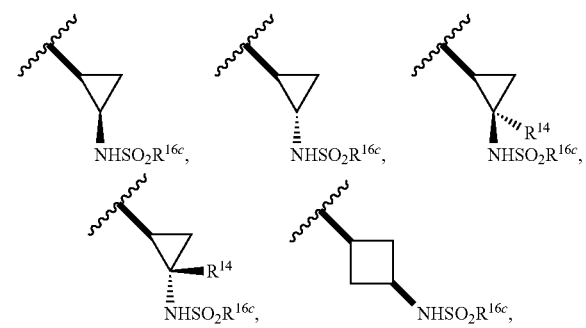

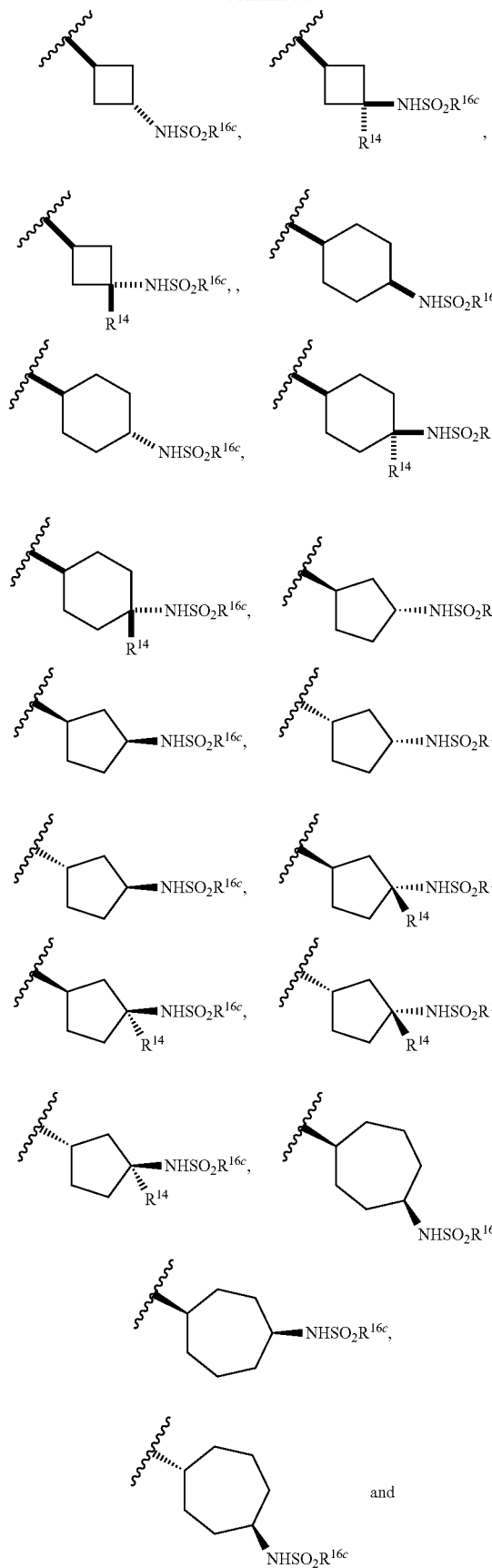

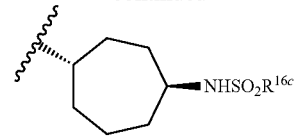

wherein:
R[14] is selected from the group consisting of methyl, ethyl, propyl, isopropyl, and cyclopropyl; and R[16c] is selected from the group consisting of methyl, trifluoromethyl, ethyl, propyl, isopropyl, and cyclopropyl.

In certain embodiments, compounds of Formula II or a pharmaceutically acceptable salt, solvate, or prodrug thereof are provided, wherein R[5] is selected from the group consisting of:

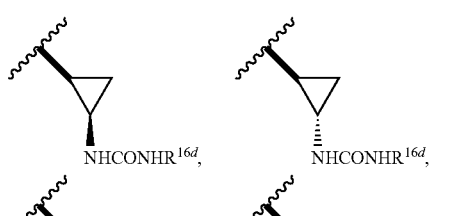

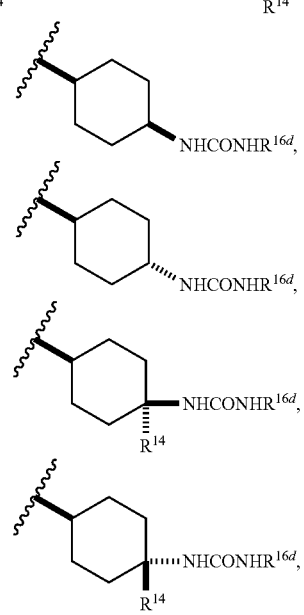

-continued

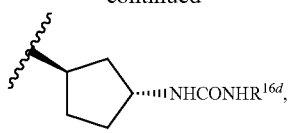
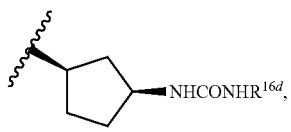
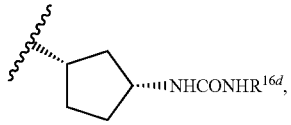
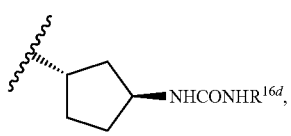
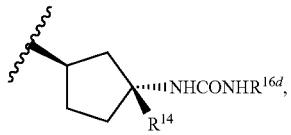
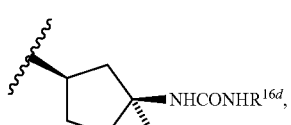
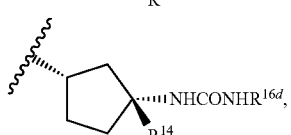
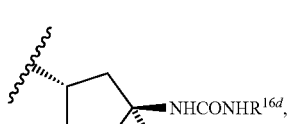
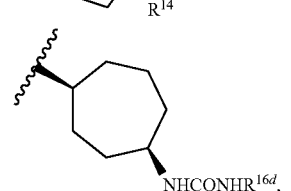
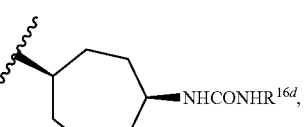

and

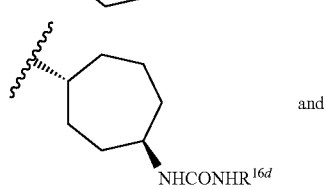

-continued

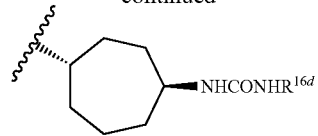

wherein:

$R^{14}$ is selected from the group consisting of methyl, ethyl, propyl, isopropyl, and cyclopropyl; and $R^{16d}$ is selected from the group consisting of methyl, trifluoromethyl, ethyl, propyl, isopropyl, and cyclopropyl.

In another embodiment, compounds of Formula XVIIIa are provided:

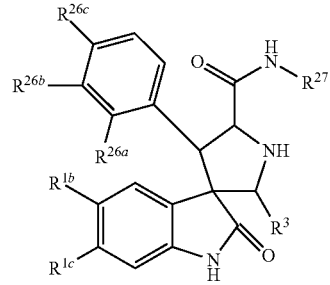

XVIIIa wherein:

$R^{1b}$ and $R^{1c}$ are independently selected from the group consisting of hydrogen, fluoro, and chloro;

$R^3$ is selected from the group consisting of optionally substituted alkyl, optionally substituted (cycloalkyl)alkyl, and optionally substituted cycloalkyl;

$R^{26a}$, $R^{26b}$, and $R^{26c}$ are independently selected from the group consisting of hydrogen, fluoro, and chloro; and $R^{27}$ is selected from the group consisting of:

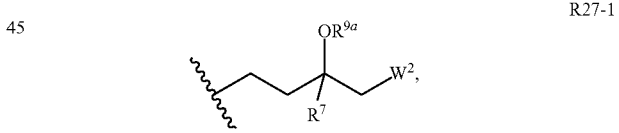

R27-1

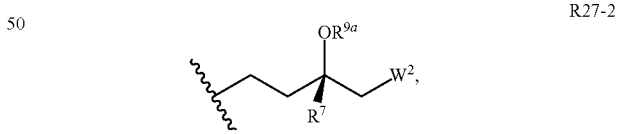

R27-2

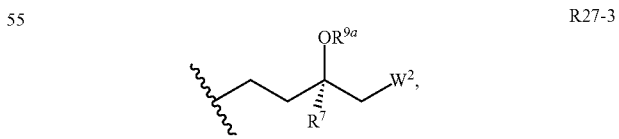

R27-3

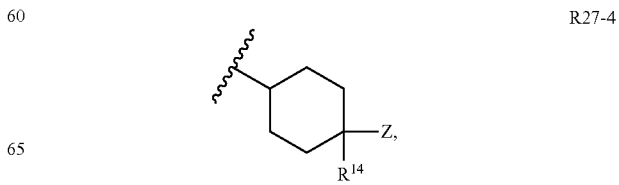

R27-4

R27-5
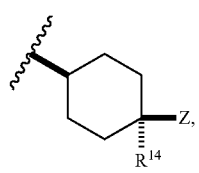
R27-6
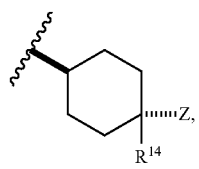
R27-7
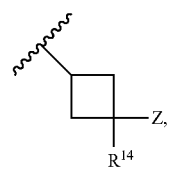
R27-8
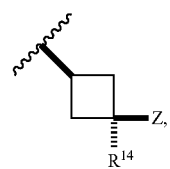
R27-9
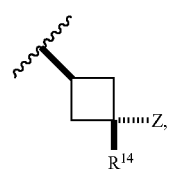
R27-10
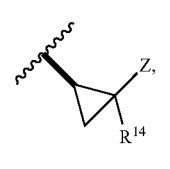
R27-11
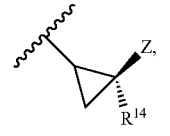
R27-12
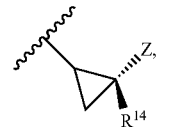
R27-13
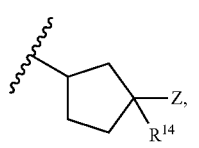
R27-14
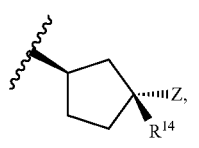
R27-15
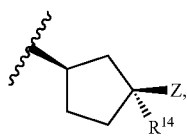
R27-16
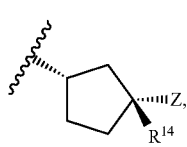
R27-17
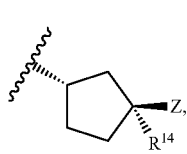
R27-18
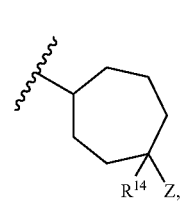
R27-19
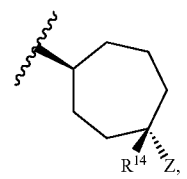
R27-20
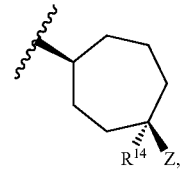
R27-21
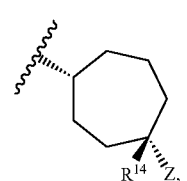
R27-22
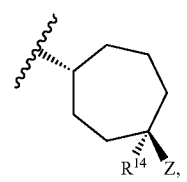
R27-23
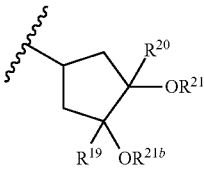

R27-24 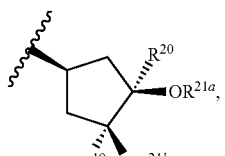

R27-25 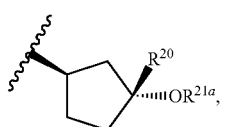

R27-26 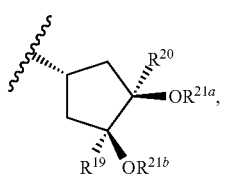

R27-27 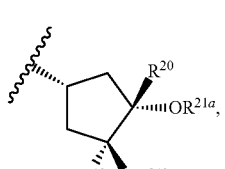

R27-28 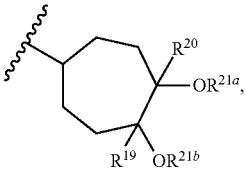

R27-29 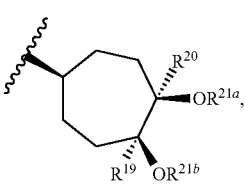

R27-30 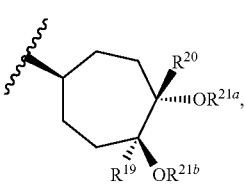

R27-31 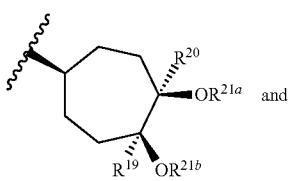

and

R27-32 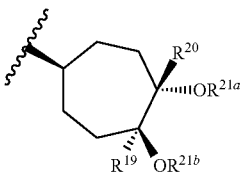

wherein:

$R^7$ is optionally substituted $C_1$-$C_4$ alkyl;

$W^2$ is selected from the group consisting of —$OR^{10}$ and —$NR^{11a}R^{11b}$;

$R^{9a}$ and $R^{10}$ are each hydrogen; or one of $R^{9a}$ and $R^{10}$ is hydrogen and the other is a metabolically cleavable group;

$R^{11a}$ is selected from the group consisting of hydrogen, optionally substituted alkyl, optionally substituted cycloalkyl, optionally substituted aryl, optionally substituted heteroaryl, —$SO_2R^{11c}$, and —$CONR^{11d}R^{11e}$;

$R^{11b}$ is selected from the group consisting of hydrogen, optionally substituted alkyl, optionally substituted cycloalkyl, optionally substituted aryl, and optionally substituted heteroaryl; or $R^{11a}$ and $R^{11b}$ taken together with the nitrogen atom to which they are attached form a 4- to 8-membered optionally substituted heterocyclo;

$R^{11c}$ is selected from the group consisting of optionally substituted alkyl and optionally substituted cycloalkyl;

$R^{11d}$ and $R^{11e}$ are each independently selected from the group consisting of hydrogen, optionally substituted alkyl, and optionally substituted cycloalkyl; or $R^{11d}$ and $R^{11e}$ taken together with the nitrogen atom to which they are attached form a 4- to 8-membered optionally substituted heterocyclo;

$R^{14}$ is selected from the group consisting of hydrogen, optionally substituted $C_1$-$C_4$ alkyl, and optionally substituted cycloalkyl;

Z is selected from the group consisting of —$OR^{15}$ and —$NR^{16a}R^{16b}$;

$R^{15}$ is selected from the group consisting of hydrogen and metabolically cleavable group;

$R^{16a}$ is selected from the group consisting of —$SO_2R^{16c}$ and —$CONR^{16d}R^{16e}$;

$R^{16b}$ is selected from the group consisting of hydrogen and optionally substituted alkyl;

$R^{16c}$ is selected from the group consisting of optionally substituted alkyl, optionally substituted cycloalkyl, optionally substituted aryl, and optionally substituted heteroaryl;

$R^{16d}$ and $R^{16e}$ are each independently selected from the group consisting of hydrogen, optionally substituted alkyl, optionally substituted cycloalkyl, optionally substituted aryl, and optionally substituted heteroaryl; or $R^{16d}$ and $R^{16e}$ taken together with the nitrogen atom to which they are attached form a 4- to 8-membered heterocyclo;

$R^{19}$ is selected from the group consisting of hydrogen, optionally substituted $C_1$-$C_6$ alkyl, and optionally substituted cycloalkyl;

$R^{20}$ is selected from the group consisting of hydrogen, optionally substituted $C_1$-$C_6$ alkyl, and optionally substituted cycloalkyl;

$R^{21a}$ and $R^{21b}$ are each hydrogen; or one of $R^{21a}$ and $R^{21b}$ is hydrogen and the other is metabolically cleavable group;

or a pharmaceutically acceptable salt, solvate, or prodrug thereof.

In another embodiment, compounds of Formula XVIIIb are provided:

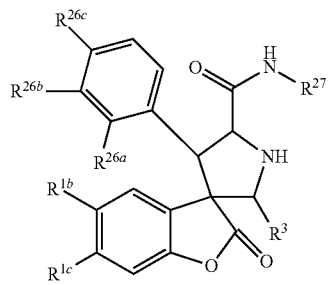

XVIIIb wherein $R^{1b}$, $R^{1b}$, $R^3$, $R^{26a}$, $R^{26b}$, $R^{26c}$, and $R^{27}$ have the meanings as described above for Formula XVIIIa, or a pharmaceutically acceptable salt, solvate, or prodrug thereof.

In another embodiment, compounds of Formula XVIIIc are provided:

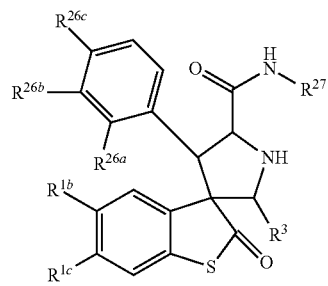

XVIIIc wherein $R^{1b}$, $R^{1b}$, $R^3$, $R^{26a}$, $R^{26b}$, $R^{26c}$, and $R^{27}$ have the meanings as described above for Formula XVIIIa, or a pharmaceutically acceptable salt, solvate, or prodrug thereof.

In certain embodiments, $R^{27}$ is selected from the group consisting of R27-2, R27-3, R27-5, R27-6, R27-8, R27-9, R27-11, R27-12, R27-14, R27-15, R27-16, R27-17, R27-19, R27-20, R27-21, R27-22, R27-24, R27-25, R27-27, R27-29, R27-30, R27-31, and R27-32. In certain embodiments, $R^{27}$ is selected from the group consisting of R27-2, R27-3, R27-5, and R27-6, R27-8, R27-9, R27-14, R27-15, R27-16, and R27-17. In certain embodiments, $R^{27}$ is a hydroxycycloalkyl group.

In certain embodiments, $R^{9a}$ is hydrogen; $W^2$ is OH; Z is OH; $R^2$ is $C_1$-$C_4$ alkyl, e.g., methyl, ethyl, propyl, or isopropyl, or cyclopropyl; $R^{14}$, $R^{19}$, and $R^{20}$ are each independently hydrogen, $C_1$-$C_4$ alkyl, e.g., methyl, ethyl, propyl, or isopropyl, or cyclopropyl; and $R^{21a}$ and $R^{21b}$ are each hydrogen.

In certain embodiments, $R^{9a}$ is hydrogen, $R^7$ is hydrogen, $C_1$-$C_4$ alkyl, or cyclopropyl; $W^2$ is —$NHR^{11a}$; $R^{11a}$ is $C_1$-$C_4$ alkyl, e.g., methyl, trifluoromethyl, ethyl, propyl, or isopropyl, or cyclopropyl; $R^{14}$ is hydrogen, $C_1$-$C_4$ alkyl, e.g., methyl, ethyl, propyl, or isopropyl, or cyclopropyl; Z is —$NHSO_2R^{16c}$ or —$NHCONHR^{16d}$; and $R^{16c}$ and $R^{16d}$ are each independently optionally substituted $C_1$-$C_4$ alkyl, e.g., methyl, trifluoromethyl, ethyl, propyl, or isopropyl, or cyclopropyl.

In certain embodiments, compounds of Formulae XIX-XXXIV are provided:

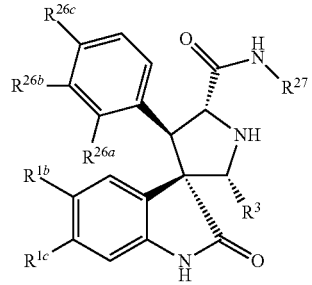

XIX

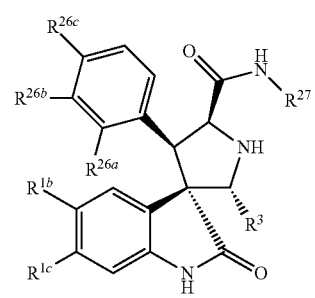

XX

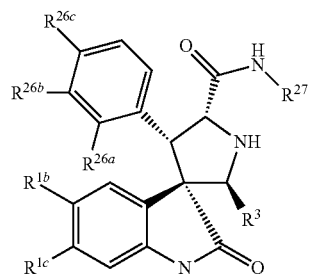

XXI

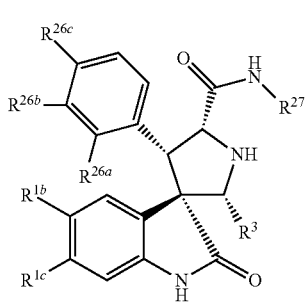

XXII

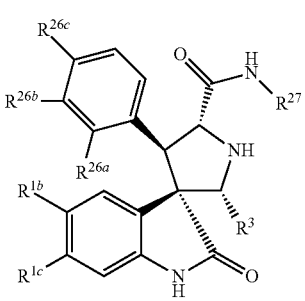

XXIII

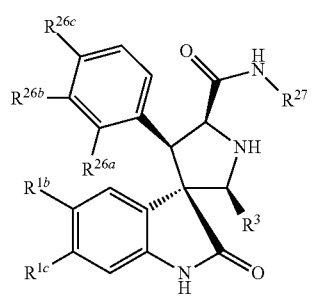
XXIV
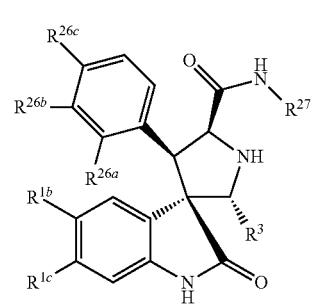
XXV
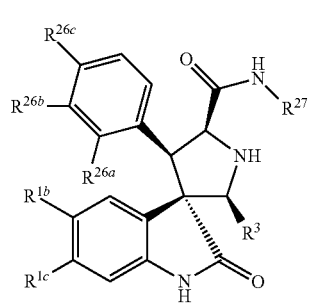
XXVI
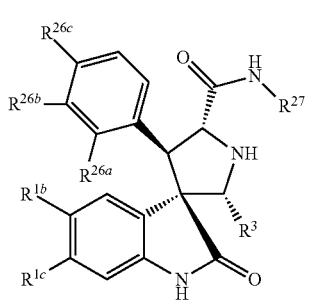
XXVII
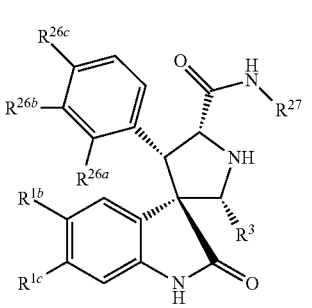
XXVIII
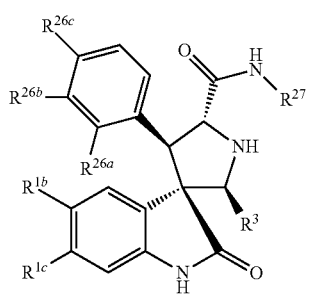
XXIX
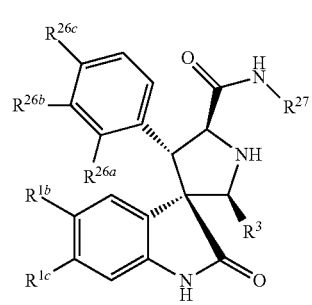
XXX
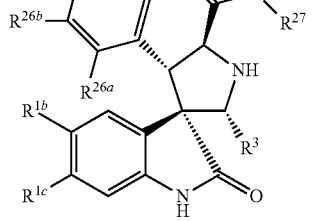
XXXI
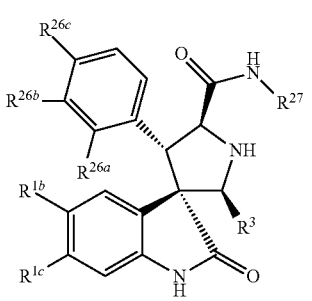
XXXII
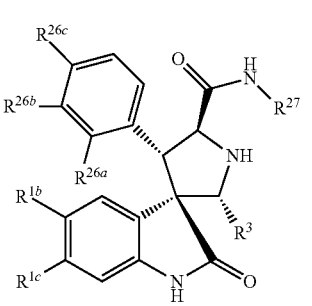
XXXIII -continued

XXXIV

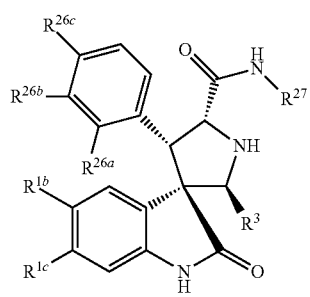

wherein $R^{1b}$, $R^{1c}$, $R^3$, $R^{26a}$, $R^{26b}$, $R^{26c}$, and $R^{27}$ have the meanings as described above in connection with Formula XVIIIa, or a pharmaceutically acceptable salt, solvate, or prodrug thereof.

In certain embodiments, compounds of Formula XIX are provided, wherein $R^{1b}$, $R^{1c}$, $R^3$, $R^{26a}$, $R^{26b}$, $R^{26c}$, and $R^{27}$ have the meanings as described above in connection with Formula XVIIIa, or a pharmaceutically acceptable salt, solvate, or prodrug thereof.

In certain embodiments, compounds of Formula XIX are provided, wherein $R^{27}$ is selected from the group consisting of:

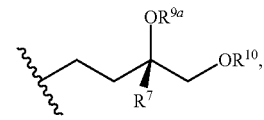
R27-33

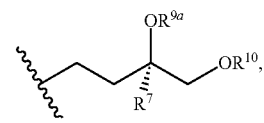
R27-34

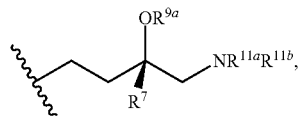
R27-35

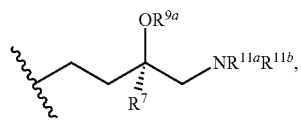
R27-36

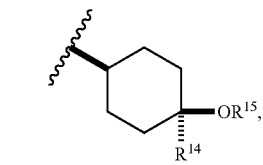
R27-37

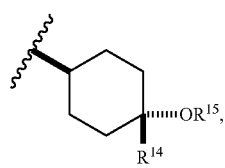
R27-38

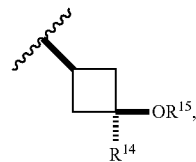
R27-39

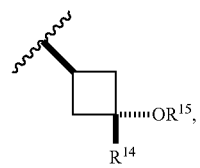
R27-40

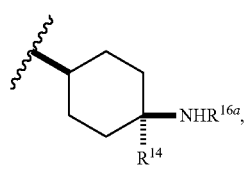
R27-41

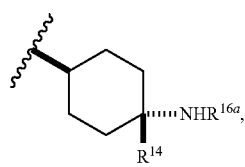
R27-42

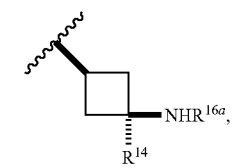
R27-43

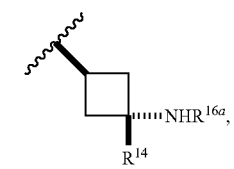
R27-44

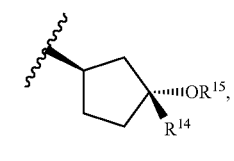
R27-45

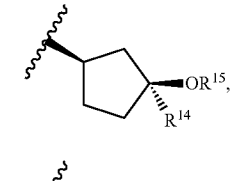
R27-46

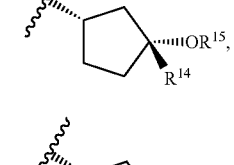
R27-47

R27-48

-continued

R27-49 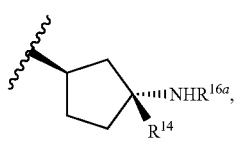

R27-50 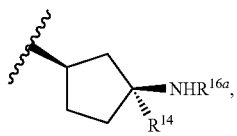

R27-51 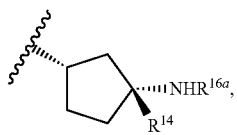

R27-52 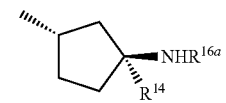

R27-53 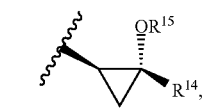

R27-54 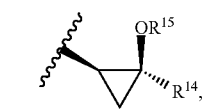

R27-55 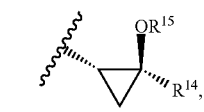

R27-56 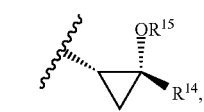

R27-57 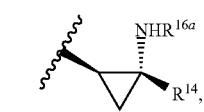

R27-58 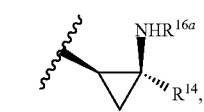

-continued

R27-59 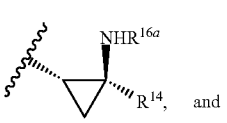 and

R27-60 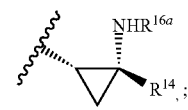;

wherein:
$R^7$ is $C_1$-$C_4$ alkyl;
$R^{9a}$ and $R^{10}$ are hydrogen; or
one of $R^{9a}$ and $R^{10}$ is hydrogen and the other is metabolically cleavable group;
$R^{11a}$ and $R^{11b}$ are each independently selected from the group consisting of hydrogen, optionally substituted $C_1$-$C_4$ alkyl, optionally substituted cycloalkyl, optionally substituted aryl, and optionally substituted heteroaryl; or
$R^{11a}$ and $R^{11b}$ taken together with the nitrogen atom to which they are attached form a 4- to 8-membered optionally substituted heterocyclo;
$R^{14}$ is selected from the group consisting of hydrogen and $C_1$-$C_4$ alkyl;
$R^{15}$ is hydrogen or a metabolically cleavable group; and
$R^{16a}$ is selected from the group consisting of —$SO_2R^{16c}$ and —$CONR^{16d}R^{16e}$;
$R^{16c}$ is selected from the group consisting of optionally substituted $C_1$-$C_4$ alkyl or cyclopropyl;
$R^{16d}$ and $R^{16e}$ are each independently selected from the group consisting of hydrogen, optionally substituted $C_1$-$C_4$ alkyl or cyclopropyl; or
$R^{16d}$ and $R^{16e}$ taken together with the nitrogen atom to which they are attached form a 4- to 8-membered heterocyclo, or a pharmaceutically acceptable salt, solvate, or prodrug thereof.

In certain embodiments, compounds of Formula XIX are provided, wherein $R^{27}$ is selected from the group consisting of:

R27-61 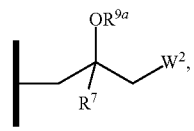

R27-62 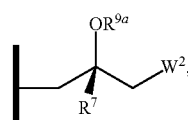

R27-63 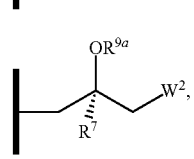

R27-64 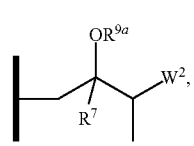

-continued

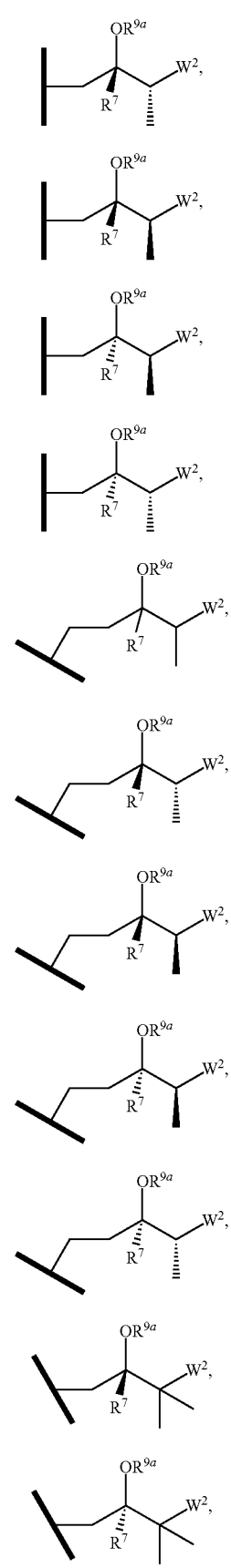

R27-65
R27-66
R27-67
R27-68
R27-69
R27-70
R27-71
R27-72
R27-73
R27-74
R27-75

-continued

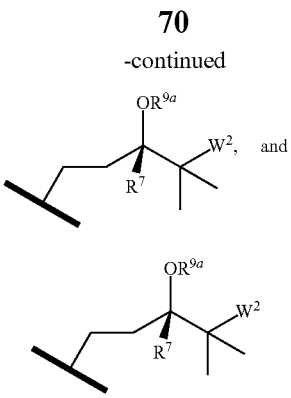

R27-76
R27-77 and wherein:

$R^7$ is optionally substituted $C_1$-$C_4$ alkyl;

$W^2$ is selected from the group consisting of —$OR^{10}$ and —$NR^{11a}R^{11b}$;

$R^{9a}$ and $R^{10}$ are each hydrogen; or one of $R^{9a}$ and $R^{10}$ is hydrogen and the other is a metabolically cleavable group;

$R^{11a}$ is selected from the group consisting of hydrogen, optionally substituted alkyl, optionally substituted cycloalkyl, optionally substituted aryl, optionally substituted heteroaryl, —$SO_2R^{11c}$, and —$CONR^{11d}R^{11e}$;

$R^{11b}$ is selected from the group consisting of hydrogen, optionally substituted alkyl, optionally substituted cycloalkyl, optionally substituted aryl, and optionally substituted heteroaryl; or $R^{11a}$ and $R^{11b}$ taken together with the nitrogen atom to which they are attached form a 4- to 8-membered optionally substituted heterocyclo;

$R^{11c}$ is selected from the group consisting of optionally substituted alkyl and optionally substituted cycloalkyl;

$R^{11d}$ and $R^{11e}$ are each independently selected from the group consisting of hydrogen, optionally substituted alkyl, and optionally substituted cycloalkyl; or $R^{11d}$ and $R^{11e}$ taken together with the nitrogen atom to which they are attached form a 4- to 8-membered optionally substituted heterocyclo;

or a pharmaceutically acceptable salt, solvate, or prodrug thereof.

In certain embodiments, compounds of Formula XIX are provided, wherein $R^{27}$ is selected from the group consisting of:

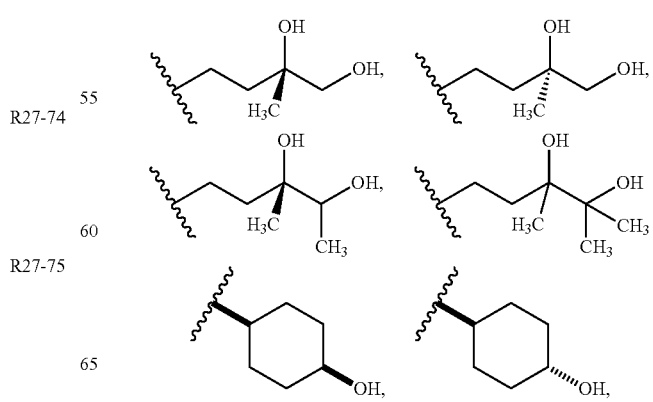

-continued

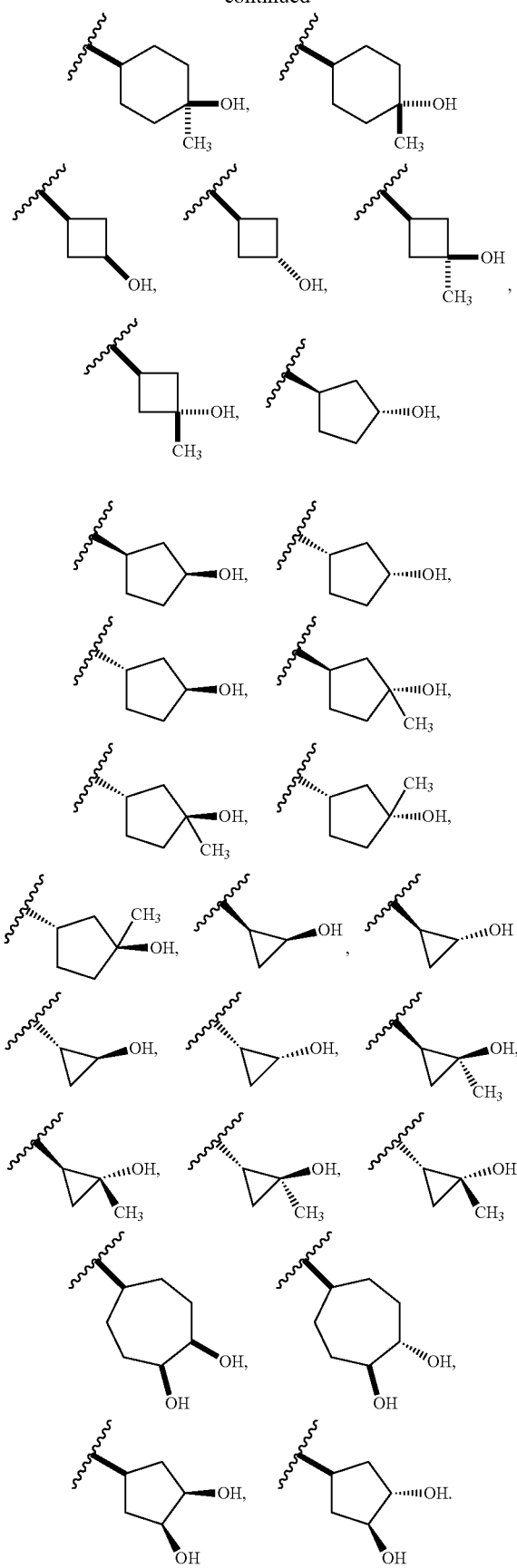

In certain embodiments, compounds of Formula XIX are provided, wherein $R^{27}$ is selected from the group consisting of:

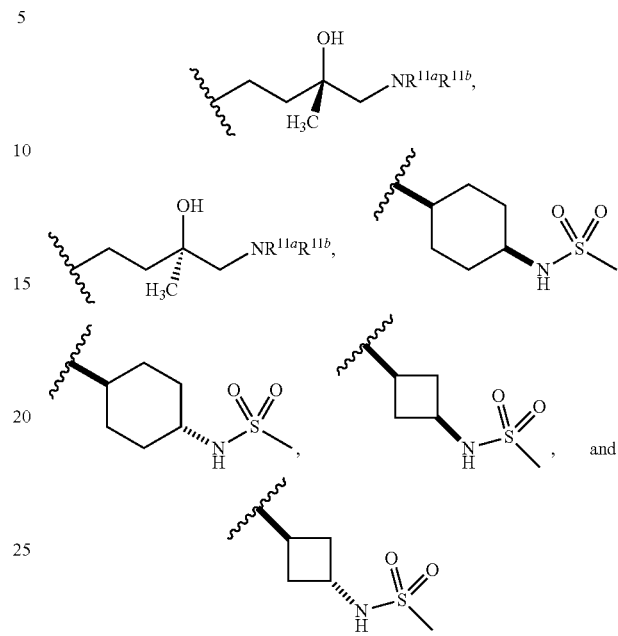

wherein $R^{11a}$ and $R^{11b}$ taken together with the nitrogen to which they are attached form a 5- or 6-membered optionally substituted heterocyclo.

In certain embodiments, compounds of Formula XIX are provided, wherein $R^{27}$ is selected from the group consisting of:

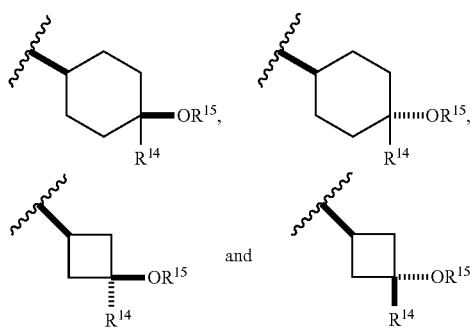

wherein:
$R^{14}$ is selected from the group consisting of hydrogen and $C_1$-$C_4$ alkyl; and
$R^{15}$ is a metabolically cleavable group.

In certain embodiments, compounds of Formulae II and XIX are provided, wherein $R^{15}$ is a metabolically cleavable group selected from the group consisting of:

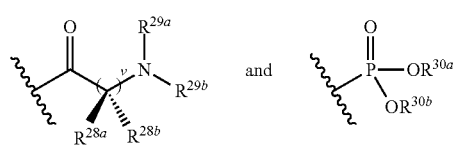

wherein:

each $R^{28a}$ and $R^{28b}$ is independently selected from the group consisting of hydrogen, optionally substituted alkyl, and aralkyl;

$R^{29a}$ and $R^{29b}$ are each selected from the group consisting of hydrogen and optionally substituted alkyl;

v is 1, 2, 3, or 4; and $R^{30a}$ and $R^{30b}$ are each selected from the group consisting of hydrogen, optionally substituted alkyl, aralkyl, optionally substituted aryl, and monovalent pharmaceutically acceptable cation; or taken together $R^{30a}$ and $R^{30b}$ represent a divalent pharmaceutically acceptable cation or an optionally substituted alkylenyl.

In certain embodiments, $R^{15}$ is the residue of a natural or unnatural amino acid. In other embodiments, $R^{15}$ is the residue of glycine, isoleucine alanine, leucine, asparagine, lysine, aspartic acid, methionine, cysteine, phenylalanine, glutamic acid, threonine, glutamine, tryptophan, valine, proline, serine, tyrosine, arginine, and histidine In certain embodiments, compounds of Formulae II and XIX are provided, wherein $R^3$ is $C_1$-$C_{10}$ alkyl.

In certain embodiments, compounds of Formulae II and XIX are provided, wherein $R^3$ is selected from the group consisting of —$CH_2C(CH_3)_3$, —$CH_2C(CH_3)_2CH_2CH_3$, —$CH_2C(CH_3)_2CH_2CH_2CH_3$, —$CH_2C(CH_3)_2CH_2CH_2CH_3$, —$CH_2C(CH_2CH_3)_2CH_3$, and —$CH_2C(CH_3)_2CH_2CH(CH_3)_2$. In certain embodiments, $R^3$ is —$CH_2C(CH_3)_3$ In certain embodiments, compounds of Formula I are provided having the structure:

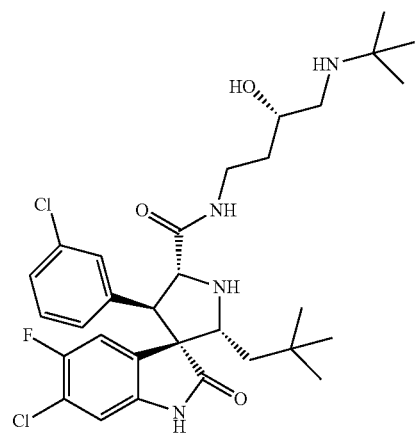

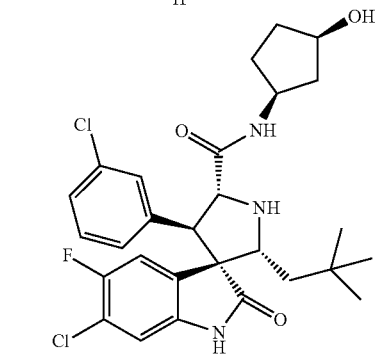

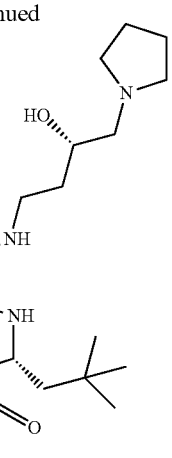

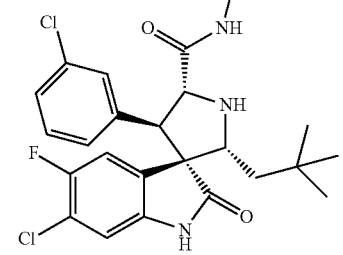

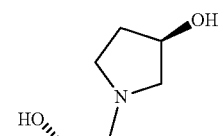

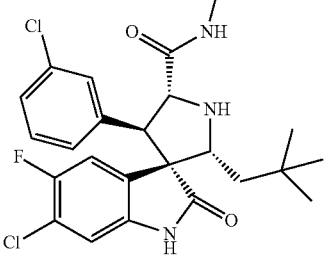

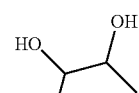

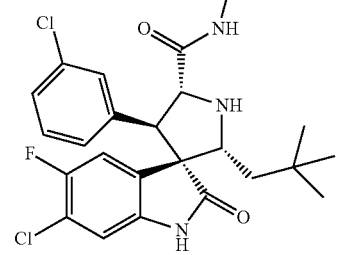

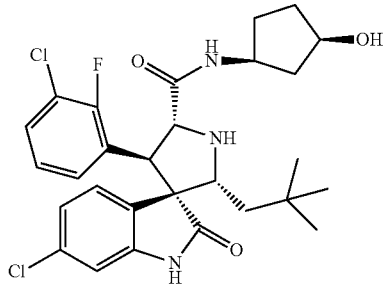

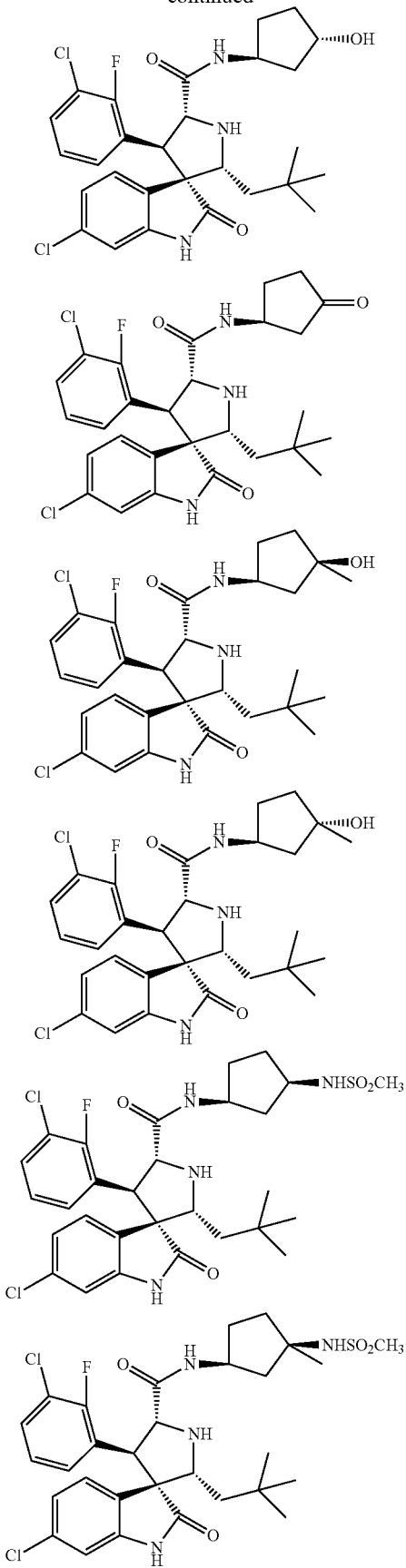
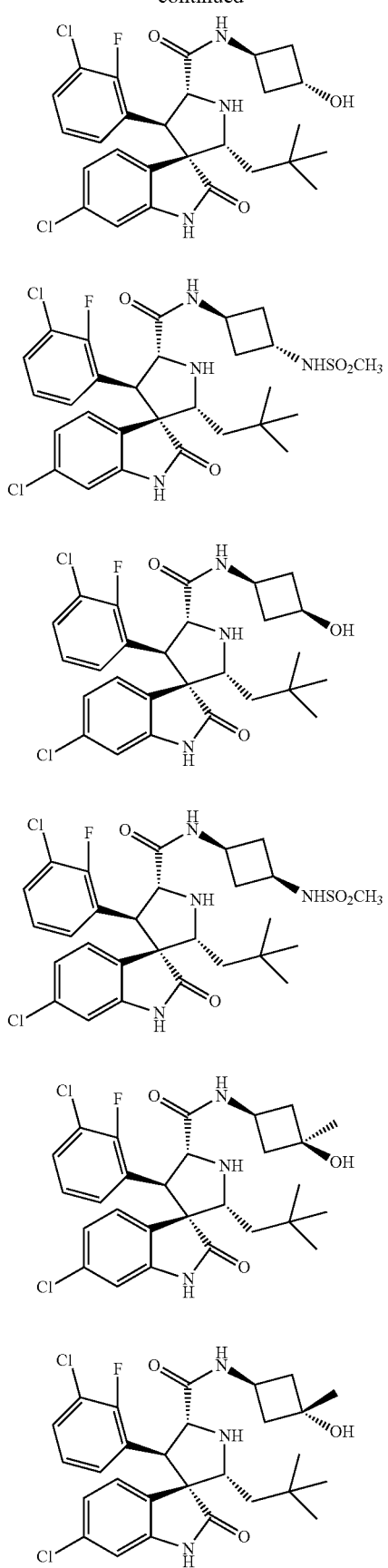

77
-continued
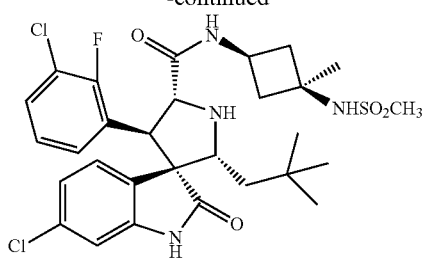
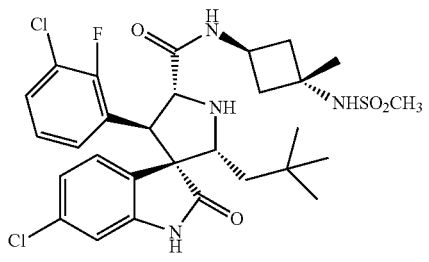
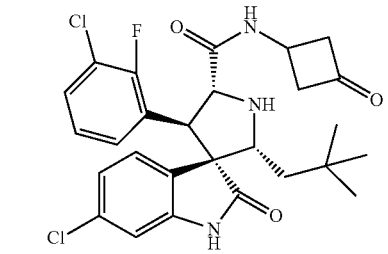
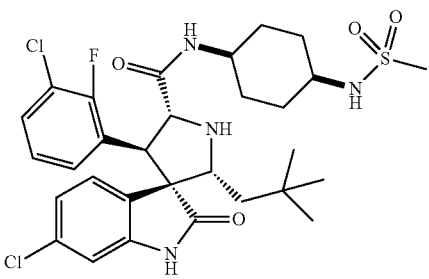
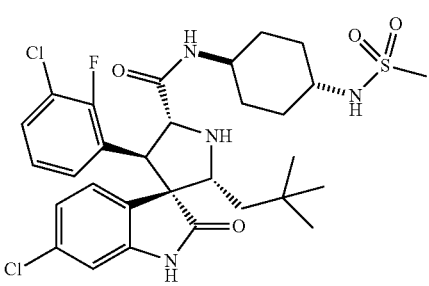
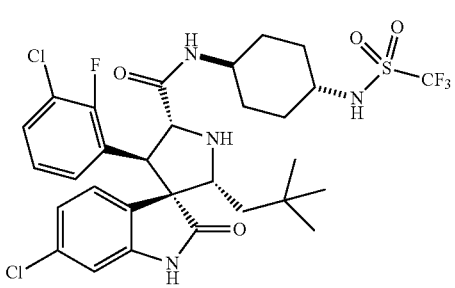
78
-continued
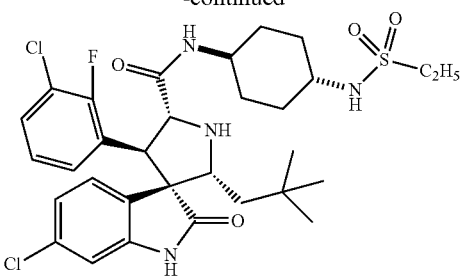
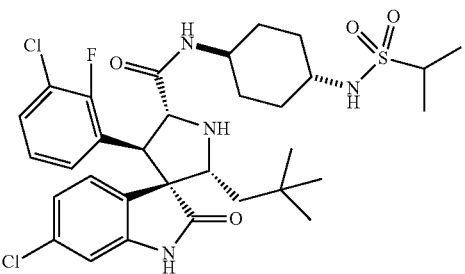
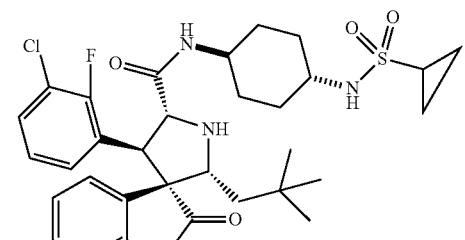
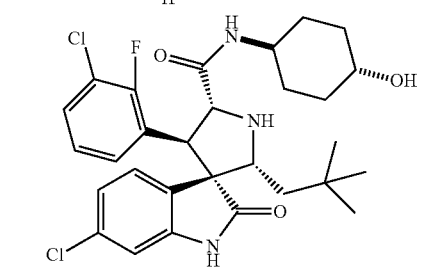
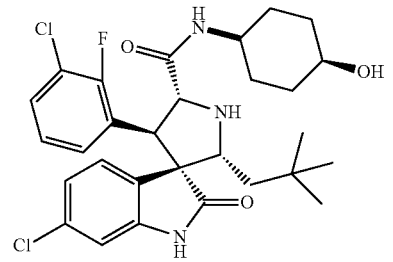
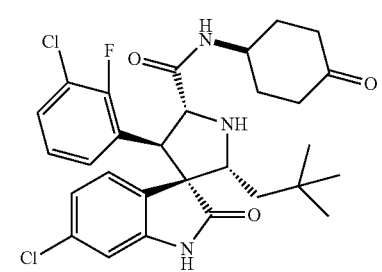

-continued
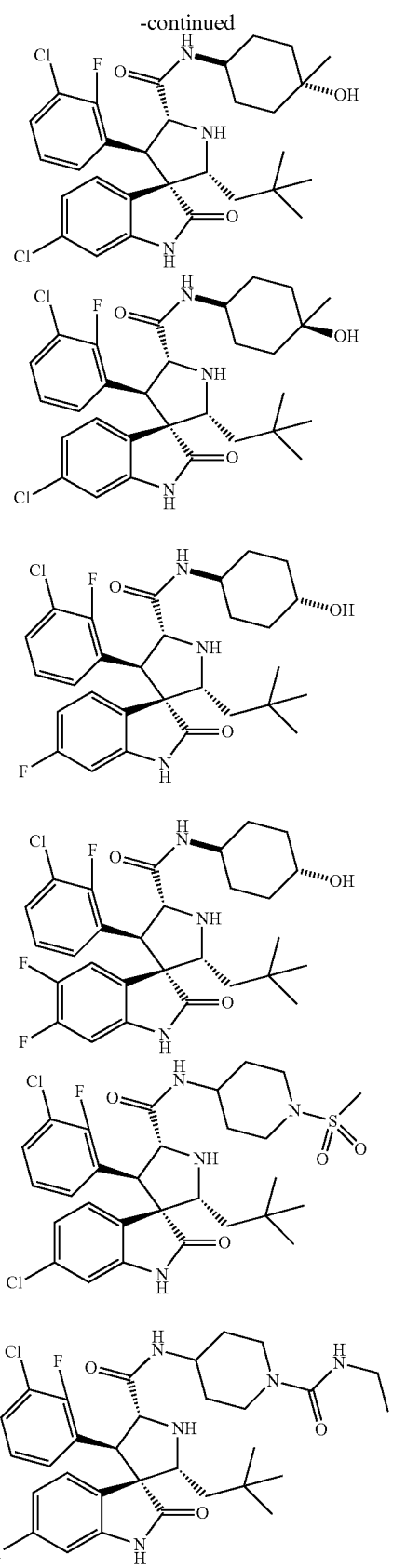
or a pharmaceutically acceptable salt, solvate, or prodrug thereof ("Ms"=—SO$_2$CH$_3$).
In certain embodiments, compounds of Formula I are provided having the following structures:
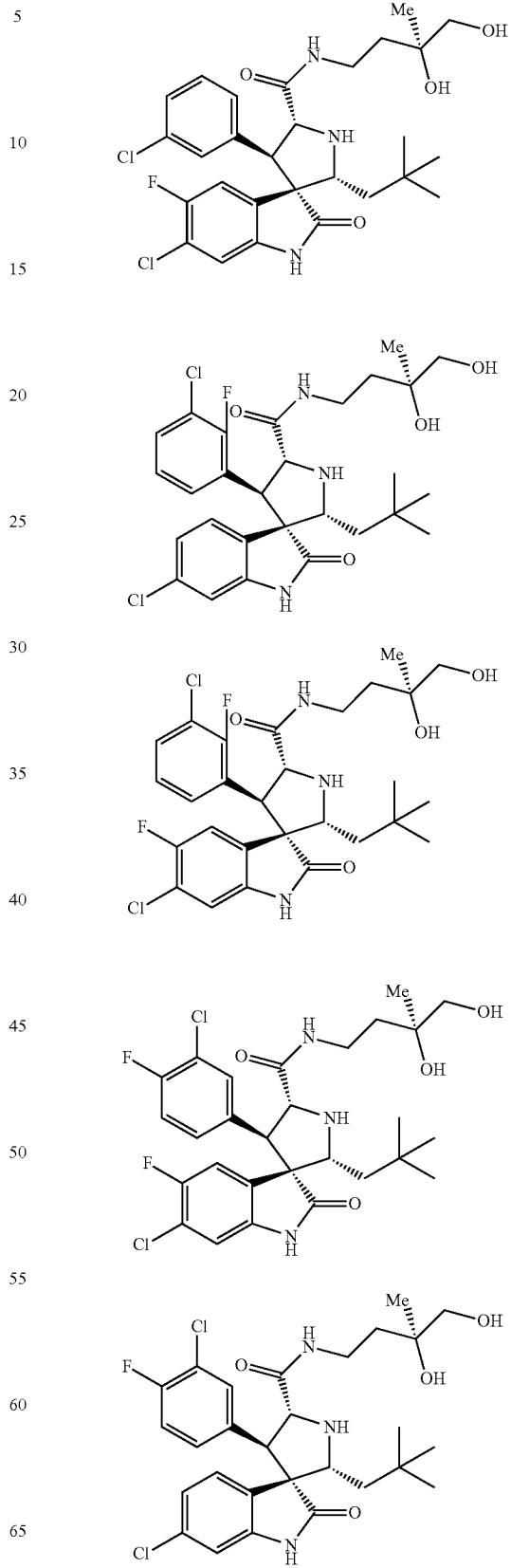

81
-continued
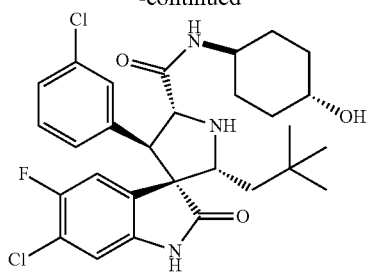
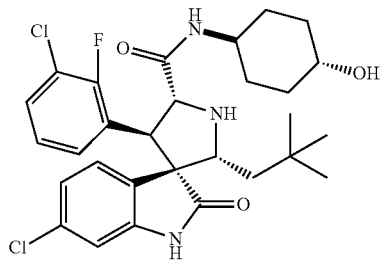
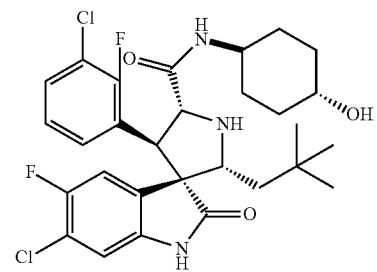
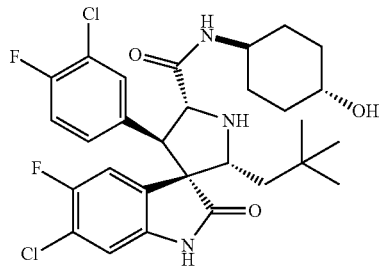
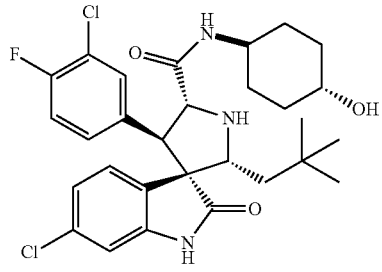
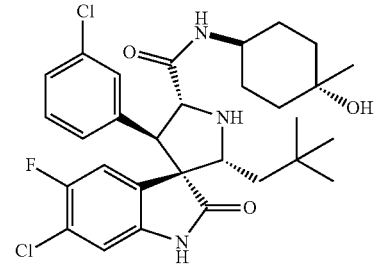
82
-continued
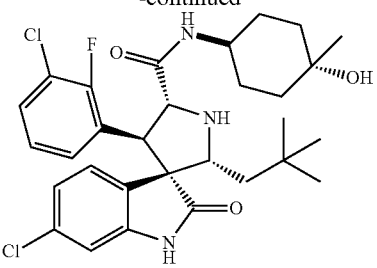
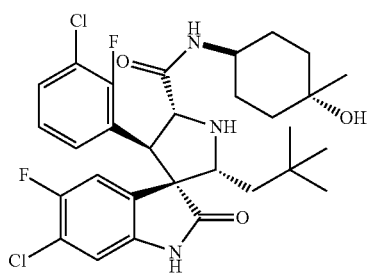
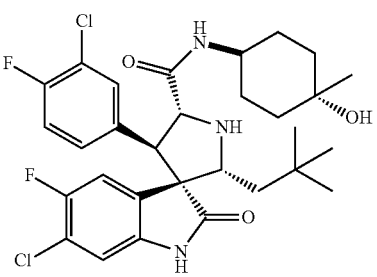
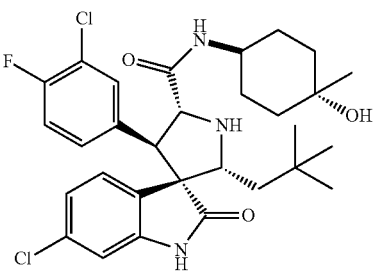
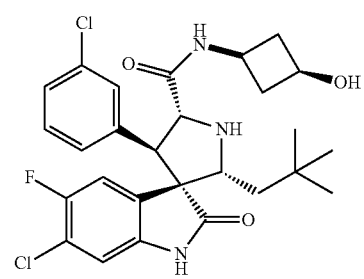
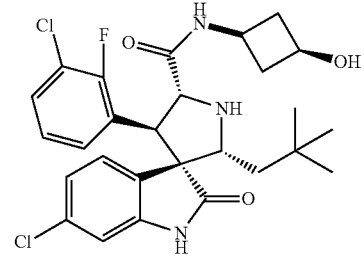

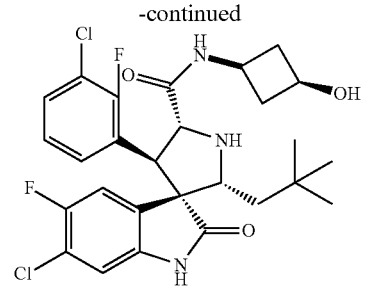
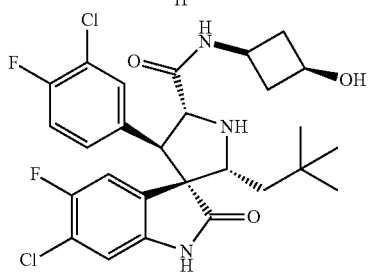
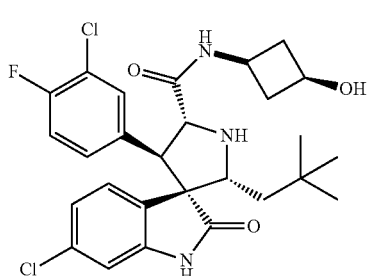
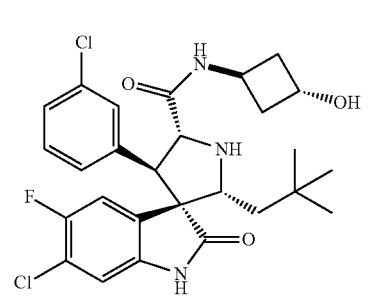
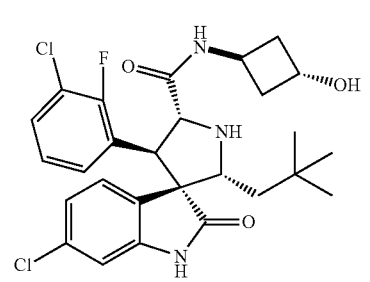
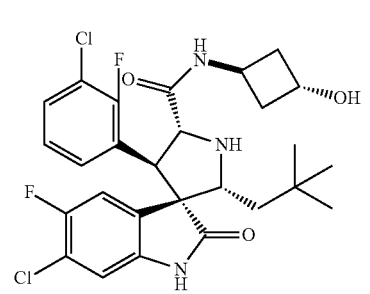
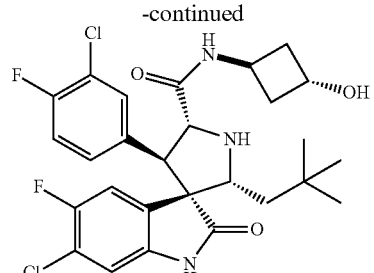
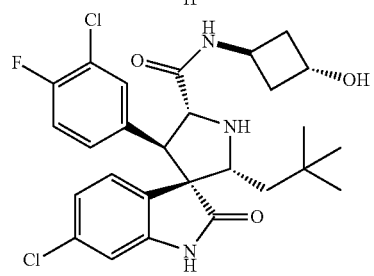
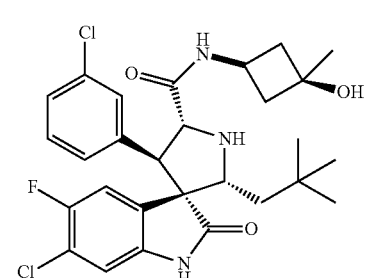
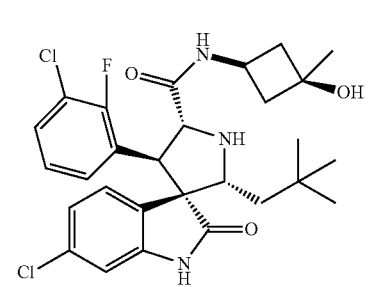
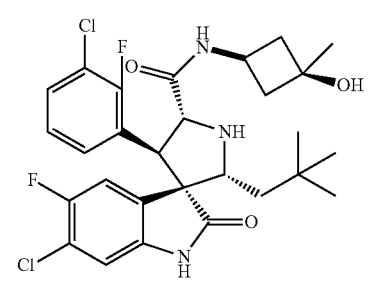

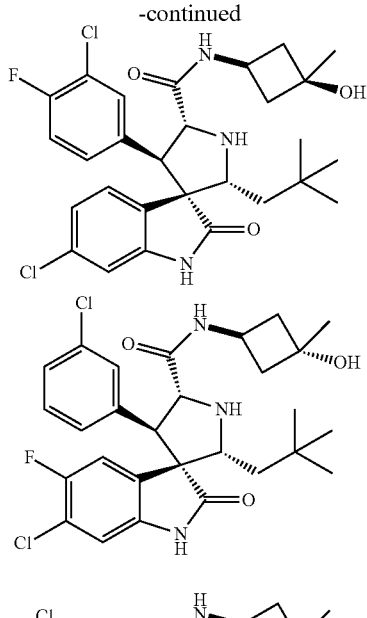
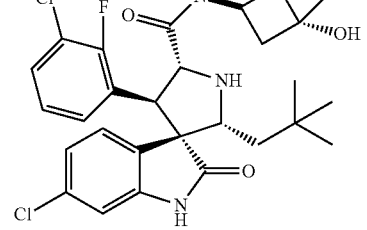
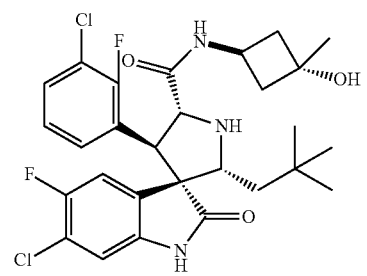
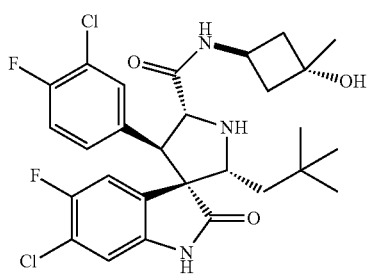
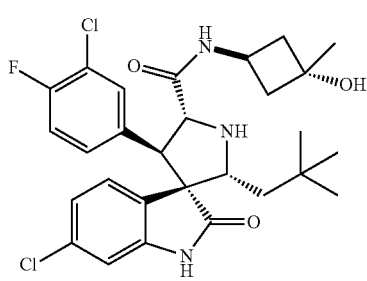
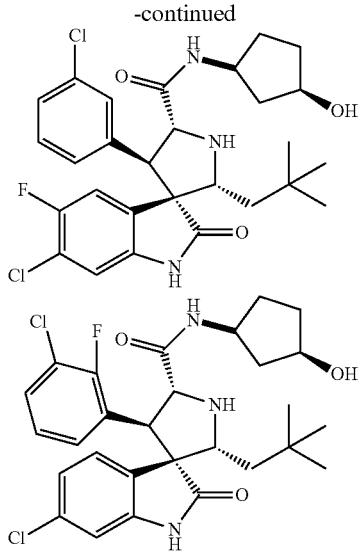
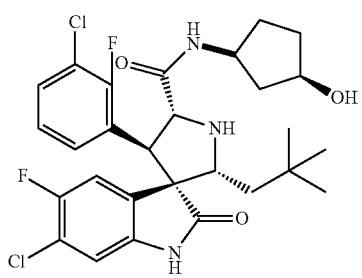
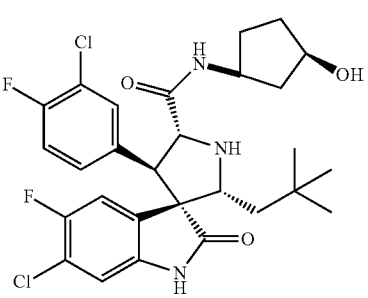
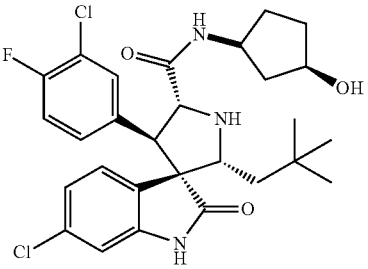
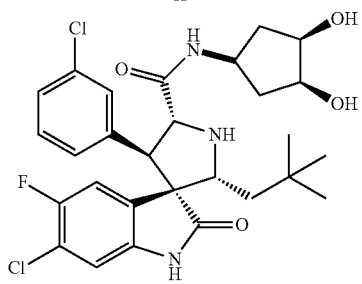

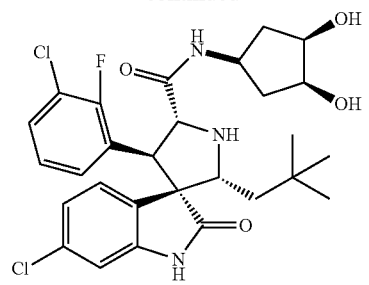
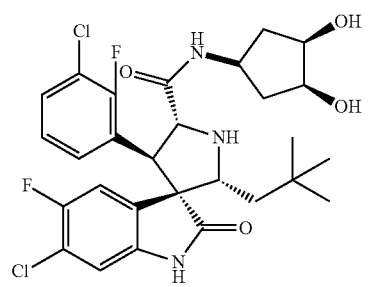
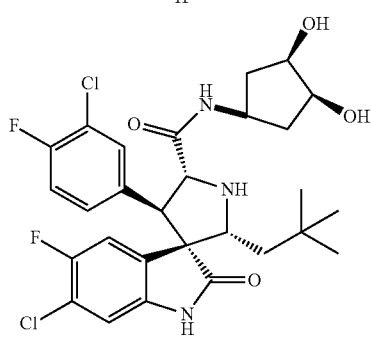
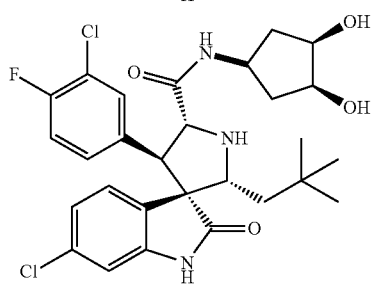
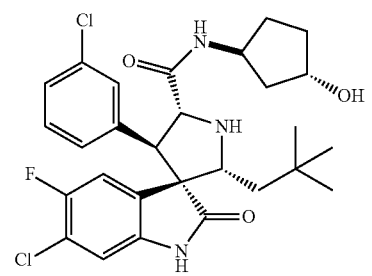
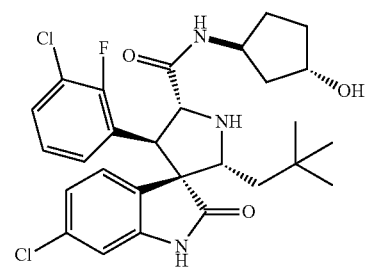
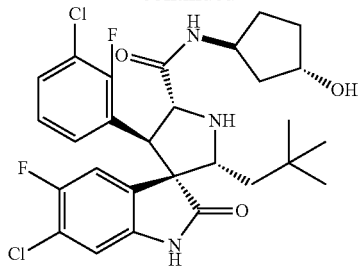
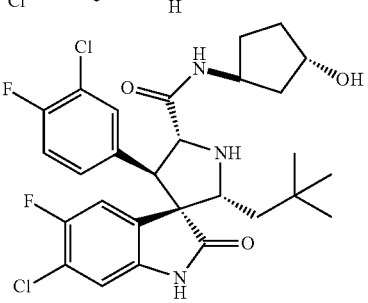
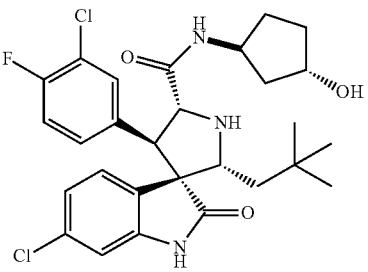
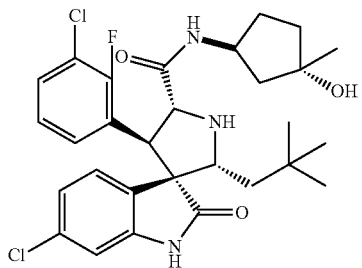
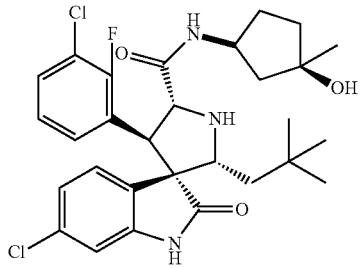
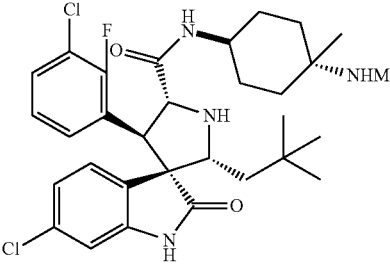

89
-continued
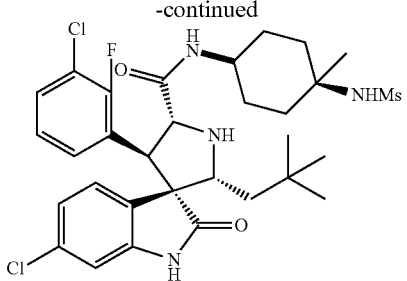
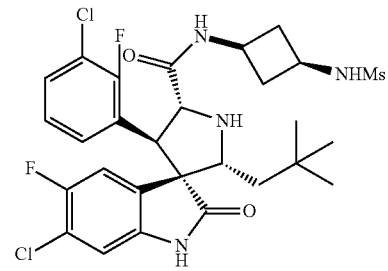
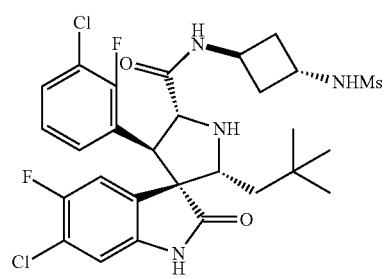
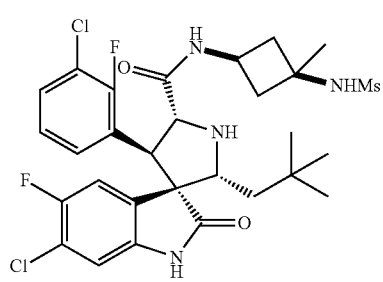
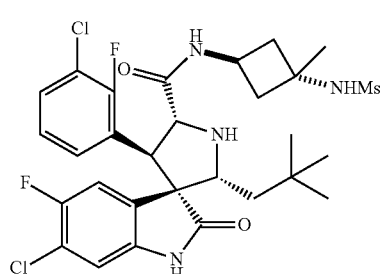
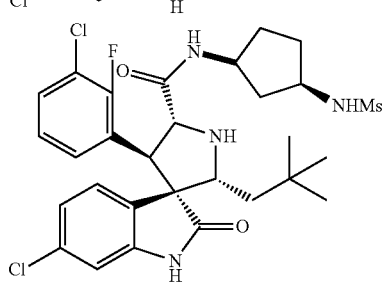
90
-continued
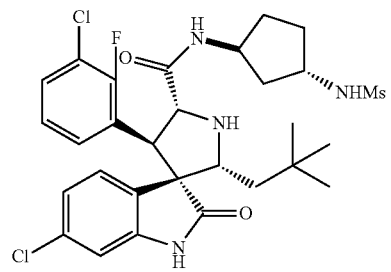
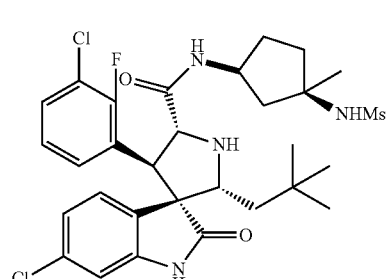
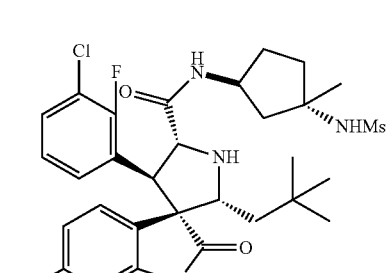
or a pharmaceutically acceptable salt, solvate, or prodrug thereof ("Ms"=—SO₂CH₃).
In certain embodiments, compounds of Formula I are provided having the following structures, which contain metabolically cleavable amino acid esters or phosphate esters as prodrugs:
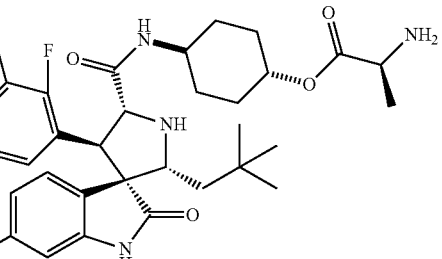
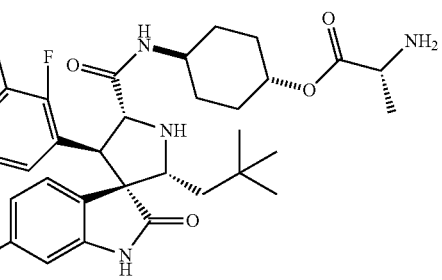

91
-continued
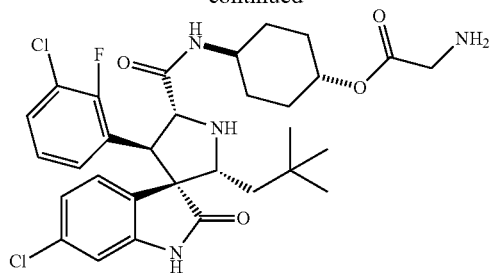
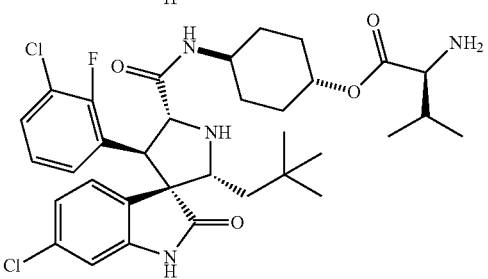
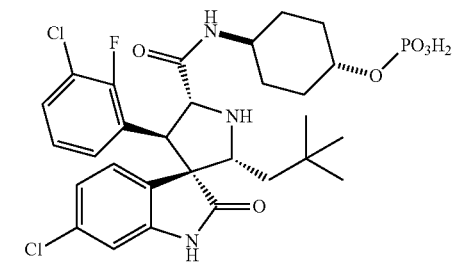
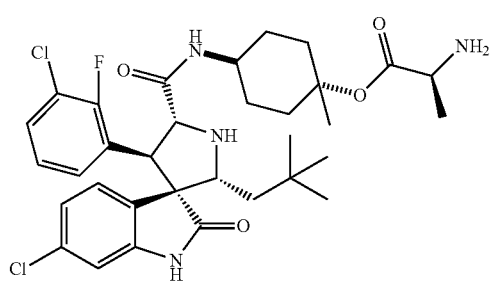
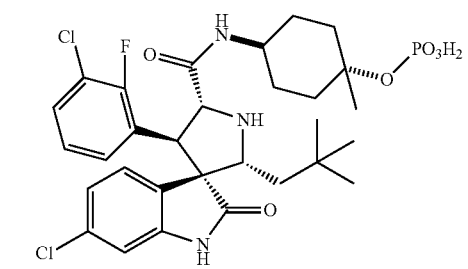
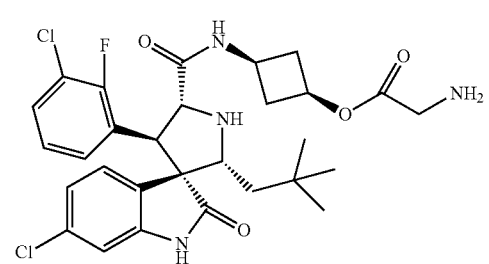
92
-continued
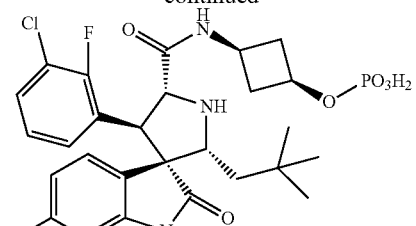
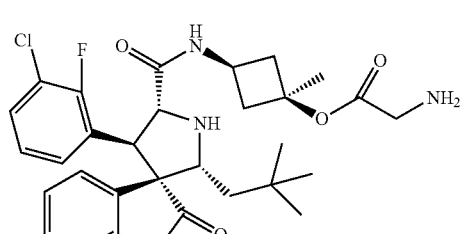
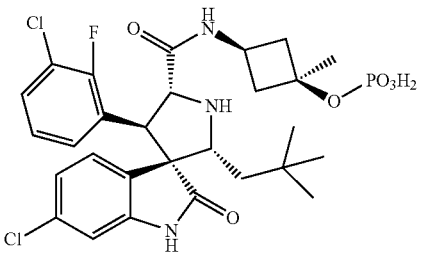
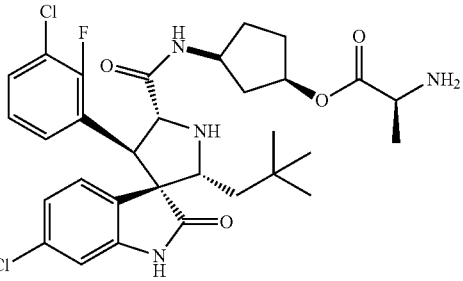
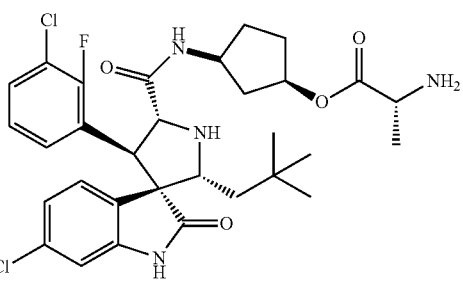
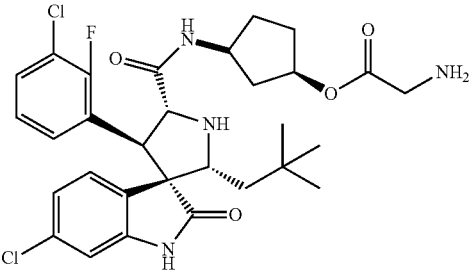

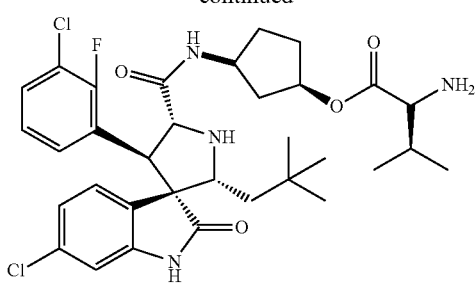
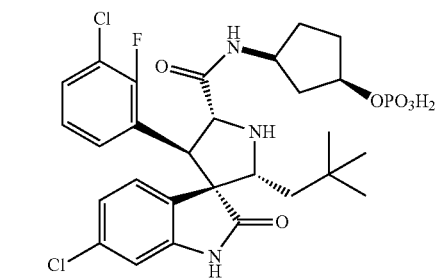
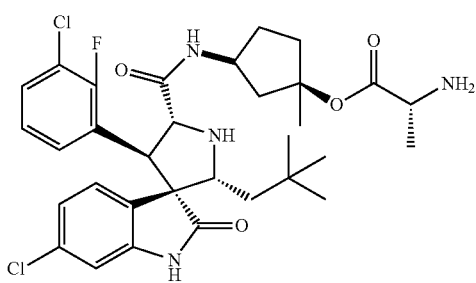
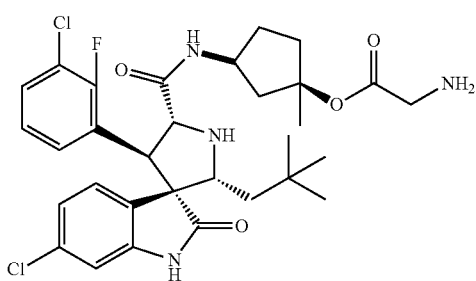
or a pharmaceutically acceptable salt or solvate thereof.
In certain embodiments, compounds having the following structure:
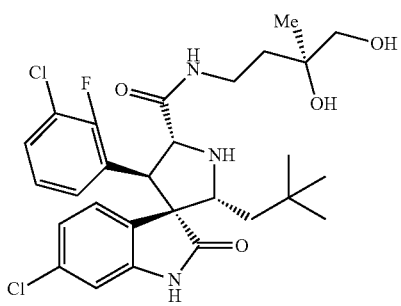
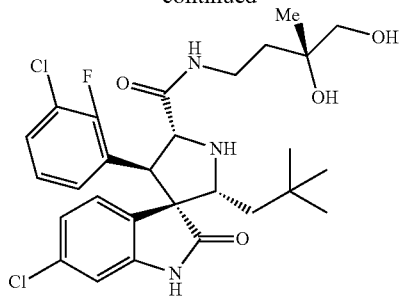
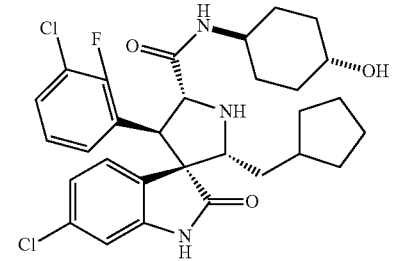
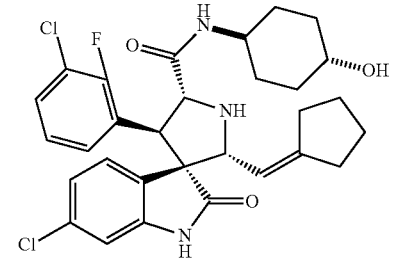
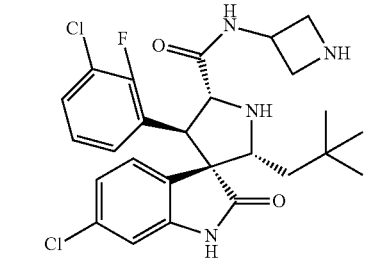
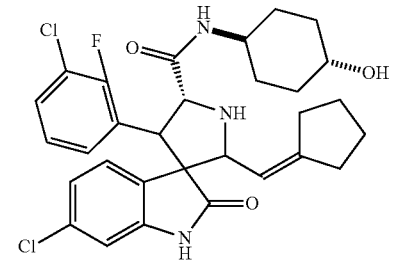
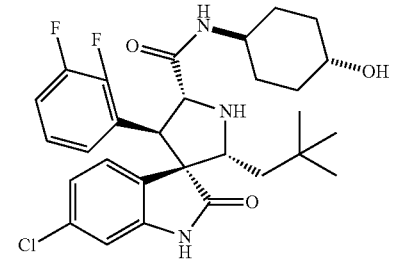

95
-continued
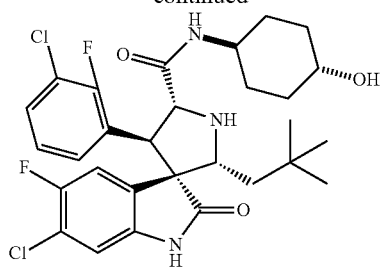
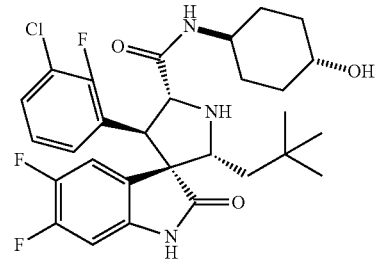
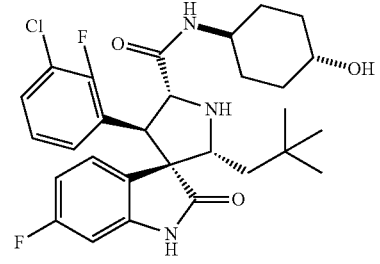
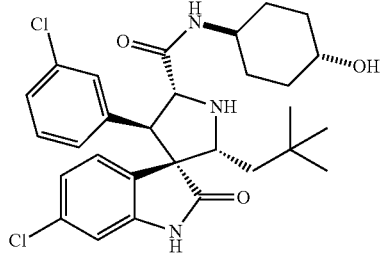
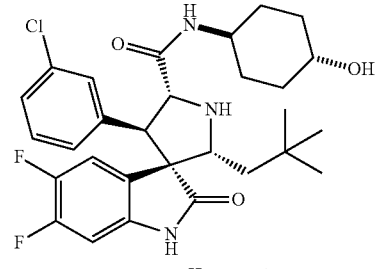
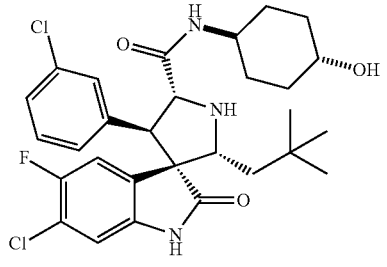
96
-continued
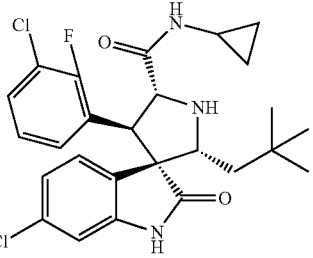
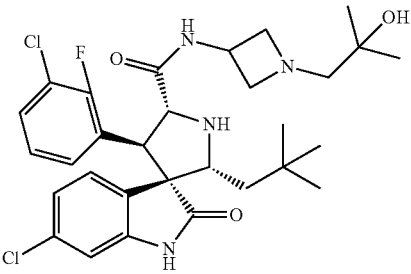
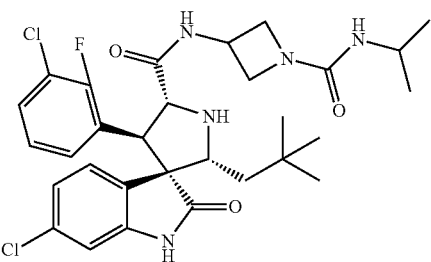
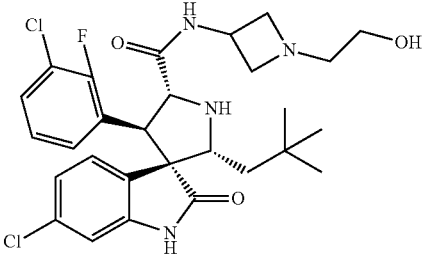
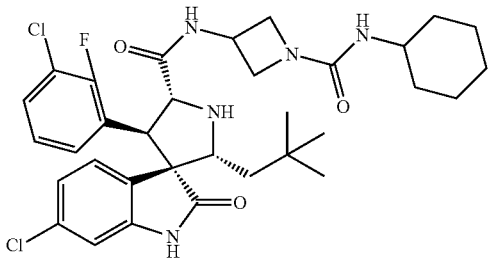
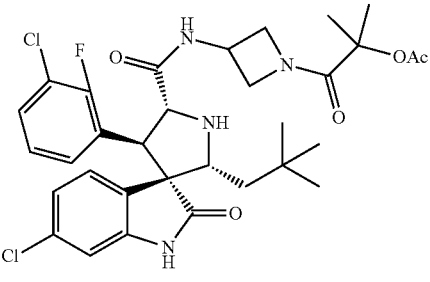

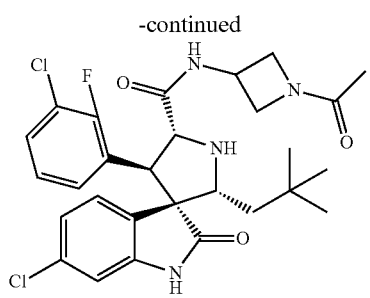
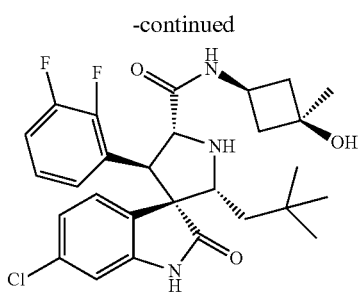
or a pharmaceutically acceptable salt or solvate thereof are provided.
In certain embodiments, compounds having the following structure:
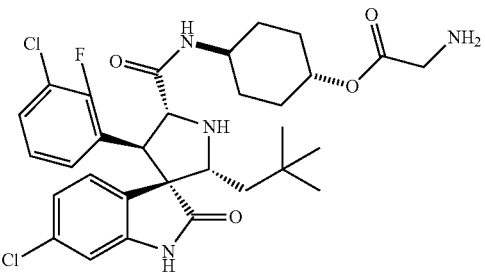

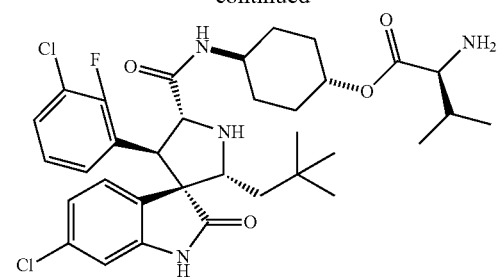
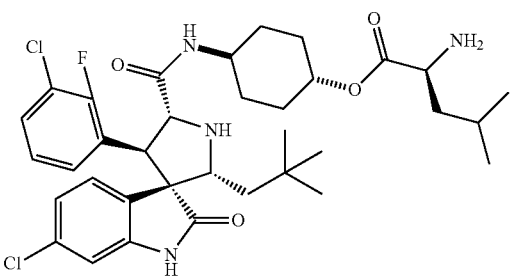
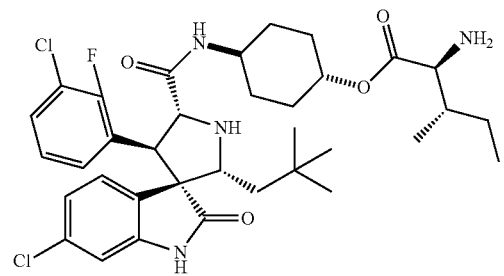
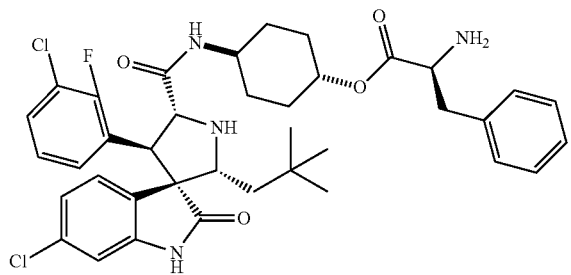
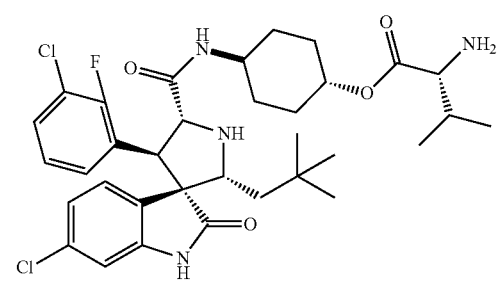
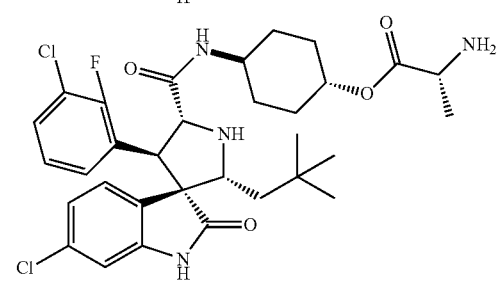
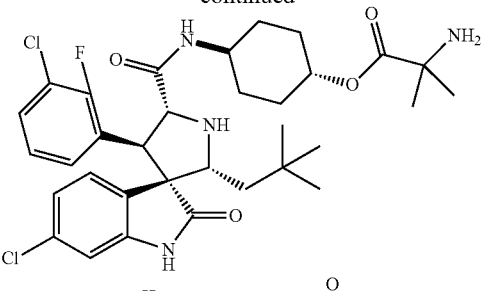
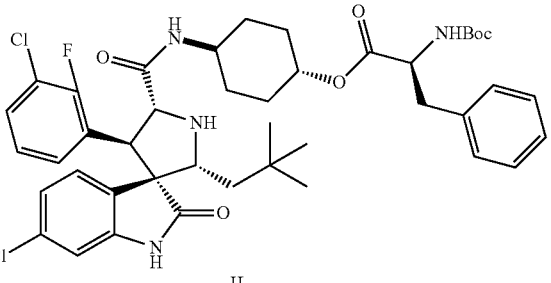
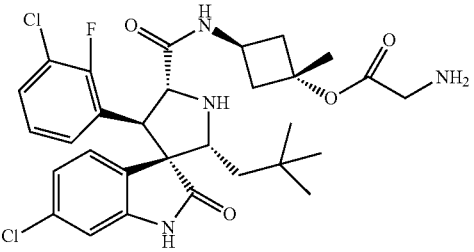
or a pharmaceutically acceptable salt or solvate thereof are provided.
In certain embodiments, compounds having the following structure:
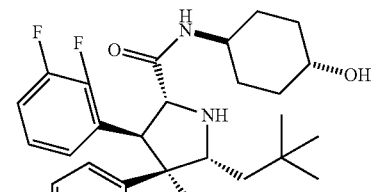
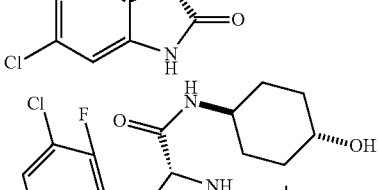
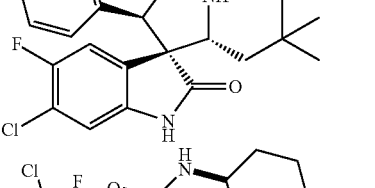
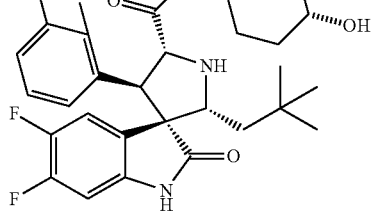

-continued
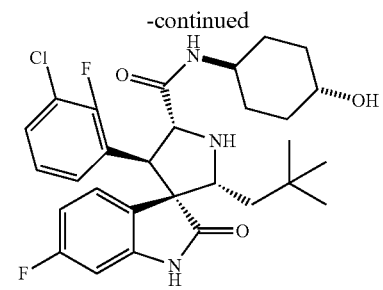
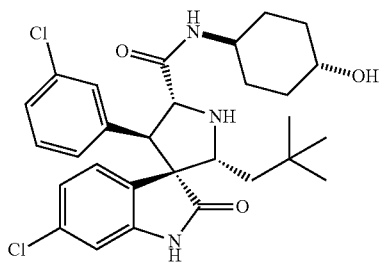
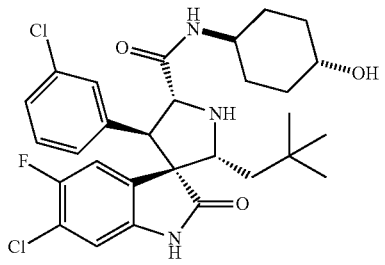
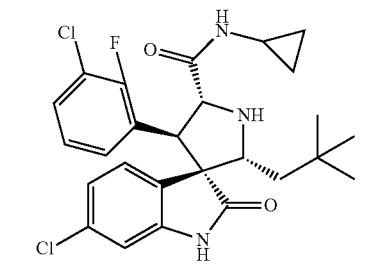
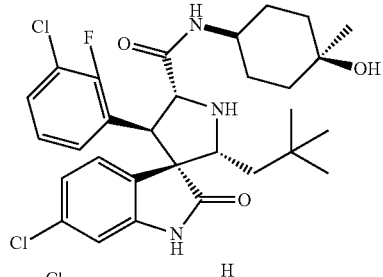
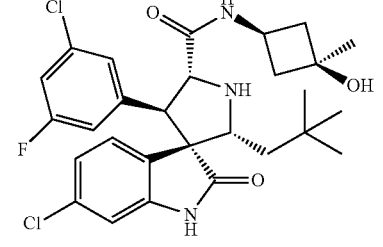
or a pharmaceutically acceptable salt or solvate thereof are provided.
In certain embodiments, compounds having the following structure:
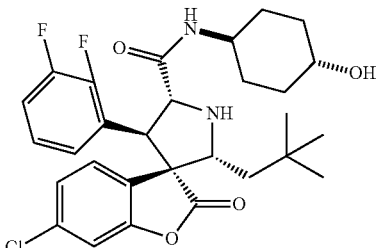
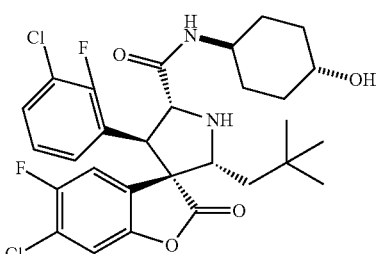
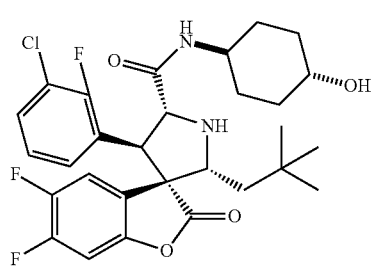
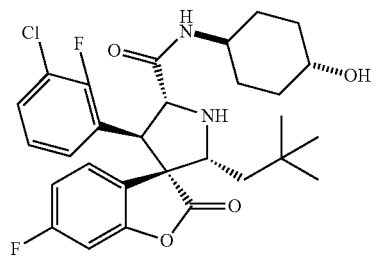
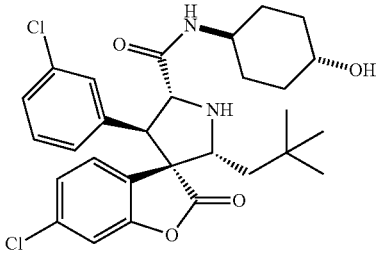
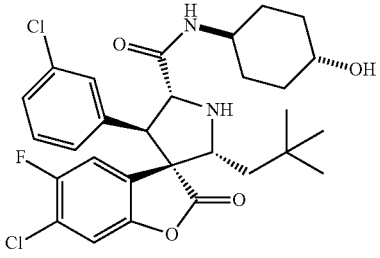

103
-continued
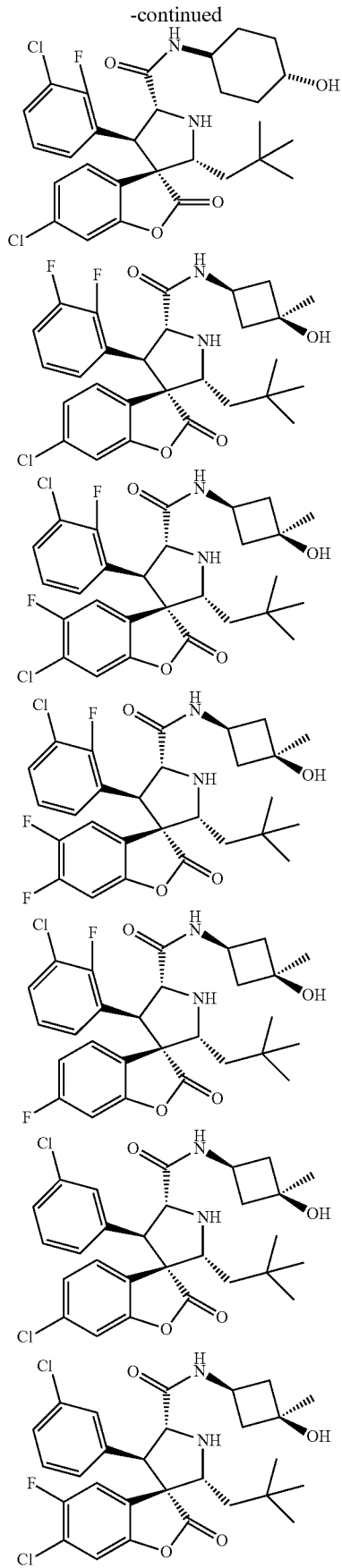
104
-continued
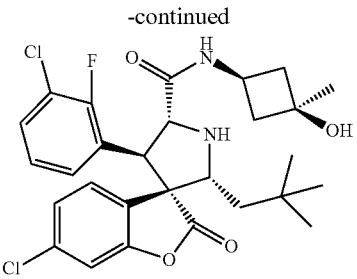
or a pharmaceutically acceptable salt or solvate thereof are provided.
In certain embodiments, compounds having the following structure:
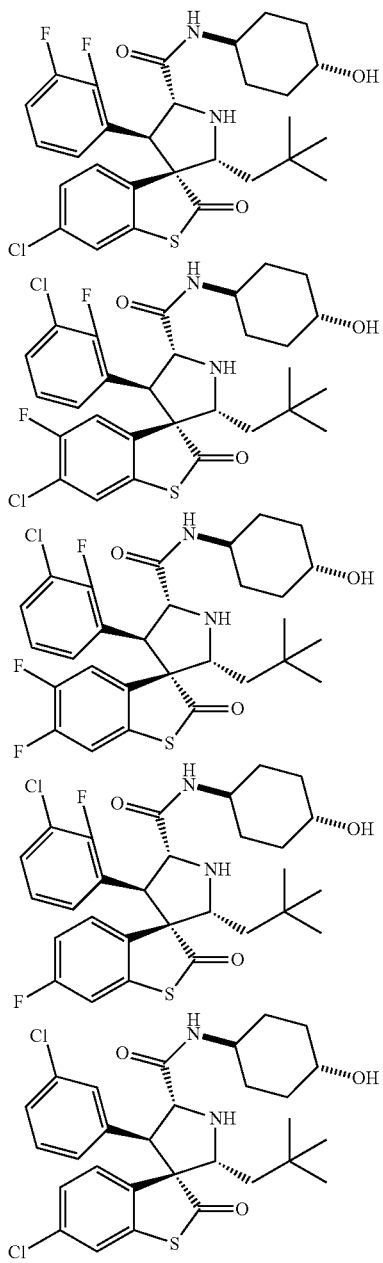

105
-continued
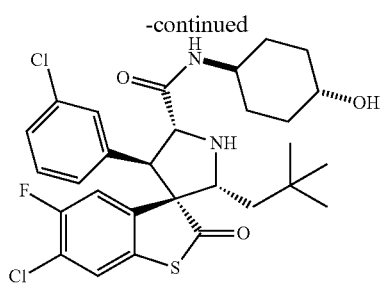
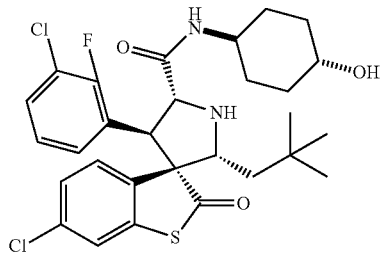
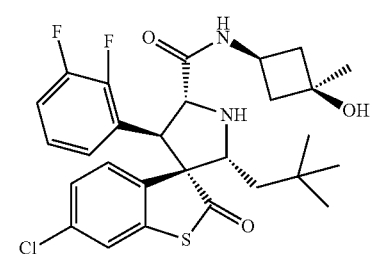
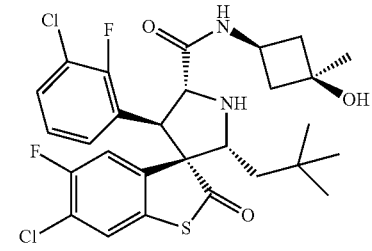
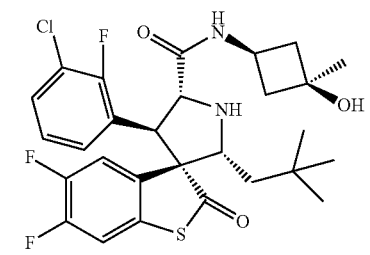
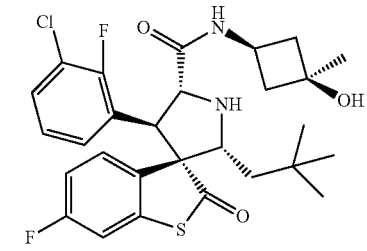
106
-continued
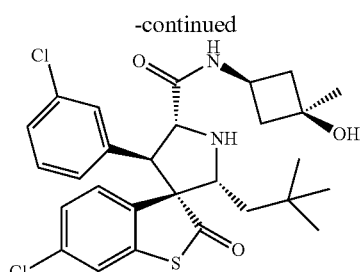
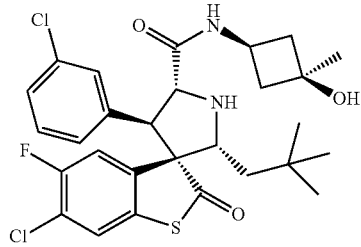
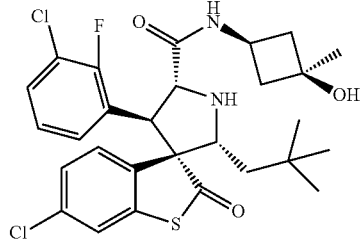
or a pharmaceutically acceptable salt or solvate thereof are provided.
In certain embodiments, compounds having the following structure:
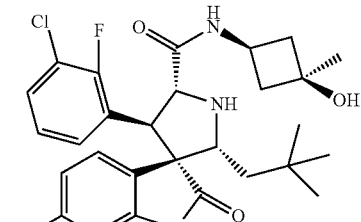
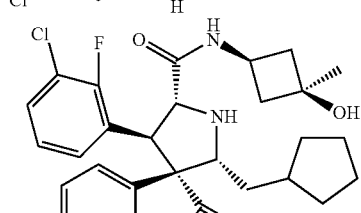
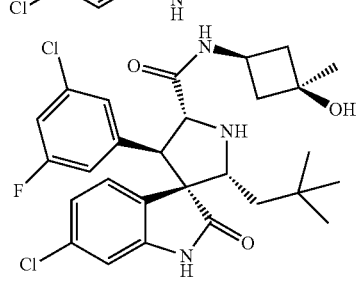

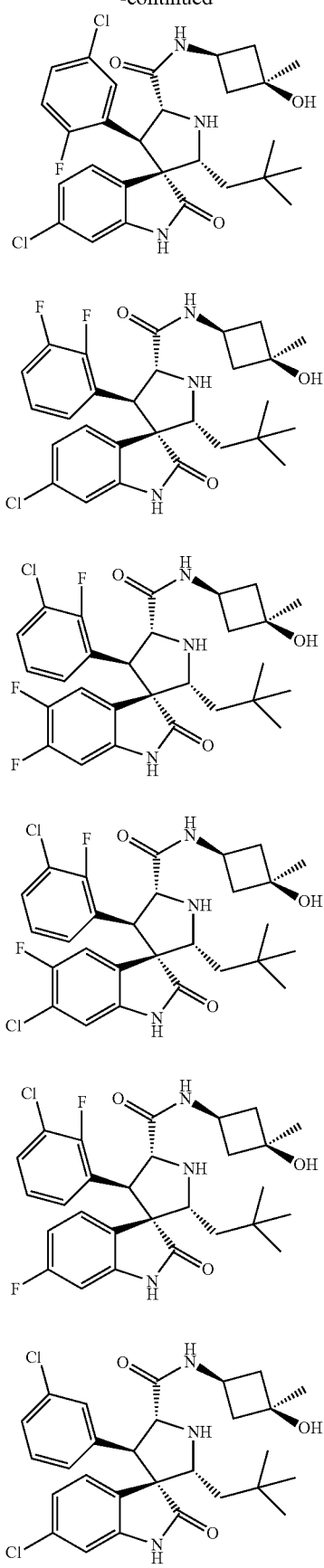
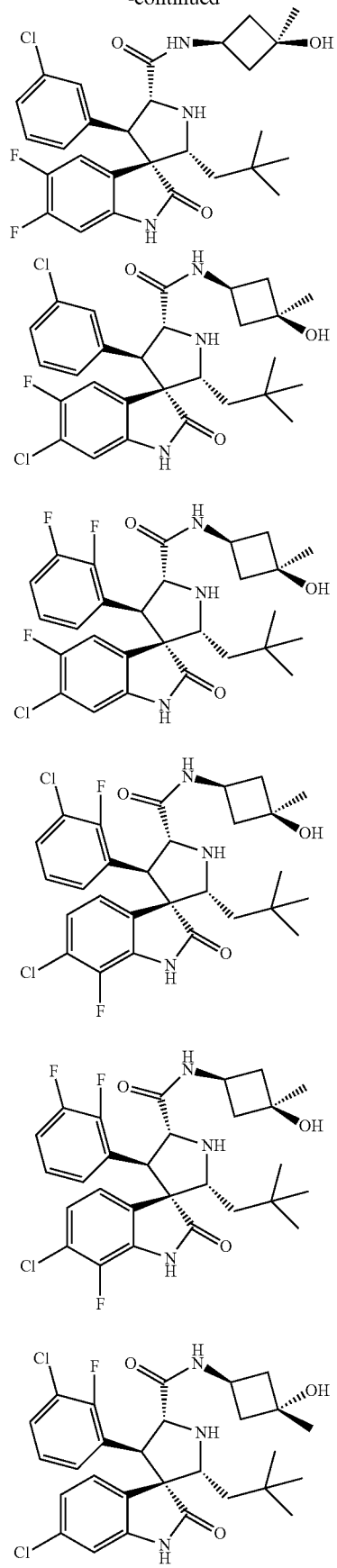

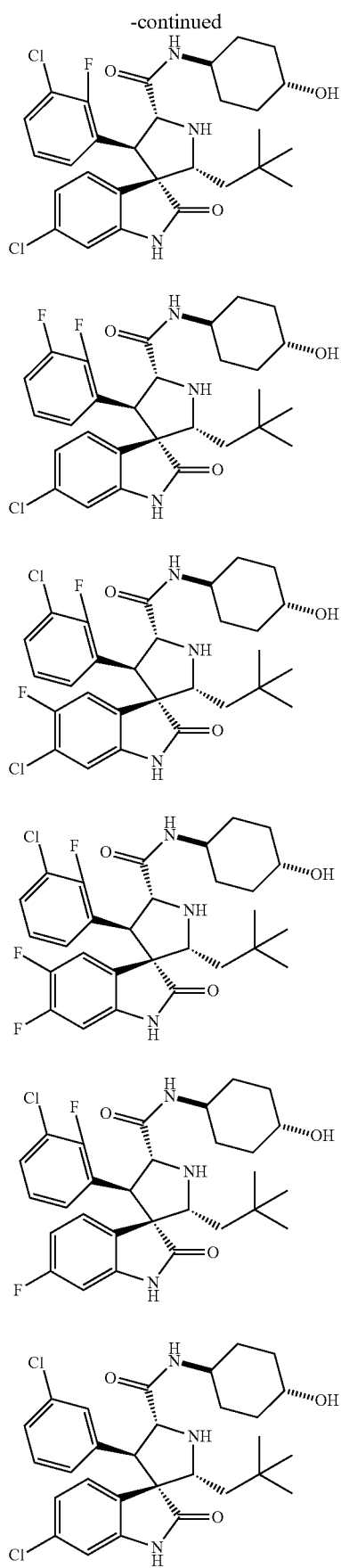
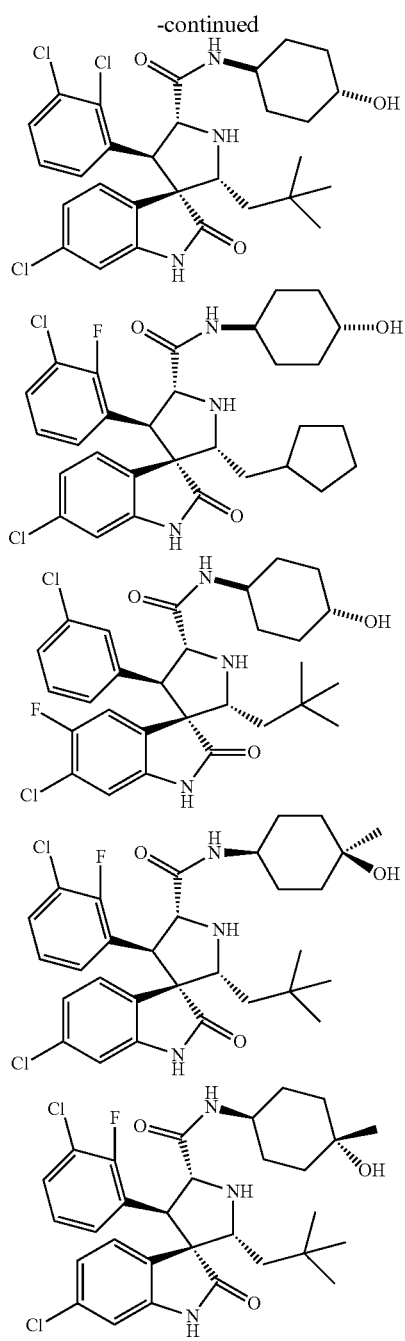
or a pharmaceutically acceptable salt or solvate thereof are provided.
In certain embodiments, compounds having the following structure:
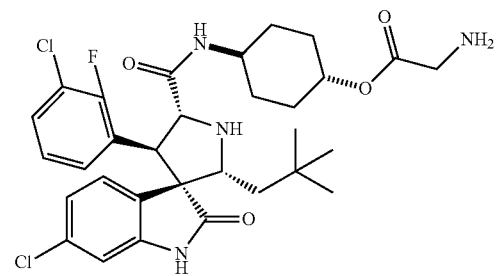

111
-continued
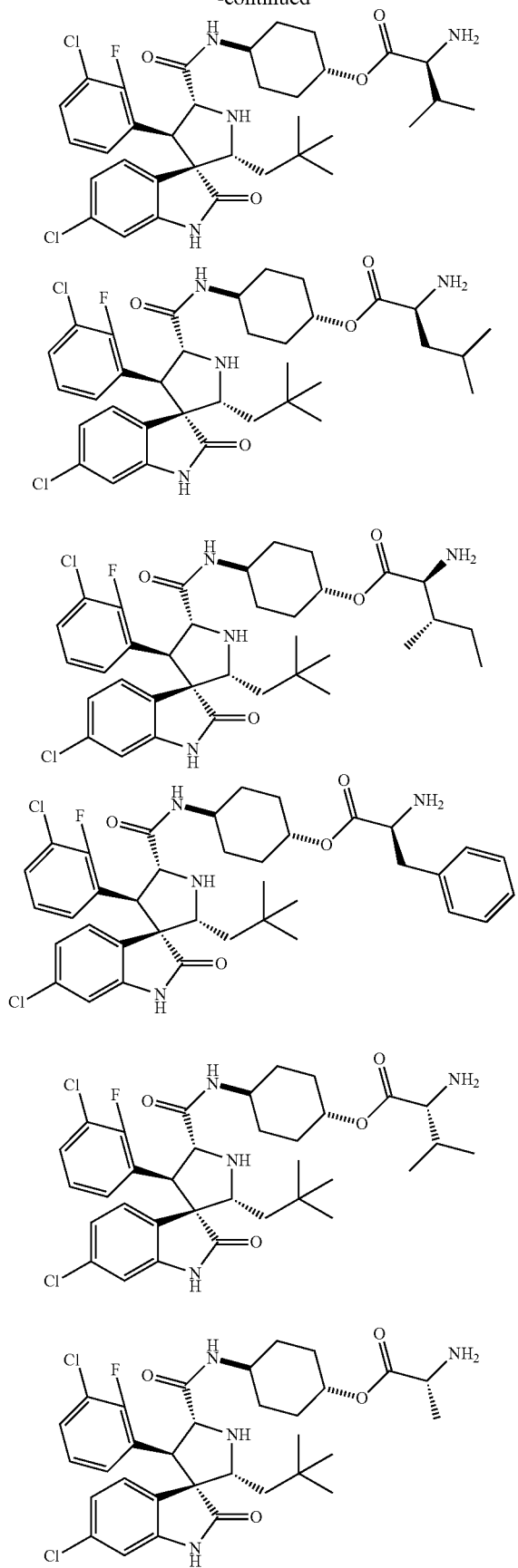
112
-continued
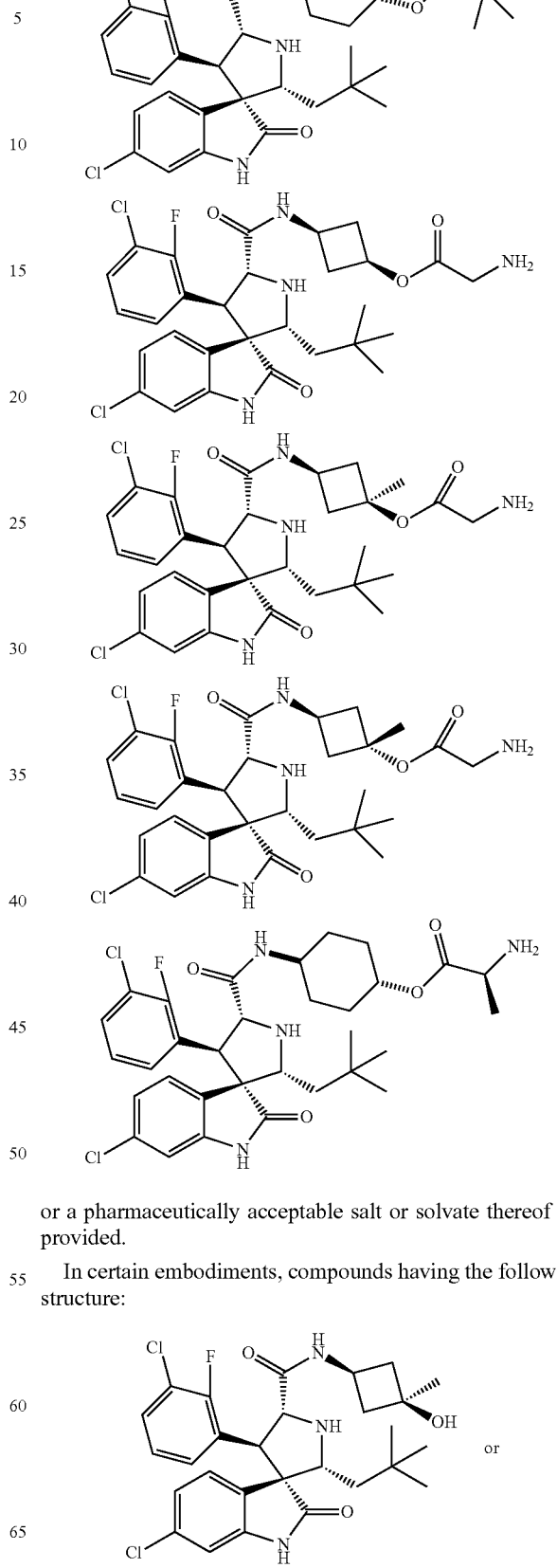
or a pharmaceutically acceptable salt or solvate thereof are provided.
In certain embodiments, compounds having the following structure:
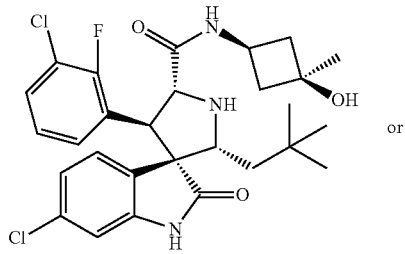
or 113
-continued

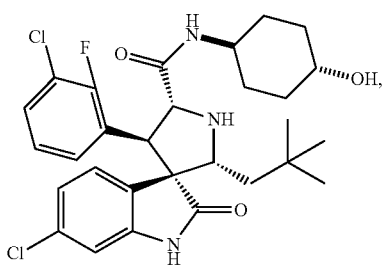

or a pharmaceutically acceptable salt or solvate thereof are provided.

The compounds and processes provided herein will be better understood in connection with the following synthetic schemes which illustrate the methods by which the compounds provided herein may be prepared. Starting materials can be obtained from commercial sources or prepared by well-established literature methods known to those of ordinary skill in the art. It will be readily apparent to one of ordinary skill in the art that the compounds defined above can be synthesized by substitution of the appropriate reagents and agents in the syntheses shown below.

Compounds of Formula Ia wherein Y is NH can be synthesized as described in Schemes 2 and 3.

Scheme 2

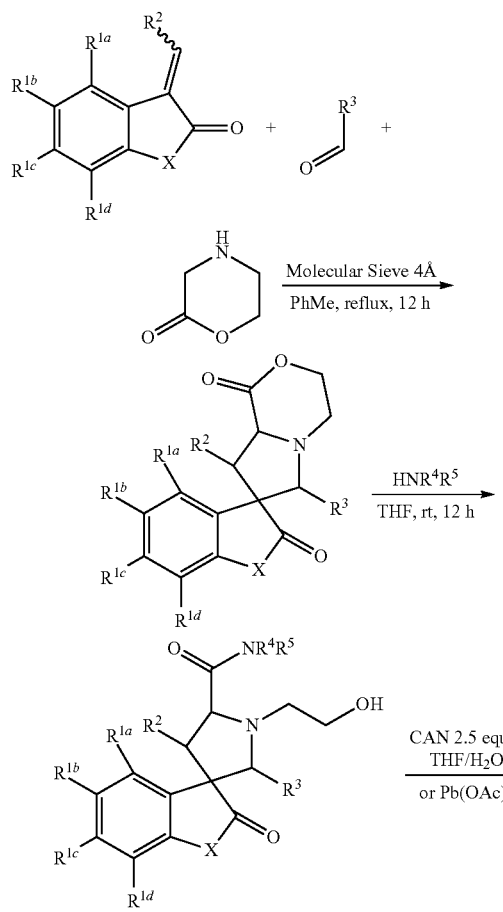

114
-continued

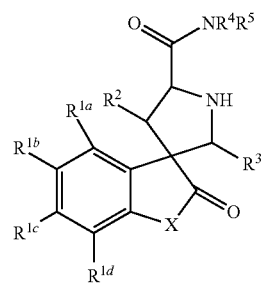

Formula Ia
(wherein Y is NH)

Scheme 3

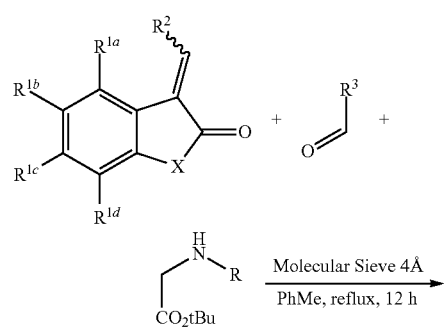

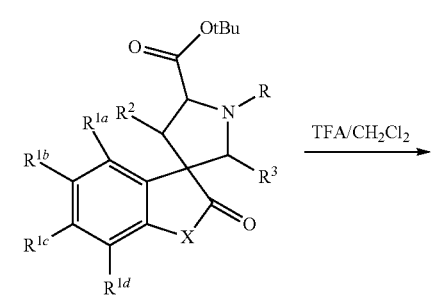

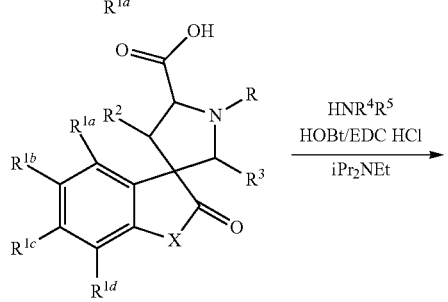

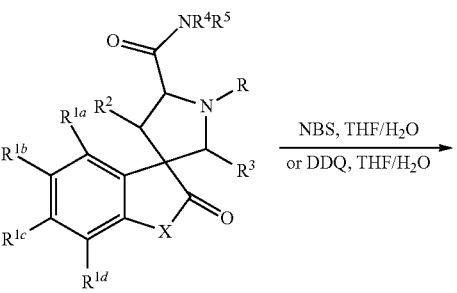

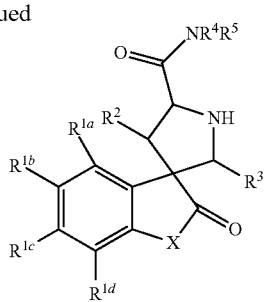

Formula Ia
(wherein Y is NH)

R = p-OMeBn——, Bn——, Me—— or other alkyl group

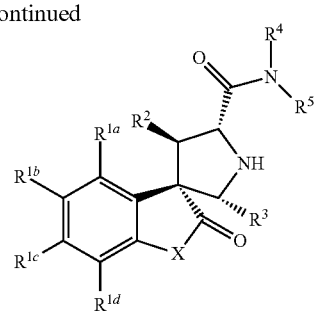

Formula II
(wherein Y = NH)

Reagents and conditions: a) CH$_2$Cl$_2$—CH$_3$CN, KF—Al$_2$O$_3$, microwave, or methanol, piperidine reflux; b 4Å molecular sieves, toluene, 70° C.; c) HNR$^4$R$^5$, r.t.; d) Pb(OAc)$_4$, CH$_2$Cl$_2$—MeOH (1:1), 0° C., or ammonium cerium(IV) nitrate (CAN), CH$_3$CN, K$_2$CO$_3$, r.t.

Compounds of Formula Ia can be separated by chiral resolution methods well know in the art, e.g., chiral column chromatography, to give compounds of Formulae II-XVII. Suitable chiral columns for use in chiral resolutions include, for example, Daicel CHIRALCEL® OD-H, Daicel CHIRAKPAK® AD-H and Regis Technologies ULMO chiral columns. Other chiral resolution methods are also possible. Compounds of Formulae II-XVII can also be prepared by asymmetric synthetic methods. For example, compounds of Formula II, wherein Y is NH, can be synthesized by using a asymmetric 1,3-dipolar cycloaddition as the key step as previously described (See U.S. Pat. Nos. 7,759,383 B2 and 7,737,174 B2, and Ding et al., *J. Am. Chem. Soc.* 127:10130-10131 (2005)) (Scheme 4).

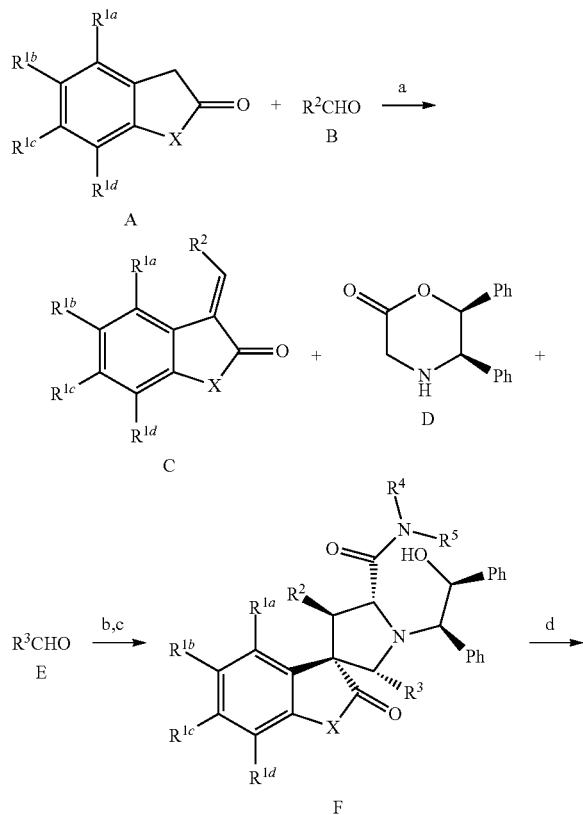

Briefly, compound A reacts with aldehyde B to give C. Compound C reacts with aldehyde E and compound D to give F (a compound of Formula I wherein R" is aralkyl). Treatment of F with Pb(OAc)$_4$ or CAN gives the compound of Formula II wherein Y is NH.

Methods

In some embodiments, compounds provided herein induce cell cycle arrest and/or apoptosis and also potentiate the induction of cell cycle arrest and/or apoptosis either alone or in response to additional apoptosis induction signals. Therefore, it is contemplated that these compounds sensitize cells to induction of cell cycle arrest and/or apoptosis, including cells that are resistant to such inducing stimuli. By inhibiting the interaction between p53 or p53-related proteins and MDM2 or MDM2-realted proteins, the compounds provided herein can be used to induce apoptosis in any disorder that can be treated, ameliorated, or prevented by the induction of apoptosis. In one embodiment, the inhibitors can be used to induce apoptosis in cells comprising functional p53 or p53-related proteins.

In another embodiment, the disclosure pertains to modulating apoptosis with compounds provided herein in combination with one or more additional apoptosis-modulating agents. Examples of apoptosis-modulating agents include, but are not limited to, Fas/CD95, TRAMP, TNF R1, DR1, DR2, DR3, DR4, DR5, DR6, FADD, RIP, TNFα, Fas ligand, TRAIL, antibodies to TRAIL-R1 or TRAIL-R2, Bcl-2, p53, BAX, BAD, Akt, CAD, PI3 kinase, PP1, and caspase proteins. Other agents involved in the initiation, decision and degradation phase of apoptosis are also included. Examples of apoptosis-modulating agents include agents, the activity, presence, or change in concentration of which, can modulate apoptosis in a subject. Apoptosis-modulating agents include those which are inducers of apoptosis, such as TNF or a TNF-related ligand, particularly a TRAMP ligand, a Fas/CD95 ligand, a TNFR-1 ligand, or TRAIL.

In some embodiments, the compositions and methods provided herein are used to treat diseased cells, tissues, organs, or pathological conditions and/or disease states in an animal (e.g., a mammalian patient including, but not limited to, humans and veterinary animals). In this regard, various diseases and pathologies are amenable to treatment or prophylaxis using the present methods and compositions. A non-limiting exemplary list of these diseases and conditions includes, but is not limited to, breast cancer, prostate cancer, lymphoma, skin cancer, pancreatic cancer, colon cancer, melanoma, malignant melanoma, ovarian cancer, brain cancer, primary brain carcinoma, head-neck cancer, glioma, glioblastoma, liver cancer, bladder cancer, non-small cell lung cancer, head or neck carcinoma, breast carcinoma, ovarian carcinoma, lung carcinoma, small-cell lung carcinoma, Wilms' tumor, cervical carcinoma, testicular carcinoma, bladder carcinoma, pancreatic carcinoma, stomach carcinoma, colon carcinoma, prostatic carcinoma, genitourinary carcinoma, thyroid carcinoma, esophageal carcinoma, myeloma, multiple myeloma, adrenal carcinoma, renal cell carcinoma, endometrial carcinoma, adrenal cortex carcinoma, malignant pancreatic insulinoma, malignant carcinoid carcinoma, choriocarcinoma, mycosis fungoides, malignant hypercalcemia, cervical hyperplasia, leukemia, acute lymphocytic leukemia, chronic lymphocytic leukemia (CLL) including B-CLL, acute myelogenous leukemia, chronic myelogenous leukemia, chronic granulocytic leukemia, acute granulocytic leukemia, hairy cell leukemia, neuroblastoma, sarcoma such as liposarcoma malignant fibrous histiocytoma, osteosarcoma, Ewing's sarcoma, leiomyosarcoma, and rhabdomyosarcoma, Kaposi's sarcoma, polycythemia vera, essential thrombocytosis, Hodgkin's disease, non-Hodgkin's lymphoma, soft-tissue sarcomas such as lipoma, and malignant Schwannoma, osteogenic sarcoma, primary macroglobulinemia, and retinoblastoma, and the like, T and B cell mediated autoimmune diseases; inflammatory diseases; infections; hyperproliferative diseases; AIDS; degenerative conditions, vascular diseases, and the like. In some embodiments, the cancer cells being treated are metastatic. In other embodiments, the cancer cells being treated are resistant to other anticancer agents.

In some embodiments, the compositions and methods provided herein are used to treat cancers that express functional or wild type p53 or p53-related proteins. In some embodiments, the compositions and methods provided herein are used to treat cancers that express elevated levels of MDM2 or MDM2-related proteins.

In some embodiments, the methods, compounds, and compositions provided herein can be used to treat a patient having a sarcoma, including, for example, liposarcoma, malignant fibrous histiocytoma, osteosarcoma, and rhabdomyosarcoma. In some embodiments, the methods, compounds, and compositions provided herein can be used to treat a patient having a soft tissue tumor, including, for example, Ewing's sarcoma, leiomyosarcoma, lipoma, and malignant Schwannomas. In some embodiments, the methods, compounds, and compositions provided herein can be used to treat a patient having lung, breast, liver, or colon cancer. In some embodiments, the methods, compounds, and compositions provided herein can be used to treat a patient having B-cell chronic lymphocytic leukemia and acute myeloid leukemia.

In some embodiments, infections suitable for treatment with the compositions and methods provided herein include, but are not limited to, infections caused by viruses, bacteria, fungi, mycoplasma, prions, and the like.

In some embodiments, methods are provided for administering an effective amount of a compound provided herein and at least one additional therapeutic agent (including, but not limited to, chemotherapeutic antineoplastics, apoptosis-modulating agents, antimicrobials, antivirals, antifungals, and anti-inflammatory agents) and/or therapeutic technique (e.g., surgical intervention, and/or radiotherapies). In a particular embodiment, the additional therapeutic agent(s) is a anticancer agent.

A number of suitable therapeutic or anticancer agents are contemplated for use in the methods provided herein. Indeed, the methods provided herein can include but are not limited to, administration of numerous therapeutic agents such as: agents that induce apoptosis; polynucleotides (e.g., antisense, ribozymes, siRNA); polypeptides (e.g., enzymes and antibodies); biological mimetics (e.g., gossypol or BH3 mimetics); agents that bind (e.g., oligomerize or complex) with a Bcl-2 family protein such as Bax; alkaloids; alkylating agents; antitumor antibiotics; antimetabolites; hormones; platinum compounds; monoclonal or polyclonal antibodies (e.g., antibodies conjugated with anticancer drugs, toxins, defensins), toxins; radionuclides; biological response modifiers (e.g., interferons (e.g., IFN-α) and interleukins (e.g., IL-2)); adoptive immunotherapy agents; hematopoietic growth factors; agents that induce tumor cell differentiation (e.g., all-trans-retinoic acid); gene therapy reagents (e.g., antisense therapy reagents and nucleotides); tumor vaccines; angiogenesis inhibitors; proteosome inhibitors: NF-κB modulators; anti-CDK compounds; HDAC inhibitors; and the like. Numerous other examples of therapeutic agents such as chemotherapeutic compounds and anticancer therapies suitable for co-administration with the disclosed compounds are known to those skilled in the art.

In certain embodiments, anticancer agents comprise agents that induce or stimulate apoptosis. Agents that induce or stimulate apoptosis include, for example, agents that interact with or modify DNA, such as by intercalating, cross-linking, alkylating, or otherwise damaging or chemically modifying DNA. Agents that induce apoptosis include, but are not limited to, radiation (e.g., X-rays, gamma rays, UV); tumor necrosis factor (TNF)-related factors (e.g., TNF family receptor proteins, TNF family ligands, TRAIL, antibodies to TRAIL-R1 or TRAIL-R2); kinase inhibitors (e.g., epidermal growth factor receptor (EGFR) kinase inhibitor. Additional anticancer agents include: vascular growth factor receptor (VGFR) kinase inhibitor, fibroblast growth factor receptor (FGFR) kinase inhibitor, platelet-derived growth factor receptor (PDGFR) kinase inhibitor, and Bcr-Abl kinase inhibitors (such as GLEEVEC)); antisense molecules; antibodies (e.g., HERCEPTIN, RITUXAN, ZEVALIN, and AVASTIN); anti-estrogens (e.g., raloxifene and tamoxifen); anti-androgens (e.g., flutamide, bicalutamide, finasteride, aminoglutethamide, ketoconazole, and corticosteroids); cyclooxygenase 2 (COX-2) inhibitors (e.g., celecoxib, meloxicam, NS-398, and non-steroidal anti-inflammatory drugs (NSAIDs)); anti-inflammatory drugs (e.g., butazolidin, DECADRON, DELTASONE, dexamethasone, dexamethasone intensol, DEXONE, HEXADROL, hydroxychloroquine, METICORTEN, ORADEXON, ORASONE, oxyphenbutazone, PEDIAPRED, phenylbutazone, PLAQUENIL, prednisolone, prednisone, PRELONE, and TANDEARIL); and cancer chemotherapeutic drugs (e.g., irinotecan (CAMPTOSAR), CPT-11, fludarabine (FLUDARA), dacarbazine (DTIC), dexamethasone, mitoxantrone, MYLOTARG, VP-16, cisplatin, carboplatin, oxaliplatin, 5-FU, doxorubicin, gemcitabine, bortezomib, gefitinib, bevacizumab, TAXOTERE or TAXOL); cellular signaling molecules; ceramides and cytokines; staurosporine, and the like.

In still other embodiments, the compositions and methods provided herein include one or more compounds provided herein and at least one anti-hyperproliferative or antineoplastic agent selected from alkylating agents, antimetabolites, and natural products (e.g., herbs and other plant and/or animal derived compounds).

Alkylating agents suitable for use in the present compositions and methods include, but are not limited to: 1) nitrogen mustards (e.g., mechlorethamine, cyclophosphamide, ifosfamide, melphalan (L-sarcolysin); and chlorambucil); 2) ethylenimines and methylmelamines (e.g., hexamethylmelamine and thiotepa); 3) alkyl sulfonates (e.g., busulfan); 4)

nitrosoureas (e.g., carmustine (BCNU); lomustine (CCNU); semustine (methyl-CCNU); and streptozocin (streptozotocin)); and 5) triazenes (e.g., dacarbazine (DTIC; dimethyl-triazenoimid-azolecarboxamide).

In some embodiments, antimetabolites suitable for use in the present compositions and methods include, but are not limited to: 1) folic acid analogs (e.g., methotrexate (amethopterin)); 2) pyrimidine analogs (e.g., fluorouracil (5-fluorouracil; 5-FU), floxuridine (fluorode-oxyuridine; FudR), and cytarabine (cytosine arabinoside)); and 3) purine analogs (e.g., mercaptopurine (6-mercaptopurine; 6-MP), thioguanine (6-thioguanine; TG), and pentostatin (2'-deoxycoformycin)).

In still further embodiments, chemotherapeutic agents suitable for use in the compositions and methods of the present disclosure include, but are not limited to: 1) vinca alkaloids (e.g., vinblastine (VLB), vincristine); 2) epipodophyllotoxins (e.g., etoposide and teniposide); 3) antibiotics (e.g., dactinomycin (actinomycin D), daunorubicin (daunomycin; rubidomycin), doxorubicin, bleomycin, plicamycin (mithramycin), and mitomycin (mitomycin C)); 4) enzymes (e.g., L-asparaginase); 5) biological response modifiers (e.g., interferon-alfa); 6) platinum coordinating complexes (e.g., cisplatin (cis-DDP) and carboplatin); 7) anthracenediones (e.g., mitoxantrone); 8) substituted ureas (e.g., hydroxyurea); 9) methylhydrazine derivatives (e.g., procarbazine (N-methylhydrazine; MIH)); 10) adrenocortical suppressants (e.g., mitotane (o,p'-DDD) and aminoglutethimide); 11) adreno-corticosteroids (e.g., prednisone); 12) progestins (e.g., hydroxyprogesterone caproate, medroxyprogesterone acetate, and megestrol acetate); 13) estrogens (e.g., diethylstilbestrol and ethinyl estradiol); 14) antiestrogens (e.g., tamoxifen); 15) androgens (e.g., testosterone propionate and fluoxymesterone); 16) antiandrogens (e.g., flutamide): and 17) gonadotropin-releasing hormone analogs (e.g., leuprolide).

Any oncolytic agent that is routinely used in a cancer therapy context finds use in the compositions and methods of the present disclosure. For example, the U.S. Food and Drug Administration maintains a formulary of oncolytic agents approved for use in the United States. International counterpart agencies to the U.S.F.D.A. maintain similar formularies. Table 1 provides a list of exemplary antineoplastic agents approved for use in the U.S. Those skilled in the art will appreciate that the "product labels" required on all U.S. approved chemotherapeutics describe approved indications, dosing information, toxicity data, and the like, for the exemplary agents.

TABLE 1

| | |
|---|---|
| Aldesleukin (des-alanyl-1, serine-125 human interleukin-2) | Proleukin |
| Alemtuzumab (IgG1κ anti CD52 antibody) | Campath |
| Alitretinoin (9-cis-retinoic acid) | Panretin |
| Allopurinol (1,5-dihydro-4H-pyrazolo[3,4-d]pyrimidin-4-one monosodium salt) | Zyloprim |
| Altretamine (N,N,N',N',N'',N'',-hexamethyl-1,3,5-triazine-2,4,6-triamine) | Hexalen |
| Amifostine (ethanethiol, 2-[(3-aminopropyl)amino]-, dihydrogen phosphate (ester)) | Ethyol |
| Anastrozole (1,3-Benzenediacetonitrile, a,a,a',a'-tetramethyl-5-(1H-1,2,4-triazol-1-ylmethyl)) | Arimidex |
| Arsenic trioxide | Trisenox |
| Asparaginase (L-asparagine amidohydrolase, type EC-2) | Elspar |
| BCG Live (lyophilized preparation of an attenuated strain of *Mycobacterium bovis* (*Bacillus Calmette-Gukin* [BCG], substrain Montreal) | TICE BCG |
| bexarotene capsules (4-[1-(5,6,7,8-tetrahydro-3,5,5,8,8-pentamethyl-2-napthalenyl) ethenyl] benzoic acid) | Targretin |
| bexarotene gel | Targretin |
| Bleomycin (cytotoxic glycopeptide antibiotics produced by *Streptomyces verticillus*; bleomycin $A_2$ and bleomycin $B_2$) | Blenoxane |
| Capecitabine (5'-deoxy-5-fluoro-N-[(pentyloxy)carbonyl]-cytidine) | Xeloda |
| Carboplatin (platinum, diammine [1,1-cyclobutanedicarboxylato(2-)-0, 0']-,(SP-4-2)) | Paraplatin |
| Carmustine (1,3-bis(2-chloroethyl)-1-nitrosourea) | BCNU, BiCNU |
| Carmustine with Polifeprosan 20 Implant | Gliadel Wafer |
| Celecoxib (as 4-[5-(4-methylphenyl)-3-(trifluoromethyl)-1H-pyrazol-1-yl] benzenesulfonamide) | Celebrex |
| Chlorambucil (4-[bis(2chlorethyl)amino]benzenebutanoic acid) | Leukeran |
| Cisplatin ($PtCl_2H_6N_2$) | Platinol |
| Cladribine (2-chloro-2'-deoxy-b-D-adenosine) | Leustatin, 2-CdA |

TABLE 1-continued

| | |
|---|---|
| Cyclophosphamide (2-[bis(2-chloroethyl)amino]tetrahydro-2H-13,2-oxazaphosphorine 2-oxide monohydrate) | Cytoxan, Neosar |
| Cytarabine (1-b-D-Arabinofuranosylcytosine, $C_9H_{13}N_3O_5$) | Cytosar-U |
| cytarabine liposomal | DepoCyt |
| Dacarbazine (5-(3,3-dimethyl-1-triazeno)-imidazole-4-carboxamide (DTIC)) | DTIC-Dome |
| Dactinomycin, actinomycin D (actinomycin produced by *Streptomyces parvullus*, $C_{62}H_{86}N_{12}O_{16}$) | Cosmegen |
| Darbepoetin alfa (recombinant peptide) | Aranesp |
| daunorubicin liposomal ((8S-cis)-8-acetyl-10-[(3-amino-2,3,6-trideoxy-á-L-lyxo-hexopyranosyl)oxy]-7,8,9,10-tetrahydro-6,8,11-trihydroxy-1-methoxy-5,12-naphthacenedione hydrochloride) | DanuoXome |
| Daunorubicin HCl, daunomycin ((1S,3S)-3-Acetyl-1,2,3,4,6,11-hexahydro-3,5,12-trihydroxy-10-methoxy-6,11-dioxo-1-naphthacenyl 3-amino-2,3,6-trideoxy-(alpha)-L-lyxo-hexopyranoside hydrochloride) | Cerubidine |
| Denileukin diftitox (recombinant peptide) | Ontak |
| Dexrazoxane ((S)-4,4'-(1-methyl-1,2-ethanediyl)bis-2,6-piperazinedione) | Zinecard |
| Docetaxel ((2R,3S)-N-carboxy-3-phenylisoserine, N-tert-butyl ester, 13-ester with 5b-20-epoxy-12a,4,7b,10b,13a-hexahydroxytax-11-en-9-one 4-acetate 2-benzoate, trihydrate) | Taxotere |
| Doxorubicin HCl (8S,10S)-10-[(3-amino-2,3,6-trideoxy-a-L-lyxo-hexopyranosyl)oxy]-8-glycolyl-7,8,9,10-tetrahydro-6,8,11-trihydroxy-1-methoxy-5,12-naphthacenedione hydrochloride) | Adriamycin, Rubex |
| doxorubicin | Adriamycin PFS Intravenous injection |
| doxorubicin liposomal | Doxil |
| dromostanolone propionate (17b-Hydroxy-2a-methyl-5a-androstan-3-one propionate) | Dromostanolone |
| dromostanolone propionate | Masterone injection |
| Elliott's B Solution | Elliott's B Solution |
| Epirubicin ((8S-cis)-10-[(3-amino-2,3,6-trideoxy-a-L-arabino-hexopyranosyl)oxy]-7,8,9,10-tetrahydro-6,8,11-trihydroxy-8-(hydroxyacetyl)-1-methoxy-5,12-naphthacenedione hydrochloride) | Ellence |
| Epoetin alfa (recombinant peptide) | Epogen |
| Estramustine (estra-1,3,5(10)-triene-3,17-diol(17(beta))-, 3-[bis(2-chloroethyl)carbamate] 17-(dihydrogen phosphate), disodium salt, monohydrate, or estradiol 3-[bis(2-chloroethyl)carbamate] 17-(dihydrogen phosphate), disodium salt, monohydrate) | Emcyt |
| Etoposide phosphate (4'-Demethylepipodophyllotoxin 9-[4,6-O-(R)-ethylidene-(beta)-D-glucopyranoside], 4'-(dihydrogen phosphate)) | Etopophos |
| etoposide, VP-16 (4'-demethylepipodophyllotoxin 9-[4,6-0-(R)-ethylidene-(beta)-D-glucopyranoside)] | Vepesid |
| Exemestane (6-methylenandrosta-1,4-diene-3, 17-dione) | Aromasin |
| Filgrastim (r-metHuG-CSF) | Neupogen |
| floxuridine(intraarterial) (2'-deoxy-5-fluorouridine) | FUDR |
| Fludarabine (fluorinated nucleotide analog of the antiviral agent vidarabine, 9-b-D-arabinofuranosyladenine (ara-A)) | Fludara |
| Fluorouracil, 5-FU (5-fluoro-2,4(1H,3H)-pyrimidinedione) | Adrucil |
| Fulvestrant (7-alpha-[9-(4,4,5,5,5-penta fluoropentylsulphinyl) nonyl]estra-1,3,5-(10)-triene-3,17-beta-diol) | Faslodex |
| Gemcitabine (2'-deoxy-2', 2'-difluorocytidine monohydrochloride(b-isomer)) | Gemzar |

TABLE 1-continued

| | |
|---|---|
| Gemtuzumab Ozogamicin (anti-CD33 hP67.6) | Mylotarg |
| Goserelin acetate | Zoladex Implant |
| Hydroxyurea | Hydrea |
| Ibritumomab Tiuxetan (immunoconjugate resulting from a thiourea covalent bond between the monoclonal antibody Ibritumomab and the linker-chelator tiuxetan[N-[2-bis(carboxymethyl)amino]-3-(p-isothiocyanatophenyl)-propyl]-[N-[2-bis(carboxymethyl)amino]-2-(methyl)-ethyl]glycine) | Zevalin |
| Idarubicin (5,12-Naphthacenedione, 9-acetyl-7-[(3-amino-2,3,6-trideoxy-(alpha)-L-lyxo-hexopyranosyl)oxy]-7,8,9,10-tetrahydro-6,9,11-trihydroxyhydrochloride, (7S-cis)) | Idamycin |
| Ifosfamide (3-(2-chloroethyl)-2-[(2-chloroethyl)amino]tetrahydro-2H-1,3,2-oxazaphosphorine 2-oxide) | IFEX |
| Imatinib Mesilate (4-[(4-Methyl-1-piperazinyl)methyl]-N-[4-methyl-3-[[4-(3-pyridinyl)-2-pyrimidinyl]amino]-phenyl]benzamide methanesulfonate) | Gleevec |
| Interferon alfa-2a (recombinant peptide) | Roferon-A |
| Interferon alfa-2b (recombinant peptide) | Intron A (Lyophilized Betaseron) |
| Irinotecan HCl ((4S)-4,11-diethyl-4-hydroxy-9-[(4-piperi-dinopiperidino)carbonyloxy]-1H-pyrano[3',4':6,7] indolizino[1,2-b] quinoline-3,14(4H, 12H) dione hydrochloride trihydrate) | Camptosar |
| Letrozole (4,4'-(1H-1,2,4-Triazol-1-ylmethylene) dibenzonitrile) | Femara |
| Leucovorin (L-Glutamic acid, N[4[[(2amino-5-formyl1,4,5,6,7,8-hexahydro4oxo6-pteridinyl)methyl]amino]benzoyl], calcium salt(1:1)) | Wellcovorin, Leucovorin |
| Levamisole HCl ((-)-(S)-2,3,5,6-tetrahydro-6-phenylimidazo [2,1-b] thiazole monohydrochloride $C_{11}H_{12}N_2S \cdot HCl$) | Ergamisol |
| Lomustine (1-(2-chloro-ethyl)-3-cyclohexyl-1-nitrosourea) | CeeNU |
| Meclorethamine, nitrogen mustard (2-chloro-N-(2-chloroethyl)-N-methylethanamine hydrochloride) | Mustargen |
| Megestrol acetate 17α(acetyloxy)-6-methylpregna-4,6-diene-3,20-dione | Megace |
| Melphalan, L-PAM (4-[bis(2-chloroethyl)amino]-L-phenylalanine) | Alkeran |
| Mercaptopurine, 6-MP (1,7-dihydro-6H-purine-6-thione monohydrate) | Purinethol |
| Mesna (sodium 2-mercaptoethane sulfonate) | Mesnex |
| Methotrexate (N-[4-[[(2,4-diamino-6-pteridinyl)methyl]methylamino]benzoyl]-L-glutamic acid) | Methotrexate |
| Methoxsalen (9-methoxy-7H-furo[3,2-g][1]-benzopyran-7-one) | Uvadex |
| Mitomycin C | Mutamycin |
| mitomycin C | Mitozytrex |
| Mitotane (1,1-dichloro-2-(o-chlorophenyl)-2-(p-chlorophenyl) ethane) | Lysodren |
| Mitoxantrone (1,4-dihydroxy-5,8-bis[[2-[(2-hydroxyethyl)amino]ethyl]amino]-9,10-anthracenedione dihydrochloride) | Novantrone |
| Nandrolone phenpropionate | Durabolin-50 |
| Nofetumomab | Verluma |
| Oprelvekin (IL-11) | Neumega |
| Oxaliplatin (cis-[(1R,2R)-1,2-cyclohexanediamine-N,N'] [oxalato(2-)-O,O'] platinum) | Eloxatin |
| Paclitaxel (5β,20-Epoxy-1,2a,4,7β,10β,13a-hexahydroxytax-11-en-9-one 4,10-diacetate 2-benzoate 13-ester with (2R, 3S)-N-benzoyl-3-phenylisoserine) | TAXOL |
| Pamidronate (phosphonic acid (3-amino-1-hydroxypropylidene) bis-, disodium salt, pentahydrate, (APD)) | Aredia |

TABLE 1-continued

| | |
|---|---|
| Pegademase<br>((monomethoxypolyethylene glycol succinimidyl) 11-17-<br>adenosine deaminase) | Adagen (Pegademase<br>Bovine) |
| Pegaspargase<br>(monomethoxypolyethylene glycol succinimidyl L-<br>asparaginase) | Oncaspar |
| Pegfilgrastim<br>(covalent conjugate of recombinant methionyl human G-<br>CSF(Filgrastim) and monomethoxypolyethylene glycol) | Neulasta |
| Pentostatin | Nipent |
| Pipobroman | Vercyte |
| Plicamycin, Mithramycin<br>(antibiotic produced by *Streptomyces plicatus*) | Mithracin |
| Porfimer sodium | Photofrin |
| Procarbazine<br>(N-isopropyl-μ-(2-methylhydrazino)-p-toluamide<br>monohydrochloride) | Matulane |
| Quinacrine<br>(6-chloro-9-(1-methyl-4-diethyl-amine) butylamino-2-<br>methoxyacridine) | Atabrine |
| Rasburicase<br>(recombinant peptide) | Elitek |
| Rituximab<br>(recombinant anti-CD20 antibody) | Rituxan |
| Sargramostim<br>(recombinant peptide) | Prokine |
| Streptozocin<br>(streptozocin 2-deoxy-2-<br>[[(methylnitrosoamino)carbonyl]amino]-a(and b)-D-<br>glucopyranose and 220 mg citric acid anhydrous) | Zanosar |
| Talc<br>($Mg_3Si_4O_{10}(OH)_2$) | Sclerosol |
| Tamoxifen<br>((Z)2-[4-(1,2-diphenyl-1-butenyl) phenoxy]-N,N-<br>dimethylethanamine 2-hydroxy-1,2,3-<br>propanetricarboxylate (1:1)) | Nolvadex |
| Temozolomide<br>(3,4-dihydro-3-methy-4-oxoimidazo[5,1-d]-as-tetrazine-8-<br>carboxamide) | Temodar |
| teniposide, VM-26<br>(4'-demethylepipodophyllotoxin 9-[4,6-0-(R)-2-<br>thenylidene-(beta)-D-glucopyranoside]) | Vumon |
| Testolactone<br>(13-hydroxy-3-oxo-13,17-secoandrosta-1,4-dien-17-oic<br>acid [dgr]-lactone) | Teslac |
| Thioguanine, 6-TG<br>(2-amino-1,7-dihydro-6 H-purine-6-thione) | Thioguanine |
| Thiotepa<br>(Aziridine,1,1',1''-phosphinothioylidynetris-, or Tris(1-<br>aziridinyl)phosphine sulfide) | Thioplex |
| Topotecan HCl<br>((S)-10-[(dimethylamino)methyl]-4-ethyl-4,9-dihydroxy-<br>1H-pyrano[3',4':6,7]indolizino [1,2-b] quinoline-3,14-<br>(4H,12H)-dione monohydrochloride) | Hycamtin |
| Toremifene<br>(2-(p-[(Z)-4-chloro-1,2-diphenyl-1-butenyl]-phenoxy)-N,N-<br>dimethylethylamine citrate (1:1)) | Fareston |
| Tositumomab, I 131 Tositumomab<br>(recombinant murine immunotherapeutic monoclonal $IgG_{2a}$<br>lambda anti-CD20 antibody (I 131 is a<br>radioimmunotherapeutic antibody)) | Bexxar |
| Trastuzumab<br>(recombinant monoclonal $IgG_1$ kappa anti-HER2 antibody) | Herceptin |
| Tretinoin, ATRA<br>(all-trans retinoic acid) | Vesanoid |
| Uracil Mustard | Uracil Mustard Capsules |
| Valrubicin, N-trifluoroacetyladriamycin-14-valerate<br>((2S-cis)-2-[1,2,3,4,6,11-hexahydro-2,5,12-trihydroxy-7<br>methoxy-6,11-dioxo-[[2,3,6-trideoxy-3-[(trifluoroacetyl)-<br>amino-α-L-lyxo-hexopyranosyl]oxyl]]-2-naphthacenyl]-2-<br>oxoethyl pentanoate) | Valstar |
| Vinblastine, Leurocristine<br>($C_{46}H_{56}N_4O_{10} \cdot H_2SO_4$) | Velban |
| Vincristine<br>($C_{46}H_{56}N_4O_{10} \cdot H_2SO_4$) | Oncovin |
| Vinorelbine<br>(3',4'-didehydro-4'-deoxy-C'-norvincaleukoblastine [R-<br>(R*,R*)-2,3-dihydroxybutanedioate (1:2)(salt)]) | Navelbine |

| | |
|---|---|
| Zoledronate, Zoledronic acid ((1-Hydroxy-2-imidazol-1-yl-phosphonoethyl) phosphonic acid monohydrate) | Zometa |

Anticancer agents further include compounds which have been identified to have anticancer activity. Examples include, but are not limited to, 3-AP, 12-O-tetradecanoylphorbol-13-acetate, 17AAG, 852A, ABI-007, ABR-217620, ABT-751, ADI-PEG 20, AE-941, AG-013736, AGRO100, alanosine, AMG 706, antibody G250, antineoplastons, AP23573, apaziquone, APC8015, atiprimod, ATN-161, atrasenten, azacitidine, BB-10901, BCX-1777, bevacizumab, BG00001, bicalutamide, BMS 247550, bortezomib, bryostatin-1, buserelin, calcitriol, CCI-779, CDB-2914, cefixime, cetuximab, CG0070, cilengitide, clofarabine, combretastatin A4 phosphate, CP-675,206, CP-724,714, CpG 7909, curcumin, decitabine, DENSPM, doxercalciferol, E7070, E7389, ecteinascidin 743, efaproxiral, eflornithine, EKB-569, enzastaurin, erlotinib, exisulind, fenretinide, flavopiridol, fludarabine, flutamide, fotemustine, FR901228, G17DT, galiximab, gefitinib, genistein, glufosfamide, GTI-2040, histrelin, HKI-272, homoharringtonine, HSPPC-96, hu14.18-interleukin-2 fusion protein, HuMax-CD4, iloprost, imiquimod, infliximab, interleukin-12, IPI-504, irofulven, ixabepilone, lapatinib, lenalidomide, lestaurtinib, leuprolide, LMB-9 immunotoxin, lonafarnib, luniliximab, mafosfamide, MB07133, MDX-010, MLN2704, monoclonal antibody 3F8, monoclonal antibody J591, motexafin, MS-275, MVA-MUC1-IL2, nilutamide, nitrocamptothecin, nolatrexed dihydrochloride, nolvadex, NS-9,06-benzylguanine, oblimersen sodium, ONYX-015, oregovomab, OSI-774, panitumumab, paraplatin, PD-0325901, pemetrexed, PHY906, pioglitazone, pirfenidone, pixantrone, PS-341, PSC 833, PXD101, pyrazoloacridine, R115777, RAD001, ranpirnase, rebeccamycin analogue, rhuAngiostatin protein, rhuMab 2C4, rosiglitazone, rubitecan, S-1, S-8184, satraplatin, SB-, 15992, SGN-0010, SGN-40, sorafenib, SR31747A, ST1571, SU011248, suberoylanilide hydroxamic acid, suramin, talabostat, talampanel, tariquidar, temsirolimus, TGFa-PE38 immunotoxin, thalidomide, thymalfasin, tipifarnib, tirapazamine, TLK286, trabectedin, trimetrexate glucuronate, TroVax, UCN-1, valproic acid, vinflunine, VNP40101M, volociximab, vorinostat, VX-680, ZD1839, ZD6474, zileuton, and zosuquidar trihydrochloride.

For a more detailed description of anticancer agents and other therapeutic agents, those skilled in the art are referred to any number of instructive manuals including, but not limited to, the Physician's Desk Reference and to Goodman and Gilman's "Pharmaceutical Basis of Therapeutics" tenth edition, Eds. Hardman et al., 2002.

In some embodiments, methods provided herein comprise administering one or more compounds provided herein with radiation therapy. The methods provided herein are not limited by the types, amounts, or delivery and administration systems used to deliver the therapeutic dose of radiation to an animal. For example, the animal may receive photon radiotherapy, particle beam radiation therapy, other types of radiotherapies, and combinations thereof. In some embodiments, the radiation is delivered to the animal using a linear accelerator. In still other embodiments, the radiation is delivered using a gamma knife.

The source of radiation can be external or internal to the animal. External radiation therapy is most common and involves directing a beam of high-energy radiation to a tumor site through the skin using, for instance, a linear accelerator. While the beam of radiation is localized to the tumor site, it is nearly impossible to avoid exposure of normal, healthy tissue. However, external radiation is usually well tolerated by animals. Internal radiation therapy involves implanting a radiation-emitting source, such as beads, wires, pellets, capsules, particles, and the like, inside the body at or near the tumor site including the use of delivery systems that specifically target cancer cells (e.g., using particles attached to cancer cell binding ligands). Such implants can be removed following treatment, or left in the body inactive. Types of internal radiation therapy include, but are not limited to, brachytherapy, interstitial irradiation, intracavity irradiation, radioimmunotherapy, and the like.

The animal may optionally receive radiosensitizers (e.g., metronidazole, misonidazole, intra-arterial Budr, intravenous iododeoxyuridine (IudR), nitroimidazole, 5-substituted-4-nitroimidazoles, 2H-isoindolediones, [[(2-bromoethyl)-amino]methyl]-nitro-1H-imidazole-1-ethanol, nitroaniline derivatives, DNA-affinic hypoxia selective cytotoxins, halogenated DNA ligand, 1,2,4 benzotriazine oxides, 2-nitroimidazole derivatives, fluorine-containing nitroazole derivatives, benzamide, nicotinamide, acridine-intercalator, 5-thiotetrazole derivative, 3-nitro-1,2,4-triazole, 4,5-dinitroimidazole derivative, hydroxylated texaphrins, cisplatin, mitomycin, tiripazamine, nitrosourea, mercaptopurine, methotrexate, fluorouracil, bleomycin, vincristine, carboplatin, epirubicin, doxorubicin, cyclophosphamide, vindesine, etoposide, paclitaxel, heat (hyperthermia), and the like), radioprotectors (e.g., cysteamine, aminoalkyl dihydrogen phosphorothioates, amifostine (WR 2721), IL-1, IL-6, and the like). Radiosensitizers enhance the killing of tumor cells. Radioprotectors protect healthy tissue from the harmful effects of radiation.

Any type of radiation can be administered to an animal, so long as the dose of radiation is tolerated by the animal without unacceptable negative side-effects. Suitable types of radiotherapy include, for example, ionizing (electromagnetic) radiotherapy (e.g., X-rays or gamma rays) or particle beam radiation therapy (e.g., high linear energy radiation). Ionizing radiation is defined as radiation comprising particles or photons that have sufficient energy to produce ionization, i.e., gain or loss of electrons (as described in, for example, U.S. Pat. No. 5,770,581 incorporated herein by reference in its entirety). The effects of radiation can be at least partially controlled by the clinician. In one embodiment, the dose of radiation is fractionated for maximal target cell exposure and reduced toxicity.

In one embodiment, the total dose of radiation administered to an animal is about 0.01 Gray (Gy) to about 100 Gy. In another embodiment, about 10 Gy to about 65 Gy (e.g., about 15 Gy, 20 Gy, 25 Gy, 30 Gy, 35 Gy, 40 Gy, 45 Gy, 50 Gy, 55 Gy, or 60 Gy) are administered over the course of treatment. While in some embodiments a complete dose of radiation can be administered over the course of one day, the total dose is ideally fractionated and administered over several days. Desirably, radiotherapy is administered over the course of at least about 3 days, e.g., at least 5, 7, 10, 14, 17, 21, 25, 28, 32, 35, 38, 42, 46, 52, or 56 days (about 1-8 weeks). Accordingly, a daily dose of radiation will comprise approximately 1-5 Gy (e.g., about 1 Gy, 1.5 Gy, 1.8 Gy, 2 Gy, 2.5 Gy, 2.8 Gy, 3 Gy, 3.2 Gy, 3.5 Gy, 3.8 Gy, 4 Gy, 4.2 Gy, or 4.5 Gy), or 1-2 Gy (e.g., 1.5-2 Gy). The daily dose of radiation should be sufficient to induce destruction of the targeted cells. If stretched over a period, in one embodiment, radiation is not administered every day, thereby allowing the animal to rest and the effects of the therapy to be realized. For example, radiation desirably is administered on 5 consecutive days, and not administered on 2 days, for each week of treatment, thereby allowing 2 days of rest per week. However, radiation can be administered 1 day/week, 2 days/week, 3 days/week, 4 days/week, 5 days/week, 6 days/week, or all 7 days/week, depending on the animal's responsiveness and any potential side effects. Radiation therapy can be initiated at any time in the therapeutic period. In one embodiment, radiation is initiated in week 1 or week 2, and is administered for the remaining duration of the therapeutic period. For example, radiation is administered in weeks 1-6 or in weeks 2-6 of a therapeutic period comprising 6 weeks for treating, for instance, a solid tumor. Alternatively, radiation is administered in weeks 1-5 or weeks 2-5 of a therapeutic period comprising 5 weeks. These exemplary radiotherapy administration schedules are not intended, however, to limit the methods provided herein.

Antimicrobial therapeutic agents may also be used as therapeutic agents in combination with the compounds provided herein. Any agent that can kill, inhibit, or otherwise attenuate the function of microbial organisms may be used, as well as any agent contemplated to have such activities. Antimicrobial agents include, but are not limited to, natural and synthetic antibiotics, antibodies, inhibitory proteins (e.g., defensins), antisense nucleic acids, membrane disruptive agents and the like, used alone or in combination. Indeed, any type of antibiotic may be used including, but not limited to, antibacterial agents, antiviral agents, antifungal agents, and the like.

In some embodiments of the methods provided herein, one or more compounds provided herein and one or more therapeutic agents or anticancer agents are administered to an animal under one or more of the following conditions: at different periodicities, at different durations, at different concentrations, by different administration routes, etc. In some embodiments, the compound is administered prior to the therapeutic or anticancer agent, e.g., 0.5, 1, 2, 3, 4, 5, 10, 12, or 18 hours, 1, 2, 3, 4, 5, or 6 days, or 1, 2, 3, or 4 weeks prior to the administration of the therapeutic or anticancer agent. In some embodiments, the compound is administered after the therapeutic or anticancer agent, e.g., 0.5, 1, 2, 3, 4, 5, 10, 12, or 18 hours, 1, 2, 3, 4, 5, or 6 days, or 1, 2, 3, or 4 weeks after the administration of the anticancer agent. In some embodiments, the compound and the therapeutic or anticancer agent are administered concurrently but on different schedules, e.g., the compound is administered daily while the therapeutic or anticancer agent is administered once a week, once every two weeks, once every three weeks, or once every four weeks. In other embodiments, the compound is administered once a week while the therapeutic or anticancer agent is administered daily, once a week, once every two weeks, once every three weeks, or once every four weeks.

In some embodiments, compositions provided herein comprise one or more of the compounds provided herein in an amount which is effective to achieve its intended purpose. While individual needs vary, determination of optimal ranges of effective amounts of each component is within the skill of the art. Typically, the compounds may be administered to mammals, e.g. humans, orally at a dose of 0.0025 to 50 mg/kg, or an equivalent amount of the pharmaceutically acceptable salt thereof, per day of the body weight of the mammal being treated for disorders responsive to induction of apoptosis. In one embodiment, about 0.01 to about 25 mg/kg is orally administered to treat, ameliorate, or prevent such disorders. For intramuscular injection, the dose is generally about one-half of the oral dose. For example, a suitable intramuscular dose would be about 0.0025 to about 25 mg/kg, or from about 0.01 to about 5 mg/kg.

The unit oral dose may comprise from about 0.01 to about 1000 mg, for example, about 0.1 to about 100 mg of the compound. The unit dose may be administered one or more times daily as one or more tablets or capsules each containing from about 0.1 to about 10 mg, conveniently about 0.25 to 50 mg of the compound or its solvates.

In a topical formulation, the compound may be present at a concentration of about 0.01 to 100 mg per gram of carrier. In a one embodiment, the compound is present at a concentration of about 0.07-1.0 mg/ml, for example, about 0.1-0.5 mg/ml, and in one embodiment, about 0.4 mg/ml.

In addition to administering the compound as a raw chemical, the compounds provided herein may be administered as part of a pharmaceutical preparation. In some embodiments, the pharmaceutical preparation can include one or more pharmaceutically acceptable carrier, excipient, and/or auxiliary. In some embodiments, the one or more carriers, excipients, and auxiliaries facilitate processing of the compound into a preparation which can be used pharmaceutically. The preparations, particularly those preparations which can be administered orally or topically and which can be used for one type of administration, such as tablets, dragees, slow release lozenges and capsules, mouth rinses and mouth washes, gels, liquid suspensions, hair rinses, hair gels, shampoos and also preparations which can be administered rectally, such as suppositories, as well as suitable solutions for administration by intravenous infusion, injection, topically or orally, contain from about 0.01 to 99 percent, in one embodiment from about 0.25 to 75 percent of active compound(s), together with the one or more carriers, excipients, and/or auxiliaries.

The pharmaceutical compositions of provided herein may be administered to any patient which may experience the beneficial effects of the compounds provided herein. Foremost among such patients are mammals, e.g., humans, although the methods and compositions provided herein are not intended to be so limited. Other patients include veterinary animals (cows, sheep, pigs, horses, dogs, cats and the like).

The compounds and pharmaceutical compositions thereof may be administered by any means that achieve their intended purpose. For example, administration may be by parenteral, subcutaneous, intravenous, intramuscular, intraperitoneal, transdermal, buccal, intrathecal, intracranial, intranasal or topical routes. Alternatively, or concurrently, administration may be by the oral route. The dosage administered will be dependent upon the age, health, and weight of the recipient, kind of concurrent treatment, if any, frequency of treatment, and the nature of the effect desired.

The pharmaceutical preparations provided herein are manufactured by means of conventional mixing, granulating, dragee-making, dissolving, or lyophilizing processes. Thus, pharmaceutical preparations for oral use can be obtained by combining the active compounds with solid excipients, optionally grinding the resulting mixture and processing the mixture of granules, after adding suitable auxiliaries, if desired or necessary, to obtain tablets or dragee cores.

Suitable excipients are, in particular, fillers such as saccharides, for example lactose or sucrose, mannitol or sorbitol, cellulose preparations and/or calcium phosphates, for example tricalcium phosphate or calcium hydrogen phosphate, as well as binders such as starch paste, using, for example, maize starch, wheat starch, rice starch, potato starch, gelatin, tragacanth, methyl cellulose, hydroxypropylmethylcellulose, sodium carboxymethylcellulose, and/or polyvinyl pyrrolidone. If desired, disintegrating agents may be added such as the above-mentioned starches and also carboxymethyl-starch, cross-linked polyvinyl pyrrolidone, agar, or alginic acid or a salt thereof, such as sodium alginate. Auxiliaries can be suitable flow-regulating agents and lubricants. Suitable auxiliaries include, for example, silica, talc, stearic acid or salts thereof, such as magnesium stearate or calcium stearate, and/or polyethylene glycol. Dragee cores are provided with suitable coatings which, if desired, are resistant to gastric juices. For this purpose, concentrated saccharide solutions may be used, which may optionally contain gum arabic, talc, polyvinyl pyrrolidone, polyethylene glycol and/or titanium dioxide, lacquer solutions and suitable organic solvents or solvent mixtures. In order to produce coatings resistant to gastric juices, solutions of suitable cellulose preparations such as acetylcellulose phthalate or hydroxypropylmethyl-cellulose phthalate, are used. Dye stuffs or pigments may be added to the tablets or dragee coatings, for example, for identification or in order to characterize combinations of active compound doses.

Other pharmaceutical preparations which can be used orally include push-fit capsules made of gelatin, as well as soft, sealed capsules made of gelatin and a plasticizer such as glycerol or sorbitol. The push-fit capsules can contain the active compounds in the form of granules which may be mixed with fillers such as lactose, binders such as starches, and/or lubricants such as talc or magnesium stearate and, optionally, stabilizers. In soft capsules, the active compounds are in one embodiment dissolved or suspended in suitable liquids, such as fatty oils, or liquid paraffin. In addition, stabilizers may be added.

Possible pharmaceutical preparations which can be used rectally include, for example, suppositories, which consist of a combination of one or more of the active compounds with a suppository base. Suitable suppository bases are, for example, natural or synthetic triglycerides, or paraffin hydrocarbons. In addition, it is also possible to use gelatin rectal capsules which consist of a combination of the active compounds with a base. Possible base materials include, for example, liquid triglycerides, polyethylene glycols, or paraffin hydrocarbons.

Suitable formulations for parenteral administration include aqueous solutions of the active compounds in water-soluble form, for example, water-soluble salts and alkaline solutions. In addition, suspensions of the active compounds as appropriate oily injection suspensions may be administered. Suitable lipophilic solvents or vehicles include fatty oils, for example, sesame oil, or synthetic fatty acid esters, for example, ethyl oleate or triglycerides or polyethylene glycol-400. Aqueous injection suspensions may contain substances which increase the viscosity of the suspension include, for example, sodium carboxymethyl cellulose, sorbitol, and/or dextran. Optionally, the suspension may also contain stabilizers.

The topical compositions provided herein are formulated in one embodiment as oils, creams, lotions, ointments and the like by choice of appropriate carriers. Suitable carriers include vegetable or mineral oils, white petrolatum (white soft paraffin), branched chain fats or oils, animal fats and high molecular weight alcohol (greater than $C_{12}$). The carriers may be those in which the active ingredient is soluble. Emulsifiers, stabilizers, humectants and antioxidants may also be included as well as agents imparting color or fragrance, if desired. Additionally, transdermal penetration enhancers can be employed in these topical formulations. Examples of such enhancers can be found in U.S. Pat. Nos. 3,989,816 and 4,444,762.

Ointments may be formulated by mixing a solution of the active ingredient in a vegetable oil such as almond oil with warm soft paraffin and allowing the mixture to cool. A typical example of such an ointment is one which includes about 30% almond oil and about 70% white soft paraffin by weight.

Lotions may be conveniently prepared by dissolving the active ingredient, in a suitable high molecular weight alcohol such as propylene glycol or polyethylene glycol.

The following examples are illustrative, but not limiting, of the compounds, compositions, and methods provided herein. Other suitable modifications and adaptations of the variety of conditions and parameters normally encountered in clinical therapy and which are obvious to those skilled in the art are within the spirit and scope of the methods, compounds, and compositions provided herein.

MDM2 Inhibitors

U.S. Pat. Nos. 7,759,383 B2 and 7,737,174 B2 disclose MDM2 inhibitors including MI-219 (AT-219), MI-319 and MI-147 (Chart 1).

Chart 1

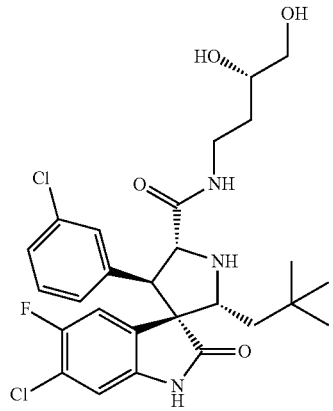

MI-219 (AT-219)

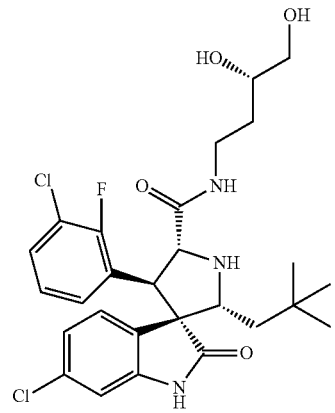

MI-147

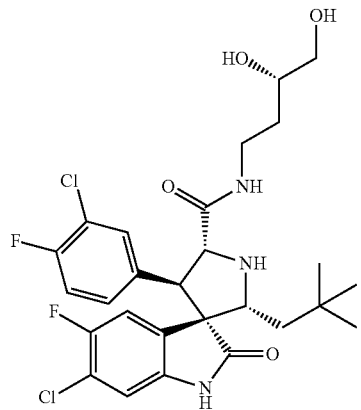

MI-319

To further evaluate MI-219, MI-147, and MI-319 as potential anticancer drug candidates for clinical development, a series of experiments were carried out to evaluate their metabolic and pharmacokinetic properties.

Incubation of MI-219, MI-147 and MI-319 with human, rat and dog microsomes in vitro showed that the concentration of each of these three compounds decreased rather quickly (Table 2). These data suggested that MI-219, MI-147 and MI-319 are metabolized fairly rapidly in vitro by rat, dog and human microsomes.

Pharmacokinetic studies (PK) of MI-219 in Male Sprague Dawley rats showed that MI-219 was orally bioavailable (Tables 3-4). For example, following oral administration of MI-219 at dose of 25 mg/kg, the mean±SD values of $C_{max}$ (maximum plasma concentration) and Tmax for MI-219 were 3751.78±1067.86 mg/L, 0.58±0.38 hr, respectively; the mean±SD values of AUC(0-∞) (area-under-the-curve) and half-life (T½) for MI-219 were 7689.94±325.86 hr*mg/L and 1.43±0.09 hr, respectively. The plasma concentrations of MI-219 decreased fairly rapidly, from 2957 ng/ml at 1 hr time-point, to 224 ng/ml at 4 hr time-point, further to 103 ng/ml at 6 hr time-point. The calculated oral bioavailability in rats for MI-219 using the 25 mg/kg oral dosing and 5 mg/kg IV dosing as the references was 65.45±2.77%.

PK studies of MI-219 in ICR mice showed that MI-219 was orally bioavailable in mice (Tables 5-7). At 50 mg/kg oral dosing, MI-219 reached the maximum concentration ($C_{max}$) of 8469 ng/ml at 2 hr time-point and had an AUC of 8469±2381 hr*ug/L. The concentrations of MI-219 were 3077±2296, 378±128 and 121±133 ng/ml at 3 h, 5 h and 9 h, respectively. The calculated oral bioavailability (F) for MI-219 in mice is 54.9±19.0%.

PK studies of MI-219 in Beagle dogs showed that MI-219 was orally bioavailable in dogs (Tables 8-11). At 10 mg/kg oral dosing, MI-219 reached the maximum concentration ($C_{max}$) of 2893±726 ng/ml at 1 hr time-point and had an AUC of 7947±2396 hr*ug/L. The concentrations of MI-219 were 1500±599, 759±314, 483±152, 327±147, 178±92 ng/ml at 2, 3, 4, 6 and 8 hr time-point, respectively. The calculated oral bioavailability (F) for MI-219 in dogs is 22.8%.

PK studies of MI-219 in Cynomolgus Monkeys showed that MI-219 was orally bioavailable in monkeys (Tables 12-13). At 50 mg/kg oral dosing, MI-219 reached the maximum concentration ($C_{max}$) of 1257±837 at 3.3 hr by curve fitting and had an AUC of 8199±5717 hr*ug/L. The concentrations of MI-219 were 1121.42±951.73, 796.07±703.14, 341.82±273.89 and 17.60±7.21 at 4, 6, 8 and 24 hr time-point, respectively. The calculated oral bioavailability (F) of MI-219 in moneys is 13.89%.

Oral administration of MI-219 in mice bearing SJSA-1 and LnCAP human xenograft tumors was indeed effective tumor growth inhibition at 200-300 mg/kg daily dosing or twice a day for a period of 2 weeks (Shangary et al. 2008, PNAS). SJSA-1 cells are derived from the primary tumor or a patient diagnosed with primitive multipotential sarcoma of the femur. SJSA-1 cells harbor an amplification of the MDM2 gene. LnCAP cells are androgen-sensitive human prostate adenocarcinoma cells derived from a metastatic tumor of a patient diagnosed with prostate cancer. These data indicate that MI-219 is an orally active MDM2 inhibitor.

These metabolic and PK studies also revealed that MI-219 is metabolized fairly quickly. Hence, further chemical modifications of MI-219 to improve upon its metabolic and PK parameters may yield new MDM2 inhibitors as better drug candidates for treatment of human cancer and other conditions through targeting human MDM2 and activation of p53.

Provided herein are new compounds that inhibit p53-MDM2 interaction. The compounds provided herein have, inter alia, improved metabolic stability and/or pharmacokinetic properties and oral bioavailability.

TABLE 2

Microsomal stability studies of MI-147, MI-219 and MI-319.

|  | Time (min) | MI-147 | MI-219 | MI-319 |
|---|---|---|---|---|
| Human | 0 | 100.00% | 100.00% | 100.00% |
|  | 5 | 78.23% | 78.76% | 82.09% |
|  | 10 | 58.01% | 58.19% | 60.88% |
|  | 15 | 41.59% | 46.46% | 43.86% |
|  | 30 | 19.67% | 26.46% | 24.79% |
|  | 45 | 10.81% | 20.88% | 10.66% |
|  | 60 | 7.18% | 11.86% | 16.31% |
| Rat | 0 | 100.00% | 100.00% | 100.00% |
|  | 5 | 68.05% | 58.19% | 64.80% |
|  | 10 | 31.04% | 40.59% | 41.96% |
|  | 15 | 16.85% | 28.11% | 30.71% |
|  | 30 | 6.18% | 18.61% | 23.11% |
|  | 45 | 4.40% | 18.42% | 23.01% |
|  | 60 | 3.43% | 18.38% | 24.01% |
| Dog | 0 | 100.00% | 100.00% | 100.00% |
|  | 5 | 77.84% | 83.38% | 108.25% |
|  | 10 | 47.98% | 71.22% | 69.29% |
|  | 15 | 44.83% | 71.51% | 57.20% |
|  | 30 | 21.52% | 54.96% | 41.84% |
|  | 45 | 17.08% | 33.81% | 29.39% |
|  | 60 | 12.15% | 32.52% | 27.06% |
| Negative | 0 | 100.00% | 100.00% | 100.00% |
|  | 5 | 94.73% | 102.63% | 95.37% |
|  | 10 | 90.77% | 105.25% | 90.75% |
|  | 15 | 93.43% | 109.19% | 96.26% |
|  | 30 | 94.14% | 111.07% | 86.12% |
|  | 45 | 91.07% | 104.13% | 91.41% |
|  | 60 | 85.38% | 109.01% | 85.90% |

TABLE 3

Plasma Concentration of MI-219 in Male Rat Following Intravenous and Oral Administration.

| Time Point (hr) | Plasma Concentration (ng/mL) | | | | | | | |
|---|---|---|---|---|---|---|---|---|
|  | IV (5 mg/kg) | | | PO (25 mg/kg) | | | | |
| Animal No. | M1 | M2 | Mean | M6 | M7 | M8 | Mean | SD |
| 0.083 | 5873.30 | 5229.30 | 5551.30 | 1526.57 | 1380.03 | 1642.42 | 1516.34 | 131.49 |
| 0.25 | 1551.07 | 1612.79 | 1581.93 | 2817.28 | 2398.33 | 4965.7 | 3393.77 | 1377.35 |
| 0.5 | 693.45 | 548.39 | 620.92 | 3332.19 | 2500.25 | 4278.56 | 3370.33 | 889.77 |
| 1 | 330.71 | 344.66 | 337.68 | 3101.06 | 2957.44 | 1779.31 | 2612.60 | 725.22 |
| 2 | 164.88 | 134.91 | 149.90 | 1064.21 | 1534.41 | 1342.18 | 1313.60 | 236.40 |
| 4 | 49.27 | 56.50 | 52.88 | 296.644 | 223.937 | 407.415 | 309.33 | 92.39 |
| 6 | 24.18 | 32.66 | 28.42 | 103.285 | 90.8093 | 131.398 | 108.50 | 20.79 |

TABLE 3-continued

Plasma Concentration of MI-219 in Male Rat Following Intravenous and Oral Administration.

| Time Point | Plasma Concentration (ng/mL) | | | | | | |
|---|---|---|---|---|---|---|---|
| | IV (5 mg/kg) | | | PO (25 mg/kg) | | | |
| Animal No. (hr) | M1 | M2 | Mean | M6 | M7 | M8 | Mean | SD |
| 8 | 11.05 | 18.98 | 15.02 | 47.5486 | 80.4445 | 66.2777 | 64.76 | 16.50 |
| 24 | 1.86 | 1.28 | 1.57 | 25.1348 | 17.5136 | 20.2154 | 20.95 | 3.86 |

BLQ: Below the limit of quantitation;
SD: Standard deviation;
NA: Nonapplicable

TABLE 4

Selected Pharmacokinetics Parameters of MI-219 in Rats Following Intravenous and Oral Administration.

| Animal Number | $AUC_{(0-t)}$ hr * ug/L | $AUC_{(0-\infty)}$ hr * ug/L | $MRT_{(0-\infty)}$ hr | $T_{1/2}$ hr | Vz L/kg | CLz L/hr/kg | Cmax ug/L | Tmax hr | F (%) |
|---|---|---|---|---|---|---|---|---|---|
| IV (5 mg/kg) | | | | | | | | | |
| 1 | 2379.54 | 2379.62 | 1.26 | 1.86 | 5.62 | 2.10 | 5873.30 | | |
| 2 | 2318.88 | 2319.77 | 1.51 | 2.54 | 7.90 | 2.16 | 5229.30 | | |
| MEAN | 2349.21 | 2349.69 | 1.38 | 2.20 | 6.76 | 2.13 | 5551.30 | | |
| PO (25 mg/kg) | | | | | | | | | |
| 6 | 7378.78 | 7378.81 | 2.64 | 1.36 | NA | NA | 3332.19 | 0.5 | 62.81 |
| 7 | 7623.45 | 7662.25 | 2.67 | 1.54 | NA | NA | 2957.44 | 1 | 65.22 |
| 8 | 8028.71 | 8028.76 | 2.62 | 1.40 | NA | NA | 4965.7 | 0.25 | 68.34 |
| MEAN | 7676.98 | 7689.94 | 2.64 | 1.43 | NA | NA | 3751.78 | 0.58 | 65.45 |
| SD | 328.26 | 325.86 | 0.03 | 0.09 | NA | NA | 1067.86 | 0.38 | 2.77 |

NA: Nonapplicable

TABLE 5

Measured concentrations of MI-219 in the plasma samples after a single p.o dose at 50 mg/kg in mice.

| Time | Group 3-8 | Group 3-10 | Group 3-12 | Mean ± SD |
|---|---|---|---|---|
| | Plasma Concentrations (ng/ml) | | | |
| 5 min | 944 | 295 | 1016 | 752 ± 397 |
| 15 min | 2927 | 1700 | 1503 | 2043 ± 772 |
| 30 min | 2312 | 5956 | 4371 | 4213 ± 1827 |
| 45 min | 3354 | 4737 | 9082 | 5724 ± 2988 |
| 1 h | 9267 | 2693 | 4800 | 5587 ± 3357 |
| 2 h | 10399 | 9201 | 5808 | 8469 ± 2381 |
| 3 h | 5719 | 1948 | 1564 | 3077 ± 2296 |
| 5 h | 522 | 277 | 334 | 378 ± 128 |
| 9 h | 272 | 26 | 64.2 | 121 ± 133 |
| 24 h | Beyond detection limit | Beyond detection limit | Beyond detection limit | |

TABLE 6

Measured concentrations of MI-219 in the plasma samples after a single i.v. dose at 10 mg/kg in mice.

| Time | Group 4-7 | Group 4-9 | Group 4-11 | Mean ± SD |
|---|---|---|---|---|
| 5 min | 14196 | 21792 | 18135 | 18041 ± 3799 |
| 15 min | 6030 | 6397 | 5042 | 5823 ± 701 |
| 30 min | 2628 | 4347 | 3735 | 3570 ± 871 |
| 45 min | 1519 | 2225 | 1449 | 1731 ± 429 |
| 1 h | 1061 | 1285 | 1322 | 1223 ± 141 |
| 2 h | 689 | 325 | 1328 | 781 ± 508 |
| 3 h | 108 | 489 | 150 | 249 ± 209 |
| 5 h | 78.5 | 52 | 38.6 | 56.4 ± 20.3 |
| 9 h | 13.4 | 37.2 | 13.9 | 21.5 ± 13.6 |
| 24 h | BLQ | BLQ | BLQ | |

TABLE 7

PK parameters of MI-219 after a p.o. dose (50 mg/kg) in mice.

| Parameter | Group 3-8 | Group 3-10 | Group 3-12 | Mean ± SD |
|---|---|---|---|---|
| | Oral dose | | | |
| Cmax (ng/mL) | 10399 | 9201 | 9082 | 9561 ± 728 |
| Tmax (h) | 2 | 2 | 0.75 | 1.58 ± 0.72 |
| AUC 0→9 h (ng · h/mL) | 26839 | 16158 | 14622 | 19206 ± 6655 |
| MRT(h) | 2.5813 | 2.04307 | 2.2585 | 2.29 ± 0.27 |
| Kel | 0.37 | 0.69 | 0.35 | 0.47 ± 0.19 |
| T½ | 1.51 | 0.99 | 1.82 | 1.61 ± 0.53 |
| F (%) | 76.7 | 46.2 | 41.8 | 54.9 ± 19.0 |

TABLE 8

Plasma concentration of MI-219 following IV administration at 2.0 mg/kg to Beagle dogs (ng/ml).

| Dog No. | Time (h) | | | | | | | | | | |
|---|---|---|---|---|---|---|---|---|---|---|---|
| | 0.117 | 0.133 | 0.20 | 0.5 | 1.0 | 3.0 | 4.0 | 6.0 | 8.0 | 12 | 24 |
| 1 | — | 7464 | 2623 | 1888 | 853 | 367 | 256 | 114.3 | 52.2 | 17.9 | 3.55 |
| 2 | 4069 | — | 2272 | 1192 | 704 | 331 | 188 | 81.1 | 39.7 | 9.75 | 1.11 |
| 3 | 7668 | — | 3918 | 1795 | 1044 | 402 | 248 | 119 | 57.8 | 19.4 | 5.62 |
| Mean | 5868 | 7464 | 2938 | 1625 | 867 | 367 | 231 | 105 | 49.9 | 15.7 | 3.42 |
| SD | 2545 | | 867 | 378 | 170 | 36 | 37 | 21 | 9.3 | 5.2 | 2.26 |
| CV % | 43.4 | | 29.5 | 23.3 | 19.6 | 9.8 | 16.0 | 19.8 | 18.6 | 33.1 | 65.9 |

TABLE 9

Plasma concentration of MI-219 following PO administration at 10 mg/kg to Beagle dogs (ng/ml).

| Dog No. | Time (h) | | | | | | | | | |
|---|---|---|---|---|---|---|---|---|---|---|
| | 0 | 0.5 | 1 | 2 | 3 | 4 | 6 | 8 | 12 | 24 |
| 1 | BLQ | 2101 | 3560 | 2165 | 1095 | 603 | 335 | 216 | 54.68 | 4.05 |
| 2 | BLQ | 1842 | 2119 | 1002 | 474 | 312 | 177 | 72.9 | 20.0 | 3.78 |
| 3 | BLQ | 3323 | 2999 | 1333 | 708 | 535 | 470 | 245 | 63.8 | 4.48 |
| Mean | | 2422 | 2893 | 1500 | 759 | 483 | 327 | 178 | 46.2 | 4.10 |
| SD | | 791 | 726 | 599 | 314 | 152 | 147 | 92 | 23.1 | 0.35 |
| CV % | | 32.7 | 25.1 | 40.0 | 41.3 | 31.5 | 44.8 | 51.8 | 50.0 | 8.6 |
| Min | | 1842 | 2119 | 1002 | 474 | 312 | 177 | 72.9 | 20.0 | 3.78 |
| Max | | 3323 | 3560 | 2165 | 1095 | 603 | 470 | 245 | 63.8 | 4.48 |

TABLE 10

Pharmacokinetic parameters of MI-219 following IV administration at 2.0 mg/kg to Beagle dogs.

| Dog No. | T½ h | AUC0-t ng · h/ml | AUC0-∞ ng · h/ml | MRT h | Vss ml/kg | CL ml/h/kg |
|---|---|---|---|---|---|---|
| 1 | 4.32 | 8490 | 8512 | 1.22 | 286 | 235 |
| 2 | 3.00 | 3884 | 3889 | 1.81 | 929 | 514 |
| 3 | 4.36 | 6272 | 6307 | 1.87 | 591 | 317 |
| Mean | 3.90 | 6216 | 6236 | 1.63 | 602 | 355 |
| SD | 0.78 | 2303 | 2312 | 0.36 | 322 | 144 |
| Min | 3.00 | 3884 | 3889 | 1.22 | 286 | 235 |
| Max | 4.36 | 8490 | 8512 | 1.87 | 929 | 514 |
| CV % | 19.9 | 37.1 | 37.1 | 22.0 | 53.5 | 40.4 |

TABLE 11

Pharmacokinetic parameters of MI-219 following PO administration at 10 mg/kg to Beagle dogs.

| Dog No. | T½ h | Tmax h | Cmax ng/ml | AUC0-t ng · h/ml | AUC0-∞ ng · h/ml | MRT h | F % |
|---|---|---|---|---|---|---|---|
| 1 | 2.77 | 1.0 | 3560 | 9665 | 9681 | 3.09 | 22.8 |
| 2 | 3.03 | 1.0 | 2119 | 5210 | 5226 | 2.71 | 26.8 |
| 3 | 2.81 | 0.5 | 3323 | 8967 | 8985 | 3.33 | 28.6 |
| Mean | 2.87 | 0.83 | 3001 | 7947 | 7964 | 3.04 | 26.1 |
| SD | 0.14 | 0.29 | 773 | 2396 | 2396 | 0.31 | 3.0 |
| Min | 2.77 | 0.5 | 2119 | 5210 | 5226 | 2.71 | 22.8 |
| Max | 3.03 | 1.0 | 3560 | 9665 | 9681 | 3.33 | 28.6 |
| CV % | 4.9 | 35 | 25.8 | 30.2 | 30.1 | 10.2 | 11.5 |

TABLE 12

Plasma Concentration of MI-219 in Male Cynomolgus Monkeys Following Intravenous and Oral Administration.

Sampling Time Point — Plasma Concentration (ng/mL)

IV (10 mg/kg)

| Animal Number | 1 | 2 | 3 | Mean | SD |
|---|---|---|---|---|---|
| 0.083 | 15043.60 | 18669.25 |  | 16856.43 | NA |
|  |  |  |  |  | NA |
| 0.1 |  |  | 18416.30 | 18416.30 | NA |
| 0.5 | 2188.67 | 3577.55 | 3536.46 | 3100.89 | 790.28 |
| 1 | 1564.10 | 2277.17 | 2483.63 | 2108.30 | 482.46 |
| 1.5 | 1052.84 | 1867.36 | 2128.74 | 1682.98 | 561.15 |
| 2 | 985.23 | 1277.08 | 1539.44 | 1267.25 | 277.24 |
| 3 | 1230.40 | 691.83 | 834.00 | 918.74 | 279.11 |
| 4 | 348.97 | 582.63 | 562.45 | 498.02 | 129.47 |
| 6 | 246.12 | 211.39 | 324.99 | 260.83 | 58.21 |
| 8 | 180.91 | 115.94 | 202.16 | 166.34 | 44.92 |
| 24 | 5.91 | 8.00 | 8.34 | 7.42 | 1.32 |

PO (50 mg/kg)

| Animal Number | 4 | 5 | 6 | Mean | SD |
|---|---|---|---|---|---|
| 0.083 | 1.35 | 1.32 | BLQ | 1.33 | NA |
| 0.25 | 7.31 | 73.42 | 60.99 | 47.24 | 35.13 |
| 0.5 | 9.90 | 107.48 | 165.45 | 94.28 | 78.61 |
| 1 | 192.53 | 186.66 | 241.02 | 206.74 | 29.83 |
| 1.5 | 521.16 | 226.37 | 208.41 | 318.65 | 175.61 |
| 2 | 399.35 | 326.78 | 807.19 | 511.11 | 258.97 |
| 3 | 1497.78 | 691.63 | 859.30 | 1016.24 | 425.37 |
| 4 | 2219.11 | 526.86 | 618.28 | 1121.42 | 951.73 |
| 6 | 1598.28 | 503.39 | 286.55 | 796.07 | 703.14 |
| 8 | 657.93 | 175.38 | 192.15 | 341.82 | 273.89 |
| 24 | 24.18 | 18.74 | 9.89 | 17.60 | 7.21 |

BLQ: Below the limit of quantitation;
SD: Standard deviation;
NA: Nonapplicable

TABLE 13

Selected Pharmacokinetics Parameters of MI-219 in Male Cynomolgus Monkeys Following Intravenous and Oral Administration

| Animal No. | $AUC_{(0-t)}$ h * μg/L | $AUC_{(0-\infty)}$ h * μg/L | $MRT_{(0-\infty)}$ h | $T_{1/2}$ h | Vz L/kg | CLz L/h/kg | Cmax μg/L | Tmax h | F (%) |
|---|---|---|---|---|---|---|---|---|---|
| IV |  |  |  |  |  |  |  |  |  |
| 1 | 10271.39 | 10300.28 | 2.68 | 3.38 | 4.73 | 0.97 | 15043.60 |  |  |
| 2 | 11610.30 | 11647.87 | 2.12 | 3.25 | 4.03 | 0.86 | 18669.25 |  |  |
| 3 | 13662.84 | 13703.99 | 2.44 | 3.43 | 3.62 | 0.73 | 18416.30 |  |  |
| MEAN | 11848.18 | 11884.05 | 2.41 | 3.35 | 4.12 | 0.85 | 17376.38 |  |  |
| SD | 1708.19 | 1714.10 | 0.28 | 0.09 | 0.56 | 0.12 | 2024.20 |  |  |
| Oral |  |  |  |  |  |  |  |  |  |
| 1 | 14799.10 | 14905.54 | 6.25 | 3.03 | NA | NA | 2219.11 | 4.00 | 25.08 |
| 2 | 4724.43 | 4732.32 | 6.38 | 2.52 | NA | NA | 691.63 | 3.00 | 7.96 |
| 3 | 5075.71 | 5128.70 | 5.57 | 3.72 | NA | NA | 859.30 | 3.00 | 8.63 |
| MEAN | 8199.74 | 8255.52 | 6.06 | 3.09 | NA | NA | 1256.68 | 3.33 | 13.89 |
| SD | 5717.91 | 5762.50 | 0.44 | 0.60 | NA | NA | 837.69 | 0.58 | 9.70 |

NA: Nonapplicable

Detailed studies were performed to determine the metabolism of MI-219 in vitro using human and rat microsomes and in vivo using rats.

Metabolite Identification

Sample Preparation:

Metabolites in Liver Microsome Incubation:

MI-219 (or other compounds) was incubated with pooled liver microsomes in phosphate buffer at 37° C. The final concentrations of the compound, HLM, beta-NADPH, phosphate buffer and $MgCl_2$ were 20-50 μM, 1 mg/ml, 1 mM, 0.1 M and 3.3 mM, respectively, in 0.4 ml of mixture solution. The percentage of MeOH in the incubation mixture was kept less than 0.2% (v/v). Samples were incubated for 60 min and the reaction was terminated with 1.2 mL of ice-cold acetonitrile to precipitate proteins. Two different controls were prepared by using boiled microsomes (100° C. for 5 min) or spiking MI-219 after protein precipitation. Samples were subsequently centrifuged at 14,000 rpm for 5 min. The supernatant was analyzed by LC/MS/MS.

Metabolites in rat plasma: MI-219 was i.v. injected into male Sprague-Dawley rats (n=6, weight range 200-220 g) sat a dose of 5 mg/kg. MI-219 was i.v. injected at a dose of 5 mg/kg. Blood samples were collected from the retro-orbital plexus of rats under light ether anesthesia into microfuge tubes containing heparin as an anti-coagulant at 0.166, 0.5, 1, 2, 4, 6, 8, and 24 h post-injection. Plasma was harvested by centrifuging the blood at 13000 rpm for 5 min at 4° C. and stored frozen at −80±10° C. until analysis.

Screening and characterization of metabolites with LC-MS/MS: MI-219 and other compounds were injected into mass spectrometer to obtain their MS, $MS^2$ and $MS^3$ spectra. Based on the similarities and difference among their mass spectra, the possible fragmentation pathways of protonated MI-219 and several lead compounds were proposed. Three characteristic product ions were selected to generate 240 ion channels for MRM screening by using Metabolite ID software (Applied Biosystems), including 40 common biotransformation processes. To search all the metabolites, two other scan modes, EMS full scan and precursor scan were also conducted. Only the components detected in the sample and absent in all the control samples were regarded as possible metabolites. To identify the possible metabolites, both the sample and controls were injected on the LC-MS for EPI and $MS^3$ scans to obtain their $MS^2$ and $MS^3$ spectra. Based on the $M5^2$, $MS^3$ spectra of the metabolites and the proposed fragmentation pathways of MI-219 and other compounds, the metabolites were characterized.

FIG. 13A-D shows the MS/MS spectra of protonated MI-219, MI-142, MI-63 and MI-708B. Based on these MS/MS spectra and $MS^3$ spectra of the major product ions such as m/z 496, 419, 363, 320, 285, 188, the fragmentation pathways of protonated MI-219 were proposed (Scheme 5). Supporting evidence for the proposed fragmentation was obtained by tracking the functional groups of the MI-219 derivatives. The presence and absence of mass shifts of the product ions provide the structural information the product ions.

Scheme 5. Proposed fragmentation pathways of protonated MI-219.

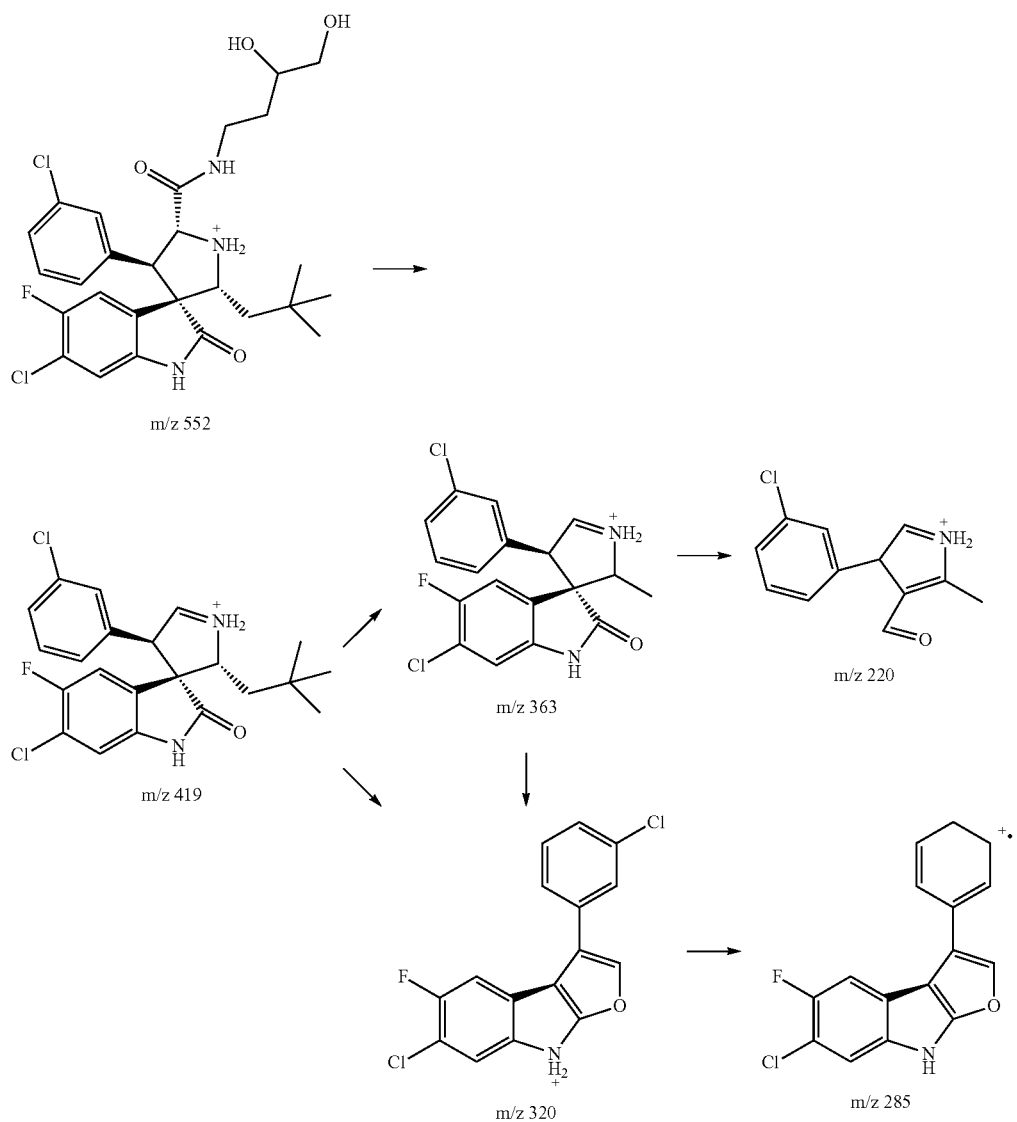

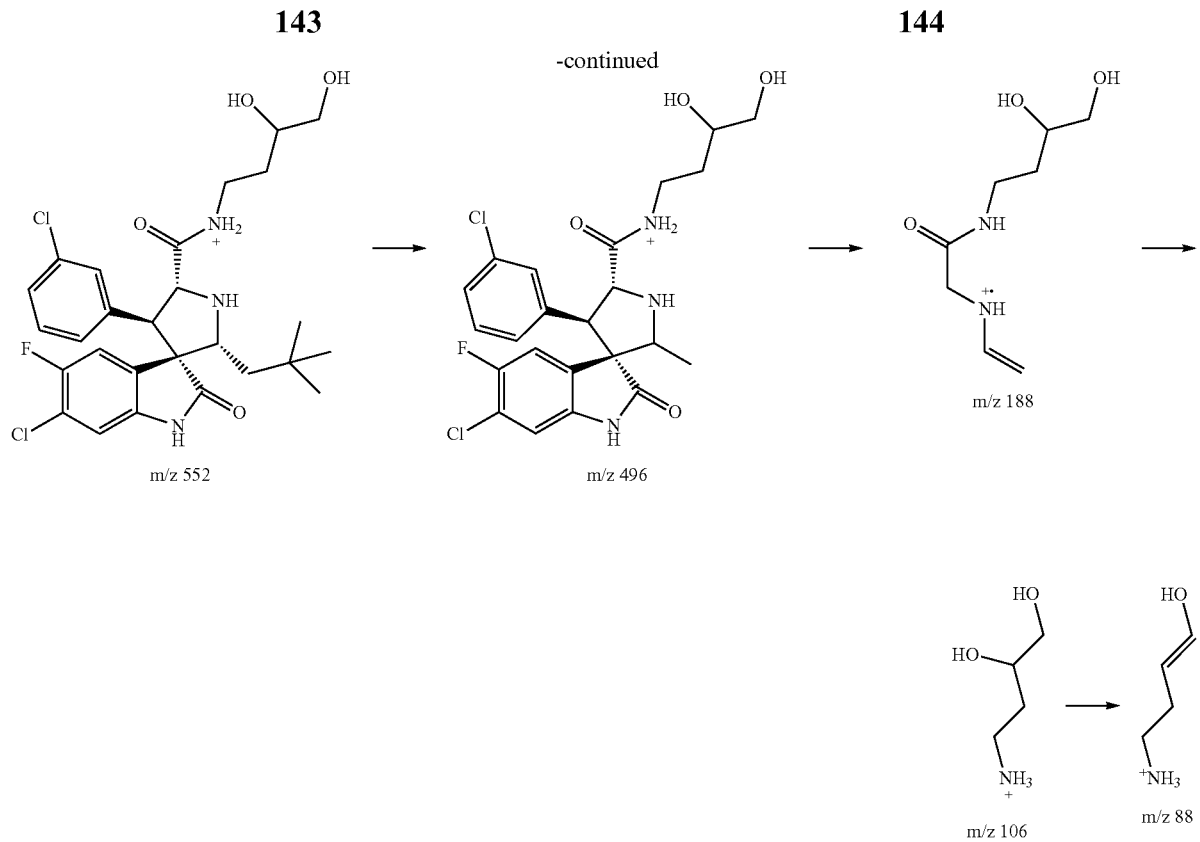

Figure 14A:
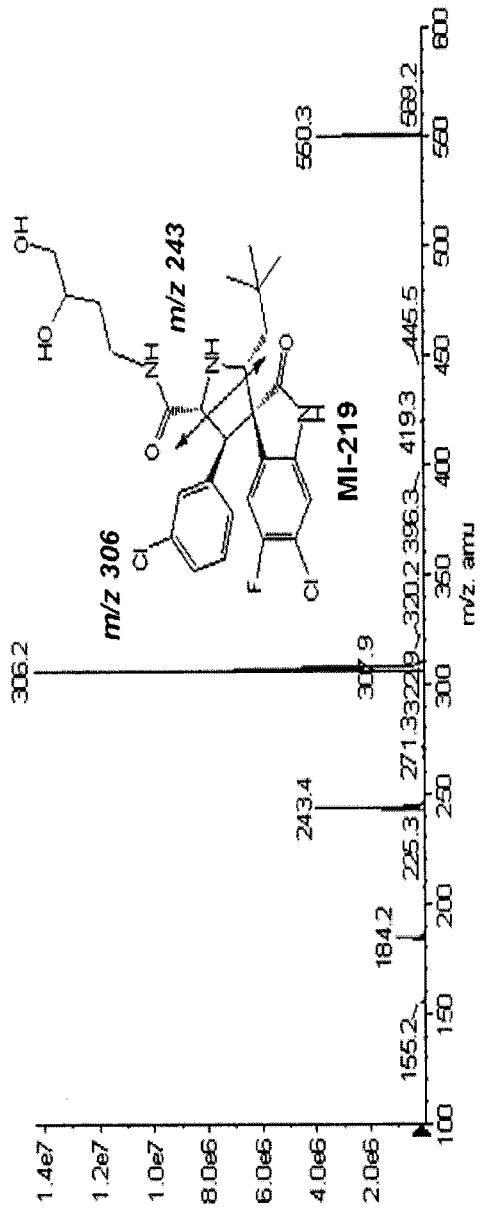
FIG. 14A-B are two MS/MS spectra of deprotonated MI-219 and MI-142, respectively.
Figure 14B:
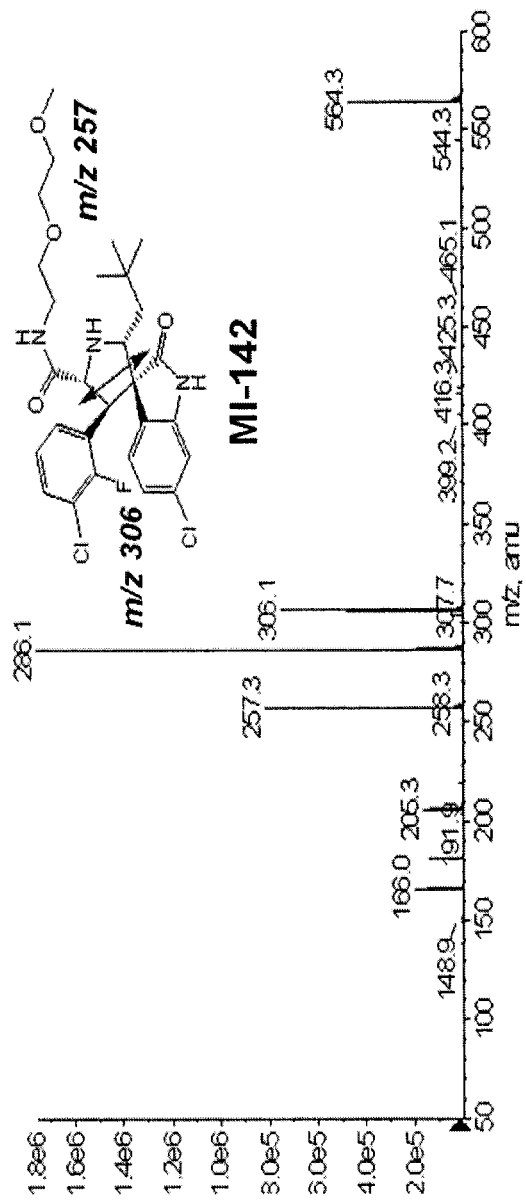

FIG. 14A-B shows the MS/MS spectra of deprotonated MI-219 and MI-142. The product ion m/z 306 was detected in the MS/MS spectra of both two compounds. The product ion of MI-219 at m/z 243 and the product ion of MI-142 at m/z 257 suggested the product ions of MI-219 at m/z 306 and 243 were generated by cleaving the pyrrolidine ring. The metabolites of MI-219 were tentatively elucidated by comparing their major product ions with that of MI-219.

Figure 15A:
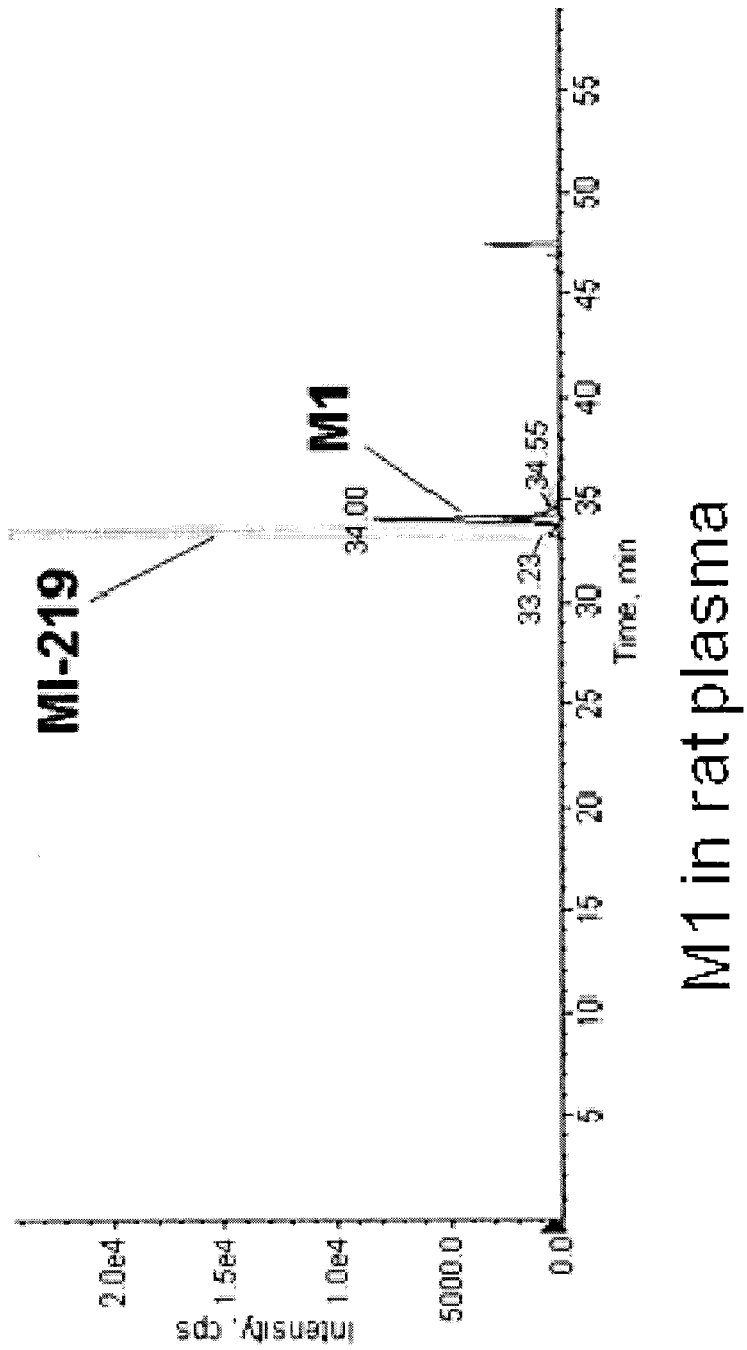
FIG. 15A-D are four LC-MS chromatograms and MS/MS spectra of Ml in rat plasma (A and B) and synthetic Ml (C and D).
Figure 15B:
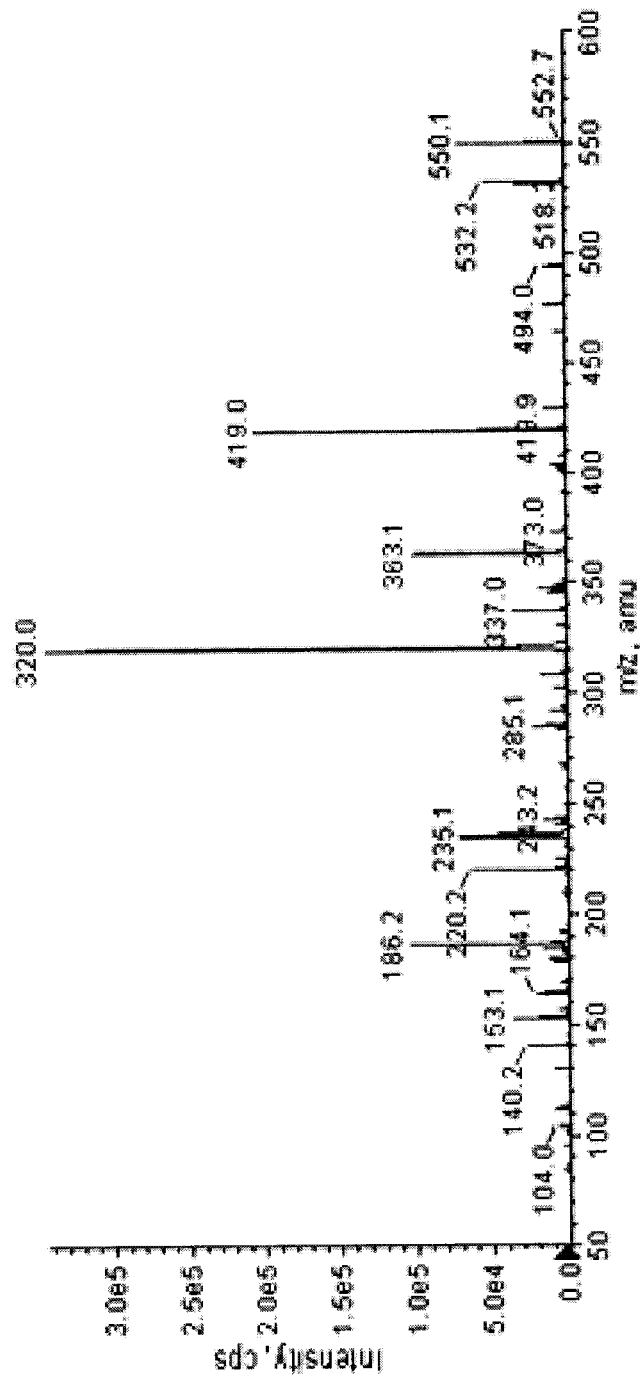
Figure 15C:
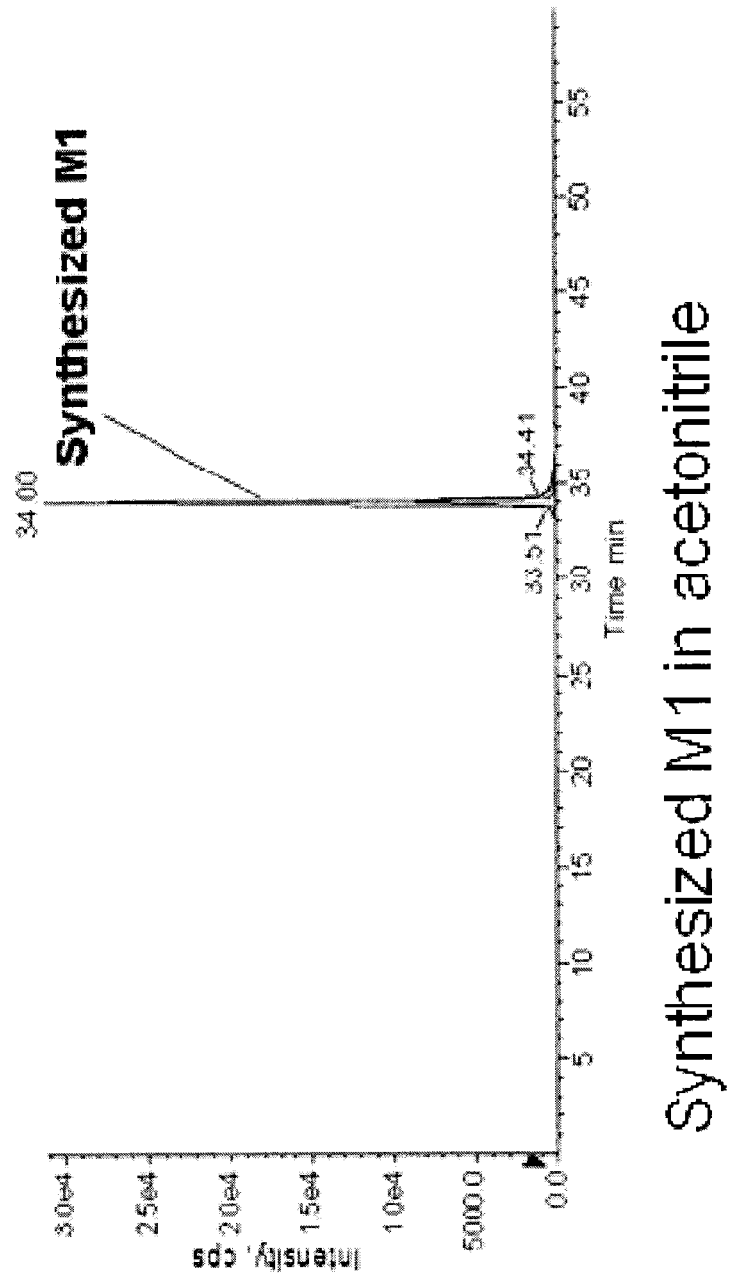
Figure 15D:
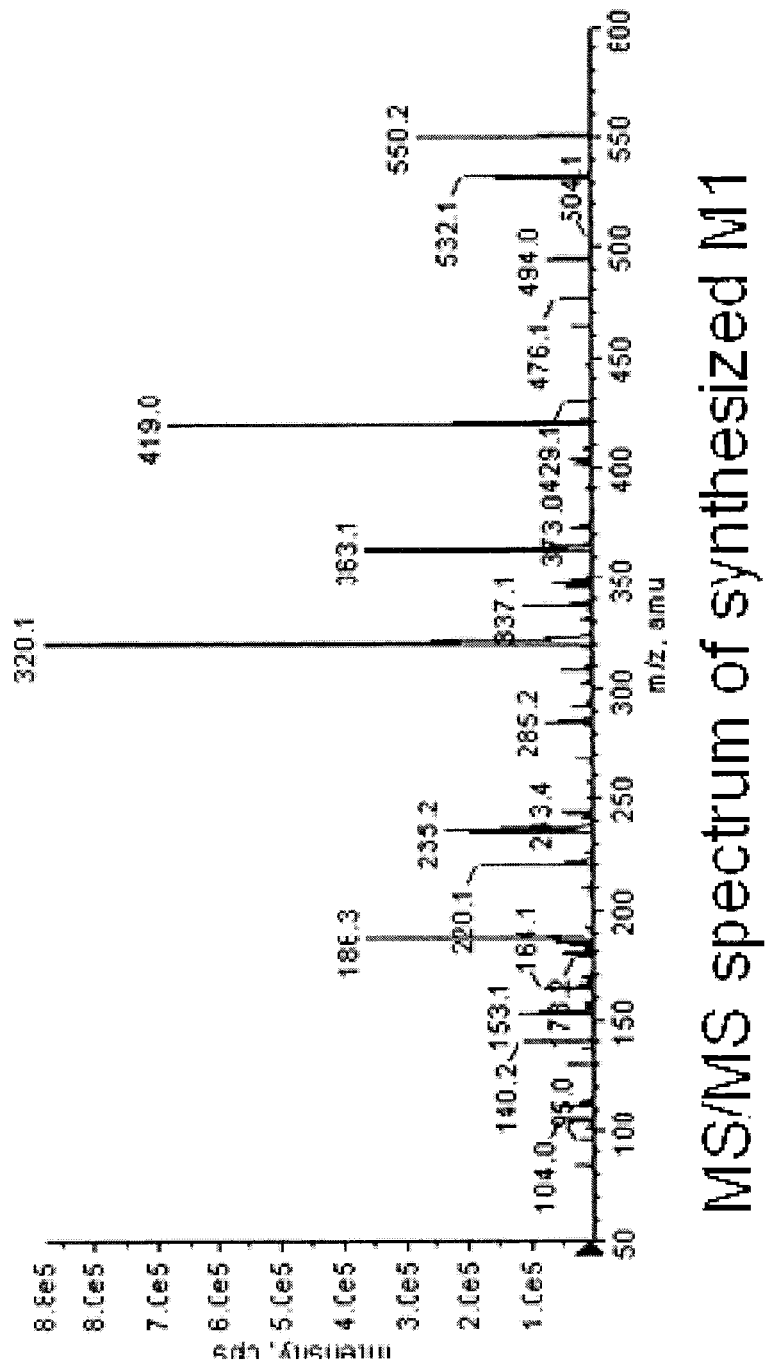

FIG. 15B shows the MS/MS spectrum of M1. The presence of m/z 419, 363, 320 and 285 suggested that the metabolic site was not on the core structure. The detection of product ions at m/z 186 and 104, which have a mass shift of 2 Da compared with m/z 188 and 106 of MI-219, suggested that the dehydrogenation occurred on the side chain. To confirm the structure of M1, two ketone compounds were synthesized by oxidizing either hydroxyl group of MI-219. The two compounds were found to be interconvertible. FIGS. 15A and 15C show that the synthesized compound exhibited the same HPLC retention time and mass spectral pattern, suggesting that M1 is derived from the oxidation of one hydroxyl group of MI-219.

Figure 16:
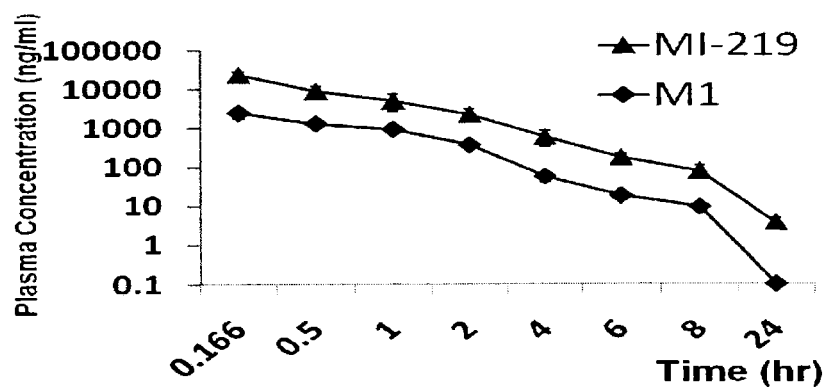
FIG. 16 is a line graph showing plasma concentrations of MI-219 and Ml in the rats.

FIG. 16 shows the plasma concentrations of MI-219 and M1 in the rats. The elimination rates of the two compounds are similar.

Figure 17A:
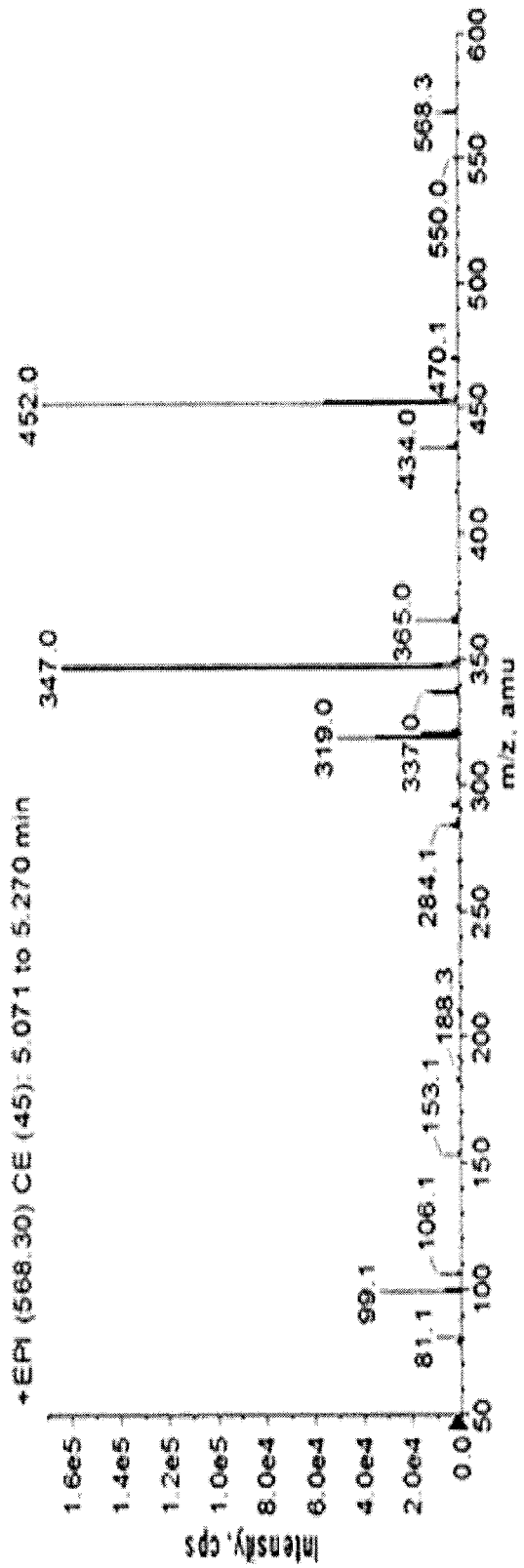
FIG. 17A-B are two MS/MS spectra of protonated M2 (A) and deprotonated M2 (B).
Figure 17B:
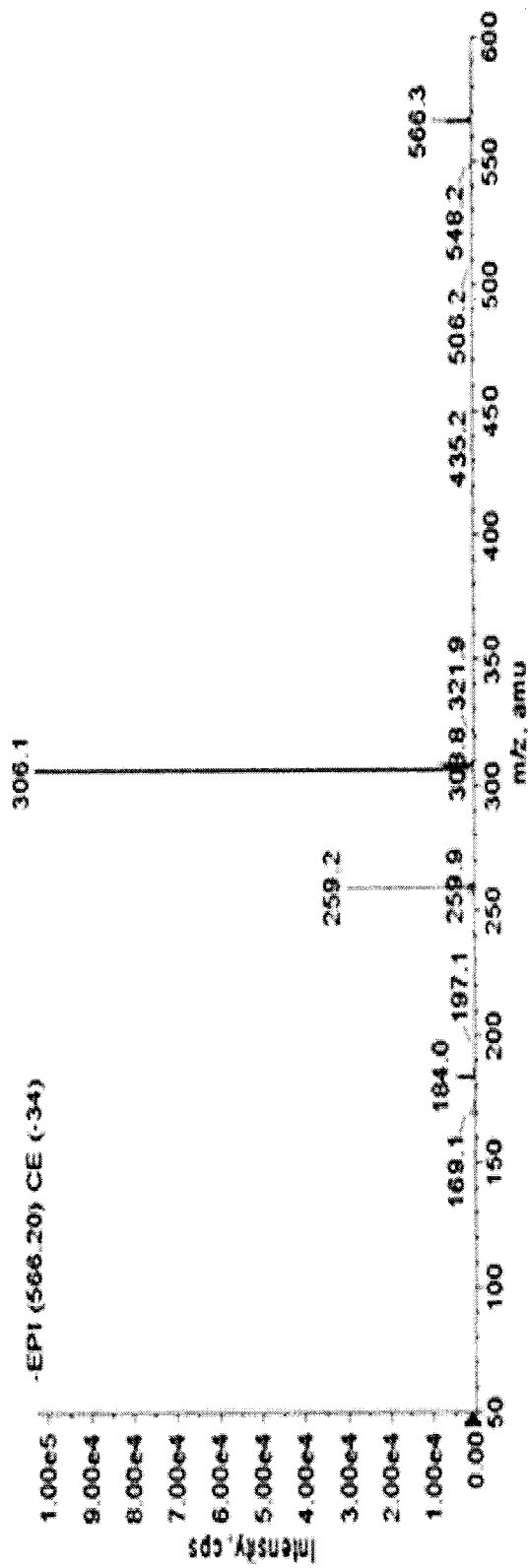
Figure 18A:
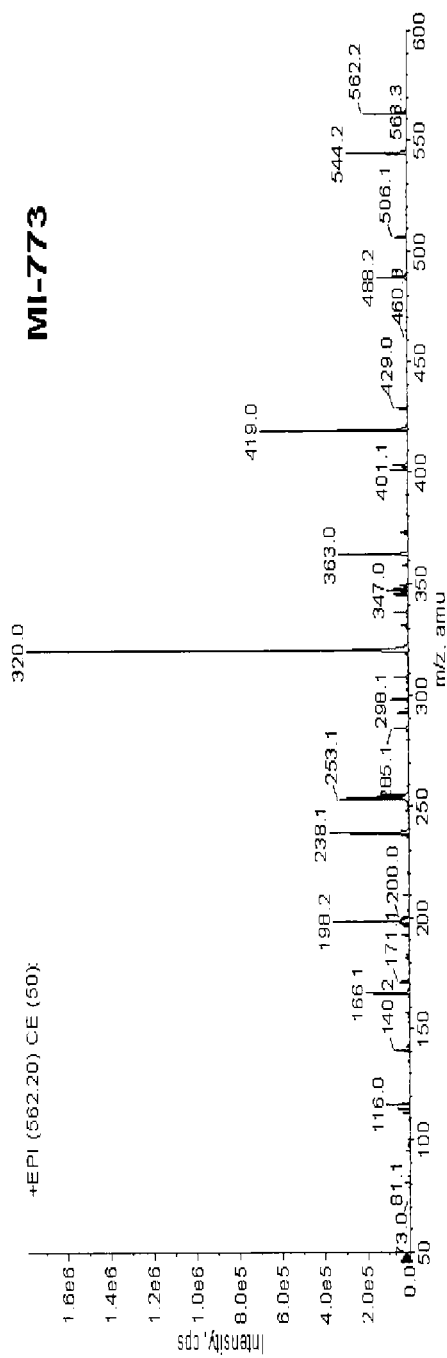
FIG. 18A-D are four MS/MS spectra of protonated MI-773 and three metabolites M1, M2 and M3.
Figure 18B:
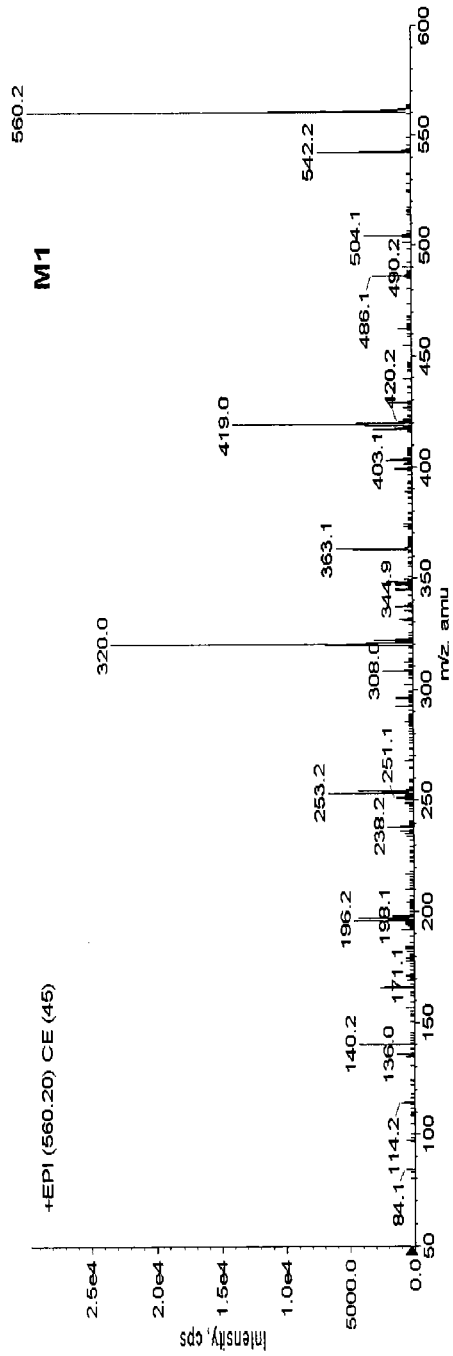
Figure 18C:
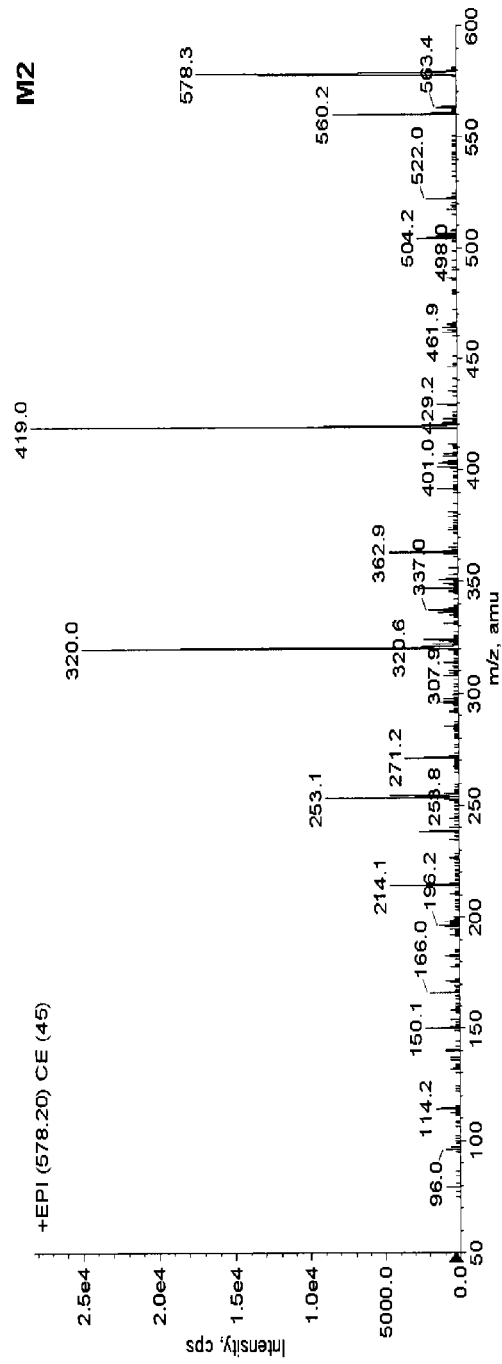
Figure 18D:
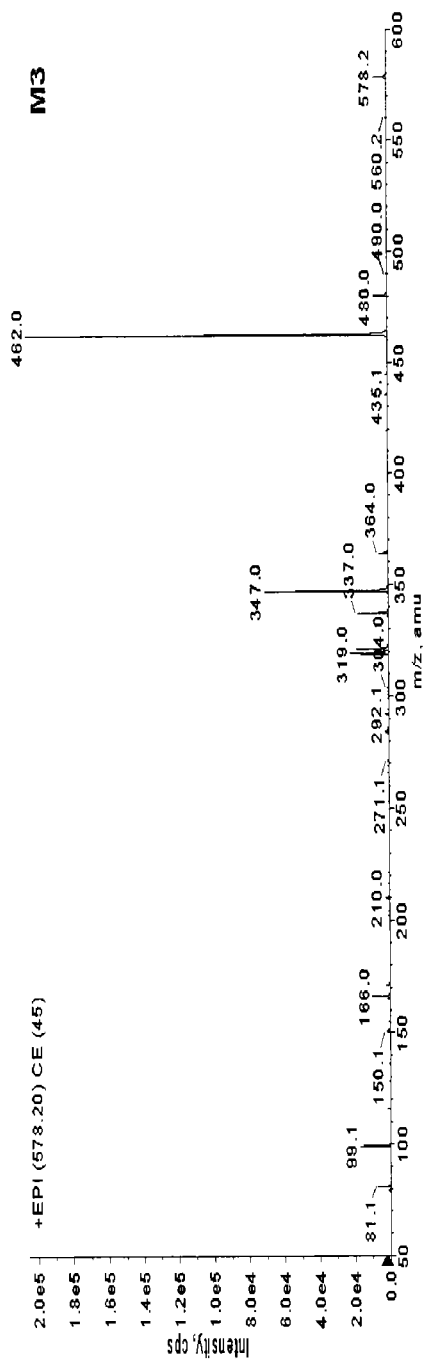

Besides M1, another metabolite (M2) with a molecular weight of 567 Da was detected at 4.76 min on the chromatogram. FIG. 17 shows the MS/MS spectra of protonated M2 (A) and deprotonated M2 (B). M2 showed a mass shift of 16 Da compared with MI-219, suggesting that the biotransformation was probably hydroxylation. The absence of m/z 419 and 320 in FIG. 17A suggested that the hydroxylation occurred on the core structure. The presence m/z 306 and 259 in FIG. 17B indicated that the hydroxylation occurred on the m/z 243 moiety of MI-219. Hence, it is inferred that the hydroxylation occurred on the 3,3-dimethylbutan-1-amine moiety. The loss of 116 Da from m/z 568 to m/z 452 is attributed to the elimination of hydroxylized 3,3-dimethylbutan-1-amine radical. This radical loss of 116 Da was also detected in the hydroxylized metabolites of other MI-219 analogues such as MI-773, MI-519-63 and MI-519-64, which is discussed later. The hydroxylation of the amine is expected to facilitate the homolysis of the N—C bond. Hence, the hydroxyl group is assigned to the amine of pyrrolidine ring.

Besides M1 and M2, the other 6 metabolites of MI-219 in human liver microsome incubation were tentatively characterized. Their possible structures, chromatographic retention times, characteristic product ions and peak areas are listed in Table 14.

TABLE 14

Metabolites of MI-219 in human liver microsome incubations

| Metabolites | Peak area (counts) | Retention time (min) | [M + H]+ and product ions |
|---|---|---|---|
| M1 | 5.7 × 10⁸ | 6.52 | 550 [M + H]+ 419 363 320 235 186 104 |
| M2 | 8.1 × 10⁷ | 4.76 | 568 [M + H]+ 452 347 319 |

TABLE 14-continued
Metabolites of MI-219 in human liver microsome incubations
| Metabolites | Peak area (counts) | Retention time (min) | $[M + H]^+$ and product ions |
|---|---|---|---|
| 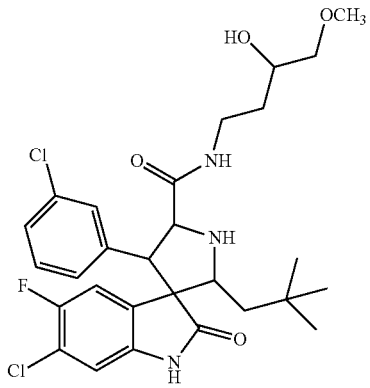 [SMILES: COCC(O)CCNC(=O)C1NC(CC(C)(C)C)C2(C(=O)Nc3cc(Cl)c(F)cc32)C1c1cccc(Cl)c1] | $7.7 \times 10^6$ $1.1 \times 10^7$ | 6.19 and 6.28 | 566 $[M + H]^+$ 492 419 320 210 182 |
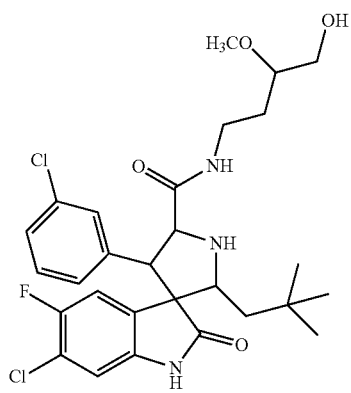 [SMILES: COC(CO)CCNC(=O)C1NC(CC(C)(C)C)C2(C(=O)Nc3cc(Cl)c(F)cc32)C1c1cccc(Cl)c1]
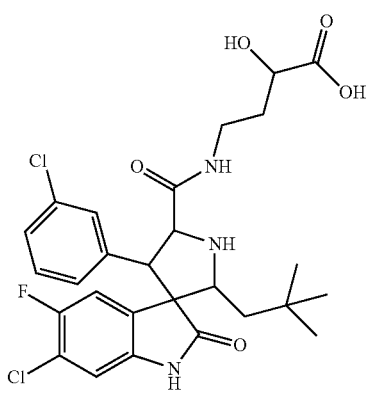
M3

TABLE 14-continued
Metabolites of MI-219 in human liver microsome incubations
| Metabolites | Peak area (counts) | Retention time (min) | [M + H]+ and product ions |
|---|---|---|---|
| 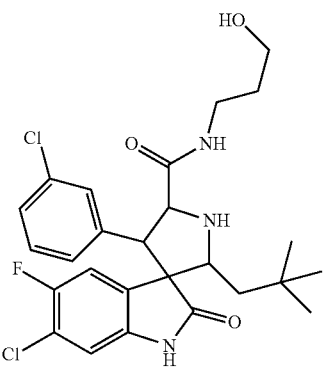 M4 | $2.4 \times 10^6$ | 6.77 | 522 [M + H]+ 419 320 235 220 158 |
| 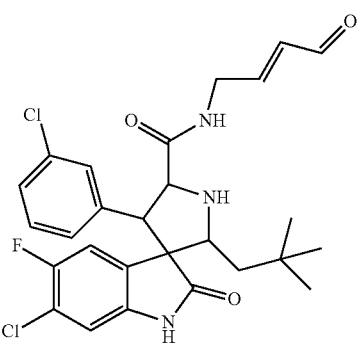 M5 | $4.1 \times 10^7$ | 6.55 | 532 [M + H]+ 419 320 220 |
| 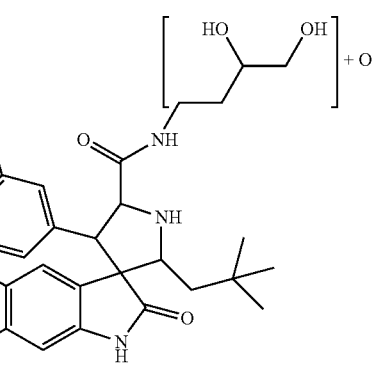 M6 | $2.4 \times 10^7$ | 6.20 | 568 [M + H]+ 464 419 320 204 122 |

TABLE 14-continued

Metabolites of MI-219 in human liver microsome incubations

| Metabolites | Peak area (counts) | Retention time (min) | [M + H]+ and product ions |
|---|---|---|---|
| 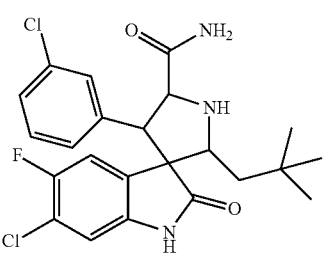M7 | 8.9 × 10⁶<br>1.5 × 10⁷<br>5.9 × 10⁶ | 6.34, 6.76, and 7.05 | 464<br>[M + H]+<br>419<br>320<br>285<br>153 |
| 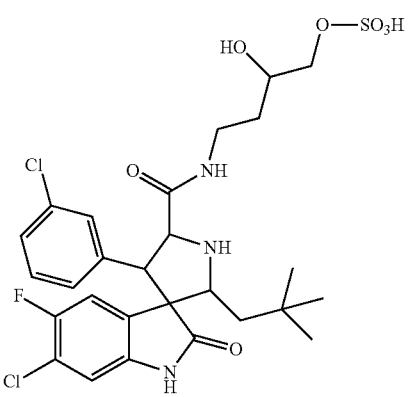 | 3.2 × 10⁷ | 6.57 | 632<br>[M + H]+<br>550<br>533<br>419<br>320<br>225<br>168 |
| 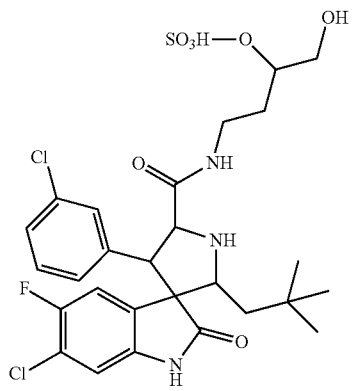M8 | | | |

Metabolism studies thus established that the primary metabolic site in MI-219 is on its "tail." Furthermore, since two other promising MDM2 inhibitors, MI-147 and MI-319, also contain the same diol tail, their tail is also susceptible for quick metabolism. The compounds provided herein include new MDM2 inhibitors with different tails that may afford improved metabolic stability. In addition, for the purpose of drug development, it is highly desirable to obtain new MDM2 inhibitors with not only improved metabolic stability but also good oral bioavailability.

Direct modifications on the "diol" tail, which led to a series of new compounds, e.g., MI-519-24, MI-519-28, MI-519-29, MI-519-31, and MI-758. Binding experiments showed that these new analogues bind to MDM2 with good affinities (Table 19A). Furthermore, they also effectively inhibit cell growth in tumor cell lines with wild-type p53 and show selectivity over tumor cell lines with mutated or deleted p53, consistent with their mechanism of action.

Microsomal stability studies showed that MI-758, MI-519-24, MI-519-28 and MI-519-29 have an improved stability over MI-219 in rat liver microsomes. MI-758 and MI-519-28 also have an improved stability over MI-219 in human liver microsomes. These data indicate that the microsomal stabilities for the same compounds may be quite different between rat and human microsomes (Table 15).

TABLE 15

Microsomal stability studies of MDM2 inhibitors. The microsomal stability of these compounds was evaluated together using the same batch of rat or human liver microsomes.

|  | Time (min) | AT-219 | MI-758 | MI-519-24 | MI-519-28 | MI-519-29 | MI-519-31 |
|---|---|---|---|---|---|---|---|
| Rat Microsome | 0 | 100.00% | 100.00% | 100.00% | 100.00% | 100.00% | 100.00% |
|  | 5 | 90.48% | 96.52% | 102.16% | 92.34% | 93.42% | 80.22% |
|  | 10 | 80.58% | 92.93% | 86.33% | 87.59% | 84.91% | 65.69% |
|  | 15 | 72.12% | 82.50% | 75.72% | 86.13% | 82.81% | 57.57% |
|  | 30 | 53.75% | 73.32% | 68.24% | 71.97% | 70.75% | 42.91% |
|  | 45 | 48.85% | 69.33% | 66.08% | 65.40% | 71.89% | 34.31% |
|  | 60 | 49.62% | 66.93% | 61.51% | 61.79% | 69.91% | 32.81% |
|  | T(½) min | 33.15 | 79.82 | 48.52 | 74.56 | 61.30 | 18.69 |
| Human Microsome | 0 | 100.00% | 100.00% | 100.00% | 100.00% | 100.00% | 100.00% |
|  | 5 | 97.51% | 95.88% | 57.08% | 91.87% | 70.67% | 78.11% |
|  | 10 | 88.37% | 89.21% | 53.92% | 89.02% | 56.31% | 58.15% |
|  | 15 | 81.51% | 81.61% | 49.62% | 77.40% | 49.52% | 45.42% |
|  | 30 | 58.25% | 65.20% | 47.41% | 66.83% | 45.48% | 22.75% |
|  | 45 | 50.70% | 54.52% | 41.18% | 55.85% | 40.08% | 13.25% |
|  | 60 | 42.15% | 51.45% | 41.42% | 53.78% | 35.28% | 8.56% |
|  | T(½) min | 37.03 | 49.47 | 11.24 | 54.11 | 12.07 | 13.01 |

Analogues containing different "tail" groups (Chart 2) were also investigated to further examine what kinds of tails would be more stable in rat or human liver microsomes. The microsomal stability data for these analogues are summarized in Table 16. The microsomal stability data showed that MI-122 and MI-126 have an improved rat microsomal stability over MI-219.

Chart 2

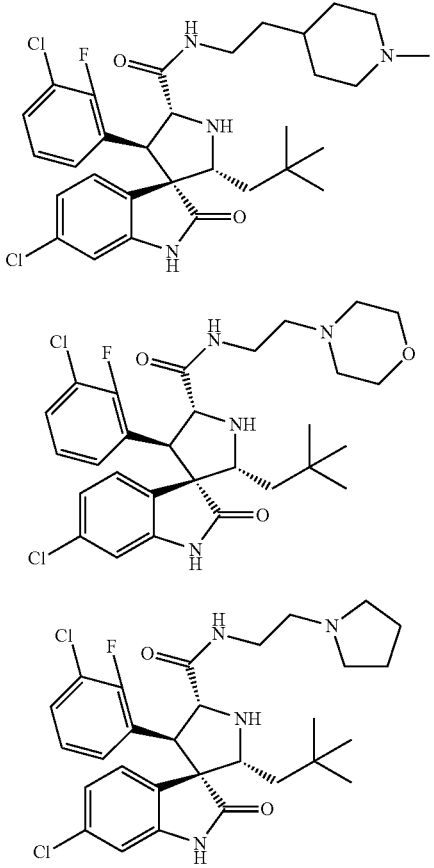

MI-122

MI-63

MI-120

-continued

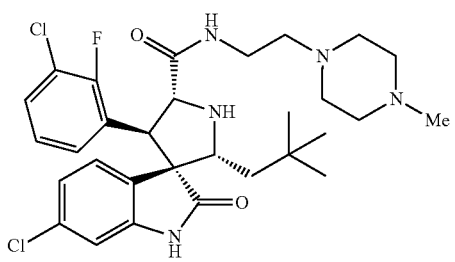

MI-126

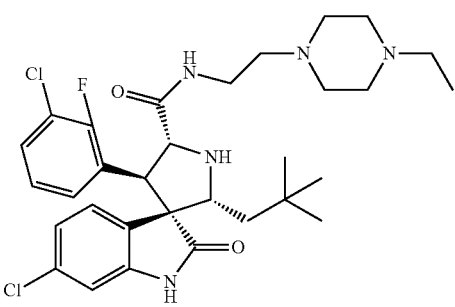

MI-129

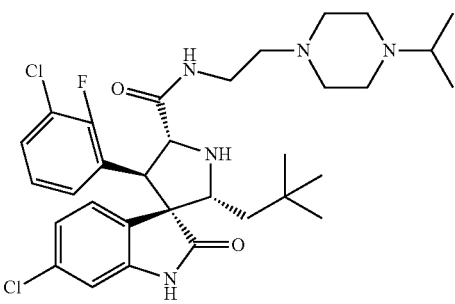

MI-130

-continued

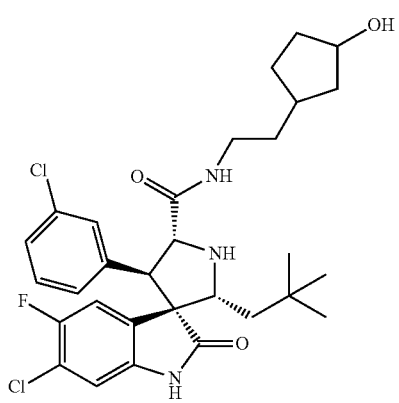

MI-225

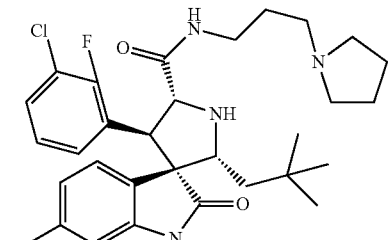

M-519-43

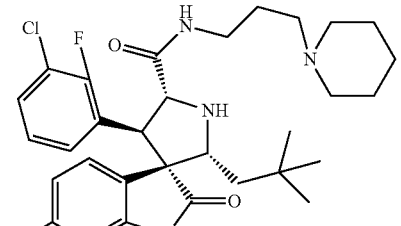

M-519-44

TABLE 16

Microsomal stability of MDM2 inhibitors in rat liver microsomes.

| | % of compound remaining When incubated in rat liver microsomes at indicated time (min) | | | | | |
|---|---|---|---|---|---|---|
| | 0 | 4 | 6 | 10 | 15 | 30 |
| MI-219 (AT-219) | 100 | 76.6 | 64.3 | 57.3 | 51.9 | 49.3 |
| MI-63 | 100 | 76 | 57.9 | 35.4 | 27.7 | 21 |
| MI-120 | 100 | 95.1 | 88.1 | 84.7 | 82.1 | 79 |
| MI-122 | 100 | 96.3 | 95.6 | 87.8 | 86.5 | 82.7 |
| MI-130 | 100 | 77.2 | 60.1 | 48 | 42.3 | 34.1 |
| MI-126 | 100 | 88.4 | 77.2 | 65.6 | 62.3 | 60.4 |
| MI-129 | 100 | 74.4 | 52.5 | 41.1 | 36.7 | 33.1 |
| MI-225 | 100 | 63.1 | 56.6 | 44.4 | 30.9 | 30.2 |

Based upon the improved microsomal stability, a series of new analogues were designed and synthesized (Chart 3). The microsomal stability test showed that MI-519-40, MI-519-43 and MI-763 have an improved microsomal stability over MI-219, whereas several others have comparable or inferior microsomal stability as compared to MI-219 (Table 17).

Chart 3

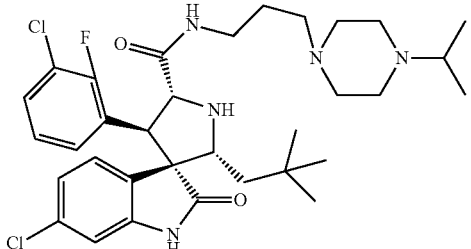

M-519-45

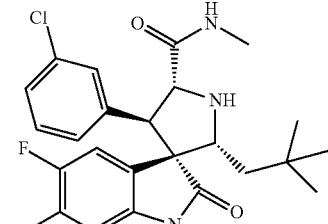

M-519-40

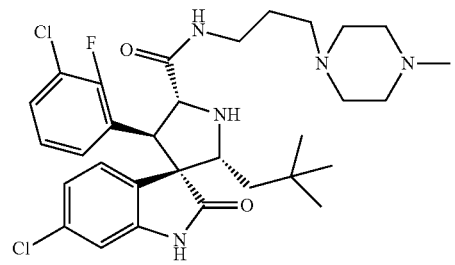

M-519-46

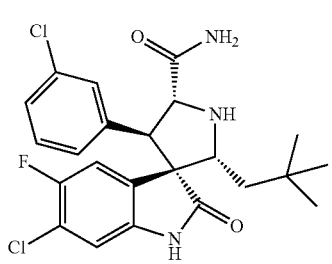

M-519-41

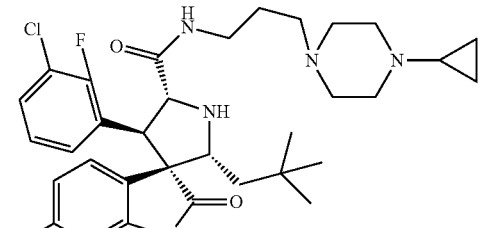

M-519-47

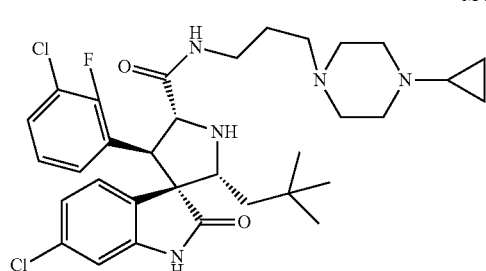

M-519-48

M-748
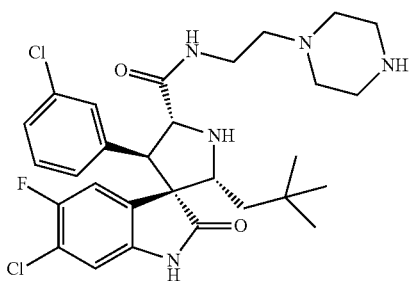

M-749
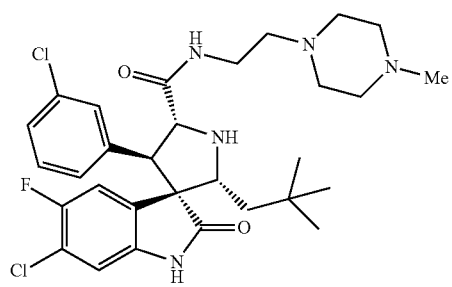

MI-751
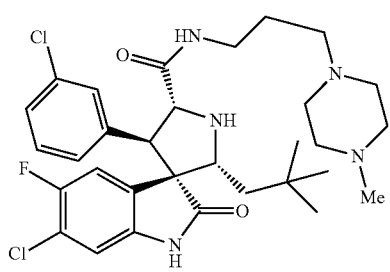

MI-763
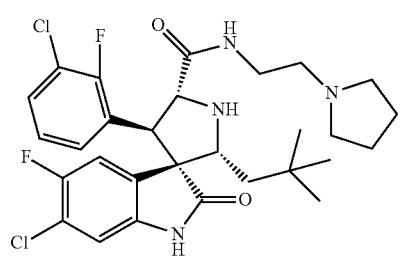

MI-764
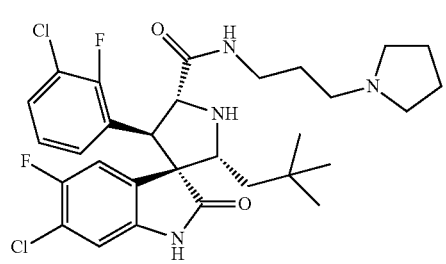

TABLE 17

Microsomal stability of previous synthesized MDM2 inhibitors in rat liver microsomes.

| | % of compound remaining When incubated in rat liver microsomes at indicated time (min) | | | | | |
|---|---|---|---|---|---|---|
| | 0 | 4 | 6 | 10 | 15 | 30 |
| MI-219 (AT-219) | 100 | 76.6 | 64.3 | 57.3 | 51.9 | 49.3 |
| MI-519-40 | 100 | 84.2 | 70.1 | 59.6 | 58.7 | 57.6 |
| MI-519-41 | 100 | 84.2 | 80.4 | 66.1 | 55.4 | 42.9 |
| MI-519-43 | 100 | 92.3 | 86.1 | 70.6 | 69.9 | 62.5 |
| MI-519-44 | 100 | 85.6 | 74.7 | 66.4 | 61.2 | 42.5 |
| MI-519-45 | 100 | 81.1 | 59.6 | 50.7 | 44.3 | 38.5 |
| MI-519-46 | 100 | 83.8 | 70.9 | 53.9 | 53.4 | 38.3 |
| MI-519-47 | 100 | 80.1 | 61.1 | 45.3 | 38.1 | 34.3 |
| MI-519-48 | 100 | 79.8 | 64.8 | 48.5 | 45.2 | 43.7 |
| MI-748 | 100 | 79.1 | 69.7 | 61.5 | 49.9 | 43.7 |
| MI-749 | 100 | 82.9 | 58.4 | 54.2 | 42.7 | 23 |
| MI-751 | 100 | 83.1 | 62.9 | 50.1 | 41.6 | 31.1 |
| MI-763 | 100 | 96.8 | 97.3 | 85.6 | 72.1 | 61.5 |
| MI-764 | 100 | 87.8 | 76.5 | 66.5 | 63.9 | 55.8 |

Since it is highly desirable to obtain orally bioavailable compounds, several MDM2 inhibitors were evaluated for their pharmacokinetic properties in rats. The data are summarized in Table 18. Unfortunately, MI-122, MI-126, MI-519-24, MI-519-28 and MI-519-29, which have an improved microsomal stability over MI-219, have much inferior oral pharmacokinetic parameters in rats as compared to AT-219. One exception is MI-758, which shows good oral bioavailability and pharmacokinetic parameters. These data indicate that it is difficult to design MDM2 inhibitors with an improved microsomal stability and good pharmacokinetic properties when dosing orally. Interestingly, MI-225, which has an inferior microsomal stability to MI-219, has a good oral bioavailability.

TABLE 18

Pharmacokinetic parameters of MDM2 inhibitors in male rats with oral dosing.

| Compounds | Oral Dose (mg/kg) | $C_{max}$ (ng/ml) | $AUC_{(0-t)}$ (hr * mg/L) | $T_{1/2}$ (hr) | % F |
|---|---|---|---|---|---|
| MI-219 | 25 | 3751 ± 1068 | 7677 ± 328 | 1.4 ± 0.1 | 65 |
| MI-122 | 25 | 120 ± 112 | 1078 ± 891 | 7.1 ± 1.8 | 14 |
| MI-126 | 25 | 274 ± 82 | 1888 ± 515 | 3.8 ± 0.5 | 31 |
| MI-519-24 | 15 | 35 ± 23 | 101 ± 62 | 3.2 ± 1.4 | 1.1 |
| MI-519-28 | 15 | 102 ± 46 | 419 ± 239 | 1.6 ± 0.2 | 8.4 |
| MI-519-29 | 15 | 51 ± 30 | 28 ± 15 | 6.9 ± 7.5 | <1 |
| MI-758 | 15 | 1494 ± 1125 | 4282 ± 2690 | 1.9 ± 0.1 | 38 |

Based upon these data, it is proposed that in order to achieve good oral bioavailability for MDM2 inhibitors, a charge neutral "tail" is preferred. Furthermore, MI-225 achieved a good oral bioavailability, although it has an inferior microsomal stability to MI-219. Therefore, a number of compounds containing a 4-, 5- and 6-membered ring with a hydroxyl group attached to it for the "tail" were prepared.

Biological testing showed that the configuration of the hydroxyl group plays an important role for cellular activity, which was not expected. For example, MI-519-60 is more potent than its epimer MI-519-63, and MI-519-64 is more potent than its epimer MI-519-65, in inhibition of cell growth in multiple cancer cell lines with wild-type p53 (Table 19A).

Microsomal stability studies showed that while MI-519-51 has an inferior stability to MI-219 in both human and rat liver microsomes, MI-773 is more stable than MI-219 in human liver microsomes and MI-519-63 has a comparable microsomal stability to MI-219 (Tables 21-24).

Pharmacokinetic studies were performed on MI-519-51 and MI-773 and the data are summarized in Tables 25-26. The PK data showed that while MI-519-51 has inferior overall PK parameters to MI-219 in both intravenous and oral routes of dosing, MI-773 has improved PK parameters over MI-219 in both intravenous and oral routes of dosing. For example, the AUC values in both routes of administration for MI-773 are 2-times higher than that for MI-219 at the same dose. These data indicated that MI-773 has a good pharmacokinetic profile in both intravenous and oral routes of dosing in rats and a good oral bioavailability. Furthermore, the major difference in their pharmacokinetic parameters between MI-519-51 and MI-773 cannot be predicted based upon their chemical structures.

To facilitate the design of new MDM2 inhibitors to further improve their overall PK profiles, metabolism studies on MI-773 and MI-519-63 were performed.

The major metabolites of MI-773 in human liver microsome incubation were characterized. FIGS. 18A-D show the MS/MS spectra of protonated MI-773 and three metabolites of MI-773 (M1, M2 and M3). As shown in the MS/MS spectra of M1 and M2, the presence of m/z 419 and 320 suggested the dehydrogenation and hydroxylation did not occur on the core structure. The presence of m/z 114, a mass shift of 2 Da compared with m/z 116 of protonated MI-773, indicated that the metabolic sites located on the cyclohexane side chain. The chemical structures of MI-773 and M1 are shown in Chart 4.

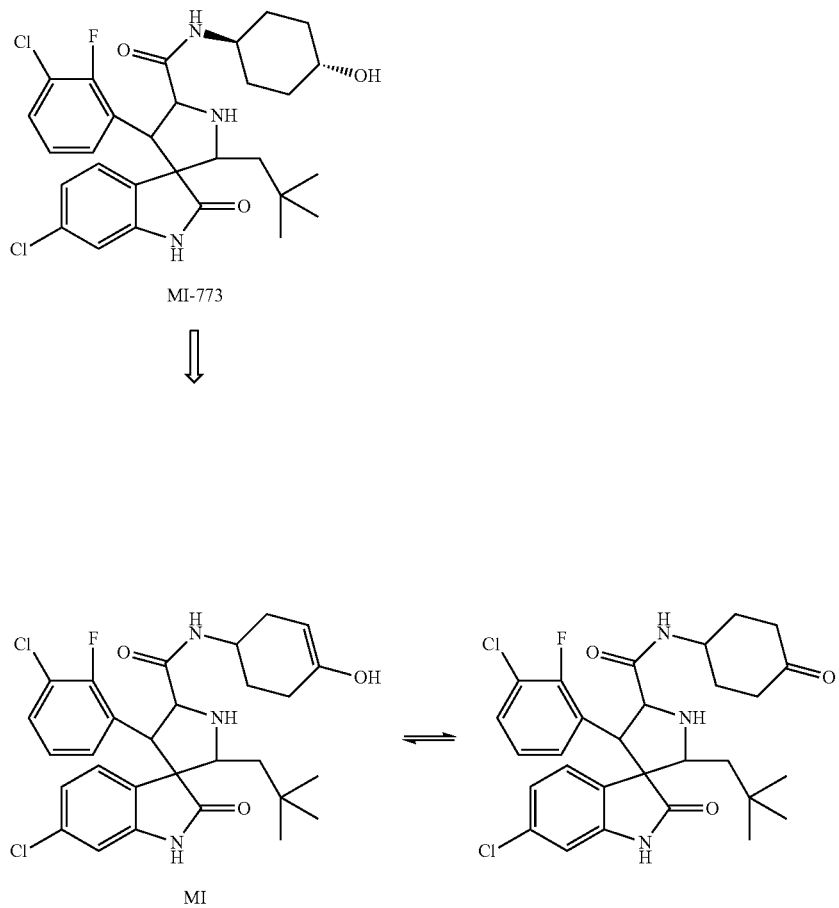

Figure 19A:
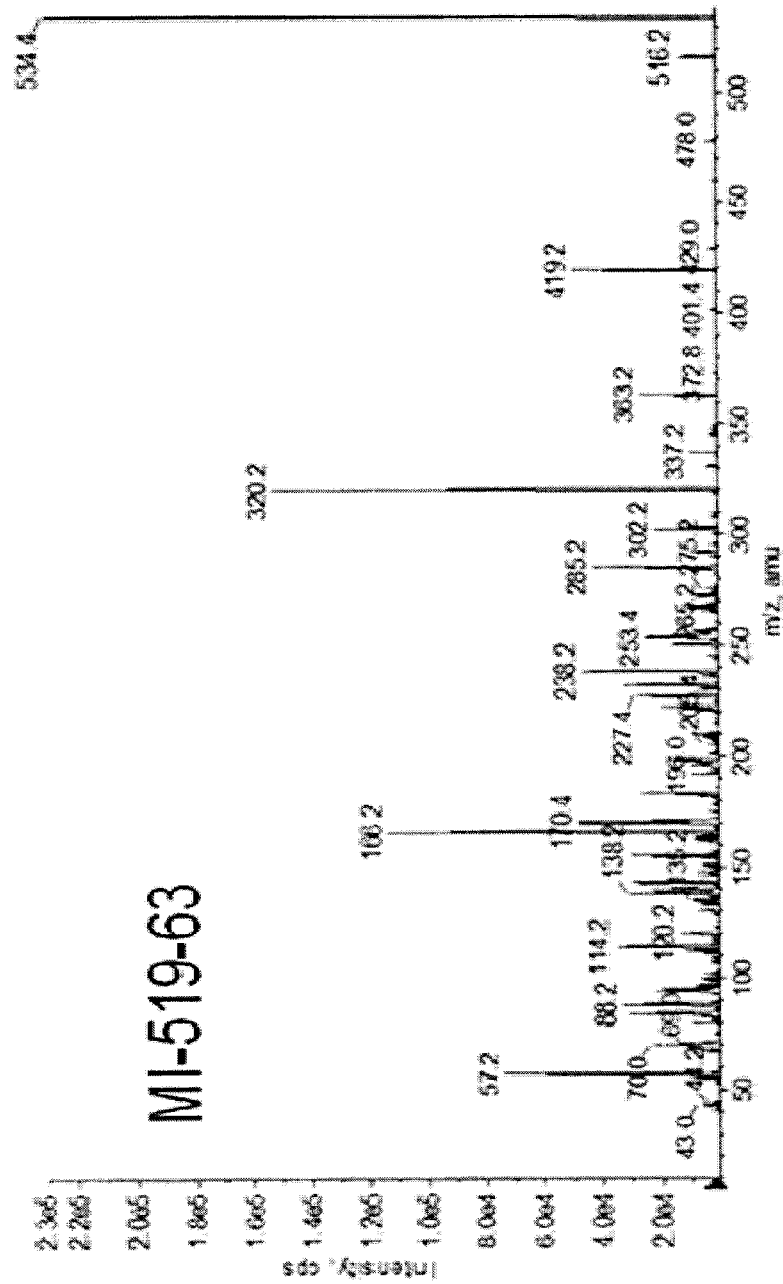
FIG. 19A-C are three MS/MS spectra of protonated MI-519-63 and its metabolites M1 and M2.
Figure 19B:
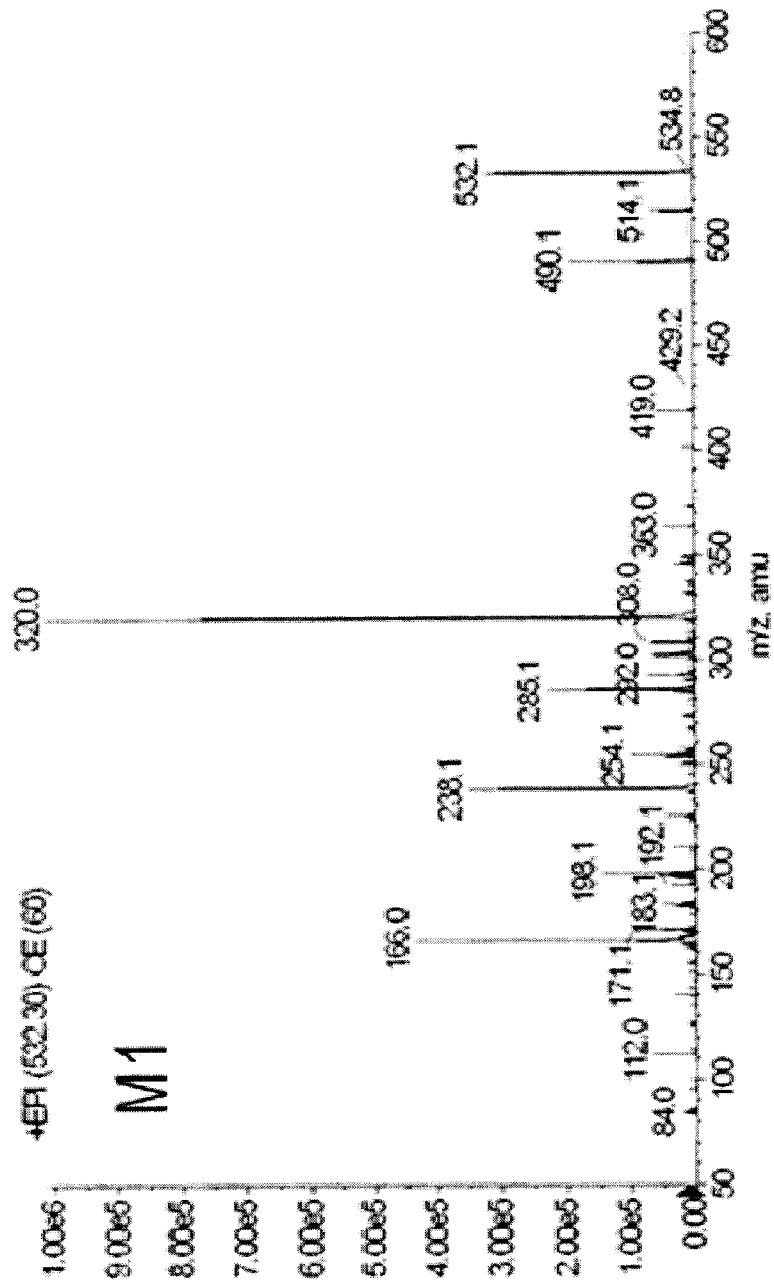
Figure 19C:
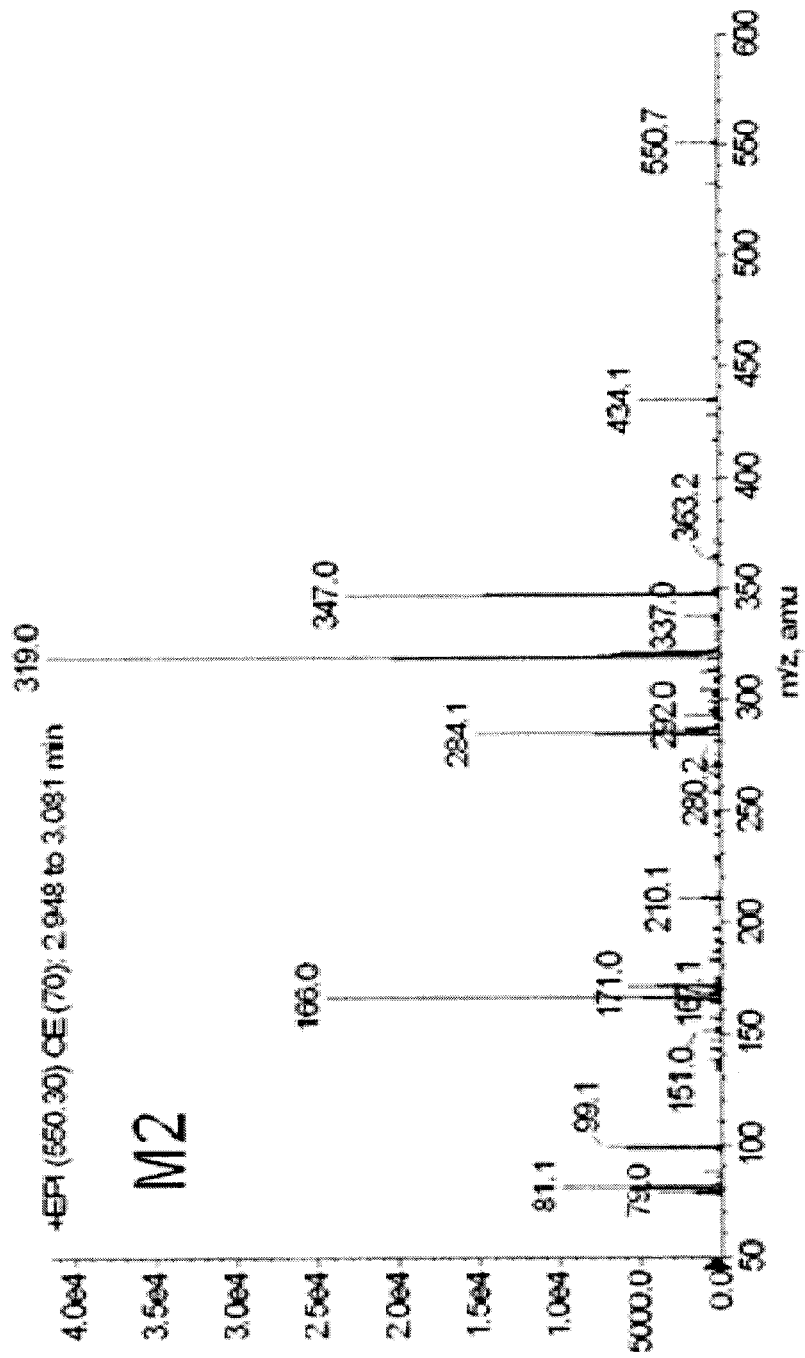

The biotransformation pathways of MI-519-63 in human liver microsome incubation were investigated. The detection of m/z 419, 363, 320 and 285 in MS/MS spectra (FIGS. 19A-C) of both protonated MI-519-63 and M1 indicated that the dehydrogenation occurred on the cyclobutane side chain, which was further confirmed by the detection of the product ion of M1 at m/z 112, showing a mass shift of 2 Da compared with the product ion of MI-519-63 at m/z 114. The MS/MS spectrum of M2 showed a very similar pattern to that of MI-773-M3 and MI219-M2. The hydroxylation was inferred to occur on the amine of pyrrolidine ring. The proposed biotranformations of MI-519-63 are shown in Chart 5.

microsomal stability (Tables 21 and 23). The microsomal stability data on MI-772 and its epimer MI-771 show that the configuration of the —NHSO$_2$Me group has a substantial impact on the microsomal stability of these compounds, which was not expected.

Pharmacokinetic studies in rats showed that MI-772 has a long half-life in rats in both intravenous and oral routes of dosing (Tables 25 and 26) and has a modest oral bioavailability. In comparison, MI-771 has a very poor pharmacokinetic profile in both intravenous and oral routes of dosing. Thus, the configuration of the —NHSO$_2$Me group in MI-771 and MI-772 has a substantial impact on their pharmacokinetic profiles.

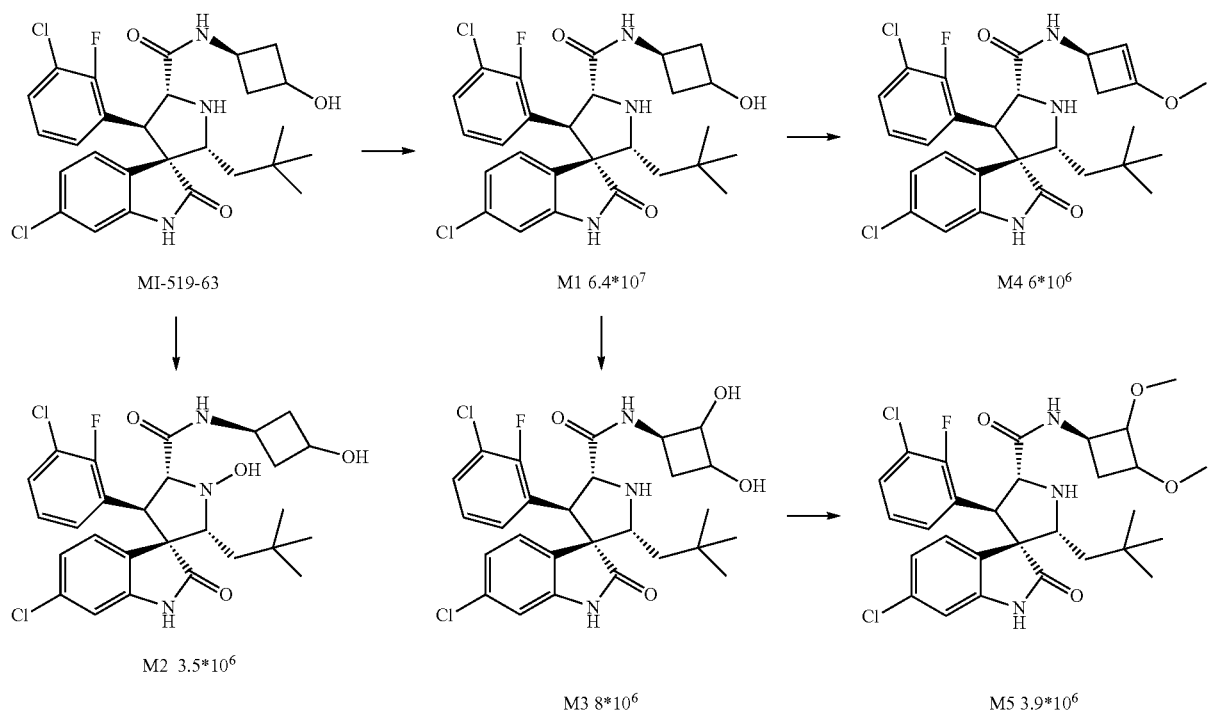

Chart 5. Biotransformation pathways of MI-519-63 in human liver microsome incubation.

Compounds provided herein include spiro-oxindole MDM2 inhibitors that were designed based upon these metabolism studies of MI-773 and MI-519-63.

Binding and cellular studies showed that while MI-519-64 and MI-519-65 bind to human MDM2 protein with high affinities and effectively inhibit cancer cell growth in cancer cell lines with wild-type p53, MI-519-64 is several times more potent than MI-519-65.

Microsomal stability studies showed that MI-519-64 has an improved microsomal stability over MI-519-63 (Tables 22-24).

Since the hydroxyl group in MI-773 and MI-519-63 can be metabolized to give a ketone, replacement of this hydroxyl with a sulphonylamide group was investigated as a means to generate MDM2 inhibitors with improved microsomal stability and/or good oral bioavailability (see MI-771 and MI-772).

Binding and cellular studies showed that while both MI-771 and MI-772 bind to human MDM2 protein with high affinities and effectively inhibit cell growth in cancer cell lines with wild-type p53, MI-772 is several times more potent than MI-771.

Microsomal stability studies showed that MI-772 is very stable, much more stable than MI-773 and also MI-219 (Tables 21 and 23). Surprisingly, MI-771 has a very poor Example 1

Analytical Data for Compounds

MI-219-M1(b)

TFA Salt

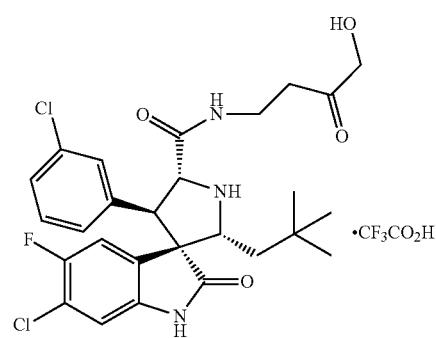 [SMILES: CC(C)(C)C[C@H]1N[C@@H](C(=O)NCCC(=O)CO)[C@H](c2cccc(Cl)c2)[C@@]12C(=O)Nc1cc(Cl)c(F)cc12 ; "·CF3CO2H"]

¹H NMR (300 MHz, CD₃OD) δ 7.72 (d, J=8.5 Hz, 1H), 7.32-7.21 (m, 3H), 7.08 (d, J=7.7 Hz, 1H), 6.87 (d, J=6.0 Hz, 1H), 5.25 (d, J=11.2 Hz, 1H), 4.50-4.47 (m, 1H), 4.11 (d, J=11.2 Hz, 1H), 4.05-3.97 (m, 2H), 3.67-3.38 (m, 2H), 2.61-2.56 (m, 2H), 1.92 (dd, J=15.5, 8.2 Hz, 1H), 1.20 (dd, J=15.5, 2.0 Hz, 1H), 0.92 (s, 9H); MS (ESI) m/z 550 [M+H]⁺.

MI-519-24

TFA Salt

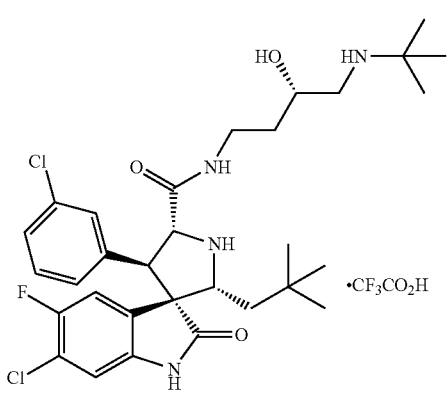 [SMILES: CC(C)(C)C[C@H]1N[C@@H](C(=O)NCC[C@H](O)CNC(C)(C)C)[C@H](c2cccc(Cl)c2)[C@@]12C(=O)Nc1cc(Cl)c(F)cc12 ; "·CF3CO2H"]

¹H NMR (300 MHz, CD₃OD) δ 7.70 (m, 1H), 7.31-7.02 (m, 4H), 6.88-6.83 (m, 1H), 5.28 (d, J=11.3 Hz, 1H), 4.48-4.45 (m, 1H), 4.18-4.13 (m, 1H), 3.75-3.72 (m, 2H), 3.36-3.31 (m, 1H), 3.05-3.03 (m, 1H), 2.83-2.76 (m, 1H), 1.92 (dd, J=15.4, 8.4 Hz, 1H), 1.65-1.53 (2H), 1.36 (s, 9H), 1.17 (d, J=15.4 Hz, 1H), 0.92 (s, 9H); MS (ESI) m/z 607 [M+H]⁺.

MI-519-27

TFA Salt

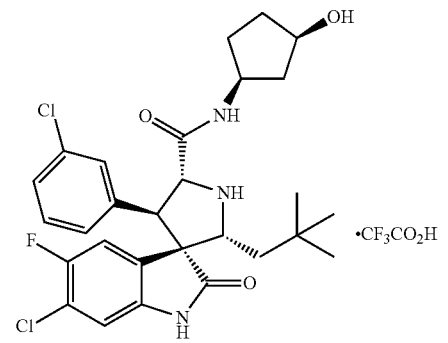 [SMILES: CC(C)(C)C[C@H]1N[C@@H](C(=O)N[C@H]2CC[C@@H](O)C2)[C@H](c2cccc(Cl)c2)[C@@]12C(=O)Nc1cc(Cl)c(F)cc12 ; "·CF3CO2H"]

¹H NMR (300 MHz, CD₃OD) δ 7.68 (d, J=8.5 Hz, 1H), 7.32-7.20 (m, 3H), 7.08 (d, J=7.7 Hz, 1H), 6.87 (d, J=6.0 Hz, 1H), 5.20 (d, J=11.2 Hz, 1H), 4.38 (d, J=7.8 Hz, 1H), 4.24-4.20 (m, 2H), 4.08 (d, J=11.2 Hz, 1H), 2.19-2.12 (m, 1H), 1.90-1.70 (m, 3H), 1.53-1.48 (m, 2H), 1.39-1.31 (m, 1H), 1.20-1.16 (m, 1H), 0.91 (s, 9H); MS (ESI) m/z 548 [M+H]⁺.

MI-519-29

TFA Salt

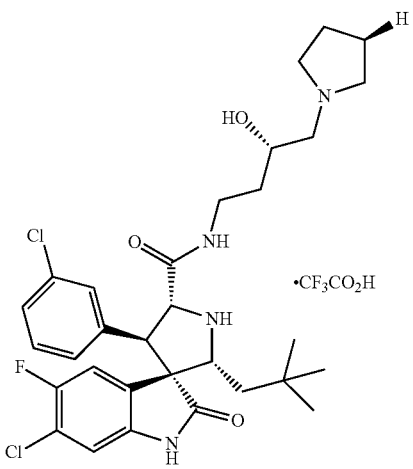

¹H NMR (300 MHz, CD₃OD) δ 7.70 (d, J=8.5 Hz, 1H), 7.33-7.21 (m, 3H), 7.09 (d, J=7.6 Hz, 1H), 6.87 (d, J=6.0 Hz, 1H), 5.27 (d, J=11.2 Hz, 1H), 4.56 (s, 1H), 4.46-4.44 (m, 1H), 4.15 (d, J=11.2 Hz, 1H), 3.75-3.65 (4H), 3.42-3.28 (m, 2H), 3.15 (m, 3H), 2.30-2.05 (m, 2H), 1.90 (dd, J=15.4, 8.5 Hz, 1H).

MI-519-30

TFA Salt

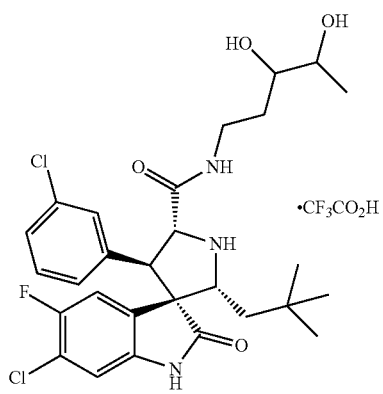 [SMILES: CC(O)C(O)CCNC(=O)[C@@H]1N[C@H](CC(C)(C)C)[C@]2(C(=O)Nc3cc(Cl)c(F)cc32)[C@H]1c1cccc(Cl)c1 ; "·CF3CO2H"]

¹H NMR (300 MHz, CD₃OD) δ 7.55 (d, J=8.7 Hz, 1H), 7.23-7.14 (m, 2H), 7.08 (s, 1H), 7.02-6.99 (m, 1H), 6.85 (d, J=6.2 Hz, 1H), 4.87 (d, J=11.0 Hz, 1H), 4.27-4.24 (m, 1H), 4.11-4.06 (m, 1H), 3.50-3.47 (m, 1H), 3.40-3.32 (m, 2H), 3.19-3.16 (m, 1H), 1.58-1.48 (m, 3H), 1.12-1.04 (m, 4H), 0.92 (s, 9H); MS (ESI) m/z 566 [M+H]⁺.

MI-519-35

TFA Salt

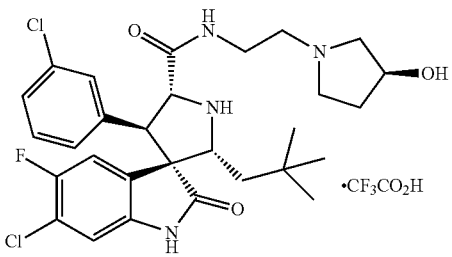 [SMILES: CC(C)(C)C[C@H]1N[C@@H](C(=O)NCCN2CC[C@H](O)C2)[C@H](c2cccc(Cl)c2)[C@@]12C(=O)Nc1cc(Cl)c(F)cc12 ; "·CF3CO2H"]

¹H NMR (300 MHz, CD₃OD) δ 7.68 (d, J=8.5 Hz, 1H), 7.31-7.20 (m, 3H), 7.10-7.08 (m, 1H), 6.86 (d, J=6.0 Hz, 1H), 5.26 (d, J=11.2 Hz, 1H), 5.10-5.03 (m, 1H), 4.50 (m, 1H), 4.40-4.37 (m, 1H), 4.16 (d, J=11.2 Hz, 1H), 3.63-3.51 (m, 4H), 3.44-3.32 (m, 3H), 2.21-2.18 (m, 1H), 2.01-1.95 (m, 1H), 1.89 (dd, J=15.4, 8.6 Hz, 1H), 1.18-1.03 (m, 1H), 0.92 (s, 9H); MS (ESI) m/z 577 [M+H]⁺.

MI-519-36

TFA Salt

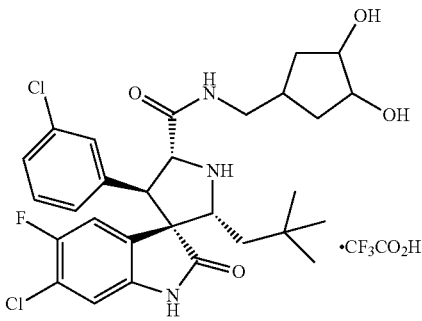 [SMILES: CC(C)(C)C[C@H]1N[C@@H](C(=O)NCC2CC(O)C(O)C2)[C@H](c2cccc(Cl)c2)[C@@]12C(=O)Nc1cc(Cl)c(F)cc12 ; "·CF3CO2H"]

¹H NMR (300 MHz, CD₃OD) δ 7.53 (m, 1H), 7.27-7.17 (m, 2H), 7.07 (s, 1H), 7.00-6.98 (m, 1H), 6.86 (d, J=6.2 Hz, 1H), 4.98 (d, J=12.4 Hz, 1H), 4.45-4.41 (m, 1H), 4.10 (d, J=12.4 Hz, 1H), 3.85-3.81 (m, 1H), 3.28-3.22 (m, 1H), 3.04-2.96 (m, 1H), 2.33-2.29 (m, 1H), 1.74 (dd, J=15.2, 7.3 Hz, 1H), 1.64-1.51 (m, 2H), 1.30-1.21 (m, 3H), 0.90 (s, 9H); MS (ESI) m/z 578 [M+H]⁺.

MI-519-37

TFA Salt

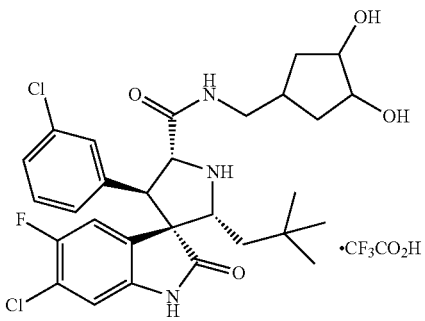 [SMILES: CC(C)(C)C[C@H]1N[C@@H](C(=O)NCC2CC(O)C(O)C2)[C@H](c2cccc(Cl)c2)[C@@]12C(=O)Nc1cc(Cl)c(F)cc12 ; "·CF3CO2H"]

¹H NMR (300 MHz, CD₃OD) δ 7.71 (d, J=8.5 Hz, 1H), 7.33-7.22 (m, 3H), 7.08 (d, J=7.6 Hz, 1H), 6.87 (d, J=6.0 Hz, 1H), 5.26 (d, J=11.3 Hz, 1H), 4.49-4.46 (m, 1H), 4.10 (d, J=11.3 Hz, 1H), 3.85-3.78 (m, 2H), 3.33-3.22 (m, 1H), 3.00-2.93 (m, 1H), 2.31-2.28 (m, 1H), 1.92 (dd, J=15.5, 8.2 Hz, 1H), 1.60-1.52 (m, 2H), 1.28-1.18 (m, 3H), 0.92 (s, 9H); MS (ESI) m/z 578 [M+H]⁺.

MI-519-41

TFA Salt

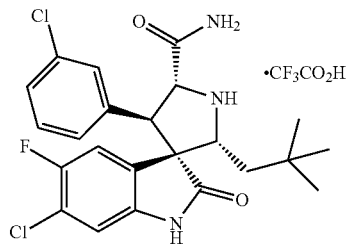 [SMILES: CC(C)(C)C[C@H]1N[C@@H](C(N)=O)[C@H](c2cccc(Cl)c2)[C@@]12C(=O)Nc1cc(Cl)c(F)cc12 ; "·CF3CO2H"]

¹H NMR (300 MHz, CD₃OD) δ 7.68 (d, J=8.5 Hz, 1H), 7.33-7.24 (m, 3H), 7.10 (d, J=7.7 Hz, 1H), 6.87 (d, J=6.0 Hz, 1H), 5.28 (d, J=11.2 Hz, 1H), 4.44 (m, 1H), 4.11 (d, J=11.2 Hz, 1H), 1.90 (dd, J=15.5, 8.3 Hz, 1H), 1.20 (dd, J=15.5, 2.0 Hz, 1H), 0.92 (s, 9H); MS (ESI) m/z 464 [M+H]⁺.

MI-519-43

TFA Salt

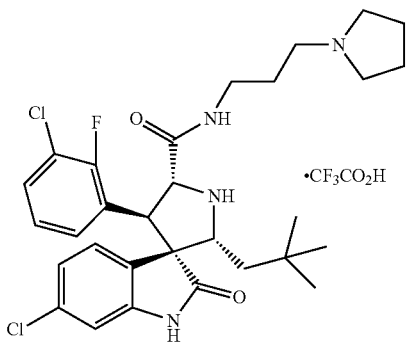 [SMILES: CC(C)(C)C[C@H]1N[C@@H](C(=O)NCCCN2CCCC2)[C@H](c2cccc(Cl)c2F)[C@@]12C(=O)Nc1cc(Cl)ccc12 ; "·CF3CO2H"]

¹H NMR (300 MHz, CD₃OD) δ 7.57-7.54 (m, 2H), 7.46-7.40 (m, 1H), 7.22-7.14 (m, 2H), 6.81 (d, J=1.8 Hz, 1H), 5.34 (d, J=11.4 Hz, 1H), 4.66 (d, J=11.4 Hz, 1H), 4.55-4.52 (m, 1H), 3.60 (m, 2H), 3.32-3.26 (m, 2H), 3.03-2.93 (m, 4H), 2.11-1.81 (m, 7H), 1.15 (dd, J=15.4, 1.7 Hz, 1H), 0.90 (s, 9H); MS (ESI) m/z 575 [M+H]⁺.

MI-519-44

TFA Salt

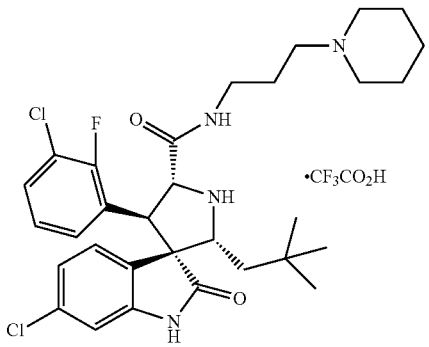 [SMILES: CC(C)(C)C[C@H]1N[C@@H](C(=O)NCCCN2CCCCC2)[C@H](c2cccc(Cl)c2F)[C@@]12C(=O)Nc1cc(Cl)ccc12 ; "·CF3CO2H"]

¹H NMR (300 MHz, CD₃OD) δ 7.63-7.57 (m, 2H), 7.46-7.41 (m, 1H), 7.23-7.14 (m, 2H), 6.81 (m, 1H), 5.30 (d, J=11.3 Hz, 1H), 4.64 (d, J=11.3 Hz, 1H), 4.50 (d, J=8.3 Hz, 1H), 3.43-3.19 (m, 4H), 2.94-2.75 (m, 4H), 1.95-1.71 (m, 8H), 1.53-1.43 (m, 1H), 1.14 (d, J=15.2 Hz, 1H), 0.92 (s, 9H); MS (ESI) m/z 589 [M+H]⁺.

MI-519-49

TFA Salt

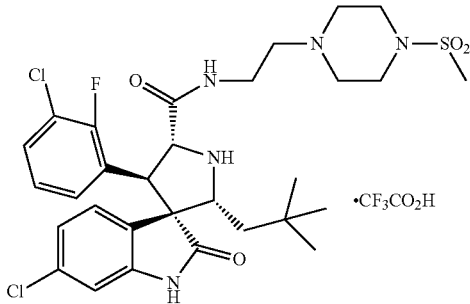 [SMILES: CC(C)(C)C[C@H]1N[C@@H](C(=O)NCCN2CCN(S(C)(=O)=O)CC2)[C@H](c2cccc(Cl)c2F)[C@@]12C(=O)Nc1cc(Cl)ccc12 ; "·CF3CO2H"]

¹H NMR (300 MHz, CD₃OD) δ 7.60-7.55 (m, 2H), 7.44-7.39 (m, 1H), 7.20-7.15 (m, 2H), 6.80 (d, J=1.8 Hz, 1H), 5.33 (d, J=11.4 Hz, 1H), 4.64 (d, J=11.4 Hz, 1H), 4.48 (d, J=7.1 Hz, 1H), 3.72-3.64 (m, 1H), 3.55-3.52 (m, 5H), 3.38-3.30 (m, 6H), 2.95 (s, 3H), 1.93 (dd, J=15.3, 8.6 Hz, 1H), 1.13 (d, J=15.3 Hz, 1H), 0.90 (s, 9H); MS (ESI) m/z 654 [M+H]⁺.

MI-519-50

TFA Salt

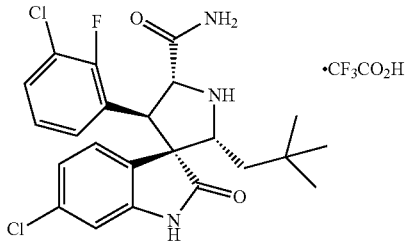 [SMILES: CC(C)(C)C[C@H]1N[C@@H](C(N)=O)[C@H](c2cccc(Cl)c2F)[C@@]12C(=O)Nc1cc(Cl)ccc12 ; "·CF3CO2H"]

¹H NMR (300 MHz, CD₃OD) δ 7.58-7.55 (m, 2H), 7.45-7.39 (m, 1H), 7.22-7.14 (m, 2H), 6.80 (d, J=1.8 Hz, 1H), 5.29 (d, J=11.3 Hz, 1H), 4.60 (d, J=11.3 Hz, 1H), 4.50 (dd, J=8.6, 1.9 Hz, 1H), 1.88 (dd, J=15.4, 8.4 Hz, 1H), 1.15 (dd, J=15.4, 1.9 Hz, 1H), 0.90 (s, 9H); MS (ESI) m/z 464 [M+H]⁺.

MI-519-51

TFA Salt

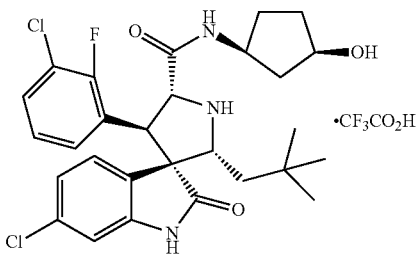

¹H NMR (300 MHz, CD₃OD) δ 7.54 (d, J=8.1 Hz, 1H), 7.36-7.31 (m, 1H), 7.15-7.12 (m, 1H), 7.02-6.91 (m, 2H), 6.81-6.80 (m, 1H), 4.98 (d, J=11.9 Hz, 1H), 4.47 (d, J=11.8 Hz, 1H), 4.41-4.37 (m, 1H), 4.22-4.19 (m, 2H), 2.18-2.08 (m, 1H), 1.85-1.49 (m, 5H), 1.37-1.33 (m, 1H), 1.14 (dd, J=15.2, 3.6 Hz, 1H), 0.91 (s, 9H); MS (ESI) m/z 548 [M+H]⁺.

MI-519-51-epi

TFA Salt

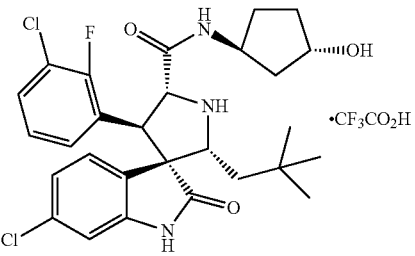

¹H NMR (300 MHz, CD₃OD) δ 7.63-7.56 (m, 2H), 7.45-7.40 (m, 1H), 7.21-7.14 (m, 2H), 6.82 (m, 1H), 5.19 (d, J=11.3 Hz, 1H), 4.59 (d, J=11.3 Hz, 1H), 4.54-4.51 (m, 1H), 4.35-4.32 (m, 1H), 4.24-4.21 (m, 1H), 2.02-1.85 (m, 3H), 1.73-1.63 (m, 2H), 1.51 (m, 1H), 1.19-1.14 (m, 1H), 1.09-1.04 (m, 1H), 0.90 (s, 9H); MS (ESI) m/z 548 [M+H]⁺.

MI-519-60

TFA Salt

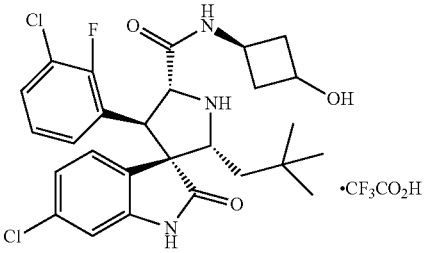

(epimer of MI-519-63)

¹H NMR (300 MHz, CD₃OD) δ 7.61-7.56 (m, 1H), 7.41-7.36 (m, 1H), 7.23-7.18 (m, 1H), 6.88 (m, 1H), 6.80-6.76 (m, 1H), 6.66-6.60 (m, 1H), 4.82-4.77 (m, 1H), 4.43-4.15 (m, 2H), 4.05-3.80 (m, 2H), 3.75-3.51 (m, 3H), 2.35-2.09 (m, 1H), 1.88 (dd, J=15.0, 8.0 Hz, 1H), 1.24-1.18 (m, 1H), 0.82 (s, 9H); MS (ESI) m/z 534 [M+H]⁺.

MI-519-56

TFA Salt

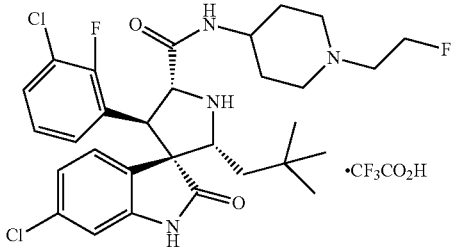 [SMILES: CC(C)(C)C[C@H]1N[C@@H](C(=O)NC2CCN(CCF)CC2)[C@H](c2cccc(Cl)c2F)[C@@]12C(=O)Nc1cc(Cl)ccc12 ; "·CF3CO2H"]

¹H NMR (300 MHz, CD₃OD) δ 7.63-7.57 (m, 2H), 7.44-7.39 (m, 1H), 7.21-7.15 (m, 2H), 6.81 (m, 1H), 5.26 (d, J=10.9 Hz, 1H), 4.75-4.73 (m, 1H), 4.64 (d, J=11.4 Hz, 1H), 4.52-4.50 (m, 1H), 3.98-3.94 (m, 1H), 3.75-3.60 (m, 1H), 3.55-3.52 (m, 1H), 3.46-3.42 (m, 1H), 3.31-3.13 (m, 1H), 2.31-2.20 (m, 1H), 1.95-1.87 (m, 3H), 1.80-1.50 (m, 1H), 1.18-1.13 (m, 1H), 0.90 (s, 9H); MS (ESI) m/z 593 [M+H]⁺.

MI-519-62

TFA Salt

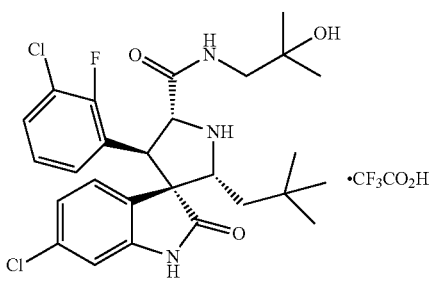 [SMILES: CC(C)(C)C[C@H]1N[C@@H](C(=O)NCC(C)(C)O)[C@H](c2cccc(Cl)c2F)[C@@]12C(=O)Nc1cc(Cl)ccc12 ; "·CF3CO2H"]

¹H NMR (300 MHz, CD₃OD) δ 7.57-7.53 (m, 1H), 7.41-7.38 (m, 1H), 7.22-7.17 (m, 1H), 6.87-6.82 (m, 3H), 5.02 (d, J=10.1 Hz, 1H), 4.44 (d, J=10.1 Hz, 1H), 4.11 (dd, J=7.4, 2.8 Hz, 1H), 3.41-3.36 (m, 1H), 3.12-3.07 (m, 1H), 1.97 (dd, J=15.2, 7.5 Hz, 1H), 1.32 (dd, J=15.2, 2.9 Hz, 1H), 1.07 (s, 3H), 0.98 (s, 3H), 0.90 (s, 9H); MS (ESI) m/z 536 [M+H]⁺.

MI-519-63

TFA Salt

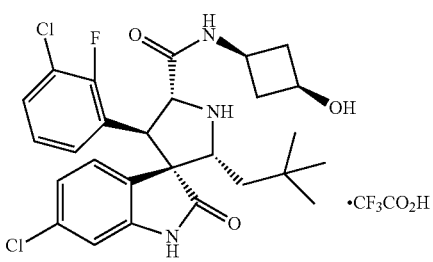 [SMILES: CC(C)(C)C[C@H]1N[C@@H](C(=O)N[C@H]2C[C@@H](O)C2)[C@H](c2cccc(Cl)c2F)[C@@]12C(=O)Nc1cc(Cl)ccc12 ; "·CF3CO2H"]

¹H NMR (300 MHz, CD₃OD) δ 7.55-7.51 (m, 1H), 7.43-7.38 (m, 1H), 7.24-7.18 (m, 1H), 6.88 (m, 1H), 6.81 (m, 1H), 6.79-6.73 (m, 1H), 4.93 (d, J=9.7 Hz, 1H), 4.40 (d, J=9.7 Hz, 1H), 4.11 (dd, J=7.7, 2.7 Hz, 1H), 3.98-3.93 (m, 1H), 3.87-3.32 (m, 1H), 2.72-2.56 (m, 2H), 2.03-1.87 (m, 2H), 1.77-1.71 (m, 1H), 1.25 (dd, J=15.4, 2.6 Hz, 1H), 0.89 (s, 9H); MS (ESI) m/z 534 [M+H]⁺.

MI-519-68

TFA Salt

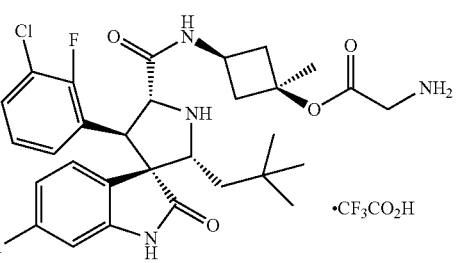

¹H NMR (300 MHz, CD₃OD) δ 7.58-7.55 (m, 1H), 7.38-7.35 (m, 1H), 7.21-7.16 (m, 1H), 6.87 (s, 1H), 6.82-6.78 (m, 2H), 5.08 (d, J=10.0 Hz, 1H), 4.45 (d, J=10.0 Hz, 1H), 4.17-4.07 (m, 2H), 3.78 (s, 2H), 2.68-2.58 (m, 2H), 2.44-2.40 (m, 1H), 2.30-2.27 (m, 1H), 1.98 (dd, J=15.4, 7.7 Hz, 1H), 1.58 (s, 1H), 1.26 (dd, J=15.4, 2.5 Hz, 1H), 0.82 (s, 9H); MS (ESI) m/z 464 [M+H]⁺.

MI-519-69

TFA Salt

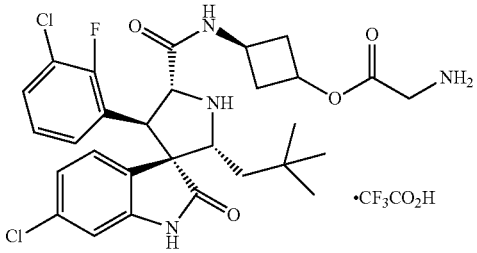

¹H NMR (300 MHz, CD₃OD) δ 7.62-7.57 (m, 1H), 7.41-7.35 (m, 1H), 7.22-7.17 (m, 1H), 6.88 (s, 1H), 6.79 (m, 2H), 5.11 (d, J=10.1 Hz, 1H), 4.47 (d, J=10.1 Hz, 1H), 4.19 (dd, J=7.6, 2.6 Hz, 1H), 4.07-4.02 (m, 1H), 3.82 (s, 2H), 2.87-2.74 (m, 2H), 2.22-2.18 (m, 1H), 2.07-1.96 (m, 2H), 1.27 (dd, J=15.3, 2.6 Hz, 1H), 0.82 (s, 9H); MS (ESI) m/z 591 [M+H]⁺.

MI-519-70

TFA Salt

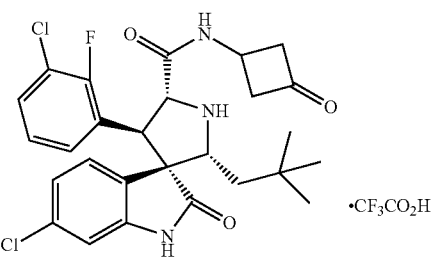 [SMILES: CC(C)(C)C[C@H]1N[C@@H](C(=O)NC2CC(=O)C2)[C@H](c2cccc(Cl)c2F)[C@@]12C(=O)Nc1cc(Cl)ccc12 ; "·CF3CO2H"]

¹H NMR (300 MHz, CD₃OD) δ 7.58-7.53 (m, 1H), 7.44-7.39 (m, 1H), 7.26-7.21 (m, 1H), 6.90-6.89 (m, 1H), 6.80-6.77 (m, 1H), 6.60 (d, J=8.1 Hz, 1H), 5.00 (d, J=9.0 Hz, 1H), 4.50-4.40 (m, 2H), 4.08 (d, J=5.5 Hz, 1H), 3.43-3.32 (m, 2H), 3.17-3.06 (m, 2H), 1.96 (dd, J=15.2, 7.9 Hz, 1H), 1.18 (dd, J=15.2, 1.9 Hz, 1H), 0.83 (s, 9H); MS (ESI) m/z 532 [M+H]⁺.

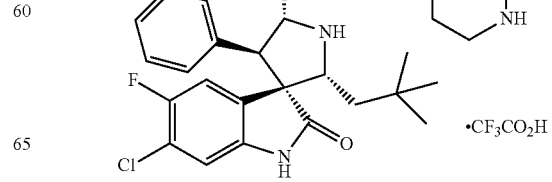

¹H NMR (300 MHz, CD₃OD) δ 7.65 (d, J=8.4 Hz, 1H), 7.29 (d, J=7.8 Hz, 1H), 7.27 (s, 1H), 7.21 (t, J=7.8 Hz, 1H), 7.04 (d, J=7.5 Hz, 1H), 6.83 (d, J=6.0 Hz, 1H), 5.27 (d, J=11.4 Hz, 1H), 4.41 (d, J=6.6 Hz, 1H), 4.10 (d, J=11.4 Hz, 1H), 3.39-3.53 (m, 1H), 3.11-3.22 (m, 1H), 3.00 (s, 4H), 2.53 (s, 4H), 2.41 (dd, J=6.6, 12.0 Hz, 1H), 1.86 (dd, J=8.1, 15.3 Hz, 1H), 1.09-1.38 (m, 2H), 0.93 (s, 9H).

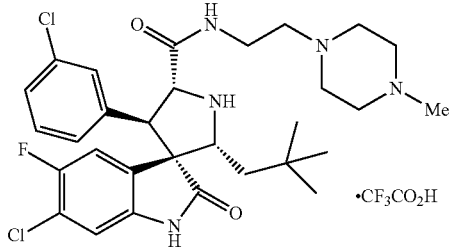 [SMILES: CN1CCN(CCNC(=O)[C@@H]2N[C@H](CC(C)(C)C)[C@]3(C(=O)Nc4cc(Cl)c(F)cc43)[C@H]2c2cccc(Cl)c2)CC1 ; "·CF3CO2H"]

¹H NMR (300 MHz, CD₃OD) δ 7.66 (d, J=8.4 Hz, 1H), 7.15-7.33 (m, 3H), 7.05 (d, J=7.5 Hz, 1H), 6.81 (d, J=6.0 Hz, 1H), 5.31 (d, J=11.4 Hz, 1H), 4.44 (dd, J=1.8, 8.4 Hz, 1H), 4.12 (d, J=11.4 Hz, 1H), 3.33-3.45 (m, 1H), 3.18 (dd, J=7.5, 14.7 Hz, 4H), 2.95-3.10 (m, 1H), 2.80 (s, 3H), 2.66 (dd, J=7.5, 13.8 Hz, 4H), 2.46 (dd, J=6.6, 12.6 Hz, 2H), 1.88 (dd, J=8.4, 15.3 Hz, 1H), 1.23-1.38 (m, 1H), 0.85 (s, 9H).

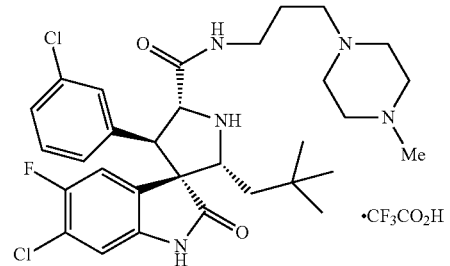 [SMILES: CN1CCN(CCCNC(=O)[C@@H]2N[C@H](CC(C)(C)C)[C@]3(C(=O)Nc4cc(Cl)c(F)cc43)[C@H]2c2cccc(Cl)c2)CC1 ; "·CF3CO2H"]

¹H NMR (300 MHz, CD₃OD) δ 7.68 (d, J=8.4 Hz, 1H), 7.13-7.30 (m, 3H), 7.04 (d, J=7.2 Hz, 1H), 6.84 (d, J=6.0 Hz, 1H), 5.32 (d, J=11.4 Hz, 1H), 4.41 (dd, J=1.8, 8.4 Hz, 1H), 4.11 (d, J=11.4 Hz, 1H), 3.31-3.46 (m, 1H), 3.16 (dd, J=7.5, 14.7 Hz, 4H), 2.95-3.10 (m, 1H), 2.78 (s, 3H), 2.67 (dd, J=7.5, 14.1 Hz, 4H), 2.46 (dd, J=6.6, 12.6 Hz, 2H), 2.09-2.38 (m, 2H), 1.67-1.78 (m, 1H), 1.23-1.38 (m, 1H), 0.86 (s, 9H).

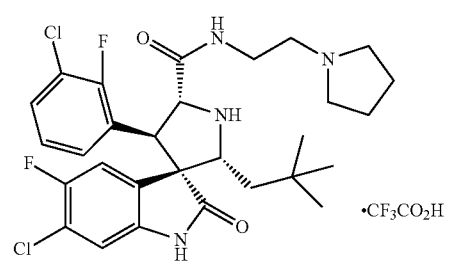 [SMILES: CC(C)(C)C[C@H]1N[C@@H](C(=O)NCCN2CCCC2)[C@H](c2cccc(Cl)c2F)[C@@]12C(=O)Nc1cc(Cl)c(F)cc12 ; "·CF3CO2H"]

¹H NMR (300 MHz, CD₃OD) δ 7.70 (d, J=8.4 Hz, 1H), 7.58 (t, J=7.2 Hz, 1H), 7.42 (t, J=7.5 Hz, 1H), 7.18 (t, J=8.1 Hz, 1H), 6.88 (d, J=6.0 Hz, 1H), 5.31 (d, J=11.4 Hz, 1H), 4.67 (d, J=11.4 Hz, 1H), 4.48 (d, J=7.8 Hz, 1H), 3.52-3.80 (m, 2H), 3.00-3.48 (m, 6H), 1.95-2.30 (m, 4H), 1.93 (dd, J=8.4, 15.3 Hz, 1H), 1.13 (d, J=15.6 Hz, 1H), 0.92 (s, 9H).

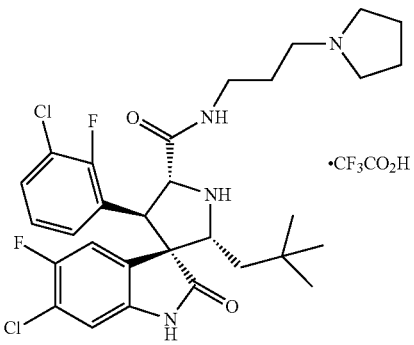 [SMILES: CC(C)(C)C[C@H]1N[C@@H](C(=O)NCCCN2CCCC2)[C@H](c2cccc(Cl)c2F)[C@@]12C(=O)Nc1cc(Cl)c(F)cc12 ; "·CF3CO2H"]

¹H NMR (300 MHz, CD₃OD) δ 7.71 (d, J=8.1 Hz, 1H), 7.60 (t, J=7.2 Hz, 1H), 7.45 (t, J=6.9 Hz, 1H), 7.21 (t, J=7.8 Hz, 1H), 6.89 (d, J=6.0 Hz, 1H), 5.30 (d, J=11.4 Hz, 1H), 4.66 (d, J=11.4 Hz, 1H), 4.52 (d, J=8.1 Hz, 1H), 3.55-3.80 (m, 2H), 3.18-3.46 (m, 2H), 2.82-3.15 (m, 4H), 1.74-2.33 (m, 7H), 1.16 (d, J=15.6 Hz, 1H), 0.92 (s, 9H).

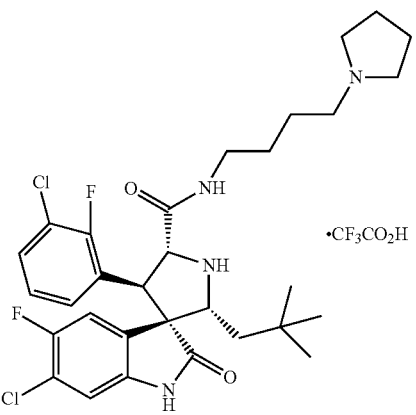 [SMILES: CC(C)(C)C[C@H]1N[C@@H](C(=O)NCCCCN2CCCC2)[C@H](c2cccc(Cl)c2F)[C@@]12C(=O)Nc1cc(Cl)c(F)cc12 ; "·CF3CO2H"]

¹H NMR (300 MHz, CD₃OD) δ 7.71 (d, J=8.7 Hz, 1H), 7.59 (t, J=6.6 Hz, 1H), 7.44 (t, J=6.9 Hz, 1H), 7.20 (t, J=8.1 Hz, 1H), 6.88 (d, J=6.0 Hz, 1H), 5.28 (d, J=11.4 Hz, 1H), 4.65 (d, J=11.4 Hz, 1H), 4.52 (d, J=8.4 Hz, 1H), 3.55-3.70 (m, 2H), 3.08-3.27 (m, 4H), 2.88-3.08 (m, 2H), 1.98-2.28 (m, 5H), 1.91 (dd, J=8.4, 15.3 Hz, 1H), 1.40-1.65 (m, 4H), 1.15 (d, J=15.3 Hz, 1H), 0.91 (s, 9H), 0.82 (d, J=9.9 Hz, 1H).

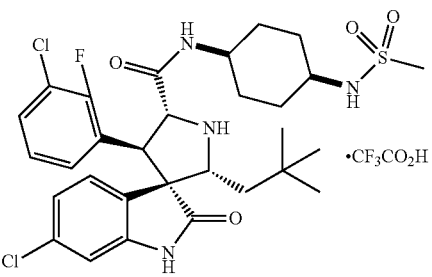

¹H NMR (300 MHz, CD₃OD) δ 8.33 (d, J=7.5 Hz, 1H), 7.45 (t, J=6.9 Hz, 1H), 7.34 (t, J=7.8 Hz, 1H), 7.15 (t, J=8.7 Hz, 1H), 6.83 (d, J=1.5 Hz, 1H), 6.75 (dd, J=1.8, 8.1 Hz, 1H), 6.66 (d, J=8.1 Hz, 1H), 4.79 (d, J=9.9 Hz, 1H), 4.32 (d, J=9.6 Hz, 1H), 3.99 (d, J=5.4 Hz, 1H), 3.55-3.70 (m, 1H), 3.05-3.20 (m, 1H), 2.89 (s, 3H), 1.78-2.06 (m, 4H), 1.67 (d, J=12.6 Hz, 1H), 1.15-1.45 (m, 6H), 0.86 (d, J=6.3 Hz, 1H), 0.78 (s, 9H).

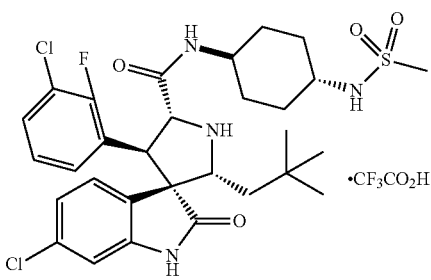

¹H NMR (300 MHz, CD₃OD) δ 8.31 (d, J=7.8 Hz, 1H), 7.46 (t, J=6.9 Hz, 1H), 7.34 (t, J=7.8 Hz, 1H), 7.15 (t, J=8.7 Hz, 1H), 6.83 (d, J=1.5 Hz, 1H), 6.75 (dd, J=1.8, 8.1 Hz, 1H), 6.66 (d, J=8.1 Hz, 1H), 4.79 (d, J=9.9 Hz, 1H), 4.32 (d, J=9.6 Hz, 1H), 3.99 (d, J=5.4 Hz, 1H), 3.55-3.70 (m, 1H), 3.05-3.20 (m, 1H), 2.89 (s, 3H), 1.78-2.06 (m, 4H), 1.67 (d, J=12.6 Hz, 1H), 1.15-1.45 (m, 6H), 0.86 (d, J=6.3 Hz, 1H), 0.78 (s, 9H).

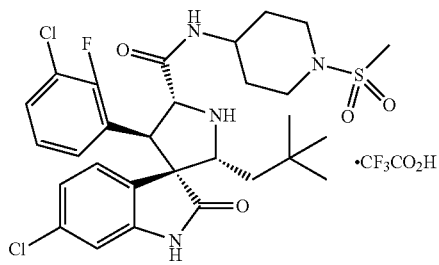 [SMILES: CC(C)(C)C[C@H]1N[C@@H](C(=O)NC2CCN(S(C)(=O)=O)CC2)[C@H](c2cccc(Cl)c2F)[C@@]12C(=O)Nc1cc(Cl)ccc12 ; "·CF3CO2H"]

¹H NMR (300 MHz, CD₃OD) δ 7.48 (t, J=6.6 Hz, 1H), 7.35 (t, J=6.9 Hz, 1H), 7.16 (t, J=7.8 Hz, 1H), 6.83 (d, J=1.8 Hz, 1H), 6.75 (dd, J=1.8, 8.1 Hz, 1H), 6.65 (d, J=8.1 Hz, 1H), 4.33 (d, J=9.3 Hz, 1H), 4.02 (d, J=5.4 Hz, 1H), 3.70-3.88 (m, 1H), 3.62 (d, J=12.3 Hz, 1H), 3.53 (d, J=12.9 Hz, 1H), 2.77 (s, 3H), 2.65-2.90 (m, 2H), 1.79-2.06 (m, 2H), 1.65-1.78 (m, 1H), 1.47-1.63 (m, 1H), 1.32-1.47 (m, 1H), 1.10-1.24 (m, 1H), 0.86 (d, J=6.0 Hz, 1H), 0.78 (s, 9H), 0.76 (d, J=11.7 Hz, 1H).

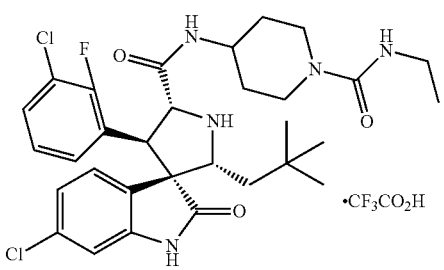 [SMILES: CCNC(=O)N1CCC(NC(=O)[C@@H]2N[C@H](CC(C)(C)C)[C@]3(C(=O)Nc4cc(Cl)ccc43)[C@H]2c2cccc(Cl)c2F)CC1 ; "·CF3CO2H"]

¹H NMR (300 MHz, CD₃OD) δ 8.53 (d, J=7.5 Hz, 1H), 7.55 (t, J=7.5 Hz, 1H), 7.39 (t, J=7.2 Hz, 1H), 7.19 (t, J=8.1 Hz, 1H), 6.88 (s, 1H), 6.82 (s, 2H), 5.04 (d, J=9.9 Hz, 1H), 4.46 (d, J=9.9 Hz, 1H), 4.20 (dd, J=2.7, 7.2 Hz, 1H), 3.73-4.05 (m, 2H), 3.07-3.22 (m, 2H), 2.86 (dd, J=13.8, 26.1 Hz, 2H), 2.03 (dd, J=7.2, 15.3 Hz, 1H), 1.78-1.96 (m, 2H), 1.56-1.68 (m, 1H), 1.16-1.53 (m, 3H), 1.10 (t, J=7.2 Hz, 3H), 0.90 (d, J=4.5 Hz, 1H), 0.82 (s, 9H), 0.80 (d, J=12.9 Hz, 1H).

C027

TFA Salt

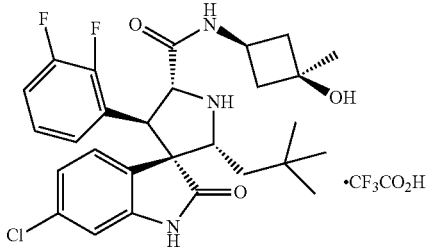 [SMILES: CC(C)(C)C[C@H]1N[C@@H](C(=O)N[C@H]2C[C@@](C)(O)C2)[C@H](c2cccc(F)c2F)[C@@]12C(=O)Nc1cc(Cl)ccc12 ; "·CF3CO2H"]

¹H NMR (300 MHz, MeOH-d4): 7.50-7.36 (m, 1H), 7.24-7.10 (m, 2H), 6.88-6.76 (m, 3H), 5.12 (d, J=10.17 Hz, 1H), 4.49 (d, J=10.17 Hz, 1H), 4.23 (dd, J=6.83, 2.09 Hz, 1H), 3.98-3.83 (m, 1H), 2.49-2.36 (m, 1H), 2.36-2.22 (m, 1H), 2.10-1.96 (m, 2H), 1.94-1.82 (m, 1H), 1.35-1.28 (m, 1H), 1.29 (s, 3H), 0.80 (s, 9H); ¹³C NMR (75 MHz, MeOH-d4): 108.1, 166.0, 145.4, 136.9, 127.9, 126.1 (t, J_{C-F}=5.6 Hz), 125.4, 123.4 118.8 (d, J_{C-F}=17.3 Hz), 112.0, 67.4, 64.5, 63.7, 61.6, 49.5, 45.6, 45.5, 42.4, 38.5, 30.9, 29.5, 27.6; ESI-MS calculated for C₂₈H₃₃³⁵ClF₂N₃O₃ [M+H]⁺: 532.2179, Found: 532.42.

C029

TFA Salt

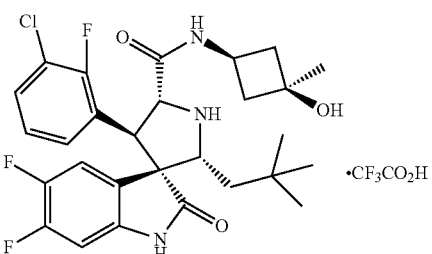

¹H NMR (300 MHz, MeOH-d4): 8.84 (d, J=6.80 Hz, 1H), 7.58 (t, J=6.80 Hz, 1H), 7.39 (t, J=7.11 Hz, 1H), 7.22 (t, J=7.80 Hz, 1H), 6.88 (dd, J=9.81, 7.80 Hz, 1H), 6.78 (d, J=10.13, 6.63 Hz, 1H), 5.11 (d, J=10.37 Hz, 1H), 4.48 (d, J=10.37 Hz, 1H), 4.21 (d, J=10.37 Hz, 1H), 4.21 (dd, J=7.32, 2.66 Hz, 1H), 3.95-3.75 (m, 1H), 2.46-2.22 (m, 2H), 2.12-1.96 (m, 2H), 1.94-1.80 (m, 1H), 1.34-1.28 (m, 1), 1.29 (s, 3H), 0.81 (s, 9H); ¹³C NMR (75 MHz, MeOH-d4): 180.2, 169.2, 132.2, 128.7 (d, J_{C-F}=2.2 Hz), 126.5 (d, J_{C-F}=4.6 Hz), 124.7 (dd, J_{C-F}=33.5, 19.2 Hz), 122.6 (d, J_{C-F}=18.1 Hz), 101.5 (d, J_{C-F}=23.0 Hz), 67.4, 64.4, 63.5, 61.9, 49.8, 45.6, 45.5, 42.4, 38.6, 30.9, 29.5, 27.6; ESI-MS calculated for C₂₈H₃₂³⁵ClF₃N₃O₃ [M+H]⁺: 550.2084, Found: 550.33.

C031

TFA Salt

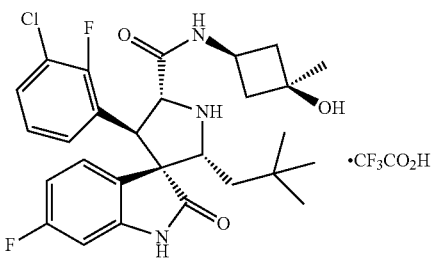 [SMILES: CC(C)(C)C[C@H]1N[C@@H](C(=O)N[C@H]2C[C@@](C)(O)C2)[C@H](c2cccc(Cl)c2F)[C@@]12C(=O)Nc1cc(F)ccc12 ; "·CF3CO2H"]

$^1$H NMR (300 MHz, MeOH-d4): 7.68-7.54 (m, 1H), 7.38-7.26 (m, 1H), 7.22-7.12 (m, 1H), 6.90-6.76 (m, 1H), 6.70-6.60 (m, 1H), 6.56-6.42 (m, 1H), 5.30-5.20 (m, 1H), 4.49 (d, J=10.03 Hz, 1H), 4.25 (dd, J=71.9, 2.39 Hz, 1H), 4.00-3.82 (m, 1H), 2.50-2.21 (m, 2H), 2.18-2.00 (m, 2H), 1.98-1.82 (m, 1H), 1.40-1.30 (m, 1H), 1.28 (s, 3H), 0.79 (s, 9H); $^{13}$C NMR (75 MHz, MeOH-d4): 180.6, 165.1 (d, $J_{C-F}$=246.7 Hz), 166.1, 157.7 (d, $J_{C-F}$=247.9 Hz), 145.6 (d, $J_{C-F}$=12.0 Hz), 132.0, 128.6, 128.2 (d, $J_{C-F}$=10.2 Hz), 126.3 (d, $J_{C-F}$=4.5 Hz), 125.0 (d, $J_{C-F}$=14.0 Hz), 122.4 (d, $J_{C-F}$=18.4 Hz), 122.3, 109.8 (d, $J_{C-F}$=23.2 Hz), 99.9 (d, $J_{C-F}$=27.8 Hz), 67.4, 64.5, 63.5, 61.5, 49.2, 45.6, 45.5, 42.3, 38.4, 30.9, 29.5, 27.5; ESI-MS calculated for $C_{28}H_{33}{}^{35}ClF_2N_3O_3$ [M+H]$^+$: 532.2179, Found: 532.42.

C034

TFA Salt

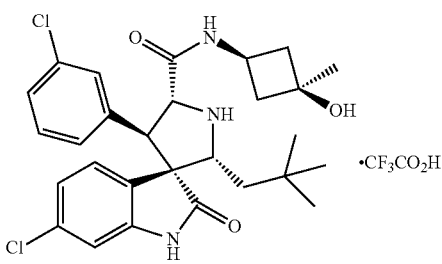 [SMILES: CC(C)(C)C[C@H]1N[C@@H](C(=O)N[C@H]2C[C@@](C)(O)C2)[C@H](c2cccc(Cl)c2)[C@@]12C(=O)Nc1cc(Cl)ccc12 ; "·CF3CO2H"]

$^1$H NMR (300 MHz, MeOH-d4): 7.28-7.10 (m, 5H), 6.92-6.84 (m, 1H), 6.80-6.76 (m, 1H), 5.40-5.20 (m, 1H), 5.08 (d, J=10.96 Hz, 1H), 4.40-4.20 (m, 1H), 3.90-3.60 (m, 1H), 2.50-2.30 (m, 1H), 2.30-2.15 (m, 1H), 2.15-2.00 (m, 2H), 1.90-1.75 (m, 1H), 1.57 (dd, J=15.3, 3.71 Hz, 1H), 1.25 (s, 3H), 0.79 (s, 9H); $^{13}$C NMR (75 MHz, MeOH-d4): 180.0, 165.9, 144.7, 136.7, 136.6, 135.8, 131.3, 130.1, 129.8, 128.1, 128.1, 126.8, 123.5, 112.0, 67.4, 64.3, 64.0, 62.2, 57.2, 45.7, 45.6, 42.7, 38.3, 31.0, 29.6, 27.5; ESI-MS calculated for $C_{28}H_{34}{}^{35}Cl_2N_3O_3$ [M+H]$^+$: 530.1977, Found: 530.50.

C035

TFA Salt

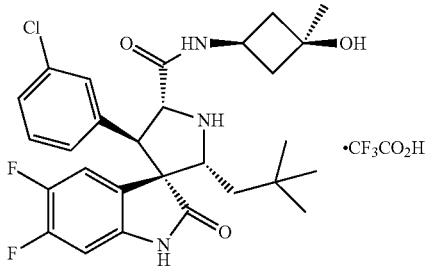 [SMILES: CC(C)(C)C[C@H]1N[C@@H](C(=O)N[C@H]2C[C@@](C)(O)C2)[C@H](c2cccc(Cl)c2)[C@@]12C(=O)Nc1cc(F)c(F)cc12 ; "·CF3CO2H"]

$^1$H NMR (300 MHz, MeOH-d4): 7.40-7.00 (m, 5H), 6.80-6.40 (m, 1H), 5.60-5.00 (m, 2H), 4.60-4.20 (m, 1H), 4.00-3.80 (m, 1H), 2.60-2.40 (m, 1H), 2.40-2.20 (m, 1H), 2.20-2.00 (m, 2H), 2.00-1.80 (m, 1H), 1.70-1.50 (m, 1H), 1.28 (s, 3H), 0.83 (s, 9H); $^{13}$C NMR (75 MHz, MeOH-d4): 180.0, 165.8, 160.0-145.0 (m, 2×$C_{sp2}$-F), 136.5, 135.9, 131.4, 130.0, 129.9, 128.0, 124.1 (d, $J_{C-F}$=6.3 Hz), 119.1, 116.7 (d, $J_{C-F}$=20.4 Hz), 101.4 (d, $J_{C-F}$=23.0 Hz), 67.4, 64.2, 63.8, 62.5, 57.4, 45.6, 45.5, 42.7, 38.3, 31.0, 29.5, 27.5; ESI-MS calculated for $C_{28}H_{33}{}^{35}ClF_2N_3O_3$ [M+H]$^+$: 532.2179, Found: 532.42.

MI-519-73

TFA Salt

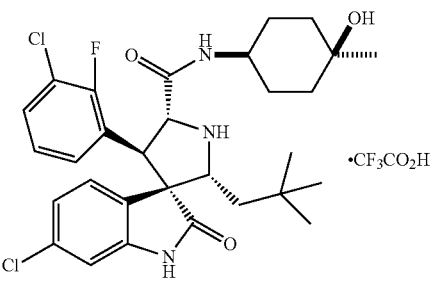

$^1$H NMR (300 MHz, MeOH-d4): 7.50-7.30 (m, 2H), 7.20-7.10 (m, 1H), 6.90-6.70 (m, 3H), 5.00-4.70 (m, 1H), 4.36 (d, J=9.76 Hz, 1H), 4.05-3.96 (m, 1H), 3.70-3.50 (m, 1H), 1.94 (dd, J=14.98, 7.30 Hz, 1H), 1.80-1.00 (m, 8H), 1.16 (s, 3H), 0.90-0.70 (m, 1H), 0.80 (s, 9H); ESI-MS calculated for $C_{30}H_{37}{}^{35}Cl_2FN_3O_3$ [M+H]$^+$: 576.2196, Found: 576.58.

MI-519-74

TFA Salt

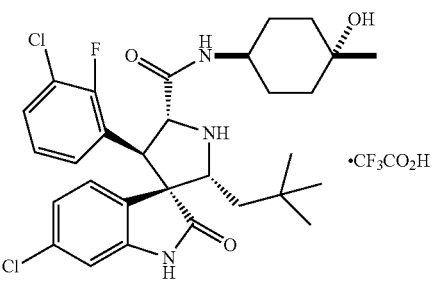

¹H NMR (300 MHz, MeOH-d4): 7.50-7.30 (m, 2H), 7.25-7.10 (m, 1H), 6.85-6.70 (m, 3H), 5.00-4.70 (m, 1H), 4.32 (d, J=9.69 Hz, 1H), 4.10-3.95 (m, 1H), 3.85-3.70 (m, 1H), 2.00-1.80 (m, 2H), 1.75-1.20 (m, 7H), 1.13 (s, 3H), 0.95-0.75 (m, 1H), 0.81 (s, 9H); ESI-MS calculated for $C_{30}H_{32}{}^{35}Cl_2FN_3O_3$ [M+H]$^+$: 576.2196, Found: 576.58.

MI-7102

TFA Salt

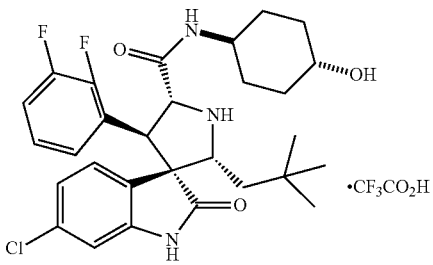

¹H NMR (300 MHz, MeOH-d4): 7.36-7.25 (m, 1H), 7.24-7.11 (m, 2H), 6.86 (d, J=1.8 Hz, 1H), 6.80 (dd, J=1.8, 8.1 Hz, 1H), 6.72 (d, J=8.1 Hz, 1H), 4.82 (d, J=9.6 Hz, 1H), 4.36 (d, J=9.6 Hz, 1H), 4.04 (dd, J=2.4, 7.4 Hz, 1H), 3.74-3.56 (m, 1H), 3.56-3.40 (m, 1H), 2.05-1.78 (m, 5H), 1.75-1.59 (m, 1H), 1.43-1.04 (m, 5H), 0.81 (s, 9H); ESI-MS calculated for $C_{29}H_{35}ClF_2N_3O_3$ (M+H)$^+$ requires 546.23, found 546.58.

MI-7103

TFA Salt

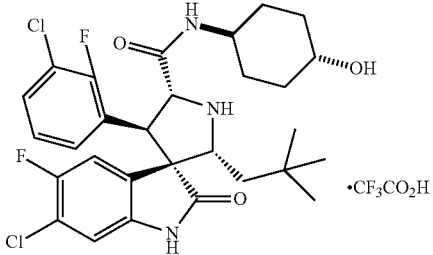

¹H NMR (300 MHz, MeOH-d4): 8.38 (d, J=7.7 Hz, 1H), 7.54 (t, J=6.7 Hz, 1H), 7.40 (d, J=7.1 Hz, 1H), 7.20 (t, J=7.9 Hz, 1H), 6.93 (d, J=6.1 Hz, 1H), 6.86 (d, J=8.7 Hz, 1H), 4.45 (d, J=10.3 Hz, 1H), 4.13 (dd, J=2.8, 7.5 Hz, 1H), 3.77-3.55 (m, 1H), 3.55-3.42 (m, 1H), 2.09-1.71 (m, 4H), 1.70-1.56 (m, 1H), 1.45-1.02 (m, 5H), 0.82 (s, 9H); ESI-MS calculated for $C_{29}H_{34}Cl_2F_2N_3O_3$ (M+H)$^+$ requires 580.19, found 580.67.

MI-7104

TFA Salt

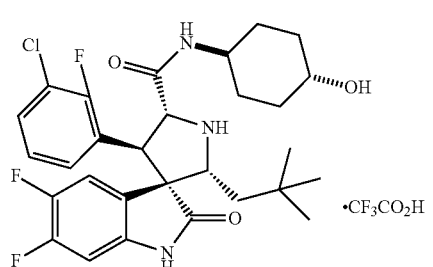

¹H NMR (300 MHz, MeOH-d4): 7.49 (t, J=7.2 Hz, 1H), 7.45-7.38 (m, 1H), 7.22 (t, J=8.0 Hz, 1H), 6.85-6.68 (m, 2H), 4.80 (d, J=9.8 Hz, 1H), 4.36 (d, J=9.9 Hz, 1H), 4.01 (dd, J=2.4, 7.6 Hz, 1H), 3.74-3.57 (m, 1H), 3.55-3.39 (m, 1H), 2.04-1.77 (m, 4H), 1.74-1.59 (m, 1H), 1.44-1.04 (m, 5H), 0.90 (d, J=4.5 Hz, 1H), 0.82 (s, 9H); ESI-MS calculated for $C_{29}H_{34}ClF_3N_3O_3$ (M+H)$^+$ requires 564.22, found 564.58.

MI-7105

TFA Salt

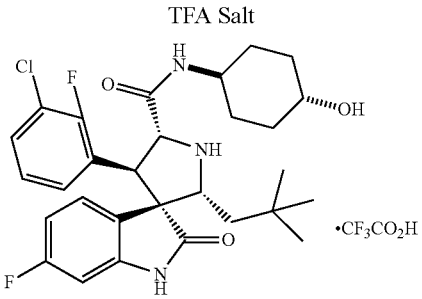

¹H NMR (300 MHz, MeOH-d4): 7.49 (t, J=7.2 Hz, 1H), 7.45-7.38 (m, 1H), 7.22 (t, J=8.0 Hz, 1H), 6.85-6.68 (m, 2H), 4.80 (d, J=9.8 Hz, 1H), 4.36 (d, J=9.9 Hz, 1H), 4.01 (dd, J=2.4, 7.6 Hz, 1H), 3.74-3.57 (m, 1H), 3.55-3.39 (m, 1H), 2.04-1.77 (m, 4H), 1.74-1.59 (m, 1H), 1.44-1.04 (m, 5H), 0.90 (d, J=4.5 Hz, 1H), 0.82 (s, 9H); ESI-MS calculated for $C_{29}H_{35}ClF_2N_3O_3$ (M+H)$^+$ requires 546.23, found 546.58.

MI-7106

TFA Salt

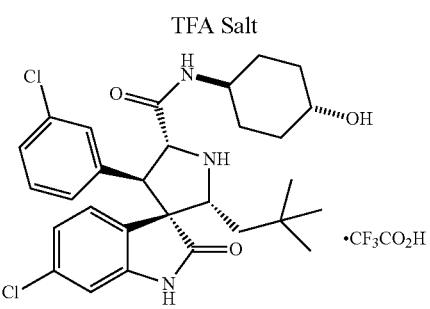

¹H NMR (300 MHz, MeOH-d4): 8.36 (d, J=7.0 Hz, 1H), 7.59 (d, J=8.1 Hz, 1H), 7.41-7.11 (m, 4H), 7.04 (d, J=7.6 Hz, 1H), 6.78 (d, J=1.8 Hz, 1H), 5.19 (d, J=11.3 Hz, 1H), 4.44 (J=8.1 Hz, 1H), 4.07 (d, J=11.3 Hz, 1H), 3.74-3.53 (m, 1H), 3.53-3.37 (m, 1H), 2.08-1.83 (m, 3H), 1.83-1.69 (m, 1H), 1.61-1.44 (m, 1H), 1.44-1.08 (m, 4H), 1.07-0.72 (m, 1H), 0.88 (s, 9H); ESI-MS calculated for $C_{29}H_{36}Cl_2N_3O_3$ (M+H)$^+$ requires 544.21, found 544.67.

MI-7108

TFA Salt

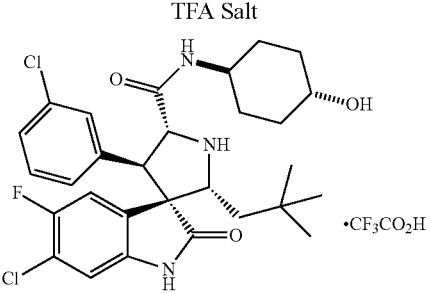

¹H NMR (300 MHz, MeOH-d4/DMSO-d6): 10.15 (s, 1H), 7.76 (d, J=8.2 Hz, 1H), 7.22 (s, 1H), 7.17-7.00 (m, 3H), 6.94 (d, J=7.1 Hz, 1H), 6.81 (d, J=6.0 Hz, 1H), 4.42 (d, J=8.3 Hz, 1H), 4.09 (d, J=3.0 Hz, 1H), 3.79 (d, J=8.3 Hz, 1H), 3.73-3.49 (m, 2H), 3.35 (d, J=9.5 Hz, 1H), 2.10-1.84 (m, 4H), 1.52-1.11 (m, 5H), 0.87 (s, 9H); ¹³C NMR (75 MHz, MeOH-d4/DMSO-d6): 177.1, 172.4, 153.6 (d, $J_{C-F}$=242.7 Hz), 138.7, 138.5 (d, $J_{C-F}$=2.4 Hz), 133.2, 129.0, 127.544, 127.541 (d, $J_{C-F}$=6.7 Hz), 126.8, 126.5, 119.7 (d, $J_{C-F}$=19.2 Hz), 111.3, 110.4 (d, $J_{C-F}$=24.1 Hz), 68.4, 66.6, 65.7, 64.0, 58.6, 46.8, 42.2, 33.26, 33.20, 30.4, 30.2, 29.7, 29.5; ESI-MS calculated for $C_{29}H_{35}Cl_2FN_3O_3$ (M+H)+ requires 562.20, found 562.67.

MI-7109

TFA Salt

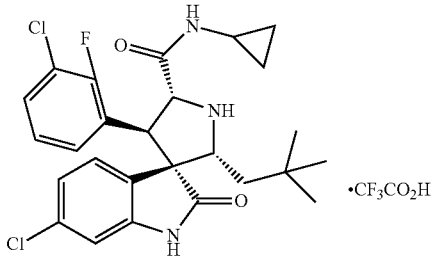 [SMILES: CC(C)(C)C[C@H]1N[C@@H](C(=O)NC2CC2)[C@H](c2cccc(Cl)c2F)[C@@]12C(=O)Nc1cc(Cl)ccc12 ; "·CF3CO2H"]

¹H NMR (300 MHz, MeOH-d4): 7.47 (t, J=6.7 Hz, 1H), 7.42-7.33 (m, 1H), 7.18 (t, J=7.7 Hz, 1H), 6.87 (d, J=1.8 Hz, 1H), 6.78 (dd, J=1.8, 8.1 Hz, 1H), 6.70 (d, J=8.1 Hz, 1H), 4.40 (d, J=9.7 Hz, 1H), 4.11 (dd, J=2.5, 7.6 Hz, 1H), 2.77-2.65 (m, 1H), 1.99 (dd, J=7.6, 15.3 Hz, 1H), 1.24 (dd, J=2.5, 15.3 Hz, 1H), 0.92-0.62 (m, 2H), 0.81 (s, 9H), 0.56-0.30 (m, 2H); ESI-MS calculated for $C_{26}H_{29}Cl_2FN_3O_2$ (M+H)+ requires 504.1₆, found 504.58.

B049

TFA Salt

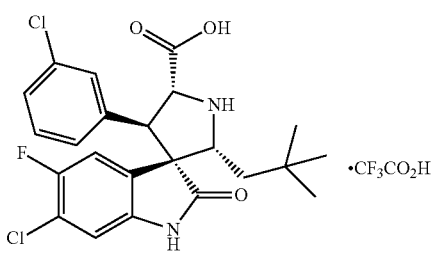 [SMILES: CC(C)(C)C[C@H]1N[C@@H](C(=O)O)[C@H](c2cccc(Cl)c2)[C@@]12C(=O)Nc1cc(Cl)c(F)cc12 ; "·CF3CO2H"]

¹H NMR (300 MHz, CD₃OD): 7.597 (d, J=8.73 Hz, 1H), 7.30-7.10 (m, 3H), 7.10-7.00 (m, 1H), 6.84 (d, J=6.14 Hz, 1H), 5.35 (d, J=12.85 Hz, 1H), 4.40 (dd, J=7.62, 3.80 Hz, 1H), 4.15 (d, J=12.92 Hz, 1H), 1.71 (dd, J=15.32, 7.68 Hz, 1H), 1.12 (dd, J=15.32, 3.79 Hz, 1H), 0.92 (s, 9H); ESI-MS calculated for $C_{23}H_{24}{}^{35}Cl_2FN_2O_3$ [M+H]+: 465.1148, Found: 465.50.

B053

TFA Salt

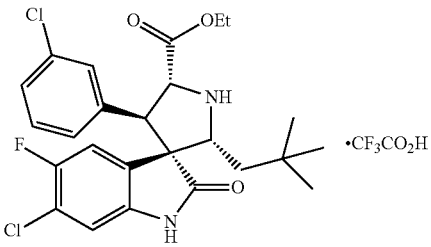 [SMILES: CCOC(=O)[C@@H]1N[C@H](CC(C)(C)C)[C@]2(C(=O)Nc3cc(Cl)c(F)cc32)[C@H]1c1cccc(Cl)c1 ; "·CF3CO2H"]

¹H NMR (300 MHz, CD₃OD): 7.67 (d, J=8.41 Hz, 1H), 7.35-7.18 (m, 3H), 7.10-7.00 (m, 1H), 6.87 (d, J=6.03 Hz, 1H), 5.62 (d, J=12.10 Hz, 1H), 4.42 (dd, J=8.54, 1.92 Hz, 1H), 4.30-4.15 (m, 2H), 4.23 (d, J=12.00 Hz, 1H), 1.96 (dd, J=15.44, 8.61 Hz, 1H), 1.24-1.15 (m, 1H), 1.13 (t, J=7.13 Hz, 3H), 0.91 (s, 9H); ESI-MS calculated for $C_{25}H_{28}{}^{35}Cl_2FN_2O_3$ [M+H]+: 493.1461, Found: 493.30.

B059

TFA Salt

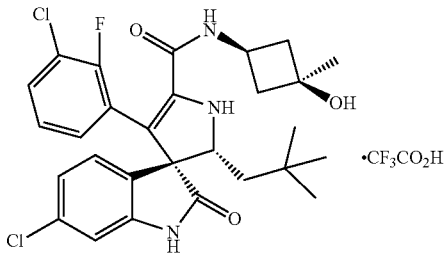 [SMILES: CC(C)(C)C[C@H]1NC(C(=O)N[C@H]2C[C@@](C)(O)C2)=C(c2cccc(Cl)c2F)[C@@]12C(=O)Nc1cc(Cl)ccc12 ; "·CF3CO2H"]

¹H NMR (300 MHz, CD₃OD): 7.45-7.34 (m, 1H), 7.26-7.12 (m, 1H), 7.04-6.93 (m, 1H), 6.90 (d, J=1.80 Hz, 1H), 6.65 (dd, J=8.08, 1.80 Hz, 1H), 4.41 (d, J=9.25 Hz, 1H), 3.96 (quint, J=8.13 Hz, 1H), 2.51-2.07 (m, 2H), 2.40-2.20 (m, 2H), 1.88 (dd, J=14.20, 9.91 Hz, 1H), 1.32 (s, 3H), 1.20-0.80 (m, 1H), 0.88 (s, 9H); ¹³C NMR (75 MHz, CD₃OD): 181.3, 172.9 (d, $J_{C-F}$=266.9 Hz), 168.6, 162.7, 145.3, 135.8, 131.7, 130.7 (d, $J_{C-F}$=38.6 Hz), 126.2 (d, $J_{C-F}$=4.5 Hz), 126.1, 123.6, 122.9, 122.7, 111.4, 78.4, 67.7, 63.4, 46.0, 45.8, 44.3, 38.0, 31.4, 30.2, 27.6; ESI-MS calculated for $C_{28}H_{31}{}^{35}Cl_2FN_3O_3$ [M+H]+: 546.1727, Found: 546.50.

B066-15

TFA Salt

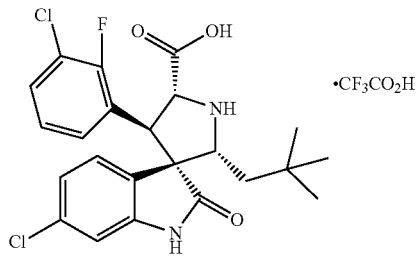 [SMILES: CC(C)(C)C[C@H]1N[C@@H](C(=O)O)[C@H](c2cccc(Cl)c2F)[C@@]12C(=O)Nc1cc(Cl)ccc12 ; "·CF3CO2H"]

¹H NMR (300 MHz, CD₃OD): 7.60-7.45 (m, 1H), 7.45-7.35 (m, 1H), 7.22 (t, J=7.96 Hz, 1H), 6.90 (d, J=1.80 Hz, 1H), 6.75 (dd, J=8.14, 1.92 Hz, 1H), 6.41 (d, J=8.13 Hz, 1H), 5.07 (d, J=8.40 Hz, 1H), 4.39 (d, J=8.40 Hz, 1H), 4.01 (dd, J=7.76, 2.17 Hz, 1H), 1.95 (dd, J=15.35, 7.83 Hz, 1H), 1.12 (dd, J=15.35, 2.17 Hz, 1H), 0.82 (s, 9H); ESI-MS calculated for $C_{23}H_{24}{}^{35}Cl_2FN_2O_3$ [M+H]⁺: 465.1148, Found: 465.42.

MI-519-72

TFA Salt

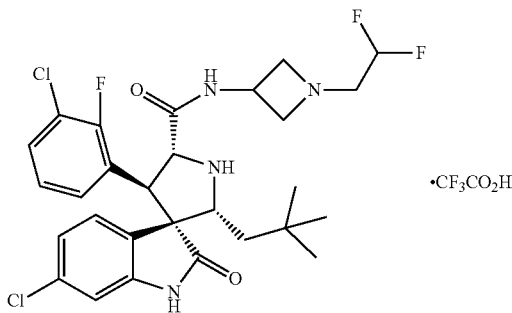 [SMILES: CC(C)(C)C[C@H]1N[C@@H](C(=O)NC2CN(CC(F)F)C2)[C@H](c2cccc(Cl)c2F)[C@@]12C(=O)Nc1cc(Cl)ccc12 ; "·CF3CO2H"]

•CF₃CO₂H

ESI-MS calculated for $C_{28}H_{32}{}^{35}Cl_2F_3N_4O_2$ [M+H]⁺: 583.1854, Found: 583.42.

MI-519-75

TFA Salt

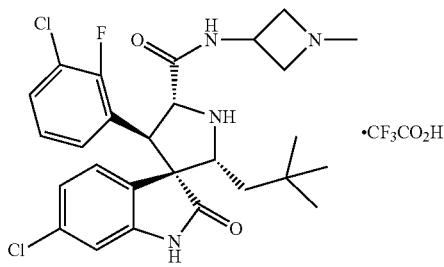 [SMILES: CN1CC(NC(=O)[C@@H]2N[C@H](CC(C)(C)C)[C@]3(C(=O)Nc4cc(Cl)ccc43)[C@H]2c2cccc(Cl)c2F)C1 ; "·CF3CO2H"]

•CF₃CO₂H

¹H NMR (300 MHz, CD₃OD): 7.64-7.54 (m, 1H), 7.42-7.60 (m, 1H), 7.26-7.18 (m, 1H), 6.88 (s, 1H), 6.80-6.70 (m, 1H), 6.50-6.40 (m, 1H), 5.20-5.00 (m, 1H), 4.80-4.30 (m, 4H), 4.30-4.10 (m, 2H), 4.10-4.00 (m, 1H), 3.98 (s, 3H), 1.90 (dd, J=14.96, 7.33 Hz, 1H), 1.11 (d, J=14.96 Hz, 1H), 0.81 (s, 9H); ESI-MS calculated for $C_{27}H_{32}{}^{35}Cl_2FN_4O_2$ [M+H]⁺: 533.1886, Found: 533.58.

MI-519-76

TFA Salt

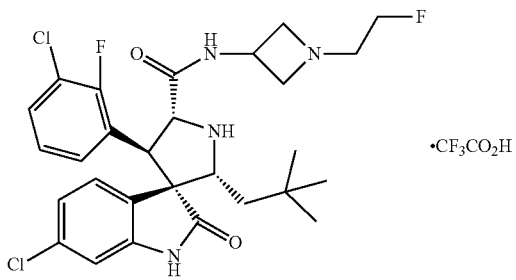 [SMILES: CC(C)(C)C[C@H]1N[C@@H](C(=O)NC2CN(CCF)C2)[C@H](c2cccc(Cl)c2F)[C@@]12C(=O)Nc1cc(Cl)ccc12 ; "·CF3CO2H"]

•CF₃CO₂H

ESI-MS calculated for $C_{28}H_{33}{}^{35}Cl_2F_2N_4O_2$ [M+H]⁺: 565.1949, Found: 565.42.

MI-519-77

TFA Salt

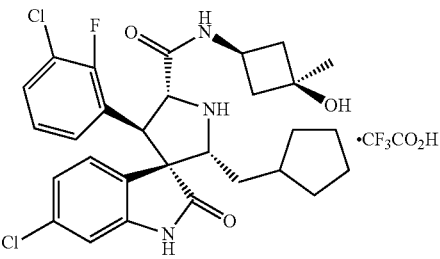 [SMILES: C[C@]1(O)C[C@@H](NC(=O)[C@@H]2N[C@H](CC3CCCC3)[C@]3(C(=O)Nc4cc(Cl)ccc43)[C@H]2c2cccc(Cl)c2F)C1 ; "·CF3CO2H"]

•CF₃CO₂H

¹H NMR (300 MHz, CD₃OD): 7.50-7.40 (m, 1H), 7.40 (m, 1H), 7.20-7.10 (m, 1H), 6.85 (d, J=1.40 Hz, 1H), 6.84-6.72 (m, 2H), 5.00-4.80 (m, 1H), 4.45 (d, J=10.10 Hz, 1H), 4.02 (t, J=6.61 Hz, 1H), 3.90 (quintet, J=8.07 Hz, 1H), 2.50-2.25 (m, 2H), 2.10-1.82 (m, 3H), 1.81-1.31 (m, 8H), 1.30 (s, 3H), 1.10-0.91 (m, 1H), 0.91-0.81 (m 1H); ESI-MS calculated for $C_{29}H_{33}{}^{35}Cl_2FN_3O_3$ [M+H]⁺: 560.1883, Found: 560.50.

MI-519-78

TFA Salt

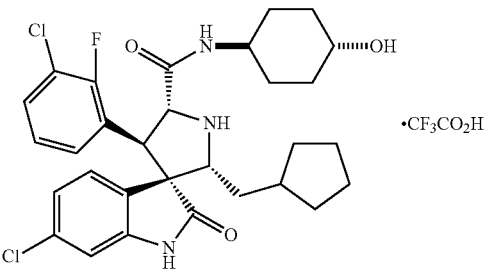

•CF₃CO₂H

¹H NMR (300 MHz, CD₃OD): 7.45-7.31 (m, 2H), 7.20-7.11 (m, 1H), 6.86-6.82 (m, 1H), 6.81-6.78 (m, 2H), 4.90-4.80 (m, 1H), 4.45 (d, J=10.33 Hz, 1H), 4.10-3.95 (m, 1H), 3.70-3.60 (m, 1H), 3.50-3.40 (m, 1H), 2.10-1.05 (m, 17H), 1.05-0.95 (m, 1H), 0.95-0.80 (m, 1H); ESI-MS calculated for $C_{30}H_{35}{}^{35}Cl_2FN_3O_3$ [M+H]⁺: 574.2040, Found: 574.58.

MI-519-79

TFA Salt

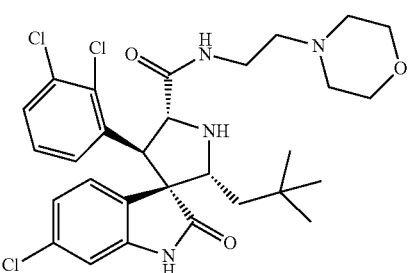

•CF₃CO₂H

¹H NMR (300 MHz, CD₃OD): 7.78 (d, J=6.92 Hz, 1H), 7.56-7.42 (m, 2H), 6.90 (d, J=1.89 Hz, 1H), 6.68 (dd, J=8.15, 1.84 Hz, 1H), 6.03 (dd, J=8.13, 3.66 Hz, 1H), 4.80-4.70 (m, 1H), 4.58 (d, J=5.51 Hz, 1H), 4.10-3.70 (m, 7H), 3.54 (dt, J=15.10, 5.20 Hz, 2H), 3.40-3.20 (m, 3H), 1.79 (ddd, J=14.60, 8.49, 1.59 Hz, 1H), 1.00-0.80 (m, 1H), 0.81 (s, 9H); ESI-MS calculated for $C_{29}H_{36}{}^{35}Cl_3N_4O_3$ [M+H]⁺: 593.1853, Found: 593.75.

MI-519-80

TFA Salt

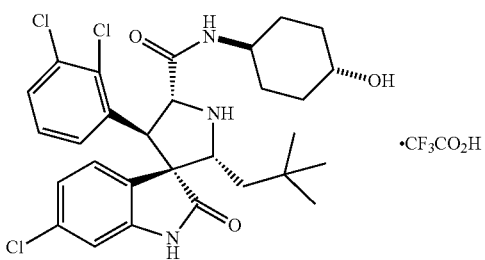

¹H NMR (300 MHz, CD₃OD): 7.80-7.72 (m, 1H), 7.50-7.38 (m, 2H), 6.87 (d, J=1.81 Hz, 1H), 6.71 (dd, J=8.16, 1.81 Hz, 1H), 6.52-6.40 (m, 1H), 4.96-4.80 (m, 1H), 4.62 (d, J=8.69 Hz, 1H), 4.10-3.95 (m, 1H), 3.70-3.55 (m, 1H), 3.50-3.45 (m, 1H), 2.00-1.80 (m, 3H), 1.80-1.60 (m, 1H), 1.40-1.00 (m, 5H), 0.95-0.85 (m, 1H), 0.80 (s, 9H); ESI-MS calculated for $C_{29}H_{35}{}^{35}Cl_3N_3O_3$ [M+H]⁺: 578.1744, Found: 578.75.

C02701

TFA Salt

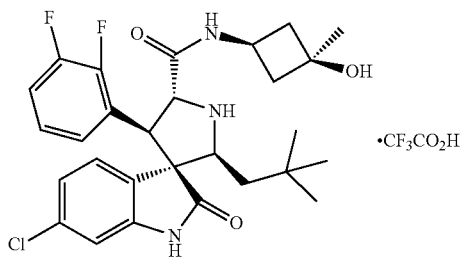 [SMILES: CC(C)(C)C[C@@H]1N[C@@H](C(=O)N[C@H]2C[C@@](C)(O)C2)[C@H](c2cccc(F)c2F)[C@]12C(=O)Nc1cc(Cl)ccc12 ; "·CF3CO2H"]

¹H NMR (300 MHz, MeOH-d4): 8.82 (d, J=6.83 Hz, 1H), 7.65-7.55 (m, 1H), 7.45-7.30 (m, 1H), 7.20-7.05 (m, 3H), 6.80-6.75 (m, 1H), 5.40-5.10 (m, 1H), 4.61 (d, J=11.39 Hz, 1H), 4.50 (d, J=7.66 Hz, 1H), 3.95-3.80 (m, 1H), 2.45-2.30 (m, 1H), 2.30-2.15 (m, 1H), 2.05-1.80 (m, 2H), 1.80-1.60 (m, 1H), 1.27 (s, 3H), 1.20-1.08 (m, 1H), 0.86 (s, 9H); ¹³C NMR (75 MHz, MeOH-d4): 177.8, 167.0, 160.0-148.0 (m, 2×$C_{sp2}$-F), 145.2, 137.2, 126.8, 126.5-126.0 (m), 125.0, 124.1, 123.5, 122.1 (d, $J_{C-F}$=9.74 Hz), 119.1 (d, $J_{C-F}$=17.1 Hz), 112.1, 67.3, 64.5, 64.2, 62.6, 48.5, 45.6, 45.5, 43.3, 38.3, 31.0, 29.5, 27.5; ESI-MS calculated for $C_{28}H_{33}{}^{35}ClF_2N_3O_3$ [M+H]⁺: 532.2179, Found: 532.50.

C02901

TFA Salt

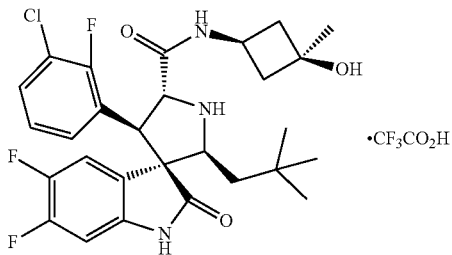 [SMILES: CC(C)(C)C[C@@H]1N[C@@H](C(=O)N[C@H]2C[C@@](C)(O)C2)[C@H](c2cccc(Cl)c2F)[C@]12C(=O)Nc1cc(F)c(F)cc12 ; "·CF3CO2H"]

¹H NMR (300 MHz, MeOH-d4): 7.80-7.65 (m, 1H), 7.60-7.50 (m, 1H), 7.40-7.30 (m, 1H), 7.20-7.10 (m, 1H), 6.80-6.65 (m, 1H), 5.50-5.10 (m, 1H), 4.60 (d, J=11.39 Hz, 1H), 4.50 (d, J=6.96 Hz, 1H), 3.95-3.80 (m, 1H), 2.50-2.30 (m, 1H), 2.30-2.20 (m, 1H), 2.10-1.80 (m, 2H), 1.80-1.65 (m, 1H), 1.27 (s, 3H), 1.20-1.05 (m, 1H), 0.87 (s, 9H); ¹³C NMR (75 MHz, MeOH-d4): 177.8, 167.0, 160.0-145.0 (m, 3×$C_{sp2}$-F), 132.6, 128.6, 126.6, 122.5 (d, $J_{C-F}$=18.9 Hz), 121.3 (d, $J_{C-F}$=13.0 Hz), 118.8, 115.4 (d, $J_{C-F}$=21.7 Hz), 115.1, 101.8 (d, $J_{C-F}$=23.3 Hz), 67.3, 64.6, 64.3, 62.5, 48.7, 45.6, 45.5, 43.4, 38.3, 31.0, 29.5, 27.5; ESI-MS calculated for $C_{28}H_{32}{}^{35}ClF_3N_3O_3$ [M+H]⁺: 550.2084, Found: 550.33.

C03001

TFA Salt

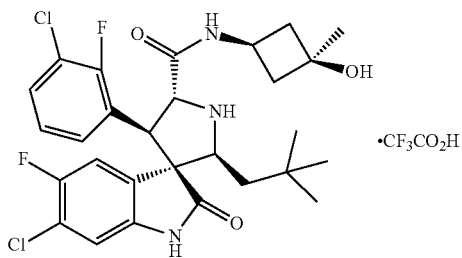 [SMILES: CC(C)(C)C[C@@H]1N[C@@H](C(=O)N[C@H]2C[C@@](C)(O)C2)[C@H](c2cccc(Cl)c2F)[C@]12C(=O)Nc1cc(Cl)c(F)cc12 ; "·CF3CO2H"]

¹H NMR (300 MHz, MeOH-d4): 7.70 (d, J=7.30 Hz, 1H), 7.60-7.50 (m, 1H), 7.45-7.35 (m, 1H), 7.25-7.15 (m, 1H), 6.88 (d, J=6.00 Hz, 1H), 5.21 (d, J=11.35 Hz, 1H), 4.61 (d, J=11.37 Hz, 1H), 4.53 (d, J=8.19 Hz, 1H), 3.95-3.80 (m, 1H), 2.50-2.35 (m, 1H), 2.35-2.15 (m, 1H), 2.00-1.80 (m, 2H), 1.80-1.60 (m, 1H), 1.29 (s, 3H), 1.25-1.05 (m, 1H), 0.89 (s, 9H); ¹³C NMR (75 MHz, MeOH-d4): 177.3, 166.7, 157.6 (d, $J_{C-F}$=249.5 Hz), 155.7 (d, $J_{C-F}$=243.5 Hz), 140.4 (d, $J_{C-F}$=2.8 Hz), 132.5, 128.4, 126.4 (d, $J_{C-F}$=4.9 Hz), 125.0 (d, $J_{C-F}$=7.4 Hz), 123.4 (d, $J_{C-F}$=19.5 Hz), 122.3 (d, $J_{C-F}$=18.9 Hz), 121.0 (d, $J_{C-F}$=13.0 Hz), 114.5 (d, $J_{C-F}$=25.1 Hz), 104.8, 67.1, 64.6, 64.2, 62.4, 47.3, 45.4, 45.3, 43.2, 38.2, 30.8, 29.2, 27.3; ESI-MS calculated for $C_{28}H_{32}{}^{35}Cl_2F_2N_3O_3$ [M+H]⁺: 566.1789, Found: 566.50.

C03401

TFA Salt

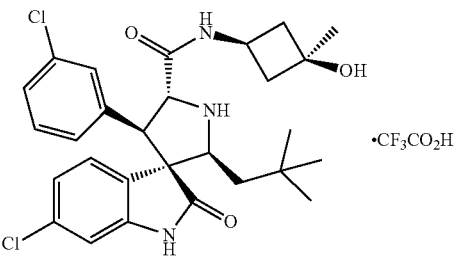 [SMILES: CC(C)(C)C[C@@H]1N[C@@H](C(=O)N[C@H]2C[C@@](C)(O)C2)[C@H](c2cccc(Cl)c2)[C@]12C(=O)Nc1cc(Cl)ccc12 ; "·CF3CO2H"]

¹H NMR (300 MHz, MeOH-d4): 7.58 (d, J=8.07 Hz, 1H), 7.30-7.10 (m, 4H), 7.02 (d, J=7.67 Hz, 1H), 6.77 (d, J=1.54 Hz, 1H), 5.40-5.20 (m, 1H), 4.44 (d, J=7.09 Hz, 1H), 4.10 (d, J=11.25 Hz, 1H), 3.95-3.80 (m, 1H), 2.45-2.30 (m, 1H), 2.30-2.15 (m, 1H), 2.05-1.85 (m, 2H), 1.80-1.70 (m, 1H), 1.27 (s, 3H), 1.20-1.10 (m, 1H), 0.86 (s, 9H); ¹³C NMR (75 MHz, MeOH-d4): 177.8, 167.3, 145.3, 137.1, 135.8, 134.4, 131.4, 130.4, 129.5, 128.3, 126.3, 124.2, 124.1, 112.2, 67.3, 64.9, 64.2, 62.8, 57.2, 45.7, 45.6, 43.4, 38.3, 31.0, 29.5, 27.5; ESI-MS calculated for $C_{28}H_{34}{}^{35}Cl_2N_3O_3$ [M+H]⁺: 530.1977, Found: 530.58.

C03701

TFA Salt

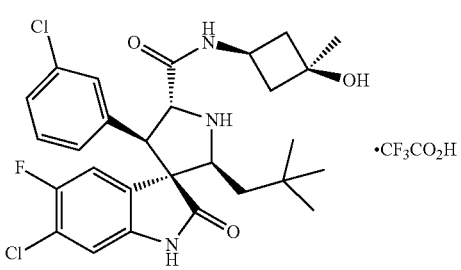 [SMILES: CC(C)(C)C[C@@H]1N[C@@H](C(=O)N[C@H]2C[C@@](C)(O)C2)[C@H](c2cccc(Cl)c2)[C@]12C(=O)Nc1cc(Cl)c(F)cc12 ; "·CF3CO2H"]

¹H NMR (300 MHz, MeOH-d4): 9.00-8.80 (m, 1H), 7.73 (d, J=8.42 Hz, 1H), 7.40-7.20 (m, 3H), 7.15-7.05 (m, 1H), 6.89 (d, J=6.00 Hz, 1H), 5.32 (d, J=11.34 Hz, 1H), 4.52 (d, J=7.91 Hz, 1H), 4.20 (d, J=11.28 Hz, 1H), 4.00-3.80 (m, 1H), 2.50-2.35 (m, 1H), 2.35-2.20 (m, 1H), 2.20-1.90 (m, 2H), 1.90-1.80 (m, 1H), 1.31 (s, 3H), 1.30-1.15 (m, 1H), 0.91 (s, 9H); ¹³C NMR (75 MHz, MeOH-d4): 178.8, 168.2, 157.3 (d, $J_{C-F}$=255.8 Hz), 142.1 (d, $J_{C-F}$=2.6 Hz), 137.1, 135.5, 132.8, 131.7, 130.7, 129.6, 127.2 (d, $J_{C-F}$=7.2 Hz), 124.7 (d, $J_{C-F}$=19.3 Hz), 115.5 (d, $J_{C-F}$=24.9 Hz), 114.8, 68.6, 66.6, 65.3, 64.0, 58.2, 47.0, 46.8, 44.7, 39.5, 32.2, 30.8, 28.8; ESI-MS calculated for $C_{28}H_{33}{}^{35}Cl_2FN_3O_3$ [M+H]⁺: 548.1883, Found: 548.42

C04801

TFA Salt

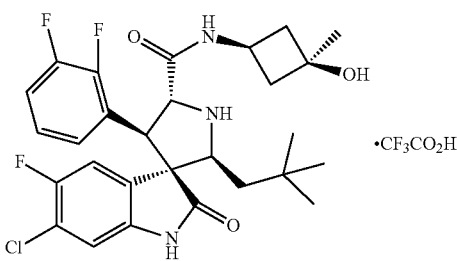 [SMILES: CC(C)(C)C[C@@H]1N[C@@H](C(=O)N[C@H]2C[C@@](C)(O)C2)[C@H](c2cccc(F)c2F)[C@]12C(=O)Nc1cc(Cl)c(F)cc12 ; "·CF3CO2H"]

¹H NMR (300 MHz, MeOH-d4): 9.00-8.80 (m, 1H), 7.70 (d, J=8.35 Hz, 1H), 7.50-7.35 (m, 1H), 7.30-7.10 (m, 2H), 6.88 (d, J=6.88 Hz, 1H), 5.30 (d, J=11.32 Hz, 1H), 4.66 (d, J=11.33 Hz, 1H), 4.56 (d, J=7.43 Hz, 1H), 4.00-3.80 (m, 1H), 2.50-2.35 (m, 1H), 2.35-2.20 (m, 1H), 2.10-1.90 (m, 2H), 1.80-1.70 (m, 1H), 1.30 (s, 3H), 1.16 (d, J=15.34 Hz, 1H), 0.90 (s, 9H); ¹³C NMR (75 MHz, MeOH-d4): 177.5, 166.9, 160-145 (m, 2×$C_{sp2}$-F), 155.9 (d, $J_{C-F}$=243.4 Hz), 140.7 (d, $J_{C-F}$=2.69 Hz), 126.5-126.1 (m), 125.6 (d, $J_{C-F}$=7.6 Hz), 125.0 (d, $J_{C-F}$=3.4 Hz), 123.6 (d, $J_{C-F}$=19.5 Hz), 122.0 (d, $J_{C-F}$=9.8 Hz), 119.1 (d, $J_{C-F}$=17.1 Hz), 114.7 (d, $J_{C-F}$=25.0 Hz), 113.4, 67.3, 64.7, 64.3, 62.5, 48.2, 45.6, 45.6, 43.4, 38.3, 31.0, 29.5, 27.5; ESI-MS calculated for $C_{28}H_{32}{}^{35}ClF_3N_3O_3$ [M+H]⁺: 550.2084, Found: 550.42.

MI-710201

TFA Salt

¹H NMR (300 MHz, MeOH-d4): 7.57 (d, J=8.0 Hz, 1H), 7.50-7.36 (m, 1H), 7.27-7.07 (m, 3H), 6.79 (s, 1H), 5.11 (d, J=11.1 Hz, 1H), 4.55 (d, J=11.0 Hz, 1H), 4.39 (d, J=7.7 Hz, 1H), 3.71-3.52 (m, 1H), 3.52-3.37 (m, 1H), 3.21 (dd, J=7.4, 14.5 Hz, 1H), 1.92 (d, J=9.6 Hz, 1H), 1.86-1.70 (m, 2H), 1.58 (d, J=11.8 Hz, 1H), 1.43-1.18 (m, 4H), 1.12 (d, J=15.5 Hz, 1H), 0.99 (d, J=13.0 Hz, 1H), 0.88 (s, 9H); ESI-MS calculated for $C_{29}H_{35}ClF_2N_3O_3$ (M+H)⁺ requires 546.23, found 546.58.

MI-710401

TFA Salt

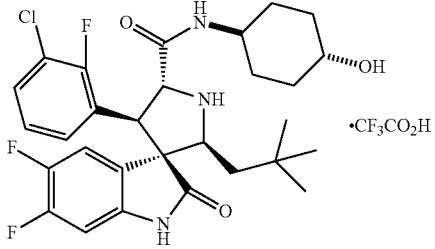

¹H NMR (300 MHz, MeOH-d4): 7.67 (t, J=8.6 Hz, 1H), 7.57 (t, J=6.8 Hz, 1H), 7.38 (t, J=6.8 Hz, 1H), 7.15 (t, J=7.8 Hz, 1H), 6.71 (dd, J=6.6, 10.1 Hz, 1H), 5.01 (d, J=10.8 Hz, 1H), 4.52 (d, J=10.8 Hz, 1H), 4.40-4.21 (m, 1H), 3.74-3.56 (m, 1H), 3.56-3.40 (m, 1H), 2.08-1.87 (m, 2H), 1.87-1.68 (m, 2H), 1.68-1.53 (m, 1H), 1.45-1.18 (m, 3H), 1.17-0.97 (m, 2H), 0.89 (s, 9H); ESI-MS calculated for $C_{29}H_{34}ClF_3N_3O_3$ (M+H)⁺ requires 564.22, found 564.58.

MI-710501

TFA Salt

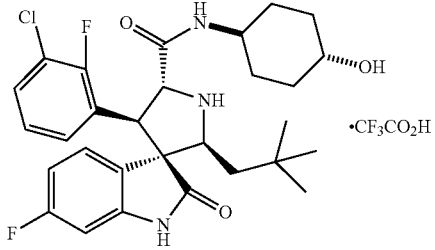

¹H NMR (300 MHz, MeOH-d4): 7.66-7.53 (m, 1H), 7.44-7.33 (m, 1H), 7.22-7.09 (m, 1H), 6.93-6.79 (m, 1H), 6.59-6.51 (m, 1H), 5.40-5.31 (m, 1H), 4.63-4.48 (m, 1H), 4.41-4.30 (m, 1H), 2.41-2.20 (m, 2H), 2.15-1.97 (m, 2H), 1.95-1.85 (m, 1H), 1.85-1.71 (m, 1H), 1.71-1.47 (m, 3H), 1.19-1.07 (m, 1H), 0.88 (s, 9H); ESI-MS calculated for $C_{29}H_{34}ClF_3N_3O_3$ (M+H)⁺ requires 546.23, found 546.58.

MI-710901

TFA Salt

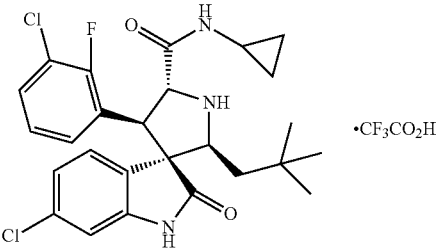 [SMILES: CC(C)(C)C[C@@H]1N[C@@H](C(=O)NC2CC2)[C@H](c2cccc(Cl)c2F)[C@]12C(=O)Nc1cc(Cl)ccc12 ; "·CF3CO2H"]

¹H NMR (300 MHz, MeOH-d4): 7.61 (d, J=8.1 Hz, 1H), 7.53 (t, J=6.7 Hz, 1H), 7.40 (t, J=7.0 Hz, 1H), 7.21-7.08 (m, 2H), 6.79 (d, J=1.6 Hz, 1H), 5.14 (d, J=11.3 Hz, 1H), 4.60 (d, J=11.3 Hz, 1H), 4.48 (d, J=7.0 Hz, 1H), 2.78-2.58 (m, 1H), 1.86 (dd, J=8.4, 15.4 Hz, 1H), 1.13 (d, J=15.4 Hz, 1H), 0.88 (s, 9H), 0.78-0.60 (m, 2H), 0.47-0.16 (m, 2H); ¹³C NMR (75 MHz, MeOH-d4): 177.9, 169.5, 157.8 (d, $J_{C\text{-}F}$=249.4 Hz), 145.2, 137.2, 132.6, 128.7, 126.8 (d, $J_{C\text{-}F}$=1.6 Hz), 126.6 (d, $J_{C\text{-}F}$=4.9 Hz), 124.2, 123.6, 122.5 (d, $J_{C\text{-}F}$=18.8 Hz), 121.8 (d, $J_{C\text{-}F}$=13.1 Hz), 64.7, 64.4, 62.9, 43.5, 31.0, 29.6, 23.9, 6.7, 6.5; ESI-MS calculated for $C_{26}H_{29}Cl_2FN_3O_2$ (M+H)⁺ requires 504.16, found 504.58.

Example 2

Fluorescence-Polarization MDM2 Binding Assay

The binding affinity of the MDM2 inhibitors was determined using an optimized, sensitive and quantitative fluorescence polarization-based (FP-based) binding assay using a recombinant human His-tagged MDM2 protein (residues 1-118) and a fluorescently tagged p53-based peptide.

The design of the fluorescence probe was based upon a previously reported high-affinity p53-based peptidomimetic compound (5-FAM-βAla-βAla-Phe-Met-Aib-pTyr-(6-Cl-LTrp)-Glu-Ac3c-Leu-Asn-NH2 (SEQ ID NO: 1)) García-Echeverria et al., *J. Med. Chem.* 43: 3205-3208 (2000)). This tagged peptide is called PMDM6-F. The $K_d$ value of PMDM6-F with the recombinant MDM2 protein was determined from the saturation curve. MDM2 protein was serially double diluted in a Dynex 96-well, black, round-bottom plate, and the PMDM6-F peptide was added at 1 nM concentration. The assay was performed in the buffer: 100 mM potassium phosphate, pH 7.5; 100 μg/mL bovine gamma globulin; 0.02% sodium azide, 0.01% Triton X-100) and the polarization values were measured after 3 h of incubation using an ULTRA READER (Tecan U.S. Inc., Research Triangle Park, N.C.). The $IC_{50}$ value was obtained by fitting the mP values in a sigmoidal dose-response curve (variable slope) with a non-linear regression, and was determined to be 1.40 nM±0.25. The $K_d$ value was calculated using the equation: $K_d$ value =$IC_{50}$-L0/2. L0/2 is the concentration of the free ligand (PMDM6-F). Since PMDM6-F was used at a final concentration of 1 nM, L0/2 was 0.5 nM.

Figure 23:
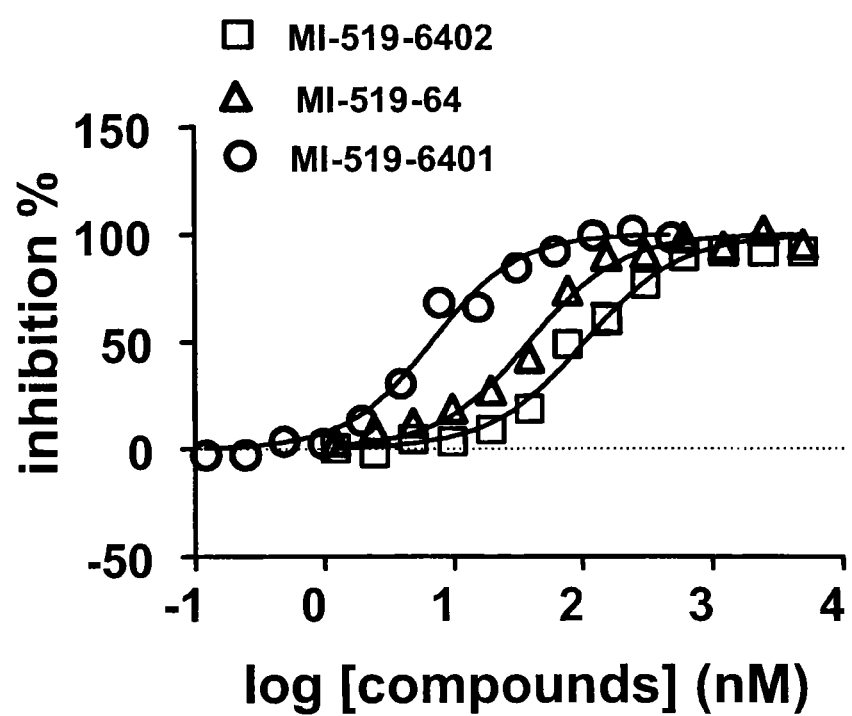
FIG. 23 is a line graph showing the binding affinities of MI-519-64, MI-519-6401, and MI-519-6402 to human MDM2 protein, as determined using a fluorescence-polarization binding assay. The purity of each isomer used in this experiment (as determined by RP-HPLC) are as follows: MI-519-6402: 90% (with 10% of MI-519-64); MI-519-64: 93% (with 3% of MI-519-6402 and 4% of MI-519-6401); and MI-519-6401: >99%. The log $EC_{50}$ values for MI-519-6402, MI-519-64, and MI-519-6401 are 2.030 nM, 1.598 nM, and 0.8354 nM, respectively.
Figure 24:
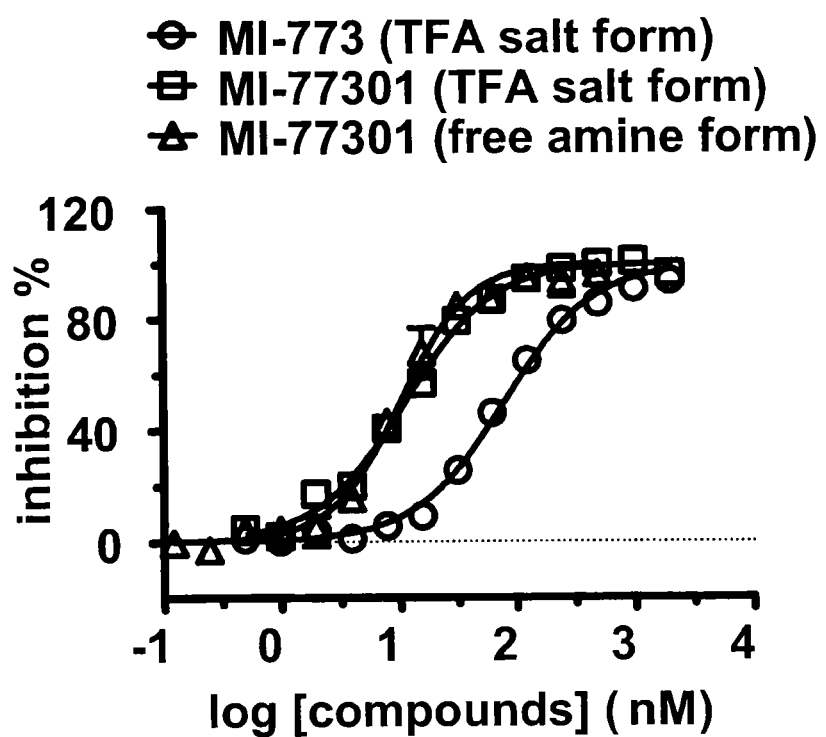
FIG. 24 is a line graph show the binding affinities of MI-773 and MI-77301 to human MDM2 protein, as determined using a fluorescence-polarization binding assay.

Dose-dependent, competitive binding experiments were performed with serial dilutions of a tested compound in DMSO. A 5 μL sample of the tested compound and pre-incubated MDM2 protein (10 nM) and PMDM6-F peptide (1 nM) in the assay buffer (100 mM potassium phosphate, pH 7.5; 100 μg/mL bovine gamma globulin; 0.02% sodium azide, 0.01% Triton X-100), were added in a Dynex 96-well, black, round-bottom plate to produce a final volume of 125 μL. For each assay, the controls included the MDM2 protein and PMDM6-F (equivalent to 0% inhibition), PMDM6-F peptide alone (equivalent to 100% inhibition). The polarization values were measured after 3 h of incubation. The $IC_{50}$ values, i.e. the inhibitor concentration at which 50% of bound peptide is displaced, were determined from a plot using non-linear least-squares analysis. Curve fitting was performed using GRAPHPAD PRISM software (GraphPad Software, Inc., San Diego, Calif.). As presented in Tables 19A-D and FIGS. 23 and 24, compounds provided herein are potent MDM2 antagonists. Compounds shown in Tables 19A-D as the free base were tested either as the free base or as the $CF_3CO_2H$ (TFA) or HCl salt. In general, comparable assay responses are expected between the free base and salt form of a compound.

Example 3

Cell Growth Assay

Isogenic HCT-116 colon cancer cell lines were a kind gift from Prof. Bert Vogelstein (Johns Hopkins, Baltimore, Md.) and were maintained in McCoy's 5A medium containing 10% FBS. All other cell lines were obtained from ATCC, (Manassas, Va.) and were maintained in RPMI-1640 medium containing 10% FBS.

Cells were seeded in 96-well flat bottom cell culture plates at a density of 2-3×10³ cells/well with compounds and incubated for 4 days. The rate of cell growth inhibition after treatment with increasing concentrations of the tested compounds was determined by WST-8 (2-(2-methoxy-4-nitrophenyl)-3-(4-nitrophenyl)-5-(2,4-disulfophenyl)-2H-tetrazolium monosodium salt (Dojindo Molecular Technologies Inc., Gaithersburg, Md.). WST-8 was added at a final concentration of 10% to each well, and then the plates were incubated at 37° C. for 2-3 hrs. The absorbance of the samples was measured at 450 nm using a TECAN ULTRA Reader. The concentration of the compounds that inhibited cell growth by 50% ($IC_{50}$) was calculated by comparing absorbance in the untreated cells and the cells treated with the compounds using the GraphPad Prism software (GraphPad Software, La Jolla, Calif. 92037, USA). The results of this assay are presented in Tables 19A-D.

TABLE 19A

| | | | $IC_{50}$ (μM) | | | | |
|---|---|---|---|---|---|---|---|
| Example | Chemical Structure | MDM2 | SJSA-1 (p53 wild-type) | HCT-116 (p53 wild-type) | LNCAP (p53 wild-type) | HCT-116 (p3-/-) | PC-3 (deleted p53) |
| MI-219-M1 (a) | | <1 | NT | <3 | <3 | >10 | >10 |

TABLE 19A-continued

| Example | Chemical Structure | MDM2 | SJSA-1 (p53 wild-type) | HCT-116 (p53 wild-type) | LNCAP (p53 wild-type) | HCT-116 (p3-/-) | PC-3 (deleted p53) |
|---|---|---|---|---|---|---|---|
| MI-219-M1 (b) | 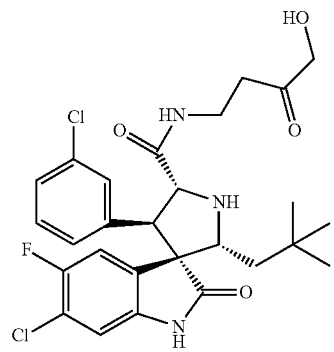 [SMILES: CC(C)(C)C[C@H]1N[C@@H](C(=O)NCCC(=O)CO)[C@H](c2cccc(Cl)c2)[C@@]12C(=O)Nc1cc(Cl)c(F)cc12] | <1 | NT | <3 | <3 | >10 | >10 |
| MI-519-24 | 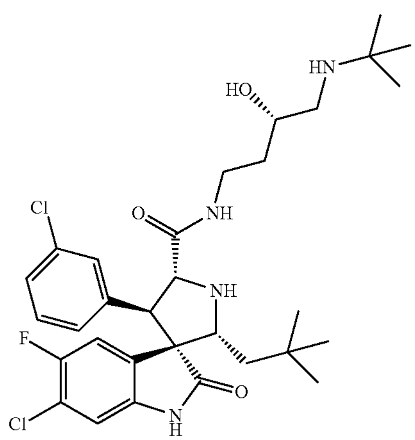 [SMILES: CC(C)(C)C[C@H]1N[C@@H](C(=O)NCC[C@H](O)CNC(C)(C)C)[C@H](c2cccc(Cl)c2)[C@@]12C(=O)Nc1cc(Cl)c(F)cc12] | <2 | NT | <2 | <3 | 6.5 ± 0.7 | 3.7 ± 0.2 |
| MI-519-27 | 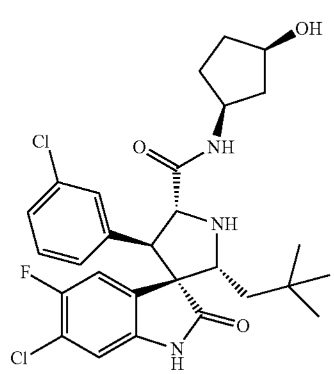 [SMILES: CC(C)(C)C[C@H]1N[C@@H](C(=O)N[C@H]2CC[C@@H](O)C2)[C@H](c2cccc(Cl)c2)[C@@]12C(=O)Nc1cc(Cl)c(F)cc12] | <1 | <3 | <2 | <2 | >10 | >5 |

TABLE 19A-continued

| Example | Chemical Structure | MDM2 | SJSA-1 (p53 wild-type) | HCT-116 (p53 wild-type) | LNCAP (p53 wild-type) | HCT-116 (p3-/-) | PC-3 (deleted p53) |
|---|---|---|---|---|---|---|---|
| MI-519-28 | 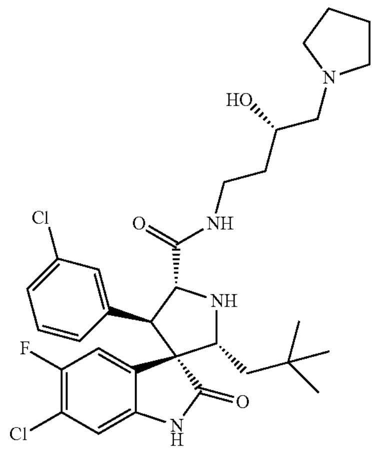 [SMILES: CC(C)(C)C[C@H]1N[C@@H](C(=O)NCC[C@H](O)CN2CCCC2)[C@H](c2cccc(Cl)c2)[C@@]12C(=O)Nc1cc(Cl)c(F)cc12] | <2 | NT | <2 | <2 | >5 | 4.1 ± 0.2 |
| MI-519-29 | 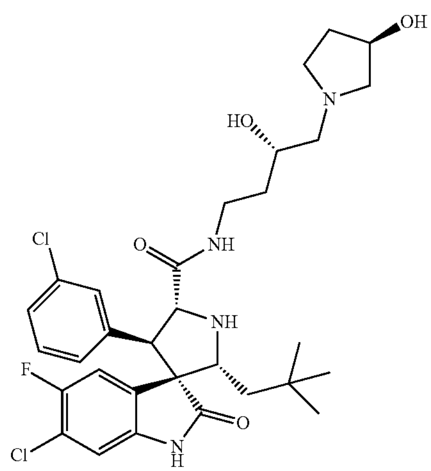 [SMILES: CC(C)(C)C[C@H]1N[C@@H](C(=O)NCC[C@H](O)CN2CC[C@@H](O)C2)[C@H](c2cccc(Cl)c2)[C@@]12C(=O)Nc1cc(Cl)c(F)cc12] | <1 | NT | <5 | <5 | >10 | >10 |
| MI-519-30 | 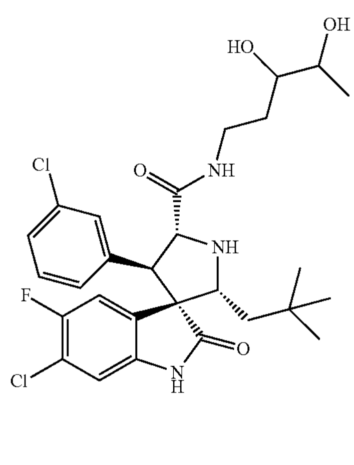 [SMILES: CC(O)C(O)CCNC(=O)[C@@H]1N[C@H](CC(C)(C)C)[C@]2(C(=O)Nc3cc(Cl)c(F)cc32)[C@H]1c1cccc(Cl)c1] | <2 | NT | 1.3 ± 0.3 | 1.1 ± 0.0 | 19.6 ± 5.2 | 19.1 ± 2.4 |

TABLE 19A-continued

| | | | IC$_{50}$ (μM) | | | | |
|---|---|---|---|---|---|---|---|
| Example | Chemical Structure | MDM2 | SJSA-1 (p53 wild-type) | HCT-116 (p53 wild-type) | LNCAP (p53 wild-type) | HCT-116 (p3-/-) | PC-3 (deleted p53) |
| MI-519-31 (isomer of MI-519-30) | | <2 | NT | 2.0 ± 0.8 | 1.3 ± 0.2 | 20.1 ± 2.5 | 24.7 ± 2.0 |
| MI-519-35 | | <1 | NT | 1.8 ± 0.5 | 1.4 ± 0.5 | 5.3 ± 0.6 | 6.7 ± 0.9 |
| MI-519-36 | | <1 | NT | 1.2 ± 0.6 | 0.9 ± 0.1 | 29.8 ± 6.5 | 20.6 ± 5.3 |
| MI-519-37 | | <1 | NT | 1.0 ± 0.5 | 0.6 ± 0.1 | 14.9 ± 2.0 | 14.0 ± 2.2 |

TABLE 19A-continued

| Example | Chemical Structure | MDM2 | SJSA-1 (p53 wild-type) | HCT-116 (p53 wild-type) | LNCAP (p53 wild-type) | HCT-116 (p3-/-) | PC-3 (deleted p53) |
|---|---|---|---|---|---|---|---|
| MI-519-38 | 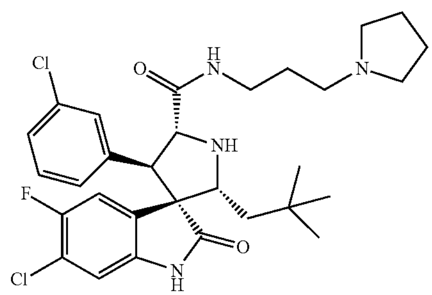 [SMILES: CC(C)(C)C[C@H]1N[C@@H](C(=O)NCCCN2CCCC2)[C@H](c2cccc(Cl)c2)[C@@]12C(=O)Nc1cc(Cl)c(F)cc12] | <1 | 2.1 ± 0.1 | 1.4 ± 0.6 | 1.0 ± 0.3 | 5.3 ± 1.6 | 3.1 ± 0.4 |
| MI-519-40 | 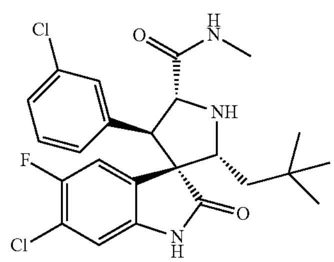 [SMILES: CNC(=O)[C@@H]1N[C@H](CC(C)(C)C)[C@]2(C(=O)Nc3cc(Cl)c(F)cc32)[C@H]1c1cccc(Cl)c1] | <1 | 1.3 ± 0.3 | 1.0 ± 0.1 | 1.0 ± 0.1 | 18.5 ± 5.5 | 14.6 ± 2.7 |
| MI-519-41 | 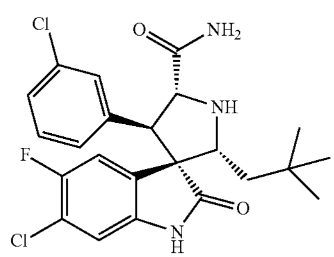 [SMILES: CC(C)(C)C[C@H]1N[C@@H](C(N)=O)[C@H](c2cccc(Cl)c2)[C@@]12C(=O)Nc1cc(Cl)c(F)cc12] | <1 | 1.3 ± 0.4 | 1.0 ± 0.3 | 1.2 ± 0.0 | 17.9 ± 2.2 | 14.9 ± 1.1 |
| MI-519-43 | 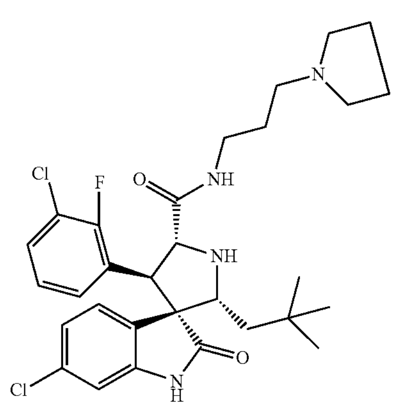 [SMILES: CC(C)(C)C[C@H]1N[C@@H](C(=O)NCCCN2CCCC2)[C@H](c2cccc(Cl)c2F)[C@@]12C(=O)Nc1cc(Cl)ccc12] | <10 | 0.9 ± 0.1 | 0.9 ± 0.0 | 1.0 ± 0.0 | 4.1 ± 0.5 | 3.4 ± 0.0 |

TABLE 19A-continued

| Example | Chemical Structure | MDM2 | SJSA-1 (p53 wild-type) | HCT-116 (p53 wild-type) | LNCAP (p53 wild-type) | HCT-116 (p3-/-) | PC-3 (deleted p53) |
|---|---|---|---|---|---|---|---|
| MI-519-44 | 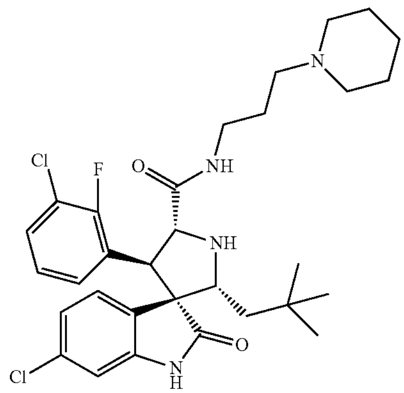 [SMILES: CC(C)(C)C[C@H]1N[C@@H](C(=O)NCCCN2CCCCC2)[C@H](c2cccc(Cl)c2F)[C@@]12C(=O)Nc1cc(Cl)ccc12] | <10 | 0.9 ± 0.1 | 0.8 ± 0.0 | 1.3 ± 0.2 | 2.8 ± 0.7 | 2.6 ± 0.1 |
| MI-519-45 | 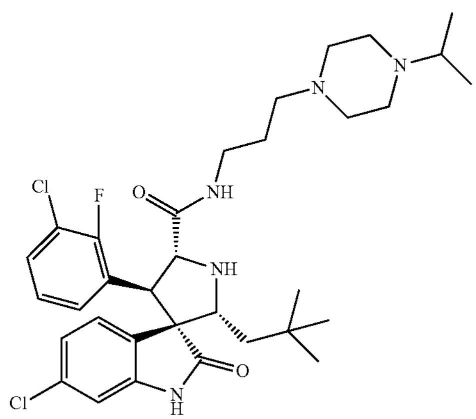 [SMILES: CC(C)N1CCN(CCCNC(=O)[C@@H]2N[C@H](CC(C)(C)C)[C@]3(C(=O)Nc4cc(Cl)ccc43)[C@H]2c2cccc(Cl)c2F)CC1] | <10 | 0.8 ± 0.2 | 0.9 ± 0.3 | 1.0 ± 0.2 | 6.9 ± 1.9 | 5.1 ± 0.9 |
| MI-519-46 | 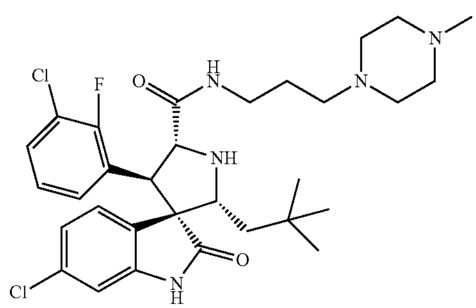 [SMILES: CN1CCN(CCCNC(=O)[C@@H]2N[C@H](CC(C)(C)C)[C@]3(C(=O)Nc4cc(Cl)ccc43)[C@H]2c2cccc(Cl)c2F)CC1] | <1 | 0.5 ± 0.3 | 0.4 ± 0.1 | 0.5 ± 0.3 | 4.3 ± 0.4 | 3.7 ± 0.4 |
| MI-519-47 | 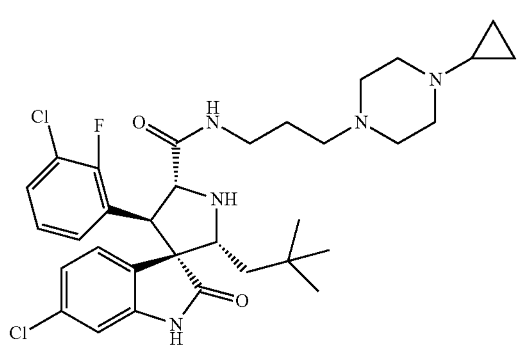 [SMILES: CC(C)(C)C[C@H]1N[C@@H](C(=O)NCCCN2CCN(C3CC3)CC2)[C@H](c2cccc(Cl)c2F)[C@@]12C(=O)Nc1cc(Cl)ccc12] | <10 | 1.1 ± 0.0 | 1.1 ± 0.2 | 1.1 ± 0.3 | 7.8 ± 0.9 | 5.7 ± 0.6 |

TABLE 19A-continued

| Example | Chemical Structure | MDM2 | SJSA-1 (p53 wild-type) | HCT-116 (p53 wild-type) | LNCAP (p53 wild-type) | HCT-116 (p3-/-) | PC-3 (deleted p53) |
|---|---|---|---|---|---|---|---|
| MI-519-49 | 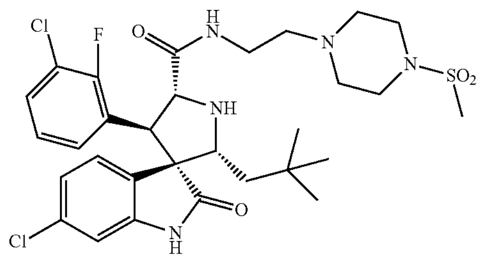 [SMILES: CC(C)(C)C[C@H]1N[C@@H](C(=O)NCCN2CCN(S(C)(=O)=O)CC2)[C@H](c2cccc(Cl)c2F)[C@@]12C(=O)Nc1cc(Cl)ccc12] | <1 | NT | 0.84 | 0.85 | 12.7 | 8.1 |
| MI-519-50 | 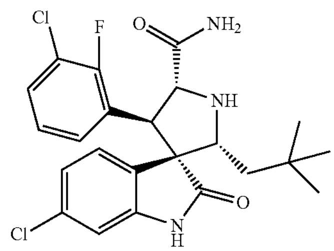 [SMILES: CC(C)(C)C[C@H]1N[C@@H](C(N)=O)[C@H](c2cccc(Cl)c2F)[C@@]12C(=O)Nc1cc(Cl)ccc12] | <1 | 1.7 ± 1.7 | 0.9 ± 0.2 | 1.3 ± 0.4 | 23.71 | 16.9 ± 4.5 |
| MI-519-51 | 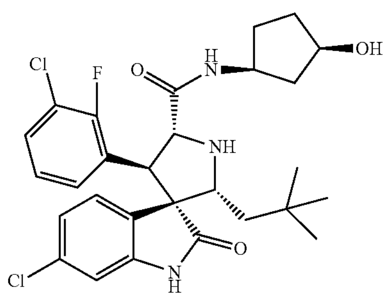 [SMILES: CC(C)(C)C[C@H]1N[C@@H](C(=O)N[C@H]2CC[C@@H](O)C2)[C@H](c2cccc(Cl)c2F)[C@@]12C(=O)Nc1cc(Cl)ccc12] | <1 | 0.6 ± 0.2 | 0.6 ± 0.3 | 0.6 ± 0.2 | 13.4 ± 0.8 | 8.2 ± 2.5 |
| MI-519-51-epi | 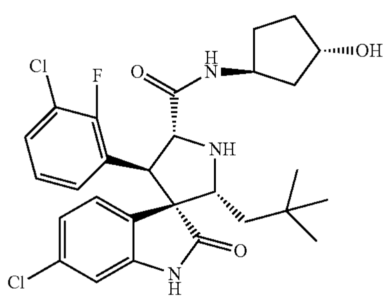 [SMILES: CC(C)(C)C[C@H]1N[C@@H](C(=O)N[C@H]2CC[C@H](O)C2)[C@H](c2cccc(Cl)c2F)[C@@]12C(=O)Nc1cc(Cl)ccc12] | <1 | NT | NT | <2 | NT | >10 |
| MI-519-56 | 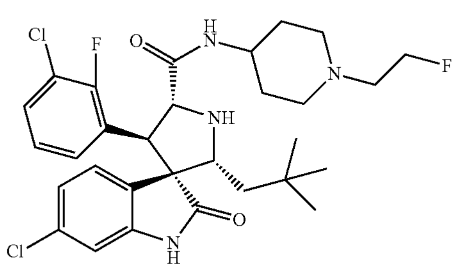 [SMILES: CC(C)(C)C[C@H]1N[C@@H](C(=O)NC2CCN(CCF)CC2)[C@H](c2cccc(Cl)c2F)[C@@]12C(=O)Nc1cc(Cl)ccc12] | <1 | <1 | <1 | <1 | >10 | |

TABLE 19A-continued

| Example | Chemical Structure | MDM2 | SJSA-1 (p53 wild-type) | HCT-116 (p53 wild-type) | LNCAP (p53 wild-type) | HCT-116 (p3-/-) | PC-3 (deleted p53) |
|---|---|---|---|---|---|---|---|
| MI-519-60 | 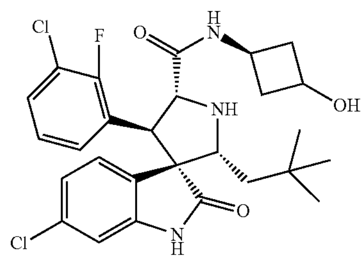 | <1 | <3 | <3 | <3 | NT | NT |
| MI-519-61 | 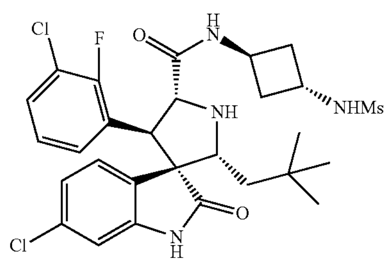 | <1 | <3 | <3 | <3 | NT | NT |
| MI-519-62 | 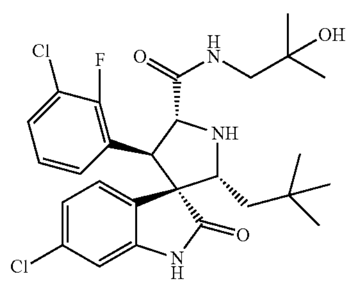 [SMILES: CC(C)(C)C[C@H]1N[C@@H](C(=O)NCC(C)(C)O)[C@H](c2cccc(Cl)c2F)[C@@]12C(=O)Nc1cc(Cl)ccc12] | <1 | <3 | <3 | <3 | >10 | >10 |
| MI-519-63 | (epimer of MI-519-60) | <1 | 2.1 | 2.0 | 2.3 | NT | NT |
| MI-519-64 | 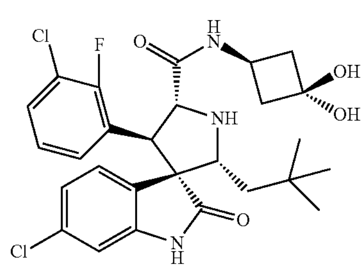 | <1 | <1 | <1 | <1 | >10 | NT |

TABLE 19A-continued

| Example | Chemical Structure | MDM2 | SJSA-1 (p53 wild-type) | HCT-116 (p53 wild-type) | LNCAP (p53 wild-type) | HCT-116 (p3-/-) | PC-3 (deleted p53) |
|---|---|---|---|---|---|---|---|
| MI-519-65 | 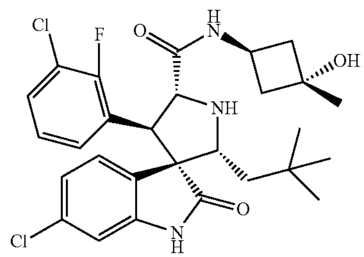 [SMILES: CC(C)(C)C[C@H]1N[C@@H](C(=O)N[C@H]2C[C@](C)(O)C2)[C@H](c2cccc(Cl)c2F)[C@@]12C(=O)Nc1cc(Cl)ccc12] | <1 | <3 | <3 | <3 | >10 | NT |
| MI-519-68 | 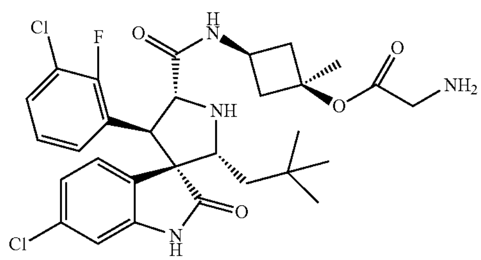 [SMILES: CC(C)(C)C[C@H]1N[C@@H](C(=O)N[C@H]2C[C@@](C)(OC(=O)CN)C2)[C@H](c2cccc(Cl)c2F)[C@@]12C(=O)Nc1cc(Cl)ccc12] | NT | NT | NT | NT | NT | NT |
| MI-519-69 | (From MI-519-63) | NT | <5 | <5 | <5 | >10 | >10 |
| MI-519-70 | 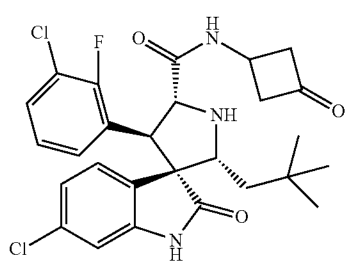 [SMILES: CC(C)(C)C[C@H]1N[C@@H](C(=O)NC2CC(=O)C2)[C@H](c2cccc(Cl)c2F)[C@@]12C(=O)Nc1cc(Cl)ccc12] | NT | <5 | <5 | <5 | >10 | >10 |
| MI-748 | 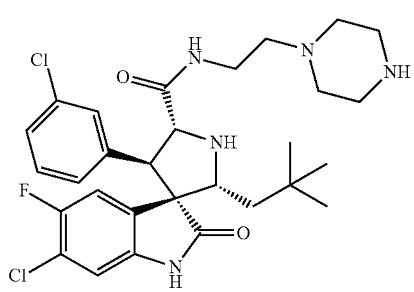 [SMILES: CC(C)(C)C[C@H]1N[C@@H](C(=O)NCCN2CCNCC2)[C@H](c2cccc(Cl)c2)[C@@]12C(=O)Nc1cc(Cl)c(F)cc12] | <1 | NT | 0.9 ± 0.7 | 0.8 ± 0.0 | 7.6 ± 1.0 | 4.1 ± 0.1 |

TABLE 19A-continued
| Example | Chemical Structure | MDM2 | SJSA-1 (p53 wild-type) | HCT-116 (p53 wild-type) | LNCAP (p53 wild-type) | HCT-116 (p3-/-) | PC-3 (deleted p53) |
|---|---|---|---|---|---|---|---|
| MI-749 | 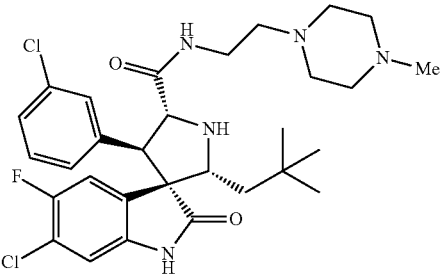 [SMILES: CN1CCN(CCNC(=O)[C@@H]2N[C@H](CC(C)(C)C)[C@]3(C(=O)Nc4cc(Cl)c(F)cc43)[C@H]2c2cccc(Cl)c2)CC1] | <1 | NT | 1.2 ± 0.4 | 1.0 ± 0.1 | 7.8 ± 1.3 | 5.0 ± 0.5 |
| MI-751 | 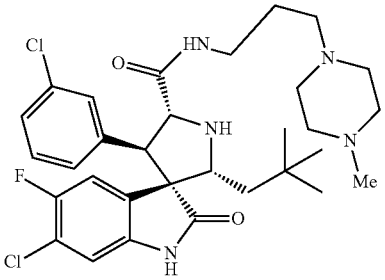 [SMILES: CN1CCN(CCCNC(=O)[C@@H]2N[C@H](CC(C)(C)C)[C@]3(C(=O)Nc4cc(Cl)c(F)cc43)[C@H]2c2cccc(Cl)c2)CC1] | <1 | NT | 1.0 ± 0.2 | 0.7 ± 0.2 | 6.2 ± 1.2 | 3.9 ± 0.9 |
| MI-758 | 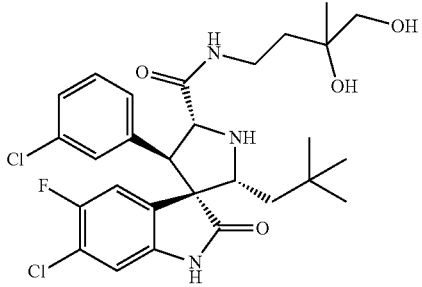<br>Single isomer | <1 | NT | 0.6 ± 0.0 | 0.6 ± 0.0 | 19.1 ± 3.6 | 18.7 ± 7.1 |
| MI-764 | 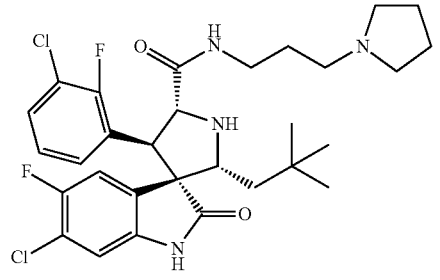 [SMILES: CC(C)(C)C[C@H]1N[C@@H](C(=O)NCCCN2CCCC2)[C@H](c2cccc(Cl)c2F)[C@@]12C(=O)Nc1cc(Cl)c(F)cc12] | <1 | 1.2 ± 0.3 | 0.5 ± 0.2 | 1.0 ± 0.4 | 3.8 ± 0.7 | 2.4 ± 0.4 |

TABLE 19A-continued

| | | | IC$_{50}$ (μM) | | | | |
|---|---|---|---|---|---|---|---|
| Example | Chemical Structure | MDM2 | SJSA-1 (p53 wild-type) | HCT-116 (p53 wild-type) | LNCAP (p53 wild-type) | HCT-116 (p3-/-) | PC-3 (deleted p53) |
| MI-765 | | NT. | 1.4 ± 0.1 | 1.1 ± 0.2 | 1.5 ± 0.9 | 4.7 ± 2.0 | 2.6 ± 0.2 |
| MI-771 | | <1 | 1.2 ± 0.3 | 1.0 ± 0.3 | 1.1 ± 0.1 | 12.0 ± 1.1 | 13.7 ± 4.4 |
| MI-772 | | <1 | <1 | <1 | <1 | >5 | >5 |
| MI-773 | | <1 | <1 | <1 | <1 | >10 | >10 |
| MI-779 | | <0.1 | 1.0 | 2.5 | 1.3 | 13.6 | 11.6 |

TABLE 19A-continued

| | | IC$_{50}$ (μM) | | | | | |
|---|---|---|---|---|---|---|---|
| Example | Chemical Structure | MDM2 | SJSA-1 (p53 wild-type) | HCT-116 (p53 wild-type) | LNCAP (p53 wild-type) | HCT-116 (p3-/-) | PC-3 (deleted p53) |
| MI-781 | | <0.1 | 0.7 | 0.4 | NT | 10.1 | NT |
| MI-739 | | <5 | NT | 2.1 ± 0.6 | 1.5 ± 0.5 | 3.0 ± 0.2 | 3.2 ± 0.7 |
| MI-740 | | <5 | NT | 2.8 ± 0.1 | 2.0 ± 0.3 | 5.4 ± 1.9 | 4.8 ± 0.8 |
| MI-742 | | <10 | NT | 1.7 ± 0.1 | 2.2 ± 0.3 | 19.9 ± 10.3 | 10.2 ± 4.8 |

TABLE 19A-continued

| | | | IC$_{50}$ (µM) | | | | |
|---|---|---|---|---|---|---|---|
| Example | Chemical Structure | MDM2 | SJSA-1 (p53 wild-type) | HCT-116 (p53 wild-type) | LNCAP (p53 wild-type) | HCT-116 (p3-/-) | PC-3 (deleted p53) |
| MI-744 | | <10 | NT | 2.4 ± 0.2 | 1.7 ± 0.1 | 5.7 ± 3.4 | 7.7 ± 3.1 |
| MI-746 | | <10 | NT | 2.3 ± 0.1 | 2.2 ± 0.4 | 6.7 ± 1.8 | 6.9 ± 1.2 |
| MI-747 | | NT. | NT | 1.3 | 1.3 | 3.9 | 3.7 |
| MI-759 | | <1 | NT | 1.4 ± 0.6 | 1.4 ± 0.1 | 5.2 ± 1.0 | 5.5 ± 2.3 |

TABLE 19A-continued

| Example | Chemical Structure | MDM2 | SJSA-1 (p53 wild-type) | HCT-116 (p53 wild-type) | LNCAP (p53 wild-type) | HCT-116 (p3-/-) | PC-3 (deleted p53) |
|---|---|---|---|---|---|---|---|
| MI-766 | 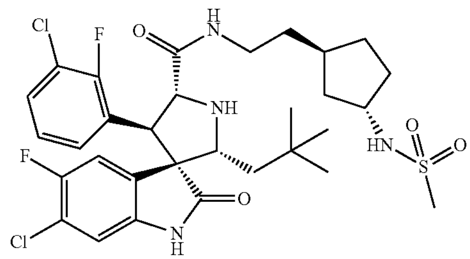 [SMILES: CC(C)(C)C[C@H]1N[C@@H](C(=O)NCC[C@H]2CC[C@H](NS(C)(=O)=O)C2)[C@H](c2cccc(Cl)c2F)[C@@]12C(=O)Nc1cc(Cl)c(F)cc12] | <1 | 1.7 ± 1.4 | 0.7 ± 0.0 | 0.9 ± 0.0 | 6.9 ± 1.4 | 5.9 ± 2.2 |
| MI-767 | 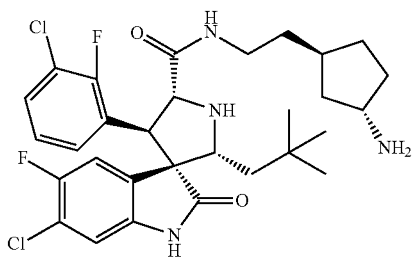 [SMILES: CC(C)(C)C[C@H]1N[C@@H](C(=O)NCC[C@H]2CC[C@H](N)C2)[C@H](c2cccc(Cl)c2F)[C@@]12C(=O)Nc1cc(Cl)c(F)cc12] | <1 | 0.9 ± 0.6 | 0.7 ± 0.2 | 0.9 ± 0.2 | 2.4 ± 1.0 | 2.2 ± 0.1 |
| MI-768 | 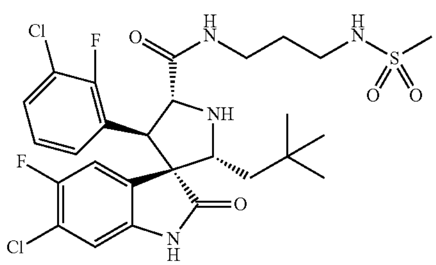 [SMILES: CC(C)(C)C[C@H]1N[C@@H](C(=O)NCCCNS(C)(=O)=O)[C@H](c2cccc(Cl)c2F)[C@@]12C(=O)Nc1cc(Cl)c(F)cc12] | <1 | 0.8 ± 0.1 | 0.5 ± 0.2 | 0.7 ± 0.2 | 9.8 ± 0.4 | 7.3 ± 0.8 |
| MI-769 | 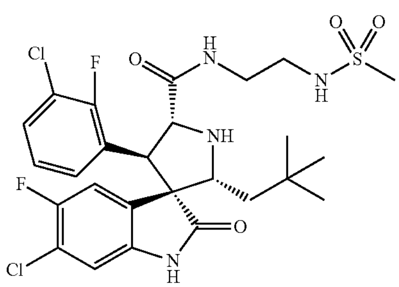 [SMILES: CC(C)(C)C[C@H]1N[C@@H](C(=O)NCCNS(C)(=O)=O)[C@H](c2cccc(Cl)c2F)[C@@]12C(=O)Nc1cc(Cl)c(F)cc12] | <1 | 0.6 | 1.6 | 1.5 | 10.2 | 13.0 |
| MI-774 | 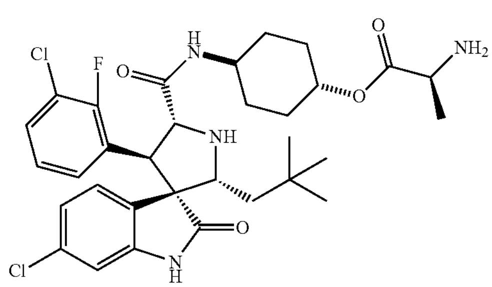 | <0.1 | 0.3 ± 0.1 | 0.3 ± 0.1 | 0.3 | 5.6 | NT |

TABLE 19A-continued

| Example | Chemical Structure | MDM2 | SJSA-1 (p53 wild-type) | HCT-116 (p53 wild-type) | LNCAP (p53 wild-type) | HCT-116 (p3-/-) | PC-3 (deleted p53) |
|---|---|---|---|---|---|---|---|
| MI-776 | 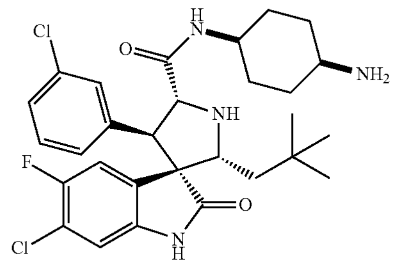 | <1 | 3.2 | 2.7 | 2.4 | NT | NT |
| MI-782 | 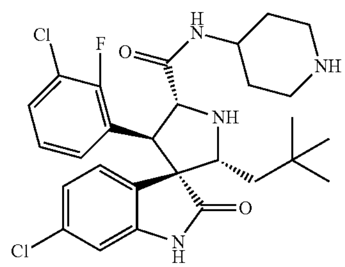 [SMILES: CC(C)(C)C[C@H]1N[C@@H](C(=O)NC2CCNCC2)[C@H](c2cccc(Cl)c2F)[C@@]12C(=O)Nc1cc(Cl)ccc12] | <1 | 1.2 | 0.7 | NT | 4.7 | NT |
| MI-783 | 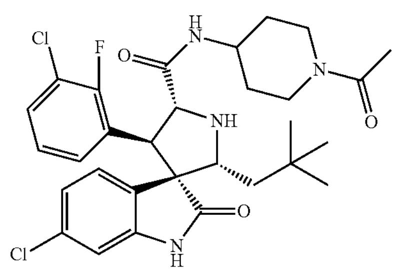 [SMILES: CC(=O)N1CCC(NC(=O)[C@@H]2N[C@H](CC(C)(C)C)[C@]3(C(=O)Nc4cc(Cl)ccc43)[C@H]2c2cccc(Cl)c2F)CC1] | <0.5 | 1.1 | 0.9 | NT | 18.5 | NT |
| MI-784 | 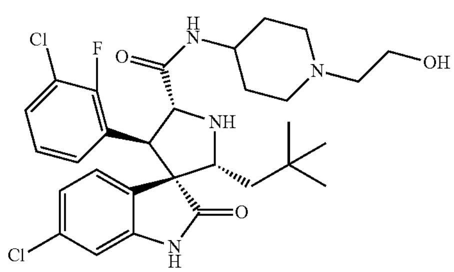 [SMILES: CC(C)(C)C[C@H]1N[C@@H](C(=O)NC2CCN(CCO)CC2)[C@H](c2cccc(Cl)c2F)[C@@]12C(=O)Nc1cc(Cl)ccc12] | <0.5 | 0.7 | 0.4 | NT | 10.3 | NT |
| MI-785 | 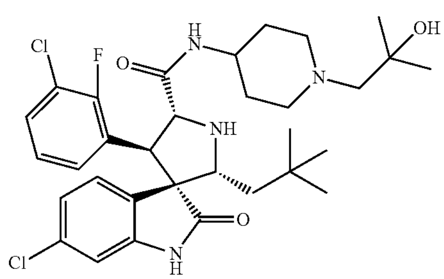 [SMILES: CC(C)(C)C[C@H]1N[C@@H](C(=O)NC2CCN(CC(C)(C)O)CC2)[C@H](c2cccc(Cl)c2F)[C@@]12C(=O)Nc1cc(Cl)ccc12] | <0.5 | 0.7 | 0.5 | NT | 8.0 | NT |

TABLE 19A-continued

| Example | Chemical Structure | MDM2 | SJSA-1 (p53 wild-type) | HCT-116 (p53 wild-type) | LNCAP (p53 wild-type) | HCT-116 (p3-/-) | PC-3 (deleted p53) |
|---|---|---|---|---|---|---|---|
| MI-786 | 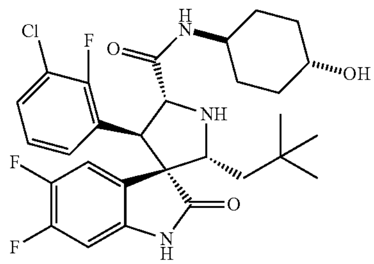 | <1 | 0.8 | 0.5 | 1.2 | NT | 14.4 |
| MI-777 | 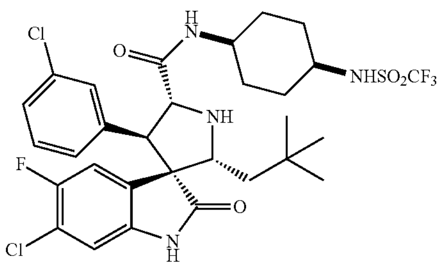 | <5 | 9.2 | 8.9 | 6.6 | | 7.8 |
| MI-780 | 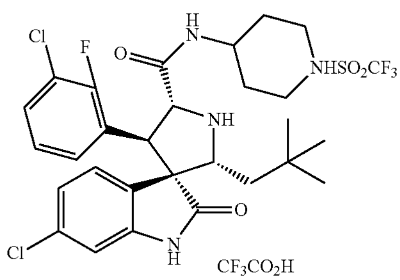 | <3 | <5 | | | | |
| C027 | 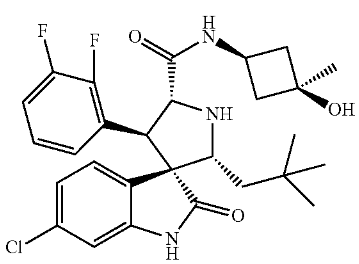 [SMILES: CC(C)(C)C[C@H]1N[C@@H](C(=O)N[C@H]2C[C@@](C)(O)C2)[C@H](c2cccc(F)c2F)[C@@]12C(=O)Nc1cc(Cl)ccc12] | <1 | <3 | <3 | <3 | >10 | >10 |
| C029 | 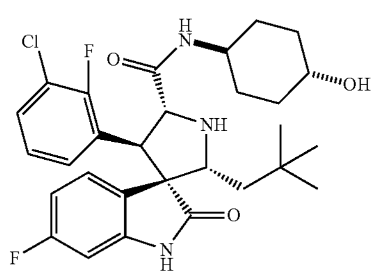 | <5 | <3 | <3 | <3 | >5 | >5 |

TABLE 19A-continued

| Example | Chemical Structure | MDM2 | SJSA-1 (p53 wild-type) | HCT-116 (p53 wild-type) | LNCAP (p53 wild-type) | HCT-116 (p3-/-) | PC-3 (deleted p53) |
|---|---|---|---|---|---|---|---|
| C031 | 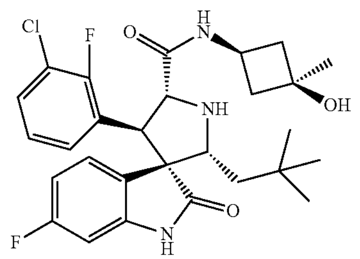 [SMILES: CC(C)(C)C[C@H]1N[C@@H](C(=O)N[C@H]2C[C@@](C)(O)C2)[C@H](c2cccc(Cl)c2F)[C@@]12C(=O)Nc1cc(F)ccc12] | <5 | <3 | <3 | <3 | >10 | >10 |
| C034 | 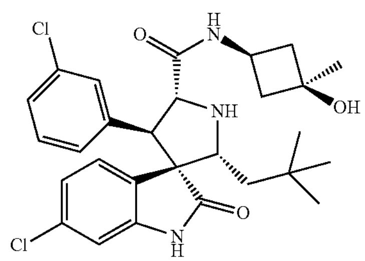 [SMILES: CC(C)(C)C[C@H]1N[C@@H](C(=O)N[C@H]2C[C@@](C)(O)C2)[C@H](c2cccc(Cl)c2)[C@@]12C(=O)Nc1cc(Cl)ccc12] | <1 | <3 | <3 | <3 | >10 | >10 |
| C035 | 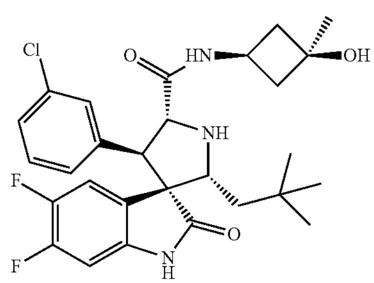 [SMILES: CC(C)(C)C[C@H]1N[C@@H](C(=O)N[C@H]2C[C@@](C)(O)C2)[C@H](c2cccc(Cl)c2)[C@@]12C(=O)Nc1cc(F)c(F)cc12] | <3 | <5 | <5 | <5 | >10 | >10 |
| C086 | 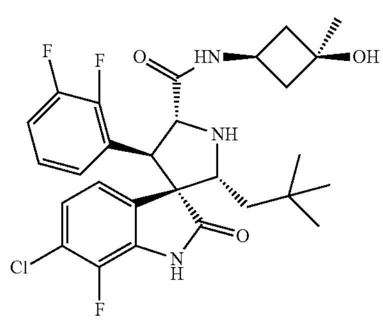 [SMILES: CC(C)(C)C[C@H]1N[C@@H](C(=O)N[C@H]2C[C@@](C)(O)C2)[C@H](c2cccc(F)c2F)[C@@]12C(=O)Nc1c2ccc(Cl)c1F] | <3 | | | | | |
| MI-7102 | 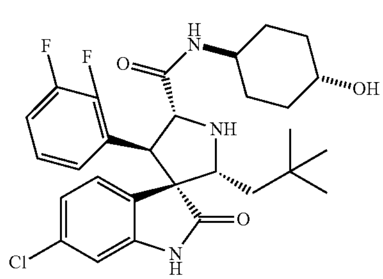 | <3 | <3 | <3 | <3 | >10 | >10 |

TABLE 19A-continued

| Example | Chemical Structure | MDM2 | SJSA-1 (p53 wild-type) | HCT-116 (p53 wild-type) | LNCAP (p53 wild-type) | HCT-116 (p3-/-) | PC-3 (deleted p53) |
|---|---|---|---|---|---|---|---|
| MI-7104 | 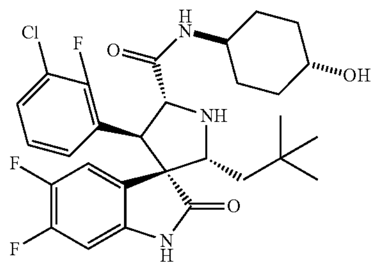 | <3 | <3 | <3 | <3 | >10 | >10 |
| MI-7105 | 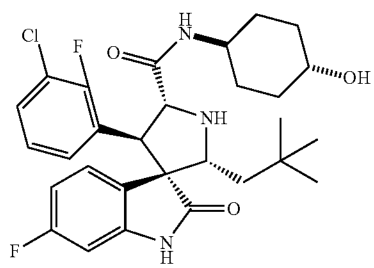 | <3 | <3 | <3 | <3 | >10 | >10 |
| MI-789 | 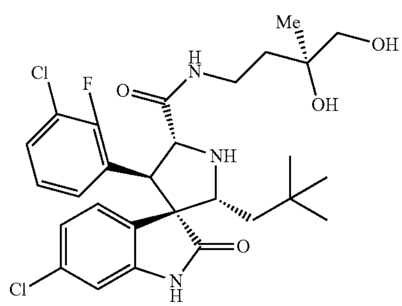 [SMILES: CC(C)(C)C[C@H]1N[C@@H](C(=O)NCC[C@](C)(O)CO)[C@H](c2cccc(Cl)c2F)[C@@]12C(=O)Nc1cc(Cl)ccc12] | <3 | <3 | <3 | <3 | >10 | >10 |
| MI-790 | 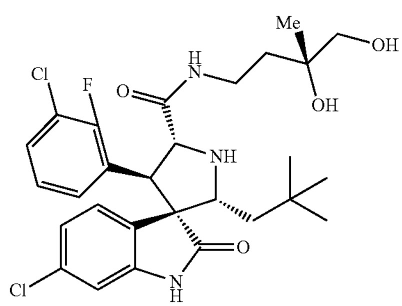 [SMILES: CC(C)(C)C[C@H]1N[C@@H](C(=O)NCC[C@@](C)(O)CO)[C@H](c2cccc(Cl)c2F)[C@@]12C(=O)Nc1cc(Cl)ccc12] | <3 | <3 | <3 | <3 | >10 | >10 |
| MI-791 | 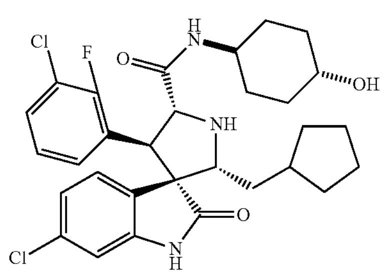 | <3 | <3 | <3 | <3 | >10 | >10 |

TABLE 19A-continued

| Example | Chemical Structure | MDM2 | SJSA-1 (p53 wild-type) | HCT-116 (p53 wild-type) | LNCAP (p53 wild-type) | HCT-116 (p3-/-) | PC-3 (deleted p53) |
|---|---|---|---|---|---|---|---|
| MI-792 | 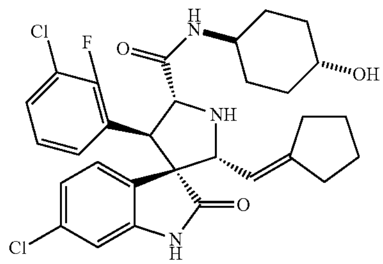 | <5 | <10 | <10 | <10 | >20 | >20 |
| MI-909 | 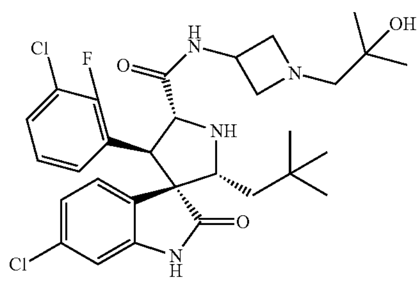 [SMILES: CC(C)(C)C[C@H]1N[C@@H](C(=O)NC2CN(CC(C)(C)O)C2)[C@H](c2cccc(Cl)c2F)[C@@]12C(=O)Nc1cc(Cl)ccc12] | <1 | <3 | <3 | <3 | >5 | >5 |
| MI-911 | 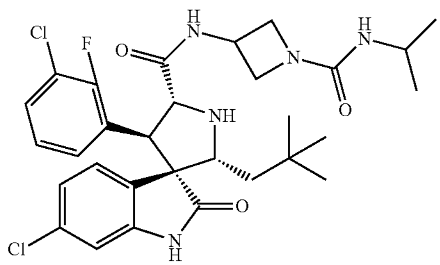 [SMILES: CC(C)NC(=O)N1CC(NC(=O)[C@@H]2N[C@H](CC(C)(C)C)[C@]3(C(=O)Nc4cc(Cl)ccc43)[C@H]2c2cccc(Cl)c2F)C1] | <3 | <5 | <5 | <5 | >10 | >10 |
| MI-912 | 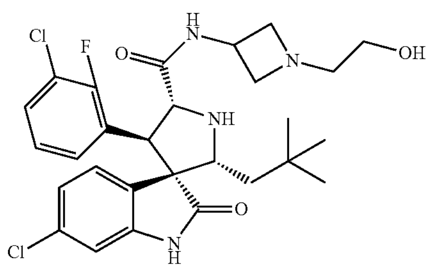 [SMILES: CC(C)(C)C[C@H]1N[C@@H](C(=O)NC2CN(CCO)C2)[C@H](c2cccc(Cl)c2F)[C@@]12C(=O)Nc1cc(Cl)ccc12] | <3 | <5 | <5 | <5 | >10 | >5 |
| MI-913 | 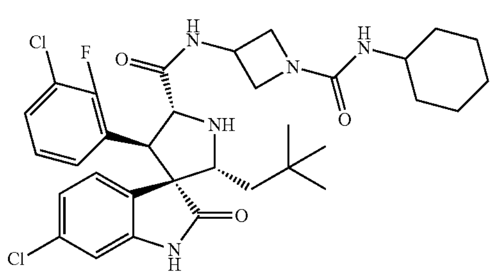 [SMILES: CC(C)(C)C[C@H]1N[C@@H](C(=O)NC2CN(C(=O)NC3CCCCC3)C2)[C@H](c2cccc(Cl)c2F)[C@@]12C(=O)Nc1cc(Cl)ccc12] | <3 | <5 | <5 | <5 | 8.8 | 4.9 |

TABLE 19A-continued

| Example | Chemical Structure | MDM2 | SJSA-1 (p53 wild-type) | HCT-116 (p53 wild-type) | LNCAP (p53 wild-type) | HCT-116 (p3-/-) | PC-3 (deleted p53) |
|---|---|---|---|---|---|---|---|
| MI-914 | 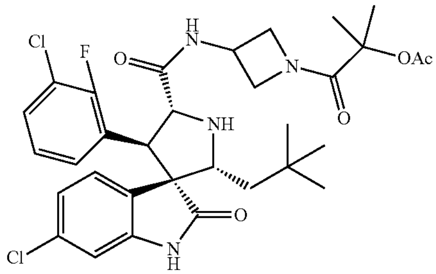 [SMILES: CC(=O)OC(C)(C)C(=O)N1CC(NC(=O)[C@@H]2N[C@H](CC(C)(C)C)[C@]3(C(=O)Nc4cc(Cl)ccc43)[C@H]2c2cccc(Cl)c2F)C1] | <1 | <3 | <3 | <3 | >10 | >5 |
| MI-915 | 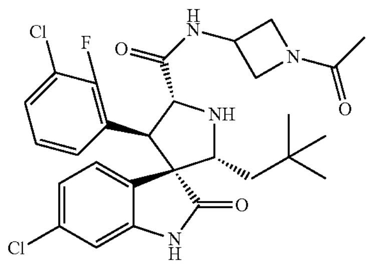 [SMILES: CC(=O)N1CC(NC(=O)[C@@H]2N[C@H](CC(C)(C)C)[C@]3(C(=O)Nc4cc(Cl)ccc43)[C@H]2c2cccc(Cl)c2F)C1] | <3 | <10 | <10 | <10 | >30 | >30 |
| MI-916 | 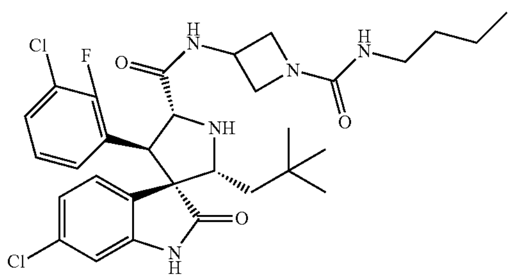 [SMILES: CCCCNC(=O)N1CC(NC(=O)[C@@H]2N[C@H](CC(C)(C)C)[C@]3(C(=O)Nc4cc(Cl)ccc43)[C@H]2c2cccc(Cl)c2F)C1] | <0.1 | <5 | <3 | <3 | >5 | >5 |
| MI-917 | 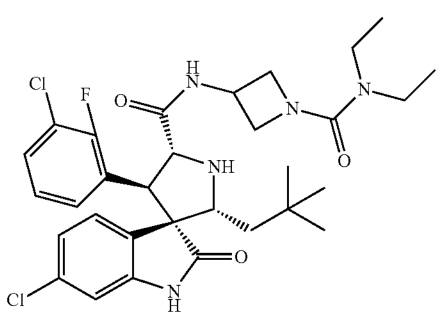 [SMILES: CCN(CC)C(=O)N1CC(NC(=O)[C@@H]2N[C@H](CC(C)(C)C)[C@]3(C(=O)Nc4cc(Cl)ccc43)[C@H]2c2cccc(Cl)c2F)C1] | <1 | 1.4 <3 | <3 | <3 | >10 | >5 |
| MI-901 | 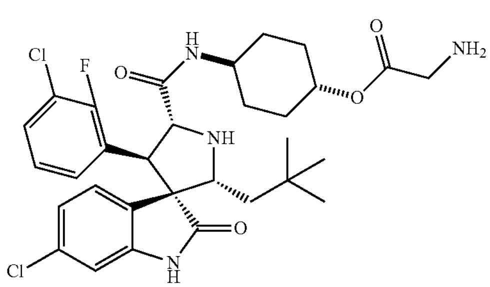 | <1 | <3 | <3 | <3 | >10 | >5 |

TABLE 19A-continued

| | | IC$_{50}$ (µM) | | | | | |
|---|---|---|---|---|---|---|---|
| Example | Chemical Structure | MDM2 | SJSA-1 (p53 wild-type) | HCT-116 (p53 wild-type) | LNCAP (p53 wild-type) | HCT-116 (p3-/-) | PC-3 (deleted p53) |
| MI-902 | | <3 | <3 | <3 | <3 | 5.9 | 4.0 |
| MI-903 | | <3 | <3 | <3 | <3 | 12.1 | 3.5 |
| MI-904 | | <1 | <3 | <3 | <3 | 6.1 | 3.1 |
| MI-910 | | <1 | <3 | <3 | <3 | 9.8 | 7.0 |
| MI-905 | | <1 | <3 | <3 | <3 | 8.0 | 3.9 |

TABLE 19A-continued

| Example | Chemical Structure | MDM2 | SJSA-1 (p53 wild-type) | HCT-116 (p53 wild-type) | LNCAP (p53 wild-type) | HCT-116 (p3-/-) | PC-3 (deleted p53) |
|---|---|---|---|---|---|---|---|
| MI-906 | 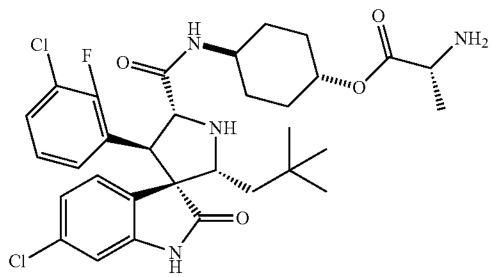 | <1 | <3 | <3 | <3 | 9.1 | 3.6 |
| MI-907 | 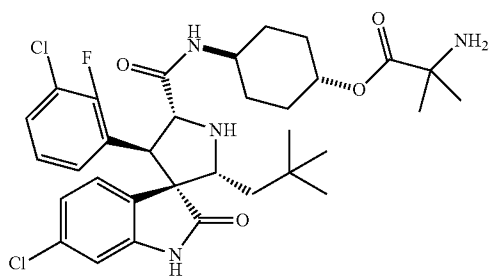 | <1 | <3 | <3 | <3 | 7 | 3.0 |
| MI-908 | 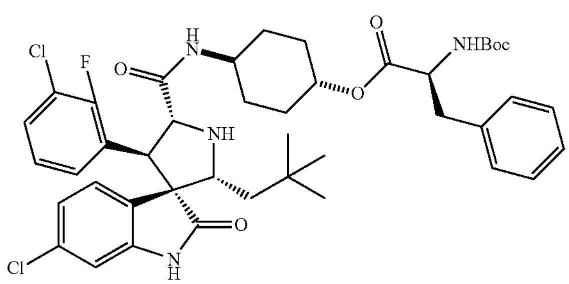 | >10 | 22.5 | 5.3 | 4.3 | >30 | ~30 |
| MI-519-6401 | 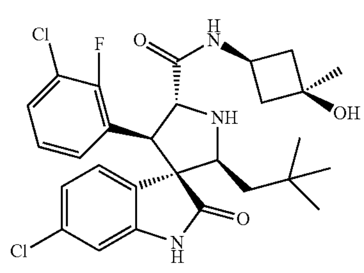 | <0.1 | 0.4 | 0.1 | 0.3 | 12.2 | 10.5 |
| MI-77301 | 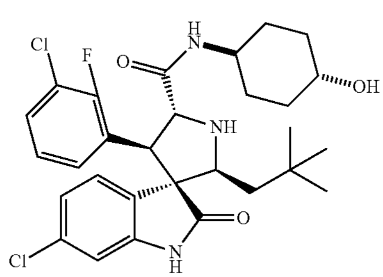 | <0.1 | 0.8 | 0.1 | 0.1 | 12.9 | 13.0 |

TABLE 19A-continued

| Example | Chemical Structure | MDM2 | SJSA-1 (p53 wild-type) | HCT-116 (p53 wild-type) | LNCAP (p53 wild-type) | HCT-116 (p3-/-) | PC-3 (deleted p53) |
|---|---|---|---|---|---|---|---|
| C02701 | 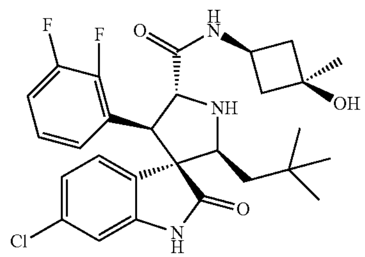 [SMILES: CC(C)(C)C[C@@H]1N[C@@H](C(=O)N[C@H]2C[C@@](C)(O)C2)[C@H](c2cccc(F)c2F)[C@]12C(=O)Nc1cc(Cl)ccc12] | <0.1 | 0.2 | 0.2 | 0.3 | 13.2 | 12.9 |
| C02901 | 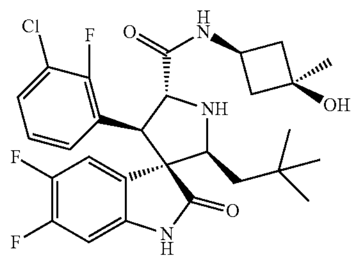 [SMILES: CC(C)(C)C[C@@H]1N[C@@H](C(=O)N[C@H]2C[C@@](C)(O)C2)[C@H](c2cccc(Cl)c2F)[C@]12C(=O)Nc1cc(F)c(F)cc12] | <0.1 | 0.5 | 0.6 | 0.2 | 16.4 | 15.6 |
| C03001 | 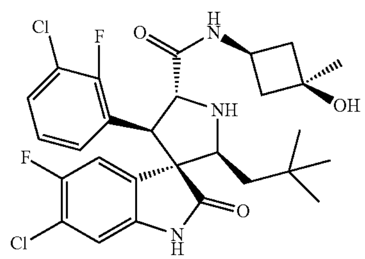 [SMILES: CC(C)(C)C[C@@H]1N[C@@H](C(=O)N[C@H]2C[C@@](C)(O)C2)[C@H](c2cccc(Cl)c2F)[C@]12C(=O)Nc1cc(Cl)c(F)cc12] | <0.1 | 0.2 | 0.2 | 0.1 | 14.2 | 29.8 |
| C03401 | 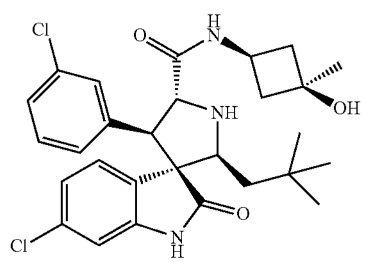 [SMILES: CC(C)(C)C[C@@H]1N[C@@H](C(=O)N[C@H]2C[C@@](C)(O)C2)[C@H](c2cccc(Cl)c2)[C@]12C(=O)Nc1cc(Cl)ccc12] | <0.1 | 0.3 | 0.6 | 0.3 | 17.3 | 17.4 |
| C03701 | 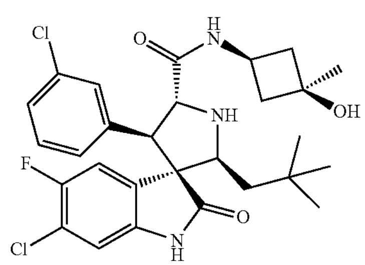 [SMILES: CC(C)(C)C[C@@H]1N[C@@H](C(=O)N[C@H]2C[C@@](C)(O)C2)[C@H](c2cccc(Cl)c2)[C@]12C(=O)Nc1cc(Cl)c(F)cc12] | <0.1 | 0.7 | 0.2 | 0.4 | 21.0 | 26.7 |

TABLE 19A-continued

| | | IC$_{50}$ (μM) | | | | | |
|---|---|---|---|---|---|---|---|
| Example | Chemical Structure | MDM2 | SJSA-1 (p53 wild-type) | HCT-116 (p53 wild-type) | LNCAP (p53 wild-type) | HCT-116 (p3-/-) | PC-3 (deleted p53) |
| C08301 | | <0.1 | | | | | |
| C08601 | | <0.5 | | | | | |
| C091 | | <0.1 | | | | | |
| C096 | | <0.1 | | | | | |
| MI-710201 | | <0.1 | 0.6 | 0.3 | 0.3 | 27.6 | 19.3 |

TABLE 19A-continued

| Example | Chemical Structure | MDM2 | SJSA-1 (p53 wild-type) | HCT-116 (p53 wild-type) | LNCAP (p53 wild-type) | HCT-116 (p3-/-) | PC-3 (deleted p53) |
|---|---|---|---|---|---|---|---|
| MI-710301 | 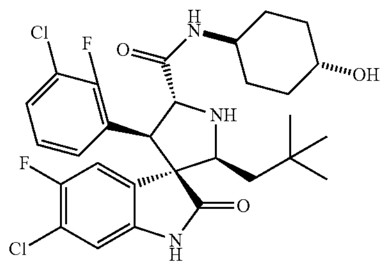 | <0.1 | 0.1 | 0.1 | 0.1 | 11.9 | 12.5 |
| MI-710401 | 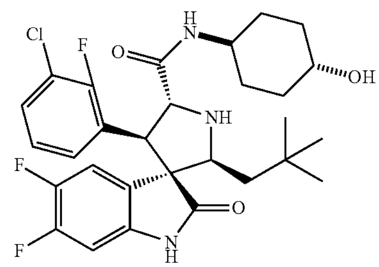 | <0.5 | 0.8 | 0.4 | 0.4 | 13.0 | 12.7 |
| MI-710601 | 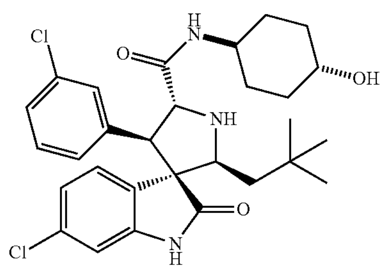 | <0.1 | 0.4 | 0.3 | 0.2 | 11.5 | 18.4 |

TABLE 19B

| ID | Structure | MW | Binding affinities to MDM2 protein as determined by FP based assay $IC_{50}$ [uM] | Inhibition of cell growth in different cancer cell lines ($IC_{50}$, uM) | | | |
|---|---|---|---|---|---|---|---|
| | | | | LNCaP | PC3 | HCT116 p53 WT | HCT116 p53 KO |
| MI-701 | 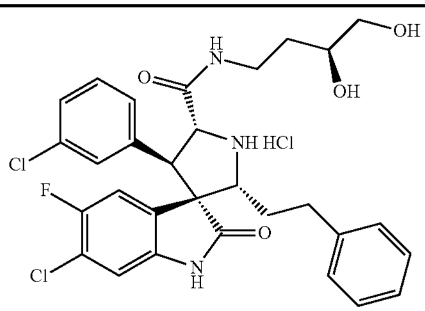 | 622.94 | >10 | 3.0 ± 3.5 | 48.9 ± 22.4 | 16.7 ± 13.0 | 33.8 ± 14.6 |

TABLE 19B-continued

| ID | Structure | MW | Binding affinities to MDM2 protein as determined by FP based assay IC$_{50}$ [uM] | Inhibition of cell growth in different cancer cell lines (IC$_{50}$, μM) | | | |
|---|---|---|---|---|---|---|---|
| | | | | LNCaP | PC3 | HCT116 p53 WT | HCT116 p53 KO |
| MI-702 | 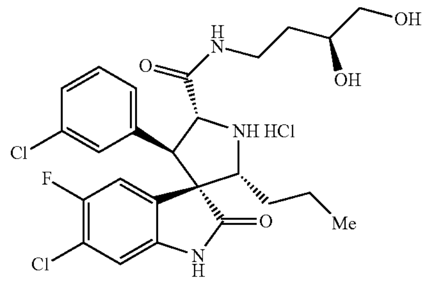 | 560.87 | >1 | 1.9 ± 0.3 | 14.3 ± 2.9 | 5.8 ± 1.7 | 12.7 ± 2.3 |
| MI-703 | 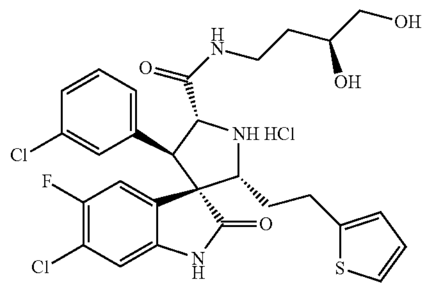 | 628.97 | >1 | 0.2 ± 0.0 | 3.9 ± 0.5 | 1.0 ± 0.2 | 4.3 ± 1.6 |
| MI-704 | 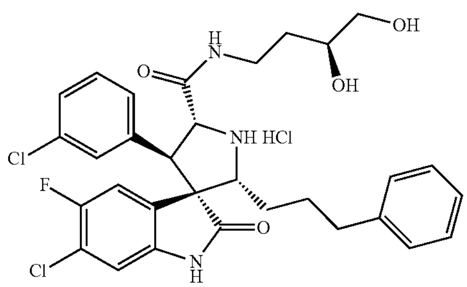 | 636.97 | >1 | 6.8 ± 0.2 | 18.0 ± 5.1 | 3.0 ± 0.9 | 12.1 ± 1.0 |
| MI-705 | 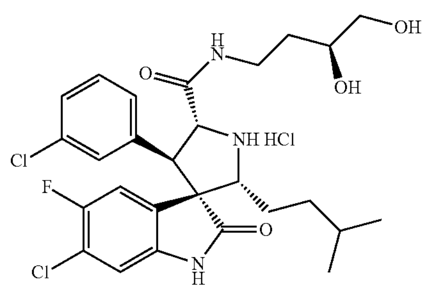 | 588.93 | <10 | 1.4 ± 0.8 | 43.9 ± 31.7 | 4.4 ± 4.0 | 32.0 ± 33.3 |
| MI-706 | 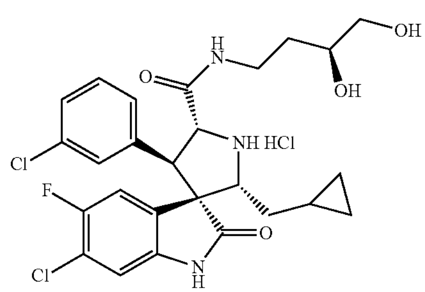 | 572.88 | <10 | 0.3 ± 0.0 | 4.6 ± 2.9 | 0.6 ± 0.1 | 1.3 ± 0.2 |

TABLE 19B-continued

| ID | Structure | MW | Binding affinities to MDM2 protein as determined by FP based assay IC$_{50}$ [uM] | Inhibition of cell growth in different cancer cell lines (IC$_{50}$, μM) | | | |
|---|---|---|---|---|---|---|---|
| | | | | LNCaP | PC3 | HCT116 p53 WT | HCT116 p53 KO |
| MI-707 | 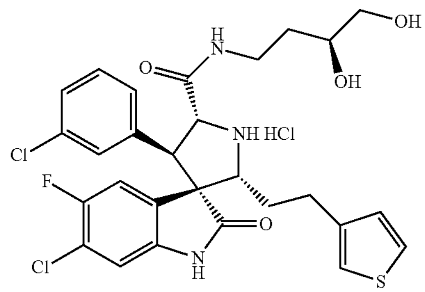 | 581.49 | <5 | 0.3 ± 0.0 | 4.6 ± 2.9 | 0.6 ± 0.1 | 1.3 ± 0.2 |
| MI-708A | 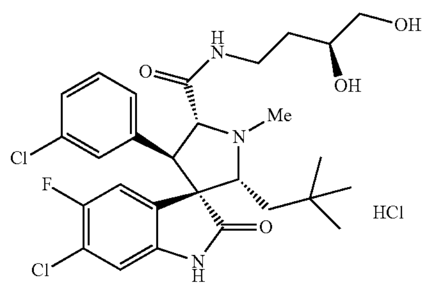 [SMILES: CN1[C@@H](C(=O)NCC[C@H](O)CO)[C@H](c2cccc(Cl)c2)[C@@]2(C(=O)Nc3cc(Cl)c(F)cc32)[C@H]1CC(C)(C)C ; Cl] | 602.95 | >3 | 3.5 ± 0.0 | 83.8 ± 11.3 | 3.8 ± 1.0 | 95.6 ± 18.2 |
| MI-708B | 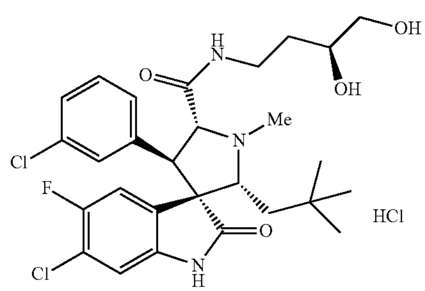 [SMILES: CN1[C@@H](C(=O)NCC[C@H](O)CO)[C@H](c2cccc(Cl)c2)[C@@]2(C(=O)Nc3cc(Cl)c(F)cc32)[C@H]1CC(C)(C)C ; Cl] | 602.95 | >3 | 6.0 ± 0.3 | 84.5 ± 18.3 | 6.6 ± 2.2 | 96.9 ± 17.8 |
| MI-709 | 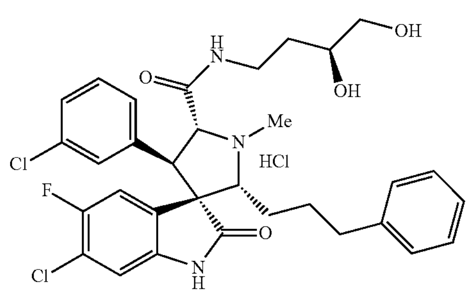 [SMILES: CN1[C@@H](C(=O)NCC[C@H](O)CO)[C@H](c2cccc(Cl)c2)[C@@]2(C(=O)Nc3cc(Cl)c(F)cc32)[C@H]1CCCc1ccccc1 ; Cl] | 651.00 | >10 | 5.6 ± 1.1 | 7.2 ± 1.4 | 9.9 ± 1.7 | 9.4 ± 1.2 |
| MI-710 | 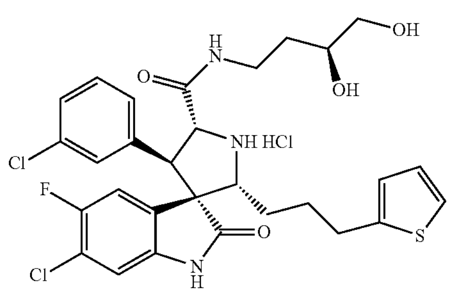 | 643.00 (4.18) | >1 | 1.2 ± 0.2 | 12.4 ± 1.9 | 1.3 ± 0.3 | 12.4 ± 1.2 |

TABLE 19B-continued

| ID | Structure | MW | Binding affinities to MDM2 protein as determined by FP based assay IC$_{50}$ [uM] | Inhibition of cell growth in different cancer cell lines (IC$_{50}$, μM) | | | |
|---|---|---|---|---|---|---|---|
| | | | | LNCaP | PC3 | HCT116 p53 WT | HCT116 p53 KO |
| MI-711 | 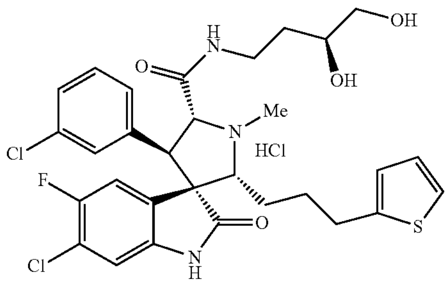 [SMILES: CN1[C@@H](C(=O)NCC[C@H](O)CO)[C@H](c2cccc(Cl)c2)[C@@]2(C(=O)Nc3cc(Cl)c(F)cc32)[C@H]1CCCc1cccs1 ; Cl] | 657.02 (4.56) | >5 | 4.8 ± 1.1 | 9.3 ± 2.5 | 8.6 ± 1.2 | 6.3 ± 2.9 |
| MI-712 | 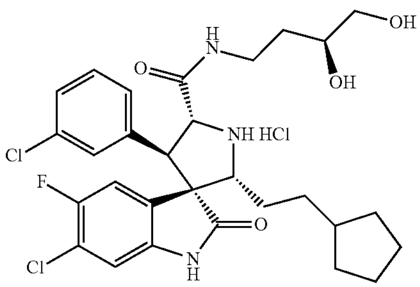 | 614.96 (3.82) | <3 | 1.0 ± 0.0 | 7.9 ± 0.2 | 1.8 ± 0.4 | 9.1 ± 1.0 |
| MI-713 | 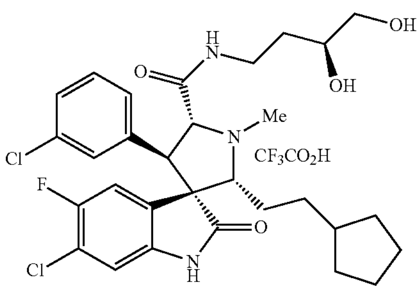 [SMILES: CN1[C@@H](C(=O)NCC[C@H](O)CO)[C@H](c2cccc(Cl)c2)[C@@]2(C(=O)Nc3cc(Cl)c(F)cc32)[C@H]1CCC1CCCC1 ; "CF3CO2H"] | 706.55 (4.19) | <10 | 2.7 ± 0.7 | 6.1 ± 2.1 | 4.9 ± 1.4 | 4.3 ± 0.7 |
| MI-714 | 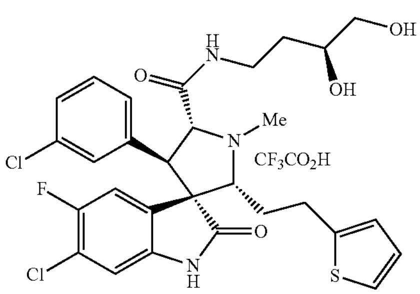 [SMILES: CN1[C@@H](C(=O)NCC[C@H](O)CO)[C@H](c2cccc(Cl)c2)[C@@]2(C(=O)Nc3cc(Cl)c(F)cc32)[C@H]1CCc1cccs1 ; "CF3CO2H"] | 720.56 (4.14) | >10 | 4.3 ± 0.0 | 7.7 ± 1.6 | 8.6 ± 0.1 | 7.5 ± 0.3 |
| MI-715B | 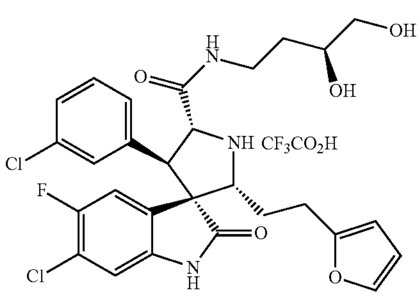 [SMILES: O=C(NCC[C@H](O)CO)[C@@H]1N[C@H](CCc2ccco2)[C@]2(C(=O)Nc3cc(Cl)c(F)cc32)[C@H]1c1cccc(Cl)c1 ; "CF3CO2H"] | 690.47 | <5 | 3.0 ± 0.7 | >10 | 2.7 ± 1.0 | >10 |

TABLE 19B-continued

| ID | Structure | MW | Binding affinities to MDM2 protein as determined by FP based assay IC$_{50}$ [uM] | Inhibition of cell growth in different cancer cell lines (IC$_{50}$, μM) | | | |
|---|---|---|---|---|---|---|---|
| | | | | LNCaP | PC3 | HCT116 p53 WT | HCT116 p53 KO |
| MI-715C | 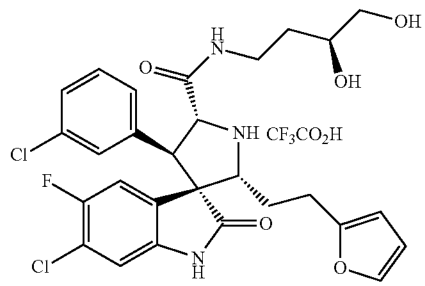 [SMILES: O=C(NCC[C@H](O)CO)[C@@H]1N[C@H](CCc2ccco2)[C@]2(C(=O)Nc3cc(Cl)c(F)cc32)[C@H]1c1cccc(Cl)c1 ; "CF3CO2H"] | 690.47 | <5 | 2.2 ± 1.2 | >10 | 2.9 ± 0.6 | >10 |
| MI-716A | 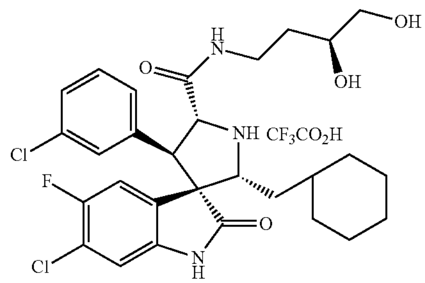 [SMILES: O=C(NCC[C@H](O)CO)[C@@H]1N[C@H](CC2CCCCC2)[C@]2(C(=O)Nc3cc(Cl)c(F)cc32)[C@H]1c1cccc(Cl)c1 ; "CF3CO2H"] | 692.52 | <3 | 1.1 ± 0.5 | 11.5 ± 0.5 | 1.0 ± 0.5 | >10 |
| MI-716B | 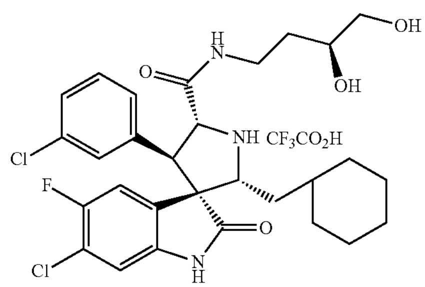 [SMILES: O=C(NCC[C@H](O)CO)[C@@H]1N[C@H](CC2CCCCC2)[C@]2(C(=O)Nc3cc(Cl)c(F)cc32)[C@H]1c1cccc(Cl)c1 ; "CF3CO2H"] | 692.52 | <1 | 0.86 ± 0.3 | 9.0 ± 2.8 | 0.6 ± 0.2 | 11.5 ± 0.7 |
| MI-716C | 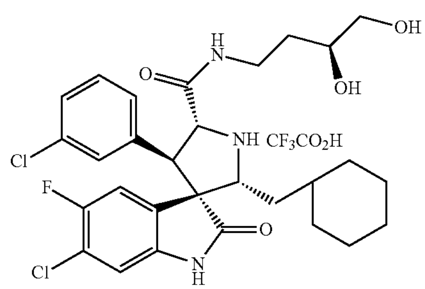 [SMILES: O=C(NCC[C@H](O)CO)[C@@H]1N[C@H](CC2CCCCC2)[C@]2(C(=O)Nc3cc(Cl)c(F)cc32)[C@H]1c1cccc(Cl)c1 ; "CF3CO2H"] | 692.52 | <1 | 0.8 ± 0.1 | 8.0 ± 2 | 0.7 ± 0.2 | 12.0 ± 3.4 |
| MI-717 | 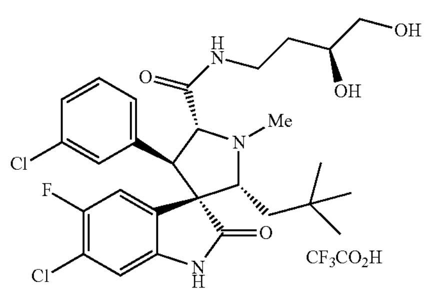 [SMILES: CN1[C@@H](C(=O)NCC[C@H](O)CO)[C@H](c2cccc(Cl)c2)[C@@]2(C(=O)Nc3cc(Cl)c(F)cc32)[C@H]1CC(C)(C)C ; "CF3CO2H"] | 680.52 | >3 | 2.7 ± 0.6 | 31.5 ± 1.4 | 2.2 ± 0.1 | 47.8 ± 1.4 |

TABLE 19B-continued

| ID | Structure | MW | Binding affinities to MDM2 protein as determined by FP based assay IC$_{50}$ [uM] | Inhibition of cell growth in different cancer cell lines (IC$_{50}$, μM) | | | |
|---|---|---|---|---|---|---|---|
| | | | | LNCaP | PC3 | HCT116 p53 WT | HCT116 p53 KO |
| MI-718 | 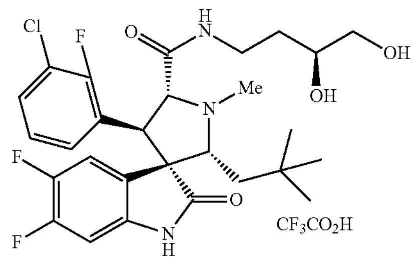 [SMILES: CN1[C@@H](C(=O)NCC[C@H](O)CO)[C@H](c2cccc(Cl)c2F)[C@@]2(C(=O)Nc3cc(F)c(F)cc32)[C@H]1CC(C)(C)C ; "CF3CO2H"] | 682.05 | >3 | 3.7 ± 0.3 | 34.2 ± 0.4 | 3.0 ± 1.1 | 47.2 ± 5.0 |
| MI-719 | 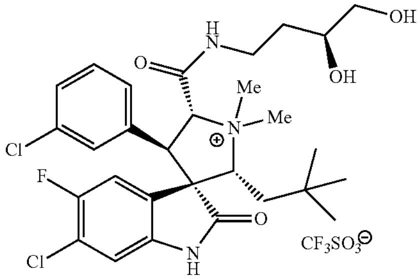 | 730.60 | >10 | 51.2 | >100 | 58.6 ± 14.9 | >100 |
| MI-720 | 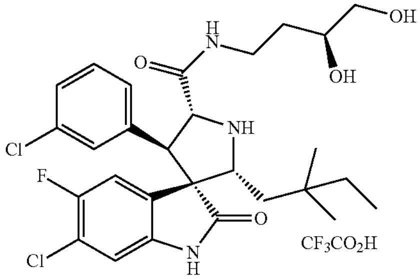 [SMILES: CCC(C)(C)C[C@H]1N[C@@H](C(=O)NCC[C@H](O)CO)[C@H](c2cccc(Cl)c2)[C@@]12C(=O)Nc1cc(Cl)c(F)cc12 ; "CF3CO2H"] | 680.52 | <1 | 0.76 ± 0.1 | 15.2 ± 3.2 | 0.69 ± 0.0 | 19.5 ± 5.6 |
| MI-721 | 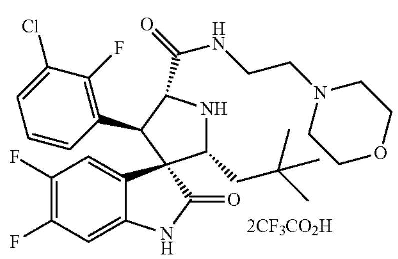 [SMILES: CC(C)(C)C[C@H]1N[C@@H](C(=O)NCCN2CCOCC2)[C@H](c2cccc(Cl)c2F)[C@@]12C(=O)Nc1cc(F)c(F)cc12 ; "2CF3CO2H"] | 807.10 | <3 | 1.4 ± 0.0 | 15.2 ± 1.4 | 1.5 ± 0.3 | 18.4 ± 5.4 |
| MI-722 | 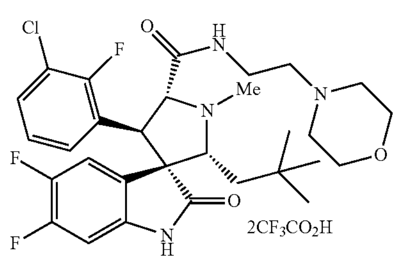 [SMILES: CN1[C@@H](C(=O)NCCN2CCOCC2)[C@H](c2cccc(Cl)c2F)[C@@]2(C(=O)Nc3cc(F)c(F)cc32)[C@H]1CC(C)(C)C ; "2CF3CO2H"] | 821.13 | | >100 | >100 | >100 | >100 |

TABLE 19B-continued

| ID | Structure | MW | Binding affinities to MDM2 protein as determined by FP based assay IC$_{50}$ [uM] | Inhibition of cell growth in different cancer cell lines (IC$_{50}$, µM) | | | |
|---|---|---|---|---|---|---|---|
| | | | | LNCaP | PC3 | HCT116 p53 WT | HCT116 p53 KO |
| MI-723 | 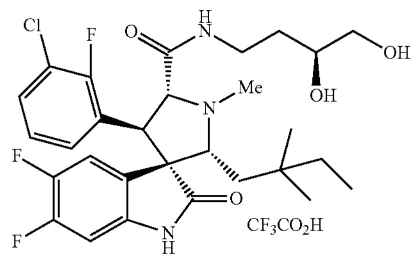 [SMILES: CCC(C)(C)C[C@H]1N(C)[C@@H](C(=O)NCC[C@H](O)CO)[C@H](c2cccc(Cl)c2F)[C@@]12C(=O)Nc1cc(F)c(F)cc12 ; "CF3CO2H"] | 695.22 | <5 | 2.301 | 24.65 | 2.422 | 51.31 |
| MI-724 | 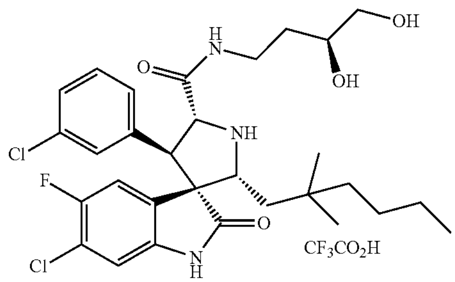 [SMILES: CCCCC(C)(C)C[C@H]1N[C@@H](C(=O)NCC[C@H](O)CO)[C@H](c2cccc(Cl)c2)[C@@]12C(=O)Nc1cc(Cl)c(F)cc12 ; "CF3CO2H"] | 708.57 | <1 | 1.2 ± 0.4 | 3.9 ± 0.2 | 1.1 ± 0.5 | 5.3 ± 0.3 |
| MI-725 | 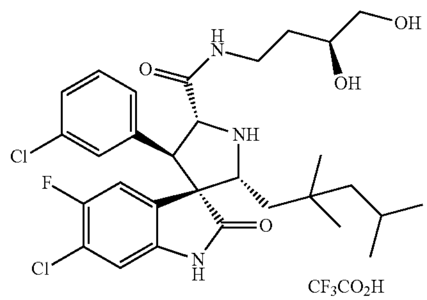 [SMILES: CC(C)CC(C)(C)C[C@H]1N[C@@H](C(=O)NCC[C@H](O)CO)[C@H](c2cccc(Cl)c2)[C@@]12C(=O)Nc1cc(Cl)c(F)cc12 ; "CF3CO2H"] | 708.57 | <1 | 0.8 ± 0.1 | 4.7 ± 1.0 | 0.7 ± 0.0 | 5.8 ± 2.9 |
| MI-726 | 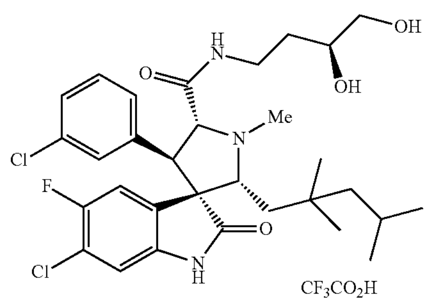 [SMILES: CC(C)CC(C)(C)C[C@H]1N(C)[C@@H](C(=O)NCC[C@H](O)CO)[C@H](c2cccc(Cl)c2)[C@@]12C(=O)Nc1cc(Cl)c(F)cc12 ; "CF3CO2H"] | 722.59 | <5 | 2.3 ± 0.3 | 5.1 ± 1.4 | 2.3 ± 0.8 | 8.0 ± 0.8 |
| MI-727 | 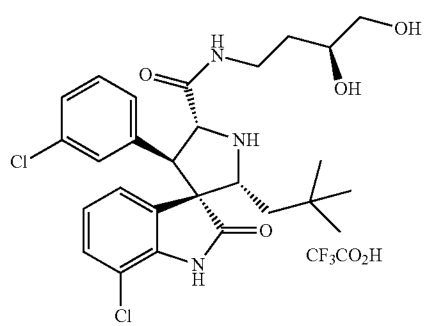 [SMILES: CC(C)(C)C[C@H]1N[C@@H](C(=O)NCC[C@H](O)CO)[C@H](c2cccc(Cl)c2)[C@@]12C(=O)Nc1c(Cl)cccc12 ; "CF3CO2H"] | 648.50 | >10 | 12.2 ± 0.5 | 21.4 ± 4.8 | 24.1 ± 0.7 | 20.9 ± 1.1 |

TABLE 19B-continued

| ID | Structure | MW | Binding affinities to MDM2 protein as determined by FP based assay IC$_{50}$ [uM] | Inhibition of cell growth in different cancer cell lines (IC$_{50}$, μM) | | | |
|---|---|---|---|---|---|---|---|
| | | | | LNCaP | PC3 | HCT116 p53 WT | HCT116 p53 KO |
| MI-728 | 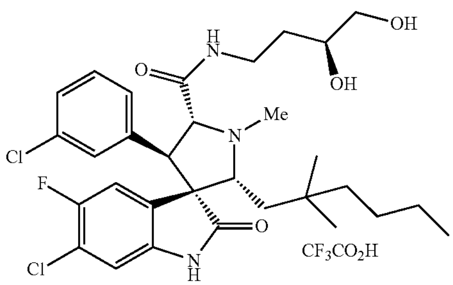 [SMILES: CCCCC(C)(C)C[C@H]1N(C)[C@@H](C(=O)NCC[C@H](O)CO)[C@H](c2cccc(Cl)c2)[C@@]12C(=O)Nc1cc(Cl)c(F)cc12 ; "CF3CO2H"] | 722.59 | <5 | 2.1 ± 0.1 | 7.1 ± 2.0 | 4.0 ± 0.8 | 16.9 ± 5.6 |
| MI-729 | 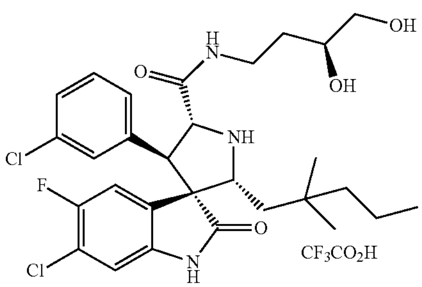 [SMILES: CCCC(C)(C)C[C@H]1N[C@@H](C(=O)NCC[C@H](O)CO)[C@H](c2cccc(Cl)c2)[C@@]12C(=O)Nc1cc(Cl)c(F)cc12 ; "CF3CO2H"] | 694.54 | <1 | 1.0 ± 0.0 | 6.1 ± 1.6 | 0.8 ± 0.2 | 8.9 ± 0.1 |
| MI-730 | 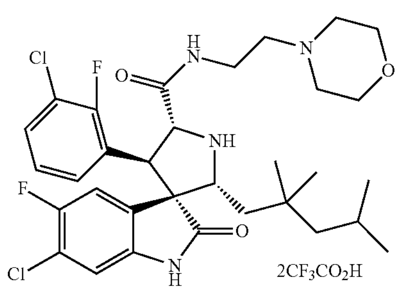 [SMILES: CC(C)CC(C)(C)C[C@H]1N[C@@H](C(=O)NCCN2CCOCC2)[C@H](c2cccc(Cl)c2F)[C@@]12C(=O)Nc1cc(Cl)c(F)cc12 ; "2CF3CO2H"] | 865.63 | <1 | 1.7 ± 0.5 | 6.3 ± 1.4 | 1.4 ± 0.3 | 7.8 ± 0.7 |
| MI-731 | 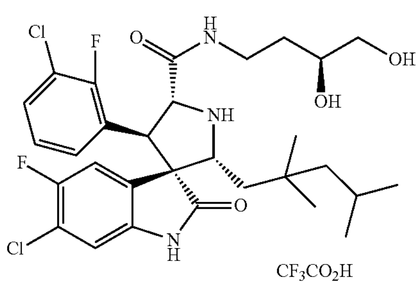 [SMILES: CC(C)CC(C)(C)C[C@H]1N[C@@H](C(=O)NCC[C@H](O)CO)[C@H](c2cccc(Cl)c2F)[C@@]12C(=O)Nc1cc(Cl)c(F)cc12 ; "CF3CO2H"] | 726.56 | <1 | 0.8 ± 0.5 | 5.6 ± 1.9 | 0.9 ± 0.5 | 6.4 ± 1.7 |
| MI-732 | 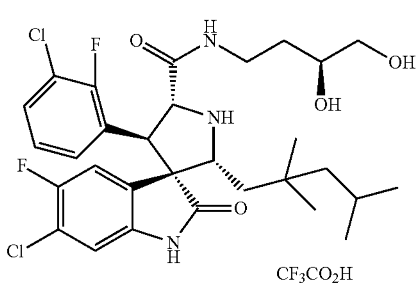 [SMILES: CC(C)CC(C)(C)C[C@H]1N[C@@H](C(=O)NCC[C@H](O)CO)[C@H](c2cccc(Cl)c2F)[C@@]12C(=O)Nc1cc(Cl)c(F)cc12 ; "CF3CO2H"] | 710.10 | <1 | 0.7 ± 0.0 | 5.8 ± 0.0 | 0.7 ± 0.1 | 10.2 ± 4.8 |

TABLE 19B-continued

| ID | Structure | MW | Binding affinities to MDM2 protein as determined by FP based assay IC$_{50}$ [uM] | Inhibition of cell growth in different cancer cell lines (IC$_{50}$, μM) | | | |
|---|---|---|---|---|---|---|---|
| | | | | LNCaP | PC3 | HCT116 p53 WT | HCT116 p53 KO |
| MI-733 | 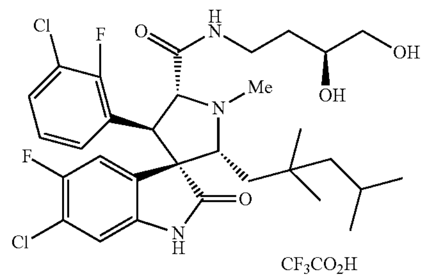 [SMILES: CC(C)CC(C)(C)C[C@H]1N(C)[C@@H](C(=O)NCC[C@H](O)CO)[C@H](c2cccc(Cl)c2F)[C@@]12C(=O)Nc1cc(Cl)c(F)cc12 ; "CF3CO2H"] | 740.58 | >1 | 2.2 ± 0.5 | 5.4 ± 1.7 | 2.4 ± 0.3 | 8.7 ± 0.9 |
| MI-734 | 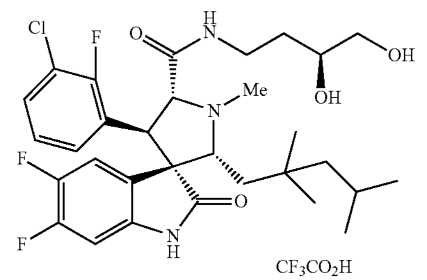 | 724.13 | >5 | 3.7 ± 1.1 | 7.4 ± 1.8 | 5.5 ± 2.1 | 8.2 ± 3.5 |
| MI-735 | 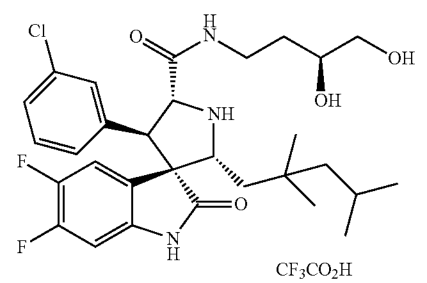 [SMILES: CC(C)CC(C)(C)C[C@H]1N[C@@H](C(=O)NCC[C@H](O)CO)[C@H](c2cccc(Cl)c2)[C@@]12C(=O)Nc1cc(F)c(F)cc12 ; "CF3CO2H"] | 692.11 | <1 | 1.1 ± 0.4 | 8.6 ± 0.9 | 1.2 ± 0.3 | 8.5 ± 1.1 |
| MI-736 | 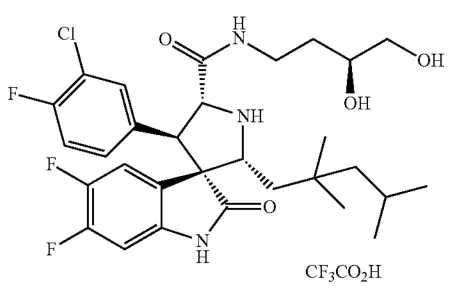 | 710.10 | <1 | 0.9 ± 0.0 | 6.3 ± 1.2 | 1.0 ± 0.2 | 4.4 ± 0.9 |
| MI-737 | 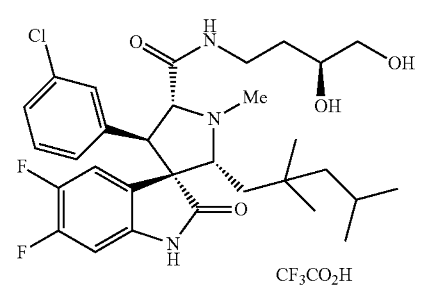 [SMILES: CC(C)CC(C)(C)C[C@H]1N(C)[C@@H](C(=O)NCC[C@H](O)CO)[C@H](c2cccc(Cl)c2)[C@@]12C(=O)Nc1cc(F)c(F)cc12 ; "CF3CO2H"] | 706.14 | >1 | 3.53<br>3.73 | 11.3<br>11.6 | 5.0<br>4.5 | 24.4<br>15.0 |

TABLE 19B-continued
| ID | Structure | MW | Binding affinities to MDM2 protein as determined by FP based assay IC$_{50}$ [uM] | Inhibition of cell growth in different cancer cell lines (IC$_{50}$, μM) | | | |
|---|---|---|---|---|---|---|---|
| | | | | LNCaP | PC3 | HCT116 p53 WT | HCT116 p53 KO |
| MI-738 | 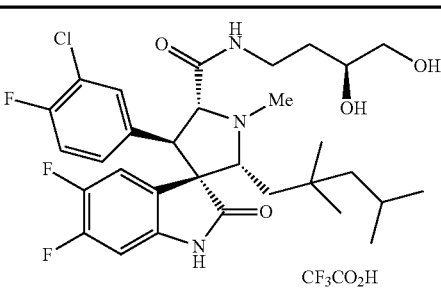 | 724.13 | >3 | 4.8 ± 1.0 | 8.5 ± 0.6 | 8.5 ± 2.1 | 8.2 ± 0.6 |
| MI-743 | 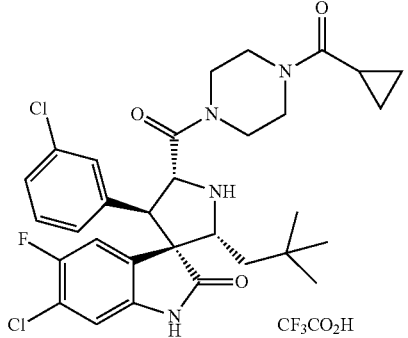 [SMILES: CC(C)(C)C[C@H]1N[C@@H](C(=O)N2CCN(C(=O)C3CC3)CC2)[C@H](c2cccc(Cl)c2)[C@@]12C(=O)Nc1cc(Cl)c(F)cc12 ; "CF3CO2H"] | 715.56 | >1 | 2.5 ± 0.5 | 7.7 ± 3.1 | 2.4 ± 0.2 | 5.7 ± 3.4 |
| MI-743B | 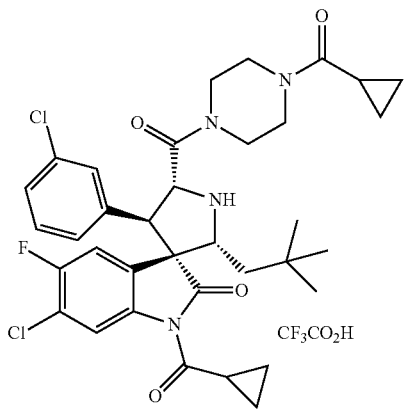 [SMILES: CC(C)(C)C[C@H]1N[C@@H](C(=O)N2CCN(C(=O)C3CC3)CC2)[C@H](c2cccc(Cl)c2)[C@@]12C(=O)N(C(=O)C1CC1)c1cc(Cl)c(F)cc12 ; "CF3CO2H"] | 783.64 | >100 | >1 | >1 | >1 | >1 |
| MI-753 | 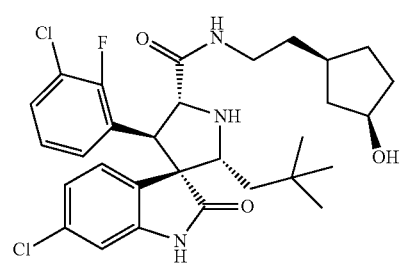 [SMILES: CC(C)(C)C[C@H]1N[C@@H](C(=O)NCC[C@H]2CC[C@@H](O)C2)[C@H](c2cccc(Cl)c2F)[C@@]12C(=O)Nc1cc(Cl)ccc12] | 576.53 | | 3.2 ± 0.3 | 24.7 ± 2.7 | 2.9 ± 0.1 | 21.8 ± 4.9 |

TABLE 19B-continued

| ID | Structure | MW | Binding affinities to MDM2 protein as determined by FP based assay IC$_{50}$ [uM] | Inhibition of cell growth in different cancer cell lines (IC$_{50}$, μM) | | | |
|---|---|---|---|---|---|---|---|
| | | | | LNCaP | PC3 | HCT116 p53 WT | HCT116 p53 KO |
| MI-754 | 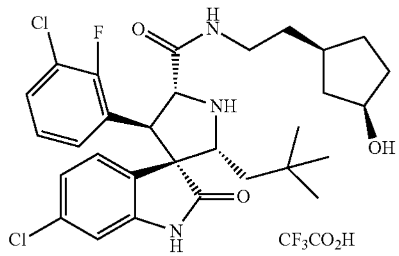 [SMILES: CC(C)(C)C[C@H]1N[C@@H](C(=O)NCC[C@H]2CC[C@@H](O)C2)[C@H](c2cccc(Cl)c2F)[C@@]12C(=O)Nc1cc(Cl)ccc12 ; "CF3CO2H"] | 690.55 | <1 | <3 | >5 | <3 | >5 |
| MI-755 | 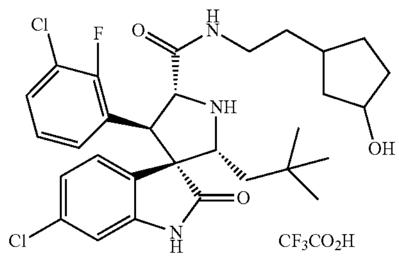 [SMILES: CC(C)(C)C[C@H]1N[C@@H](C(=O)NCCC2CCC(O)C2)[C@H](c2cccc(Cl)c2F)[C@@]12C(=O)Nc1cc(Cl)ccc12 ; "CF3CO2H"] | 690.55 | <1 | <3 | >10 | <3 | >10 |

TABLE 19C

| Compound ID | structure | Binding affinities to MDM2 as determined using FP assay IC$_{50}$ [uM] | Cell growth inhibition using WST assay (IC50 value, uM) | | | |
|---|---|---|---|---|---|---|
| | | | LNCaP IC$_{50}$ | PC3 IC$_{50}$ | HCT116 p53WT IC$_{50}$ | HCT116 p53KO IC$_{50}$ |
| MI-319-23 | 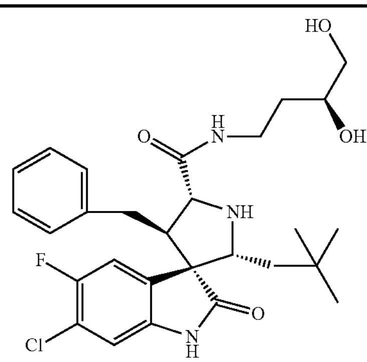 | >10 | >10 | >10 | >10 | >10 |
| MI-319-24 | 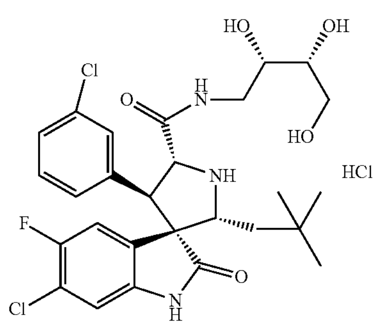 [SMILES: CC(C)(C)C[C@H]1N[C@@H](C(=O)NC[C@H](O)[C@H](O)CO)[C@H](c2cccc(Cl)c2)[C@@]12C(=O)Nc1cc(Cl)c(F)cc12 ; Cl] | <1 | <5 | >10 | <5 | >10 |

TABLE 19C-continued

| Compound ID | structure | Bidning affinities to MDM2 as determined using FP assay IC$_{50}$ [uM] | Cell growth inhibition using WST assay (IC50 value, uM) | | | |
|---|---|---|---|---|---|---|
| | | | LNCaP IC$_{50}$ | PC3 IC$_{50}$ | HCT116 p53WT IC$_{50}$ | HCT116 p53KO IC$_{50}$ |
| MI-319-25 | 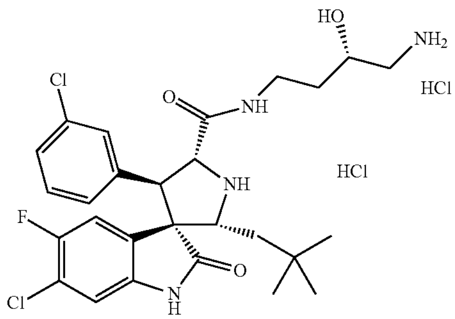 [SMILES: CC(C)(C)C[C@H]1N[C@@H](C(=O)NCC[C@H](O)CN)[C@H](c2cccc(Cl)c2)[C@@]12C(=O)Nc1cc(Cl)c(F)cc12 ; Cl ; Cl] | <1 | <5 | >10 | <5 | >10 |
| MI-319-26 | 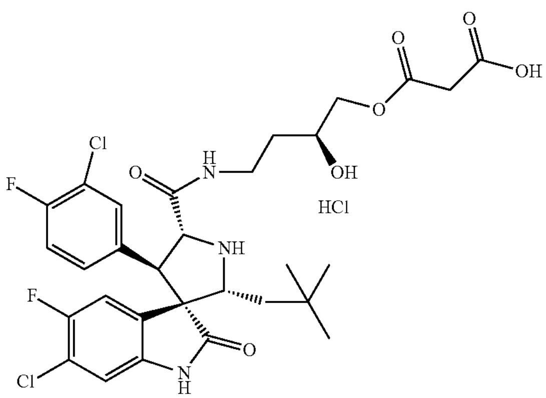 [SMILES: CC(C)(C)C[C@H]1N[C@@H](C(=O)NCC[C@H](O)COC(=O)CC(=O)O)[C@H](c2ccc(F)c(Cl)c2)[C@@]12C(=O)Nc1cc(Cl)c(F)cc12 ; Cl] | <1 | <5 | >10 | <5 | >10 |
| MI-319-27 | 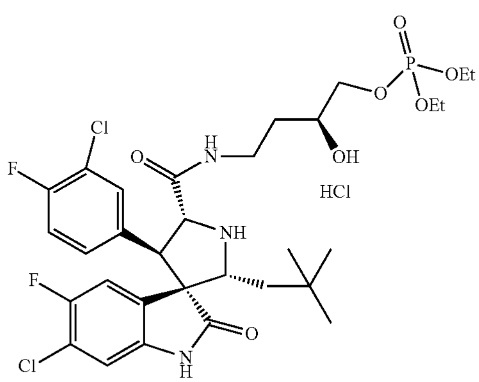 [SMILES: CCOP(=O)(OCC)OC[C@@H](O)CCNC(=O)[C@@H]1N[C@H](CC(C)(C)C)[C@]2(C(=O)Nc3cc(Cl)c(F)cc32)[C@H]1c1ccc(F)c(Cl)c1 ; Cl] | <5 | <5 | >10 | <5 | >10 |
| MI-319-28 | 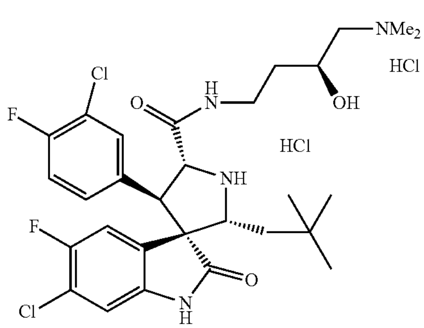 [SMILES: CN(C)C[C@@H](O)CCNC(=O)[C@@H]1N[C@H](CC(C)(C)C)[C@]2(C(=O)Nc3cc(Cl)c(F)cc32)[C@H]1c1ccc(F)c(Cl)c1 ; Cl ; Cl] | <5 | <5 | >5 | <5 | >5 |

TABLE 19C-continued

| Compound ID | structure | Bidning affinities to MDM2 as determined using FP assay IC$_{50}$ [uM] | Cell growth inhibition using WST assay (IC50 value, uM) | | | |
|---|---|---|---|---|---|---|
| | | | LNCaP IC$_{50}$ | PC3 IC$_{50}$ | HCT116 p53WT IC$_{50}$ | HCT116 p53KO IC$_{50}$ |
| MI-319-29 | 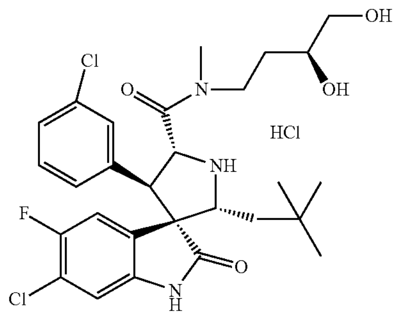 [SMILES: CN(CC[C@H](O)CO)C(=O)[C@@H]1N[C@H](CC(C)(C)C)[C@]2(C(=O)Nc3cc(Cl)c(F)cc32)[C@H]1c1cccc(Cl)c1 ; Cl] | >5 | >10 | >10 | >10 | >10 |
| MI-319-30 | 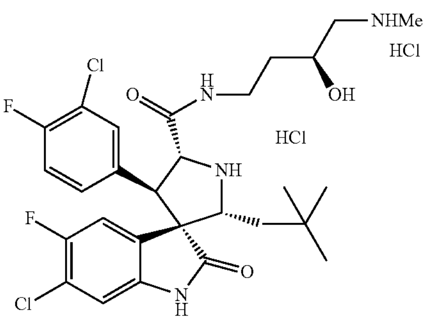 [SMILES: CNC[C@@H](O)CCNC(=O)[C@@H]1N[C@H](CC(C)(C)C)[C@]2(C(=O)Nc3cc(Cl)c(F)cc32)[C@H]1c1ccc(F)c(Cl)c1 ; Cl ; Cl] | <5 | >5 | >10 | >10 | >10 |
| MI-319-33 | 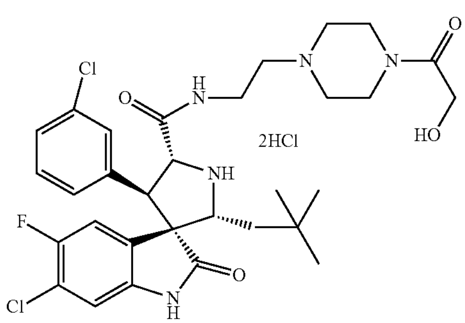 [SMILES: CC(C)(C)C[C@H]1N[C@@H](C(=O)NCCN2CCN(C(=O)CO)CC2)[C@H](c2cccc(Cl)c2)[C@@]12C(=O)Nc1cc(Cl)c(F)cc12 ; "2HCl"] | <1 | 1.4 ± 0.2 | 23.6 ± 5.5 | 2.1 ± 0.2 | 25.3 ± 2.8 |
| MI-319-34 | 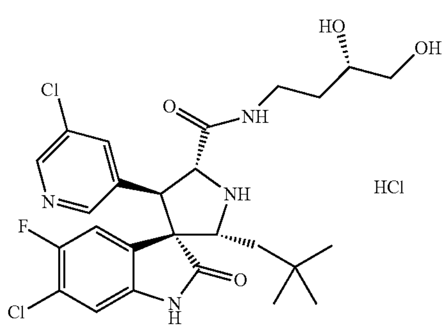 [SMILES: CC(C)(C)C[C@H]1N[C@@H](C(=O)NCC[C@H](O)CO)[C@H](c2cncc(Cl)c2)[C@@]12C(=O)Nc1cc(Cl)c(F)cc12 ; Cl] | <10 | <10 | >30 | 9.5 ± 2.1 | >30 |

TABLE 19C-continued

| Compound ID | structure | Bidning affinities to MDM2 as determined using FP assay IC$_{50}$ [uM] | Cell growth inhibition using WST assay (IC50 value, uM) | | | |
|---|---|---|---|---|---|---|
| | | | LNCaP IC$_{50}$ | PC3 IC$_{50}$ | HCT116 p53WT IC$_{50}$ | HCT116 p53KO IC$_{50}$ |
| MI-319-35 | 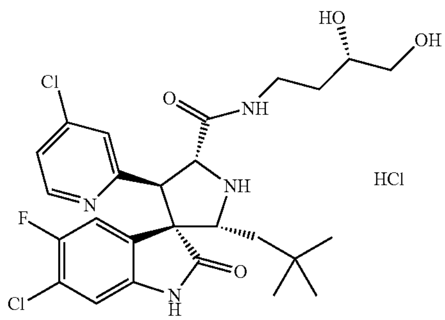 [SMILES: CC(C)(C)C[C@H]1N[C@@H](C(=O)NCC[C@H](O)CO)[C@H](c2cc(Cl)ccn2)[C@@]12C(=O)Nc1cc(Cl)c(F)cc12 ; Cl] | <10 | 3.2 ± 0.3 | >10 | 4.8 ± 0.5 | >10 |
| MI-319-36 | 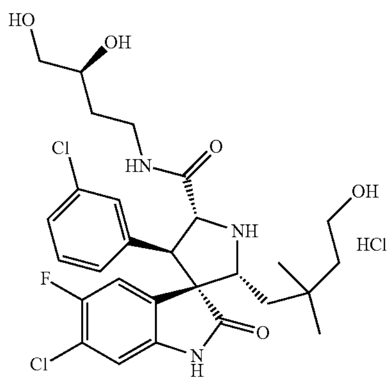 [SMILES: CC(C)(CCO)C[C@H]1N[C@@H](C(=O)NCC[C@H](O)CO)[C@H](c2cccc(Cl)c2)[C@@]12C(=O)Nc1cc(Cl)c(F)cc12 ; Cl] | <5 | 6.4 ± 1.4 | >30 | 12.2 ± 1.7 | >30 |
| MI-319-37 | 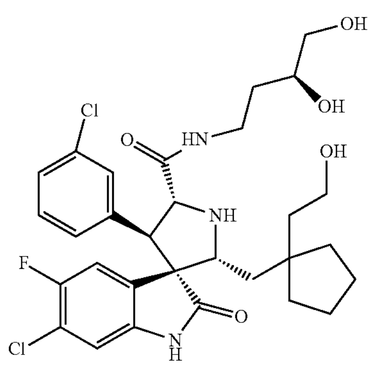 [SMILES: O=C(NCC[C@H](O)CO)[C@@H]1N[C@H](CC2(CCO)CCCC2)[C@]2(C(=O)Nc3cc(Cl)c(F)cc32)[C@H]1c1cccc(Cl)c1] | <1 | <5 | >30 | <10 | >30 |
| MI-319-38 | 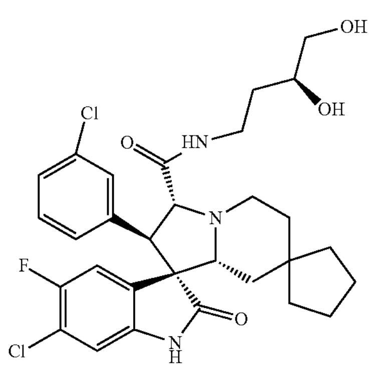 [SMILES: O=C(NCC[C@H](O)CO)[C@H]1[C@H](c2cccc(Cl)c2)[C@@]2(C(=O)Nc3cc(Cl)c(F)cc32)[C@H]2CC3(CCCC3)CCN12] | >3 | >5 | >10 | >10 | >10 |

TABLE 19C-continued
| Compound ID | structure | Bidning affinities to MDM2 as determined using FP assay IC$_{50}$ [uM] | Cell growth inhibition using WST assay (IC50 value, uM) | | | |
|---|---|---|---|---|---|---|
| | | | LNCaP IC$_{50}$ | PC3 IC$_{50}$ | HCT116 p53WT IC$_{50}$ | HCT116 p53KO IC$_{50}$ |
| MI-319-39 | 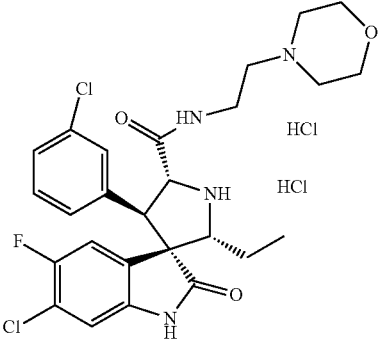 [SMILES: CC[C@H]1N[C@@H](C(=O)NCCN2CCOCC2)[C@H](c2cccc(Cl)c2)[C@@]12C(=O)Nc1cc(Cl)c(F)cc12 ; Cl ; Cl] | >10 | >3 | >10 | >3 | >10 |
TABLE 19D
| Compounds | structure | MDM2 Binding Affinities IC$_{50}$ [uM] | LNCaP IC$_{50}$ (uM) | PC3 IC$_{50}$ (uM) | HCT116p53WT IC$_{50}$ (uM) | HCT116p53KO IC$_{50}$ (uM) | SJSA-1 |
|---|---|---|---|---|---|---|---|
| MI-519-8 | 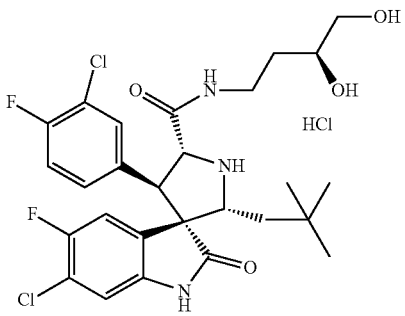 [SMILES: CC(C)(C)C[C@H]1N[C@@H](C(=O)NCC[C@H](O)CO)[C@H](c2ccc(F)c(Cl)c2)[C@@]12C(=O)Nc1cc(Cl)c(F)cc12 ; Cl] | <3 | <5 | >10 | <5 | >10 | |
| MI-519-9 | 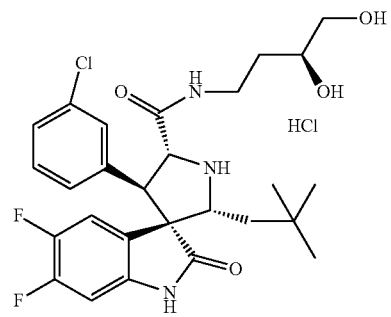 [SMILES: CC(C)(C)C[C@H]1N[C@@H](C(=O)NCC[C@H](O)CO)[C@H](c2cccc(Cl)c2)[C@@]12C(=O)Nc1cc(F)c(F)cc12 ; Cl] | <3 | <3 | >10 | <3 | >10 | |

TABLE 19D-continued

| Compounds | structure | MDM2 Binding Affinities IC$_{50}$ [uM] | LNCaP IC$_{50}$ (uM) | PC3 IC$_{50}$ (uM) | HCT116p5 3WT IC$_{50}$ (uM) | HCT116p5 3KO IC$_{50}$ (uM) | SJSA-1 |
|---|---|---|---|---|---|---|---|
| MI-519-10 | 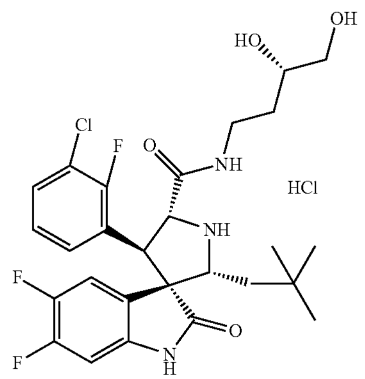 [SMILES: CC(C)(C)C[C@H]1N[C@@H](C(=O)NCC[C@H](O)CO)[C@H](c2cccc(Cl)c2F)[C@@]12C(=O)Nc1cc(F)c(F)cc12 ; Cl] | <3 | <3 | >10 | <3 | >10 | |
| MI-519-10-me | 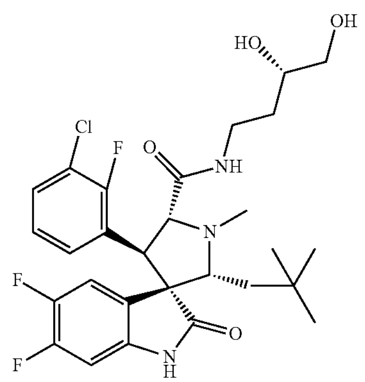 [SMILES: CN1[C@@H](C(=O)NCC[C@H](O)CO)[C@H](c2cccc(Cl)c2F)[C@@]2(C(=O)Nc3cc(F)c(F)cc32)[C@H]1CC(C)(C)C] | <10 | >1 | >30 | >1 | >30 | |
| MI-519-11 | 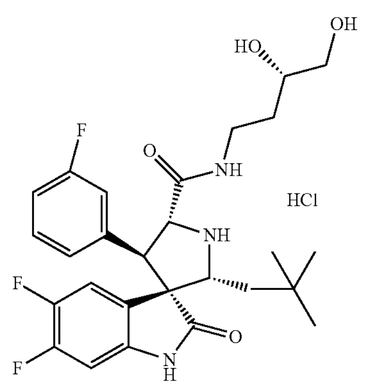 [SMILES: CC(C)(C)C[C@H]1N[C@@H](C(=O)NCC[C@H](O)CO)[C@H](c2cccc(F)c2)[C@@]12C(=O)Nc1cc(F)c(F)cc12 ; Cl] | >5 | >5 | >10 | >5 | >10 | |
| MI-519-12 | 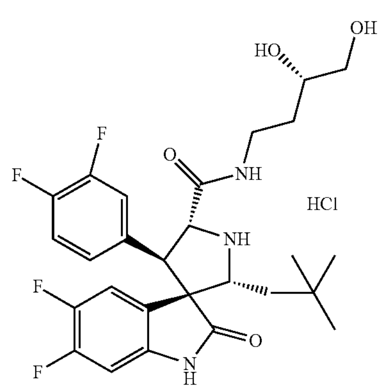 [SMILES: CC(C)(C)C[C@H]1N[C@@H](C(=O)NCC[C@H](O)CO)[C@H](c2ccc(F)c(F)c2)[C@@]12C(=O)Nc1cc(F)c(F)cc12 ; Cl] | <10 | <3 | >10 | <3 | >10 | |

TABLE 19D-continued
| Compounds | structure | MDM2 Binding Affinities IC$_{50}$ [uM] | LNCaP IC$_{50}$ (uM) | PC3 IC$_{50}$ (uM) | HCT116p5 3WT IC$_{50}$ (uM) | HCT116p5 3KO IC$_{50}$ (uM) | SJSA-1 |
|---|---|---|---|---|---|---|---|
| MI-519-13 | 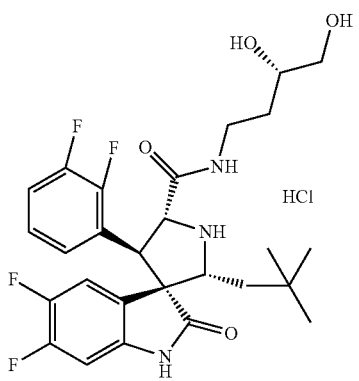 [SMILES: CC(C)(C)C[C@H]1N[C@@H](C(=O)NCC[C@H](O)CO)[C@H](c2cccc(F)c2F)[C@@]12C(=O)Nc1cc(F)c(F)cc12 ; Cl] | | | | | | |
| MI-519-14 | 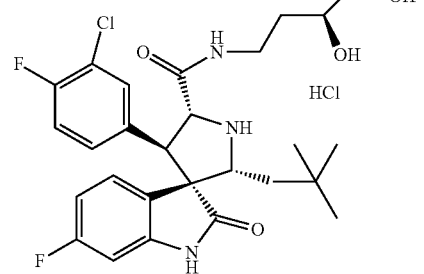 | <1 | <5 | >10 | <5 | >10 | |
| MI-519-15 | 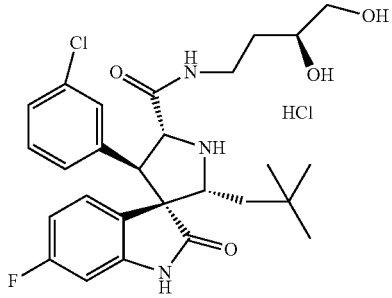 [SMILES: CC(C)(C)C[C@H]1N[C@@H](C(=O)NCC[C@H](O)CO)[C@H](c2cccc(Cl)c2)[C@@]12C(=O)Nc1cc(F)ccc12 ; Cl] | <1 | <5 | >10 | <3 | >10 | |
| MI-519-15-me | 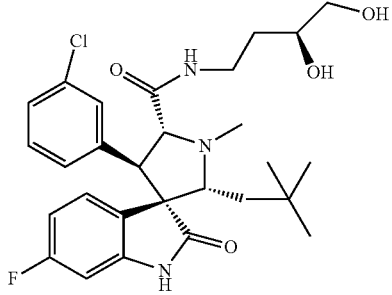 [SMILES: CN1[C@@H](C(=O)NCC[C@H](O)CO)[C@H](c2cccc(Cl)c2)[C@@]2(C(=O)Nc3cc(F)ccc32)[C@H]1CC(C)(C)C] | <5 | 6.4 | >10 | 5.2 | >10 | |

TABLE 19D-continued

| Compounds | structure | MDM2 Binding Affinities IC$_{50}$ [uM] | LNCaP IC$_{50}$ (uM) | PC3 IC$_{50}$ (uM) | HCT116p53WT IC$_{50}$ (uM) | HCT116p53KO IC$_{50}$ (uM) | SJSA-1 |
|---|---|---|---|---|---|---|---|
| MI-219-M8 | 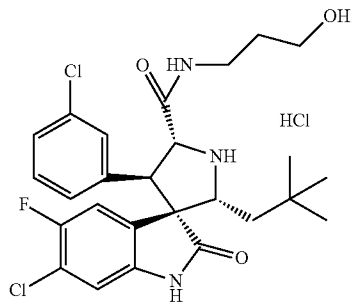 [SMILES: CC(C)(C)C[C@H]1N[C@@H](C(=O)NCCCO)[C@H](c2cccc(Cl)c2)[C@@]12C(=O)Nc1cc(Cl)c(F)cc12 ; Cl] | <1 | 1.1 ± 0.5 | 9.2 ± 1.6 | 1.4 ± 0.9 | 18.0 ± 4.1 | |
| MI-519-20 | 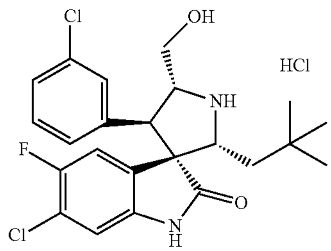 [SMILES: CC(C)(C)C[C@H]1N[C@@H](CO)[C@H](c2cccc(Cl)c2)[C@@]12C(=O)Nc1cc(Cl)c(F)cc12 ; Cl] | <5 | 2.2 ± 0.2 | 9.0 ± 1.1 | 1.9 ± 0.1 | 13.4 ± 0.8 | |
| MI-519-21 | 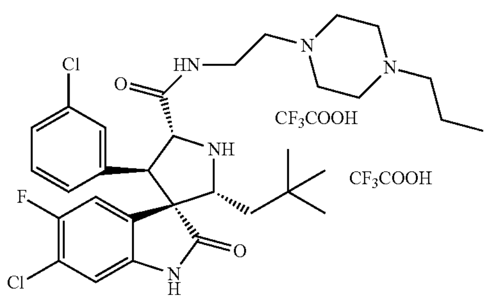 | <3 | 1.5 ± 0.6 | 4.8 ± 0.4 | 1.4 ± 0.5 | 5.8 ± 1.9 | |
| MI-519-22 | 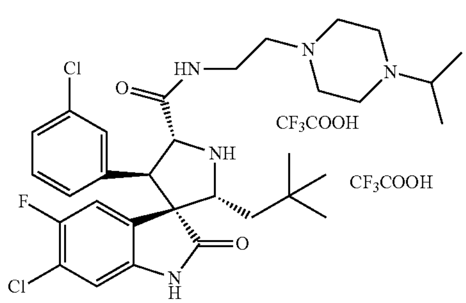 | | | | | | |
| MI-519-25 | 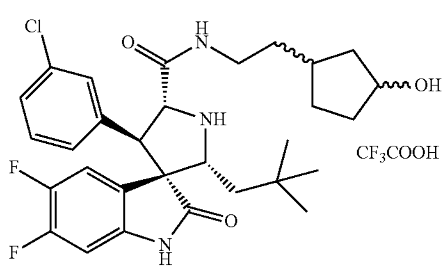 [SMILES: CC(C)(C)C[C@H]1N[C@@H](C(=O)NCCC2CCC(O)C2)[C@H](c2cccc(Cl)c2)[C@@]12C(=O)Nc1cc(F)c(F)cc12 ; "CF3COOH"] | <3 | <5 | >10 | <3 | >10 | |

TABLE 19D-continued

| Compounds | structure | MDM2 Binding Affinities IC$_{50}$ [uM] | LNCaP IC$_{50}$ (uM) | PC3 IC$_{50}$ (uM) | HCT116p53WT IC$_{50}$ (uM) | HCT116p53KO IC$_{50}$ (uM) | SJSA-1 |
|---|---|---|---|---|---|---|---|
| MI-519-26 | 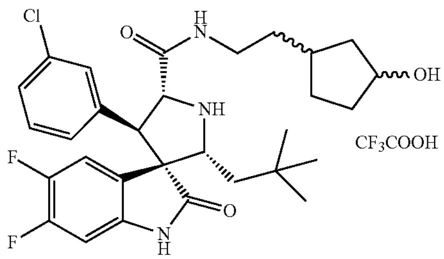 [SMILES: CC(C)(C)C[C@H]1N[C@@H](C(=O)NCCC2CCC(O)C2)[C@H](c2cccc(Cl)c2)[C@@]12C(=O)Nc1cc(F)c(F)cc12 ; "CF3COOH"] | <10 | <5 | >10 | <5 | >10 | |
| MI-519-52 | 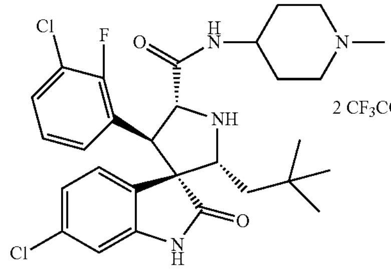 | <1 | <1 | >3 | <1 | >5 | <1 |
| MI-519-53-1 | 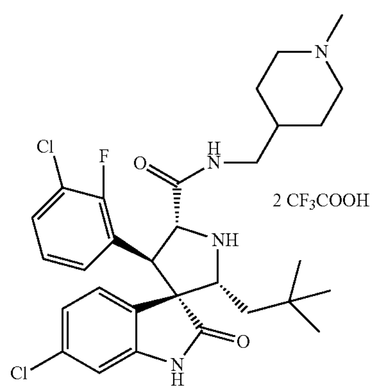 [SMILES: CN1CCC(CNC(=O)[C@@H]2N[C@H](CC(C)(C)C)[C@]3(C(=O)Nc4cc(Cl)ccc43)[C@H]2c2cccc(Cl)c2F)CC1 ; "2 CF3COOH"] | <1 | <1 | >3 | <1 | >3 | <1 |
| MI-519-53-2 | 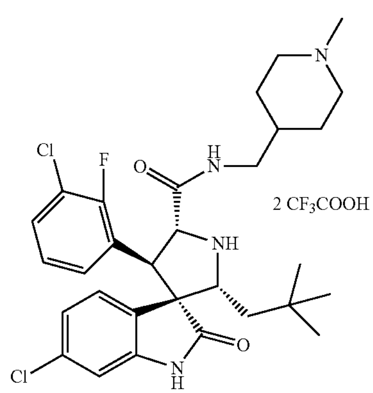 [SMILES: CN1CCC(CNC(=O)[C@@H]2N[C@H](CC(C)(C)C)[C@]3(C(=O)Nc4cc(Cl)ccc43)[C@H]2c2cccc(Cl)c2F)CC1 ; "2 CF3COOH"] | <1 | <1 | >3 | <1 | >3 | <1 |

TABLE 19D-continued

| Compounds | structure | MDM2 Binding Affinities IC$_{50}$ [uM] | LNCaP IC$_{50}$ (uM) | PC3 IC$_{50}$ (uM) | HCT116p53WT IC$_{50}$ (uM) | HCT116p53KO IC$_{50}$ (uM) | SJSA-1 |
|---|---|---|---|---|---|---|---|
| MI-519-55 | 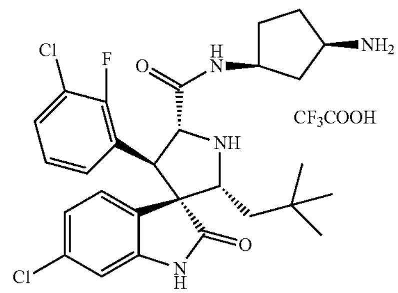 [SMILES: CC(C)(C)C[C@H]1N[C@@H](C(=O)N[C@H]2CC[C@@H](N)C2)[C@H](c2cccc(Cl)c2F)[C@@]12C(=O)Nc1cc(Cl)ccc12 ; "CF3COOH"] | <1 | <2 | >3 | <2 | >5 | <3 |
| MI-519-57-1 | 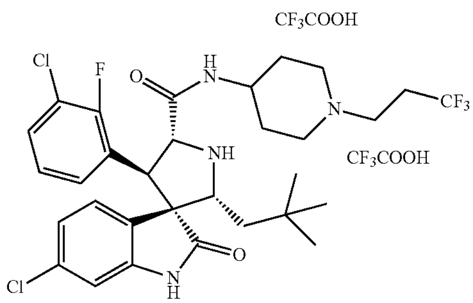 | <1 | <3 | 8.8 | <3 | 9.5 | <3 |
| MI-519-58 | 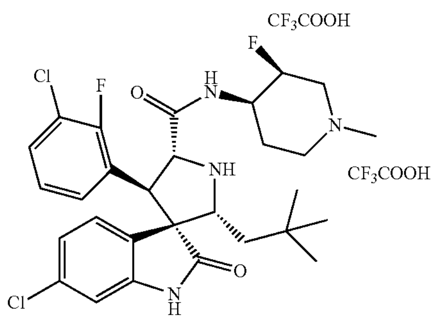 | <1 | <3 | >10 | <3 | >10 | <3 |
| MI-519-59 | 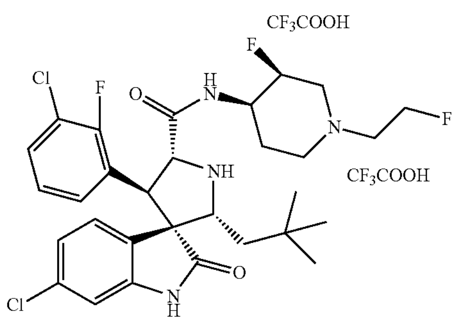 | <1 | <3 | >10 | <1 | >10 | <3 |
| MI-519-66 | 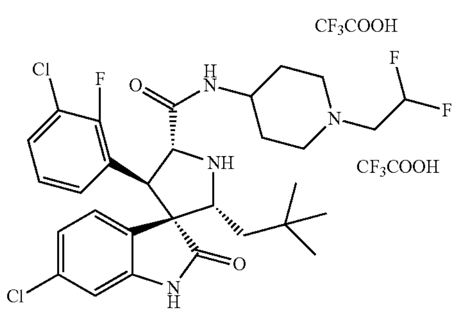 | <3 | 6.89 | <2 | 5.512 | <3 | |

TABLE 19D-continued

| Compounds | structure | MDM2 Binding Affinities IC$_{50}$ [uM] | LNCaP IC$_{50}$ (uM) | PC3 IC$_{50}$ (uM) | HCT116p53WT IC$_{50}$ (uM) | HCT116p53KO IC$_{50}$ (uM) | SJSA-1 |
|---|---|---|---|---|---|---|---|
| MI-519-67 | 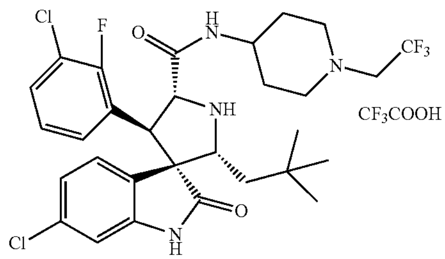 | | | | | | |
| MI-519-72 | 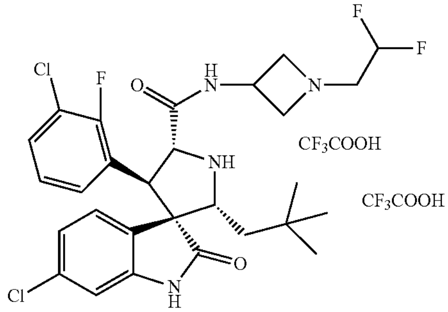 [SMILES: CC(C)(C)C[C@H]1N[C@@H](C(=O)NC2CN(CC(F)F)C2)[C@H](c2cccc(Cl)c2F)[C@@]12C(=O)Nc1cc(Cl)ccc12 ; "CF3COOH" ; "CF3COOH"] | <1 | | | | | |

Example 4

Cell Death Assay

Cell death assays were performed using trypan blue staining Cells were treated in the presence and absence of indicated compounds. Both the floating and adherent cells were stained with trypan blue. Cells that stained blue or the morphologically unhealthy cells were scored as dead cells. At least 100 cells were counted in each of three separate areas under microscope.

Figure 30:
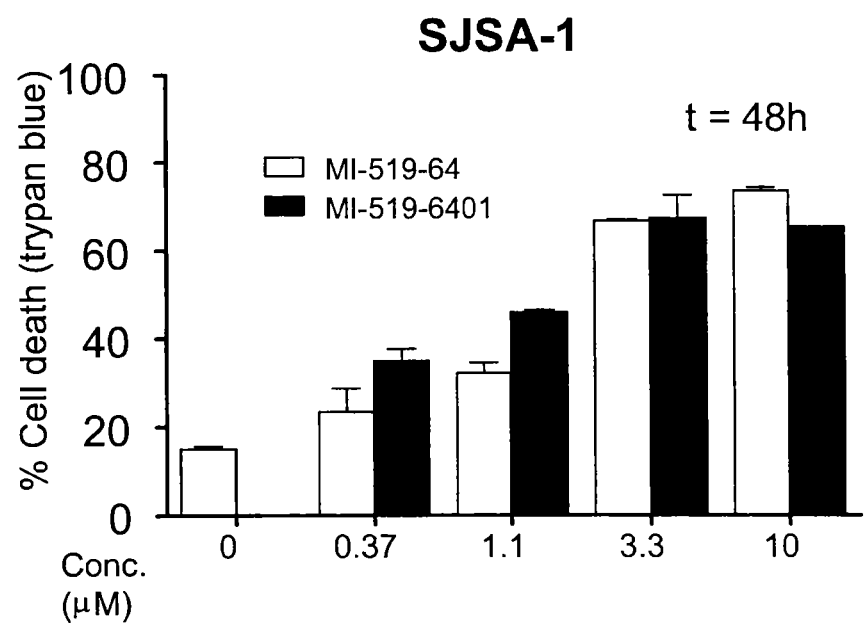
FIG. 30 is a bar graph showing cell death induced by MI-519-64 and MI-519-6401 in the SJSA-1 cell line.
Figure 31:
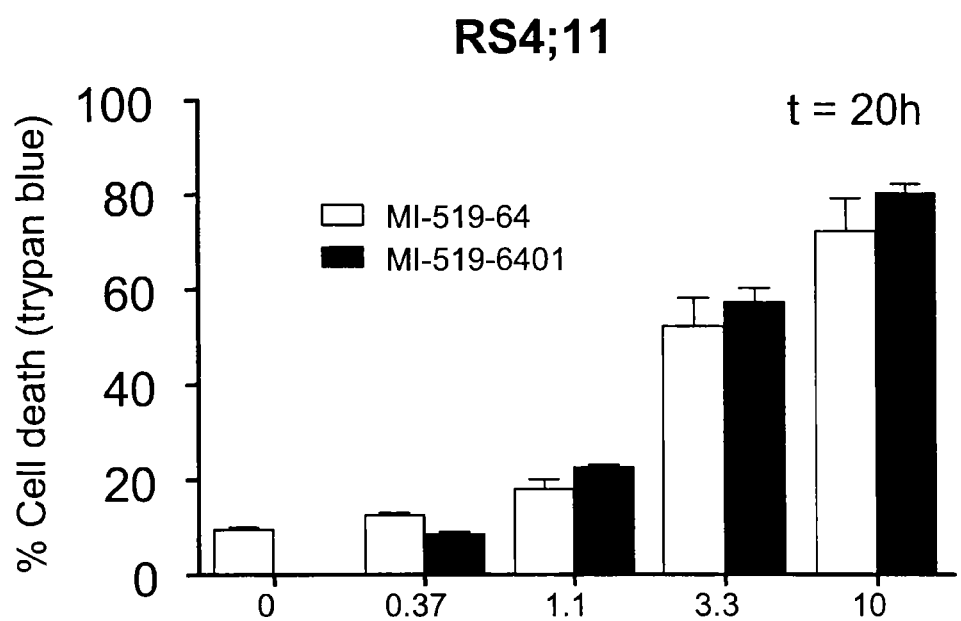
FIG. 31 is a bar graph showing cell death induced by MI-519-64 and MI-519-6401 in the RS4; 11 cell line.
Figure 32:
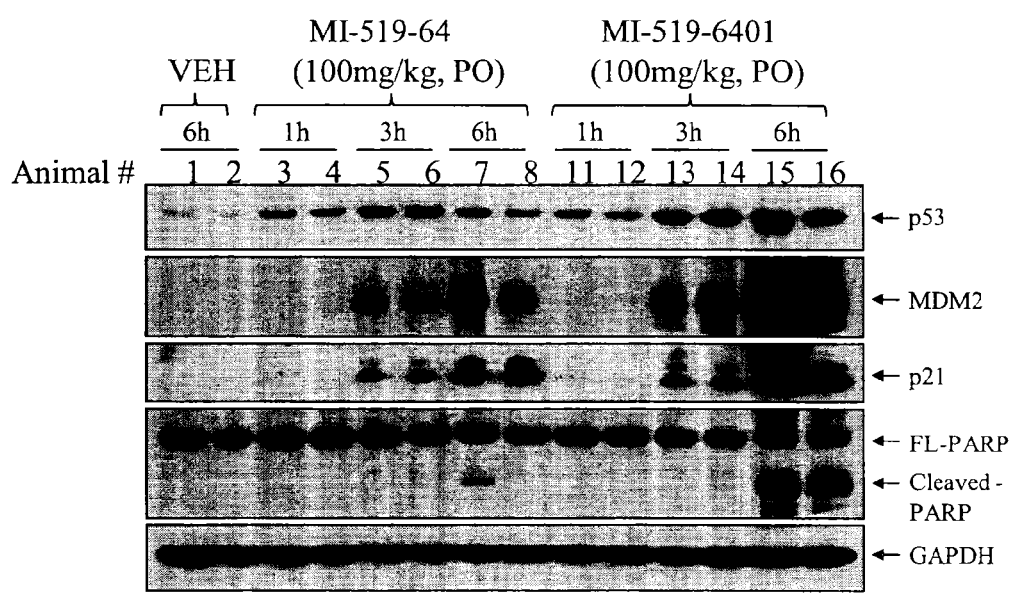
FIG. 32 is an illustration showing western blot analysis of in vivo activation of p53 and PARP cleavage induced by MI-519-64 and MI-519-6401 in SJSA-1 tumors in mice.
Figure 33:
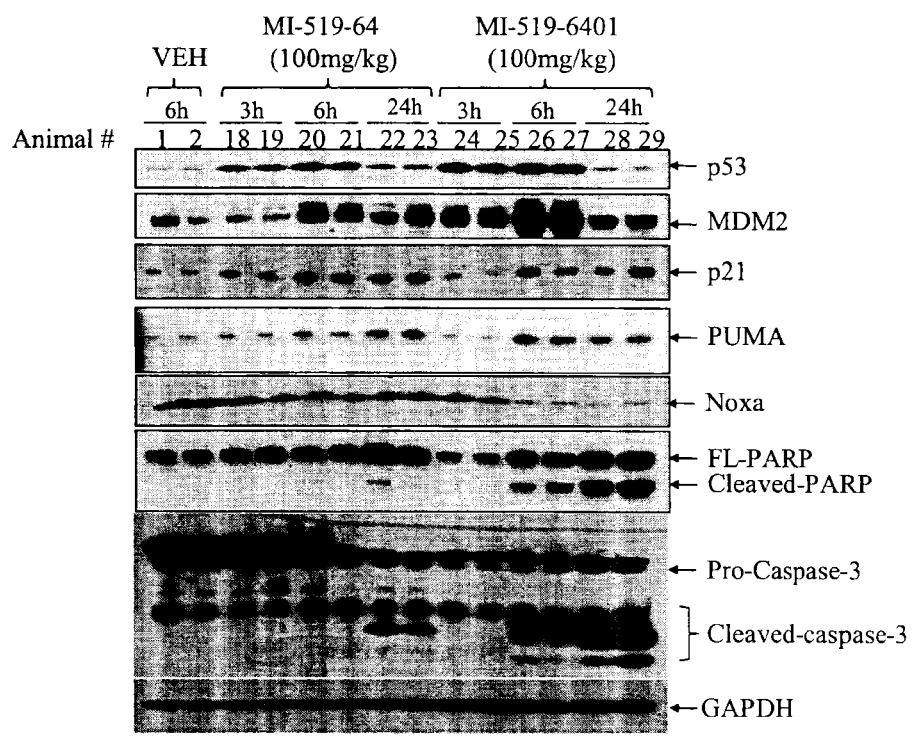
FIG. 33 is an illustration showing western blot analysis of in vivo activation of p53 and PARP cleavage induced by MI-519-64 and MI-519-6401 in RS4; 11 tumors in mice.
Figure 34:
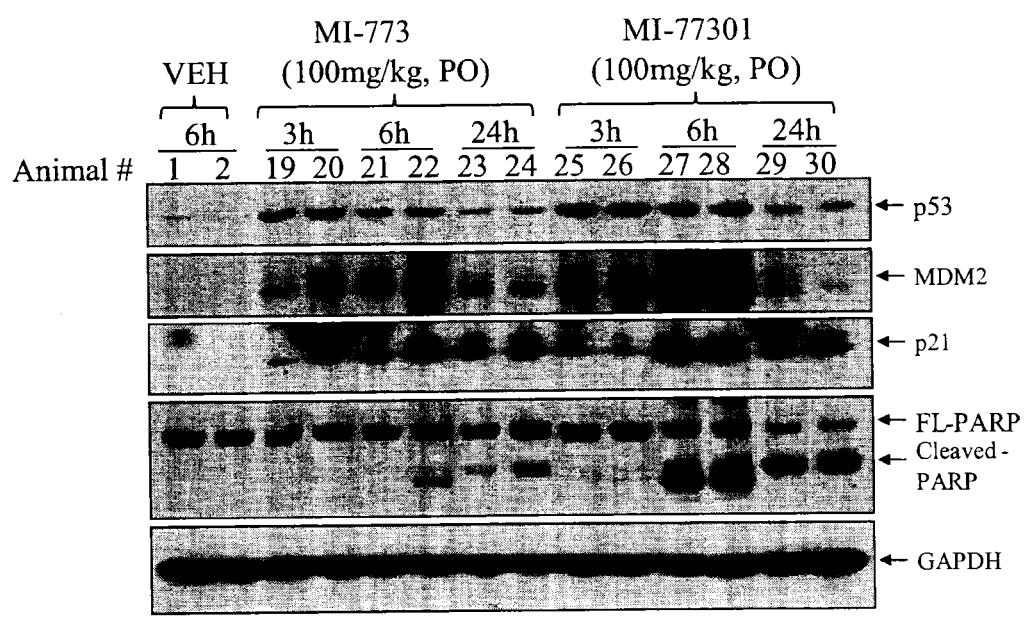
FIG. 34 is an illustration showing western blot analysis of in vivo activation of p53 and PARP cleavage induced by MI-773 and MI-77301 in SJSA-1 tumors in mice.
Figure 35:
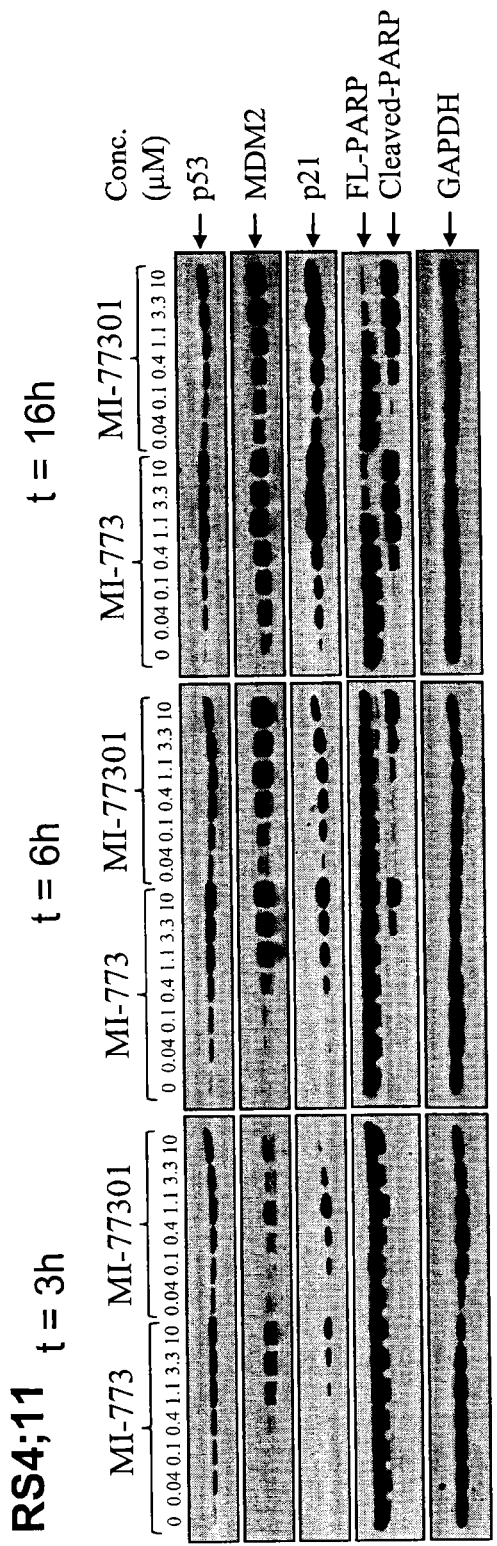
FIG. 35 is an illustration showing three western blot analyses of p53 activation and apoptosis induced by MI-773 and MI-77301 in the RS4; 11 cell line.
Figure 36:
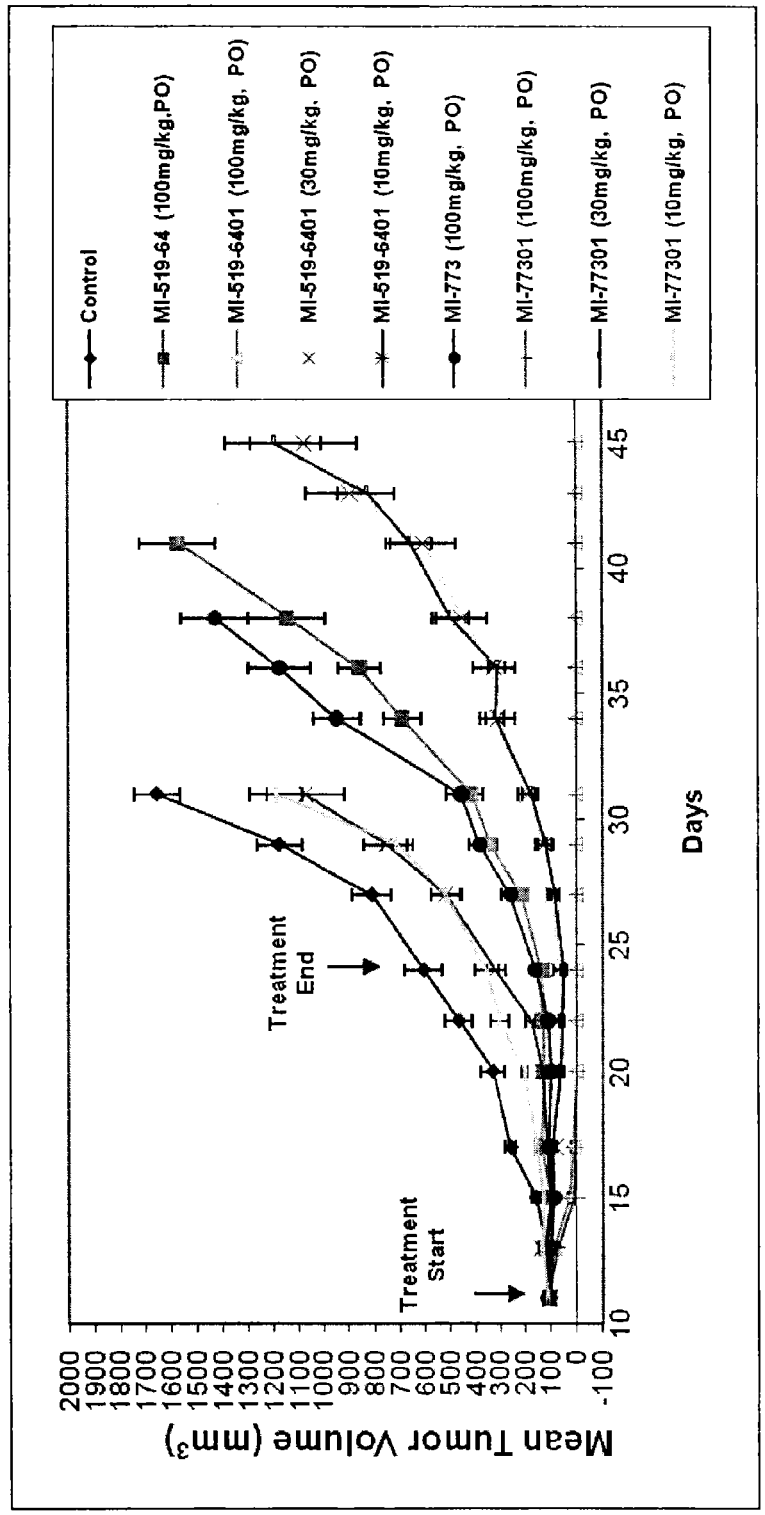
FIG. 36 is a line graph showing in vivo antitumor activity of MI-519-64, MI-519-6401, MI-773, and MI-77301 in the SJSA-1 xenograft model in mice.
Figure 37:
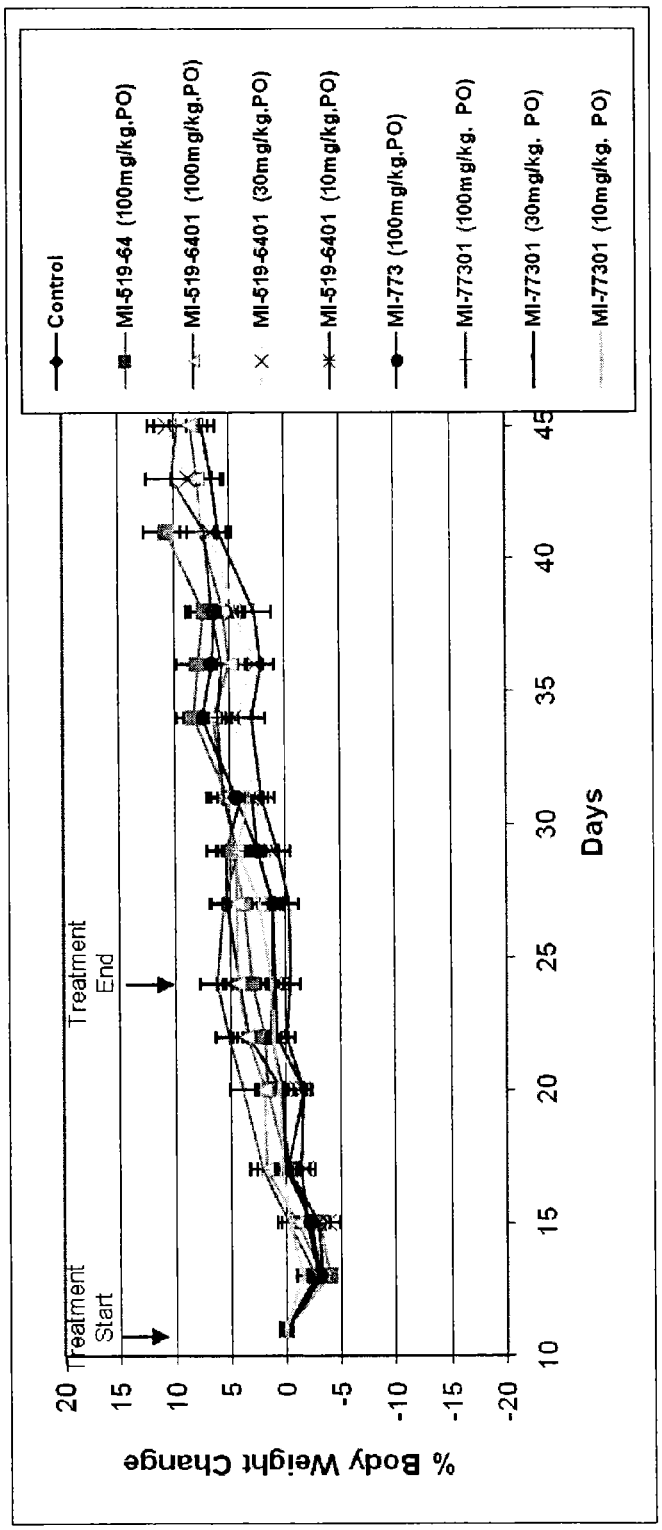
FIG. 37 is a line graph showing the animal weight following administration of MI-519-64, MI-519-6401, MI-773, and MI-77301 in mice.

As shown in FIGS. 1, 30, and 31 MDM2 inhibitors provided herein induce cell death in SJSA-1 and RS4; 11 cancer cells with wild-type p53.

Example 5

Western Blotting

For Western blot analysis, cells were lyzed in ice-cold RIPA buffer: 20 mM Tris-HCl (pH 7.5), 150 mM NaCl, 1 mM EDTA, 1 mM EGTA, 1% sodium deoxycholate, 2.5 mM sodium pyrophosphate, 1 mM b-glycerophosphate, 1 mM sodium orthovanadate and 1 μg/ml leupeptin. The proteins in the whole cell lysates were detected by Western blot analysis using the following antibodies: anti-p53 (clone DO-1), anti-MDM2 (clone SMP-14), anti-p21 (clone SX118), anti-β-actin (clone AC-40) and glyceraldehyde-3-phosphate dehydrogenase (GAPDH; HRP conjugated). As shown in FIGS. 2-4, 27, 28, and 32-25, MDM2 inhibitors provided herein are active in this assay.

Example 6

In Vitro Microsomal Stability

The in vitro stability of the MDM2 inhibitors provided herein was determined using rat and/or human liver microsomes as shown in Tables 20-24.

TABLE 20

| | % of compound remaining when incubated in rat liver microsomes at indicated time (min) | | | | | |
|---|---|---|---|---|---|---|
| compound | 0 | 4 | 6 | 10 | 15 | 30 |
| MI-519-31 | 100 | 80.1 | 69.4 | 54.3 | 47.7 | 31 |
| MI-519-38 | 100 | 91.5 | 85.4 | 82.4 | 80.8 | 73.2 |
| MI-519-40 | 100 | 84.2 | 70.1 | 59.6 | 58.7 | 57.6 |
| MI-519-41 | 100 | 84.2 | 80.4 | 66.1 | 55.4 | 42.9 |
| MI-519-44 | 100 | 85.6 | 74.7 | 66.4 | 61.2 | 42.5 |
| MI-519-45 | 100 | 81.1 | 59.6 | 50.7 | 44.3 | 38.5 |
| MI-519-46 | 100 | 83.8 | 70.9 | 53.9 | 53.4 | 38.3 |
| MI-519-47 | 100 | 80.1 | 61.1 | 45.3 | 38.1 | 34.3 |
| MI-518-48 | 100 | 79.8 | 64.8 | 48.5 | 45.2 | 43.7 |
| MI-748 | 100 | 79.1 | 69.7 | 61.5 | 49.9 | 43.7 |
| MI-749 | 100 | 82.9 | 58.4 | 54.2 | 42.7 | 23 |
| MI-751 | 100 | 83.1 | 62.9 | 50.1 | 41.6 | 31.1 |
| MI-752 | 100 | 84.3 | 70.3 | 60.6 | 52.2 | 46.4 |
| MI-763 | 100 | 96.8 | 97.3 | 85.6 | 72.1 | 61.5 |
| MI-764 | 100 | 87.8 | 76.5 | 66.5 | 63.9 | 55.8 |

TABLE 21

% of compound remaining when incubated in rat liver microsomes with NADPH at indicated time (min)

| (min) Time | MI-758 | MI-519-19 | MI-519-23 | MI-519-24 | MI-519-27 | MI-519-28 | MI-519-29 (TFA) |
|---|---|---|---|---|---|---|---|
| 0 | 100.00% | 100.00% | 100.00% | 100.00% | 100.00% | 100.00% | 100.00% |
| 5 | 96.52% | 8.14% | 43.92% | 102.16% | 57.28% | 92.34% | 93.42% |
| 10 | 92.93% | 1.61% | 34.46% | 86.33% | 31.78% | 87.59% | 84.91% |
| 15 | 82.50% | 0.64% | 18.06% | 75.72% | 19.34% | 86.13% | 82.81% |
| 30 | 73.32% | 0.00% | 9.01% | 68.24% | 5.81% | 71.97% | 70.75% |
| 45 | 69.33% | 0.00% | 5.70% | 66.08% | 2.49% | 65.40% | 71.89% |
| 60 | 66.93% | 0.00% | 4.76% | 61.51% | 2.13% | 61.79% | 69.91% |
| $t_{1/2}$ | 79.82 | 1.38 | 6.5 | 48.52 | 6.05 | 74.56 | 61.30 |

% of compound remaining when incubated in rat liver microsomes with NADPH at indicated time (min)

| (min) Time | MI-519-31 | MI-771 | MI-772 | MI-773 | MI-519-51 | AT-219 |
|---|---|---|---|---|---|---|
| 0 | 100.00% | 100.00% | 100.00% | 100.00% | 100.00% | 100.00% |
| 5 | 80.22% | 20.48% | 93.46% | 81.32% | 12.77% | 84.05% |
| 10 | 65.69% | 7.59% | 91.15% | 60.00% | 2.84% | 60.28% |
| 15 | 57.57% | 3.57% | 89.04% | 56.58% | 0.83% | 56.91% |
| 30 | 42.91% | 1.22% | 88.27% | 46.11% | 0.00% | 52.38% |
| 45 | 34.31% | 0.66% | 78.65% | 41.18% | 0.00% | 28.04% |
| 60 | 32.81% | 0.46% | 75.96% | 33.26% | 0.00% | 18.59% |
| $t_{1/2}$ | 18.69 | 2.69 | >60 | 17.28 | 2.18 | 27.94 |

TABLE 22

% of compound remaining when incubated in rat liver microsomes with NADPH at indicated time (min)

| (min) Time | MI-519-63 | MI-519-60 | MI-519-64 | MI-519-31 |
|---|---|---|---|---|
| 0 | 100% | 100% | 100% | 100% |
| 5 | 66.01% | 79.93% | 71.95% | 80.22% |
| 10 | 53.79% | 63.72% | 64.86% | 65.69% |
| 15 | 46.44% | 51.52% | 48.47% | 57.57% |
| 30 | 29.41% | 40.6% | 43.38% | 42.91% |
| 45 | 27.72% | 35.16% | 41.19% | 34.31% |
| 60 | 23.28% | 29.15% | 43.03% | 32.81% |

TABLE 23

% of compound remaining when incubated in human liver microsomes with NADPH at indicated time (min)

| (min) Time | MI-758 | MI-519-19 | MI-519-23 | MI-519-24 | MI-519-27 | MI-519-28 | MI-519-29 |
|---|---|---|---|---|---|---|---|
| 0 | 100.00% | 100.00% | 100.00% | 100.00% | 100.00% | 100.00% | 100.00% |
| 5 | 95.88% | 9.68% | 30.98% | 57.08% | 52.96% | 91.87% | 70.67% |
| 10 | 89.21% | 0.89% | 13.14% | 53.92% | 25.03% | 89.02% | 56.31% |
| 15 | 81.61% | 0.00% | 2.60% | 49.62% | 11.38% | 77.40% | 49.52% |
| 30 | 65.20% | 0.00% | 0.55% | 47.41% | 2.30% | 66.83% | 45.48% |
| 45 | 54.52% | 0.00% | 0.17% | 41.18% | 1.42% | 55.85% | 40.08% |
| 60 | 51.45% | 0.00% | 0.00% | 41.42% | 0.77% | 53.78% | 35.28% |
| $t_{1/2}$ | 49.47 | 1.48 | 3.42 | 11.24 | 5.00 | 54.11 | 12.07 |

% of compound remaining when incubated in human liver microsomes with NADPH at indicated time (min)

| (min) Time | MI-519-31 | MI-771 | MI-772 | MI-773 | MI-519-51 | AT-219 |
|---|---|---|---|---|---|---|
| 0 | 100.00% | 100.00% | 100.00% | 100.00% | 100.00% | 100.00% |
| 5 | 78.11% | 27.98% | 95.37% | 83.70% | 36.05% | 90.98% |
| 10 | 58.15% | 10.82% | 86.87% | 82.97% | 9.88% | 71.93% |
| 15 | 45.42% | 4.30% | 82.24% | 69.38% | 3.95% | 59.84% |
| 30 | 22.75% | 0.82% | 77.91% | 52.36% | 0.00% | 43.20% |
| 45 | 13.25% | 0.00% | 63.28% | 42.57% | 0.00% | 18.69% |
| 60 | 8.56% | 0.00% | 56.87% | 28.77% | 0.00% | 10.41% |
| $t_{1/2}$ | 13.01 | 3.12 | >60 | 31.51 | 3.15 | 23.96 |

TABLE 24

% of compound remaining when incubated in human liver microsomes with NADPH at indicated time (min)

| Time (min) | MI-519-63 | MI-519-60 | MI-519-64 | MI-519-31 |
|---|---|---|---|---|
| 0 | 100.00% | 100% | 100% | 100.00% |
| 5 | 77.75% | 83.26% | 83.66% | 78.11% |
| 10 | 59.66% | 68.14% | 80.61% | 58.15% |
| 15 | 50.42% | 51.54% | 65.86% | 45.42% |
| 30 | 31.21% | 49.28% | 61.26% | 22.75% |
| 45 | 26.74% | 40.97% | 55.9% | 13.25% |
| 60 | 21.5% | 37.55% | 53.21% | 8.56% |

Example 7

Pharmacokinetic Studies in Rats

Figure 5:
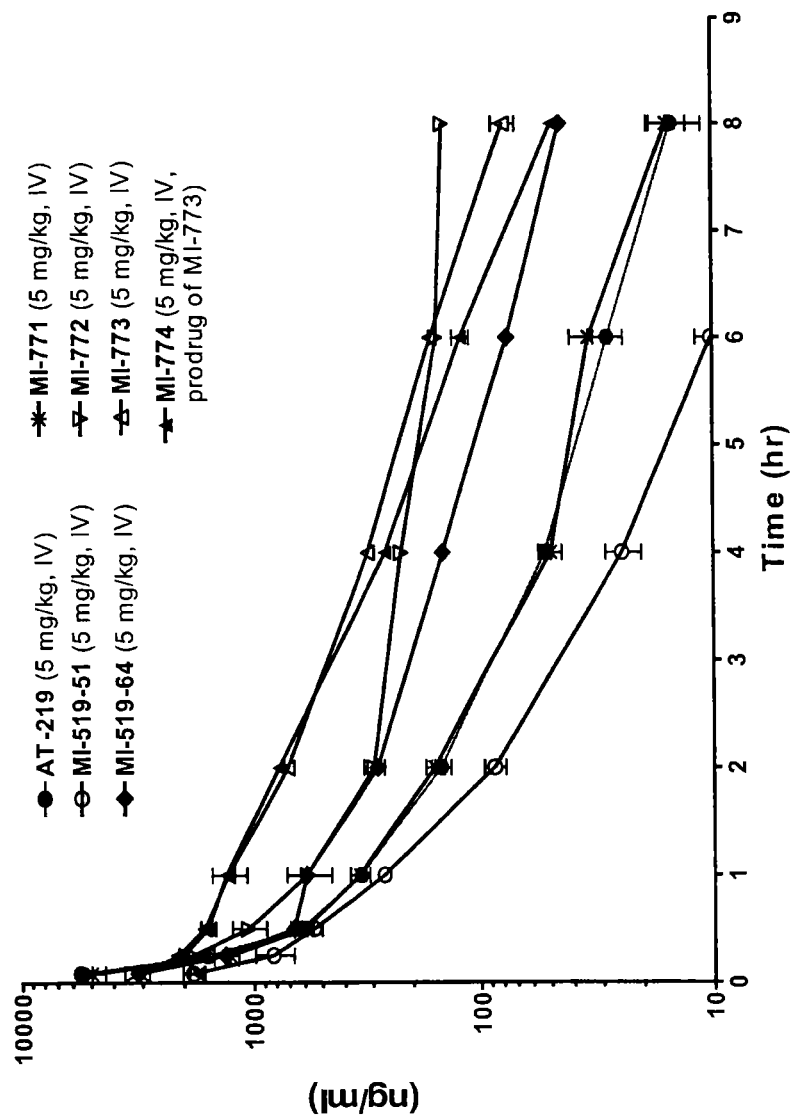
FIG. 5 is a line graph showing the plasma concentration vs. time curves following intravenous (IV) dosing of MDM2 inhibitors in rat.
Figure 6:
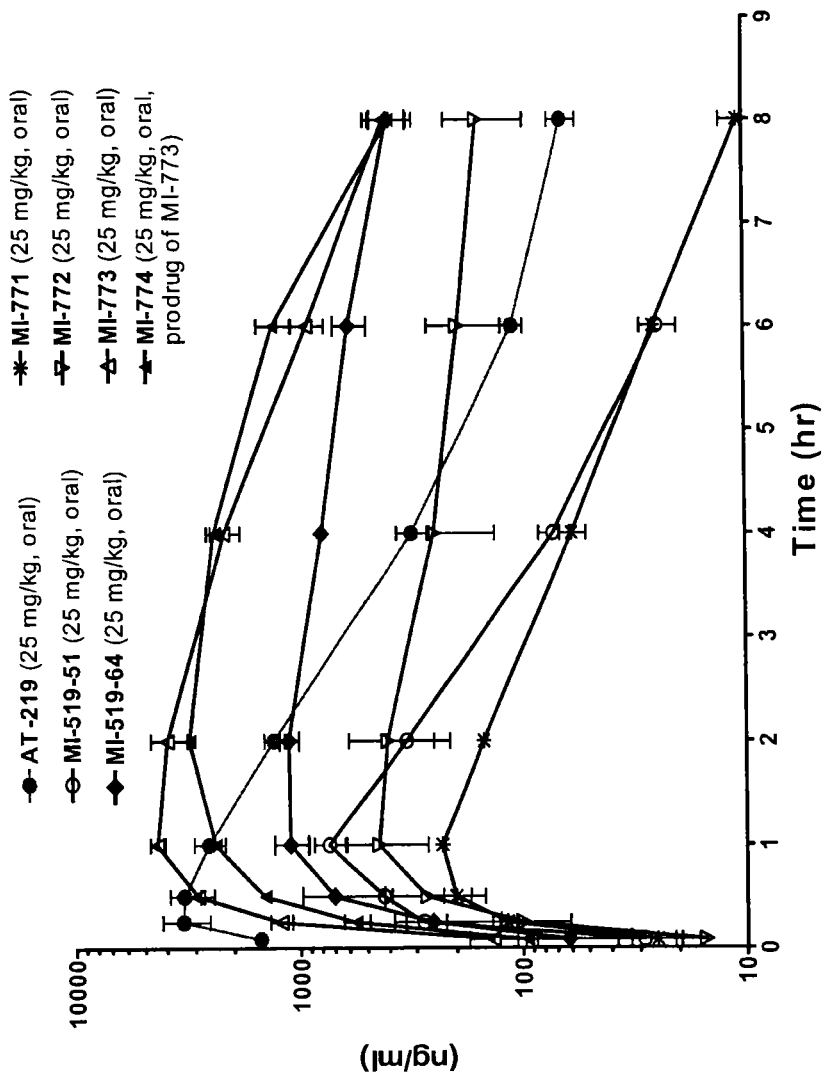
FIG. 6 is a line graph showing the plasma concentration vs. time curves following oral dosing of MDM2 inhibitors in rat.
Figure 7:
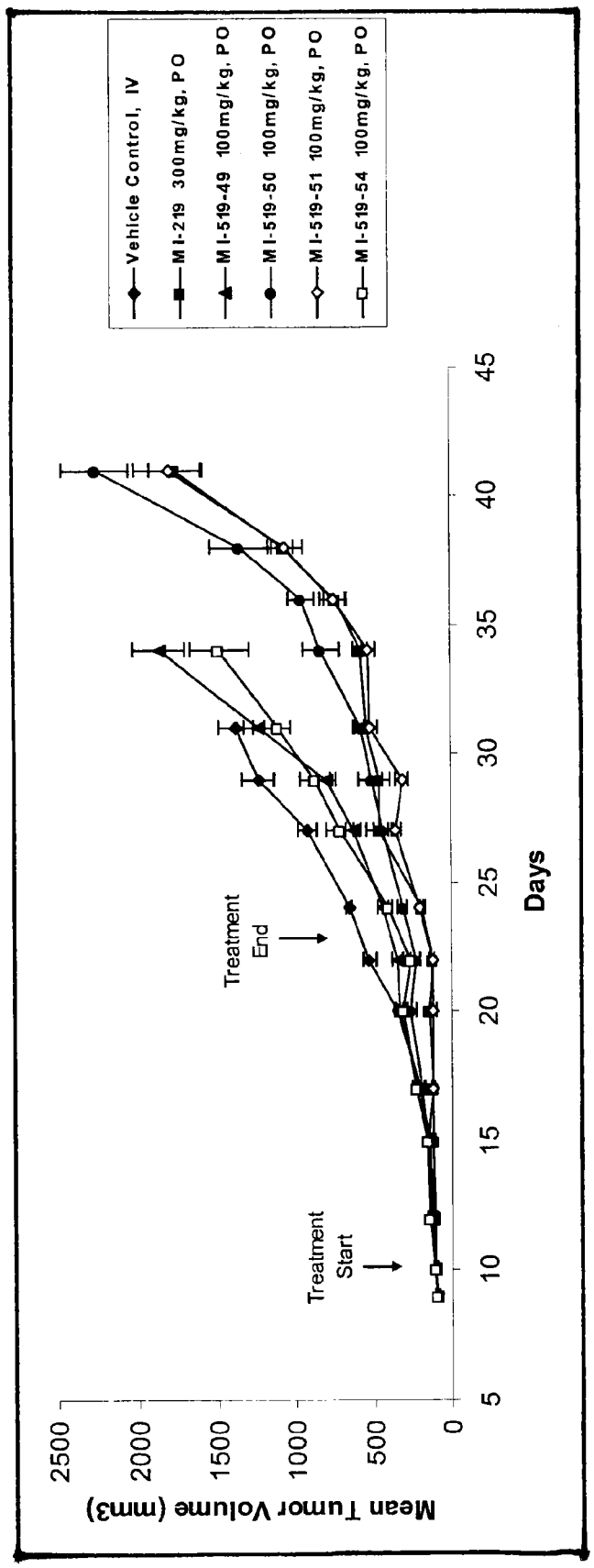
FIG. 7 is a line graph showing in vivo antitumor activity of MDM2 inhibitors in the SJSA-1 xenograft model in mice.
Figure 8:
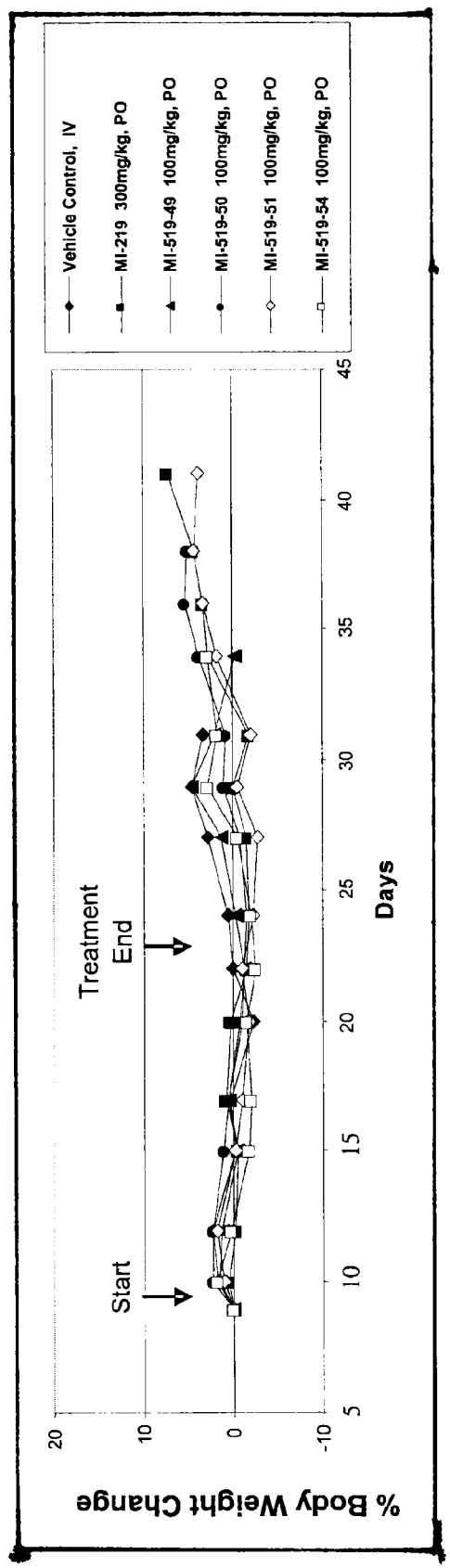
FIG. 8 is a line graph showing the animal weight following administration of MDM2 inhibitors in mice.
Figure 9:
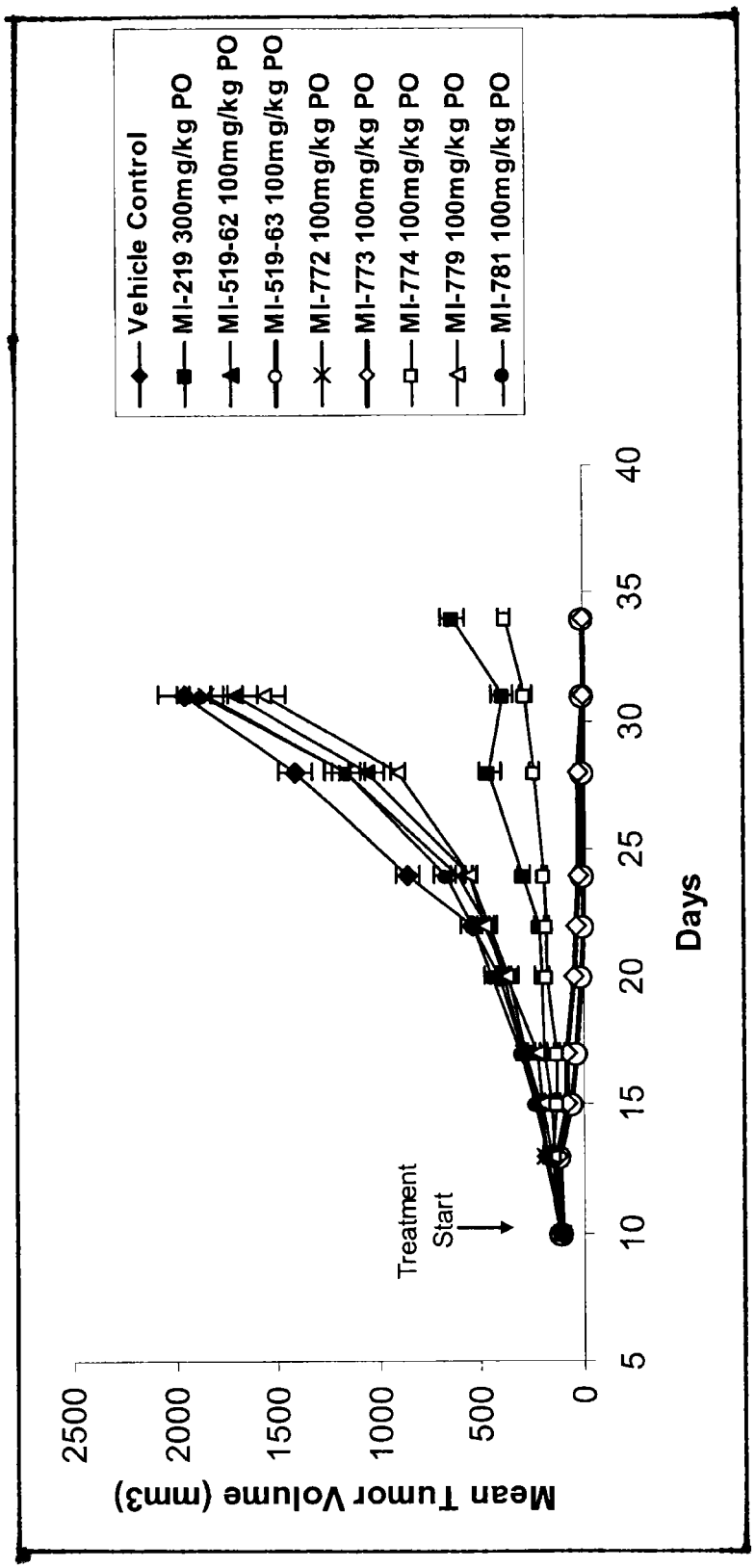
FIG. 9 is a line graph showing in vivo antitumor activity of MDM2 inhibitors in the SJSA-1 xenograft model in mice.
Figure 10:
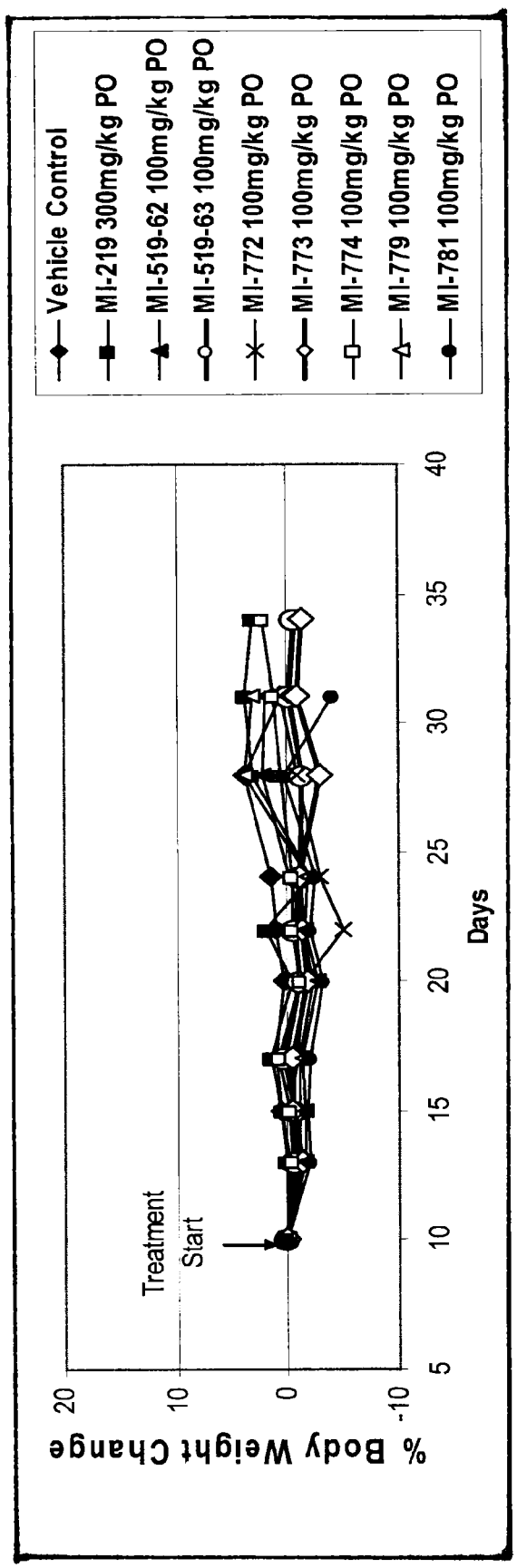
FIG. 10 is a line graph showing the animal weight following administration of MDM2 inhibitors in mice.
Figure 11:
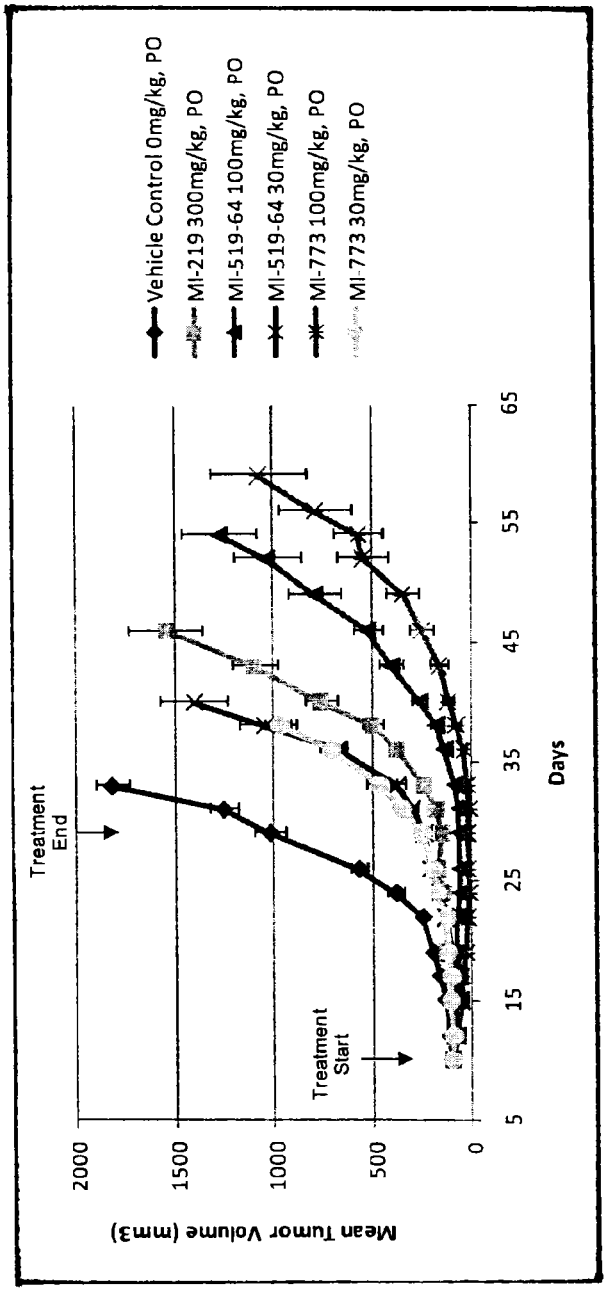
FIG. 11 is a line graph showing in vivo antitumor activity of MDM2 inhibitors in the SJSA-1 xenograft model in mice.
Figure 12:
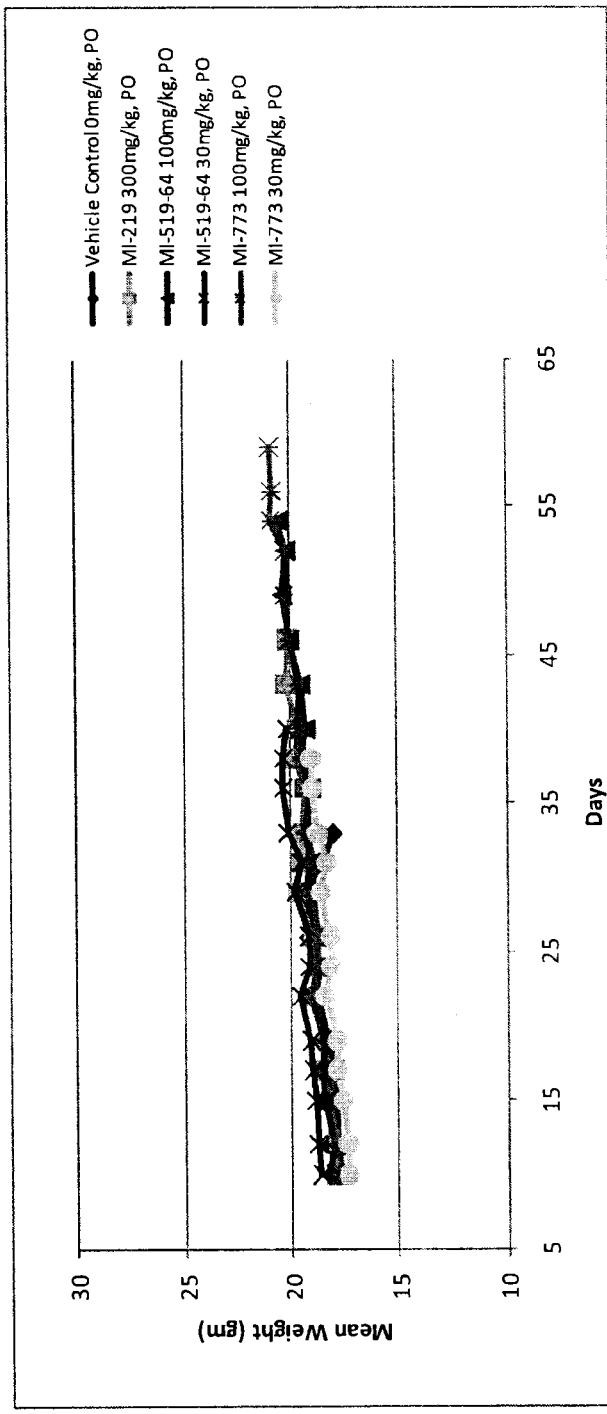
FIG. 12 is a line graph showing the animal weight following administration of MDM2 inhibitors in mice.
Figure 13A:
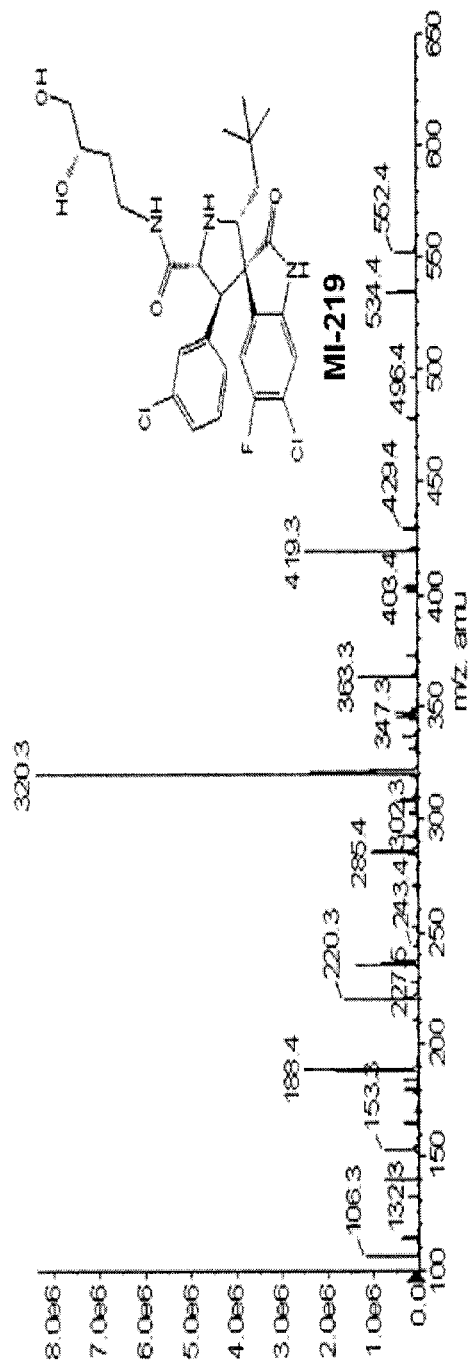
FIG. 13A-D are four MS/MS spectra of protonated MI-219, MI-142, MI-63 and MI-708B, respectively.
Figure 13B:
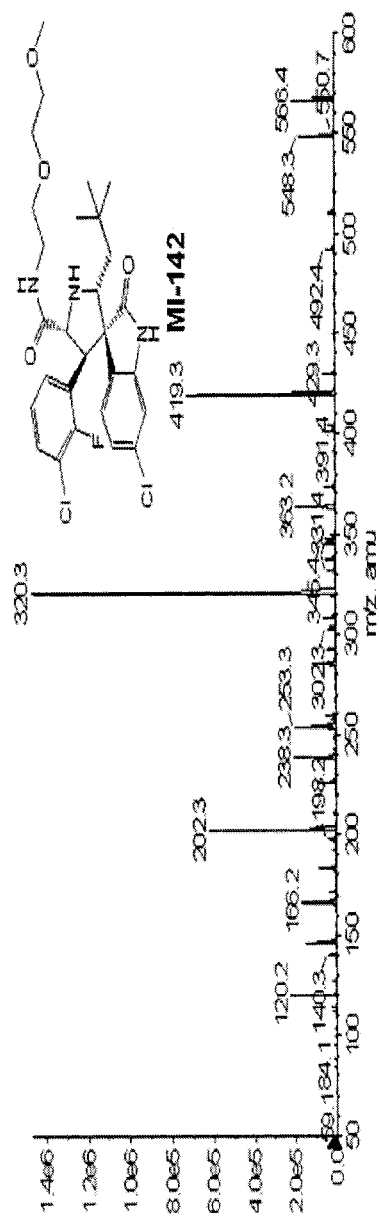
Figure 13C:
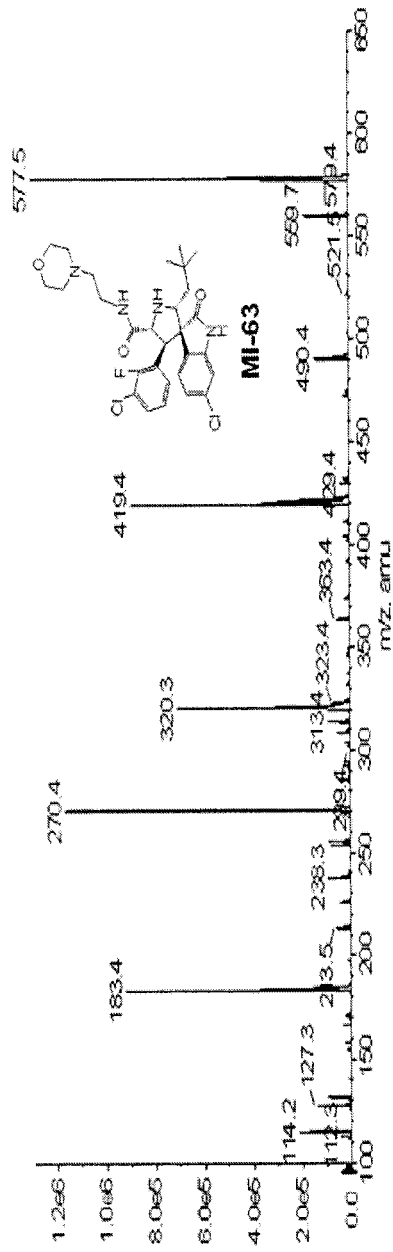
Figure 13D:
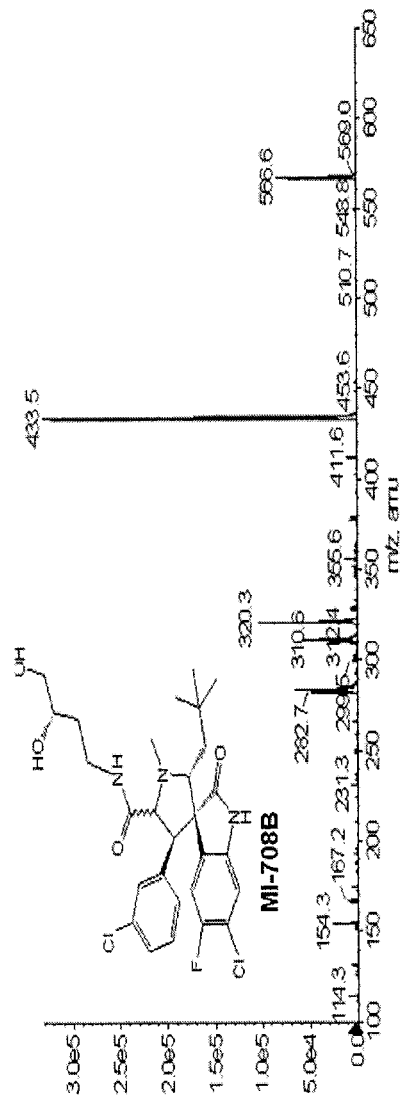

Pharmacokinetic studies on MDM2 inhibitors were carried out in rat. For comparison, the MDM2 inhibitor, AT-219, was also studied. As shown in FIGS. 5 and 6, and summarized in Tables 25 and 26, MDM2 inhibitors provided herein have promising ADME properties in rat. In particular, MI-773 displays high oral bioavailability; MI-772 displays a long plasma half-life. MI-774, the amino acid ester prodrug of MI-773, also has good oral bioavailability. Of note, in the pharmacokinetic evaluation of MI-774, the concentration of MI-773 was measured.

TABLE 25

IV dosing in rat. Plasma concentrations of the parent compound were measured with the exception of MI-774. MI-774 is an amino ester prodrug of MI-773. Accordingly, the plasma concentrations of MI-773 were measured for PK data of MI-774.

| Rat | Dosing (IV, mg/kg) | AUC (0 -> t) (µg/L * hr) | t½z (hr) | CLz (L/h/kg) | Vz (L/kg) |
|---|---|---|---|---|---|
| AT-219 | 5 | 2349 | 2.2 | 2.13 | 6.7 |
| MI-519-51 | 5 | 1110 | 1.2 | 4.5 | 7.5 |
| MI-771 | 5 | 2200 | 2.2 | 2.2 | 7.1 |
| MI-772 | 5 | 4577 | 7.4 | 1.0 | 10.9 |
| MI-773 | 5 | 4630 | 2.0 | 1.0 | 3.0 |
| MI-774 | 5 | 4195 | 1.6 | | |
| MI-519-64 | 5 | 2669 | 3.5 | 1.8 | 9.0 |

TABLE 26

Oral dosing in rat. Plasma concentrations of the parent compound were measured with the exception of MI-774. MI-774 is an amino ester prodrug of MI-773. Accordingly, the plasma concentrations of MI-773 were measured for PK data of MI-774.

| Rat | Dosing (oral, mg/kg) | AUC (0->t) (µg/L * hr) | t1/2 z (hr) | Tmax (hr) | Cmax (µg/L) | F (%) |
|---|---|---|---|---|---|---|
| AT-219 | 25 | 7677 ± 328 | 1.4 ± 0.1 | 0.6 ± 0.4 | 3752 ± 1068 | 65 ± 3 |
| MI-519-51 | 25 | 1463 ± 463 | 1.1 ± 0.1 | 1.0 ± 0.0 | 740 ± 219 | 26 ± 8 |
| MI-771 | 25 | 677 ± 41 | 1.6 ± 0.1 | 0.8 ± 0.3 | 241 ± 11 | 6.2 ± 0.4 |
| MI-772 | 25 | 3593 ± 2410 | 8.8 ± 4.2 | 1.0 ± 0.0 | 445 ± 311 | 16 ± 9 |
| MI-773 | 25 | 17230 ± 4330 | 1.6 ± 0.1 | 1.3 ± 0.6 | 4547 ± 809 | 75 ± 17 |
| MI-774 | 25 | 15115 ± 1303 | 1.5 ± 0.3 | 2.0 ± 0.0 | 3177 ± 142 | 75 ± 8 |
| MI-519-64 | 25 | 7742 ± 1317 | 3.3 ± 1.4 | 1.3 ± 0.6 | 1317 ± 82 | 56 ± 9 |

Example 8

In Vivo Efficacy Studies Using SJSA-1 Xenograft Model

SJSA-1 tumor cells were harvested with Trypsin (0.05%)-EDTA (0.53 mM) (GIBCO™, Invitrogen Corp.), growth medium added and cells placed on ice. A cell sample was mixed 1:1 with Trypan Blue (GIBCO™, Invitrogen Corp.) and counted on a hemocytometer to determine the number of live/dead cells. Cells were washed once with 1×PBS (GIBCO™, Invitrogen Corp.) and resuspended in PBS. For Matrigel injections, after washing in PBS, cells are resuspended in an ice cold mixture of 1:1 PBS and Matrigel (BD Biosciences, Invitrogen Corp.) for a final Matrigel protein concentration of 5 mg/ml. SJSA-1 tumors were inoculated into C.B-17 SCID mice at $5 \times 10^6$ cells in 0.1 ml with Matrigel. Cells were injected s.c. into the flank region of each mouse using a 27 gauge needle.

The size of tumors growing in the mice was measured in two dimensions using calipers. Tumor volume $(mm^3)=(A \times B^2)/2$ where A and B are the tumor length and width (in mm), respectively. During treatment, tumor volume and body weight was measured three times a week. After the treatment was stopped, tumor volume (FIGS. 7, 9, 11, and 36) and body weight (FIGS. 8, 10, 12, and 37) was measured at least once a week. Mice were kept for an additional 60 days for further observation of tumor growth and toxicity.

Before treatment began, tumors were allowed to grow to 60-140 $mm^3$ in volume, at which point the blood vessel supplies to the tumor should have been established. Mice with tumors within acceptable size range were randomized into treatment groups of 8 mice for experimental compounds and 10 mice for the Control group. Experimental compounds were given orally, once per day for 2-3 weeks. The Control group received vehicle alone (10% PEG 400: 3% Cremophor: 87% PBS). Statistical analyses of the in vivo efficacy of MDM2 inhibitors on SJSA-1 tumors are presented in Tables 27-29.

These data indicate good in vivo efficacy for certain MDM2 inhibitors of the disclosure, particularly MI-519-63, MI-773 and MI-519-64, without significant weight loss in the animals.

TABLE 27

| Exp. No. 1 PO dose | % Tumor Growth Inhib. T/C Control 750 mm³ D27 | t-test P value Control vs: End of Treatment D24 | t-test P value Control vs: Control 750 mm³ D27 |
|---|---|---|---|
| MI-219 300 mg/kg | 44.3% | <0.0001 | 0.0004 |
| MI-519-49 100 mg/kg | 63.8% | <0.0001 | 0.0028 |
| MI-519-50 100 mg/kg | 41.1% | <0.0001 | <0.0001 |
| MI-519-51 100 mg/kg | 34.0% | <0.0001 | <0.0001 |

TABLE 28

| Exp. No. 2 PO dose | % Tumor Growth Inhib. T/C Control 750 mm³ D24 | t-test P value Control vs: End of Treatment D31 | t-test P value Control vs: Control 750 mm³ D24 |
|---|---|---|---|
| MI-219 300 mg/kg | 30.1% | <0.0001 | <0.0001 |
| MI-519-62 100 mg/kg | 59.5% | 0.2122 | 0.0015 |
| MI-519-63 100 mg/kg | 0.0% | <0.0001 | <0.0001 |
| MI-772 100 mg/kg | 71.1% | 0.5673 | 0.0093 |
| MI-773 100 mgkg | 3.2% | <0.0001 | <0.0001 |
| MI-774 100 mg/kg | 21.4% | <0.0001 | <0.0001 |
| MI-779 100 mg/kg | 66.1% | 0.0487 | 0.0015 |
| MI-781 100 mg/kg | 75.5% | 0.6687 | 0.0554 |

TABLE 29

| Exp. No. 3 PO dose | % Tumor Growth Inhib. T/C Control 750 mm³ D29 | t-test P value Control vs: End of Treatment D31 | t-test P value Control v/s: Control 750 mm³ D29 |
|---|---|---|---|
| MI-219 300 mg/kg | 15.8% | <0.0001 | <0.0001 |
| MI-519-64 100 mg/kg | 5.3% | <0.0001 | <0.0001 |
| MI-519-64 30 mg/kg | 20.7% | <0.0001 | <0.0001 |
| MI-773 100 mg/kg | 1.2% | <0.0001 | <0.0001 |
| MI-773 30 mg/kg | 24.3% | <0.0001 | <0.0001 |

Example 9

Synthesis of MI-519-64 and MI-519-65

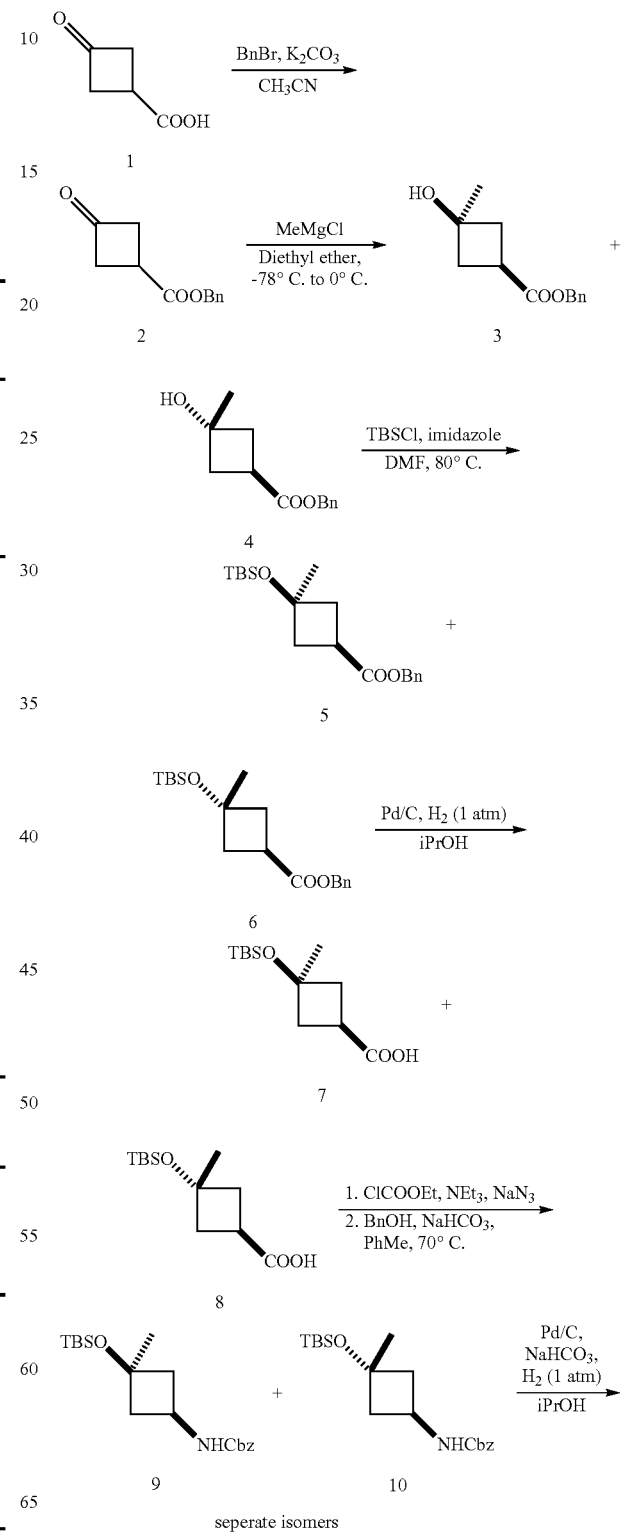

Scheme 6 seperate isomers

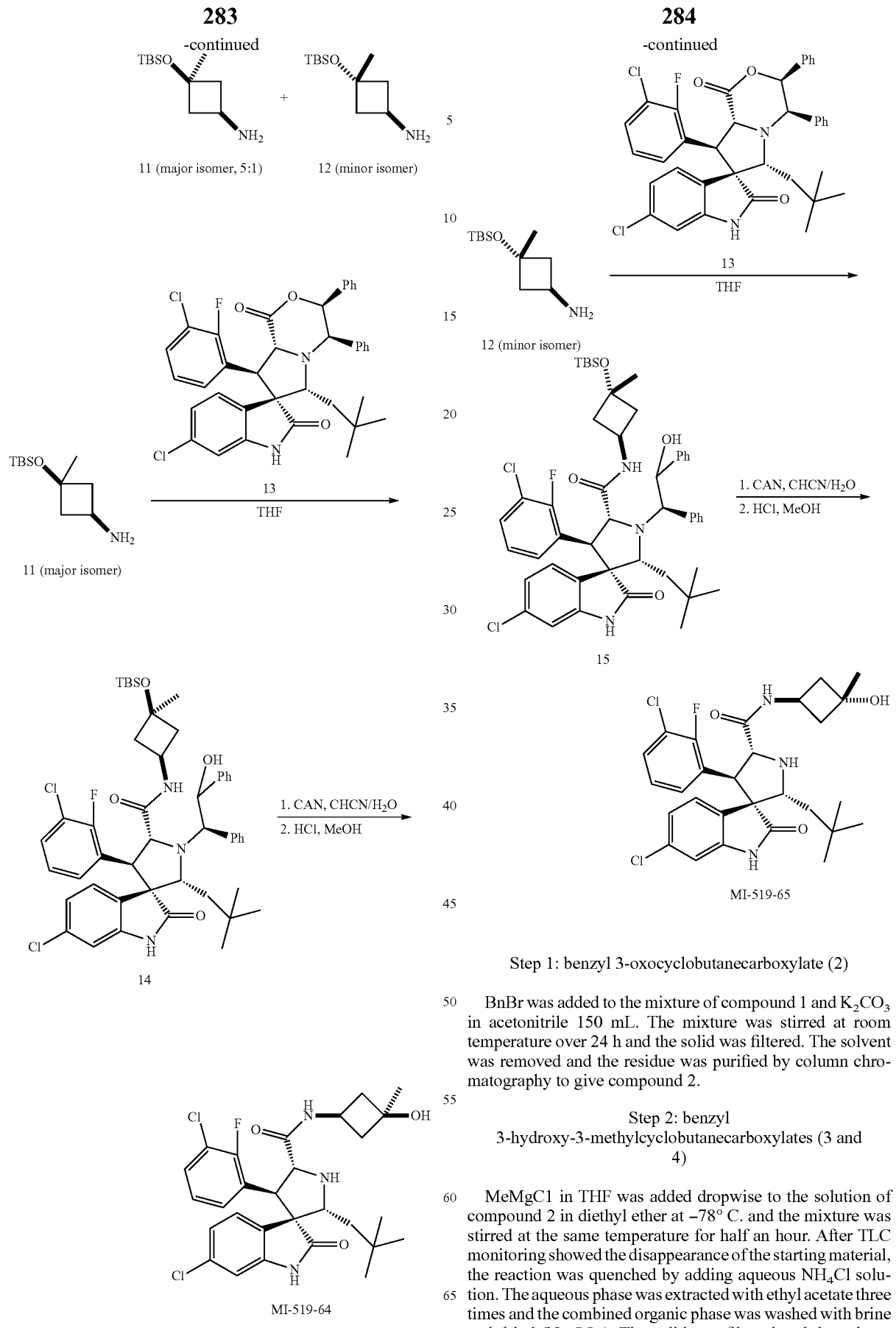

Step 1: benzyl 3-oxocyclobutanecarboxylate (2)

BnBr was added to the mixture of compound 1 and K₂CO₃ in acetonitrile 150 mL. The mixture was stirred at room temperature over 24 h and the solid was filtered. The solvent was removed and the residue was purified by column chromatography to give compound 2.

Step 2: benzyl 3-hydroxy-3-methylcyclobutanecarboxylates (3 and 4)

MeMgCl in THF was added dropwise to the solution of compound 2 in diethyl ether at −78° C. and the mixture was stirred at the same temperature for half an hour. After TLC monitoring showed the disappearance of the starting material, the reaction was quenched by adding aqueous NH₄Cl solution. The aqueous phase was extracted with ethyl acetate three times and the combined organic phase was washed with brine and dried (Na₂SO₄). The solid was filtered and the solvent was removed. The residue was purified by column chromatography to give compounds 3 and 4 (5:1 based on TLC analysis).

Step 3: benzyl 3-(tert-butyldimethylsilyloxy)-3-methylcyclobutane carboxylates (5 and 6)

To the mixture of compounds 3 and 4 in DMF (10 mL) was added immidazole and TBSC1, and the resulting mixture was stirred at 80° C. for 30 h. After cooling to room temperature, water was added and the aqueous phase was extracted with ethyl acetate three times. The combined organic phase was washed with brine and dried ($Na_2SO_4$). The solid was filtered and the solvent was removed. The residue was purified by column chromatography to get compounds 5 and 6.

Step 4: 3-(tert-butyldimethylsilyloxy)-3-methylcyclobutanecarboxylic acids (7 and 8)

To the mixture of compounds 5 and 6 in isopropanol was added Pd/C. The resulting mixture was stirred under 1 atm hydrogen for 1 h. TLC showed the disappearance of the starting material and the solid was filtered. The solvent was removed to give compounds 7 and 8.

Step 5: benzyl-3-(tert-butyldimethylsilyloxy)-3-methylcyclobutylcarbamates 9 and 10

To a 0° C. stirring solution of compounds 7 and 8 and $Et_3N$ in acetone was added ClCOOEt dropwise. The resulting mixture was stirred at 0° C. for 30 min. A solution $NaN_3$ in water was added, and the resulting mixture was stirred at 0° C. for an additional 20 min. Water was added, and the aqueous phase was extracted with ethyl acetate three times. The combined organic phase was washed with brine and dried ($Na_2SO_4$). The solvent was removed and the residue was dissolved in toluene. Benzyl alcohol and $NaHCO_3$ were added. The resulting mixture was stirred at 80° C. for 2 h. All the solvent was removed and the residue was purified by column chromatography to obtain two isomers 9 and 10 in a 5:1 ratio.

Step 6: 3-(tert-butyldimethylsilyloxy)-3-methylcyclobutanamine (11)

To a mixture of the major isomer 9 and $NaHCO_3$ in isopropanol was added Pd/C and the resulting mixture was stirred under 1 atm hydrogen for 1 h. The solid was filtered and the solvent was removed to give compound 11.

Step 7: 3-(tert-butyldimethylsilyloxy)-3-methylcyclobutanamine (12)

To a mixture of the minor isomer 10 and $NaHCO_3$ in isopropanol was added Pd/C and the resulting mixture was stirred under 1 atm hydrogen for 1 h. The solid was filtered and the solvent was removed to give compound 12.

Step 8: MI-519-64

To a solution of compound 11 in THF was added compound 13 and the resulting solution was stirred overnight. The solvent was removed and the residue thus obtained was dissolved in $CH_3CN/H_2O$ (1:1). CAN was added and the reaction mixture was stirred for 30 min. Water was added and the aqueous phase was extracted with ethyl acetate three times. The combined organic layers were dried ($Na_2SO_4$), filtered, and concentrated. The residue was purified by column chromatography on silica gel to give compound 14. Compound 14 was dissolved in methanol, 12M HCl in water was added, and the reaction mixture was stirred for 1 h at room temperature. The solvent was removed and the residue was purified by HPLC to give MI-519-64 as the TFA salt. $^1$H NMR (300 MHz, $CD_3OD$) δ 7.54-7.52 (m, 1H), 7.42-7.38 (m, 1H), 7.23-7.18 (m, 1H), 6.88-6.75 (m, 3H), 5.04 (d, J=9.9 Hz, 1H), 4.45 (d, J=9.9 Hz, 1H), 4.19-4.16 (m, 1H), 3.92-3.89 (m, 1H), 2.42-2.11 (m, 2H), 2.10-1.87 (m, 3H), 1.32-1.24 (m, 4H), 0.82 (s, 9H); MS (ESI) m/z 548 [M+H]$^+$.

Step 9: MI-519-65

To a solution of compound 12 in THF was added compound 13 and the resulting solution was stirred overnight. The solvent was removed and the residue was dissolved in $CH_3CN/H_2O$ (1:1). CAN was added and the reaction mixture was stirred for 30 min. Water was added and the aqueous phase was extracted with ethyl acetate three times. The combined organic layers were dried ($Na_2SO_4$), filtered, and concentrated. The residue was purified by column chromatography on silica gel to give compound 15. Compound 15 was dissolved in methanol, 12M HCl in water was added, and the reaction mixture was stirred for 1 h at room temperature. The solvent was removed and the residue was purified by HPLC to give MI-519-65 as the TFA salt. $^1$H NMR (300 MHz, $CD_3OD$) δ 7.50 (m, 1H), 7.44-7.38 (m, 1H), 7.24-7.20 (m, 1H), 6.89-6.88 (m, 1H), 6.80 (m, 1H), 6.71 (m, 1H), 4.91-4.88 (m, 1H), 4.40-4.36 (m, 2H), 4.10-4.06 (m, 1H), 2.41-2.33 (m, 2H), 2.07-1.87 (m, 3H), 1.25-1.21 (m, 4H), 0.82 (s, 9H); MS (ESI) m/z 548 [M+H]$^+$.

Example 11

Synthesis of MI-519-6401

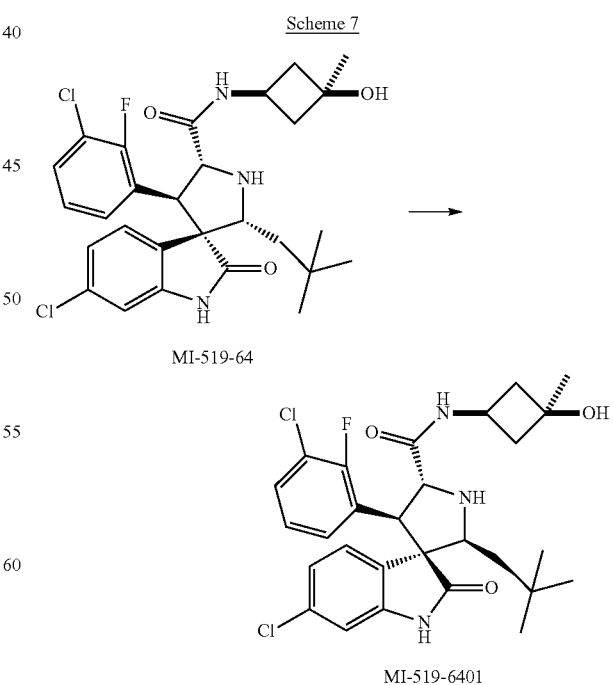

with magnetic stirring bar. Acetonitrile (20 mL) was added to fully dissolve the compound and deionized water (7 to 10 mL) was added. NaHCO$_3$ saturated aqueous solution (ca 0.5 mL) was then added to adjust the pH value between 7 and 8. This solution was allowed to stir at room temperature for at least 12 h. TFA (0.1 mL) and another 10 mL of deionized water were added to the solution and the solution was purified by semi-preparative RP-HPLC immediately using acetonitrile and water as the eluents to give MI-519-6401 as the TFA salt. $^1$H NMR (300 MHz, MeOH-d4): 7.62-7.53 (m, 2H), 7.45-7.35 (m, 1H), 7.20-7.10 (m, 2H), 6.80-6.85 (m, 1H), 5.11 (d, J=11.07 Hz, 1H), 4.57 (d, J=11.11 Hz, 1H), 4.40 (d, J=7.39 Hz, 1H), 4.00-3.80 (m, 1H), 2.50-2.35 (m, 1H), 2.35-2.20 (m, 1H), 2.10-1.90 (m, 1H), 1.90-1.60 (m, 2H), 1.30 (s, 3H), 1.20-1.05 (m, 1H), 0.88 (s, 9H); $^{13}$C NMR (75 MHz, MeOH-d4): 177.8, 168.0, 157.6 (d, J$_{C-F}$=249 Hz), 144.9, 136.8, 132.2, 128.5, 126.5, 126.3 (d, J$_{C-F}$=4.76), 123.9, 123.7, 122.3 (d, J$_{C-F}$=18.97 Hz), 122.0 (d, J$_{C-F}$=13.1 Hz), 111.8, 67.1, 64.6, 64.5, 62.9, 49.0, 45.5, 45.4, 43.3, 38.0, 30.8, 29.5, 27.3; ESI-MS calculated for C$_{28}$H$_{33}$$^{35}$Cl$_2$FN$_3$O$_3$ [M+H]$^+$: 548.1883, Found: 548.25.

Figure 20:
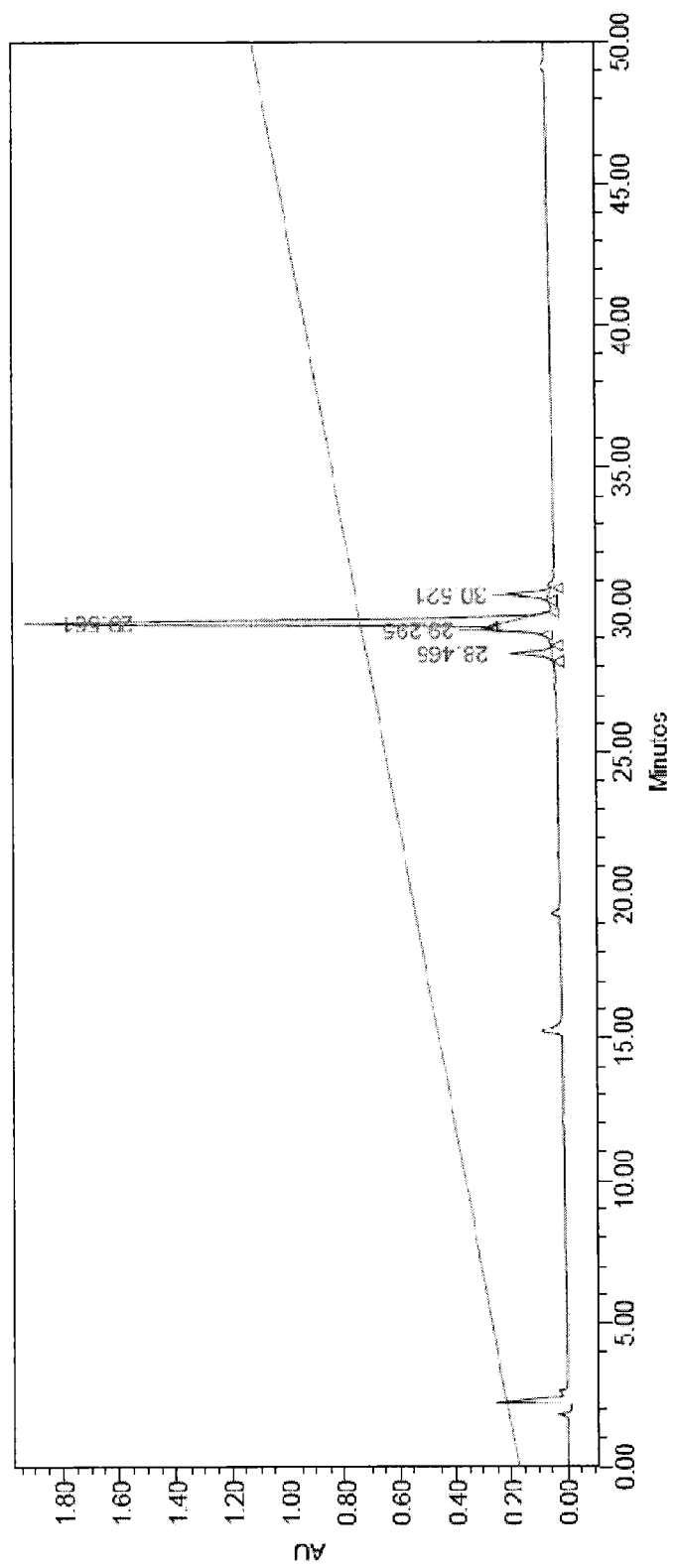
FIG. 20 is a reverse phase HPLC chromatogram of MI-519-64 after isolation by column chromatography on silica gel.
Figure 21:
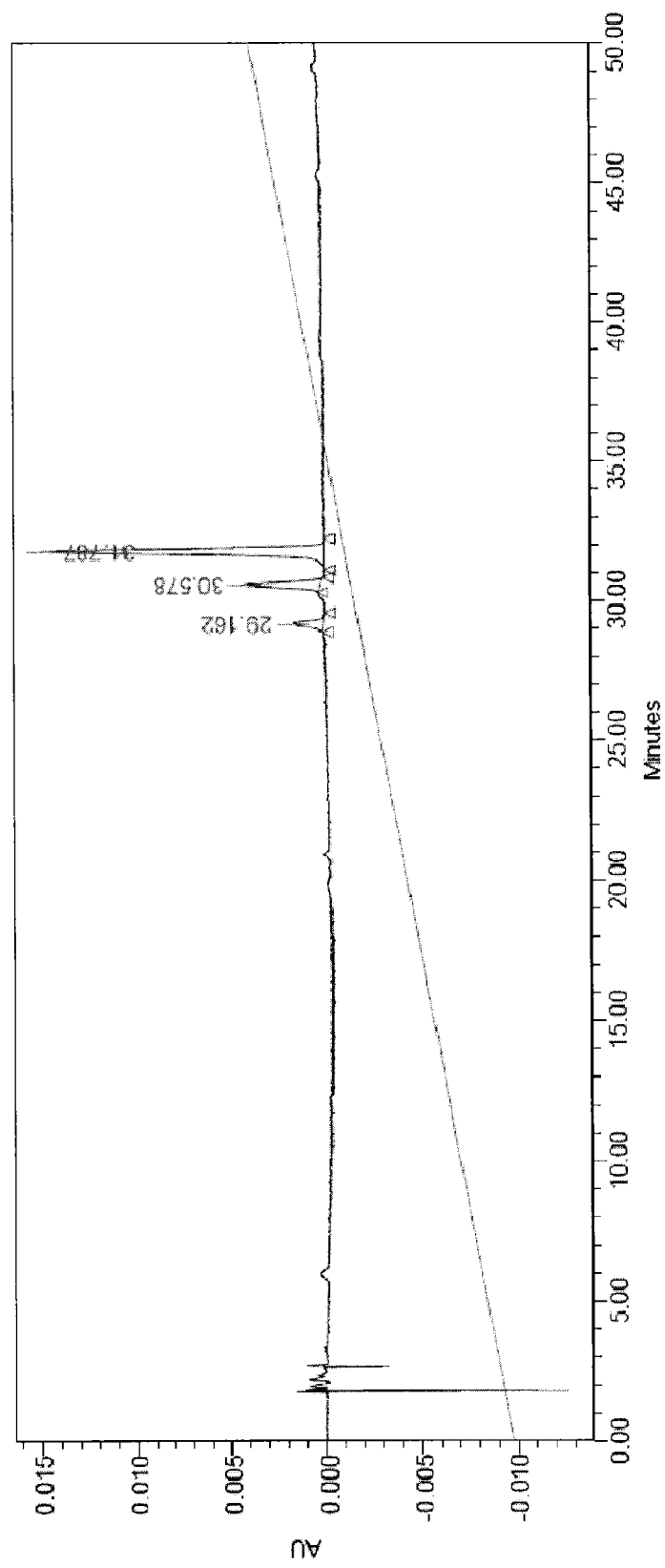
FIG. 21 is reverse phase HPLC chromatogram of MI-519-64 after treatment with acetonitrile/water for 12 h. Three isomers are present. MI-519-64 and MI-519-6401 correspond to RP-HPLC peaks at 30.578 minutes, and 31.787 minutes, respectively. The isomer eluting at 29.162 minutes has not been fully characterized (referred to as MI-519-6402).
Figure 22:
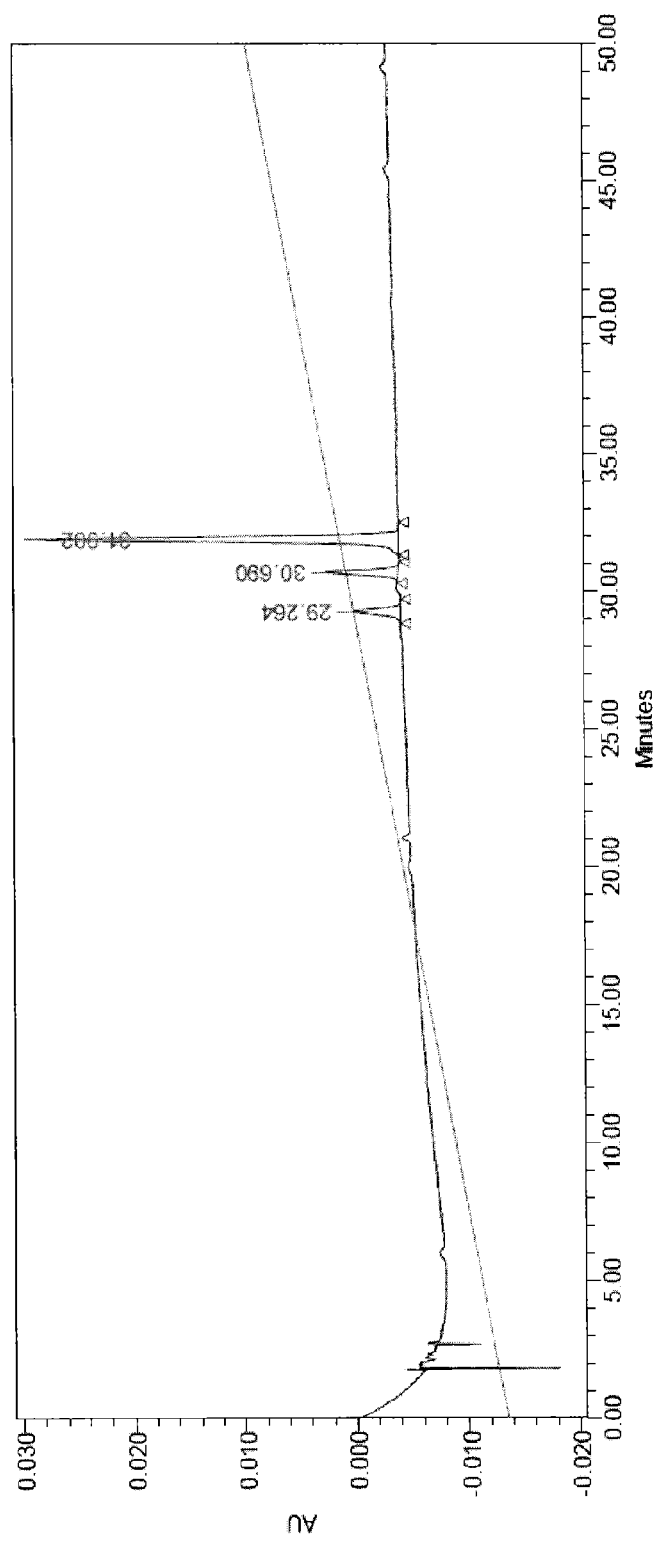
FIG. 22 is reverse phase HPLC chromatogram of MI-519-64 after treatment with acetonitrile/water for 3 days.

Analytical RP-HPLC spectra are presented in FIGS. 20-22. Referring to FIG. 21, MI-519-6401 corresponds to the RP-HPLC peak at 31.787 minutes.

In an alternate procedure, MI-519-64 (100 mg) purified by flash chromatography on silica gel was placed in a 50 mL round-bottom-flask equipped with magnetic stirring bar. Methanol (20 mL) was added to fully dissolve the compound and deionized water (10 to 20 mL) was added. NaHCO$_3$ saturated aqueous solution (ca 0.5 mL) was then added to adjust the pH value between 7 and 8. This solution was allowed to stir at room temperature for at least 12 h. TFA (0.1 mL) and another 10 mL of deionized water were added to the solution and the solution was purified by semi-preparative RP-HPLC immediately using acetonitrile and water as the eluents to give MI-519-6401 as the TFA salt.

C02701, C02901, C03001, C03401, C03701, and C04801 of Example 1 were prepared using procedures similar to that used to prepare MI-519-6401.

Example 11

Synthesis of MI-758

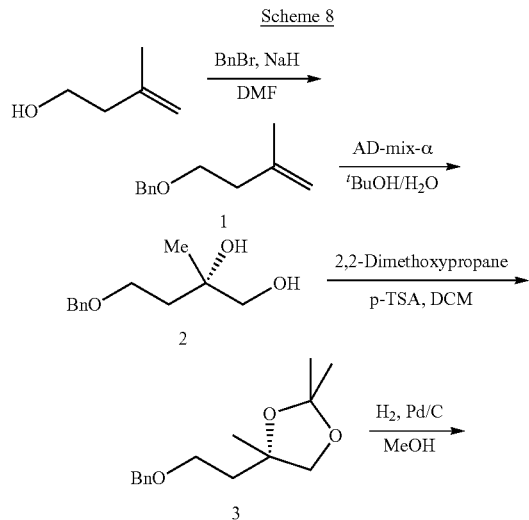

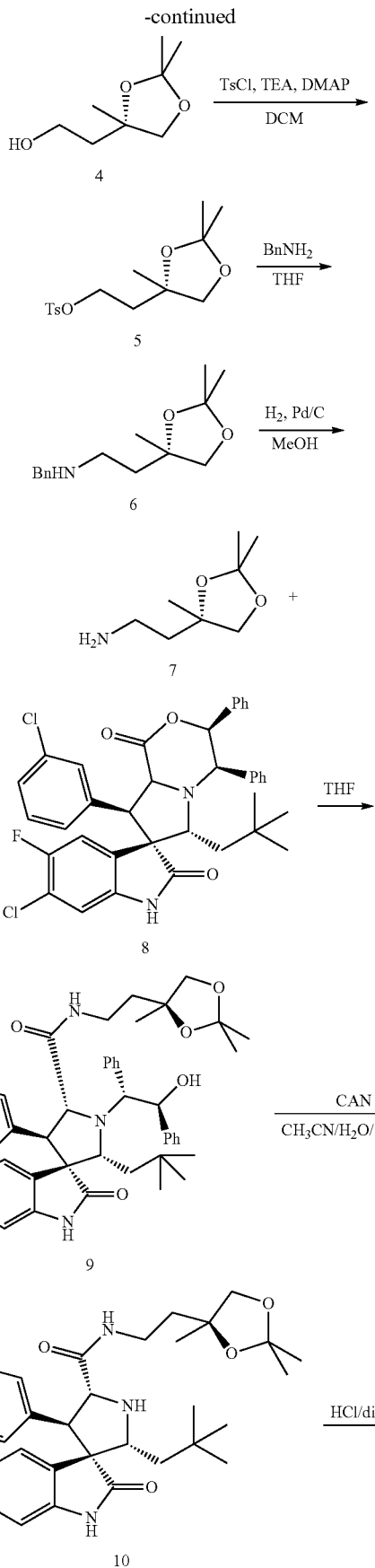

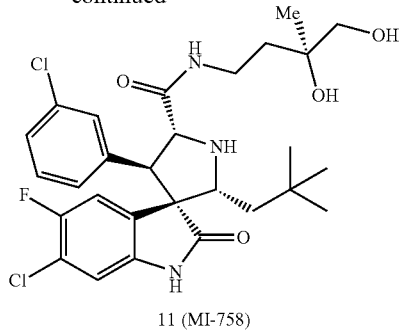

11 (MI-758)

Step 1: ((3-methylbut-3-enyloxy)methyl)benzene (1)

BnBr was added to the mixture of alcohol and NaH in DMF cooled in an ice bath. The mixture was stirred at room temperature overnight and the solid was filtered. The solvent was removed and the residue was purified by column chromatography to give compound 1.

Step 2: (S)-4-(benzyloxy)-2-methylbutane-1,2-diol (2)

Compound 1 was added to a solution of AD-mix-α in tBuOH/H$_2$O (1:1) cooled in an ice bath. After TCL monitoring showed the disappearance of the starting material, the reaction was quenched by adding Na$_2$SO$_3$. The aqueous phase was extracted with ethyl acetate three times and the combined organic phase was washed with brine and dried (Na$_2$SO$_4$). The solid was filtered and the solvent was removed. The residue was purified by column chromatography to give compound 2.

Step 3: (S)-4-(2-(benzyloxy)ethyl)-2,2,4-trimethyl-1,3-dioxolane (3)

To the mixture of compound 2 and 2,2-dimethoxypropane in DCM was added p-TSA. After TLC monitoring showed the disappearance of the starting material, aqueous NaHCO$_3$ solution was added and then extracted with ethyl acetate three times. The combined organic phase was washed with brine and dried (Na$_2$SO$_4$). The solid was filtered and the solvent was removed. The residue was purified by column chromatography to give compound 3.

Step 4: (S)-2-(2,2,4-trimethyl-1,3-dioxolan-4-yl) ethanol (4)

To a solution of 3 in MeOH was added Pd/C. The resulting mixture was stirred under 1 atm hydrogen overnight. TLC showed the disappearance of the starting material and the solid was filtered. The solvent was removed to give compound 4.

Step 5: (S)-2-(2,2,4-trimethyl-1,3-dioxolan-4-yl) ethyl 4-methylbenzene sulfonate (5)

To a solution of compound 4 and Et$_3$N in DCM was added TsCl dropwise. The resulting mixture was stirred at 0° C. for 30 min. The solid was filtered and the solvent was removed. The residue was purified by column chromatography to give compound 5.

Step 6: (S)—N-benzyl-2-(2,2,4-trimethyl-1,3-dioxolan-4-yl) ethanamine (6)

A solution of 5 and BnNH$_2$ in THF was heated to reflux overnight. The solvent was removed. The residue was purified by column chromatography to give compound 6.

Step 7: (S)-2-(2,2,4-trimethyl-1,3-dioxolan-4-yl) ethanamine (7)

To a solution of 6 in MeOH was added Pd/C. The resulting mixture was stirred under 1 atm hydrogen overnight. TLC showed the disappearance of the starting material and the solid was filtered. The solvent was removed to give compound 7.

Step 8: MI-758 (11)

To a solution of compound 7 in THF was added compound 8 and the resulting solution was stirred overnight. The solvent was removed and the residue was dissolved in CH$_3$CN/H$_2$O (1:1). CAN was added and the reaction mixture was stirred for 5 min. K$_2$CO$_3$ was added and the aqueous phase was extracted with ethyl acetate three times. The combined organic layers were dried (Na$_2$SO$_4$), filtered, and concentrated. The residue was purified by column chromatography on silica gel to give compound 11. Compound 11 was dissolved in dioxane, 4M HCl in dioxane was added, and the reaction mixture was stirred for 0.5 h at room temperature. The solvent was removed and the residue was purified by HPLC to give MI-758 as the TFA salt. $^1$H NMR (300 MHz, CD$_3$OD) δ 8.44 (s, 1H), 7.72 (d, J=8.4 Hz, 1H), 7.19-7.36 (m, 3H), 7.09 (d, J=7.5 Hz, 1H), 6.89 (d, J=6.0 Hz, 1H), 5.28 (d, J=11.1 Hz, 1H), 4.50 (d, J=6.6 Hz, 1H), 4.16 (d, J=11.1 Hz, 1H), 3.30 (s, 2H), 1.94 (dd, J=8.4, 15.3 Hz, 1H), 1.47-1.68 (m, 2H), 1.18 (d, J=15.6 Hz, 1H), 1.07 (s, 3H), 0.93 (s, 9H).

Example 12

Synthesis of MI-773

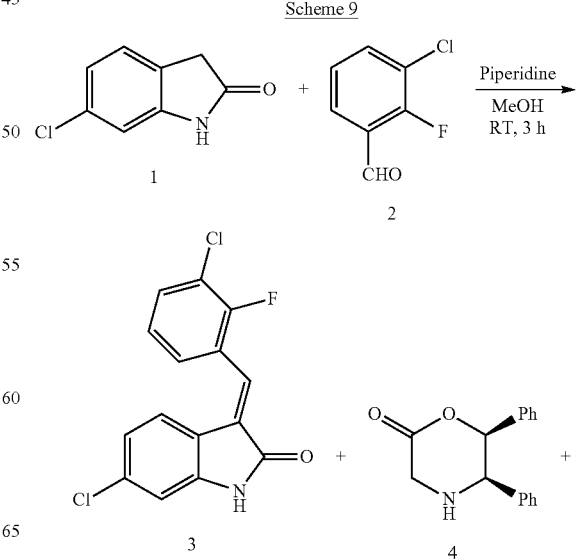

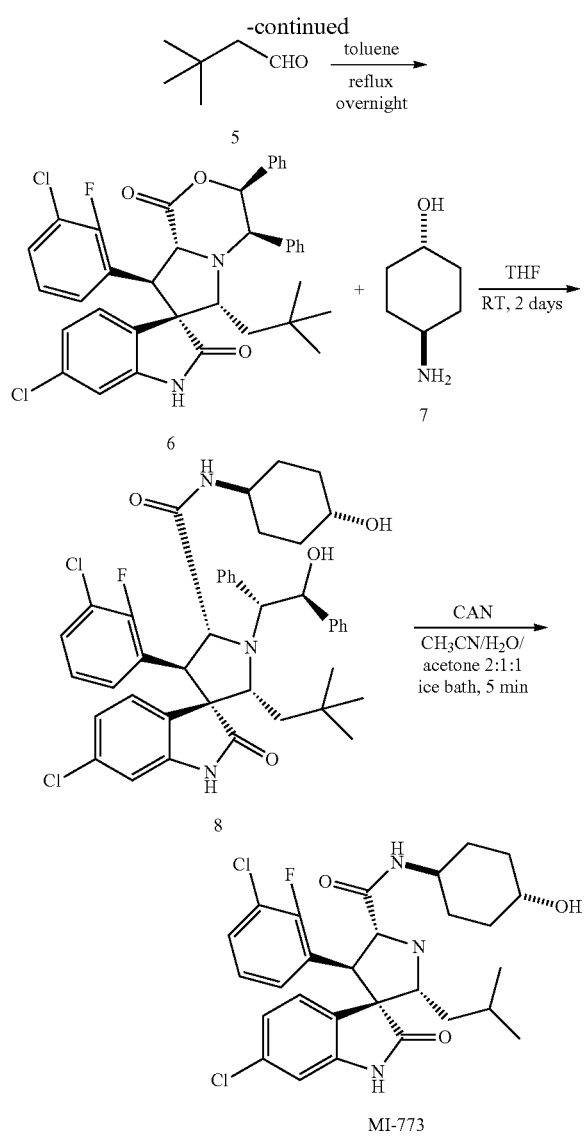

Step 4

To an ice-bath cooled solution of compound 8 (800 mg, 1.05 mmol) in CH$_3$CN (8 ml), H$_2$O (4 ml) and acetone (4 ml) was added CAN (ammonium cerium) (1.15 g, 2.1 mmol). Progress of the reaction was monitored by TLC. When all the starting material disappeared (around 5 min), 100 mg of NaHCO$_3$ powder was added and the reaction mixture was diluted with 50 mL of ethyl acetate. The organic phase was dried over anhydrous Na$_2$SO$_4$, filtered, and concentrated. The residue was purified by silica gel flash column chromatography (methylene chloride/methanol/triethylamine=200:1:1 to 200:10:1) to give (2'R,3S,4'S,5R)-6-chloro-4'-(3-chloro-2-fluorophenyl)-N-((trans-4-hydroxycyclohexyl)-2'-neopentyl-2-oxospiro[indoline-3,3'-pyrrolidine]-5'-carboxamide (MI-773) (402 mg, 68% yield). The absolute stereochemical configuration of MI-773 was determined by x-ray analysis.

MI-773 was dissolved in DCM and added TFA and then evaporated. The residue was further purified by chromatography on a C18 reverse phase semi-preparative HPLC column with solvent A (0.1% of TFA in water) and solvent B (0.1% of TFA in methanol) as eluents (gradient: 45% of solvent A and 55% of solvent B to 30% of solvent A and 70% of solvent B in 30 min) to give MI-773 as the TFA salt. NMR for MI-773 TFA: $^1$H NMR (300 MHz, CD$_3$OD) δ 7.47 (t, J=7.0 Hz, 1H), 7.34 (t, J=7.4 Hz, 1H), 7.14 (t, J=7.9 Hz, 1H), 6.83 (s, 1H), 6.80 (s, 2H), 4.39 (d, J=10.0 Hz, 1H), 4.15-4.05 (m, 1H), 3.72-3.53 (m, 1H), 3.53-3.85 (m, 2H), 2.10-1.75 (m, 4H), 1.62 (d, J=12.2 Hz, 1H), 1.45-1.05 (m, 5H), 0.78 (s, 9H).

Figure 25:
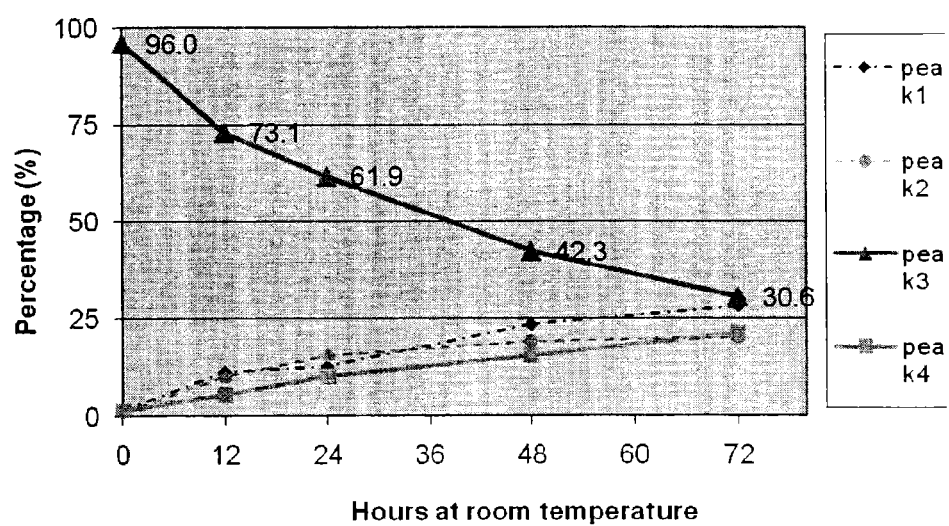
FIG. 25 is a line graph showing the stability of MI-773 (TFA salt) at various time points. The compounds corresponding to peaks 1 and 2 have not been fully characterized. The compound corresponding to peak 3 is MI-77301.

Stability of MI-773 (TFA salt): MI-773 (TFA salt) was dissolved in a water/methanol mixture (water/methanol=1:1 with 0.1% of TFA). The solution was allowed to stand at room temperature. The purity was tested using a C18 reverse phase analytical HPLC column at the time points of 0, 12 h, 24 h, 48 h, and 72 h. The results showed transformation of MI-773 to three compounds having the same molecular weight (FIG. 25). The purity of an identical sample solution stored at 4° C. was also tested at 0 and 36 h. The results showed comparably slow transformation of MI-773 at 4° C.

Example 14

Synthesis of MI-77301

Scheme 10

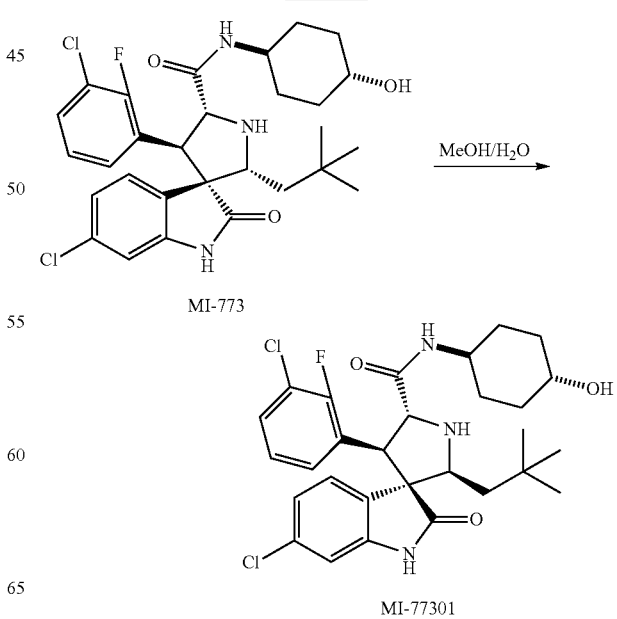

Step 1

To a stirred solution of oxindole 1 (4.19 g, 25 mmol) in methanol (50 mL) was added aldehyde 2 (3.96 g, 25 mmol) and piperidine (2.45 mL, 25 mmol). The reaction mixture was stirred at room temperature for 3 h and the yellow precipitate was collected, washed successively with methanol, hexanes, and ethyl ether and dried to give compound 3 (6.25 g, 81% yield).

Step 2

To a solution of compound 3 (6.25 g, 21 mmol) in toluene (75 ml) was added compound 4 (5.43 g, 21 mmol), compound 5 (2.15 g, 21 mmol) and 4 Å molecular sieves (4 g). The reaction mixture was heated at reflux overnight and filtrated. The filtrate was evaporated and the residue was purified by silica gel flash column chromatography (n-hexane/ethyl acetate=9:1 to 5:1) to give compound 6 (8.78 g, 65% yield).

Step 3

The solution of compound 6 (965 mg, 1.5 mmol) and amine 7 (346 mg, 3 mmol) in 5 mL of THF was stirred at room temperature for 2 days and the solvent was removed under reduced pressure. The residue was purified by silica gel flash column chromatography (n-hexane/ethyl acetate=1:1 to 1:4) to give compound 8 (819 mg, 72% yield).

MI-773 (as the TFA salt) was dissolved in MeOH/H$_2$O (1:1 v/v ratio) and allowed to stand at room temperature for 1-4 days. The solution was purified by chromatography on a C18 reverse phase semi-preparative HPLC column with solvent A (0.1% of TFA in water) and solvent B (0.1% of TFA in methanol) as eluents (gradient: 45% of solvent A and 55% of solvent B to 30% of solvent A and 70% of solvent B in 30 min) MI-77301 was isolated as the TFA salt.

$^1$H NMR (300 MHz, MeOH-d4): 8.35 (d, J=7.8 Hz, 1H), 7.54-7.62 (m, 2H), 7.37-7.43 (m, 1H), 7.12-7.20 (m, 2H), 6.80 (d, J=1.5 Hz, 1H), 5.20 (d, J=11.4 Hz, 1H), 4.58 (d, J=11.4 Hz, 1H), 4.51 (d, J=7.2 Hz, 1H), 3.50-3.75 (m, 1H), 3.30-3.50 (m, 1H), 1.82-2.00 (m, 3H), 1.76 (d, J=10.5 Hz, 1H), 1.52 (d, J=12.3 Hz, 1H), 1.05-1.42 (m, 4H), 0.88-1.00 (m, 1H), 0.88 (s, 9H); $^{13}$C NMR (75 MHz, MeOH-d4): 177.7, 166.9, 157.6 (d, JC-F=248.0 Hz), 145.0, 137.0, 132.4, 128.6, 126.6, 126.4 (d, JC-F=4.9), 124.0, 123.4, 122.3 (d, JC-F=18.8 Hz), 121.5 (d, JC-F=12.8 Hz), 111.9, 69.9, 64.4, 64.0, 62.8, 49.7, 34.3, 34.2, 30.9, 30.82, 30.77, 29.4; Purity (HPLC): >95%.

In an alternative procedure, MI-773 (77 mg) was dissolved in 15 mL MeOH/H$_2$O (v/v=1:1). After 3 days, the needle crystals that had formed were collected, washed with cold MeOH/H$_2$O (v/v=1:1) and dried in vacuum to give MI-77301 as the free amine (20 mg; >95% purity as determined by HPLC).

$^1$H NMR (300 MHz, MeOH-d4): 7.49-7.55 (m, 1H), 7.25-7.31 (m, 1H), 7.10-7.16 (m, 1H), 6.82 (d, J=1.8 Hz, 1H), 6.50-6.71 (m, 1H), 6.49 (d, J=8.4 Hz, 1H), 4.32 (d, J=9.0 Hz, 1H), 4.09 (d, J=8.7 Hz, 1H), 3.57-3.69 (m, 1H), 3.49 (d, J=9.2 Hz, 1H), 3.46-3.57 (m, 1H), 1.83-2.07 (m, 3H), 1.68-1.80 (m, 1H), 1.54 (dd, J=9.0, 14.3 Hz, 1H), 1.12-1.45 (m, 5H), 0.80 (s, 9H). The absolute stereochemical configuration of MI-77301 was determined by X-ray analysis.

Figure 26:
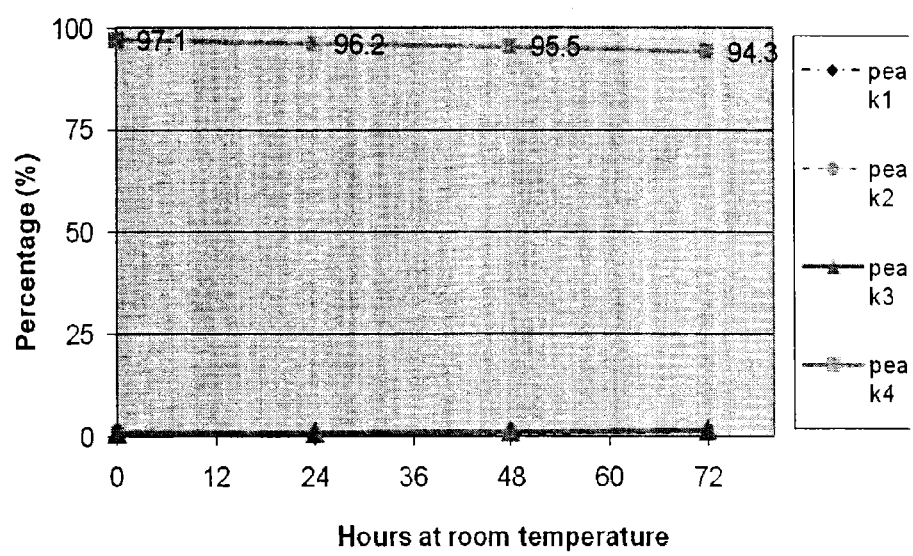
FIG. 26 is a line graph showing the stability of MI-77301 (TFA salt) at various time points.
Figure 27:
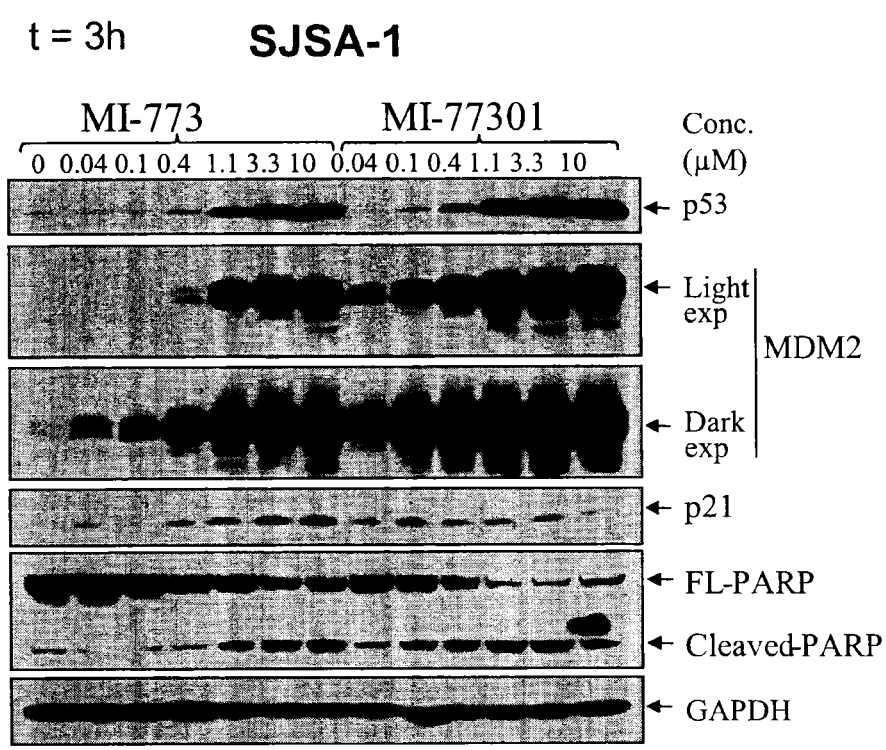
FIG. 27 is an illustration showing western blot analysis of p53 activation and apoptosis induced by MI-773 and MI-77301 in the SJSA-1 cell line.
Figure 28:
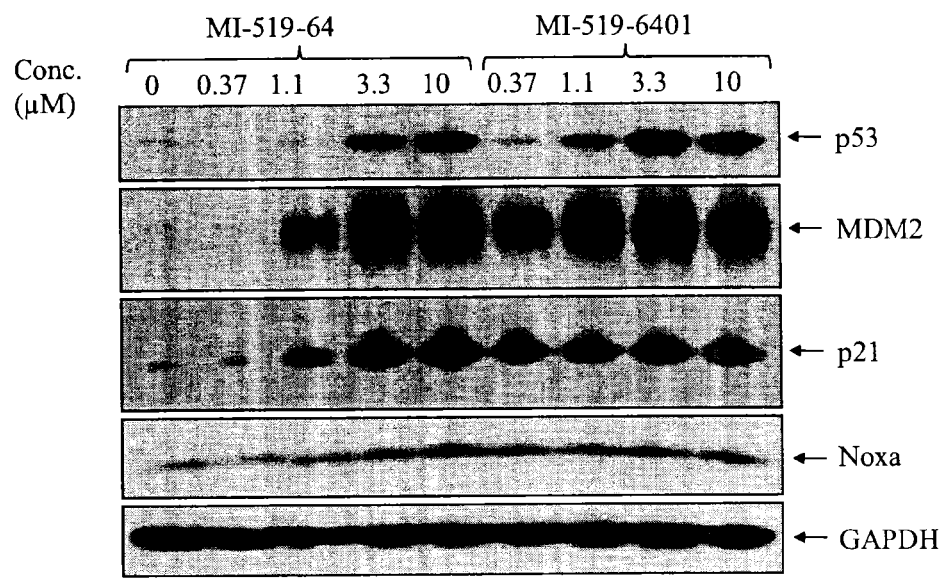
FIG. 28 is an illustration showing western blot analysis of p53 activation and apoptosis induced by MI-519-64 and MI-519-6401 in the SJSA-1 cell line.
Figure 29:
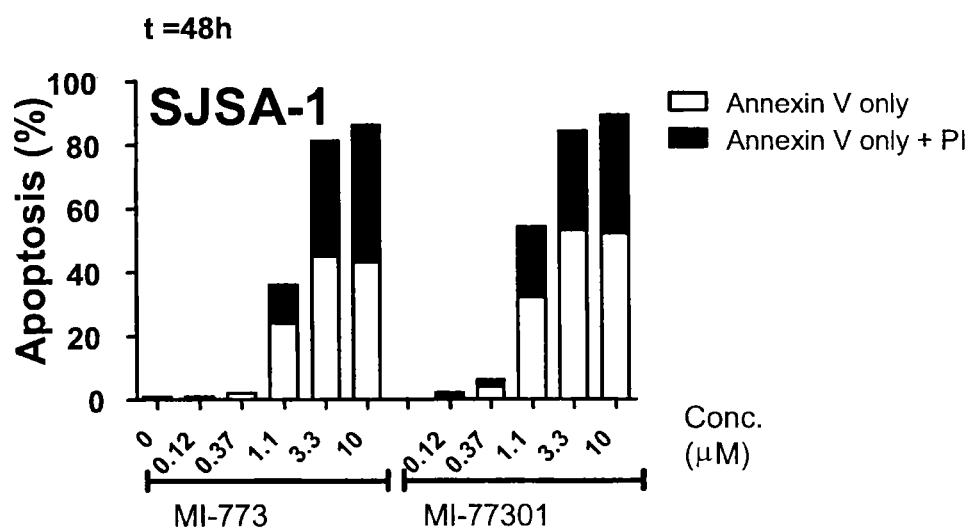
FIG. 29 is a bar graph showing apoptosis induced by MI-773 and MI-77301 in the SJSA-1 cell line.

Stability of MI-77301 (TFA salt): MI-77301 (TFA salt) was dissolved in a water/methanol mixture (water/methanol=1:1 with 0.1% of TFA). The solution was allowed to stand at room temperature. The purity was tested using a C18 reverse phase analytical HPLC column at the time points of 0, 12 h, 48 h, and 72 h. The results showed slow transformation of MI-77301 to three compounds having the same molecular weight (FIG. 26).

MI-71201, MI-710401, MI-710501, and MI-710901 of Example 1 were prepared using procedures similar to that used to prepare MI-519-6401.

Having now fully described the methods, compounds, and compositions of matter provided herein, it will be understood by those of skill in the art that the same can be performed within a wide and equivalent range of conditions, formulations, and other parameters without affecting the scope of the methods, compounds, and compositions provided herein or any embodiment thereof. All patents, patent applications and publications cited herein are fully incorporated by reference herein in their entirety.

What is claimed is:

1. A compound having Formula I:

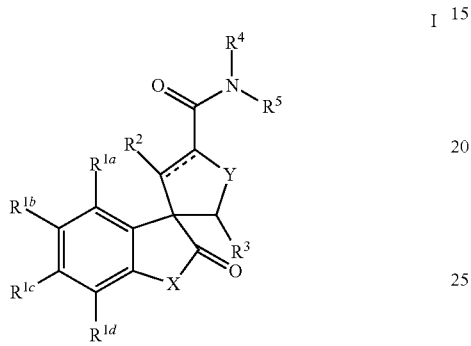

wherein:

$R^{1a}$, $R^{1b}$, $R^{1c}$, and $R^{1d}$ are independently selected from the group consisting of hydrogen, halogen, hydroxy, amino, nitro, cyano, alkoxy, aryloxy, optionally substituted alkyl, haloalkyl, optionally substituted cycloalkyl, optionally substituted alkenyl, optionally substituted cycloalkenyl, optionally substituted aryl, optionally substituted heteroaryl, carboxamido, and sulfonamido;

$R^2$ is selected from the group consisting of optionally substituted aryl and optionally substituted heteroaryl;

$R^3$ is selected from the group consisting of optionally substituted alkyl, optionally substituted (cycloalkyl) alkyl, optionally substituted cycloalkyl, optionally substituted alkenyl, optionally substituted cycloalkenyl, optionally substituted aryl, and optionally substituted heteroaryl;

$R^4$ is selected from the group consisting of hydrogen and optionally substituted $C_1$-$C_6$ alkyl;

$R^5$ is selected from the group consisting of:

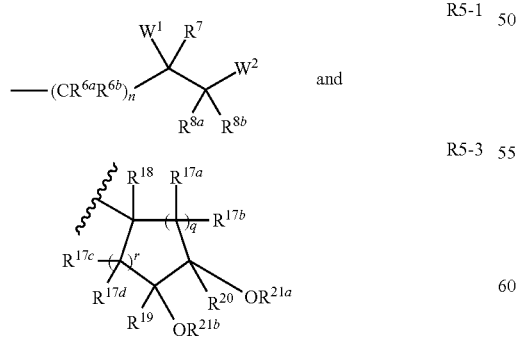

wherein:
each $R^{6a}$ and $R^{6b}$ is independently selected from the group consisting of hydrogen and optionally substituted $C_1$-$C_6$ alkyl;

$R^7$ is selected from the group consisting of hydrogen, optionally substituted $C_1$-$C_6$ alkyl, and optionally substituted cycloalkyl;

$R^{8a}$ and $R^{8b}$ are each independently selected from the group consisting of hydrogen, optionally substituted $C_1$-$C_6$ alkyl, and optionally substituted cycloalkyl; or $R^{8a}$ and $R^{8b}$ taken together with the carbon that they are attached form a 3- to 8-membered optionally substituted cycloalkyl;

$W^1$ is selected from the group consisting of —$OR^{9a}$ and —$NR^{9b}R^{9c}$;

$R^{9a}$ is hydrogen;

$R^{9b}$ is selected from the group consisting of hydrogen, optionally substituted alkyl, optionally substituted cycloalkyl, optionally substituted aryl, optionally substituted heteroaryl, —$SO_2R^{9d}$, and —$CONR^{9e}R^{9f}$;

$R^{9c}$ is selected from the group consisting of hydrogen, optionally substituted alkyl, optionally substituted cycloalkyl, optionally substituted aryl, and optionally substituted heteroaryl; or $R^{9b}$ and $R^{9c}$ taken together with the nitrogen atom to which they are attached form a 4- to 8-membered optionally substituted heterocyclo;

$R^{9d}$ is selected from the group consisting of optionally substituted alkyl and optionally substituted cycloalkyl;

$R^{9e}$ and $R^{9f}$ are each independently selected from the group consisting of hydrogen, optionally substituted alkyl, and optionally substituted cycloalkyl; or $R^{9e}$ and $R^{9f}$ taken together with the nitrogen atom to which they are attached form a 4- to 8-membered optionally substituted heterocyclo;

$W^2$ is selected from the group consisting of —$OR^{10}$ and —$NR^{11a}R^{11b}$;

$R^{10}$ is hydrogen; or one of $R^{9a}$ and $R^{10}$ is hydrogen and the other is a metabolically cleavable group;

with the proviso that when $W^1$ is —$OR^{9a}$ and $W^2$ is —$OR^{10}$ then at least one of $R^7$, $R^{8a}$, and $R^{8b}$ is other than hydrogen;

$R^{11a}$ is selected from the group consisting of hydrogen, optionally substituted alkyl, optionally substituted cycloalkyl, optionally substituted aryl, optionally substituted heteroaryl, —$SO_2R^{11c}$, and —$CONR^{11d}R^{11e}$;

$R^{11b}$ is selected from the group consisting of hydrogen, optionally substituted alkyl, optionally substituted cycloalkyl, optionally substituted aryl, and optionally substituted heteroaryl; or $R^{11a}$ and $R^{11b}$ taken together with the nitrogen atom to which they are attached form a 4- to 8-membered optionally substituted heterocyclo;

$R^{11c}$ is selected from the group consisting of optionally substituted alkyl and optionally substituted cycloalkyl;

$R^{11d}$ and $R^{11e}$ are each independently selected from the group consisting of hydrogen, optionally substituted alkyl, and optionally substituted cycloalkyl; or $R^{11d}$ and $R^{11e}$ together with the nitrogen atom to which they are attached form a 4- to 8-membered optionally substituted heterocyclo;

n is 1, 2, 3, 4, or 5;

each $R^{17a}$, $R^{17b}$, $R^{17c}$ and $R^{17d}$ is independently selected from the group consisting of hydrogen and optionally substituted $C_1$-$C_6$ alkyl;

$R^{18}$ is selected from the group consisting of hydrogen and optionally substituted $C_1$-$C_6$ alkyl;

$R^{19}$ is selected from the group consisting of hydrogen, optionally substituted $C_1$-$C_6$ alkyl, and optionally substituted cycloalkyl;

$R^{20}$ is selected from the group consisting of hydrogen, optionally substituted $C_1$-$C_6$ alkyl, and optionally substituted cycloalkyl;

$R^{21a}$ and $R^{21b}$ are each hydrogen; or one of $R^{21a}$ and $R^{21b}$ is hydrogen and the other is metabolically cleavable group;

q is 0, 1, 2, or 3;

r is 1, 2, or 3;

X is selected from the group consisting of O, S, and NR;

Y is selected from the group consisting of O, S, and NR";

R' is selected from the group consisting of hydrogen, optionally substituted alkyl, aralkyl, and optionally substituted cycloalkyl;

R" is selected from the group consisting of hydrogen, optionally substituted alkyl, aralkyl, and optionally substituted cycloalkyl; and represents a single or a double bond, or a pharmaceutically acceptable salt or solvate thereof.

2. The compound of claim 1, wherein represents a single bond or a pharmaceutically acceptable salt or solvate thereof.

3. The compound of claim 1 having Formula II:

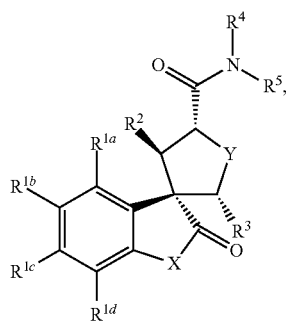

or a pharmaceutically acceptable salt or solvate thereof.

4. The compound of claim 1, wherein:

$R^{1a}$, $R^{1b}$, $R^{1c}$, and $R^{1d}$ are each independently selected from the group consisting of hydrogen, fluoro, and chloro;

$R^2$ is optionally substituted aryl;

$R^3$ is optionally substituted alkyl;

$R^4$ is hydrogen; and

X and Y are NH, or a pharmaceutically acceptable salt or solvate thereof.

5. The compound of claim 1, wherein $R^5$ is selected from the group consisting of:

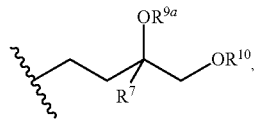

R5-5

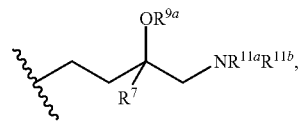

R5-6

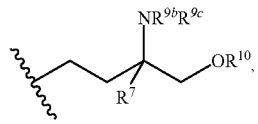

R5-7

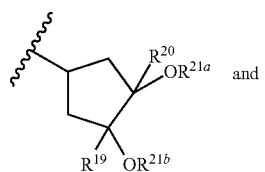

R5-16 and

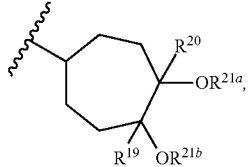

R5-17 or a pharmaceutically acceptable salt or solvate thereof.

6. The compound of claim 5, wherein:

$R^7$ is optionally substituted $C_1$-$C_4$ alkyl;

$R^{8a}$ is selected from the group consisting of hydrogen and $C_1$-$C_4$ alkyl;

$R^{9a}$ and $R^{10}$ are each hydrogen; or one of $R^9$ and $R^{10}$ is hydrogen and the other is a metabolically cleavable group;

$R^{9b}$ is selected from the group consisting of hydrogen, $C_1$-$C_4$ alkyl, —$SO_2R^{9d}$, and —$CONR^{9e}R^{9f}$;

$R^{9c}$ is selected from the group consisting of hydrogen, $C_1$-$C_4$ alkyl, and cycloalkyl; or $R^{9b}$ and $R^{9c}$ taken together with the nitrogen atom to which they are attached form a 4- to 8-membered optionally substituted heterocyclo;

$R^{9d}$ is selected from the group consisting of optionally $C_1$-$C_6$ alkyl and optionally substituted $C_3$-$C_6$ cycloalkyl;

$R^{9e}$ and $R^{9f}$ are each independently selected from the group consisting of hydrogen, optionally substituted $C_1$-$C_6$ alkyl, and optionally substituted $C_3$-$C_6$ cycloalkyl; or $R^{9e}$ and $R^{9f}$ taken together with the nitrogen atom to which they are attached form a 4- to 8-membered optionally substituted heterocyclo;

$R^{11a}$ is selected from the group consisting of hydrogen, $C_1$-$C_4$ alkyl, —$SO_2R^{11c}$, and —$CONR^{11d}R^{11e}$;

$R^{11b}$ is selected from the group consisting of hydrogen, $C_1$-$C_4$ alkyl, optionally substituted cycloalkyl; or $R^{11a}$ and $R^{11b}$ taken together with the nitrogen atom to which they are attached form a 4- to 8-membered optionally substituted heterocyclo;

$R^{11c}$ is selected from the group consisting of optionally substituted $C_1$-$C_6$ alkyl and optionally substituted $C_3$-$C_6$ cycloalkyl;

$R^{11d}$ and $R^{11e}$ are each independently selected from the group consisting of hydrogen, optionally substituted $C_1$-$C_6$ alkyl, and optionally substituted $C_3$-$C_6$ cycloalkyl; or $R^{11d}$ and $R^{11e}$ together with the nitrogen atom to which they are attached form a 4- to 8-membered optionally substituted heterocyclo;

$R^{19}$ is selected from the group consisting of hydrogen, optionally substituted $C_1$-$C_6$ alkyl, and optionally substituted $C_3$-$C_6$ cycloalkyl;

$R^{20}$ is selected from the group consisting of hydrogen, optionally substituted $C_1$-$C_6$ alkyl, and optionally substituted $C_3$-$C_6$ cycloalkyl; and $R^{21a}$ and $R^{21b}$ are each hydrogen; or one of $R^{21a}$ and $R^{21b}$ is hydrogen and the other is metabolically cleavable group, or a pharmaceutically acceptable salt or solvate thereof.

7. The compound of claim 1 having Formula XVIIIa:

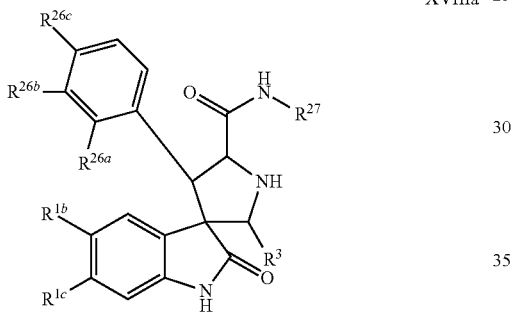

XVIIIa wherein:
$R^{1b}$ and $R^{1c}$ are independently selected from the group consisting of hydrogen, fluoro, and chloro;

$R^3$ is selected from the group consisting of optionally substituted alkyl, optionally substituted (cycloalkyl)alkyl, and optionally substituted cycloalkyl;

$R^{26a}$, $R^{26b}$, and $R^{26c}$ are independently selected from the group consisting of hydrogen, fluoro, and chloro; and $R^{27}$ is selected from the group consisting of:

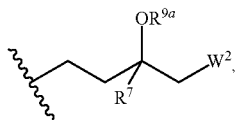

R27-1

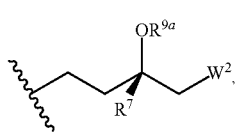

R27-2

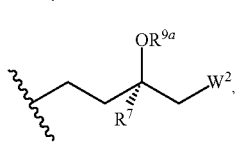

R27-3

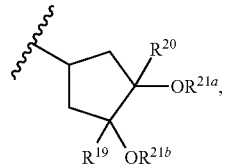

R27-23

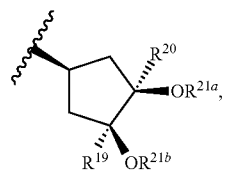

R27-24

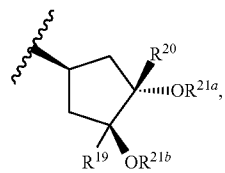

R27-25

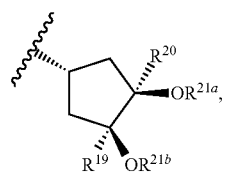

R27-26

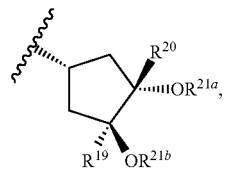

R27-27

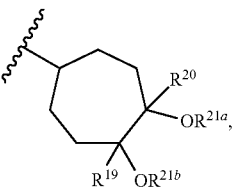

R27-28

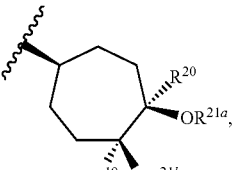

R27-29

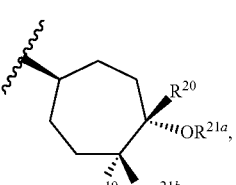

R27-30

-continued

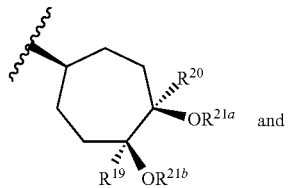

R27-31

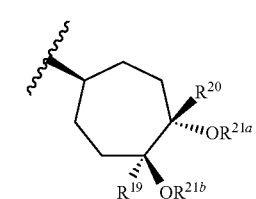

R27-32 wherein:

$R^7$ is optionally substituted $C_1$-$C_4$ alkyl;

$W^2$ is selected from the group consisting of —$OR^{10}$ and —$NR^{11a}R^{11b}$;

$R^{9a}$ and $R^{10}$ are each hydrogen; or one of $R^{9a}$ and $R^{10}$ is hydrogen and the other is a metabolically cleavable group;

$R^{11a}$ is selected from the group consisting of hydrogen, optionally substituted $C_1$-$C_4$ alkyl, optionally substituted $C_3$-$C_6$ cycloalkyl, —$SO_2R^{11c}$, and —$CONR^{11d}R^{11e}$;

$R^{11b}$ is selected from the group consisting of hydrogen, optionally substituted $C_1$-$C_4$ alkyl, optionally substituted $C_3$-$C_6$ cycloalkyl; or $R^{11a}$ and $R^{11b}$ taken together with the nitrogen atom to which they are attached form a 4- to 8-membered optionally substituted heterocyclo;

$R^{11c}$ is selected from the group consisting of optionally substituted $C_1$-$C_6$ alkyl and optionally substituted $C_3$-$C_6$ cycloalkyl;

$R^{11d}$ and $R^{11e}$ are each independently selected from the group consisting of hydrogen, optionally substituted $C_1$-$C_6$ alkyl, and optionally substituted $C_3$-$C_6$ cycloalkyl; or $R^{11d}$ and $R^{11e}$ together with the nitrogen atom to which they are attached form a 4- to 8-membered optionally substituted heterocyclo;

$R^{19}$ is selected from the group consisting of hydrogen, optionally substituted $C_1$-$C_6$ alkyl, and optionally substituted $C_3$-$C_6$ cycloalkyl;

$R^{20}$ is selected from the group consisting of hydrogen, optionally substituted $C_1$-$C_6$ alkyl, and optionally substituted $C_3$-$C_6$ cycloalkyl;

$R^{21a}$ and $R^{21b}$ are each hydrogen; or one of $R^{21a}$ and $R^{21b}$ is hydrogen and the other is metabolically cleavable group, or a pharmaceutically acceptable salt or solvate thereof.

8. The compound of claim 7 having Formula XIX:

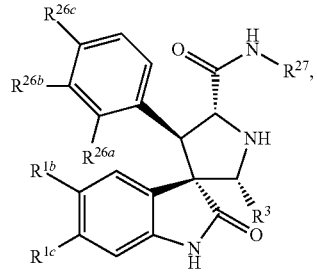

XIX or a pharmaceutically acceptable salt or solvate thereof.

9. The compound of claim 8, wherein $R^3$ is alkyl, or a pharmaceutically acceptable salt or solvate thereof.

10. The compound of claim 8, wherein $R^{27}$ is selected from the group consisting of:

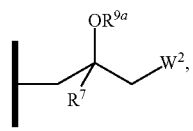

R27-61

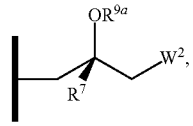

R27-62

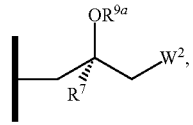

R27-63

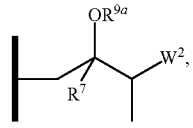

R27-64

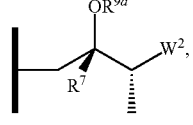

R27-65

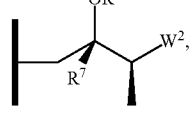

R27-66

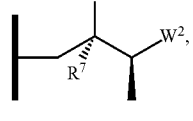

R27-67

-continued

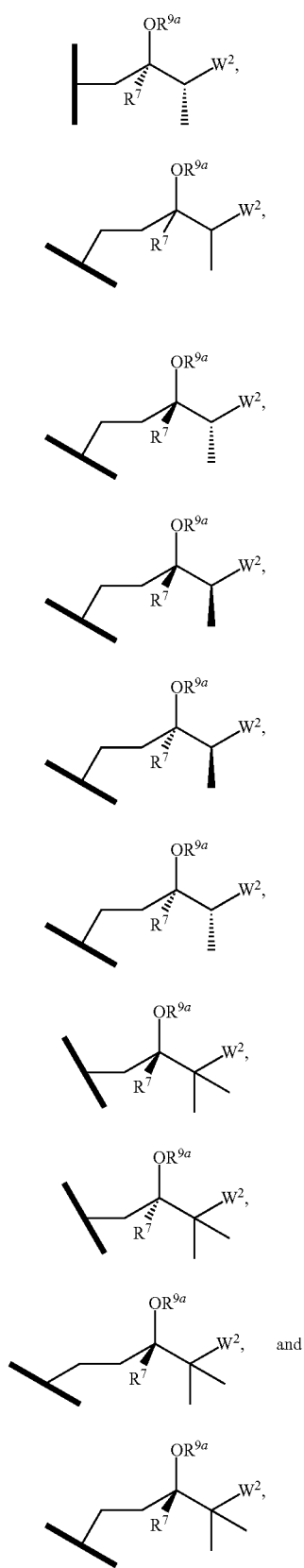

or a pharmaceutically acceptable salt or solvate thereof.

11. The compound of claim 8, wherein $R^{27}$ is selected from the group consisting of:

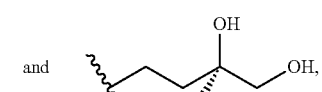

or a pharmaceutically acceptable salt or solvate thereof.

12. The compound of claim 8, wherein $R^{27}$ is selected from the group consisting of:

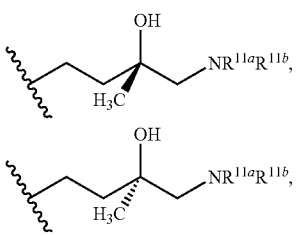

wherein $R^{11a}$ and $R^{11b}$ taken together with the nitrogen to which they are attached form a 5- or 6-membered optionally substituted heterocyclo, or a pharmaceutically acceptable salt or solvate thereof.

13. The compound of claim 10, wherein $R^3$ is —CH$_2$C(CH$_3$)$_3$, or a pharmaceutically acceptable salt or solvate thereof.

14. A pharmaceutical composition comprising the compound, or pharmaceutically acceptable salt or solvate thereof, of claim 1 and a pharmaceutically acceptable carrier.

15. A method of treating a patient comprising administering to the patient a therapeutically effective amount of the compound, or a pharmaceutically acceptable salt or solvate thereof, of claim 1, wherein the patient has cancer.

16. The method of claim 15, wherein cells of the cancer express functional p53.

17. The method of claim 15, further comprising administering to the patient one or more anticancer agents.

18. The method of claim 17, wherein the anticancer agent is a chemotherapeutic agent.

19. The method of claim 17, wherein the anticancer agent is radiation therapy.

20. A kit comprising a compound of claim 1, or a pharmaceutically acceptable salt or solvate thereof, and instructions for administering the compound to a patient having cancer.

21. The kit of claim 20, further comprising one or more anticancer agents.

22. The kit of claim 21, wherein the instructions direct co-administration of the compound together with the one or more anticancer agents.

23. The compound of claim 1 selected from the group consisting of:

305
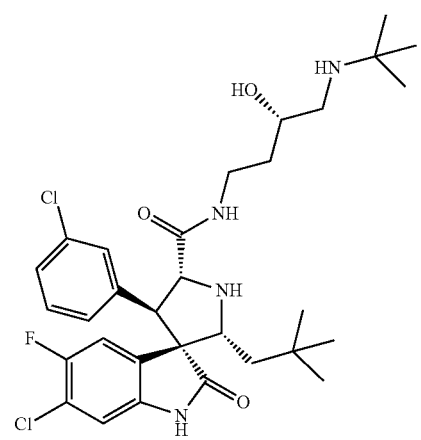
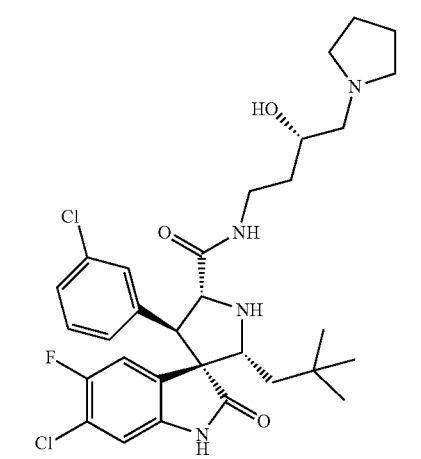
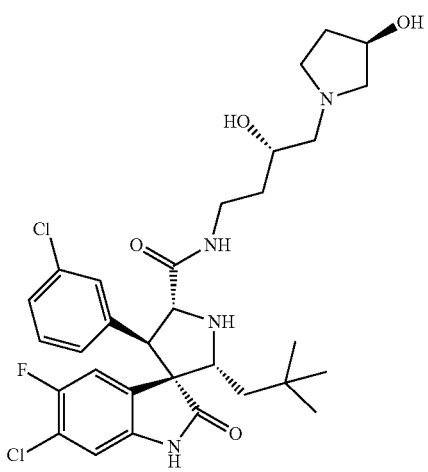
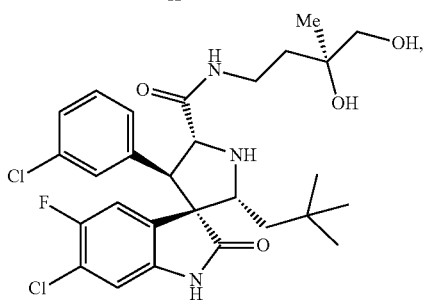
306
-continued
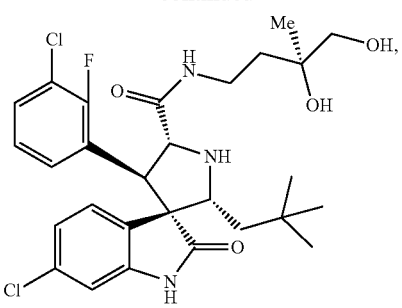
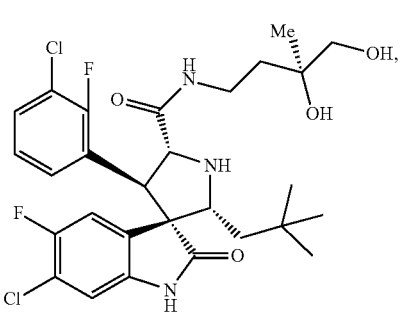
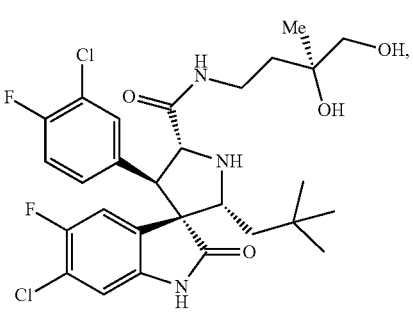
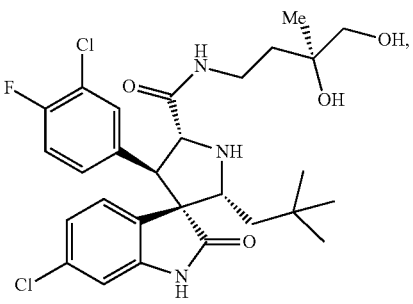
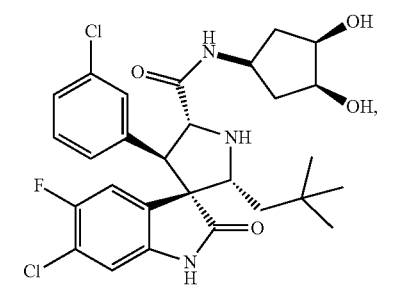

307
-continued
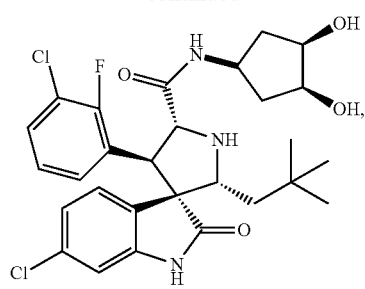
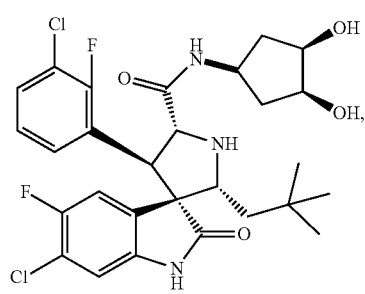
308
-continued
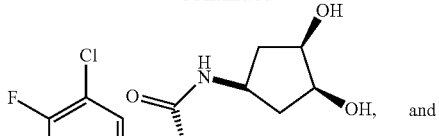 and
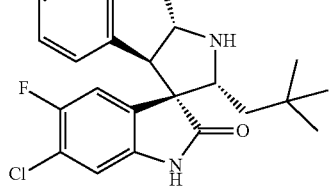
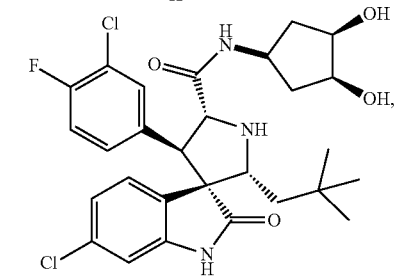
or a pharmaceutically acceptable salt or solvate thereof.
* * * * *

SEQUENCE LISTING

```
<160> NUMBER OF SEQ ID NOS: 1

<210> SEQ ID NO 1
<211> LENGTH: 11
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: The residue at this position is linked to 5-
      Carboxyfluorescein
<220> FEATURE:
<221> NAME/KEY: MISC_FEATURE
<222> LOCATION: (1)..(2)
<223> OTHER INFORMATION: The residues at these positions are beta-
      alanine
<220> FEATURE:
<221> NAME/KEY: MISC_FEATURE
<222> LOCATION: (5)..(5)
<223> OTHER INFORMATION: The residue at this position is alpha-
      aminoisobutyric acid
<220> FEATURE:
<221> NAME/KEY: MISC_FEATURE
<222> LOCATION: (6)..(6)
<223> OTHER INFORMATION: The residue at this position is phosphotyrosine
<220> FEATURE:
<221> NAME/KEY: MISC_FEATURE
<222> LOCATION: (7)..(7)
<223> OTHER INFORMATION: The residue at this position is 6-Cl-LTrp
<220> FEATURE:
<221> NAME/KEY: MISC_FEATURE
<222> LOCATION: (9)..(9)
<223> OTHER INFORMATION: The residue at this position is 1-amino-
      cyclopropanecarboxylic acid
```

```
<220> FEATURE:
<221> NAME/KEY: MISC_FEATURE
<222> LOCATION: (11)..(11)
<223> OTHER INFORMATION: The residue at this position is linked to NH2

<400> SEQUENCE: 1

Ala Ala Phe Met Xaa Tyr Trp Glu Xaa Leu Asn
1               5                   10
```